US011548944B2

(12) United States Patent
Moore et al.

(10) Patent No.: US 11,548,944 B2
(45) **Date of Patent: *Jan. 10, 2023**

(54) MATRIX METALLOPROTEASE-CLEAVABLE AND SERINE PROTEASE-CLEAVABLE SUBSTRATES AND METHODS OF USE THEREOF

(71) Applicant: CytomX Therapeutics, Inc., South San Francisco, CA (US)

(72) Inventors: Stephen James Moore, Danville, CA (US); Margaret Thy Luu Nguyen, San Francisco, CA (US); Daniel Robert Hostetter, Palo Alto, CA (US); Olga Vasiljeva, Cupertino, CA (US); Jason Gary Sagert, San Mateo, CA (US); Jonathan Alexander Terrett, Cupertino, CA (US); James William West, Bend, OR (US)

(73) Assignee: CytomX Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/360,809

(22) Filed: Jun. 28, 2021

(65) Prior Publication Data

US 2021/0355208 A1 Nov. 18, 2021
US 2022/0380453 A9 Dec. 1, 2022

Related U.S. Application Data

(62) Division of application No. 15/002,131, filed on Jan. 20, 2016, now Pat. No. 11,046,759.

(60) Provisional application No. 62/278,713, filed on Jan. 14, 2016, provisional application No. 62/277,771, filed on Jan. 12, 2016, provisional application No. 62/258,015, filed on Nov. 20, 2015, provisional application No. 62/105,490, filed on Jan. 20, 2015.

(51) Int. Cl.

| | |
|---|---|
| ***C07K 7/08*** | (2006.01) |
| ***C07K 14/00*** | (2006.01) |
| ***C07K 16/28*** | (2006.01) |
| ***A61K 38/05*** | (2006.01) |
| ***A61K 47/68*** | (2017.01) |
| ***A61K 49/00*** | (2006.01) |
| ***C07K 16/40*** | (2006.01) |
| *A61K 39/00* | (2006.01) |

(52) U.S. Cl.
CPC .............. *C07K 16/28* (2013.01); *A61K 38/05* (2013.01); *A61K 47/6849* (2017.08); *A61K 47/6851* (2017.08); *A61K 49/0058* (2013.01); *C07K 7/08* (2013.01); *C07K 14/00* (2013.01); *C07K 16/2863* (2013.01); *C07K 16/2896* (2013.01); *C07K 16/40* (2013.01); *A61K 2039/505* (2013.01); *A61K 2039/507* (2013.01); *C07K 2317/51* (2013.01); *C07K 2317/515* (2013.01); *C07K 2317/92* (2013.01); *C07K 2319/50* (2013.01); *C07K 2319/74* (2013.01)

(58) Field of Classification Search
CPC .... C07K 16/28; C07K 16/2863; C07K 16/40; C07K 2317/51; C07K 2317/515; C07K 2317/92; C07K 2319/50; A61K 47/6849; A61K 47/6851; A61K 2039/505
See application file for complete search history.

(56) References Cited

U.S. PATENT DOCUMENTS

| | | | |
|---|---|---|---|
| 3,773,919 | A | 11/1973 | Boswell |
| 4,485,045 | A | 11/1984 | Regen |
| 4,522,811 | A | 6/1985 | Eppstein et al. |
| 4,544,545 | A | 10/1985 | Ryan et al. |
| 5,013,556 | A | 5/1991 | Woodle et al. |
| 5,030,719 | A | 7/1991 | Umemeto et al. |
| 5,151,510 | A | 9/1992 | Stec et al. |
| 6,551,795 | B1 | 4/2003 | Rubenfield et al. |
| 6,558,728 | B1 | 5/2003 | Poulsen et al. |
| 7,276,497 | B2 | 10/2007 | Chari et al. |
| 7,439,319 | B2 | 10/2008 | Smith et al. |

(Continued)

FOREIGN PATENT DOCUMENTS

| | | | |
|---|---|---|---|
| BR | 112017001579 | A2 | 11/2017 |
| EP | 1 523 503 | B1 | 4/2009 |

(Continued)

OTHER PUBLICATIONS

Paul, Fundamental Immunology, 3rd Edition, 1993, pp. 292-295.*

(Continued)

*Primary Examiner* — Hong Sang

(74) *Attorney, Agent, or Firm* — Rothwell, Figg, Ernst & Manbeck, P.C.

(57) ABSTRACT

The invention relates generally to polypeptides that include at least a first cleavable moiety (CM1) that is a substrate for at least one matrix metalloprotease (MMP) and at least a second cleavable moiety (CM2) that is a substrate for at least one serine protease (SP), to activatable antibodies and other larger molecules that include these polypeptides that include at least a CM1 that is a substrate for at least one MMP protease and at least a CM2 that is a substrate for at least one SP protease, and to methods of making and using these polypeptides that include at least a CM1 that is a substrate for at least one MMP protease and at least a CM2 that is a substrate for at least one SP protease in a variety of therapeutic, diagnostic and prophylactic indications.

10 Claims, 12 Drawing Sheets

Specification includes a Sequence Listing.

(56) References Cited

U.S. PATENT DOCUMENTS

| | | | |
|---|---|---|---|
| 7,442,159 B1 | 10/2008 | Riechmann et al. | |
| 7,465,790 B2 | 12/2008 | Waldmann et al. | |
| 7,666,817 B2 | 2/2010 | Daugherty et al. | |
| 7,935,785 B2 | 5/2011 | Smith et al. | |
| 8,513,390 B2 | 8/2013 | Stagliano et al. | |
| 8,518,404 B2 | 8/2013 | Daugherty et al. | |
| 8,524,220 B1 | 9/2013 | Bermudes | |
| 8,529,898 B2 | 9/2013 | Daugherty et al. | |
| 8,541,203 B2 | 9/2013 | Daugherty et al. | |
| 8,563,269 B2 | 10/2013 | Stagliano et al. | |
| 8,809,504 B2 | 8/2014 | Lauermann | |
| 9,120,853 B2 | 9/2015 | Lowman et al. | |
| 9,127,053 B2 | 9/2015 | West et al. | |
| 9,169,321 B2 | 10/2015 | Daugherty et al. | |
| 9,309,510 B2 | 4/2016 | La Porte et al. | |
| 9,453,078 B2 | 9/2016 | Stagliano et al. | |
| 9,562,073 B2 | 2/2017 | Moore et al. | |
| 10,059,762 B2 | 8/2018 | Stagliano et al. | |
| 10,077,300 B2 | 9/2018 | Daugherty et al. | |
| 10,118,961 B2 | 11/2018 | Stagliano et al. | |
| 10,138,272 B2 | 11/2018 | Moore et al. | |
| 10,179,817 B2 * | 1/2019 | Sagert | A61K 39/3955 |
| 10,233,244 B2 * | 3/2019 | Sagert | A61P 35/00 |
| 10,336,824 B2 | 7/2019 | West et al. | |
| 10,513,558 B2 * | 12/2019 | Tipton | C07K 16/3015 |
| 10,669,337 B2 | 6/2020 | Irving et al. | |
| 10,669,339 B2 | 6/2020 | West et al. | |
| 10,745,481 B2 * | 8/2020 | West | A61K 47/6849 |
| 10,875,913 B2 | 12/2020 | Stagliano et al. | |
| 2003/0219402 A1 | 11/2003 | Rutter | |
| 2004/0109855 A1 | 6/2004 | Waldmann et al. | |
| 2004/0123343 A1 | 6/2004 | La Rosa et al. | |
| 2007/0218074 A1 | 9/2007 | Man | |
| 2009/0304719 A1 | 12/2009 | Daugherty et al. | |
| 2010/0041588 A1 | 2/2010 | Keay et al. | |
| 2010/0189651 A1 | 7/2010 | Stagliano et al. | |
| 2010/0221212 A1 | 9/2010 | Stagliano | |
| 2011/0214205 A1 | 9/2011 | Dietrich et al. | |
| 2011/0287517 A1 | 11/2011 | Steward et al. | |
| 2012/0149061 A1 | 6/2012 | Stagliano et al. | |
| 2012/0207756 A1 | 8/2012 | Stagliano et al. | |
| 2012/0237512 A1 | 9/2012 | Daugherty et al. | |
| 2012/0237977 A1 | 9/2012 | Daugherty et al. | |
| 2012/0244154 A1 | 9/2012 | Daugherty et al. | |
| 2013/0150558 A1 | 6/2013 | Williams et al. | |
| 2013/0309230 A1 | 11/2013 | Stagliano et al. | |
| 2014/0010810 A1 | 1/2014 | West et al. | |
| 2014/0023664 A1 | 1/2014 | Lowman et al. | |
| 2014/0024810 A1 | 1/2014 | Stagliano et al. | |
| 2014/0045195 A1 | 2/2014 | Daugherty et al. | |
| 2014/0363430 A1 | 12/2014 | West et al. | |
| 2015/0087810 A1 | 3/2015 | Moore et al. | |
| 2016/0122425 A1 | 5/2016 | Daugherty et al. | |
| 2016/0194399 A1 | 7/2016 | Irving | |
| 2016/0228546 A1 | 8/2016 | Stagliano et al. | |
| 2016/0311903 A1 | 10/2016 | West et al. | |
| 2016/0355587 A1 | 12/2016 | West et al. | |
| 2016/0355592 A1 | 12/2016 | Sagert et al. | |
| 2016/0355599 A1 * | 12/2016 | Sagert | A61K 47/6849 |
| 2017/0044259 A1 | 2/2017 | Tipton et al. | |
| 2017/0081397 A1 | 3/2017 | Stagliano et al. | |
| 2017/0204139 A1 | 7/2017 | Moore et al. | |
| 2018/0303952 A1 | 10/2018 | Sagert et al. | |
| 2019/0016814 A1 | 1/2019 | Humphrey et al. | |
| 2019/0119370 A1 | 4/2019 | Stagliano et al. | |
| 2019/0135864 A1 | 5/2019 | Moore et al. | |
| 2019/0211089 A1 | 7/2019 | Daugherty et al. | |
| 2019/0359714 A1 | 11/2019 | Tipton et al. | |
| 2019/0382493 A1 | 12/2019 | West et al. | |
| 2021/0284721 A1 | 9/2021 | Stagliano et al. | |

FOREIGN PATENT DOCUMENTS

| | | | |
|---|---|---|---|
| EP | 1 324 771 | B1 | 6/2011 |
| JP | 2010-536370 | A | 12/2010 |
| JP | 2012-506408 | A | 3/2012 |
| JP | 2012-514982 | A | 7/2012 |
| WO | 1994011026 | A2 | 5/1994 |
| WO | WO 1999/15563 | A1 | 4/1999 |
| WO | WO 2001/57182 | A2 | 8/2001 |
| WO | WO 2001/91798 | A2 | 12/2001 |
| WO | WO 2002/12475 | A2 | 2/2002 |
| WO | WO 2002/30460 | A2 | 4/2002 |
| WO | 2002038796 | A3 | 5/2002 |
| WO | WO 2003/038083 | A1 | 5/2003 |
| WO | WO 2004/009638 | A1 | 1/2004 |
| WO | WO 2006/110599 | A2 | 10/2006 |
| WO | WO 2007/105027 | A1 | 9/2007 |
| WO | WO 2008/052187 | A1 | 5/2008 |
| WO | WO 2009/025846 | A2 | 2/2009 |
| WO | 2010046628 | A1 | 4/2010 |
| WO | WO 2010/081173 | A2 | 7/2010 |
| WO | WO 2010/088691 | A2 | 8/2010 |
| WO | WO 2010/096838 | A2 | 8/2010 |
| WO | WO 2010/129609 | A2 | 11/2010 |
| WO | WO 2011/028698 | A2 | 3/2011 |
| WO | 2012156919 | A1 | 11/2012 |
| WO | WO 2013/163631 | A2 | 10/2013 |
| WO | WO 2013/192546 | A2 | 12/2013 |
| WO | WO 2013/192550 | A2 | 12/2013 |
| WO | WO 2014/026136 | A2 | 2/2014 |
| WO | 2014052462 | A2 | 4/2014 |
| WO | WO 2014/107599 | A2 | 7/2014 |
| WO | WO 2014/176284 | A1 | 10/2014 |
| WO | WO 2014/193973 | A2 | 12/2014 |
| WO | 2015048329 | A2 | 4/2015 |
| WO | 2015116933 | A2 | 8/2015 |
| WO | 2016014974 | A2 | 1/2016 |
| WO | 2016118629 | A1 | 7/2016 |
| WO | 2016179257 | A2 | 11/2016 |
| WO | 2020118109 | A2 | 6/2020 |

OTHER PUBLICATIONS

Rudikoff et al., Proc. Natl. Acad. Sci. USA, 1982, 79(6):1979-1983.*

Colman, Research in Immunology, 1994, 145:33-36.*

Bendig, Methods: A Companion to Methods in Enzymology, 1995; 8:83-93.*

Khantasup et al., Monoclonal Antibodies in Immunodiagnosis and Immunotherapy, 2015, 34(6): 404-417.*

Murphy et al., Journal of Immunological Methods, vol. 463, p. 127-133, 2018.*

Harris JL et al. "Rapid and general profiling of protease specificity by using combinatorial fluoreogenic substrate libraries." PNAS vol. 97(14):7754-59 (2000).

Prudova A, auf dem Keller U, Butler GS, Overall CM. Multiplex N-terminome analysis of MMP-2 and MMP-9 substrate degradomes by iTRAQ-TAILS quantitative proteomics. Mol Cell Proteomics. May 2010;9(5):894-911. doi: 10.1074/mcp.M000050-MCP201. Epub Mar. 20, 2010.

Ratnikov et al., "Basis for substrate recognition and distinction by matrix metalloproteinases." Proc. Natl. Acad. Sci., vol. 111(4): E4148-55 (2014).

Takeuchi T et al. "Cellular Location of Membrane-type Serine Protease 1 and Identification of Protease-activated Receptor-2 and Single-chain Urokinase-type Plasminogen Activator as Substrates." J Biol Chem vol. 275(34): 26333-26342 (2000).

ADC Review, "Maytansine" [online]. Retrieved from: http://adcreview.com/adc-university/adcs-101/cytotoxic-agents/maytansine/, on Mar. 17, 2016, 4 pages.

BLAST search of SEQ ID No. 362 from U.S. Pat. No. 9,562,073 (retrieved from http://blast.ncbi.nlm.nih.gov/Blast.cgi on Mar. 17, 2016, 8 pages).

BLAST search of SEQ ID No. 363 from U.S. Pat. No. 9,562,073 (retrieved from http://blast.ncbi.nlm.nih.gov/Blast.cgi on Mar. 17, 2016, 7 pages).

BLAST search of SEQ ID No. 364 from U.S. Pat. No. 9,562,073 (retrieved from http://blast.ncbi.nlm.nih.gov/Blast.cgi on Mar. 17, 2016, 8 pages).

(56) References Cited

OTHER PUBLICATIONS

Casadaban et al., "Analysis of gene control signals by DNA fusion and cloning in *Escherichia coli*" J Mol Biol, 138(2):179-207 (1980).
Donaldson, J.M. et al., "Design and development of masked therapeutic antibodies to limit off-target effects: application to anti-EGFR antibodies", Cancer Biology & Therapy, vol. 8, No. 22, 2009, p. 2147-2152.
GenBank Accession No. ADA97619, "Sequence 28102 from U.S. Pat. No. 6,551,795" Rubenfield, 2009, 1 page.
GenBank Accession No. AEL07912.1, "conserved hypothetical protein [*Xanthomonas campestris* pv. *raphani* 756C]" [retrieved on Dec. 28, 2017]. Retrieved from internet: https://www.ncbi.nlm.nih.gov/protein/AEL07912, 1 page.
GenBank Accession No. AF099373, "protein ITFG3 [*Callorhinchus milii*]" 2013, 1 page.
GenBank Accession No. AKP45152, "wall-associated receptor-like kinase 2 [*Zea mays*]" [online]. Retrieved on Jul. 25, 2018 from tire Internet: <https://www.ncbi.nlm.nih.gov/protein/Akp45152>, 2 pages.
GenBank Accession No. YP 005352726.1. "petG gene product (chloroplast [*Ginko biloba*]" [online]. [retrieved on Dec. 28, 2017]. Retrieved from the Internet:<https://www.ncbi.nlm.nih.gov/protein/YP_005352726.1>, 1 page.
Geneseq Accession No. AAB46481, "*B. brevis* tyrocidin synthetase activating domain 9" [online] First entry Apr. 9, 2001, revised Sep. 11, 2003, 2 pages.
GenPept Accession No. YP_008873205 "Hypothetical protein [*Pseudomonas* phage PPpW-3]" Kawato et al.; submitted Dec. 9, 2013, 1 page.
Gerspach et al. "Restoration of membrane TNF-like activity by cell surface targeting and matrix metalloproteinase-mediated processing of a TNF prodrug" Cell Death and Differentiation. 2006.13:273-284.
Henikoff, S et al. (1992) "Amino acid substitution matrices from protein blocks" *Proc Natl Acad Sci U S A*, 89:10915-10919.
Jabaiah, A. and P.S. Daugherty, "Directed evolution of protease beacons that enable sensitive detection of endogenous MT1-MMP activity in tumor cell lines" *Chem Biol*, Mar. 25, 2011;18(3):392-401.
Ke, S-H. et al. "Distinguishing the specificities of closely related proteases" J Biol Chem, Jun. 26, 1997; vol. 272, No. 26, pp. 16603-16609.
Ke, S-H. et al., "Optimal subsite occupancy and design of a selective inhibitor of urokinase", J Biol Chem, Aug. 15, 1997; vol. 272, No. 33, pp. 20456-20462.
Kridel, S.J. et al. "Substrate hydrolysis by matrix metalloproteinase-9" J Biol Chem, Jun. 8, 2001; vol. 276, No. 23, pp. 20572-20578. Epub Mar. 14, 2001.
Liu, S. et al. "Intermolecular complementation achieves high-specificity tumor targeting by anthrax toxin", Nature Biotechnology, vol. 23, No. 6, p. 725-730 (2005).
Lopez-Otin, C. et al. "Protease degradomics: a new challenge for proteomics", Nature Reviews: Molecular Cell Biology, vol. 3, p. 509-519, (2002).
Rothberg, J.M. et al. "An integrated semiconductor device enabling non-optical genome sequencing" Nature. Jul. 20, 2011;475(7356):348-352.
Turk, B.E. et al. "Determination of protease cleavage site motifs using mixture-based oriented peptide libraries" Nat Biotechnol, Jul. 2001; 19(7):661-667.
Uniprot Accession No. B8J087, "Uncharacterized protein" Mar. 3, 2009, 2 pages.
Uniprot Accession No. Q9ZZR8, "Cytochrome b" May 1, 1999, 2 pages.
UniprotKB Accession No. B1FZS3 (B1FZS3_9BURK), "Major facilitator superfamily MFS_1" [online]. Retrieved from the Internet on Jul. 25, 2018 from: <https://www.ncbi.nlm.nih.gov/protein/Akp45152>, 4 pages.
Venkatesh, B. et al. (2014) "Elephant shark genome provides unique insights into gnathostome evolution", Nature, vol. 505, No. 7482, pp. 174-179.
Villacres, E. et al. (1993) "Cloning, Chromosomal Mapping, and Expression of Human Fetal Brain Type I Adenylyl Cyclase" Genomics, vol. 16, No. 2, 1993, p. 473-478.
Waterhouse, A.M. et al. (2009) "Jalview Version 2—a multiple sequence alignment editor and analysis workbench" Bioinformatics, 25(9):1189-1191.
EMBL Database (Jan. 2, 2014) "*Callorhinchus milii* (elephant shark) protein ITFG3" ID AFO99373, 2 pages.
Lebeau et al. (2013) "Imaging a functional tumorigenic biomarker in the transformed epithelium", Proc. Natl. Acad. Sci. USA, 110(1):93-98.
List et al. (2005) "Deregulated matriptase causes ras-independent multistage carcinogenesis and promotes ras-mediated malignant transformation" Genes & Develop., 19:1934-1950.
Vasiljeva et al. (2019) "The Multifaceted Roles of Tumor-Associated Proteases and Harnessing Their Activity for Prodrug Activation", Biol. Chem. [online]. Retrieved from: https://doi.org/10.1515/hsz-2018-0451 (Accepted Mar. 18, 2019).
Kopylov, A. et al. (2007) "Methods of quantitative proteomics" *Biomed Chem*, 53(6):613-643. Russian; English abstract on p. 643.
"Derivative (chemistry)", Wikipedia, a free online encyclopedia, accessed Sep. 11, 2017, 1 page. Downloaded from: https://en.wikipedia.org/w/index.php?title=Derivative (chemistry)&oldid=779855519.
Jeong K. et al. "Recombinant antibodies: Engineering and production in yeast and bacteria hosts", Biotechnology Journal (2011), vol. 6, p. 16-27.
"Maytansinoid", Wikipedia, a free online encyclopedia, accessed Sep. 11, 2017, 2 pages. Downloaded from: https://en.wikipedia.org/w/index.php?title=Maytansinoid&oldid=732417913.
Kridel et al., "A Unique Substrate Binding Mode Discriminates Membrane Type-I Matrix Metalloproteinase from Other Matrix Metalloproteinases", J. Biol. Chem. (2002) 277(26): 23788-23793.
Portolano et al., Journal of Immunology, 1993, 150(3): 1993, 880-887.
Genpept Accession No. POC9K2, "RecName: Full=Protein MGF 110-14L; Flags: Precursor" May 5, 2009; Database DDBJ/EMBL/Genbank [ online]. Retrieved from the Internet: <https://www.ncbi.nlm.nih.gov/protein/229544532?sat=12&satkey= 1040226>; retrieved on Sep. 28, 2018, 3 pages.
Nangia-Makker P., et al. (Dec. 15, 2007) "Galectin-3 cleavage: a novel surrogate marker for matrix metalloproteinase activity in growing breast cancers" Cancer Res, 67(24): 11760-11768. NIH Public Access Author Manuscript; available in PMC Apr. 2, 2013 [online]. Retrieved from the Internet: https://www.ncbi.nlm.nih.gov/pmc/articles/PMC36I3979; 17 pages.
Zhao T. et al. (May 21, 2010) "A novel strategy to tag matrix metalloproteinasespositive cells for in vivo imagine of invasive and metastatic activity of tumor cells" J Control Release, 144(1):109-114. doi: 10.1016/j.jcomel.2010.01.023. Epub Jan. 21, 2010; abstract.
Irving, "Probodies Empower a New Generation of Antibody Immunotherapies," presented at Keystone Symposia on Molecular and Cellular Biology, Feb. 2015.
Gerspach et al., "Target-selective activation of a TNF prodrug by urokinase-type plasminogen activator (uPA) mediated proteolytic processing at the cell surface." Cancer Immunol Immunother, vol. 55: 1590-1600 (2006).
Tateno, H. et al. (Jul. 24, 1998) "Isolation and Characterization ofRharnnose-binding Lectins from Eggs of Steelhead Trout (*Oncorhynchus mykiss*) Homologous to Low Density Lipoprotein Receptor Superfamily" J Biol Chem, vol. 273, No. 30, pp. 19190-19197.
Baldrick P. "Pharmaceutical excipient development: the need for preclinical guidance." Regul. Toxicol Pharmacol. (2000) 32(2):210-218.
Bowie et al., "A method to identify protein sequences that fold into a known three-dimensional structure", Science (1991) 253(5016):164-170.
Charman WN, "Lipids, lipophilic drugs, and oral drug delivery—some emerging concepts." J. Pharm. Sci. (2000) 89(8):967-978.
Chen et al, "Selective Antibody Activation Through Protease-Activated Pro-Antibodies that Mask Binding Sites with Inhibitory Domains", Scientific Reports, (2017) 7(1): 11587 (1-12).

(56) References Cited

OTHER PUBLICATIONS

Chothia & Lesk, "Canonical Structures for the Hypervariable Regions of Immunoglobulins", J. Mol. Biol. (1987) 196:901-917.
Chothia et al., "Conformations of immunoglobulin hypervariable regions", Nature (1989) 342:877-883.
Database EMBL, Accession No. OVF07168 (Jun. 15, 2017) "Clavispora lusitaniae hypothetical protein" Durrens et al. [online]; XP055665684, Retrieved from Internet on Feb. 23, 2021 (2 pages): https://www.ebi.ac.uk/ena/browser/ api/embl/OVF07168.1?lineLimit=1000.
Database UniProtKB, Accession No. A0A0D8BN56 (Jun. 17, 2020) "Uncharacterized protein from Frankia torreyi", Oshone et al. [online]; UniProt Consortium, www.uniprot.org; Retrieved from Internet on Feb. 23, 2021 (1 page): https://www.uniprot.org/uniprot/A0A0D8BN56.txt.
Database UniProtKB, Accession No. T0RF53 (Oct. 13, 2013), "Uncharacterized protein from Saprolegnia diclina", Russ et al [online]; UniProt Consortium, www.uniprot.org; Retrieved from Internet: https://www.uniprot.org/uniprot/T0RF53.txt (Feb. 23, 2021); 1 page.
Davies et al., "Antibody-antigen complexes", Annual Rev. Biochem. (1990) 59:439-473.
Eppstein et al., "Biological activity of liposome-encapsulated murine interferon gamma is mediated by a cell membrane receptor", Proc. Natl. Acad. Sci. USA, (1985) 82(11):3688-3692.
Hwang et al., "Hepatic uptake and degradation of unilamellar sphingomyelin/cholesterol liposomes: a kinetic study", Proc. Natl Acad. Sci. USA (1980) 77(7):4030-4034.
Jansen et al., "Immunotoxins: hybrid molecules combining high specificity and potent cytotoxicity", Immunological Reviews (1982) 62:185-216.
Killen and Lindstrom, "Specific killing of lymphocytes that cause experimental autoimmune myasthenia gravis by ricin toxin-acetylcholine receptor conjugates", J. Immunol. (1984) 133(5):2549-2553.
Kukreja at al., "The High Throughput Multiplexed Peptide-Centric Profiling Illustrates Both the Substrate Cleavage Redundancy and Specificity in the MMP Family", Chem. Biol., (2015) 22(8):1122-1133.
LaPlanche et al., "Phosphorothioate-modified oligodeoxyribonucleotides. III. NMR and UV spectroscopic studies of the Rp-Rp, Sp-Sp, and Rp-Sp duplexes, [d(GGSAATTCC)]2, derived from diastereomeric O-ethyl phosphorothioates", Nucl. Acids Res. (1986) 14(22):9081-9093.
Malmqvist M., "Biospecific interaction analysis using biosensor technology", Nature (1993) 361(6408):186-187.
Marasco et al., "Design, intracellular expression, and activity of a human anti-human immunodeficiency virus type 1 gp120 single-chain antibody", Proc. Natl. Acad. Sci. USA (1993) 90(16):7889-7893.
Martin et al., "Irreversible coupling of immunoglobulin fragments to preformed vesicles. An improved method for liposome targeting", J. Biol. Chem. (1982) 257(1):286-288.
Mitra and Lawton, "Reagents for the crosslinking of proteins by equilibrium transfer alkylation", J. Amer. Chem. Soc. (1979) 101(11):3097-3110.
Powell et al. "Compendium of excipients for parenteral formulations" PDA J Pharm Sci Technol. (1998) 52(5):238-311.
Ramakrishnan et al., "Comparison of the Selective Cytotoxic Effects of Immunotoxins Containing Ricin A Chain or Pokeweed Antiviral Protein and Anti-Thy 1.1 Monoclonal Antibodies", Cancer Res. (1984) 44:201-208.
Scheraga, H.A., "Predicting Three-Dimensional Structures of Oligopeptides" Rev. Computational Chem., (vol. 3, K. B. Lipkowitz and D.B. Boyd (Eds.), John Wiley & Sons, Inc., Hoboken, NJ, (1992)).
Stec et al., "Automated solid-phase synthesis, separation, and stereochemistry of phosphorothioate analogs of oligodeoxyribonucleotides", J. Am. Chem. Soc. (1984) 106(20):6077-6079.
Stein et al., "Physicochemical properties of phosphorothioate oligodeoxynucleotides", Nucl. Acids Res. (1988) 16(8):3209-3221.
Thornton et al., "Prediction of progress at last", Nature (1991) 354:105-106.
Takeuchi et al., "Cellular Localization of Membrane-type Serine Protease 1 and Identification of Protease-activated Receptor-2 and Single-chain Urokinase-type Plasminogen Activator as Substrates", J. Biol. Chem. (2000) 275(34):26333-26342.
Uhlmann and Peyman, "Antisense Oligonucleotides: A New Therapeutic Principle", Chemical Reviews (1990) 90(4):543-584.
Vitetta et al., "Redesigning nature's poisons to create anti-tumor reagents", Science (1987) 238(4830): 1098-1104.
Wang W., "Lyophilization and development of solid protein pharmaceuticals", Int. J. Pharm. (2000) 203(1-2):1-60.
Zon et al., "Phosphorothioate oligonucleotides: chemistry, purification, analysis, scale-up and future directions", Anticancer Drug Des. (1991) 6(6):539-568.
Office Action dated Jan. 24, 2022 in U.S. Appl. No. 17/360,754, 18 pages.
Office Action dated Jan. 7, 2022 in U.S. Appl. No. 17/360,855, 30 pages.

* cited by examiner

H292 Efficacy Study

IVIG

Cetuximab

2001

2003

2005

PBS

C225v5-3954-2001

C225v5-3954-2006

C225v5-3954-2007

C225v5-3954-2008

C225v5-3954-2009

C225v5-3954-2010

C225v5-3954-2013

MATRIX METALLOPROTEASE-CLEAVABLE AND SERINE PROTEASE-CLEAVABLE SUBSTRATES AND METHODS OF USE THEREOF

RELATED APPLICATIONS

This application is a divisional of U.S. Ser. No. 15/002,131, filed Jan. 20, 2016, which claims the benefit of U.S. Provisional Application No. 62/105,490, filed Jan. 20, 2015, U.S. Provisional Application No. 62/258,015, filed Nov. 20, 2015, U.S. Provisional Application No. 62/277,771, filed Jan. 12, 2016, and U.S. Provisional Application No. 62/278,713, filed Jan. 14, 2016, the contents of each of which are incorporated herein by reference in their entirety.

INCORPORATION OF SEQUENCE LISTING

The contents of the text file named "CYTM037001US_SubSL_2.TXT", which was created on Jun. 24, 2016 and is 467,066 bytes in size, are hereby incorporated by reference in their entirety.

FIELD OF THE INVENTION

The invention relates generally to polypeptides that include at least a first cleavable moiety (CM1) that is a substrate for at least one matrix metalloprotease (MMP) and at least a second cleavable moiety (CM2) that is a substrate for at least one serine protease (SP), to activatable antibodies and other larger molecules that include these polypeptides that include at least a CM1 that is a substrate for at least one MMP protease and a CM2 that is a substrate for at least one SP protease, and to methods of making and using these polypeptides that include at least a CM1 that is a substrate for at least one MMP protease and a CM2 that is a substrate for at least one SP protease in a variety of therapeutic, diagnostic and prophylactic indications.

BACKGROUND OF THE INVENTION

Proteases are enzymes that degrade proteins by cleaving the peptide bonds between amino acid residues. Proteases occur naturally in all organisms and are involved in a variety of physiological reactions from simple degradation to highly regulated pathways. Some proteases are known to break specific peptide bonds based on the presence of a particular amino acid sequence within a protein.

Accordingly, there exists a need to identify new substrates for proteases and to use these substrates in a variety of therapeutic, diagnostic and prophylactic indications.

SUMMARY OF THE INVENTION

The disclosure provides amino acid sequences that include at least a first cleavable moiety (CM1) that is a substrate for at least one matrix metalloprotease (MMP) and at least a second cleavable moiety (CM2) that is a substrate for at least one serine protease (SP). These amino acid sequences are collectively referred to herein as "CM1-CM2 substrates." This term is not intended to convey any requirement regarding the orientation or other structural arrangement of the first cleavable moiety (CM1) that is a substrate for at least one matrix metalloprotease (MMP) and at least a second cleavable moiety (CM2) that is a substrate for at least one serine protease (SP). Thus, the term "CM1-CM2 substrates" encompasses CM1-CM2 substrates having the structural arrangement from N-terminus to C-terminus as follows: CM1-CM2 or CM2-CM1. The term "CM1-CM2 substrates" also encompasses substrates where at least a portion of the CM1 sequence overlaps with at least a portion of the CM2 sequence.

The CM1-CM2 substrates described herein are useful in a variety of therapeutic, diagnostic and prophylactic indications. For example, these CM1-CM2 substrates are useful in activatable antibodies that include antibodies or antigen-binding fragments thereof (AB) that include at least one masking moiety (MM) linked to at least one antigen- or epitope-binding domain of the AB such that coupling of the MM reduces the ability of the AB to bind its target.

In some embodiments, the activatable antibody includes at least a first CM (CM1) and a second CM (CM2). In some embodiments, at least a portion of the CM1 substrate sequence overlaps with at least a portion of the CM2 sequence. In some embodiments, the CM1 substrate sequence and the CM2 substrate sequence share at least one amino acid residue in common. In some embodiments, the CM1 substrate sequence and the CM2 substrate sequence share at least two amino acid residues in common. In some embodiments, the CM1 substrate sequence and the CM2 substrate sequence share at least three amino acid residues in common. In some embodiments, the CM1 substrate sequence and the CM2 substrate sequence share three or more amino acid residues in common.

In some embodiments, CM1 and CM2 are separate polypeptides that are operably linked together.

In some embodiments, CM1 and CM2 are separate polypeptides that are directly linked together, i.e., the N-terminus of one substrate is linked directly to the C-terminus of the other substrate polypeptide. In some embodiments, the N-terminus of the CM1 is linked directly to the C-terminus of the CM2. In some embodiments, the N-terminus of the CM2 is linked directly to the C-terminus of the CM1.

In some embodiments, CM1 and CM2 are separate polypeptides that are operably linked together via at least one linking moiety.

In some embodiments, the first cleavable moiety CM1 and the second cleavable moiety CM2 in the activatable antibody in the uncleaved state have the structural arrangement from N-terminus to C-terminus as follows: MM-CM1-CM2-AB, AB-CM2-CM1-MM, MM-CM2-CM1-AB, or AB-CM1-CM2-MM.

In some embodiments, the activatable antibody includes a linking peptide (LP') between CM1 and CM2. In some embodiments, the activatable antibody includes a linking peptide (LP'') between the masking moiety (MM) and CM1. In some embodiments, the activatable antibody includes a linking peptide (LP''') between CM2 and AB. In some embodiments, the activatable antibody includes a linking peptide (LP'') between the MM and CM1 and a linking peptide (LP''') between CM2 and AB. In some embodiments, the activatable antibody includes a linking peptide between the MM and CM1 (LP'') and a linking peptide between CM1 and CM2 (LP'). In some embodiments, the activatable antibody includes a linking peptide (LP') between CM1 and CM2 and a linking peptide (LP''') between CM2 and AB. In some embodiments, the activatable antibody includes a linking peptide (LP'') between the MM and CM1, a linking peptide (LP') between CM1 and CM2, and a linking peptide (LP''') between CM2 and AB.

In some embodiments, the activatable antibody includes a linking peptide (LP') between CM1 and CM2. In some embodiments, the activatable antibody includes a linking peptide (LP'') between the AB and CM1. In some embodiments, the activatable antibody includes a linking peptide (LP''') between CM2 and the masking moiety (MM). In some embodiments, the activatable antibody includes a linking peptide (LP'') between the AB and CM1 and a linking peptide (LP''') between CM2 and MM. In some embodiments, the activatable antibody includes a linking peptide between the AB and CM1 (LP'') and a linking peptide between CM1 and CM2 (LP'). In some embodiments, the activatable antibody includes a linking peptide (LP') between CM1 and CM2 and a linking peptide (LP''') between CM2 and MM. In some embodiments, the activatable antibody includes a linking peptide (LP'') between the AB and CM1, a linking peptide (LP') between CM1 and CM2, and a linking peptide (LP''') between CM2 and MM.

In some embodiments, LP' is GG. In some embodiments, LP' is GGSGGS (SEQ ID NO: 350).

In some embodiments, CM1 is a substrate for at least one matrix metalloprotease (MMP). Examples of MMPs include MMP1; MMP2; MMP3; MMP7; MMP8; MMP9; MMP10; MMP11; MMP12; MMP13; MMP14; MMP15; MMP16; MMP17; MMP19; MMP20; MMP23; MMP24; MMP26; and MMP27.

In some embodiments, CM1 is a substrate for MMP2, MMP9, MMP14, MMP1, MMP3, MMP13, MMP17, MMP11, and/or MMP19. In some embodiments, CM1 is a substrate for MMP2. In some embodiments, CM1 is a substrate for MMP9. In some embodiments, CM1 is a substrate for MMP14. In some embodiments, CM1 is a substrate for two or more MMPs. In some embodiments, CM1 is a substrate for at least MMP9 and MMP14. In some embodiments, CM1 is a substrate for at least MMP2 and MMP9. In some embodiments, CM1 is a substrate for at least MMP2 and MMP14. In some embodiments, CM1 is a substrate for three or more MMPs. In some embodiments, CM1 is a substrate for at least MMP2, MMP9, and MMP14. In some embodiments, the CM1 comprises two or more substrates for the same MMP. In some embodiments, the CM1 comprises at least two or more MMP2 substrates. In some embodiments, the CM1 comprises at least two or more MMP9 substrates. In some embodiments, the CM1 comprises at least two or more MMP14 substrates.

In some embodiments, CM1 is a substrate for an MMP and includes at least the sequence ISSGLLSS (SEQ ID NO: 20); QNQALRMA (SEQ ID NO: 21); AQNLLGMV (SEQ ID NO: 351); STFPFGMF (SEQ ID NO: 352); PVGYTSSL (SEQ ID NO: 353); DWLYWPGI (SEQ ID NO: 354); MIAPVAYR (SEQ ID NO: 355); RPSPMWAY (SEQ ID NO: 356); WATPRPMR (SEQ ID NO: 357); FRLLDWQW (SEQ ID NO: 358); LKAAPRWA (SEQ ID NO: 359); GPSHLVLT (SEQ ID NO: 360); LPGGLSPW (SEQ ID NO: 361); MGLFSEAG (SEQ ID NO: 362); SPLPLRVP (SEQ ID NO: 363); RMHLRSLG (SEQ ID NO: 364); LAAPLGLL (SEQ ID NO: 365); AVGLLAPP (SEQ ID NO: 366); LLAPSHRA (SEQ ID NO: 367); PAGLWLDP (SEQ ID NO: 368); ISSGLSS (SEQ ID NO: 369); ISSGL (SEQ ID NO: 480); ISSGLLS (SEQ ID NO: 481); ISSGLL (SEQ ID NO: 482); and/or VHMPLGFLGP (SEQ ID NO: 411).

In some embodiments, the CM1 comprises the amino acid sequence ISSGLLSS (SEQ ID NO: 20). In some embodiments, the CM1 comprises the amino acid sequence QNQALRMA (SEQ ID NO: 21). In some embodiments, the CM1 comprises the amino acid sequence AQNLLGMV (SEQ ID NO: 351). In some embodiments, the CM1 comprises the amino acid sequence STFPFGMF (SEQ ID NO: 352). In some embodiments, the CM1 comprises the amino acid sequence PVGYTSSL (SEQ ID NO: 353). In some embodiments, the CM1 comprises the amino acid sequence DWLYWPGI (SEQ ID NO: 354). In some embodiments, the CM1 comprises the amino acid sequence MIAPVAYR (SEQ ID NO: 355). In some embodiments, the CM1 comprises the amino acid sequence RPSPMWAY (SEQ ID NO: 356). In some embodiments, the CM1 comprises the amino acid sequence WATPRPMR (SEQ ID NO: 357). In some embodiments, the CM1 comprises the amino acid sequence FRLLDWQW (SEQ ID NO: 358). In some embodiments, the CM1 comprises the amino acid sequence LKAAPRWA (SEQ ID NO: 359). In some embodiments, the CM1 comprises the amino acid sequence GPSHLVLT (SEQ ID NO: 360). In some embodiments, the CM1 comprises the amino acid sequence LPGGLSPW (SEQ ID NO: 361). In some embodiments, the CM1 comprises the amino acid sequence MGLFSEAG (SEQ ID NO: 362). In some embodiments, the CM1 comprises the amino acid sequence SPLPLRVP (SEQ ID NO: 363). In some embodiments, the CM1 comprises the amino acid sequence RMHLRSLG (SEQ ID NO: 364). In some embodiments, the CM1 comprises the amino acid sequence LAAPLGLL (SEQ ID NO: 365). In some embodiments, the CM1 comprises the amino acid sequence AVGLLAPP (SEQ ID NO: 366). In some embodiments, the CM1 comprises the amino acid sequence LLAPSHRA (SEQ ID NO: 367). In some embodiments, the CM1 comprises the amino acid sequence PAGLWLDP (SEQ ID NO: 368). In some embodiments, the CM1 comprises the amino acid sequence ISSGLSS (SEQ ID NO: 369). In some embodiments, CM1 comprises the amino acid sequence VHMPLGFLGP (SEQ ID NO: 411). In some embodiments, CM1 comprises the amino acid sequence ISSGL (SEQ ID NO: 480). In some embodiments, CM1 comprises the amino acid sequence ISSGLLS (SEQ ID NO: 481). In some embodiments, CM1 comprises the amino acid sequence ISSGLL (SEQ ID NO: 482).

In some embodiments, CM2 is a substrate for at least one serine protease (SP). In some embodiments, the SP is selected from u-type plasminogen activator (uPA, also referred to as urokinase), matriptase (also referred to herein as MT-SP1 or MTSP1), and combinations thereof. Examples of other SP that cleave a CM2 described herein include, by way of non-limiting example, activated protein C; Cathepsin A; Cathepsin G; Chymase; a coagulation factor protease such as, e.g., FVIIa, FIXa, FXa, FXIa, FXIIa; Elastase; Granzyme B; Guanidinobenzoatase; HtrA1; Human Neutrophil Elastase; Lactoferrin; Marapsin; NS3/4A; PACE4; Plasmin; PSA; tPA; Thrombin; Tryptase; a Type II Transmembrane Serine Protease (TTSP) such as, e.g., DESC1, DPP-4, FAP, Hepsin, Matriptase-2, TMPRSS2, TMPRSS3, and/or TMPRSS4.

For example, suitable CM2 are cleaved by at least one serine protease and include the sequence TGRGPSWV (SEQ ID NO: 370); SARGPSRW (SEQ ID NO: 371); TARGPSFK (SEQ ID NO: 372); LSGRSDNH (SEQ ID NO: 18); GGWHTGRN (SEQ ID NO: 373); HTGRSGAL (SEQ ID NO: 374); PLTGRSGG (SEQ ID NO: 375); AARGPAIH (SEQ ID NO: 376); RGPAFNPM (SEQ ID NO: 377); SSRGPAYL (SEQ ID NO: 378); RGPATPIM (SEQ ID NO: 379); RGPA (SEQ ID NO: 380); LSGRSGNH (SEQ ID NO: 412); TSTSGRSANPRG (SEQ ID NO: 413); TSGRSANP (SEQ ID NO: 414); SGRSANPRG (SEQ ID NO: 468); VAGRSMRP (SEQ ID NO: 415); LSGRSDDH (SEQ ID NO: 547); LSGRSDIH (SEQ ID NO: 548); LSGRSDQH (SEQ ID NO: 549); LSGRSDTH (SEQ ID NO: 550); LSGRSDYH (SEQ ID NO: 551); LSGRSDNP (SEQ ID NO: 552); LSGRSANP (SEQ ID NO: 553); LSGRSANI (SEQ ID NO: 554); and/or LSGRSDNI (SEQ ID NO: 71).

In some embodiments, CM2 comprises the amino acid sequence TGRGPSWV (SEQ ID NO: 370). In some embodiments, CM2 comprises the amino acid sequence SARGPSRW (SEQ ID NO: 371). In some embodiments, CM2 comprises the amino acid sequence TARGPSFK (SEQ ID NO: 372). In some embodiments, CM2 comprises the amino acid sequence LSGRSDNH (SEQ ID NO: 18). In some embodiments, CM2 comprises the amino acid sequence GGWHTGRN (SEQ ID NO: 373). In some embodiments, CM2 comprises the amino acid sequence HTGRSGAL (SEQ ID NO: 374). In some embodiments, CM2 comprises the amino acid sequence PLTGRSGG (SEQ ID NO: 375). In some embodiments, CM2 comprises the amino acid sequence AARGPAIH (SEQ ID NO: 376). In some embodiments, CM2 comprises the amino acid sequence RGPAFNPM (SEQ ID NO: 377). In some embodiments, CM2 comprises the amino acid sequence SSRGPAYL (SEQ ID NO: 378). In some embodiments, CM2 comprises the amino acid sequence RGPATPIM (SEQ ID NO: 379). In some embodiments, CM2 comprises the amino acid sequence RGPA (SEQ ID NO: 380). In some embodiments, CM2 comprises the amino acid sequence LSGRSGNH (SEQ ID NO: 412). In some embodiments, CM2 comprises the amino acid sequence TSTSGRSANPRG (SEQ ID NO: 413). In some embodiments, the CM2 comprises the amino acid sequence SGRSANPRG (SEQ ID NO: 468). In some embodiments, CM2 comprises the amino acid sequence TSGRSANP (SEQ ID NO: 414). In some embodiments, CM2 comprises the amino acid sequence VAGRSMRP (SEQ ID NO: 415). In some embodiments, CM2 comprises the amino acid sequence LSGRSDDH (SEQ ID NO: 547). In some embodiments, CM2 comprises the amino acid sequence LSGRSDIH (SEQ ID NO: 548). In some embodiments, CM2 comprises the amino acid sequence LSGRSDQH (SEQ ID NO: 549). In some embodiments, CM2 comprises the amino acid sequence LSGRSDTH (SEQ ID NO: 550). In some embodiments, CM2 comprises the amino acid sequence LSGRSDYH (SEQ ID NO: 551). In some embodiments, CM2 comprises the amino acid sequence LSGRSDNP (SEQ ID NO: 552). In some embodiments, CM2 comprises the amino acid sequence LSGRSANP (SEQ ID NO: 553). In some embodiments, CM2 comprises the amino acid sequence LSGRSANI (SEQ ID NO: 554). In some embodiments, CM2 comprises the amino acid sequence LSGRSDNI (SEQ ID NO: 71).

In some embodiments, the CM1-CM2 substrate includes the sequence ISSGLLSGRSDNH (SEQ ID NO: 1); ISSGLLSSGGSGGSLSGRSDNH (SEQ ID NO: 2); AVGLLAPPGGTSTSGRSANPRG (SEQ ID NO: 3); TSTSGRSANPRGGGAVGLLAPP (SEQ ID NO: 4); VHMPLGFLGPGGTSTSGRSANPRG (SEQ ID NO: 5); TSTSGRSANPRGGGVHMPLGFLGP (SEQ ID NO: 6); AVGLLAPPGGLSGRSDNH (SEQ ID NO: 7); LSGRSDNHGGAVGLLAPP (SEQ ID NO: 8); VHMPLGFLGPGGLSGRSDNH (SEQ ID NO: 9); LSGRSDNHGGVHMPLGFLGP (SEQ ID NO: 10); LSGRSDNHGGSGGSISSGLLSS (SEQ ID NO: 11); LSGRSGNHGGSGGSISSGLLSS (SEQ ID NO: 12); ISSGLLSSGGSGGSLSGRSGNH (SEQ ID NO: 13); LSGRSDNHGGSGGSQNQALRMA (SEQ ID NO: 14); QNQALRMAGGSGGSLSGRSDNH (SEQ ID NO: 15); LSGRSGNHGGSGGSQNQALRMA (SEQ ID NO: 16); QNQALRMAGGSGGSLSGRSGNH (SEQ ID NO: 17); ISSGLLSGRSGNH (SEQ ID NO: 22); ISSGLLSGRSANPRG (SEQ ID NO: 469); AVGLLAPPTSGRSANPRG (SEQ ID NO: 470); AVGLLAPPSGRSANPRG (SEQ ID NO: 471); ISSGLLSGRSDDH (SEQ ID NO: 483); ISSGLLSGRSDIH (SEQ ID NO: 484); ISSGLLSGRSDQH (SEQ ID NO: 485); ISSGLLSGRSDTH (SEQ ID NO: 486); ISSGLLSGRSDYH (SEQ ID NO: 487); ISSGLLSGRSDNP (SEQ ID NO: 488); ISSGLLSGRSANP (SEQ ID NO: 489); ISSGLLSGRSANI (SEQ ID NO: 490); AVGLLAPPGGLSGRSDDH (SEQ ID NO: 515); AVGLLAPPGGLSGRSDIH (SEQ ID NO: 516); AVGLLAPPGGLSGRSDQH (SEQ ID NO: 517); AVGLLAPPGGLSGRSDTH (SEQ ID NO: 518); AVGLLAPPGGLSGRSDYH (SEQ ID NO: 519); AVGLLAPPGGLSGRSDNP (SEQ ID NO: 520); AVGLLAPPGGLSGRSANP (SEQ ID NO: 521); AVGLLAPPGGLSGRSANI (SEQ ID NO: 522); ISSGLLSGRSDNI (SEQ ID NO: 555); and/or AVGLLAPPGGLSGRSDNI (SEQ ID NO: 557).

In some embodiments, the CM1-CM2 substrate includes the sequence ISSGLLSGRSDNH (SEQ ID NO: 1). In some embodiments, the CM1-CM2 substrate includes the sequence ISSGLLSSGGSGGSLSGRSDNH (SEQ ID NO: 2). In some embodiments, the CM1-CM2 substrate includes the sequence AVGLLAPPGGTSTSGRSANPRG (SEQ ID NO: 3). In some embodiments, the CM1-CM2 substrate includes the sequence TSTSGRSANPRGGGAVGLLAPP (SEQ ID NO: 4). In some embodiments, the CM1-CM2 substrate includes the sequence VHMPLGFLGPGGTSTSGRSANPRG (SEQ ID NO: 5). In some embodiments, the CM1-CM2 substrate includes the sequence TSTSGRSANPRGGGVHMPLGFLGP (SEQ ID NO: 6). In some embodiments, the CM1-CM2 substrate includes the sequence AVGLLAPPGGLSGRSDNH (SEQ ID NO: 7). In some embodiments, the CM1-CM2 substrate includes the sequence LSGRSDNHGGAVGLLAPP (SEQ ID NO: 8). In some embodiments, the CM1-CM2 substrate includes the sequence VHMPLGFLGPGGLSGRSDNH (SEQ ID NO: 9). In some embodiments, the CM1-CM2 substrate includes the sequence LSGRSDNHGGVHMPLGFLGP (SEQ ID NO: 10). In some embodiments, the CM1-CM2 substrate includes the sequence LSGRSDNHGGSGGSISSGLLSS (SEQ ID NO: 11). In some embodiments, the CM1-CM2 substrate includes the sequence LSGRSGNHGGSGGSISSGLLSS (SEQ ID NO: 12). In some embodiments, the CM1-CM2 substrate includes the sequence ISSGLLSSGGSGGSLSGRSGNH (SEQ ID NO: 13). In some embodiments, the CM1-CM2 substrate includes the sequence LSGRSDNHGGSGGSQNQALRMA (SEQ ID NO: 14). In some embodiments, the CM1-CM2 substrate includes the sequence QNQALRMAGGSGGSLSGRSDNH (SEQ ID NO: 15). In some embodiments, the CM1-CM2 substrate includes the sequence LSGRSGNHGGSGGSQNQALRMA (SEQ ID NO: 16). In some embodiments, the CM1-CM2 substrate includes the sequence QNQALRMAGGSGGSLSGRSGNH (SEQ ID NO: 17). In some embodiments, the CM1-CM2 substrate includes the sequence ISSGLLSGRSGNH (SEQ ID NO: 22). In some embodiments, the CM1-CM2 substrate includes the sequence ISSGLLSGRSANPRG (SEQ ID NO: 469). In some embodiments, the CM1-CM2 substrate includes the sequence AVGLLAPPTSGRSANPRG (SEQ ID NO: 470). In some embodiments, the CM1-CM2 substrate includes the sequence AVGLLAPPSGRSANPRG (SEQ ID NO: 471). In some embodiments, the CM1-CM2 substrate includes the sequence ISSGLLSGRSDDH (SEQ ID NO: 483). In some embodiments, the CM1-CM2 substrate includes the sequence ISSGLLSGRSDIH (SEQ ID NO: 484). In some embodiments, the CM1-CM2 substrate includes the sequence ISSGLLSGRSDQH (SEQ ID NO: 485). In some embodiments, the CM1-CM2 substrate includes the sequence. In some embodiments, the CM1-CM2 substrate includes the sequence ISSGLLSGRSDTH (SEQ ID NO: 486). In some embodiments, the CM1-CM2 substrate includes the sequence ISSGLLSGRSDYH (SEQ ID NO: 487). In some embodiments, the CM1-CM2 substrate includes the sequence ISSGLLSGRSDNP (SEQ ID NO: 488). In some embodiments, the CM1-CM2 substrate includes the sequence ISSGLLSGRSANP (SEQ ID NO: 489). In some embodiments, the CM1-CM2 substrate includes the sequence ISSGLLSGRSANI (SEQ ID NO: 490). In some embodiments, the CM1-CM2 substrate includes the sequence AVGLLAPPGGLSGRSDDH (SEQ ID NO: 515). In some embodiments, the CM1-CM2 substrate includes the sequence AVGLLAPPGGLSGRSDIH (SEQ ID NO: 516). In some embodiments, the CM1-CM2 substrate includes the sequence AVGLLAPPGGLSGRSDQH (SEQ ID NO: 517). In some embodiments, the CM1-CM2 substrate includes the sequence AVGLLAPPGGLSGRSDTH (SEQ ID NO: 518). In some embodiments, the CM1-CM2 substrate includes the sequence AVGLLAPPGGLSGRSDYH (SEQ ID NO: 519). In some embodiments, the CM1-CM2 substrate includes the sequence AVGLLAPPGGLSGRSDNP (SEQ ID NO: 520). In some embodiments, the CM1-CM2 substrate includes the sequence AVGLLAPPGGLSGRSANP (SEQ ID NO: 521). In some embodiments, the CM1-CM2 substrate includes the sequence AVGLLAPPGGLSGRSANI (SEQ ID NO: 522). In some embodiments, the CM1-CM2 substrate includes the sequence ISSGLLSGRSDNI (SEQ ID NO: 555). In some embodiments, the CM1-CM2 substrate includes the sequence AVGLLAPPGGLSGRSDNI (SEQ ID NO: 557).

In some embodiments, the activatable antibody in the uncleaved state has the structural arrangement from N-terminus to C-terminus as follows: MM-CM1-CM2-AB, AB-CM2-CM1-MM, MM-CM2-CM1-AB, or AB-CM1-CM2-MM.

In some embodiments, the activatable antibody comprises a first linking peptide (LP1) and a second linking peptide (LP2), and the antibody in the uncleaved state has the structural arrangement from N-terminus to C-terminus as follows: MM1-LP1-CM1-CM2-LP2-AB, AB-LP2-CM2-CM1-LP1-MM, MM1-LP1-CM2-CM1-LP2-AB, or AB-LP2-CM1-CM2-LP1-MM. In some embodiments, each of LP1 and LP2 is a peptide of about 1 to 20 amino acids in length. In some embodiments, the two linking peptides need not be identical to each other.

In some embodiments, the activatable antibody includes a linking peptide (LP') between CM1 and CM2. In some embodiments, the activatable antibody includes a linking peptide (LP'') between the masking moiety (MM) and CM1. In some embodiments, the activatable antibody includes a linking peptide (LP''') between CM2 and AB. In some embodiments, the activatable antibody includes a linking peptide (LP'') between the MM and CM1 and a linking peptide (LP''') between CM2 and AB. In some embodiments, the activatable antibody includes a linking peptide between the MM and CM1 (LP'') and a linking peptide between CM1 and CM2 (LP'). In some embodiments, the activatable antibody includes a linking peptide (LP') between CM1 and CM2 and a linking peptide (LP''') between CM2 and AB. In some embodiments, the activatable antibody includes a linking peptide (LP'') between the MM and CM1, a linking peptide (LP') between CM1 and CM2, and a linking peptide (LP''') between CM2 and AB.

In some embodiments, the activatable antibody includes a linking peptide (LP') between CM1 and CM2. In some embodiments, the activatable antibody includes a linking peptide (LP'') between the AB and CM1. In some embodiments, the activatable antibody includes a linking peptide (LP''') between CM2 and the masking moiety (MM). In some embodiments, the activatable antibody includes a linking peptide (LP'') between the AB and CM1 and a linking peptide (LP''') between CM2 and MM. In some embodiments, the activatable antibody includes a linking peptide between the AB and CM1 (LP'') and a linking peptide between CM1 and CM2 (LP'). In some embodiments, the activatable antibody includes a linking peptide (LP') between CM1 and CM2 and a linking peptide (LP''') between CM2 and MM. In some embodiments, the activatable antibody includes a linking peptide (LP'') between the AB and CM1, a linking peptide (LP') between CM1 and CM2, and a linking peptide (LP''') between CM2 and MM.

In some embodiments, LP' is GG. In some embodiments, LP' is GGSGGS (SEQ ID NO: 350).

In some embodiments, at least one of LP1 or LP2 comprises an amino acid sequence selected from the group consisting of $(GS)_n$, $(GGS)_n$, $(GSGGS)_n$ (SEQ ID NO: 381) and $(GGGS)_n$ (SEQ ID NO: 382), where n is an integer of at least one.

In some embodiments, at least one of LP1 or LP2 comprises an amino acid sequence selected from the group consisting of GGSG (SEQ ID NO: 383), GGSGG (SEQ ID NO: 384), GSGSG (SEQ ID NO: 385), GSGGG (SEQ ID NO: 386), GGGSG (SEQ ID NO: 387), and GSSSG (SEQ ID NO: 388).

In some embodiments, LP1 comprises the amino acid sequence GSSGGSGGSGGSG (SEQ ID NO: 389), GSSGGSGGSGG (SEQ ID NO: 390), GSSGGSGGSGGS (SEQ ID NO: 391), GSSGGSGGSGGSGGGS (SEQ ID NO: 392), GSSGGSGGSG (SEQ ID NO: 393), or GSSGGSGGSGS (SEQ ID NO: 394).

In some embodiments, LP2 comprises the amino acid sequence GSS, GGS, GGGS (SEQ ID NO: 395), GSSGT (SEQ ID NO: 396) or GSSG (SEQ ID NO: 397).

In some embodiments, the AB has a dissociation constant of about 100 nM or less for binding to the target.

In some embodiments, the activatable antibody includes an antibody or antigen-binding fragment (AB) thereof that specifically binds a target. In some embodiments, the AB is a full-length antibody. In some embodiments, the AB is an immunologically active fragment. In some embodiments, the AB is an antigen-binding fragment. In some embodiments, the AB is a monoclonal antibody, domain antibody, single chain, Fab fragment, a $F(ab')_2$ fragment, a scFv, a scab, a dAb, a single domain heavy chain antibody, or a single domain light chain antibody. In some embodiments, such an AB is a mouse, other rodent, chimeric, humanized or fully human monoclonal antibody.

In some embodiments, the MMP protease is co-localized with the target in a tissue, and the MMP protease cleaves the CM1 in the antibody when the antibody is exposed to the protease. In some embodiments, the SP protease is co-localized with the target in a tissue, and the SP protease cleaves the CM2 substrate in the antibody when the antibody is exposed to the protease. In some embodiments, the MMP protease and/or the SP protease are co-localized with the target in a tissue, and the MMP protease and/or the SP protease cleave the CM1-CM2 substrate in the antibody when the antibody is exposed to the protease. In some embodiments, the MMP protease and the SP protease are co-localized with the target in a tissue, and at least one of the MMP protease and the SP protease cleave the CM1-CM2 substrate in the antibody when the antibody is exposed to the protease.

In some embodiments, each of the CM1 substrate sequence and the CM2 substrate sequence of the CM1-CM2 substrate is independently a polypeptide of up to 15 amino acids in length.

In some embodiments, the CM1 substrate sequence of the CM1-CM2 substrate is a substrate for at least one MMP and comprises a polypeptide sequence that is not substantially identical to any polypeptide sequence, e.g., any animal polypeptide sequence, that is naturally cleaved by the same MMP protease. In some embodiments, the CM1 substrate sequence of the CM1-CM2 substrate is a substrate for at least one MMP and comprises a polypeptide sequence that is not substantially identical to any mammalian polypeptide sequence that is naturally cleaved by the same MMP protease. In some embodiments, the CM1 substrate sequence of the CM1-CM2 substrate is a substrate for at least one MMP and comprises a polypeptide sequence that is not substantially identical to any human polypeptide sequence that is naturally cleaved by the same MMP protease. In some embodiments, the CM1 substrate sequence of the CM1-CM2 substrate is a substrate for at least one MMP and comprises a polypeptide sequence that is no more than 90% or more identical to any polypeptide sequence, e.g., any animal polypeptide sequence, that is naturally cleaved by the same MMP protease. In some embodiments, the CM1 substrate sequence of the CM1-CM2 substrate is a substrate for at least one MMP and comprises a polypeptide sequence that is no more than 90% or more identical to any mammalian polypeptide sequence that is naturally cleaved by the same MMP protease. In some embodiments, the CM1 substrate sequence of the CM1-CM2 substrate is a substrate for at least one MMP and comprises a polypeptide sequence that is no more than 90% or more identical to any human polypeptide sequence that is naturally cleaved by the same MMP protease.

In some embodiments, the CM2 substrate sequence of the CM1-CM2 substrate is a substrate for at least one SP and comprises a polypeptide sequence that is not substantially identical to any polypeptide sequence, e.g., any animal polypeptide sequence, that is naturally cleaved by the same SP protease. In some embodiments, the CM2 substrate sequence of the CM1-CM2 substrate is a substrate for at least one SP and comprises a polypeptide sequence that is not substantially identical to any mammalian polypeptide sequence that is naturally cleaved by the same SP protease. In some embodiments, the CM2 substrate sequence of the CM1-CM2 substrate is a substrate for at least one SP and comprises a polypeptide sequence that is not substantially identical to any human polypeptide sequence that is naturally cleaved by the same SP protease. In some embodiments, the CM2 substrate sequence of the CM1-CM2 substrate is a substrate for at least one SP and comprises a polypeptide sequence that is no more than 90% or more identical to any polypeptide sequence, e.g., any animal polypeptide sequence, that is naturally cleaved by the same SP protease. In some embodiments, the CM2 substrate sequence of the CM1-CM2 substrate is a substrate for at least one SP and comprises a polypeptide sequence that is no more than 90% or more identical to any mammalian polypeptide sequence that is naturally cleaved by the same SP protease. In some embodiments, the CM2 substrate sequence of the CM1-CM2 substrate is a substrate for at least one SP and comprises a polypeptide sequence that is no more than 90% or more identical to any human polypeptide sequence that is naturally cleaved by the same SP protease.

In some embodiments, the CM1-CM2 substrate comprises an amino acid sequence selected from the group consisting of SEQ ID NOs: 1-17, 22, 469-471, 483-490, 515-522, 555, and 557. In some embodiments, an activatable antibody comprises a CM1-CM2 substrate comprising an amino acid sequence selected from the group consisting of SEQ ID NOs: 1-17, 22, 469-471, 483-490, 515-522, 555, and 557, as well as an antibody or antigen binding fragment thereof (AB) that binds a target and a masking moiety (MM) that reduces the ability of the antigen- or epitope-binding domain of the AB to bind its target.

In some embodiments, an activatable antibody comprises a CM1-CM2 substrate comprising an amino acid sequence selected from the group consisting of SEQ ID NOs: 1-17, 22, 469-471, 483-490, 515-522, 555, and 557, and an anti-Jagged antibody comprising an amino acid sequence of an anti-Jagged antibody disclosed herein. In some embodiments, an activatable antibody comprises a CM1-CM2 substrate comprising an amino acid sequence selected from the group consisting of SEQ ID NOs: 1-17, 22, 469-471, 483-490, 515-522, 555, and 557, and an antibody having a light chain comprising amino acid sequence SEQ ID NO: 162 or SEQ ID NO: 164 and a heavy chain comprising amino acid sequence SEQ ID NO: 67 or SEQ ID NO: 163.

In some embodiments, the CM1-CM2 is included in an activatable antibody having a light chain amino acid sequence selected from the group consisting of SEQ ID NOs: 420, 422, 424, 426, 428, 430, 432, 434, 436, 439, 477, 479, 507-514, 539-546, 561, and 562, and a heavy chain amino acid sequence of SEQ ID NO: 67.

In some embodiments, the CM1-CM2 is included in an activatable antibody having a light chain amino acid sequence selected from the group consisting of SEQ ID NOs: 420, 422, 424, 426, 428, 430, 432, 434, 436, 439, 477, 479, 507-514, 539-546, 561, and 562, and a heavy chain amino acid sequence of SEQ ID NO: 163.

In some embodiments, an activatable antibody comprises a CM1-CM2 substrate comprising an amino acid sequence selected from the group consisting of SEQ ID NOs: 1-17, 22, 469-471, 483-490, 515-522, 555, and 557, and an anti-EGFR antibody comprising an amino acid sequence of an anti-EGFR antibody disclosed herein. In some embodiments, an activatable antibody comprises a CM1-CM2 substrate comprising an amino acid sequence selected from the group consisting of SEQ ID NOs: 1-17, 22, 469-471, 483-490, 515-522, 555, and 557, and an antibody having a light chain comprising amino acid sequence SEQ ID NO: 111 and a heavy chain comprising amino acid sequence SEQ ID NO: 108, SEQ ID NO: 109, or SEQ ID NO: 110.

In some embodiments, the CM1-CM2 is included in an activatable antibody having a light chain amino acid sequence selected from the group consisting of SEQ ID NOs: 449, 451, 453, 455, 457, 459, 461, 463, 465, 467, 472, 474, 499-506, 531-538, 559, and 560, and a heavy chain amino acid sequence of SEQ ID NO: 108.

In some embodiments, the CM1-CM2 is included in an activatable antibody having a light chain amino acid sequence selected from the group consisting of SEQ ID NOs: 449, 451, 453, 455, 457, 459, 461, 463, 465, 467, 472, 474, 499-506, 531-538, 559, and 560, and a heavy chain amino acid sequence of SEQ ID NO: 109.

In some embodiments, the CM1-CM2 is included in an activatable antibody having a light chain amino acid sequence selected from the group consisting of SEQ ID NOs: 449, 451, 453, 455, 457, 459, 461, 463, 465, 467, 472, 474, 499-506, 531-538, 559, and 560, and a heavy chain amino acid sequence of SEQ ID NO: 110.

In some embodiments, the CM1-CM2 substrate is also a substrate for at least one additional protease.

In some embodiments, the at least one additional protease is a different MMP protease than the MMP protease that cleaves the CM1. In some embodiments, the at least one additional protease is an MMP protease selected from the group consisting of MMP1; MMP2; MMP3; MMP7; MMP8; MMP9; MMP10; MMP11; MMP12; MMP13; MMP14; MMP15; MMP16; MMP17; MMP19; MMP20; MMP23; MMP24; MMP26; and MMP27.

In some embodiments, the at least one additional protease is a different SP protease than the SP protease that cleaves CM2. In some embodiments, the at least one additional SP protease is selected from the group consisting of uPA; matriptase; activated protein C; Cathepsin A; Cathepsin G; Chymase; a coagulation factor protease such as, e.g., FVIIa, FIXa, FXa, FXIa, FXIIa; Elastase; Granzyme B; Guanidinobenzoatase; HtrA1; Human Neutrophil Elastase; Lactoferrin; Marapsin; NS3/4A; PACE4; Plasmin; PSA; tPA; Thrombin; Tryptase; a Type II Transmembrane Serine Protease (TTSP) such as, e.g., DESC1, DPP-4, FAP, Hepsin, Matriptase-2, TMPRSS2, TMPRSS3, and TMPRSS4.

In some embodiments, the at least one additional protease is selected from the group consisting of those shown in Table 6.

TABLE 6

| Exemplary Proteases and/or Enzymes |
|---|
| ADAMS, ADAMTS, e.g. |
| ADAM8 |
| ADAM9 |
| ADAM10 |
| ADAM 12 |
| ADAM 15 |
| ADAM 17/TACE |
| ADAMDEC1 |
| ADAMTS1 |
| ADAMTS4 |
| ADAMTS5 |
| Aspartate proteases, e.g., |
| BACE |
| Renin |
| Aspartic cathepsins, e.g., |
| Cathepsin D |
| Cathepsin E |
| Caspases, e.g., |
| Caspase 1 |
| Caspase 2 |
| Caspase 3 |
| Caspase 4 |
| Caspase 5 |
| Caspase 6 |
| Caspase 7 |
| Caspase 8 |
| Caspase 9 |
| Caspase 10 |
| Caspase 14 |
| Cysteine cathepsins, e.g., |
| Cathepsin B |
| Cathepsin C |
| Cathepsin K |
| Cathepsin L |
| Cathepsin S |
| Cathepsin V/L2 |
| Cathepsin X/Z/P |
| Cysteine proteinases, e.g., |
| Cruzipain |
| Legumain |
| Otubain-2 |
| KLKs, e.g., |
| KLK4 |
| KLK5 |
| KLK6 |
| KLK7 |
| KLK8 |
| KLK10 |

TABLE 6-continued

| Exemplary Proteases and/or Enzymes |
|---|
| KLK11 |
| KLK13 |
| KLK14 |
| Metallo proteinases, e.g., |
| Meprin |
| Neprilysin |
| PSMA |
| BMP-1 |

The disclosure also provides an antibody includes at east a first CM1 an a second CM2 and is conjugated to an agent. In some embodiments, the first CM1 and the second CM2 are each polypeptides of no more than 15 amino acids long. In some embodiments, the activatable antibody is a conjugated activatable antibody that, in the uncleaved state has the structural arrangement from N-terminus to C-terminus as follows: MM-CM1-CM2-AB-Agent, Agent-AB-CM2-CM1-MM, MM-CM2-CM1-AB-Agent, or Agent-AB-CM1-CM2-MM. In some embodiments, the activatable antibody is a conjugated activatable antibody that, in the uncleaved state has the structural arrangement from N-terminus to C-terminus as follows: Agent-MM-CM1-CM2-AB, AB-CM2-CM1-MM-Agent, Agent-MM-CM2-CM1-AB, or AB-CM1-CM2-MM-Agent. In some embodiments, the activatable antibody is a conjugated activatable antibody that, in the uncleaved state has the structural arrangement from N-terminus to C-terminus as follows: Agent-MM-CM1-CM2-AB-Agent, Agent-AB-CM2-CM1-MM-Agent, Agent-MM-CM2-CM1-AB-Agent, or Agent-AB-CM1-CM2-MM-Agent.

In some embodiments, the activatable antibody is a conjugated activatable antibody that comprises a masking moiety (MM), a first linking peptide (LP1) and a second linking peptide (LP2), and the antibody in the uncleaved state has the structural arrangement from N-terminus to C-terminus as follows: MM1-LP1-CM1-CM2-LP2-AB-Agent, Agent-AB-LP2-CM2-CM1-LP1-MM, MM1-LP1-CM2-CM1-LP2-AB-Agent, or Agent-AB-LP2-CM1-CM2-LP1-MM. In some embodiments, each of LP1 and LP2 is a peptide of about 1 to 20 amino acids in length. In some embodiments, the two linking peptides need not be identical to each other.

In some embodiments, the activatable antibody is a conjugated activatable antibody that comprises a masking moiety (MM), a first linking peptide (LP1) and a second linking peptide (LP2), and the antibody in the uncleaved state has the structural arrangement from N-terminus to C-terminus as follows: Agent-MM1-LP1-CM1-CM2-LP2-AB, AB-LP2-CM2-CM1-LP1-MM-Agent, Agent-MM1-LP1-CM2-CM1-LP2-AB, or AB-LP2-CM1-CM2-LP1-MM-Agent. In some embodiments, each of LP1 and LP2 is a peptide of about 1 to 20 amino acids in length. In some embodiments, the two linking peptides need not be identical to each other.

In some embodiments, the activatable antibody is a conjugated activatable antibody that comprises a masking moiety (MM), a first linking peptide (LP1) and a second linking peptide (LP2), and the antibody in the uncleaved state has the structural arrangement from N-terminus to C-terminus as follows: Agent-MM1-LP1-CM1-CM2-LP2-AB-Agent, Agent-AB-LP2-CM2-CM1-LP1-MM-Agent, Agent-MM1-LP1-CM2-CM1-LP2-AB-Agent, or Agent-AB-LP2-CM1-CM2-LP1-MM-Agent. In some embodiments, each of LP1 and LP2 is a peptide of about 1 to 20 amino acids in length. In some embodiments, the two linking peptides need not be identical to each other.

In some embodiments, the conjugated activatable antibody includes a linking peptide (LP') between CM1 and CM2. In some embodiments, the conjugated activatable antibody includes a linking peptide (LP'') between the masking moiety (MM) and CM1. In some embodiments, the conjugated activatable antibody includes a linking peptide (LP''') between CM2 and AB. In some embodiments, the conjugated activatable antibody includes a linking peptide (LP'') between the MM and CM1 and a linking peptide (LP''') between CM2 and AB. In some embodiments, the conjugated activatable antibody includes a linking peptide between the MM and CM1 (LP'') and a linking peptide between CM1 and CM2 (LP'). In some embodiments, the conjugated activatable antibody includes a linking peptide (LP') between CM1 and CM2 and a linking peptide (LP''') between CM2 and AB. In some embodiments, the conjugated activatable antibody includes a linking peptide (LP'') between the MM and CM1, a linking peptide (LP') between CM1 and CM2, and a linking peptide (LP''') between CM2 and AB.

In some embodiments, the conjugated activatable antibody includes a linking peptide (LP') between CM1 and CM2. In some embodiments, the conjugated activatable antibody includes a linking peptide (LP'') between the AB and CM1. In some embodiments, the conjugated activatable antibody includes a linking peptide (LP''') between CM2 and the masking moiety (MM). In some embodiments, the conjugated activatable antibody includes a linking peptide (LP'') between the AB and CM1 and a linking peptide (LP''') between CM2 and MM. In some embodiments, the conjugated activatable antibody includes a linking peptide between the AB and CM1 (LP'') and a linking peptide between CM1 and CM2 (LP'). In some embodiments, the conjugated activatable antibody includes a linking peptide (LP') between CM1 and CM2 and a linking peptide (LP''') between CM2 and MM. In some embodiments, the conjugated activatable antibody includes a linking peptide (LP'') between the AB and CM1, a linking peptide (LP') between CM1 and CM2, and a linking peptide (LP''') between CM2 and MM.

In some embodiments, LP' is GG. In some embodiments, LP' is GGSGGS (SEQ ID NO: 350).

In some embodiments, at least one of LP1 or LP2 comprises an amino acid sequence selected from the group consisting of $(GS)_n$, $(GGS)_n$, $(GSGGS)_n$ (SEQ ID NO: 381) and $(GGGS)_n$ (SEQ ID NO: 382), where n is an integer of at least one.

In some embodiments, at least one of LP1 or LP2 comprises an amino acid sequence selected from the group consisting of GGSG (SEQ ID NO: 383), GGSGG (SEQ ID NO: 384), GSGSG (SEQ ID NO: 385), GSGGG (SEQ ID NO: 386), GGGSG (SEQ ID NO: 387), and GSSSG (SEQ ID NO: 388).

In some embodiments LP1 comprises the amino acid sequence

```
                                        (SEQ ID NO: 389)
GSSGGSGGSGGSG,

                                        (SEQ ID NO: 390)
GSSGGSGGSGG,

                                        (SEQ ID NO: 391)
GSSGGSGGSGGS,

                                        (SEQ ID NO: 392)
GSSGGSGGSGGSGGGS,
```

-continued

```
                                        (SEQ ID NO: 393)
GSSGGSGGSG,
or

                                        (SEQ ID NO: 394)
GSSGGSGGSGS.
```

In some embodiments, LP2 comprises the amino acid sequence GSS, GGS, GGGS (SEQ ID NO: 395), GSSGT (SEQ ID NO: 396) or GSSG (SEQ ID NO: 397).

In some embodiments, the CM1-CM2 substrate is linked or otherwise attached to an antibody. For example, the CM1-CM2 is used to link one or more agents to the antibody or antigen binding fragment thereof (AB) that binds a given target, such that the CM1-CM2 is cleaved when exposed to the MMP and/or the SP, and the agent is released from the AB. Exemplary targets include, but are not limited to the targets shown in Table 1. Exemplary ABs include, but are not limited to, the antibodies shown in Table 2.

In some embodiments, the AB has a dissociation constant of about 100 nM or less for binding to the target.

In some embodiments, the antibody includes an antibody or antigen-binding fragment thereof that specifically binds a target. In some embodiments, the antibody or immunologically active fragment thereof that binds the target is a monoclonal antibody, domain antibody, single chain, Fab fragment, a $F(ab')_2$ fragment, a scFv, a scab, a dAb, a single domain heavy chain antibody, or a single domain light chain antibody. In some embodiments, such an antibody or immunologically active fragment thereof that binds the target is a mouse, other rodent, chimeric, humanized or fully human monoclonal antibody.

In some embodiments, the MM has a dissociation constant for binding to the AB that is no more than the dissociation constant of the AB to the target.

In some embodiments, the MM does not interfere or compete with the AB for binding to the target in a cleaved state.

In some embodiments, the MM is a polypeptide of about 2 to 40 amino acids in length. For example, the MM is a polypeptide of up to about 40 amino acids in length.

In some embodiments, the MM polypeptide sequence is different from that of any natural binding partner of the AB. In some embodiments, the MM polypeptide sequence is no more than 50% identical to any natural binding partner of the AB. In some embodiments, the MM polypeptide sequence is no more than 40%, 30%, 25%, 20%, 15%, or 10% identical to any natural binding partner of the AB.

In some embodiments, the agent conjugated to the AB or the AB of an activatable antibody is a therapeutic agent. In some embodiments, the agent is an antineoplastic agent. In some embodiments, the agent is a toxin or fragment thereof. As used herein, a fragment of a toxin is a fragment that retains toxic activity. In some embodiments, the agent is conjugated to the AB via a cleavable linker. In some embodiments, the agent is conjugated to the AB via a linker that includes at least one CM1-CM2 substrate sequence. In some embodiments, the agent is conjugated to the AB via a noncleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the agent is an anti-inflammatory agent.

In some embodiments, the antibody and/or activatable antibody also includes a detectable moiety. In some embodiments, the detectable moiety is a diagnostic agent.

In some embodiments, the conjugated antibody and/or conjugated activatable antibody includes a detectable label. In some embodiments, the detectable label includes an imaging agent, a contrasting agent, an enzyme, a fluorescent label, a chromophore, a dye, one or more metal ions, or a ligand-based label. In some embodiments, the imaging agent comprises a radioisotope. In some embodiments, the radioisotope is indium or technetium. In some embodiments, the contrasting agent comprises iodine, gadolinium or iron oxide. In some embodiments, the enzyme comprises horseradish peroxidase, alkaline phosphatase, or 0-galactosidase. In some embodiments, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments, the luminescent label comprises an N-methylacrydium derivative. In some embodiments, the label comprises an Alexa Fluor® label, such as Alex Fluor® 680 or Alexa Fluor® 750. In some embodiments, the ligand-based label comprises biotin, avidin, streptavidin or one or more haptens.

In some embodiments, the antibody and/or the AB of the activatable antibody naturally contains one or more disulfide bonds. In some embodiments, the AB can be engineered to include one or more disulfide bonds.

In some embodiments, the antibody and/or conjugated antibody is monospecific. In some embodiments, the antibody and/or conjugated antibody is multispecific, referred to herein as multispecific antibodies and/or conjugated multispecific antibodies. In some embodiments, the multispecific antibody and/or conjugated multispecific antibody is bispecific or trifunctional. In some embodiments, the antibody and/or conjugated antibody is formulated as part of a pro-Bispecific T Cell Engager (pro-BITE) molecule. In some embodiments, the antibody and/or conjugated antibody is formulated as part of a pro-Chimeric Antigen Receptor (pro-CAR) modified T cell or other engineered receptor or other immune effector cell, such as a CAR modified NK cell. In some embodiments, the activatable antibody and/or conjugated activatable antibody is formulated as part of a pro-Chimeric Antigen Receptor (CAR) modified T cell. In some embodiments, the activatable antibody and/or conjugated activatable antibody is formulated as part of a pro-Chimeric Antigen Receptor (CAR) modified NK cell.

In some embodiments, the activatable antibody and/or conjugated activatable antibody is monospecific. In some embodiments, the activatable antibody and/or conjugated activatable antibody is multispecific, referred to herein as multispecific activatable antibodies and/or conjugated multispecific activatable antibodies. As used herein, terms such as "activatable antibody" and all grammatical variations thereof, unless otherwise noted, are intended to encompass, but are not limited to embodiments where the activatable antibody is a multispecific activatable antibody of the disclosure. As used herein, terms such as "conjugated activatable antibody" and all grammatical variations thereof, unless otherwise noted, are intended to encompass, but are not limited to embodiments where the conjugated activatable antibody is a conjugated multispecific activatable antibody of the disclosure. In some embodiments, the multispecific activatable antibody and/or conjugated multispecific activatable antibody is bispecific or trifunctional. In some embodiments, the activatable antibody and/or conjugated activatable antibody is formulated as part of a pro-Bispecific T Cell Engager (pro-BITE) molecule. In some embodiments, the activatable antibody and/or conjugated activatable antibody is formulated as part of a pro-Chimeric Antigen Receptor (pro-CAR) modified T cell or other engineered receptor.

In some embodiments, the antibodies, antibody conjugates, activatable antibodies, conjugated activatable antibodies, multispecific activatable antibodies, and/or conjugated multispecific activatable antibodies described herein are used in conjunction with one or more additional agents or a combination of additional agents. Suitable additional agents include current pharmaceutical and/or surgical therapies for an intended application, such as, for example, cancer. For example, the activatable antibodies, conjugated activatable antibodies, multispecific activatable antibodies, and/or conjugated multispecific activatable antibodies can be used in conjunction with an additional chemotherapeutic or anti-neoplastic agent.

In some embodiments, the activatable antibody is a multispecific activatable antibody. The multispecific activatable antibodies provided herein are multispecific antibodies that recognize two or more different antigens or epitopes and that include at least one masking moiety (MM) linked to at least one antigen- or epitope-binding domain of the multispecific antibody such that coupling of the MM reduces the ability of the antigen- or epitope-binding domain to bind its target. In some embodiments, the MM is coupled to the antigen- or epitope-binding domain of the multispecific antibody via a CM1-CM2 substrate that functions as a substrate for at least one MMP protease and at least one SP protease. The activatable multispecific antibodies provided herein are stable in circulation, activated at intended sites of therapy and/or diagnosis but not in normal, i.e., healthy tissue, and, when activated, exhibit binding to a target that is at least comparable to the corresponding, unmodified multispecific antibody.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 that sequence includes at least the amino acid sequence SYAMS (SEQ ID NO: 398); a VH CD2 sequence that includes at least the amino acid sequence SIDPEGRQTYYADSVKG (SEQ ID NO: 399); a VH CDR3 sequence that includes at least the amino acid sequence DIGGRSAFDY (SEQ ID NO: 400), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes at least the amino acid sequence RASQSISSY (SEQ ID NO: 401); a VL CDR2 sequence that includes at least the amino acid sequence AASSLQS (SEQ ID NO: 402); a VL CDR3 sequence that includes at least the amino acid sequence QQTVVAPPL (SEQ ID NO: 403), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes a sequence that is at least 90%, 91%, 92%, 93%, 94%, 95%, 96%, 97%, 98%, 99% or more identical to the amino acid sequence SYAMS (SEQ ID NO: 398); a VH CD2 sequence that includes a sequence that is at least 90%, 91%, 92%, 93%, 94%, 95%, 96%, 97%, 98%, 99% or more identical to the amino acid sequence SIDPEGRQTYYADSVKG (SEQ ID NO: 399); a VH CDR3 sequence that includes a sequence that is at least 90%, 91%, 92%, 93%, 94%, 95%, 96%, 97%, 98%, 99% or more identical to the amino acid sequence DIGGRSAFDY (SEQ ID NO: 400), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes a sequence that is at least 90%, 91%, 92%, 93%, 94%, 95%, 96%, 97%, 98%, 99% or more identical to the amino acid sequence RASQSISSY (SEQ ID NO: 401); a VL CDR2 sequence that includes a sequence that is at least 90%, 91%, 92%, 93%, 94%, 95%, 96%, 97%, 98%, 99% or more identical to the amino acid sequence AASSLQS (SEQ ID NO: 402); and a VL CDR3 sequence that includes a sequence that is at least 90%, 91%, 92%, 93%, 94%, 95%, 96%, 97%, 98%, 99% or more identical to the amino acid sequence QQTVVAPPL (SEQ ID NO: 403), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes at least the amino acid sequence SYAMS (SEQ ID NO: 398); the VH CD2 sequence includes at least the amino acid sequence SIDPEGRQTYYADSVKG (SEQ ID NO: 399); the VH CDR3 sequence includes at least the amino acid sequence DIGGRSAFDY (SEQ ID NO: 400); the VL CDR1 sequence includes at least the amino acid sequence RASQSISSY (SEQ ID NO: 401); the VL CDR2 sequence includes at least the amino acid sequence AASSLQS (SEQ ID NO: 402); and the VL CDR3 sequence includes at least the amino acid sequence QQTVVAPPL (SEQ ID NO: 403).

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes a sequence that is at least 90%, 91%, 92%, 93%, 94%, 95%, 96%, 97%, 98%, 99% or more identical to the amino acid sequence SYAMS (SEQ ID NO: 398); the VH CD2 sequence includes a sequence that is at least 90%, 91%, 92%, 93%, 94%, 95%, 96%, 97%, 98%, 99% or more identical to the amino acid sequence SIDPEGRQTYYADSVKG (SEQ ID NO: 399); the VH CDR3 sequence includes a sequence that is at least 90%, 91%, 92%, 93%, 94%, 95%, 96%, 97%, 98%, 99% or more identical to the amino acid sequence DIGGRSAFDY (SEQ ID NO: 400); the VL CDR1 sequence includes a sequence that is at least 90%, 91%, 92%, 93%, 94%, 95%, 96%, 97%, 98%, 99% or more identical to the amino acid sequence RASQSISSY (SEQ ID NO: 401); the VL CDR2 sequence includes a sequence that is at least 90%, 91%, 92%, 93%, 94%, 95%, 96%, 97%, 98%, 99% or more identical to the amino acid sequence AASSLQS (SEQ ID NO: 402); and the VL CDR3 sequence includes a sequence that is at least 90%, 91%, 92%, 93%, 94%, 95%, 96%, 97%, 98%, 99% or more identical to the amino acid sequence QQTVVAPPL (SEQ ID NO: 403).

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds Epidermal Growth Factor Receptor (EGFR) and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes at least the amino acid sequence NYGVH (SEQ ID NO: 404); a VH CD2 sequence that includes at least the amino acid sequence VIWSGGNTDYNTPFTS (SEQ ID NO: 405); a VH CDR3 sequence that includes at least the amino acid sequence ALTYYDYEFAY (SEQ ID NO: 406); and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes at least the amino acid sequence RASQSIGTNIH (SEQ ID NO: 407); a VL CDR2 sequence that includes at least the amino acid sequence KYASESIS (SEQ ID NO: 408); and a VL CDR3 sequence that includes at least the amino acid sequence QQNNNWPTT (SEQ ID NO: 409), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes a sequence that is at least 90%, 91%, 92%, 93%, 94%, 95%, 96%, 97%, 98%, 99% or more identical to the amino acid sequence NYGVH (SEQ ID NO: 404); a VH CD2 sequence that includes a sequence that is at least 90%, 91%, 92%, 93%, 94%, 95%, 96%, 97%, 98%, 99% or more identical to the amino acid sequence VIWSGGNTDYNTPFTS (SEQ ID NO: 405); a VH CDR3 sequence that includes a sequence that is at least 90%, 91%, 92%, 93%, 94%, 95%, 96%, 97%, 98%, 99% or more identical to the amino acid sequence ALTYYDYEFAY (SEQ ID NO: 406); and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes a sequence that is at least 90%, 91%, 92%, 93%, 94%, 95%, 96%, 97%, 98%, 99% or more identical to the amino acid sequence RASQSIGTNIH (SEQ ID NO: 407); a VL CDR2 sequence that includes a sequence that is at least 90%, 91%, 92%, 93%, 94%, 95%, 96%, 97%, 98%, 99% or more identical to the amino acid sequence KYASESIS (SEQ ID NO: 408); and a VL CDR3 sequence that includes a sequence that is at least 90%, 91%, 92%, 93%, 94%, 95%, 96%, 97%, 98%, 99% or more identical to the amino acid sequence QQNNNWPTT (SEQ ID NO: 409), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes at least the amino acid sequence NYGVH (SEQ ID NO: 404); the VH CD2 sequence includes at least the amino acid sequence VIWSGGNTDYNTPFTS (SEQ ID NO: 405); the VH CDR3 sequence includes at least the amino acid sequence ALTYYDYEFAY (SEQ ID NO: 406); the VL CDR1 sequence includes at least the amino acid sequence RASQSIGTNIH (SEQ ID NO: 407); the VL CDR2 sequence includes at least the amino acid sequence KYASESIS (SEQ ID NO: 408); and the VL CDR3 sequence includes at least the amino acid sequence QQNNNWPTT (SEQ ID NO: 409).

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes a sequence that is at least 90%, 91%, 92%, 93%, 94%, 95%, 96%, 97%, 98%, 99% or more identical to the amino acid sequence NYGVH (SEQ ID NO: 404); the VH CD2 sequence includes a sequence that is at least 90%, 91%, 92%, 93%, 94%, 95%, 96%, 97%, 98%, 99% or more identical to the amino acid sequence VIWSGGNTDYNTPFTS (SEQ ID NO: 405); the VH CDR3 sequence includes a sequence that is at least 90%, 91%, 92%, 93%, 94%, 95%, 96%, 97%, 98%, 99% or more identical to the amino acid sequence ALTYYDYEFAY (SEQ ID NO: 406); the VL CDR1 sequence includes a sequence that is at least 90%, 91%, 92%, 93%, 94%, 95%, 96%, 97%, 98%, 99% or more identical to the amino acid sequence RASQSIGTNIH (SEQ ID NO: 407); the VL CDR2 sequence includes a sequence that is at least 90%, 91%, 92%, 93%, 94%, 95%, 96%, 97%, 98%, 99% or more identical to the amino acid sequence KYASESIS (SEQ ID NO: 408); and the VL CDR3 sequence includes a sequence that is at least 90%, 91%, 92%, 93%, 94%, 95%, 96%, 97%, 98%, 99% or more identical to the amino acid sequence QQNNNWPTT (SEQ ID NO: 409).

In some embodiments, the activatable antibody and/or conjugated activatable antibody provided herein, including but not limited to a multispecific activatable antibody and/or conjugated multispecific activatable antibody of the disclosure, comprises a CM1-CM2 substrate comprising an amino acid sequence selected from the group consisting of SEQ ID NOs: 1-17, 22, 469-471, 483-490, 515-522, 555, and 557, and an anti-Jagged antibody comprising an amino acid sequence of an anti-Jagged antibody disclosed herein. In some embodiments, the activatable antibody and/or conjugated activatable antibody provided herein, including but not limited to a multispecific activatable antibody and/or conjugated multispecific activatable antibody of the disclosure, comprises a CM1-CM2 substrate comprising an amino acid sequence selected from the group consisting of SEQ ID NOs: 1-17, 22, 469-471, 483-490, 515-522, 555, and 557, and an antibody having a light chain comprising amino acid sequence SEQ ID NO: 162 or SEQ ID NO: 164 and a heavy chain comprising amino acid sequence SEQ ID NO: 67 or SEQ ID NO: 163.

In some embodiments, the activatable antibody and/or conjugated activatable antibody provided herein, including but not limited to a multispecific activatable antibody and/or conjugated multispecific activatable antibody of the disclosure, includes at least a heavy chain amino acid sequence of SEQ ID NO: 67 and a light chain amino acid sequence selected from the group consisting of SEQ ID NOs: 420, 422, 424, 426, 428, 430, 432, 434, 436, 439, 477, 479, 507-514, 539-546, 561, and 562.

In some embodiments, the activatable antibody and/or conjugated activatable antibody provided herein, including but not limited to a multispecific activatable antibody and/or conjugated multispecific activatable antibody of the disclosure, comprises a CM1-CM2 substrate comprising an amino acid sequence selected from the group consisting of SEQ ID NOs: 1-17, 22, 469-471, 483-490, 515-522, 555, and 557, and an anti-EGFR antibody comprising an amino acid sequence of an anti-EGFR antibody disclosed herein. In some embodiments, the activatable antibody and/or conjugated activatable antibody provided herein, including but not limited to a multispecific activatable antibody and/or conjugated multispecific activatable antibody of the disclosure, comprises a CM1-CM2 substrate comprising an amino acid sequence selected from the group consisting of SEQ ID NOs: 1-17, 22, 469-471, 483-490, 515-522, 555, and 557, and an antibody having a light chain comprising amino acid sequence SEQ ID NO: 111 and a heavy chain comprising amino acid sequence SEQ ID NO: 108, SEQ ID NO: 109, or SEQ ID NO: 110.

In some embodiments, the activatable antibody and/or conjugated activatable antibody provided herein, including but not limited to a multispecific activatable antibody and/or conjugated multispecific activatable antibody of the disclosure, includes at least a heavy chain amino acid sequence of SEQ ID NO: 108 and a light chain amino acid sequence selected from the group consisting of SEQ ID NOs: 449, 451, 453, 455, 457, 459, 461, 463, 465, 467, 472, 474, 499-506, 531-538, 559, and 560.

In some embodiments, the activatable antibody and/or conjugated activatable antibody provided herein, including but not limited to a multispecific activatable antibody and/or conjugated multispecific activatable antibody of the disclosure, includes at least a heavy chain amino acid sequence that is at least 90%, 91%, 92%, 93%, 94%, 95%, 96%, 97%, 98%, 99% or more identical to the amino acid sequence of SEQ ID NO: 67 and a light chain amino acid sequence that is at least 90%, 91%, 92%, 93%, 94%, 95%, 96%, 97%, 98%, 99% or more identical to an amino acid sequence selected from the group consisting of SEQ ID NOs: 420, 422, 424, 426, 428, 430, 432, 434, 436, 439, 477, 479, 507-514, 539-546, 561, and 562.

In some embodiments, the activatable antibody and/or conjugated activatable antibody provided herein, including but not limited to a multispecific activatable antibody and/or conjugated multispecific activatable antibody of the disclosure, includes at least a heavy chain amino acid sequence that is at least 90%, 91%, 92%, 93%, 94%, 95%, 96%, 97%, 98%, 99% or more identical to the amino acid sequence of SEQ ID NO: 108 and a light chain amino acid sequence that is at least 90%, 91%, 92%, 93%, 94%, 95%, 96%, 97%, 98%, 99% or more identical to an amino acid sequence selected from the group consisting of SEQ ID NOs: 449, 451, 453, 455, 457, 459, 461, 463, 465, 467, 472, 474, 499-506, 531-538, 559, and 560.

In some embodiments, the activatable antibody also includes an agent conjugated to the AB. In some embodiments, the agent is a therapeutic agent. In some embodiments, the agent is an antineoplastic agent. In some embodiments, the agent is a toxin or a fragment thereof. In some embodiments, the agent is conjugated to the AB via a linker. In some embodiments, the linker is a cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is conjugated to the AB via a linker that includes at least one CM1-CM2 substrate sequence. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the agent is an anti-inflammatory agent.

In some embodiments, the activatable antibody also includes a detectable moiety. In some embodiments, the detectable moiety is a diagnostic agent.

In some embodiments, the conjugated antibody includes a detectable label. In some embodiments, the detectable label includes an imaging agent, a contrasting agent, an enzyme, a fluorescent label, a chromophore, a dye, one or more metal ions, or a ligand-based label. In some embodiments, the imaging agent comprises a radioisotope. In some embodiments, the radioisotope is indium or technetium. In some embodiments, the contrasting agent comprises iodine, gadolinium or iron oxide. In some embodiments, the enzyme comprises horseradish peroxidase, alkaline phosphatase, or β-galactosidase. In some embodiments, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments, the luminescent label comprises an N-methylacrydium derivative. In some embodiments, the label comprises an Alexa Fluor® label, such as Alex Fluor® 680 or Alexa Fluor® 750. In some embodiments, the ligand-based label comprises biotin, avidin, streptavidin or one or more haptens.

In some embodiments, the activatable antibody also includes a signal peptide. In some embodiments, the signal peptide is conjugated to the activatable antibody via a spacer. In some embodiments, the spacer is conjugated to the activatable antibody in the absence of a signal peptide. In some embodiments, the spacer is joined directly to the MM of the activatable antibody. In some embodiments, the spacer is joined directly to the MM of the activatable antibody in the structural arrangement from N-terminus to C-terminus of spacer-MM-CM1-CM2 substrate-AB. An example of a spacer joined directly to the N-terminus of MM of the activatable antibody is an amino acid sequence selected from the group consisting of QGQSGQ (SEQ ID NO: 410), GQSGQ (SEQ ID NO: 416), QSGQ (SEQ ID NO: 417), SGQ (SEQ ID NO: 418), GQ, and Q. In some embodiments, the spacer includes at least the amino acid sequence QGQSGQ (SEQ ID NO: 410). In some embodiments, the spacer includes at least the amino acid sequence GQSGQ (SEQ ID NO: 416). In some embodiments, the spacer includes at least the amino acid sequence QSGQ (SEQ ID NO: 417). In some embodiments, the spacer includes at least the amino acid sequence SGQ (SEQ ID NO: 418). In some embodiments, the spacer includes at least the amino acid sequence GQ. In some embodiments, the spacer includes at least the amino acid sequence Q.

In some embodiments, the AB of the activatable antibody naturally contains one or more disulfide bonds. In some embodiments, the AB can be engineered to include one or more disulfide bonds.

In some embodiments, the serum half-life of the activatable antibody is longer than that of the corresponding antibody; e.g., the pK of the activatable antibody is longer than that of the corresponding antibody. In some embodiments, the serum half-life of the activatable antibody is similar to that of the corresponding antibody. In some embodiments, the serum half-life of the activatable antibody is at least 15 days when administered to an organism. In some embodiments, the serum half-life of the activatable antibody is at least 12 days when administered to an organism. In some embodiments, the serum half-life of the activatable antibody is at least 11 days when administered to an organism. In some embodiments, the serum half-life of the activatable antibody is at least 10 days when administered to an organism. In some embodiments, the serum half-life of the activatable antibody is at least 9 days when administered to an organism. In some embodiments, the serum half-life of the activatable antibody is at least 8 days when administered to an organism. In some embodiments, the serum half-life of the activatable antibody is at least 7 days when administered to an organism. In some embodiments, the serum half-life of the activatable antibody is at least 6 days when administered to an organism. In some embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

The disclosure also provides compositions and methods that include an activatable antibody that includes an antibody or antibody fragment (AB) that specifically binds a given target, where the AB is coupled to a masking moiety (MM) that decreases the ability of the AB to bind its target. In some embodiments, the activatable antibody further includes a CM1-CM2 substrate that is a substrate for at least one MMP and at least one SP. The compositions and methods provided herein enable the attachment of one or more agents to one or more cysteine residues in the AB without compromising the activity (e.g., the masking, activating or binding activity) of the activatable antibody. In some embodiments, the compositions and methods provided herein enable the attachment of one or more agents to one or more cysteine residues in the AB without reducing or otherwise disturbing one or more disulfide bonds within the MM. The compositions and methods provided herein produce an activatable antibody that is conjugated to one or more agents, e.g., any of a variety of therapeutic, diagnostic and/or prophylactic agents, for example, in some embodiments, without any of the agent(s) being conjugated to the MM of the activatable antibody. The compositions and methods provided herein produce conjugated activatable antibodies in which the MM retains the ability to effectively and efficiently mask the AB of the activatable antibody in an uncleaved state. The compositions and methods provided herein produce conjugated activatable antibodies in which the activatable antibody is still activated, i.e., cleaved, in the presence of a MMP that can cleave the CM1-CM2 substrate.

The activatable antibodies have at least one point of conjugation for an agent, but in the methods and compositions provided herein less than all possible points of conjugation are available for conjugation to an agent. In some embodiments, the one or more points of conjugation are sulfur atoms involved in disulfide bonds. In some embodiments, the one or more points of conjugation are sulfur atoms involved in interchain disulfide bonds. In some embodiments, the one or more points of conjugation are sulfur atoms involved in interchain sulfide bonds, but not sulfur atoms involved in intrachain disulfide bonds. In some embodiments, the one or more points of conjugation are sulfur atoms of cysteine or other amino acid residues containing a sulfur atom. Such residues may occur naturally in the antibody structure or may be incorporated into the antibody by site-directed mutagenesis, chemical conversion, or mis-incorporation of non-natural amino acids.

Also provided are methods of preparing a conjugate of an activatable antibody having one or more interchain disulfide bonds in the AB and one or more intrachain disulfide bonds in the MM, and a drug reactive with free thiols is provided. The method generally includes partially reducing interchain disulfide bonds in the activatable antibody with a reducing agent, such as, for example, TCEP; and conjugating the drug reactive with free thiols to the partially reduced activatable antibody. As used herein, the term partial reduction refers to situations where an activatable antibody is contacted with a reducing agent and less than all disulfide bonds, e.g., less than all possible sites of conjugation are reduced. In some embodiments, less than 99%, 98%, 97%, 96%, 95%, 90%, 85%, 80%, 75%, 70%, 65%, 60%, 55%, 50%, 45%, 40%, 35%, 30%, 25%, 20%, 15%, 10% or less than 5% of all possible sites of conjugation are reduced.

In some embodiments, a method of reducing and conjugating an agent, e.g., a drug, to an activatable antibody resulting in selectivity in the placement of the agent is provided. The method generally includes partially reducing the activatable antibody with a reducing agent such that any conjugation sites in the masking moiety or other non-AB portion of the activatable antibody are not reduced, and conjugating the agent to interchain thiols in the AB. The conjugation site(s) are selected so as to allow desired placement of an agent to allow conjugation to occur at a desired site. The reducing agent is, for example, TCEP. The reduction reaction conditions such as, for example, the ratio of reducing agent to activatable antibody, the length of incubation, the temperature during the incubation, the pH of the reducing reaction solution, etc., are determined by identifying the conditions that produce a conjugated activatable antibody in which the MM retains the ability to effectively and efficiently mask the AB of the activatable antibody in an uncleaved state. The ratio of reduction agent to activatable antibody will vary depending on the activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

In some embodiments, a method of reducing interchain disulfide bonds in the AB of an activatable antibody and conjugating an agent, e.g., a thiol-containing agent such as a drug, to the resulting interchain thiols to selectively locate agent(s) on the AB is provided. The method generally includes partially reducing the AB with a reducing agent to form at least two interchain thiols without forming all possible interchain thiols in the activatable antibody; and conjugating the agent to the interchain thiols of the partially reduced AB. For example, the AB of the activatable antibody is partially reduced for about 1 hour at about 37° C. at a desired ratio of reducing agent:activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

The thiol-containing reagent can be, for example, cysteine or N-acetyl cysteine. The reducing agent can be, for example, TCEP. In some embodiments, the reduced activatable antibody can be purified prior to conjugation, using for example, column chromatography, dialysis, or diafiltration. In some embodiments, the reduced antibody is not purified after partial reduction and prior to conjugation.

The disclosure also provides partially reduced activatable antibodies in which at least one interchain disulfide bond in the activatable antibody has been reduced with a reducing agent without disturbing any intrachain disulfide bonds in the activatable antibody, wherein the activatable antibody includes an antibody or an antigen binding fragment thereof (AB) that specifically binds to the target, a masking moiety (MM) that inhibits the binding of the AB of the activatable antibody in an uncleaved state to the target, and a CM1-CM2 substrate coupled to the AB, wherein the CM1-CM2 substrate is a polypeptide that functions as a substrate for at least one MMP and one SP. In some embodiments, the MM is coupled to the AB via the CM1-CM2 substrate. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM1-CM2 substrate-AB or AB-CM1-CM2 substrate-MM. In some embodiments, the reducing agent is TCEP.

The disclosure also provides partially reduced activatable antibodies, including but not limited to multispecific activatable antibodies of the disclosure, in which at least one interchain disulfide bond in the activatable antibody has been reduced with a reducing agent without disturbing or otherwise compromising the activity and/or efficacy of the activatable antibody, wherein the activatable antibody includes an antibody or an antigen binding fragment thereof (AB) that specifically binds to a target, a masking moiety (MM) that inhibits the binding of the AB of the activatable antibody in an uncleaved state to the target, and a CM1-CM2 substrate coupled to the AB, and the CM1-CM2 substrate is a polypeptide that functions as a substrate for a protease. The activity and/or efficacy of the activatable antibody is, by way of nonlimiting example, masking activity, activation of the activatable antibody, and/or binding activity of the activated activatable antibody. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM1-CM2 substrate-AB or AB-CM1-CM2 substrate-MM. In some embodiments, the reducing agent is TCEP.

The disclosure also provides conjugated activatable antibodies that include an activatable antibody linked to monomethyl auristatin D (MMAD) payload, wherein the activatable antibody includes an antibody or an antigen binding fragment thereof (AB) that specifically binds to a target, a masking moiety (MM) that inhibits the binding of the AB of the activatable antibody in an uncleaved state to the target, and CM1-CM2 substrate coupled to the AB, and the CM1-CM2 substrate is a polypeptide that functions as a substrate for at least one MMP protease and at least one SP protease.

In some embodiments, the MMAD-conjugated activatable antibody can be conjugated using any of several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB.

In some embodiments, the MMAD payload is conjugated to the AB via a linker. In some embodiments, the MMAD payload is conjugated to a cysteine in the AB via a linker. In some embodiments, the MMAD payload is conjugated to a lysine in the AB via a linker. In some embodiments, the MMAD payload is conjugated to another residue of the AB via a linker, such as those residues disclosed herein. In some embodiments, the linker is a thiol-containing linker. In some embodiments, the linker is a cleavable linker. In some embodiments, the linker is a non-cleavable linker. In some embodiments, the linker is selected from the group consisting of the linkers shown in Tables 5 and 6. In some embodiments, the activatable antibody and the MMAD payload are linked via a maleimide caproyl-valine-citrulline linker. In some embodiments, the activatable antibody and the MMAD payload are linked via a maleimide PEG-valine-citrulline linker. In some embodiments, the activatable antibody and the MMAD payload are linked via a maleimide caproyl-valine-citrulline-para-aminobenzyloxycarbonyl linker. In some embodiments, the activatable antibody and the MMAD payload are linked via a maleimide PEG-valine-citrulline-para-aminobenzyloxycarbonyl linker. In some embodiments, the MMAD payload is conjugated to the AB using the partial reduction and conjugation technology disclosed herein.

The disclosure also provides polypeptides and other larger molecules that include one or more of the CM1-CM2 substrate sequences presented herein. By way of non-limiting example, the CM1-CM2 substrate sequences presented herein are useful in prodrug compositions and methods of use thereof. These CM1-CM2 substrate sequences presented herein are also useful in probes and other detection agents and methods of use thereof. For example, the CM1-CM2 substrate sequences presented herein can be used in conjunction with fluors and other quenchers to produce detection agents, such as imaging agents and/or other diagnostic agents. Those of ordinary skill in the art will appreciate that the CM1-CM2 substrate sequences presented herein are useful in any composition and/or method in the art that would use a substrate that is cleavable by at least one MMP and at least one SP.

The disclosure also provides an isolated nucleic acid molecule encoding an antibody and/or an activatable antibody described herein, as well as vectors that include these isolated nucleic acid sequences. The disclosure provides methods of producing an antibody and/or activatable antibody by culturing a cell under conditions that lead to expression of the antibody and/or activatable antibody, wherein the cell comprises such a vector.

The disclosure provides a method of manufacturing a conjugated antibody of the disclosure that bind a given target by (a) culturing a cell comprising a nucleic acid construct that encodes the antibody under conditions that lead to expression of the antibody, (i) wherein the antibody includes a CM1-CM2 substrate, and (ii) wherein the CM1-CM2 substrate is a polypeptide that functions as a substrate for a matrix metalloprotease and a serine protease; (b) recovering the antibody; and (c) conjugating the recovered antibody to one or more additional agents.

The disclosure also provides a method of manufacturing the activatable antibodies of the disclosure that bind in an activated state a given target by (a) culturing a cell comprising a nucleic acid construct that encodes the activatable antibody under conditions that lead to expression of the activatable antibody, wherein the activatable antibody comprises a masking moiety (MM), a CM1-CM2 substrate, and an antibody or an antigen binding fragment thereof (AB) that specifically binds the target, (i) wherein the CM1-CM2 substrate is a polypeptide that functions as a substrate for a MMP and a SP; and (ii) wherein the CM1-CM2 substrate is positioned in the activatable antibody such that, in an uncleaved state, the MM interferes with specific binding of the AB to the target and in a cleaved state the MM does not interfere or compete with specific binding of the AB to the target; and (b) recovering the activatable antibody.

The disclosure also provides a method of manufacturing the conjugated activatable antibodies of the disclosure that bind in an activated state a given target by (a) culturing a cell comprising a nucleic acid construct that encodes the activatable antibody under conditions that lead to expression of the activatable antibody, wherein the activatable antibody comprises a masking moiety (MM), a CM1-CM2 substrate, and an antibody or an antigen binding fragment thereof (AB) that specifically binds the target, (i) wherein the CM1-CM2 substrate is a polypeptide that functions as a substrate for a MMP and a SP; and (ii) wherein the CM1-CM2 substrate is positioned in the activatable antibody such that, in an uncleaved state, the MM interferes with specific binding of the AB to the target and in a cleaved state the MM does not interfere or compete with specific binding of the AB to the target; (b) recovering the activatable antibody; and (c) conjugating the recovered antibody to one or more additional agents.

The disclosure provides methods of preventing, delaying the progression of, treating, alleviating a symptom of, or otherwise ameliorating a target-related disease in a subject by administering a therapeutically effective amount of a conjugated antibody, an activatable antibody and/or a conjugated activatable antibody described herein to a subject in need thereof.

The disclosure provides methods of preventing, delaying the progression of, treating, alleviating a symptom of, or otherwise ameliorating inflammation and/or an inflammatory disorder in a subject by administering a therapeutically effective amount of a conjugated antibody, an activatable antibody and/or a conjugated activatable antibody described herein to a subject in need thereof. The disclosure also provides methods of preventing, delaying the progression of, treating, alleviating a symptom of, or otherwise ameliorating cancer in a subject by administering a therapeutically effective amount of a conjugated antibody, an activatable antibody and/or a conjugated activatable antibody described herein to a subject in need thereof. The disclosure also provides methods of preventing, delaying the progression of, treating, alleviating a symptom of, or otherwise ameliorating an autoimmune disease in a subject by administering a therapeutically effective amount a conjugated antibody, an activatable antibody and/or a conjugated activatable antibody described herein to a subject in need thereof.

A conjugated antibody, an activatable antibody and/or a conjugated activatable antibody used in any of the embodiments of these methods and uses can be administered at any stage of the disease. For example, such a conjugated antibody, activatable antibody and/or conjugated activatable antibody can be administered to a patient suffering cancer of any stage, from early to metastatic. The terms subject and patient are used interchangeably herein.

In some embodiments, the subject is a mammal, such as a human, non-human primate, companion animal (e.g., cat, dog, horse), farm animal, work animal, or zoo animal. In some embodiments, the subject is a rodent. In some embodiments, the subject is a human. In some embodiments, the subject is a companion animal. In some embodiments, the subject is an animal in the care of a veterinarian.

The conjugated antibody, activatable antibody and/or conjugated activatable antibody and therapeutic formulations thereof are administered to a subject suffering from or susceptible to a disease or disorder associated with aberrant target expression and/or activity. A subject suffering from or susceptible to a disease or disorder associated with aberrant target expression and/or activity is identified using any of a variety of methods known in the art. For example, subjects suffering from cancer or other neoplastic condition are identified using any of a variety of clinical and/or laboratory tests such as, physical examination and blood, urine and/or stool analysis to evaluate health status. For example, subjects suffering from inflammation and/or an inflammatory disorder are identified using any of a variety of clinical and/or laboratory tests such as physical examination and/or bodily fluid analysis, e.g., blood, urine and/or stool analysis, to evaluate health status.

Administration of a conjugated antibody, an activatable antibody and/or a conjugated activatable antibody to a patient suffering from a disease or disorder associated with aberrant target expression and/or activity is considered successful if any of a variety of laboratory or clinical objectives is achieved. For example, administration of a conjugated antibody, an activatable antibody and/or a conjugated activatable antibody to a patient suffering from a disease or disorder associated with aberrant target expression and/or activity is considered successful if one or more of the symptoms associated with the disease or disorder is alleviated, reduced, inhibited or does not progress to a further, i.e., worse, state. Administration of a conjugated antibody, an activatable antibody and/or a conjugated activatable antibody to a patient suffering from a disease or disorder associated with aberrant target expression and/or activity is considered successful if the disease or disorder enters remission or does not progress to a further, i.e., worse, state.

In some embodiments, the antibodies, conjugated antibodies, activatable antibodies, and/or conjugated activatable antibodies described herein are used in conjunction with one or more additional agents or a combination of additional agents. Suitable additional agents include current pharmaceutical and/or surgical therapies for an intended application, such as, for example, cancer. For example, the antibodies, conjugated antibodies, activatable antibodies, and/or conjugated activatable antibodies can be used in conjunction with an additional chemotherapeutic or anti-neoplastic agent.

In some embodiments, the additional agent(s) is a chemotherapeutic agent, such as a chemotherapeutic agent selected from the group consisting of docetaxel, paclitaxel, abraxane (i.e., albumin-conjugated paclitaxel), doxorubicin, oxaliplatin, carboplatin, cisplatin, irinotecan, and gemcitabine.

In some embodiments, the additional agent(s) is a checkpoint inhibitor, a kinase inhibitor, an agent targeting inhibitors in the tumor microenvironment, and/or a T cell or NK agonist. In some embodiments, the additional agent(s) is radiation therapy, alone or in combination with another additional agent(s) such as a chemotherapeutic or anti-neoplastic agent. In some embodiments, the additional agent(s) is a vaccine, an oncovirus, and/or a DC-activating agent such as, by way of non-limiting example, a toll-like receptor (TLR) agonist and/or α-CD40. In some embodiments, the additional agent(s) is a tumor-targeted antibody designed to kill the tumor via ADCC or via direct conjugation to a toxin (e.g., an antibody drug conjugate (ADC).

In some embodiments, the checkpoint inhibitor is an inhibitor of a target selected from the group consisting of CTLA-4, LAG-3, PD-1, PD-1, TIGIT, TIM-3, B7H4, BTLA, and Vista. In some embodiments, the kinase inhibitor is selected from the group consisting of B-RAFi, MEKi, and Btk inhibitors, such as ibrutinib. In some embodiments, the kinase inhibitor is crizotinib. In some embodiments, the tumor microenvironment inhibitor is selected from the group consisting of an IDO inhibitor, an α-CSF1R inhibitor, an α-CCR4 inhibitor, a TGF-beta, a myeloid-derived suppressor cell, or a T-regulatory cell. In some embodiments, the agonist is selected from the group consisting of Ox40, GITR, CD137, ICOS, CD27, and HVEM.

In some embodiments, the inhibitor is a CTLA-4 inhibitor. In some embodiments, the inhibitor is a LAG-3 inhibitor. In some embodiments, the inhibitor is a PD-1 inhibitor. In some embodiments, the inhibitor is a PD-1 inhibitor. In some embodiments, the inhibitor is a TIGIT inhibitor. In some embodiments, the inhibitor is a TIM-3 inhibitor. In some embodiments, the inhibitor is a B7H4 inhibitor. In some embodiments, the inhibitor is a Vista inhibitor. In some embodiments, the inhibitor is a B-RAFi inhibitor. In some embodiments, the inhibitor is a MEKi inhibitor. In some embodiments, the inhibitor is a Btk inhibitor. In some embodiments, the inhibitor is ibrutinib. In some embodiments, the inhibitor is crizotinib. In some embodiments, the inhibitor is an IDO inhibitor. In some embodiments, the inhibitor is an α-CSF1R inhibitor. In some embodiments, the inhibitor is an α-CCR4 inhibitor. In some embodiments, the inhibitor is a TGF-beta. In some embodiments, the inhibitor is a myeloid-derived suppressor cell. In some embodiments, the inhibitor is a T-regulatory cell.

In some embodiments, the agonist is Ox40. In some embodiments, the agonist is GITR. In some embodiments, the agonist is CD137. In some embodiments, the agonist is ICOS. In some embodiments, the agonist is CD27. In some embodiments, the agonist is HVEM.

In some embodiments, the antibody, conjugated antibody, activatable antibody, and/or conjugated activatable antibody is administered during and/or after treatment in combination with one or more additional agents such as, for example, a chemotherapeutic agent, an anti-inflammatory agent, and/or an immunosuppressive agent. In some embodiments, the antibody, conjugated antibody, activatable antibody, and/or conjugated activatable antibody and the additional agent are formulated into a single therapeutic composition, and the antibody, conjugated antibody, activatable antibody, and/or conjugated activatable antibody and additional agent are administered simultaneously. Alternatively, the antibody, conjugated antibody, activatable antibody, and/or conjugated activatable antibody and additional agent are separate from each other, e.g., each is formulated into a separate therapeutic composition, and the antibody, conjugated antibody, activatable antibody, and/or conjugated activatable antibody and the additional agent are administered simultaneously, or the antibody, conjugated antibody, activatable antibody, and/or conjugated activatable antibody and the additional agent are administered at different times during a treatment regimen. For example, the antibody, conjugated antibody, activatable antibody, and/or conjugated activatable antibody is administered prior to the administration of the additional agent, the antibody, conjugated antibody, activatable antibody, and/or conjugated activatable antibody is administered subsequent to the administration of the additional agent, or the antibody, conjugated antibody, activatable antibody, and/or conjugated activatable antibody and the additional agent are administered in an alternating fashion. As described herein, the antibody, conjugated antibody, activatable antibody, and/or conjugated activatable antibody and additional agent are administered in single doses or in multiple doses.

In some embodiments, the antibody, conjugated antibody, activatable antibody, and/or conjugated activatable antibody and the additional agent(s) are administered simultaneously. For example, the antibody, conjugated antibody, activatable antibody, and/or conjugated activatable antibody and the additional agent(s) can be formulated in a single composition or administered as two or more separate compositions. In some embodiments, the antibody, conjugated antibody, activatable antibody, and/or conjugated activatable antibody and the additional agent(s) are administered sequentially, or the antibody, conjugated antibody, activatable antibody, and/or conjugated activatable antibody and the additional agent are administered at different times during a treatment regimen.

In some embodiments, the conjugated antibody, activatable antibody and/or conjugated activatable antibody is administered during and/or after treatment in combination with one or more additional agents such as, by way of non-limiting example, an anti-inflammatory agent, an immunosuppressive agent, a chemotherapeutic agent, such as an alkylating agent, an anti-metabolite, an anti-microtubule agent, a topoisomerase inhibitor, a cytotoxic antibiotic, and/or any other nucleic acid damaging agent. In some embodiments, the additional agent is a taxane, such as paclitaxel (e.g., Abraxane®). In some embodiments, the additional agent is an anti-metabolite, such as gemcitabine. In some embodiments, the additional agent is an alkylating agent, such as platinum-based chemotherapy, such as carboplatin or cisplatin. In some embodiments, the additional agent is a targeted agent, such as a kinase inhibitor, e.g., sorafenib or erlotinib. In some embodiments, the additional agent is a targeted agent, such as another antibody, e.g., a monoclonal antibody (e.g., bevacizumab), a bispecific antibody, or a multispecific antibody. In some embodiments, the additional agent is a proteosome inhibitor, such as bortezomib or carfilzomib. In some embodiments, the additional agent is an immune modulating agent, such as lenolidominde or IL-2. In some embodiments, the additional agent is radiation. In some embodiments, the additional agent is an agent considered standard of care by those skilled in the art. In some embodiments, the additional agent is a chemotherapeutic agent well known to those skilled in the art.

In some embodiments, the additional agent is an antibody, another conjugated antibody, another activatable antibody and/or another conjugated activatable antibody. In some embodiments the additional agent is an antibody, another conjugated antibody, another activatable antibody and/or another conjugated activatable antibody against the same target as the first conjugated antibody, activatable antibody and/or a conjugated activatable antibody. In some embodiments the additional agent is an antibody, another conjugated antibody, another activatable antibody and/or another conjugated activatable antibody against a target different than the target of the first conjugated antibody, activatable antibody and/or a conjugated activatable antibody.

In some embodiments, the conjugated antibody, activatable antibody and/or conjugated activatable antibody and the additional agent(s) are administered simultaneously. For example, the conjugated antibody, activatable antibody and/or conjugated activatable antibody and the additional agent(s) can be formulated in a single composition or administered as two or more separate compositions. In some embodiments, the conjugated antibody, activatable antibody and/or conjugated activatable antibody and the additional agent(s) are administered sequentially, or the antibody and/or conjugated antibodies and the additional agent are administered at different times during a treatment regimen. For example, the antibody and/or conjugated antibodies is administered prior to the administration of the additional agent, the antibody and/or conjugated antibodies is administered subsequent to the administration of the additional agent, or the antibody and/or conjugated antibodies and the additional agent are administered in an alternating fashion. As described herein, the antibody and/or conjugated antibodies and additional agent are in single doses or in multiple doses.

The disclosure also provides methods and kits for using the conjugated antibodies, activatable antibodies and/or conjugated activatable antibodies in a variety of diagnostic and/or prophylactic indications.

Pharmaceutical compositions according to the disclosure can include an antibody, conjugated antibody, activatable antibody and/or a conjugated activatable antibody of the disclosure and a carrier. These pharmaceutical compositions can be included in kits, such as, for example, diagnostic kits.

BRIEF DESCRIPTION OF THE DRAWINGS

FIG. 8F is a graph that plots and compares the data presented in FIGS. 8A-8E in a single graph.

DETAILED DESCRIPTION OF THE INVENTION

Figure 1A:
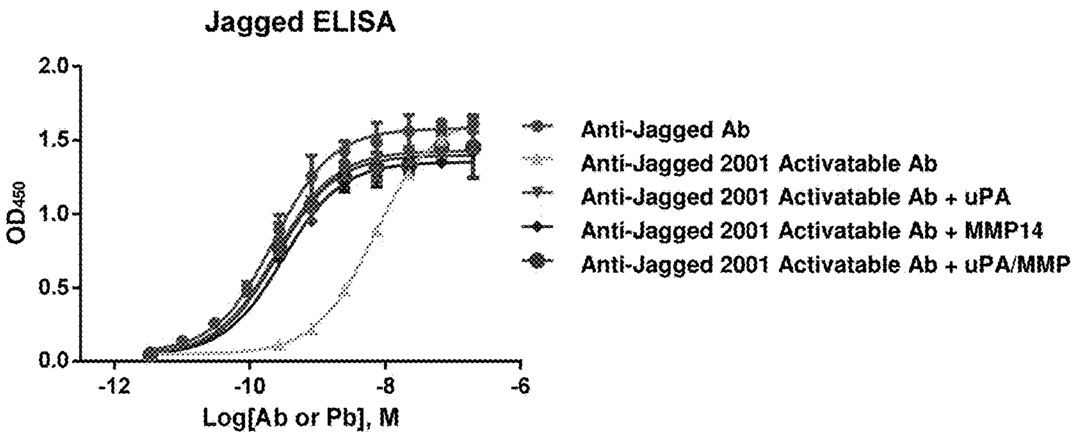
FIGS. 1A and 1B are a series of graphs depicting the results of human Jagged 1 binding ELISA assays that demonstrate the binding of the anti-Jagged antibody and the masked and activated activatable antibodies. Both the (A) 2001 and (B) 1001/LP'/0001 substrate-containing activatable antibodies were activated by uPA (a serine protease), MMP14 (an MMP), and uPA in combination with MMP14. The activated activatable antibodies showed binding equivalent to the anti-Jagged antibody.

The disclosure provides amino acid sequences that include at least a first cleavable moiety (CM1) that is a substrate for at least one matrix metalloprotease (MMP) and at least a second cleavable moiety (CM2) that is a substrate for at least one serine protease (SP). These CM1-CM2 substrates are useful in a variety of therapeutic, diagnostic and prophylactic indications. For example, these CM1-CM2 substrates are useful in activatable antibodies that include antibodies or antigen-binding fragments thereof (AB) that include at least one masking moiety (MM) linked to at least one antigen- or epitope-binding domain of the AB such that coupling of the MM reduces the ability of the AB to bind its target.

The working examples provided herein demonstrate that these CM1-CM2 substrates exhibit a number of desirable cleavage characteristics when exposed to at least one MMP protease and/or at least one SP protease under specified conditions.

The disclosure also provides antibodies that include one or more of these CM1-CM2 substrates. For example, these CM1-CM2 substrates are useful when conjugating antibodies to one or more additional agents to produce conjugated antibodies. These CM1-CM2 substrates are also useful in activatable antibodies and/or activatable antibody conjugates.

The conjugated antibodies, activatable antibodies, and/or conjugated activatable antibodies include an antibody or antigen-binding fragment thereof (AB) that specifically binds a target. Exemplary classes of targets of an AB include, but are not necessarily limited to, cell surface receptors and secreted binding proteins (e.g., growth factors), soluble enzymes, structural proteins (e.g. collagen, fibronectin) and the like. In some embodiments, conjugated antibodies and/or activatable antibodies have an AB that binds an extracellular target, usually an extracellular protein target. In some embodiments, conjugated antibodies and/or activatable antibodies are designed for cellular uptake and are switchable inside a cell.

As a non-limiting example, the AB is a binding partner for any target listed in Table 1.

TABLE 1

| Exemplary Targets | | | | | |
|---|---|---|---|---|---|
| 1-92-LFA-3 | CD52 | DL44 | HVEM | LIF-R | STEAP1 |
| Alpha-4 integrin | CD56 | DLK1 | Hyaluronidase | Lewis X | STEAP2 |

TABLE 1-continued

| Exemplary Targets | | | | | |
|---|---|---|---|---|---|
| Alpha-V integrin | CD64 | DLL4 | ICOS | LIGHT | TAG-72 |
| alpha4beta1 integrin | CD70 | DPP-4 | IFNalpha | LRP4 | TAPA1 |
| alpha4beta7 integrin | CD71 | DSG1 | IFNbeta | LRRC26 | TGFbeta |
| AGR2 | CD74 | EGFR | IFNgamma | MCSP | TIGIT |
| Anti-Lewis-Y | | EGFRviii | IgE | Mesothelin | TIM-3 |
| Apelin J receptor | CD80 | Endothelin B receptor (ETBR) | IgE Receptor (FceRI) | MRP4 | TLR2 |
| APRIL | CD81 | ENPP3 | IGF | MUC1 | TLR4 |
| B7-H4 | CD86 | EpCAM | IGF1R | Mucin-16 (MUC16, CA-125) | TLR6 |
| BAFF | CD95 | EPHA2 | IL1B | Na/K ATPase | TLR7 |
| BTLA | CD117 | EPHB 2 | IL1R | Neutrophil elastase | TLR8 |
| C5 complement | CD125 | ERBB3 | IL2 | NGF | TLR9 |
| C-242 | CD132 (IL-2RG) | F protein of RSV | IL11 | Nicastrin | TMEM31 |
| CA9 | CD133 | FAP | IL12 | Notch Receptors | TNFalpha |
| CA19-9 (Lewis a) | CD137 | FGF-2 | IL12p40 | Notch 1 | TNFR |
| Carbonic anhydrase 9 | CD138 | FGF8 | IL-12R, IL-12Rbeta1 | Notch 2 | TNFRS 12 A |
| CD2 | CD166 | FGFR1 | IL13 | Notch 3 | TRAIL-R1 |
| CD3 | CD172A | FGFR2 | IL13R | Notch 4 | TRAIL-R2 |
| CD6 | CD248 | FGFR3 | IL15 | NOV | Transferrin |
| CD9 | CDH6 | FGFR4 | IL17 | OSM-R | Transferrin receptor |
| CD11a | CEACAM5 (CEA) | Folate receptor | IL18 | OX-40 | TRK-A |
| CD19 | CEACAM6 (NCA-90) | GAL3ST1 | IL21 | PAR2 | TRK-B |
| CD20 | CLAUDIN-3 | G-CSF | IL23 | PDGF-AA | uPAR |
| CD22 | CLAUDIN-4 | G-CSFR | IL23R | PDGF-BB | VAP1 |
| CD24 | cMet | GD2 | IL27/IL27R (wsx1) | PDGFRalpha | VCAM-1 |
| CD25 | Collagen | GITR | IL29 | PDGFRbeta | VEGF |
| CD27 | Cripto | GLUT1 | IL-31R | PD-1 | VEGF-A |
| CD28 | CSFR | GLUT4 | IL31/IL31R | PD-L1 | VEGF-B |
| CD30 | CSFR-1 | GM-CSF | IL2R | PD-L2 | VEGF-C |
| CD33 | CTLA-4 | GM-CSFR | IL4 | Phosphatidyl-serine | VEGF-D |
| CD38 | CTGF | GP IIb/IIIa receptors | IL4R | P1GF | VEGFR1 |
| CD40 | CXCL10 | Gp130 | IL6, IL6R | PSCA | VEGFR2 |
| CD40L | CXCL13 | GPIIB/IIIA | Insulin Receptor | PSMA | VEGFR3 |
| CD41 | CXCR1 | GPNMB | Jagged Ligands | RAAG12 | VISTA |
| CD44 | CXCR2 | GRP78 | Jagged 1 | RAGE | WISP-1 |
| CD44v6 | | HER2/neu | Jagged 2 | SLC44A4 | WISP-2 |
| CD47 | CXCR4 | HGF | LAG-3 | Sphingosine 1 Phosphate | WISP-3 |
| CD51 | CYR61 | hGH | | | |

As a non-limiting example, the AB is or is derived from an antibody listed in Table 2.

TABLE 2

| Antibody Trade Name (antibody name) | Target |
|---|---|
| Avastin ™ (bevacizumab) | VEGF |
| Lucentis ™ (ranibizumab) | VEGF |
| Erbitux ™ (cetuximab) | EGFR |
| Vectibix ™ (panitumumab) | EGFR |
| Remicade ™ (infliximab) | TNFα |
| Humira ™ (adalimumab) | TNFα |

TABLE 2-continued

| Antibody Trade Name (antibody name) | Target |
|---|---|
| Tysabri ™ (natalizumab) | Integrinα4 |
| Simulect ™ (basiliximab) | IL2R |
| Soliris ™ (eculizumab) | Complement C5 |
| Raptiva ™ (efalizumab) | CD11a |
| Bexxar ™ (tositumomab) | CD20 |
| Zevalin ™ (ibritumomab tiuxetan) | CD20 |
| Rituxan ™ (rituximab) | CD20 |
| Ocrelizumab | CD20 |
| Arzerra ™ (ofatumumab) | CD20 |

TABLE 2-continued

| Exemplary sources for Abs | |
|---|---|
| Antibody Trade Name (antibody name) | Target |
| Gazyva ™ (Obinutuzumab) | CD20 |
| Zenapax ™ (daclizumab) | CD25 |
| Adcetris ™ (brentuximab vedotin) | CD30 |
| Myelotarg ™ (gemtuzumab) | CD33 |
| Mylotarg ™ (gemtuzumab ozogamicin) | CD33 |
| Campath ™ (alemtuzumab) | CD52 |
| ReoPro ™ (abiciximab) | Glycoprotein receptor IIb/IIIa |
| Xolair ™ (omalizumab) | IgE |
| Herceptin ™ (trastuzumab) | Her2 |
| Kadcyla ™ (trastuzumab emtansine) | Her2 |
| Synagis ™ (palivizumab) | F protein of RSV |
| (ipilimumab) | CTLA-4 |
| (tremelimumab) | CTLA-4 |
| Hu5c8 | CD40L |
| (pertuzumab) | Her2-neu |
| (ertumaxomab) | CD3/Her2-neu |
| Orencia ™ (abatacept) | CTLA-4 |
| (tanezumab) | NGF |
| (bavituximab) | Phosphatidylserine |
| (zalutumumab) | EGFR |
| (mapatumumab) | EGFR |
| (matuzumab) | EGFR |
| (nimotuzumab) | EGFR |
| ICR62 | EGFR |
| mAb 528 | EGFR |
| CH806 | EGFR |
| MDX-447 | EGFR/CD64 |
| (edrecolomab) | EpCAM |
| RAV12 | RAAG12 |
| huJ591 | PSMA |
| Enbrel ™ (etanercept) | TNF-R |
| Amevive ™ (alefacept) | 1-92-LFA-3 |
| Antril ™, Kineret ™ (ankinra) | IL-1Ra |
| GC1008 | TGFbeta |
| | Notch, e.g., Notch 1 |
| | Jagged 1 or Jagged 2 |
| (adecatumumab) | EpCAM |
| (figitumumab) | IGF1R |
| (tocilizumab) | IL-6 receptor |
| Stelara ™ (ustekinumab) | IL-12/IL-23 |
| Prolia ™ (denosumab) | RANKL |

Exemplary conjugated antibodies, activatable antibodies and/or conjugated activatable antibodies of the disclosure include, for example, antibodies that bind interleukin 6 receptor (IL-6R) and that include a heavy chain and a light chain that are, or are derived from, the antibody referred to herein as the "Av1" antibody, which binds interleukin-6 receptor (IL-6R). The amino acid sequences for the Av1 heavy chain and the Av1 light chain are shown below in SEQ ID NO: 100 and SEQ ID NO: 101, respectively.

Av1 Antibody Heavy Chain Amino Acid Sequence:

```
                                            (SEQ ID NO: 100)
QVQLQESGPGLVRPSQTLSLTCTVSGYSITSDHAWSWVRQPPGRGLEWIG

YISYSGITTYNPSLKSRVTISRDNSKNTLYLQMNSLRAEDTAVYYCARSL

ARTTAMDYWGQGSLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK
```

Av1 Antibody Light Chain Amino Acid Sequence:

```
                                            (SEQ ID NO: 101)
DIQMTQSPSSLSASVGDRVTITCRASQDISSYLNWYQQKPGKAPKLLIYY

TSRLHSGVPSRFSGSGSGTDFTFTISSLQPEDIATYYCQQGNTLPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

Exemplary activatable antibodies and/or conjugated activatable antibodies of the disclosure include, for example, antibodies that bind interleukin 6 receptor (IL-6R) and that include a heavy chain and a light chain that are, or are derived from, the Av1 antibody and a masking moiety. Exemplary activatable antibodies and/or conjugated activatable antibodies of the disclosure include an amino acid sequence attached to the N-terminus of the AV1 light chain. These N-terminal amino acid sequences include, for example, YGSCSWNYVHIFMDC (SEQ ID NO: 102); QGDFDIPFPAHWVPIT (SEQ ID NO: 103); MGVPAGCVWNYAHIFMDC (SEQ ID NO: 104); QGQSGQYGSCSWNYVHIFMDC (SEQ ID NO: 105); QGQSGQGDFDIPFPAHWVPIT (SEQ ID NO: 106); or QGQSGQMGVPAGCVWNYAHIFMDC (SEQ ID NO: 107). It is also to be appreciated that such amino acid sequences can be attached to the N-terminus of the AV1 heavy chain or to the C-terminus of the AV1 heavy or light chain.

Exemplary activatable antibodies of the disclosure include, for example, antibodies that bind Epidermal Growth Factor Receptor (EGFR) and that include a heavy chain and a light chain that are, or are derived from, an antibody selected from the group consisting of the antibody referred to herein as the "c225v5" antibody (also referred to herein as the C225v5 antibody), the antibody referred to herein as the "c225v4" antibody (also referred to herein as the C225v4 antibody), and the antibody referred to herein as the "c225v6" antibody (also referred to herein as the C225v6 antibody), each of which binds EGFR. The c225v5 antibody, the c225v4 antibody, and the c225v6 antibody share the same light chain sequence, referred to herein as "c225 light chain." The amino acid sequences for the c225v5 heavy chain, the c225v4 antibody, the c225v6 antibody, and the c225 light chain are shown below.

C225v5 Antibody Heavy Chain Amino Acid Sequence:

```
                                            (SEQ ID NO: 108)
QVQLKQSGPGLVQPSQSLSITCTVSGFSLTNYGVHWVRQSPGKGLEWLGV

IWSGGNTDYNTPFTSRLSINKDNSKSQVFFKMNSLQSQDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK
```

C225v4 Antibody Heavy Chain Amino Acid Sequence:

(SEQ ID NO: 109)
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

C225v6 Antibody Heavy Chain Amino Acid Sequence:

(SEQ ID NO: 110)
QVQLKQSGPGLVQPSQSLSITCTVSGFSLTNYGVHWVRQSPGKGLEWLGV

IWSGGNTDYNTPFTSRLSINKDNSKSQVFFKMNSLQSQDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

-continued

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYAS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

C225 Antibody Light Chain Amino Acid Sequence:

(SEQ ID NO: 111)
QILLTQSPVILSVSPGERVSFSCRASQSIGTNIHWYQQRTNGSPRLLIKY

ASESISGIPSRFSGSGSGTDFTLSINSVESEDIADYYCQQNNNWPTTFGA

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Exemplary conjugated antibodies and/or activatable antibodies of the disclosure include, for example, antibodies that bind a Jagged target, e.g., Jagged-1, Jagged-2 and/or both Jagged-1 and Jagged-2, and that include a combination of a variable heavy chain region and a variable light chain region that are, or are derived from, the variable heavy chain and variable light chain sequences shown below.

Variable Light Chain Amino Sequence Lc4
(SEQ ID NO: 112)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc4
(SEQ ID NO: 113)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable Light Chain Amino Sequence Lc5
(SEQ ID NO: 114)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc5
(SEQ ID NO: 115)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPYHGQFDYWGQGTLVTVSS

Variable Light Chain Amino Sequence Lc7
(SEQ ID NO: 116)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc7
(SEQ ID NO: 117)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc8
(SEQ ID NO: 118)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

-continued

Variable Heavy Chain Amino Sequence Hc8
(SEQ ID NO: 119)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKHIGRTNPFDYWGQGTLVTVSS

Variable Light Chain Amino Sequence Lc13
(SEQ ID NO: 120)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc13
(SEQ ID NO: 121)
EVQLLESGGGLVQPGGSLRLSCAASGFTFSSYAMSWVRQAPGKGLEWVSSIEQMGWQTEYADSV

KGRFTISRDNSKNTLYLQMNSLRAEDTAVYYCAKSAAAFDYWGQGTLVTVSS

Variable Light Chain Amino Sequence Lc16
(SEQ ID NO: 122)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc16
(SEQ ID NO: 123)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPYYGQFDYWGQGTLVTVSS

Variable Light Chain Amino Sequence Lc19
(SEQ ID NO: 124)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc19
(SEQ ID NO: 125)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc21
(SEQ ID NO: 126)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc21
(SEQ ID NO: 127)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable Light Chain Amino Sequence Lc24
(SEQ ID NO: 128)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc24
(SEQ ID NO: 129)
EVQLLESGGGLVQPGGSLRLSCAASGFTFSSYAMSWVRQAPGKGLEWVSSIEEMGWQTLYADSV

KGRFTISRDNSKNTLYLQMNSLRAEDTAVYYCAKSAAAFDYWGQGTLVTVSS

Variable Light Chain Amino Sequence Lc26
(SEQ ID NO: 130)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc26
(SEQ ID NO: 131)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

-continued

Variable Light Chain Amino Sequence Lc27
(SEQ ID NO: 132)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc27
(SEQ ID NO: 133)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFYGQFDYWGQGTLVTVSS

Variable Light Chain Amino Sequence Lc28
(SEQ ID NO: 134)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc28
(SEQ ID NO: 135)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc30
(SEQ ID NO: 136)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc30
(SEQ ID NO: 137)
EVQLLESGGGLVQPGGSLRLSCAASGFTFSSYAMSWVRQAPGKGLEWVSSIEEMGWQTLYADSV

KGRFTISRDNSKNTLYLQMNSLRAEDTAVYYAKSAAAFDYWGQGTLVTVSS

Variable Light Chain Amino Sequence Lc31
(SEQ ID NO: 138)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc31
(SEQ ID NO: 139)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable Light Chain Amino Sequence Lc32
(SEQ ID NO: 140)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc32
(SEQ ID NO: 141)
EVQLLESGGGLVQPGGSLRLSCAASGFTFSSYAMSWVRQAPGKGLEWVSSIDPEGWQTYYADSV

KGRFTISRDNSKNTLYLQMNSLRAEDTAVYYCAKSAAAFDYWGQGTLVTVSS

Variable Light Chain Amino Sequence Lc37
(SEQ ID NO: 142)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc37
(SEQ ID NO: 143)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPHNGQFDYWGQGTLVTVSS

Variable Light Chain Amino Sequence Lc39
(SEQ ID NO: 144)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

-continued

Variable Heavy Chain Amino Sequence Hc39
(SEQ ID NO: 145)
EVQLLESGGGLVQPGGSLRLSCAASGFTFSSYAMSWVRQAPGKGLEWVSSIEQMGWQTEYADSV

KGRFTISRDNSKNTLYLQMNSLRAEDTAVYYCAKSAAAFDYWGQGTLVTVSS

Variable Light Chain Amino Sequence Lc40
(SEQ ID NO: 146)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Heavy Chain Amino Sequence Hc40
(SEQ ID NO: 147)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino SequenceLc47
(SEQ ID NO: 148)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc47
(SEQ ID NO: 149)
EVQLLESGGGLVQPGGSLRLSCAASGFTFSSYAMSWVRQAPGKGLEWVSSIDEMGWQTEYADSV

KGRFTISRDNSKNTLYLQMNSLRAEDTAVYYCAKSAAAFDYWGQGTLVTVSS

Variable 4B2 Light Chain
(SEQ ID NO: 150)
DIQMTQSPSSLSASVGDRVTITCRASQSISSYLNWYQQKPGKAPKLLIYAASSLQSGVPSRFSG

SGSGTDFTLTISSLQPEDFATYYCQQTLDAPPQFGQGTKVEIKR

Variable 4B2 Heavy Chain
(SEQ ID NO: 151)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable 4D11 Light Chain
(SEQ ID NO: 152)
DIQMTQSPSSLSASVGDRVTITCRASQSISSYLNWYQQKPGKAPKLLIYAASSLQSGVPSRFSG

SGSGTDFTLTISSLQPEDFATYYCQQTVVAPPLFGQGTKVEIKR

Variable 4D11 Heavy Chain
(SEQ ID NO: 153)
EVQLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSS

Variable 4E7 Light Chain
(SEQ ID NO: 154)
DIQMTQSPSSLSASVGDRVTITCRASQSISSYLNWYQQKPGKAPKLLIYAASSLQSGVPSRFSG

SGSGTDFTLTISSLQPEDFATYYCQQSLVAPLTFGQGTKVEIKR

Variable 4E7 Heavy Chain
(SEQ ID NO: 155)
EVQLLESGGGLVQPGGSLRLSCAASGFTFSSYAMSWVRQAPGKGLEWVSSIEEMGWQTKYADSV

KGRFTISRDNSKNTLYLQMNSLRAEDTAVYYCAKSAAAFDYWGQGTLVTVSS

Variable 4E11 Light Chain
(SEQ ID NO: 156)
DIQMTQSPSSLSASVGDRVTITCRASQSISSYLNWYQQKPGKAPKLLIYAASSLQSGVPSRFSG

SGSGTDFTLTISSLQPEDFATYYCQQALDAPLMFGQGTKVEIKR

Variable 4E11 Heavy Chain
(SEQ ID NO: 157)
EVQLLESGGGLVQPGGSLRLSCAASGFTFSSYAMSWVRQAPGKGLEWVSSIEPMGQLTEYADSV

KGRFTISRDNSKNTLYLQMNSLRAEDTAVYYCAKDIGGRSAFDYWGQGTLVTVSS

-continued

Variable 6B7 Light Chain
(SEQ ID NO: 158)
DIQMTQSPSSLSASVGDRVTITCRASQSISSYLNWYQQKPGKAPKLLIYAASSLQSGVPSRFSG

SGSGTDFTLTISSLQPEDFATYYCQQALVAPLTFGQGTKVEIKR

Variable 6B7 Heavy Chain
(SEQ ID NO: 159)
EVQLLESGGGLVQPGGSLRLSCAASGFTFSSYAMSWVRQAPGKGLEWVSSIDEMGWQTYYADSV

KGRFTISRDNSKNTLYLQMNSLRAEDTAVYYCAKSAAAFDYWGQGTLVTVSS

Variable 6F8 Light Chain
(SEQ ID NO: 160)
DIQMTQSPSSLSASVGDRVTITCRASQSISSYLNWYQQKPGKAPKLLIYAASSLQSGVPSRFSG

SGSGTDFTLTISSLQPEDFATYYCQQALVAPLTFGQGTKVEIKR

Variable 6F8 Heavy Chain
(SEQ ID NO: 161)
EVQLLESGGGLVQPGGSLRLSCAASGFTFSSYAMSWVRQAPGKGLEWVSSIDEMGWQTYYADSV

KGRFTISRDNSKNTLYLQMNSLRAEDTAVYYCAKSAAAFDYWGQGTLVTVSS

Exemplary conjugated antibodies, activatable antibodies and/or conjugated activatable antibodies of the disclosure include, for example, antibodies that bind a Jagged target, e.g., Jagged-1, Jagged-2 and/or both Jagged-1 and Jagged-2, and that include a combination of a heavy chain region and a light chain region that are, or are derived from, the heavy chain and light chain sequences shown below.

4D11 Light Chain sequence:
(SEQ ID NO: 162)
DIQMTQSPSSLSASVGDRVTITCRASQSISSYLNWYQQKPGKAPKLLIYAASSLQSGVPSRFSG

SGSGTDFTLTISSLQPEDFATYYCQQTVVAPPLFGQGTKVEIKRTVAAPSVFIFPPSDEQLKSG

TASVVCLLNNFYPREAKVQWKVDNALQSGNSQESVTEQDSKDSTYSLSSTLTLSKADYEKHKVY

ACEVTHQGLSSPVTKSFNRGEC

4D11 Heavy Chain sequence:
(SEQ ID NO: 67)
EVQLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSSASTKGPSVF

PLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEALHNHYTQKSLSLSPG

K

4D11v2 Heavy Chain sequence
(SEQ ID NO: 163)
EVHLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSSASTKGPSVF

PLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEALHNHYTQKSLSLSPG

K

-continued

4D11v2 Light Chain Sequence (SEQ ID NO: 164)

```
DIQMTQSPSSLSASVGDRVTITCRASQSISSYLNWYQQKPGKAPKLLIYAASSLQSGVPSRFSG

SGSGTDFTLTISSLQPEDFATYYCQQTVVAPPLFGQGTKVEIKRTVAAPSVFIFPPSDEQLKSG

TASVVCLLNNFYPREAKVQWKVDNALQSGNSQESVTEQDSKDSTYSLSSTLTLXKADYEKHKVY

ACEVTHQGLSSPVTKSFNRGEC
```

The activatable antibodies and activatable antibody compositions provided herein contain at least an antibody or antibody fragment thereof (collectively referred to as AB throughout the disclosure) that specifically binds a target, e.g., a human target, wherein the AB is modified by a masking moiety (MM).

In some embodiments, the masking moiety is selected for use with a specific antibody or antibody fragment. For example, suitable masking moieties for use with antibodies that bind EGFR include MMs that include the sequence CISPRG (SEQ ID NO: 165). By way of non-limiting examples, the MM can include a sequence such as CISPRGC (SEQ ID NO: 166); CISPRGCG (SEQ ID NO: 167); CISPRGCPDGPYVMY (SEQ ID NO: 168); CISPRGCPDGPYVM (SEQ ID NO: 169), CISPRGCEPGTYVPT (SEQ ID NO: 170) and CISPRGCPGQIWHPP (SEQ ID NO: 171). Other suitable masking moieties include any of the EGFR-specific masks disclosed in PCT Publication No. WO 2010/081173, such as, by way of non-limiting example, GSHCLIPINMGAPSC (SEQ ID NO: 172); CISPRGCGGSSASQSGQGSHCLIPINMGAPSC (SEQ ID NO: 173); CNHHYFYTCGCISPRGCPG (SEQ ID NO: 174); ADHVFWGSYGCISPRGCPG (SEQ ID NO: 175); CHHVYWGHCGCISPRGCPG (SEQ ID NO: 176); CPHFTTTSCGCISPRGCPG (SEQ ID NO: 177); CNHHYHYYCGCISPRGCPG (SEQ ID NO: 178); CPHVSFGSCGCISPRGCPG (SEQ ID NO: 179); CPYYTLSYCGCISPRGCPG (SEQ ID NO: 180); CNHVYFGTCGCISPRGCPG (SEQ ID NO: 181); CNHFTLTTCGCISPRGCPG (SEQ ID NO: 182); CHHFTLTTCGCISPRGCPG (SEQ ID NO: 183); YNPCATPMCCISPRGCPG (SEQ ID NO: 184); CNHHYFYTCGCISPRGCG (SEQ ID NO: 185); CNHHYHYYCGCISPRGCG (SEQ ID NO: 186); CNHVYFGTCGCISPRGCG (SEQ ID NO: 187); CHHVYWGHCGCISPRGCG (SEQ ID NO: 188); CPHFTTTSCGCISPRGCG (SEQ ID NO: 189); CNHFTLTTCGCISPRGCG (SEQ ID NO: 190); CHHFTLTTCGCISPRGCG (SEQ ID NO: 191); CPYYTLSYCGCISPRGCG (SEQ ID NO: 192); CPHVSFGSCGCISPRGCG (SEQ ID NO: 193); ADHVFWGSYGCISPRGCG (SEQ ID NO: 194); YNPCATPMCCISPRGCG (SEQ ID NO: 195); CHHVYWGHCGCISPRGCG (SEQ ID NO: 196); C(N/P)H(H/V/F)(Y/T)(F/W/T/L)(Y/G/T/S)(T/S/Y/H)CGCISPRGCG (SEQ ID NO: 197); CISPRGCGQPIPSVK (SEQ ID NO: 198); CISPRGCTQPYHVSR (SEQ ID NO: 199); and/or CISPRGCNAVSGLGS (SEQ ID NO: 200).

Suitable masking moieties for use with antibodies that bind a Jagged target, e.g., Jagged 1 and/or Jagged 2, include, by way of non-limiting example, masking moieties that include a sequence such as QGQSGQCNIWLVGGDCRGWQG (SEQ ID NO: 201); QGQSGQGQQQWCNIWINGGDCRGWNG (SEQ ID NO: 202); PWCMQRQDFLRCPQP (SEQ ID NO: 203); QLGLPAYMCTFECLR (SEQ ID NO: 204); CNLWVSGGDCGGLQG (SEQ ID NO: 205); SCSLWTSGSCLPHSP (SEQ ID NO: 206); YCLQLPHYMQAMCGR (SEQ ID NO: 207); CFLYSCTDVSYWNNT (SEQ ID NO: 208); PWCMQRQDYLRCPQP (SEQ ID NO: 209); CNLWISGGDCRGLAG (SEQ ID NO: 210); CNLWVSGGDCRGVQG (SEQ ID NO: 211); CNLWVSGGDCRGLRG (SEQ ID NO: 212); CNLWISGGDCRGLPG (SEQ ID NO: 213); CNLWVSGGDCRDAPW (SEQ ID NO: 214); CNLWVSGGDCRDLLG (SEQ ID NO: 215); CNLWVSGGDCRGLQG (SEQ ID NO: 216); CNLWLHGGDCRGWQG (SEQ ID NO: 217); CNIWLVGGDCRGWQG (SEQ ID NO: 218); CTTWFCGGDCGVMRG (SEQ ID NO: 219); CNIWGPSVDCGALLG (SEQ ID NO: 220); CNIWVNGGDCRSFEG (SEQ ID NO: 221); YCLNLPRYMQDMCWA (SEQ ID NO: 222); YCLALPHYMQADCAR (SEQ ID NO: 223); CFLYSCGDVSYWGSA (SEQ ID NO: 224); CYLYSCTDSAFWNNR (SEQ ID NO: 225); CYLYSCNDVSYWSNT (SEQ ID NO: 226); CFLYSCTDVSYW (SEQ ID NO: 227); CFLYSCTDVAYWNSA (SEQ ID NO: 228); CFLYSCTDVSYWGDT (SEQ ID NO: 229); CFLYSCTDVSYWGNS (SEQ ID NO: 230); CFLYSCTDVAYWNNT (SEQ ID NO: 231); CFLYSCGDVSYWGNPGLS (SEQ ID NO: 232); CFLYSCTDVAYWSGL (SEQ ID NO: 233); CYLYSCTDGSYWNST (SEQ ID NO: 234); CFLYSCSDVSYWGNI (SEQ ID NO: 235); CFLYSCTDVAYW (SEQ ID NO: 236); CFLYSCTDVSYWGST (SEQ ID NO: 237); CFLYSCTDVAYWGDT (SEQ ID NO: 238); GCNIWLNGGDCRGWVDPLQG (SEQ ID NO: 239); GCNIWLVGGDCRGWIGDTNG (SEQ ID NO: 240); GCNIWLVGGDCRGWIEDSNG (SEQ ID NO: 241); GCNIWANGGDCRGWIDNIDG (SEQ ID NO: 242); GCNIWLVGGDCRGWLGEAVG (SEQ ID NO: 243); GCNIWLVGGDCRGWLEEAVG (SEQ ID NO: 244); GGPALCNIWLNGGDCRGWSG (SEQ ID NO: 245); GAPVFCNIWLNGGDCRGWMG (SEQ ID NO: 246); GQQQWCNIWINGGDCRGWNG (SEQ ID NO: 247); GKSEFCNIWLNGGDCRGWIG (SEQ ID NO: 248); GTPGGCNIWANGGDCRGWEG (SEQ ID NO: 249); GASQYCNLWINGGDCRGWRG (SEQ ID NO: 250); GCNIWLVGGDCRPWVEGG (SEQ ID NO: 251); GCNIWAVGGDCRPFVDGG (SEQ ID NO: 252); GCNIWLNGGDCRAWVDTG (SEQ ID NO: 253); GCNIWIVGGDCRPFINDG (SEQ ID NO: 254); GCNIWLNGGDCRPVVFGG (SEQ ID NO: 255); GCNIWLSGGDCRMFMNEG (SEQ ID NO: 256); GCNIWVNGGDCRSFVYSG (SEQ ID NO: 257); GCNIWLNGGDCRGWEASG (SEQ ID NO: 258); GCNIWAHGGDCRGFIEPG (SEQ ID NO: 259); GCNIWLNGGDCRTFVASG (SEQ ID NO: 260); GCNIWAHGGDCRGFIEPG (SEQ ID NO: 261); GFLENCNIWLNGGDCRTG (SEQ ID NO: 262); GIYENC- NIWLNGGDCRMG (SEQ ID NO: 263); and/or GIPDNCNIWINGGDCRYG (SEQ ID NO: 264).

Suitable masking moieties for use with antibodies that bind an interleukin 6 target, e.g., interleukin 6 receptor (IL-6R), include, by way of non-limiting example, masking moieties that include a sequence such as QGQSGQYGSCSWNYVHIFMDC (SEQ ID NO: 265); QGQSGQGDFDIPFPAHWVPIT (SEQ ID NO: 266); QGQSGQMGVPAGCVWNYAHIFMDC (SEQ ID NO: 267); YRSCNWNYVSIFLDC (SEQ ID NO: 268); PGAFDIPFPAHWVPNT (SEQ ID NO: 269); ESSCVWNYVHIYMDC (SEQ ID NO: 270); YPGCKWNYDRIFLDC (SEQ ID NO: 271); YRTCSWNYVGIFLDC (SEQ ID NO: 272); YGSCSWNYVHIFMDC (SEQ ID NO: 273); YGSCSWNYVHIFLDC (SEQ ID NO: 274); YGSCNWNYVHIFLDC (SEQ ID NO: 275); YTSCNWNYVHIFMDC (SEQ ID NO: 276); YPGCKWNYDRIFLDC (SEQ ID NO: 277); WRSCNWNYAHIFLDC (SEQ ID NO: 278); WSNCHWNYVHIFLDC (SEQ ID NO: 279); DRSCTWNYVRISYDC (SEQ ID NO: 280); SGSCKWDYVHIFLDC (SEQ ID NO: 281); SRSCIWNYAHIHLDC (SEQ ID NO: 282); SMSCYWQYERIFLDC (SEQ ID NO: 283); YRSCNWNYVSIFLDC (SEQ ID NO: 284); SGSCKWDYVHIFLDC (SEQ ID NO: 285); YKSCHWDYVHIFLDC (SEQ ID NO: 286); YGSCTWNYVHIFMEC (SEQ ID NO: 287); FSSCNWNYVHIFLDC (SEQ ID NO: 288); WRSCNWNYAHIFLDC (SEQ ID NO: 289); YGSCQWNYVHIFLDC (SEQ ID NO: 290); YRSCNWNYVHIFLDC (SEQ ID NO: 291); NMSCHWDYVHIFLDC (SEQ ID NO: 292); FGPCTWNYARISWDC (SEQ ID NO: 293); XXsCXWXYvhIfXdC (SEQ ID NO: 294); MGVPAGCVWNYAHIFMDC (SEQ ID NO: 295); RDTGGQCRWDYVHIFMDC (SEQ ID NO: 296); AGVPAGCTWNYVHIFMEC (SEQ ID NO: 297); VGVPNGCVWNYAHIFMEC (SEQ ID NO: 298); DGGPAGCSWNYVHIFMEC (SEQ ID NO: 299); AVGPAGCWWNYVHIFMEC (SEQ ID NO: 300); CTWNYVHIFMDCGEGEGP (SEQ ID NO: 301); GGVPEGCTWNYAHIFMEC (SEQ ID NO: 302); AEVPAGCWWNYVHIFMEC (SEQ ID NO: 303); AGVPAGCTWNYVHIFMEC (SEQ ID NO: 304); SGASGGCKWNYVHIFMDC (SEQ ID NO: 305); TPGCRWNYVHIFMECEAL (SEQ ID NO: 306); VGVPNGCVWNYAHIFMEC (SEQ ID NO: 307); PGAFDIPFPAHWVPNT (SEQ ID NO: 308); RGACDIPFPAHWIPNT (SEQ ID NO: 309); QGDFDIPFPAHWVPIT (SEQ ID NO: 310); XGafDIPFPAHWvPnT (SEQ ID NO: 311); RGDGNDSDIPFPAHWVPRT (SEQ ID NO: 312); SGVGRDRDIPFPAHWVPRT (SEQ ID NO: 313); WAGGNDCDIPFPAHWIPNT (SEQ ID NO: 314); WGDGMDVDIPFPAHWVPVT (SEQ ID NO: 315); AGSGNDSDIPFPAHWVPRT (SEQ ID NO: 316); ESRSGYADIPFPAHWVPRT (SEQ ID NO: 317); and/or RECGRCGDIPFPAHWVPRT (SEQ ID NO: 318).

When the AB is modified with a MM and is in the presence of the target, specific binding of the AB to its target is reduced or inhibited, as compared to the specific binding of the AB not modified with an MM or the specific binding of the parental AB to the target.

The $K_d$ of the AB modified with a MM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM or of the parental AB towards the target. Conversely, the binding affinity of the AB modified with a MM towards the target is at least 2, 3, 4, 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM or of the parental AB towards the target.

The dissociation constant ($K_d$) of the MM towards the AB is generally greater than the $K_d$ of the AB towards the target. The $K_d$ of the MM towards the AB can be at least 5, 10, 25, 50, 100, 250, 500, 1,000, 2,500, 5,000, 10,000, 100,000, 1,000,000 or even 10,000,000 times greater than the $K_d$ of the AB towards the target. Conversely, the binding affinity of the MM towards the AB is generally lower than the binding affinity of the AB towards the target. The binding affinity of MM towards the AB can be at least 5, 10, 25, 50, 100, 250, 500, 1,000, 2,500, 5,000, 10,000, 100,000, 1,000,000 or even 10,000,000 times lower than the binding affinity of the AB towards the target.

When the AB is modified with a MM and is in the presence of the target specific binding of the AB to its target is reduced or inhibited, as compared to the specific binding of the AB not modified with an MM or the specific binding of the parental AB to the target. When compared to the binding of the AB not modified with an MM or the binding of the parental AB to the target the AB's ability to bind the target when modified with an MM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or more when measured in vivo or in an in vitro assay.

The MM inhibits the binding of the AB to the target. The MM binds the antigen binding domain of the AB and inhibits binding of the AB to the target. The MM can sterically inhibit the binding of the AB to the target. The MM can allosterically inhibit the binding of the AB to its target. In these embodiments when the AB is modified or coupled to a MM and in the presence of target there is no binding or substantially no binding of the AB to the target, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the AB to the target, as compared to the binding of the AB not modified with an MM, the parental AB, or the AB not coupled to an MM to the target, for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

When an AB is coupled to or modified by a MM, the MM 'masks' or reduces or otherwise inhibits the specific binding of the AB to the target. When an AB is coupled to or modified by a MM, such coupling or modification can effect a structural change that reduces or inhibits the ability of the AB to specifically bind its target.

An AB coupled to or modified with an MM can be represented by the following formulae (in order from an amino (N) terminal region to carboxyl (C) terminal region:

(MM)-(AB)

(AB)-(MM)

(MM)-L-(AB)

(AB)-L-(MM)

where MM is a masking moiety, the AB is an antibody or antibody fragment thereof, and the L is a linker. In many embodiments, it may be desirable to insert one or more linkers, e.g., flexible linkers, into the composition so as to provide for flexibility.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 25% identical to any natural binding partner of the AB. In some embodiments, the MM is no more than 50% identical to any natural binding partner of the AB. In some embodiments, the MM is no more than 20% identical to any natural binding partner of the AB. In some embodiments, the MM is no more than 10% identical to any natural binding partner of the AB.

In some embodiments, the activatable antibodies include an AB that is modified by an MM and also includes at least one cleavable moiety (CM1) that is a substrate for at least one matrix metalloprotease (MMP) and at least a second cleavable moiety (CM2) that is a subject for at least one serine protease (SP). Such activatable antibodies exhibit activatable/switchable binding, to the AB's target. Activatable antibodies generally include an antibody or antibody fragment (AB), modified by or coupled to a masking moiety (MM) and a CM1-CM2 substrate.

The elements of the activatable antibodies are arranged so that the MM and CM1-CM2 substrate are positioned such that in a cleaved (or relatively active) state and in the presence of a target, the AB binds a target while in an uncleaved (or relatively inactive) state in the presence of the target, specific binding of the AB to its target is reduced or inhibited. The specific binding of the AB to its target can be reduced due to the inhibition or masking of the AB's ability to specifically bind its target by the MM.

The $K_d$ of the AB modified with a MM and a CM1-CM2 substrate towards the target is at least 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM and a CM1-CM2 substrate or of the parental AB towards the target. Conversely, the binding affinity of the AB modified with a MM and a CM1-CM2 substrate towards the target is at least 2, 3, 4, 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM and a CM1-CM2 substrate or of the parental AB towards the target.

When the AB is modified with a MM and a CM1-CM2 substrate and is in the presence of the target but not in the presence of a modifying agent (for example a MMP and a SP), specific binding of the AB to its target is reduced or inhibited, as compared to the specific binding of the AB not modified with an MM and a CM1-CM2 substrate or of the parental AB to the target. When compared to the binding of the parental AB or the binding of an AB not modified with an MM and a CM1-CM2 substrate to its target, the AB's ability to bind the target when modified with an MM and a CM1-CM2 substrate can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

As used herein, the term cleaved state refers to the condition of the activatable antibodies following modification, i.e., cleavage, of the CM1-CM2 substrate by at least one matrix metalloprotease and/or at least one serine protease. The term uncleaved state or fully uncleaved, as used herein, refers to the condition of the activatable antibodies in the absence of cleavage of the CM1-CM2 substrate by a MMP and/or a SP. As discussed above, the term "activatable antibodies" is used herein to refer to an activatable antibody in both its uncleaved (native) state, as well as in its cleaved state. An activatable antibody in its cleaved state is also referred to herein as an activated antibody and/or activated activatable antibody. It will be apparent to the ordinarily skilled artisan that in some embodiments, a cleaved activatable antibody may lack an MM due to cleavage of the CM1-CM2 substrate by protease, resulting in release of at least the MM.

By activatable or switchable is meant that the activatable antibody exhibits a first level of binding to a target when in a inhibited, masked or uncleaved state (i.e., a first conformation), and a second level of binding to the target in the uninhibited, unmasked and/or cleaved state (i.e., a second conformation), where the second level of target binding is greater than the first level of binding. In general, the access of target to the AB of the activatable antibody is greater in the presence of a cleaving agent capable of cleaving the CM1-CM2 substrate than in the absence of such a cleaving agent. Thus, when the activatable antibody is in the uncleaved state, the AB is inhibited from target binding and can be masked from target binding (i.e., the first conformation is such the AB cannot bind the target), and in the cleaved state the AB is not inhibited or is unmasked to target binding.

The CM1-CM2 substrate and AB of the activatable antibodies are selected so that the AB represents a binding moiety for a given target, and the CM1-CM2 substrate represents a substrate for a MMP and a SP, where the MMP and/or the SP are co-localized with the target at a treatment site or diagnostic site in a subject. The activatable antibodies disclosed herein find particular use where, for example, a MMP and a SP, each capable of cleaving a site in the CM1-CM2 substrate, are present at relatively higher levels in target-containing tissue of a treatment site or diagnostic site than in tissue of non-treatment sites (for example in healthy tissue).

In some embodiments, activatable antibodies provide for reduced toxicity and/or adverse side effects that could otherwise result from binding of the AB at non-treatment sites if the AB were not masked or otherwise inhibited from binding to the target.

In general, an activatable antibody can be designed by selecting an AB of interest and constructing the remainder of the activatable antibody so that, when conformationally constrained, the MM provides for masking of the AB or reduction of binding of the AB to its target. Structural design criteria can be to be taken into account to provide for this functional feature.

Activatable antibodies exhibiting a switchable phenotype of a desired dynamic range for target binding in an inhibited versus an uninhibited conformation are provided. Dynamic range generally refers to a ratio of (a) a maximum detected level of a parameter under a first set of conditions to (b) a minimum detected value of that parameter under a second set of conditions. For example, in the context of an activatable antibody, the dynamic range refers to the ratio of (a) a maximum detected level of target protein binding to an activatable antibody in the presence of a MMP and a SP that are capable of cleaving the CM1-CM2 substrate of the activatable antibodies to (b) a minimum detected level of target protein binding to an activatable antibody in the absence of the protease. The dynamic range of an activatable antibody can be calculated as the ratio of the dissociation constant of an activatable antibody cleaving agent (e.g., enzyme) treatment to the dissociation constant of the activatable antibodies cleaving agent treatment. The greater the dynamic range of an activatable antibody, the better the switchable phenotype of the activatable antibody. Activatable antibodies having relatively higher dynamic range values (e.g., greater than 1) exhibit more desirable switching phenotypes such that target protein binding by the activatable antibodies occurs to a greater extent (e.g., predominantly occurs) in the presence of a cleaving agent (e.g., enzyme) capable of cleaving the CM1-CM2 substrate of the activatable antibodies than in the absence of a cleaving agent.

Activatable antibodies can be provided in a variety of structural configurations. Exemplary formulae for activatable antibodies are provided below. It is specifically contemplated that the N- to C-terminal order of the AB, MM and CM1-CM2 substrate may be reversed within an activatable antibody. It is also specifically contemplated that the CM and MM may overlap in amino acid sequence, e.g., such that the CM1-CM2 substrate is at least partially contained within the MM.

For example, activatable antibodies can be represented by the following formula (in order from an amino (N) terminal region to carboxyl (C) terminal region:

(MM)-(CM1-CM2 substrate)-(AB)

(AB)-(CM1-CM2 substrate)-(MM)

where MM is a masking moiety, the CM1-CM2 substrate is a cleavable moiety, and AB is an antibody or fragment thereof. As noted above, the term "CM1-CM2 substrate" is not intended to convey any requirement regarding the orientation or other structural arrangement of the first cleavable moiety (CM1) that is a substrate for at least one matrix metalloprotease (MMP) and at least a second cleavable moiety (CM2) that is a substrate for at least one serine protease (SP). Thus, the term "CM1-CM2 substrates" encompasses CM1-CM2 substrates having the structural arrangement from N-terminus to C-terminus as follows: CM1-CM2 or CM2-CM1. The term "CM1-CM2 substrates" also encompasses substrates where at least a portion of the CM1 sequence overlaps with at least a portion of the CM2 sequence. It should also be noted that although MM and CM1-CM2 substrate are indicated as distinct components in the formulae above, in all exemplary embodiments (including formulae) disclosed herein it is contemplated that the amino acid sequences of the MM and the CM1-CM2 substrate could overlap, e.g., such that the CM1-CM2 substrate is completely or partially contained within the MM. In addition, the formulae above provide for additional amino acid sequences that may be positioned N-terminal or C-terminal to the activatable antibodies elements.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 50% identical to any natural binding partner of the AB. In some embodiments, the MM is no more than 25% identical to any natural binding partner of the AB. In some embodiments, the MM is no more than 20% identical to any natural binding partner of the AB. In some embodiments, the MM is no more than 10% identical to any natural binding partner of the AB.

In many embodiments, it may be desirable to insert one or more linkers, e.g., flexible linkers, into the activatable antibody construct so as to provide for flexibility at one or more of the MM-CM1-CM2 substrate junction, the CM1-CM2 substrate-AB junction, or both. For example, the AB, MM, and/or CM1-CM2 substrate may not contain a sufficient number of residues (e.g., Gly, Ser, Asp, Asn, especially Gly and Ser, particularly Gly) to provide the desired flexibility. As such, the switchable phenotype of such activatable antibody constructs may benefit from introduction of one or more amino acids to provide for a flexible linker. In addition, as described below, where the activatable antibody is provided as a conformationally constrained construct, a flexible linker can be operably inserted to facilitate formation and maintenance of a cyclic structure in the uncleaved activatable antibody.

For example, in certain embodiments, an activatable antibody comprises one of the following formulae (where the formula below represent an amino acid sequence in either N- to C-terminal direction or C- to N-terminal direction):

(MM)-L1-(CM1-CM2 substrate)-(AB)

(MM)-(CM1-CM2 substrate)-L2-(AB)

(MM)-L1-(CM1-CM2 substrate)-L2-(AB)

wherein MM, CM1-CM2 substrate, and AB are as defined above; wherein L1 and L2 are each independently and optionally present or absent, are the same or different flexible linkers that include at least 1 flexible amino acid (e.g., Gly). In addition, the formulae above provide for additional amino acid sequences that may be positioned N-terminal or C-terminal to the activatable antibodies elements. Examples include, but are not limited to, targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HAS)).

The CM1-CM2 substrate is specifically cleaved by at least one MMP at a rate of about $0.001\text{-}1500\times10^4$ $M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or $1500\times10^4$ $M^{-1}S^{-1}$ and is specifically cleaved by at least one SP at a rate of about $0.001\text{-}1500\times10^4$ $M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or $1500\times10^4$ $M^{-1}S^{-1}$.

For specific cleavage by an enzyme, contact between the enzyme and CM1-CM2 substrate is made. When the activatable antibody comprising an AB coupled to a MM and a CM1-CM2 substrate is in the presence of target and sufficient enzyme activity, the CM1-CM2 substrate can be cleaved. Sufficient enzyme activity can refer to the ability of the enzyme to make contact with the CM1-CM2 substrate and effect cleavage. It can readily be envisioned that an enzyme may be in the vicinity of the CM1-CM2 substrate but unable to cleave because of other cellular factors or protein modification of the enzyme.

Linkers suitable for use in compositions described herein are generally ones that provide flexibility of the modified AB or the activatable antibodies to facilitate the inhibition of the binding of the AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, or 20 amino acids in length.

Exemplary flexible linkers include glycine polymers (G)n, glycine-serine polymers (including, for example, (GS) n, (GSGGS)n (SEQ ID NO: 381) and (GGGS)n (SEQ ID NO: 382), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible linkers include, but are not limited to Gly-Gly-Ser-Gly (SEQ ID NO: 383), Gly-Gly-Ser-Gly-Gly (SEQ ID NO: 384, Gly-Ser-Gly-Ser-Gly (SEQ ID NO: 385), Gly-Ser-Gly-Gly-Gly (SEQ ID NO: 386), Gly-Gly-Gly-Ser-Gly (SEQ ID NO: 387), Gly-Ser-Ser-Ser-Gly (SEQ ID NO: 388), and the like. The ordinarily skilled artisan will recognize that design of an activatable antibodies can include linkers that are all or partially flexible, such that the linker can include a flexible linker as well as one or more portions that confer less flexible structure to provide for a desired activatable antibodies structure.

In some embodiments, the activatable antibodies described herein also include an agent conjugated to the activatable antibody. In some embodiments, the conjugated agent is a therapeutic agent, such as an anti-inflammatory and/or an antineoplastic agent. In such embodiments, the agent is conjugated to a carbohydrate moiety of the activatable antibody, for example, in some embodiments, where the carbohydrate moiety is located outside the antigen-binding region of the antibody or antigen-binding fragment in the activatable antibody. In some embodiments, the agent is conjugated to a sulfhydryl group of the antibody or antigen-binding fragment in the activatable antibody.

In some embodiments, the agent is a cytotoxic agent such as a toxin (e.g., an enzymatically active toxin of bacterial, fungal, plant, or animal origin, or fragments thereof), or a radioactive isotope (i.e., a radioconjugate).

In some embodiments, the agent is a detectable moiety such as, for example, a label or other marker. For example, the agent is or includes a radiolabeled amino acid, one or more biotinyl moieties that can be detected by marked avidin (e.g., streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties are attached by spacer molecules.

The disclosure also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents include, for example, dolastatins and derivatives thereof (e.g. auristatin E, AFP, MMAF, MMAE, MMAD, DMAF, DMAE). For example, the agent is monomethyl auristatin E (MMAE) or monomethyl auristatin D (MMAD). In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the agent is linked to the AB using a maleimide caproyl-valine-citrulline linker or a maleimide PEG-valine-citrulline linker. In some embodiments, the agent is linked to the AB using a maleimide caproyl-valine-citrulline linker. In some embodiments, the agent is linked to the AB using a maleimide PEG-valine-citrulline linker In some embodiments, the agent is monomethyl auristatin D (MMAD) linked to the AB using a maleimide PEG-valine-citrulline-para-aminobenzyloxycarbonyl linker, and this linker payload construct is referred to herein as "vc-MMAD." In some embodiments, the agent is monomethyl auristatin E (MMAE) linked to the AB using a maleimide PEG-valine-citrulline-para-aminobenzyloxycarbonyl linker, and this linker payload construct is referred to herein as "vc-MMAE." The structures of vc-MMAD and vc-MMAE are shown below:

vc-MMAD:

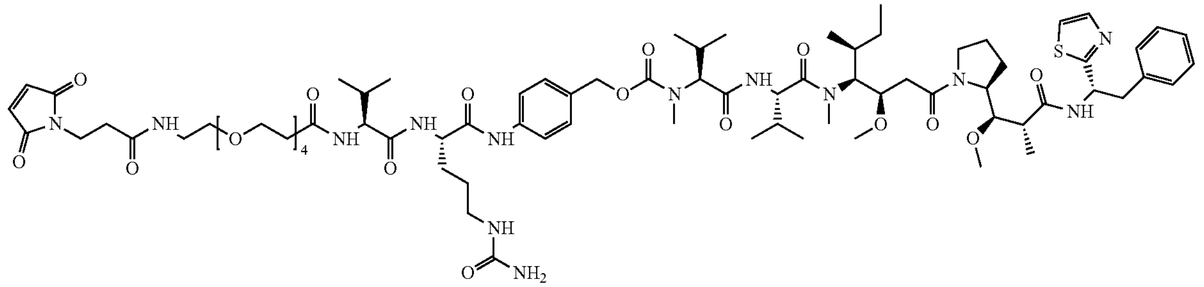

vc-MMAE:

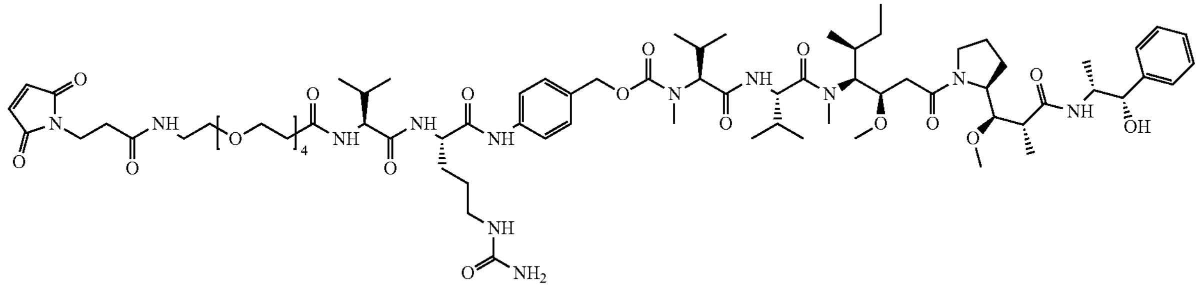

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Table 3 lists some of the exemplary pharmaceutical agents that may be employed in the herein described disclosure but in no way is meant to be an exhaustive list.

TABLE 3

| Exemplary Pharmaceutical Agents for Conjugation |
|---|
| CYTOTOXIC AGENTS |
| Auristatins |
| Auristatin E |
| Monomethyl auristatin D (MMAD) |
| Monomethyl auristatin E (MMAE) |
| Desmethyl auristatin E (DMAE) |
| Auristatin F |
| Monomethyl auristatin F (MMAF) |
| Desmethyl auristatin F (DMAF) |
| Auristatin derivatives, e.g., amides thereof |
| Auristatin tyramine |
| Auristatin quinoline |
| Dolastatins |
| Dolastatin derivatives |
| Dolastatin 16 DmJ |
| Dolastatin 16 Dpv |
| Maytansinoids, e.g. DM-1; DM-4 |
| Maytansinoid derivatives |
| Duocarmycin |
| Duocarmycin derivatives |
| Alpha-amanitin |
| Anthracyclines |
| Doxorubicin |
| Daunorubicin |
| Bryostatins |
| Camptothecin |
| Camptothecin derivatives |
| 7-substituted Camptothecin |
| 10, 11-Difluoromethylenedioxycamptothecin |
| Combretastatins |
| Debromoaplysiatoxin |
| Kahalalide-F |
| Discodermolide |
| Ecteinascidins |
| ANTIVIRALS |
| Acyclovir |
| Vira A |
| Symmetrel |

TABLE 3-continued

| Exemplary Pharmaceutical Agents for Conjugation |
|---|
| ANTIFUNGALS |
| Nystatin |
| ADDITIONAL ANTI-NEOPLASTICS |
| Adriamycin |
| Cerubidine |
| Bleomycin |
| Alkeran |
| Velban |
| Oncovin |
| Fluorouracil |
| Methotrexate |
| Thiotepa |
| Bisantrene |
| Novantrone |
| Thioguanine |
| Procarabizine |
| Cytarabine |
| ANTI-BACTERIALS |
| Aminoglycosides |
| Streptomycin |
| Neomycin |
| Kanamycin |
| Amikacin |
| Gentamicin |
| Tobramycin |
| Streptomycin B |
| Spectinomycin |
| Ampicillin |
| Sulfanilamide |
| Polymyxin |
| Chloramphenicol |
| Turbostatin |
| Phenstatins |
| Hydroxyphenstatin |
| Spongistatin 5 |
| Spongistatin 7 |
| Halistatin 1 |
| Halistatin 2 |
| Halistatin 3 |
| Modified Bryostatins |
| Halocomstatins |
| Pyrrolobenzimidazoles (PBI) |
| Cibrostatin6 |
| Doxaliform |
| Anthracycline analogues |
| Cemadotin analogue (CemCH2-SH) |
| Pseudomonas toxin A (PE38) variant |
| Pseudomonas toxin A (ZZ-PE38) variant |
| ZJ-101 |
| OSW-1 |
| 4-Nitrobenzyloxycarbonyl Derivatives of O6-Benzylguanine |
| Topoisomerase inhibitors |
| Hemiasterlin |
| Cephalotaxine |
| Homoharringtonine |
| Pyrrolobenzodiazepine (PBD) |
| Pyrrolobenzodiazepine (PBD) dimers |
| Functionalized pyrrolobenzodiazepines |
| Functionalized pyrrolobenzodiazepine dimers |
| Calicheamicins |
| Podophyllotoxins |
| Taxanes |
| Vinca alkaloids |
| CONJUGATABLE DETECTION REAGENTS |
| Fluorescein and derivatives thereof |
| Fluorescein isothiocyanate (FITC) |
| RADIOPHARMACEUTICALS |
| $^{125}I$ |
| $^{131}I$ |
| $^{89}Zr$ |
| $^{111}In$ |

TABLE 3-continued

| Exemplary Pharmaceutical Agents for Conjugation |
|---|
| $^{123}I$ |
| $^{131}In$ |
| $^{99}mTc$ |
| $^{201}Tl$ |
| $^{133}Xe$ |
| $^{11}C$ |
| $^{62}Cu$ |
| $^{18}F$ |
| $^{68}Ga$ |
| $^{13}N$ |
| $^{15}O$ |
| $^{38}K$ |
| $^{82}Rb$ |
| $^{99}mTc$ (Technetium) |
| HEAVY METALS |
| Barium |
| Gold |
| Platinum |
| ANTI-MYCOPLASMALS |
| Tylosine |
| Spectinomycin |

Those of ordinary skill in the art will recognize that a large variety of possible moieties can be coupled to the resultant antibodies of the disclosure. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. In some embodiments, the binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present disclosure, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

In some embodiments, in addition to the compositions and methods provided herein, the conjugated activatable antibody can also be modified for site-specific conjugation through modified amino acid sequences inserted or otherwise included in the activatable antibody sequence. These modified amino acid sequences are designed to allow for controlled placement and/or dosage of the conjugated agent within a conjugated activatable antibody. For example, the activatable antibody can be engineered to include cysteine substitutions at positions on light and heavy chains that provide reactive thiol groups and do not negatively impact protein folding and assembly, nor alter antigen binding. In some embodiments, the activatable antibody can be engineered to include or otherwise introduce one or more non-natural amino acid residues within the activatable antibody to provide suitable sites for conjugation. In some embodiments, the activatable antibody can be engineered to include or otherwise introduce enzymatically activatable peptide sequences within the activatable antibody sequence.

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. In some embodiments, suitable linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC. Additional linkers include, but are not limited to, SMCC, sulfo-SMCC, SPDB, or sulfo-SPDB.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In some embodiments, the linkers are cleavable. In some embodiments, the linkers are non-cleavable. In some embodiments, two or more linkers are present. The two or more linkers are all the same, i.e., cleavable or non-cleavable, or the two or more linkers are different, i.e., at least one cleavable and at least one non-cleavable.

The present disclosure utilizes several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB. According to the disclosure, ABs may be covalently attached to an agent through an intermediate linker having at least two reactive groups, one to react with AB and one to react with the agent. The linker, which may include any compatible organic compound, can be chosen such that the reaction with AB (or agent) does not adversely affect AB reactivity and selectivity. Furthermore, the attachment of linker to agent might not destroy the activity of the agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

According to the present disclosure, suitable linkers for attachment to reduced ABs include those having certain reactive groups capable of reaction with a sulfhydryl group of a reduced antibody or fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101: 3097-3110).

According to the present disclosure, suitable linkers for attachment to neither oxidized nor reduced Abs include those having certain functional groups capable of reaction with the primary amino groups present in unmodified lysine residues in the Ab. Such reactive groups include, but are not limited to, NHS carboxylic or carbonic esters, sulfo-NHS carboxylic or carbonic esters, 4-nitrophenyl carboxylic or carbonic esters, pentafluorophenyl carboxylic or carbonic esters, acyl imidazoles, isocyanates, and isothiocyanates.

According to the present disclosure, suitable linkers for attachment to neither oxidized nor reduced Abs include those having certain functional groups capable of reaction with the carboxylic acid groups present in aspartate or glutamate residues in the Ab, which have been activated with suitable reagents. Suitable activating reagents include EDC, with or without added NHS or sulfo-NHS, and other dehydrating agents utilized for carboxamide formation. In these instances, the functional groups present in the suitable linkers would include primary and secondary amines, hydrazines, hydroxylamines, and hydrazides.

The agent may be attached to the linker before or after the linker is attached to the AB. In certain applications it may be desirable to first produce an AB-linker intermediate in which the linker is free of an associated agent. Depending upon the particular application, a specific agent may then be covalently attached to the linker. In some embodiments, the AB is first attached to the MM, CM1-CM2 substrate and associated linkers and then attached to the linker for conjugation purposes.

Branched Linkers: In specific embodiments, branched linkers that have multiple sites for attachment of agents are utilized. For multiple site linkers, a single covalent attachment to an AB would result in an AB-linker intermediate capable of binding an agent at a number of sites. The sites may be aldehyde or sulfhydryl groups or any chemical site to which agents can be attached.

In some embodiments, higher specific activity (or higher ratio of agents to AB) can be achieved by attachment of a single site linker at a plurality of sites on the AB. This plurality of sites may be introduced into the AB by either of two methods. First, one may generate multiple aldehyde groups and/or sulfhydryl groups in the same AB. Second, one may attach to an aldehyde or sulfhydryl of the AB a "branched linker" having multiple functional sites for subsequent attachment to linkers. The functional sites of the branched linker or multiple site linker may be aldehyde or sulfhydryl groups, or may be any chemical site to which linkers may be attached. Still higher specific activities may be obtained by combining these two approaches, that is, attaching multiple site linkers at several sites on the AB.

Cleavable Linkers: Peptide linkers that are susceptible to cleavage by enzymes of the complement system, such as but not limited to urokinase, tissue plasminogen activator, trypsin, plasmin, or another enzyme having proteolytic activity may be used in one embodiment of the present disclosure. According to one method of the present disclosure, an agent is attached via a linker susceptible to cleavage by complement. The antibody is selected from a class that can activate complement. The antibody-agent conjugate, thus, activates the complement cascade and releases the agent at the target site. According to another method of the present disclosure, an agent is attached via a linker susceptible to cleavage by enzymes having a proteolytic activity such as a urokinase, a tissue plasminogen activator, plasmin, or trypsin. These cleavable linkers are useful in conjugated activatable antibodies that include an extracellular toxin, e.g., by way of non-limiting example, any of the extracellular toxins shown in Table 3.

Non-limiting examples of cleavable linker sequences are provided in Table 4.

TABLE 4

Exemplary Linker Sequences for Conjugation

| Types of Cleavable Sequences | Amino Acid Sequence |
|---|---|
| Plasmin cleavable sequences | |
| Pro-urokinase | PRFKIIGG (SEQ ID NO: 319) |
| | PRFRIIGG (SEQ ID NO: 320) |
| TGFβ | SSRHRRALD (SEQ ID NO: 321) |
| Plasminogen | RKSSIIIRMRDVVL (SEQ ID NO: 322) |
| Staphylokinase | SSSFDKGKYKKGDDA (SEQ ID NO: 323) |
| | SSSFDKGKYKRGDDA (SEQ ID NO: 324) |
| Factor Xa cleavable sequences | |
| | IEGR (SEQ ID NO: 325) |
| | IDGR (SEQ ID NO: 326) |
| | GGSIDGR (SEQ ID NO: 327) |
| MMP cleavable sequences | |
| Gelatinase A | PLGLWA (SEQ ID NO: 328) |
| Collagenase cleavable sequences | |
| Calf skin collagen (α1(I) chain) | GPQGIAGQ (SEQ ID NO: 329) |
| Calf skin collagen (α2(I) chain) | GPQGLLGA (SEQ ID NO: 330) |
| Bovine cartilage collagen (α1(II) chain) | GIAGQ (SEQ ID NO: 331) |
| Human liver collagen (α1(III) chain) | GPLGIAGI (SEQ ID NO: 332) |
| Human $\alpha_2$M | GPEGLRVG (SEQ ID NO: 333) |
| Human PZP | YGAGLGVV (SEQ ID NO: 334) |
| | AGLGVVER (SEQ ID NO: 335) |
| | AGLGISST (SEQ ID NO: 336) |
| Rat $\alpha_1$M | EPQALAMS (SEQ ID NO: 337) |
| | QALAMSAI (SEQ ID NO: 338) |
| Rat $\alpha_2$M | AAYHLVSQ (SEQ ID NO: 339) |
| | MDAFLESS (SEQ ID NO: 340) |
| Rat $\alpha_1I_3$(2J) | ESLPVVAV (SEQ ID NO: 341) |
| Rat $\alpha_1I_3$(27J) | SAPAVESE (SEQ ID NO: 342) |
| Human fibroblast collagenase | DVAQFVLT (SEQ ID NO: 343) |
| (autolytic cleavages) | VAQFVLTE (SEQ ID NO: 344) |
| | AQFVLTEG (SEQ ID NO: 345) |
| | PVQPIGPQ (SEQ ID NO: 346) |

In some embodiments, the linker may comprise a spacer element and a cleavable element. The spacer element serves to position the cleavable element away from the core of the AB such that the cleavable element is more accessible to the enzyme responsible for cleavage. Certain of the branched linkers described above may serve as spacer elements.

Throughout this discussion, it should be understood that the attachment of linker to agent (or of spacer element to cleavable element, or cleavable element to agent) need not be particular mode of attachment or reaction. Any reaction providing a product of suitable stability and biological compatibility is acceptable.

In addition, agents may be attached via disulfide bonds (for example, the disulfide bonds on a cysteine molecule) to the AB. Since many tumors naturally release high levels of glutathione (a reducing agent) this can reduce the disulfide bonds with subsequent release of the agent at the site of delivery. In certain specific embodiments, the reducing agent that would modify a CM1-CM2 substrate would also modify the linker of the conjugated activatable antibody.

Spacers and Cleavable Elements: In some embodiments, it may be necessary to construct the linker in such a way as to optimize the spacing between the agent and the AB of the activatable antibody. This may be accomplished by use of a linker of the general structure:

$$W\text{-}(CH_2)n\text{-}Q$$

wherein

W is either —NH—$CH_2$— or —$CH_2$—;

Q is an amino acid, peptide; and n is an integer from 0 to 20.

Serum Complement and Selection of Linkers: According to one method of the present disclosure, when release of an agent is desired, an AB that is an antibody of a class that can activate complement is used. The resulting conjugate retains both the ability to bind antigen and activate the complement cascade. Thus, according to this embodiment of the present disclosure, an agent is joined to one end of the cleavable linker or cleavable element and the other end of the linker group is attached to a specific site on the AB. For example, if the agent has an hydroxy group or an amino group, it may be attached to the carboxy terminus of a peptide, amino acid or other suitably chosen linker via an ester or amide bond, respectively. For example, such agents may be attached to the linker peptide via a carbodimide reaction. If the agent contains functional groups that would interfere with attachment to the linker, these interfering functional groups can be blocked before attachment and deblocked once the product conjugate or intermediate is made. The opposite or amino terminus of the linker is then used either directly or after further modification for binding to an AB that is capable of activating complement.

Linkers (or spacer elements of linkers) may be of any desired length, one end of which can be covalently attached to specific sites on the AB of the activatable antibody. The other end of the linker or spacer element may be attached to an amino acid or peptide linker.

Thus when these conjugates bind to antigen in the presence of complement the amide or ester bond that attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like as presented in but not limited to those in Table 3.

Linkers for Release without Complement Activation: In yet another application of targeted delivery, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates may be prepared by attaching the agent to an AB that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

Biochemical Cross Linkers: In some embodiments, the activatable antibody may be conjugated to one or more therapeutic agents using certain biochemical cross-linkers. Cross-linking reagents form molecular bridges that tie together functional groups of two different molecules. To link two different proteins in a step-wise manner, hetero-bifunctional cross-linkers can be used that eliminate unwanted homopolymer formation.

Peptidyl linkers cleavable by lysosomal proteases are also useful, for example, Val-Cit, Val-Ala or other dipeptides. In addition, acid-labile linkers cleavable in the low-pH environment of the lysosome may be used, for example: bis-sialyl ether. Other suitable linkers include cathepsin-labile substrates, particularly those that show optimal function at an acidic pH.

Exemplary hetero-bifunctional cross-linkers are referenced in Table 5.

TABLE 5

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
|---|---|---|---|
| SMPT | Primary amines<br>Sulfhydryls | Greater stability | 11.2 Å |
| SPDP | Primary amines<br>Sulfhydryls | Thiolation<br>Cleavable cross-linking | 6.8 Å |
| LC-SPDP | Primary amines<br>Sulfhydryls | Extended spacer arm | 15.6 Å |
| Sulfo-LC-SPDP | Primary amines<br>Sulfhydryls | Extender spacer arm<br>Water-soluble | 15.6 Å |
| SMCC | Primary amines<br>Sulfhydryls | Stable maleimide reactive group<br>Enzyme-antibody conjugation<br>Hapten-carrier protein conjugation | 11.6 Å |
| Sulfo-SMCC | Primary amines<br>Sulfhydryls | Stable maleimide reactive group<br>Water-soluble<br>Enzyme-antibody conjugation | 11.6 Å |
| MBS | Primary amines<br>Sulfhydryls | Enzyme-antibody conjugation<br>Hapten-carrier protein conjugation | 9.9 Å |
| Sulfo-MBS | Primary amines<br>Sulfhydryls | Water-soluble | 9.9 Å |
| SIAB | Primary amines<br>Sulfhydryls | Enzyme-antibody conjugation | 10.6 Å |
| Sulfo-SIAB | Primary amines<br>Sulfhydryls | Water-soluble | 10.6 Å |
| SMPB | Primary amines<br>Sulfhydryls | Extended spacer arm<br>Enzyme-antibody conjugation | 14.5 Å |
| Sulfo-SMPB | Primary amines<br>Sulfhydryls | Extended spacer arm<br>Water-soluble | 14.5 Å |
| EDE/Sulfo-NHS | Primary amines<br>Carboxyl groups | Hapten-Carrier conjugation | 0 |
| ABH | Carbohydrates<br>Nonselective | Reacts with sugar groups | 11.9 Å |

Non-Cleavable Linkers or Direct Attachment: In some embodiments of the disclosure, the conjugate may be designed so that the agent is delivered to the target but not released. This may be accomplished by attaching an agent to an AB either directly or via a non-cleavable linker.

These non-cleavable linkers may include amino acids, peptides, D-amino acids or other organic compounds that may be modified to include functional groups that can subsequently be utilized in attachment to ABs by the methods described herein. A-general formula for such an organic linker could be W—$(CH_2)$n-Q wherein W is either —NH—$CH_2$— or —$CH_2$—;

Q is an amino acid, peptide; and n is an integer from 0 to 20.

Non-Cleavable Conjugates: In some embodiments, a compound may be attached to ABs that do not activate complement. When using ABs that are incapable of complement activation, this attachment may be accomplished using linkers that are susceptible to cleavage by activated complement or using linkers that are not susceptible to cleavage by activated complement.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present disclosure can be conjugated to the liposomes as described in Martin et al., J. Biol. Chem., 257: 286-288 (1982) via a disulfide-interchange reaction.

Definitions

Unless otherwise defined, scientific and technical terms used in connection with the present disclosure shall have the meanings that are commonly understood by those of ordinary skill in the art. The term "a" entity or "an" entity refers to one or more of that entity. For example, a compound refers to one or more compounds. As such, the terms "a", "an", "one or more" and "at least one" can be used interchangeably. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d>10^{-6}$). Antibodies include, but are not limited to, polyclonal, monoclonal, chimeric, domain antibody, single chain, Fab, and $F(ab')_2$ fragments, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as IgG1, IgG2, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, a scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is ≤1 μM; in some embodiments, ≤100 nM and in some embodiments, ≤10 nM.

As used herein, the terms "specific binding," "immunological binding," and "immunological binding properties" refer to the non-covalent interactions of the type that occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to the target, when the binding constant ($K_d$) is ≤1 μM, in some embodiments 100 nM, in some embodiments 10 nM, and in some embodiments 100 pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide that it is not linked to in nature, or (3) does not occur in nature as part of a larger sequence. Polynucleotides in accordance with the disclosure include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the disclosure comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and that has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length and in some embodiments, 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the disclosure are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem.

Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present disclosure. Examples of unconventional amino acids include: 4 hydroxyproline, 7-carboxyglutamate, F—N,N,N-trimethyllysine, ε-N-acetyllysine, 0-phosphoserine, N-acetylserine, N-formylmethionine, 3-methylhistidine, 5-hydroxylysine, 6-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and that are 5' to the 5' end of the RNA transcript are referred to as "upstream sequences", sequence regions on the DNA strand having the same sequence as the RNA and that are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, in some embodiments, at least 90 percent sequence identity, in some embodiments, at least 95 percent sequence identity, and in some embodiments, at least 99 percent sequence identity.

In some embodiments, residue positions that are not identical differ by conservative amino acid substitutions.

As discussed herein, minor variations in the amino acid sequences of antibodies or immunoglobulin molecules are contemplated as being encompassed by the present disclosure, providing that the variations in the amino acid sequence maintain at least 75%, in some embodiments, at least 80%, 90%, 95%, and in some embodiments, 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Suitable amino- and carboxy-termini of fragments or analogs occur near boundaries of functional domains. Structural and functional domains can be identified by comparison of the nucleotide and/or amino acid sequence data to public or proprietary sequence databases. In some embodiments, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Suitable amino acid substitutions are those that: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various muteins of a sequence other than the naturally-occurring peptide sequence. For example, single or multiple amino acid substitutions (for example, conservative amino acid substitutions) may be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, in some embodiments, at least 14 amino acids long, in some embodiments, at least 20 amino acids long, usually at least 50 amino acids long, and in some embodiments, at least 70 amino acids long. The term "analog" as used herein refers to polypeptides that are comprised of a segment of at least 25 amino acids that has substantial identity to a portion of a deduced amino acid sequence and that has specific binding to the target, under suitable binding conditions. Typically, polypeptide analogs comprise a conservative amino acid substitution (or addition or deletion) with respect to the naturally-occurring sequence. Analogs typically are at least 20 amino acids long, in some embodiments, at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$) fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and in some embodiments, a substantially purified fraction is a composition wherein the object species comprises at least about 50 percent (on a molar basis) of all macromolecular species present.

Generally, a substantially pure composition will comprise more than about 80 percent of all macromolecular species present in the composition, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects.

Activatable antibodies of the disclosure specifically bind a given target, e.g., a human target protein. Also included in the disclosure are activatable antibodies that bind to the same epitope as the activatable antibodies described herein.

Those skilled in the art will recognize that it is possible to determine, without undue experimentation, if a monoclonal antibody (e.g., a murine monoclonal or humanized antibody) has the same specificity as a monoclonal antibody used in the methods described herein by ascertaining whether the former prevents the latter from binding to the target. If the monoclonal antibody being tested competes with the monoclonal antibody of the disclosure, as shown by a decrease in binding by the monoclonal antibody of the disclosure, then the two monoclonal antibodies bind to the same, or a closely related, epitope. A method for determining whether a monoclonal antibody has the specificity of a monoclonal antibody of the disclosure is to pre-incubate the monoclonal antibody of the disclosure with the target and then add the monoclonal antibody being tested to determine if the monoclonal antibody being tested is inhibited in its ability to bind the target. If the monoclonal antibody being tested is inhibited then, in all likelihood, it has the same, or functionally equivalent, epitopic specificity as the monoclonal antibody of the disclosure.

Multispecific Activatable Antibodies

The disclosure also provides multispecific activatable antibodies. The multispecific activatable antibodies provided herein are multispecific antibodies that recognize two or more different antigens or epitopes and that include at least one masking moiety (MM) linked to at least one antigen- or epitope-binding domain of the multispecific antibody such that coupling of the MM reduces the ability of the antigen- or epitope-binding domain to bind its target. In some embodiments, the MM is coupled to the antigen- or epitope-binding domain of the multispecific antibody via a CM1-CM2 substrate that functions as a substrate for at least one MMP protease and at least one SP. The activatable multispecific antibodies provided herein are stable in circulation, activated at intended sites of therapy and/or diagnosis but not in normal, i.e., healthy tissue, and, when activated, exhibit binding to a target that is at least comparable to the corresponding, unmodified multispecific antibody.

In some embodiments, the multispecific activatable antibodies are designed to engage immune effector cells, also referred to herein as immune-effector cell engaging multispecific activatable antibodies. In some embodiments, the multispecific activatable antibodies are designed to engage leukocytes, also referred to herein as leukocyte engaging multispecific activatable antibodies. In some embodiments, the multispecific activatable antibodies are designed to engage T cells, also referred to herein as T-cell engaging multispecific activatable antibodies. In some embodiments, the multispecific activatable antibodies engage a surface antigen on a leukocyte, such as on a T cell, on a natural killer (NK) cell, on a myeloid mononuclear cell, on a macrophage, and/or on another immune effector cell. In some embodiments, the immune effector cell is a leukocyte. In some embodiments, the immune effector cell is a T cell. In some embodiments, the immune effector cell is a NK cell. In some embodiments, the immune effector cell is a mononuclear cell, such as a myeloid mononuclear cell. In some embodiments, the multispecific activatable antibodies are designed to bind or otherwise interact with more than one target and/or more than one epitope, also referred to herein as multi-antigen targeting activatable antibodies. As used herein, the terms "target" and "antigen" are used interchangeably.

In some embodiments, immune effector cell engaging multispecific activatable antibodies of the disclosure include a targeting antibody or antigen-binding fragment thereof and an immune effector cell engaging antibody or antigen-binding portion thereof, where at least one of the targeting antibody or antigen-binding fragment thereof and/or the immune effector cell engaging antibody or antigen-binding portion thereof is masked. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the non-immune effector cell engaging antibody is a cancer targeting antibody. In some embodiments the non-immune cell effector antibody is an IgG. In some embodiments the immune effector cell engaging antibody is a scFv. In some embodiments the targeting antibody (e.g., non-immune cell effector antibody) is an IgG and the immune effector cell engaging antibody is a scFv. In some embodiments, the immune effector cell is a leukocyte. In some embodiments, the immune effector cell is a T cell. In some embodiments, the immune effector cell is a NK cell. In some embodiments, the immune effector cell is a myeloid mononuclear cell.

In some embodiments, T-cell engaging multispecific activatable antibodies of the disclosure include a targeting antibody or antigen-binding fragment thereof and a T-cell engaging antibody or antigen-binding portion thereof, where at least one of the targeting antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibodies include a cancer targeting antibody or antigen-binding fragment thereof and a T-cell engaging antibody or antigen-binding portion thereof, where at least one of the cancer targeting antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibodies include a cancer targeting IgG antibody or antigen-binding fragment thereof and a T-cell engaging scFv, where at least one of the cancer targeting IgG antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments of an immune effector cell engaging multispecific activatable antibody, one antigen is typically an antigen present on the surface of a tumor cell or other cell type associated with disease, such as, but not limited to, any target listed in Table 1, such as, but not limited to, EGFR, erbB2, EpCAM, Jagged, PD-L1, B7H3, or CD71 (transferrin receptor), and another antigen is typically a stimulatory or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA. In some embodiments, the antigen is a stimulatory receptor present on the surface of a T cell or NK cell; examples of such stimulatory receptors include, but are not limited to, CD3, CD27, CD28, CD137 (also referred to as 4-1BB), GITR, HVEM, ICOS, NKG2D, and OX40. In some embodiments, the antigen is an inhibitory receptor present on the surface of a T-cell; examples of such inhibitory receptors include, but are not limited to, BTLA, CTLA-4, LAG3, PD-1, TIGIT, TIM3, and NK-expressed KIRs. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PD-L1, PD-L2, or TNFSF9.

One embodiment of the disclosure is a multispecific activatable antibody that is activatable in a cancer microenvironment and that includes an antibody, for example a IgG or scFv, directed to a tumor target and an agonist antibody, for example an IgG or scFv, directed to a co-stimulatory receptor expressed on the surface of an activated T cell or NK cell, wherein at least one of the cancer target antibody and/or agonist antibody is masked. Examples of co-stimulatory receptors include, but are not limited to, CD27, CD137, GITR, HVEM, NKG2D, and OX40. In this embodiment, the multispecific activatable antibody, once activated by tumor-associated proteases, would effectively crosslink and activate the T cell or NK cell expressed co-stimulatory receptors in a tumor-dependent manner to enhance the activity of T cells that are responding to any tumor antigen via their endogenous T cell antigen or NK-activating receptors. The activation-dependent nature of these T cell or NK cell costimulatory receptors would focus the activity of the activated multispecific activatable antibody to tumor-specific T cells, without activating all T cells independent of their antigen specificity. In one embodiment, at least the co-stimulatory receptor antibody of the multispecific activatable antibody is masked to prevent activation of autoreactive T cells that may be present in tissues that also express the antigen recognized by the tumor target-directed antibody in the multispecific activatable antibody, but whose activity is restricted by lack of co-receptor engagement.

One embodiment of the disclosure is a multispecific activatable antibody that is activatable in a disease characterized by T cell overstimulation, such as, but not limited to, an autoimmune disease or inflammatory disease microenvironment. Such a multispecific activatable antibody includes an antibody, for example a IgG or scFv, directed to a target comprising a surface antigen expressed in a tissue targeted by a T cell in autoimmune or inflammatory disease and an antibody, for example a IgG or scFv, directed to an inhibitory receptor expressed on the surface of a T cell or NK cell, wherein at least one of the disease tissue target antibody and/or T cell inhibitory receptor antibody is masked. Examples of inhibitory receptors include, but are not limited to, BTLA, CTLA-4, LAG3, PD-1, TIGIT, TIM3, and NK-expressed KIRs. Examples of a tissue antigen targeted by T cells in autoimmune disease include, but are not limited to, a surface antigen expressed on myelin or nerve cells in multiple sclerosis or a surface antigen expressed on pancreatic islet cells in Type 1 diabetes. In this embodiment, the multispecific activatable antibody when localized in the tissue under autoimmune attack or inflammation is activated and co-engages the T cell or NK cell inhibitory receptor to suppress the activity of autoreactive T cells responding to any disease tissue-targeted antigens via their endogenous TCR or activating receptors. In one embodiment, at least one or multiple antibodies are masked to prevent suppression of T cell responses in non-disease tissues where the target antigen may also be expressed.

In some embodiments, the T-cell engaging multispecific activatable antibody includes an anti-CD3 epsilon (CD3ε, also referred to herein as CD3e and CD3) scFv and a targeting antibody or antigen-binding fragment thereof, where at least one of the anti-CD3ε scFv and/or the targeting antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an anti-CD3ε scFv and a cancer targeting antibody or antigen-binding fragment thereof, where at least one of the anti-CD3ε scFv and/or the cancer targeting antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CD3ε scFv and a cancer targeting IgG antibody or antigen-binding fragment thereof, where at least one of the anti-CD3ε scFv and/or the cancer targeting IgG antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody IgG or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CD3 epsilon (CD3ε) scFv that is derived from OKT3, where at least one of the targeting antibody or antigen-binding fragment thereof and/or the OKT3 scFv or OKT3-derived scFv is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an OKT3 scFv or OKT3-derived scFv and a cancer targeting antibody or antigen-binding fragment thereof, where at least one of the OKT3 scFv or OKT3-derived scFv and/or the cancer targeting antibody or antigen-binding portion thereof is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an OKT3 scFv or OKT3-derived scFv and a cancer targeting IgG antibody or antigen-binding fragment thereof, where at least one of the OKT3 scFv or OKT3-derived scFv and/or the cancer targeting IgG antibody or antigen-binding portion thereof is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3c. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody IgG or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CTLA-4 scFv, where at least one of the targeting antibody or antigen-binding fragment thereof and/or the anti-CTLA-4 scFv is masked. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an anti-CTLA-4 scFv and a targeting IgG antibody or antigen-binding fragment thereof, where at least one of the anti-CTLA-4 scFv and/or the targeting IgG antibody or antigen-binding portion thereof is masked. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4. In some embodiments, the targeting IgG antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4, and the targeting antibody IgG or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the multi-antigen targeting antibodies and/or multi-antigen targeting activatable antibodies include at least a first antibody or antigen-binding fragment thereof that binds a first target and/or first epitope and a second antibody or antigen-binding fragment thereof that binds a second target and/or a second epitope. In some embodiments, the multi-antigen targeting antibodies and/or multi-antigen targeting activatable antibodies bind two or more different targets. In some embodiments, the multi-antigen targeting antibodies and/or multi-antigen targeting activatable antibodies bind two or more different epitopes on the same target. In some embodiments, the multi-antigen targeting antibodies and/or multi-antigen targeting activatable antibodies bind a combination of two or more different targets and two or more different epitopes on the same target.

In some embodiments, a multispecific activatable antibody comprising an IgG has the IgG variable domains masked. In some embodiments, a multispecific activatable antibody comprising a scFv has the scFv domains masked. In some embodiments, a multispecific activatable antibody has both IgG variable domains and scFv domains, where at least one of the IgG variable domains is coupled to a masking moiety. In some embodiments, a multispecific activatable antibody has both IgG variable domains and scFv domains, where at least one of the scFv domains is coupled to a masking moiety. In some embodiments, a multispecific activatable antibody has both IgG variable domains and scFv domains, where at least one of the IgG variable domains is coupled to a masking moiety and at least one of the scFv domains is coupled to a masking moiety. In some embodiments, a multispecific activatable antibody has both IgG variable domains and scFv domains, where each of the IgG variable domains and the scFv domains is coupled to its own masking moiety. In some embodiments, one antibody domain of a multispecific activatable antibody has specificity for a target antigen and another antibody domain has specificity for a T-cell surface antigen. In some embodiments, one antibody domain of a multispecific activatable antibody has specificity for a target antigen and another antibody domain has specificity for another target antigen. In some embodiments, one antibody domain of a multispecific activatable antibody has specificity for an epitope of a target antigen and another antibody domain has specificity for another epitope of the target antigen.

In a multispecific activatable antibody, a scFv can be fused to the carboxyl terminus of the heavy chain of an IgG activatable antibody, to the carboxyl terminus of the light chain of an IgG activatable antibody, or to the carboxyl termini of both the heavy and light chains of an IgG activatable antibody. In a multispecific activatable antibody, a scFv can be fused to the amino terminus of the heavy chain of an IgG activatable antibody, to the amino terminus of the light chain of an IgG activatable antibody, or to the amino termini of both the heavy and light chains of an IgG activatable antibody. In a multispecific activatable antibody, a scFv can be fused to any combination of one or more carboxyl termini and one or more amino termini of an IgG activatable antibody. In some embodiments, a masking moiety (MM) linked to a CM1-CM2 substrate is attached to and masks an antigen binding domain of the IgG. In some embodiments, a masking moiety (MM) linked to a CM1-CM2 substrate is attached to and masks an antigen binding domain of at least one scFv. In some embodiments, a masking moiety (MM) linked to a CM1-CM2 substrate is attached to and masks an antigen binding domain of an IgG and a masking moiety (MM) linked to a CM1-CM2 substrate is attached to and masks an antigen binding domain of at least one scFv.

The disclosure provides examples of multispecific activatable antibody structures that include, but are not limited to, the following: $(VL-CL)_2$:(VH-CH1-CH2-CH3-L4-VH*-L3-VL*-L2-CM1-CM2 substrate-L1-$MM)_2$; $(VL-CL)_2$:(VH-CH1-CH2-CH3-L4-VL*-L3-VH*-L2-CM1-CM2 substrate-L1-$MM)_2$; (MM-L1-CM1-CM2 substrate-L2-VL-$CL)_2$:(VH-CH1-CH2-CH3-L4-VH*-L3-$VL^*)_2$; (MM-L1-CM1-CM2 substrate-L2-VL-$CL)_2$:(VH-CH1-CH2-CH3-L4-VL*-L3-$VH^*)_2$; $(VL-CL)_2$:(MM-L1-CM1-CM2 substrate-L2-VL*-L3-VH*-L4-VH-CH1-CH2-$CH3)_2$; $(VL-CL)_2$:(MM-L1-CM1-CM2 substrate-L2-VH*-L3-VL*-L4-VH-CH1-CH2-$CH3)_2$; (MM-L1-CM1-CM2 substrate-L2-VL-$CL)_2$:(VL*-L3-VH*-L4-VH-CH1-CH2-$CH3)_2$; (MM-L1-CM1-CM2 substrate-L2-VL-$CL)_2$:(VH*-L3-VL*-L4-VH-CH1-CH2-$CH3)_2$; (VL-CL-L4-VH*-L3-VL*-L2-CM1-CM2 substrate-L1-$MM)_2$:(VH-CH1-CH2-$CH3)_2$; (VL-CL-L4-VL*-L3-VH*-L2-CM1-CM2 substrate-L1-$MM)_2$:(VH-CH1-CH2-$CH3)_2$; (MM-L1-CM1-CM2 substrate-L2-VL*-L3-VH*-L4-VL-$CL)_2$:(VH-CH1-CH2-$CH3)_2$; (MM-L1-CM1-CM2 substrate-L2-VH*-L3-VL*-L4-VL-$CL)_2$:(VH-CH1-CH2-$CH3)_2$; (VL-CL-L4-VH*-L3-VL*-L2-CM1-CM2 substrate-L1-$MM)_2$: (MM-L1-CM1-

CM2 substrate-L2-VL*-L3-VH*-L4-VH-CH1-CH2-CH3)$_2$; (VL-CL-L4-VH*-L3-VL*-L2-CM1-CM2 substrate-L1-MM)$_2$: (MM-L1-CM1-CM2 substrate-L2-VH*-L3-VL*-L4-VH-CH1-CH2-CH3)$_2$; (VL-CL-L4-VL*-L3-VH*-L2-CM1-CM2 substrate-L1-MM)$_2$: (MM-L1-CM1-CM2 substrate-L2-VL*-L3-VH*-L4-VH-CH1-CH2-CH3)$_2$; (VL-CL-L4-VL*-L3-VH*-L2-CM1-CM2 substrate-L1-MM)$_2$: (MM-L1-CM1-CM2 substrate-L2-VH*-L3-VL*-L4-VH-CH1-CH2-CH3)$_2$; (VL-CL-L4-VH*-L3-VL*)$_2$: (MM-L1-CM1-CM2 substrate-L2-VL*-L3-VH*-L4-VH-CH1CH3)$_2$; (VL-CL-L4-VH*-L3-VL*)$_2$: (MM-L1-CM1-CM2 substrate-L2-VH*-L3-VL*-L4-VH-CH1-CH2-CH3)$_2$; (VL-CL-L4-VL*-L3-VH*)$_2$: (MM-L1-CM1-CM2 substrate-L2-VL*-L3-VH*-L4-VH-CH1-CH2-CH3)$_2$; (VL-CL-L4-VL*-L3-VH*)$_2$: (MM-L1-CM1-CM2 substrate-L2-VH*-L3-VL*-L4-VH-CH1-CH2-CH3)$_2$; (VL-CL-L4-VH*-L3-VL*-L2-CM1-CM2 substrate-L1-MM)$_2$: (VL*-L3-VH*-L4-VH-CH1-CH2-CH3)$_2$; (VL-CL-L4-VH*-L3-VL*-L2-CM1-CM2 substrate-L1-MM)$_2$: (VH*-L3-VL*-L4-VH-CH1-CH2-CH3)$_2$; (VL-CL-L4-VL*-L3-VH*-L2-CM1-CM2 substrate-L1-MM)$_2$: (VL*-L3-VH*-L4-VH-CH1-CH2-CH3)$_2$; or (VL-CL-L4-VL*-L3-VH*-L2-CM1-CM2 substrate-L1-MM)$_2$: (VH*-L3-VL*-L4-VH-CH1-CH2-CH3)$_2$, wherein: VL and VH represent the light and heavy variable domains of the first specificity, contained in the IgG; VL* and VH* represent the variable domains of the second specificity, contained in the scFv; L1 is a linker peptide connecting the masking moiety (MM) and the CM1-CM2 substrate; L2 is a linker peptide connecting the CM1-CM2 substrate, and the antibody; L3 is a linker peptide connecting the variable domains of the scFv; L4 is a linker peptide connecting the antibody of the first specificity to the antibody of the second specificity; CL is the light-chain constant domain; and CH1, CH2, CH3 are the heavy chain constant domains. The first and second specificities may be toward any antigen or epitope.

In some embodiments of a T-cell engaging multispecific activatable antibody, one antigen is typically an antigen present on the surface of a tumor cell or other cell type associated with disease, such as, but not limited to, any target listed in Table 1, such as, but not limited to, EGFR, erbB2, EpCAM, Jagged, PD-L1, B7H3, or CD71 (transferrin receptor), and another antigen is typically a stimulatory (also referred to herein as activating) or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137 (also referred to as TNFRSF9), CTLA-4, GITR, HVEM, ICOS, LAG3, NKG2D, OX40, PD-1, TIGIT, TIM3, or VISTA. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PD-L1, PD-L2, or TNFSF9. In some embodiments of a multi-antigen targeting activatable antibody, one antigen is selected from the group of targets listed in Table 1, and another antigen is selected from the group of targets listed in Table 1.

In some embodiments, the targeting antibody is an anti-EGFR antibody. In some embodiments, the targeting antibody is C225v5, which is specific for binding to EGFR. In some embodiments, the targeting antibody is C225, which is specific for binding to EGFR. In some embodiments, the targeting antibody is C225v4, which is specific for binding to EGFR. In some embodiments, the targeting antibody is C225v6, which is specific for binding to EGFR. In some embodiments, the targeting antibody is an anti-Jagged antibody. In some embodiments, the targeting antibody is 4D11, which is specific for binding to human and mouse Jagged 1 and Jagged 2. In some embodiments, the targeting antibody is 4D11v2, which is specific for binding to human and mouse Jagged 1 and Jagged 2.

In some embodiments, the targeting antibody can be in the form an activatable antibody. In some embodiments, the scFv(s) can be in the form of a Pro-scFv (see, e.g., WO 2009/025846, WO 2010/081173).

In some embodiments, the scFv is specific for binding CD3ε, and is or is derived from an antibody or fragment thereof that binds CD3ε, e.g., CH2527, FN18, H2C, OKT3, 2C11, UCHT1, or V9. In some embodiments, the scFv is specific for binding CTLA-4 (also referred to herein as CTLA and CTLA4).

In some embodiments, the anti-CTLA-4 scFv includes the amino acid sequence:

```
                                        (SEQ ID NO: 347)
GGGSGGGGSGSGGGSGGGGSGGGEIVLTQSPGTLSLSPGERATLSCRAS
QSVSSSYLAWYQQKPGQAPRLLIYGASSRATGIPDRFSGSGSGTDFTLT
ISRLEPEDFAVYYCQQYGSSPLTFGGGTKVEIKRSGGSTITSYNVYYTK
LSSSGTQVQLVQTGGGVVQPGRSLRLSCAASGSTFSSYAMSWVRQAPGK
GLEWVSAISGSGGSTYYADSVKGRFTISRDNSKNTLYLQMNSLRAEDTA
VYYCATNSLYWYFDLWGRGTLVTVSSAS
```

In some embodiments, the anti-CTLA-4 scFv includes the amino acid sequence that is at least 90%, 91%, 92%, 93%, 94%, 95%, 96%, 97%, 98%, 99% or more identical to the amino acid sequence of SEQ ID NO: 347.

In some embodiments, the anti-CD3E scFv includes the amino acid sequence:

```
                                        (SEQ ID NO: 349)
GGGSGGGGSGSGGGSGGGGSGGGQVQLQQSGAELARPGASVKMSCKASG
YTFTRYTMHWVKQRPGQGLEWIGYINPSRGYTNYNQKFKDKATLTTDKS
SSTAYMQLSSLTSEDSAVYYCARYYDDHYCLDYWGQGTTLTVSSGGGGS
GGGGSGGGGSQIVLTQSPAIMSASPGEKVTMTCSASSSVSYMNWYQQKS
GTSPKRWIYDTSKLASGVPAHFRGSGSGTSYSLTISGMEAEDAATYYCQ
QWSSNPFTFGSGTKLEINR
```

In some embodiments, the anti-CD3E scFv includes the amino acid sequence that is at least 90%, 91%, 92%, 93%, 94%, 95%, 96%, 97%, 98%, 99% or more identical to the amino acid sequence of SEQ ID NO: 349.

In some embodiments, the scFv is specific for binding one or more T-cells, one or more NK-cells and/or one or more macrophages. In some embodiments, the scFv is specific for binding a target selected from the group consisting of B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA.

In some embodiments, the multispecific activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the multispecific activatable antibody via a linker. In some embodiments, the agent is conjugated to the AB via a cleavable linker. In some embodiments, the agent is conjugated to the AB via a linker that includes at least one CM1-CM2 substrate sequence. In some embodiments, the linker is a non-cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is an agent selected from the group listed in Table 4. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the multispecific activatable antibody also includes a detectable moiety. In some embodiments, the detectable moiety is a diagnostic agent.

In some embodiments, the multispecific activatable antibody naturally contains one or more disulfide bonds. In some embodiments, the multispecific activatable antibody can be engineered to include one or more disulfide bonds.

The disclosure also provides an isolated nucleic acid molecule encoding a multispecific activatable antibody described herein, as well as vectors that include these isolated nucleic acid sequences. The disclosure provides methods of producing a multispecific activatable antibody by culturing a cell under conditions that lead to expression of the activatable antibody, wherein the cell comprises such a nucleic acid molecule. In some embodiments, the cell comprises such a vector.

The disclosure also provides a method of manufacturing multispecific activatable antibodies of the disclosure by (a) culturing a cell comprising a nucleic acid construct that encodes the multispecific activatable antibody under conditions that lead to expression of the multispecific activatable, and (b) recovering the multispecific activatable antibody.

The disclosure also provides multispecific activatable antibodies and/or multispecific activatable antibody compositions that include at least a first antibody or antigen-binding fragment thereof (AB1) that specifically binds a first target or first epitope and a second antibody or antigen-biding fragment thereof (AB2) that binds a second target or a second epitope, where at least AB1 is coupled or otherwise attached to a masking moiety (MM1), such that coupling of the MM1 reduces the ability of AB1 to bind its target. In some embodiments, the MM1 is coupled to AB1 via a CM1-CM2 substrate for an MMP and a SP, where at least one of the MMP and the SP is co-localized with the target of AB1 at a treatment site or a diagnostic site in a subject. The multispecific activatable antibodies provided herein are stable in circulation, activated at intended sites of therapy and/or diagnosis but not in normal, i.e., healthy tissue, and, when activated, exhibit binding to the target of AB1 that is at least comparable to the corresponding, unmodified multispecific antibody.

In some embodiments, the multispecific activatable antibody comprises a linking peptide between the MM1 and the CM1-CM2 substrate.

In some embodiments, the multispecific activatable antibody comprises a linking peptide between the CM1-CM2 substrate and the AB1.

In some embodiments, the activatable antibody comprises a first linking peptide (LP1) and a second linking peptide (LP2), and at least a portion of the multispecific activatable antibody has the structural arrangement from N-terminus to C-terminus as follows in the uncleaved state: MM1-LP1-CM1-CM2 substrate-LP2-AB1 or AB1-LP2-CM1-CM2 substrate-LP1-MM1. In some embodiments, the two linking peptides need not be identical to each other.

In some embodiments, at least one of LP1 or LP2 includes an amino acid sequence selected from the group consisting of $(GS)_n$, $(GGS)_n$, $(GSGGS)_n$ (SEQ ID NO: 381) and $(GGGS)_n$ (SEQ ID NO: 382), where n is an integer of at least one. In some embodiments, at least one of LP1 or LP2 includes an amino acid sequence selected from the group consisting of GGSG (SEQ ID NO: 383), GGSGG (SEQ ID NO: 384), GSGSG (SEQ ID NO: 385), GSGGG (SEQ ID NO: 386), GGGSG (SEQ ID NO: 387), and GSSSG (SEQ ID NO: 388).

In some embodiments, the activatable antibody includes a linking peptide (LP') between CM1 and CM2.

In some embodiments, the activatable antibody comprises a first linking peptide (LP1), a second linking peptide (LP2), and a linking peptide (LP') between CM1 and CM2, and at least a portion of the multispecific activatable antibody has the structural arrangement from N-terminus to C-terminus as follows in the uncleaved state: MM1-LP1-CM1-CM2 substrate-LP2-AB1 or AB1-LP2-CM1-CM2 substrate-LP1-MM1. In some embodiments, linking peptides need not be identical to each other.

In some embodiments, LP' is GG. In some embodiments, LP' is GGSGGS (SEQ ID NO: 350).

In some embodiments, the multispecific activatable antibody includes at least a first antibody or antigen-binding fragment thereof (AB1) that specifically binds a first target or first epitope and a second antibody or antigen-binding fragment thereof (AB2) that specifically binds a second target or second epitope. In some embodiments, each of the AB in the multispecific activatable antibody is independently selected from the group consisting of a monoclonal antibody, domain antibody, single chain, Fab fragment, a $F(ab')_2$ fragment, a scFv, a scAb, a dAb, a single domain heavy chain antibody, and a single domain light chain antibody. In some embodiments, each of the AB in the multispecific activatable antibody is a rodent (e.g., mouse or rat), chimeric, humanized or fully human monoclonal antibody.

In some embodiments, each of the AB in the multispecific activatable antibody has a dissociation constant of about 100 nM or less for binding to its corresponding target or epitope.

In some embodiments, MM1 has a dissociation constant for binding to its corresponding AB that is greater than the dissociation constant of the AB to its corresponding target or epitope.

In some embodiments, MM1 has a dissociation constant for binding to its corresponding AB that is no more than the dissociation constant of the AB to its corresponding target or epitope.

In some embodiments, MM1 does not interfere or compete with its corresponding AB for binding to the corresponding target or epitope when the multispecific activatable antibody is in a cleaved state.

In some embodiments, MM1 is a polypeptide of about 2 to 40 amino acids in length. In some embodiments, each of the MM in the multispecific activatable antibody is a polypeptide of no more than 40 amino acids in length.

In some embodiments, MM1 has a polypeptide sequence that is different from that of target of the corresponding AB.

In some embodiments, MM1 has a polypeptide sequence that is no more than 50% identical to any natural binding partner of the corresponding AB. In some embodiments, MM1 has a polypeptide sequence that is no more than 25% identical to any natural binding partner of the corresponding AB. In some embodiments, MM1 has a polypeptide sequence that is no more than 10% identical to any natural binding partner of the corresponding AB.

In some embodiments, the coupling of MM1 reduces the ability of the corresponding AB to bind its target or epitope such that the dissociation constant ($K_d$) of the AB when coupled to the MM1 towards its corresponding target or epitope is at least 20 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 40 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 100 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 1000 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 10,000 times greater than the $K_d$ of the AB when not coupled to the MM1 towards its corresponding target or epitope.

In some embodiments, MM1 is an amino acid sequence selected from a MM disclosed herein.

In some embodiments, the multispecific activatable antibody includes at least a second masking moiety (MM2) that inhibits the binding of the AB2 to its target when the multispecific activatable antibody is in an uncleaved state, and an additional cleavable moiety (CM') coupled to the AB2, wherein the CM' is either a CM1-CM2 substrate or a polypeptide that functions as a substrate for a second protease. In some embodiments, CM' is a polypeptide of no more than 15 amino acids long. In some embodiments, CM' is a CM1-CM2 substrate, wherein each of CM1 and CM2 in the CM1-CM2 substrate is independently no more than 15 amino acids long.

In some embodiments, the MMP protease, the SP protease, and/or the second protease is co-localized with the second target or epitope in a tissue, and wherein the MMP protease, the SP protease, and/or the second protease cleaves the CM' in the multispecific activatable antibody when the multispecific activatable antibody is exposed to the MMP protease, the SP protease, and/or the second protease. In some embodiments, the MMP protease, the SP protease, and/or the second protease are co-localized with the first target or epitope and the second target or epitope in a tissue. In some embodiments, the MMP protease, the SP protease, and/or the second protease are the same MMP protease and the same SP protease. In some embodiments, the MMP protease, the SP protease, and/or the second protease are not the same MMP protease and not the same SP protease. In some embodiments, the CM1-CM2 substrate and CM' are different substrates for the same MMP protease and same SP protease. In some embodiments, the protease that cleaves CM' is selected from the group consisting of those shown in Table 6.

In some embodiments, each of the MM in the multispecific activatable antibody, e.g., MM1 and at least MM2, has a dissociation constant for binding to its corresponding AB that is greater than the dissociation constant of the AB to its corresponding target or epitope.

In some embodiments, each of the MM in the multispecific activatable antibody has a dissociation constant for binding to its corresponding AB that is no more than the dissociation constant of the AB to its corresponding target or epitope.

In some embodiments, each of the MM in the multispecific activatable antibody does not interfere or compete with its corresponding AB for binding to the corresponding target or epitope when the multispecific activatable antibody is in a cleaved state.

In some embodiments, each of the MM in the multispecific activatable antibody is a polypeptide of about 2 to 40 amino acids in length. In some embodiments, each of the MM in the multispecific activatable antibody is a polypeptide of no more than 40 amino acids in length.

In some embodiments, each of the MM in the multispecific activatable antibody has a polypeptide sequence that is different from that of target of the corresponding AB.

In some embodiments, each of the MM in the multispecific activatable antibody has a polypeptide sequence that is no more than 50% identical to any natural binding partner of the corresponding AB. In some embodiments, each of the MM in the multispecific activatable antibody has a polypeptide sequence that is no more than 25% identical to any natural binding partner of the corresponding AB. In some embodiments, each of the MM in the multispecific activatable antibody has a polypeptide sequence that is no more than 10% identical to any natural binding partner of the corresponding AB.

In some embodiments, the coupling of each of the MM reduces the ability of the corresponding AB to bind its target or epitope such that the dissociation constant ($K_d$) of the AB when coupled to the MM towards its corresponding target or epitope is at least 20 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 40 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 100 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 1000 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 10,000 times greater than the $K_d$ of the AB when not coupled to the MM towards its corresponding target or epitope.

In some embodiments, each of the MM is an amino acid sequence selected from a MM disclosed herein.

In some embodiments, the protease that cleaves the CM1-CM2 substrate sequence is co-localized with the target of the AB1 in the multispecific activatable antibody in a tissue, and the MMP protease and/or SP protease, i.e., at least one of the MMP protease and the SP protease, cleave the CM1-CM2 substrate in the multispecific activatable antibody when the multispecific activatable antibody is exposed to the proteases.

In some embodiments, the multispecific activatable antibody includes more than one CM1-CM2 substrate sequence, and the MMP protease and/or the SP protease that cleaves at least one CM1-CM2 substrate sequence is co-localized with the target of at least one of the AB regions in the multispecific activatable antibody in a tissue, and the MMP protease and/or SP protease cleaves the CM1-CM2 substrate in the multispecific activatable antibody when the multispecific activatable antibody is exposed to the proteases.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least twofold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least threefold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least fourfold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least fivefold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least tenfold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least 20-fold greater than the dissociation constant of an unmodified AB binding to its target, and whereas in the cleaved state, the AB binds its target.

In some embodiments, each CM1-CM2 substrate is positioned in the multispecific activatable antibody such that in the uncleaved state, binding of the multispecific activatable antibody to a target of one of the AB regions is reduced to occur with a dissociation constant that is at least 40-fold greater than the dissociation constant of an unmodified AB binding to its target, and whereas in the cleaved state, the AB binds its target.

In some embodiments, each CM1-CM2 substrate is positioned in the multispecific activatable antibody such that in the uncleaved state, binding of the multispecific activatable antibody to a target of one of the AB regions is reduced to occur with a dissociation constant that is at least 50-fold greater than the dissociation constant of an unmodified AB binding to its target, and whereas in the cleaved state, the AB binds its target.

In some embodiments, each CM1-CM2 substrate is positioned in the multispecific activatable antibody such that in the uncleaved state, binding of the multispecific activatable antibody to a target of one of the AB regions is reduced to occur with a dissociation constant that is at least 100-fold greater than the dissociation constant of an unmodified AB binding to its target, and whereas in the cleaved state, the AB binds its target.

In some embodiments, each CM1-CM2 substrate is positioned in the multispecific activatable antibody such that in the uncleaved state, binding of the multispecific activatable antibody to a target of one of the AB regions is reduced to occur with a dissociation constant that is at least 200-fold greater than the dissociation constant of an unmodified AB binding to its target, and whereas in the cleaved state, the AB binds its target.

The disclosure also provides compositions and methods that include a multispecific activatable antibody that includes at least a first antibody or antibody fragment (AB1) that specifically binds a target and a second antibody or antibody fragment (AB2), where at least the first AB in the multispecific activatable antibody is coupled to a masking moiety (MM1) that decreases the ability of AB1 to bind its target. In some embodiments, each AB is coupled to a MM that decreases the ability of its corresponding AB to each target. For example, in bispecific activatable antibody embodiments, AB1 is coupled to a first masking moiety (MM1) that decreases the ability of AB1 to bind its target, and AB2 is coupled to a second masking moiety (MM2) that decreases the ability of AB2 to bind its target. In some embodiments, the multispecific activatable antibody comprises more than two AB regions; in such embodiments, AB1 is coupled to a first masking moiety (MM1) that decreases the ability of AB1 to bind its target, AB2 is coupled to a second masking moiety (MM2) that decreases the ability of AB2 to bind its target, AB3 is coupled to a third masking moiety (MM3) that decreases the ability of AB3 to bind its target, and so on for each AB in the multispecific activatable antibody.

In some embodiments, the multispecific activatable antibody further includes at least one CM1-CM2 substrate that is a substrate for a MMP protease and a SP protease, where the CM1-CM2 substrate links a MM to an AB. For example, in some embodiments, the multispecific activatable antibody includes at least a first antibody or antibody fragment (AB1) that specifically binds a target and a second antibody or antibody fragment (AB2), where at least the first AB in the multispecific activatable antibody is coupled via a first CM1-CM2 substrate to a masking moiety (MM1) that decreases the ability of AB1 to bind its target. In some bispecific activatable antibody embodiments, AB1 is coupled via the first CM1-CM2 substrate to MM1, and AB2 is coupled via a second CM1-CM2 substrate to a second masking moiety (MM2) that decreases the ability of AB2 to bind its target. In some embodiments, the multispecific activatable antibody comprises more than two AB regions; in some of these embodiments, AB1 is coupled via the first CM1-CM2 substrate to MM1, AB2 is coupled via the second CM1-CM2 substrate to MM2, and AB3 is coupled via a third CM1-CM2 substrate to a third masking moiety (MM3) that decreases the ability of AB3 to bind its target, and so on for each AB in the multispecific activatable antibody.

Activatable Antibodies Having Non-Binding Steric Moieties or Binding Partners for Non-Binding Steric Moieties The disclosure also provides activatable antibodies that include non-binding steric moieties (NB) or binding partners (BP) for non-binding steric moieties, where the BP recruits or otherwise attracts the NB to the activatable antibody. The activatable antibodies provided herein include, for example, an activatable antibody that includes a non-binding steric moiety (NB), a CM1-CM2 substrate and antibody or antibody fragment (AB) that binds a target; an activatable antibody that includes a binding partner for a non-binding steric moiety (BP), a CM1-CM2 substrate and an AB; and an activatable antibody that includes a BP to which an NB has been recruited, a CM1-CM2 substrate and an AB that binds the target. Activatable antibodies in which the NB is covalently linked to the CM1-CM2 substrate and AB of the activatable antibody or is associated by interaction with a BP that is covalently linked to the CM1-CM2 substrate and AB of the activatable antibody are referred to herein as "NB-containing activatable antibodies." By activatable or switchable is meant that the activatable antibody exhibits a first level of binding to a target when the activatable antibody is in an inhibited, masked or uncleaved state (i.e., a first conformation), and a second level of binding to the target when the activatable antibody is in an uninhibited, unmasked and/or cleaved state (i.e., a second conformation, i.e., activated antibody), where the second level of target binding is greater than the first level of target binding. The activatable antibody compositions can exhibit increased bioavailability and more favorable biodistribution compared to conventional antibody therapeutics.

In some embodiments, activatable antibodies provide for reduced toxicity and/or adverse side effects that could otherwise result from binding of the at non-treatment sites and/or non-diagnostic sites if the AB were not masked or otherwise inhibited from binding to such a site.

In one embodiment, the activatable antibody includes a non-binding steric moiety (NB); a CM1-CM2 substrate; and an antibody or antibody fragment (AB) that binds specifically to the target, wherein the NB is a polypeptide that does not bind specifically to the AB; the CM1-CM2 substrate is a polypeptide that includes a substrate (S) for an enzyme; the CM1-CM2 substrate is positioned such that in an uncleaved state, the NB interferes with binding of the AB to the target and in a cleaved state, the NB does not interfere with binding of the AB to the target; and the NB does not inhibit cleavage of the CM1-CM2 substrate by the enzyme. As used herein and throughout, the term polypeptide refers to any polypeptide that includes at least two amino acid residues, including larger polypeptides, full-length proteins and fragments thereof, and the term polypeptide is not limited to single-chain polypeptides and can include multi-unit, e.g., multi-chain, polypeptides. In cases where the polypeptide is of a shorter length, for example, less than 50 amino acids total, the terms peptide and polypeptide are used interchangeably herein, and in cases where the polypeptide is of a longer length, e.g., 50 amino acids or greater, the terms polypeptide and protein are used interchangeably herein.

In one embodiment, the activatable antibody includes a non-binding steric moiety (NB); a CM1-CM2 substrate; and an antibody or antibody fragment (AB) that binds specifically to the target, wherein (i) the NB includes a polypeptide that does not bind specifically to the AB; (ii) CM1-CM2 substrate is a polypeptide of up to 50 amino acids in length that includes a substrate (S) for an enzyme; (iii) the CM1-CM2 substrate is positioned such that in an uncleaved state, the NB interferes with binding of the AB to the target and in a cleaved state, the NB does not interfere with binding of the AB to the target; and (iv) the NB does not inhibit cleavage of the CM1-CM2 substrate by the enzyme. For example, each of the CM1 substrate sequence and the CM2 substrate sequence in the CM1-CM2 substrate independent has a length of up to 15 amino acids.

In one embodiment, the activatable antibody includes a non-binding steric moiety (NB); a CM1-CM2 substrate; and an antibody or antibody fragment (AB) that binds specifically to the target, wherein (i) the NB includes a polypeptide that does not bind specifically to the AB; (ii) the CM1-CM2 substrate is a polypeptide that includes a substrate (S) for an enzyme; (iii) the CM1-CM2 substrate is positioned such that in an uncleaved state, the NB interferes with binding of the AB to the target and in a cleaved state, the NB does not interfere with binding of the AB to the target; (iv) the NB does not inhibit cleavage of the CM1-CM2 substrate by the enzyme; and (v) the activatable antibody has the structural arrangement from N-terminus to C-terminus as follows in the uncleaved state: NB-CM1-CM2 substrate-AB or AB-CM1-CM2 substrate-NB.

In one embodiment, the activatable antibody includes a non-binding steric moiety (NB); a CM1-CM2 substrate; and an antibody or antibody fragment (AB) that binds specifically to the target, wherein (i) the NB includes a polypeptide that does not bind specifically to the AB; (ii) the CM1-CM2 substrate is a polypeptide that includes a substrate (S) for an enzyme; (iii) the CM1-CM2 substrate is positioned such that in an uncleaved state, the NB interferes with binding of the AB to the target and in a cleaved state, the NB does not interfere with binding of the AB to the target, and wherein the NB in the uncleaved activatable antibody reduces the ability of the AB to bind the target by at least 50%, for example, by at least 60%, by at least 70%, by at least 75%, by at least 80%, by at least 85%, by at least 90%, by at least 95%, by at least 96%, by at least 97%, by at least 98%, by at least 99%, by at least 100% as compared to the ability of the cleaved AB to bind the target; and (iv) the NB does not inhibit cleavage of the CM1-CM2 substrate by the enzyme. The reduction in the ability of the AB to bind the target is determined, e.g., using an assay as described herein or an in vitro target displacement assay such as, for example, the assay described in PCT Publication Nos. WO 2009/025846 and WO 2010/081173.

In one embodiment, the activatable antibody includes a binding partner (BP) for a non-binding steric moiety (NB); a CM1-CM2 substrate; and an antibody or antibody fragment (AB) that binds specifically to the target, wherein the BP is a polypeptide that binds to the NB when exposed thereto; the NB does not bind specifically to the AB; the CM1-CM2 substrate is a polypeptide that includes a substrate (S) for an enzyme; the CM1-CM2 substrate is positioned such that in an uncleaved state in the presence of the NB, the NB interferes with binding of the AB to the target and in a cleaved state, the NB does not interfere with binding of the AB to the target and the BP does not interfere with binding of the AB to the target; and the NB and the BP do not inhibit cleavage of the CM1-CM2 substrate by the enzyme. In some examples of this embodiment, the BP of the activatable antibody is optionally bound to the NB. In one embodiment, the NB is recruited by the BP of the activatable antibody in vivo.

In some examples of any of these activatable antibody embodiments, the activatable antibody is formulated as a composition. In some of these embodiments, the composition also includes the NB, where the NB is co-formulated with the activatable antibody that includes the BP, the CM1-CM2 substrate, and the AB. In some examples of this embodiment, the BP is selected from the group consisting of an albumin binding peptide, a fibrinogen binding peptide, a fibronectin binding peptide, a hemoglobin binding peptide, a transferrin binding peptide, an immunoglobulin domain binding peptide, and other serum protein binding peptides.

In some examples of any of these activatable antibody embodiments, the NB is a soluble, globular protein. In some examples of any of these activatable antibody embodiments, the NB is a protein that circulates in the bloodstream. In some examples of any of these activatable antibody embodiments, the NB is selected from the group consisting of albumin, fibrinogen, fibronectin, hemoglobin, transferrin, an immunoglobulin domain, and other serum proteins.

In some examples of any of these activatable antibody embodiments, the CM1-CM2 substrate is a polypeptide that includes a substrate (S) for a protease. In some examples of any of these activatable antibody embodiments, the protease is co-localized with the in a tissue, and the protease cleaves the CM1-CM2 substrate in the activatable antibody when the activatable antibody is exposed to the protease. In some examples of any of these activatable antibody embodiments, the CM1-CM2 substrate is a polypeptide of up to 50 amino acids in length. In some examples of any of these activatable antibody embodiments, the CM1-CM2 substrate is a polypeptide that includes a substrate (S) having a length of up to 15 amino acids, e.g., 3 amino acids long, 4 amino acids long, 5 amino acids long, 6 amino acids long, 7 amino acids long, 8 amino acids long, 9 amino acids long, 10 amino acids long, 11 amino acids long, 12 amino acids long, 13 amino acids long, 14 amino acids long, or 15 amino acids long.

In some examples of any of these activatable antibody embodiments, the activatable antibody has the structural arrangement from N-terminus to C-terminus as follows in the uncleaved state: NB-CM1-CM2 substrate-AB, AB-CM1-CM2 substrate-NB, BP-CM1-CM2 substrate-AB or AB-CM1-CM2 substrate-BP. In embodiments where the activatable antibody includes a BP and the activatable antibody is in the presence of the corresponding NB, the activatable antibody has a structural arrangement from N-terminus to C-terminus as follows in the uncleaved state: NB:BP-CM1-CM2-AB, NB:BP-CM2-CM1-AB, AB-CM1-CM2-BP:NB or AB-CM2-CM1-BP:NB, where ":" represents an interaction, e.g., binding, between the NB and BP.

In some examples of any of these activatable antibody embodiments, the activatable antibody includes an antibody or antigen-binding fragment thereof that specifically binds a given target and is a monoclonal antibody, domain antibody, single chain, Fab fragment, a F(ab')2 fragment, a scFv, a scab, a dAb, a single domain heavy chain antibody, or a single domain light chain antibody. In some embodiments, such an antibody or immunologically active fragment thereof that binds the target a mouse, other rodent, chimeric, humanized or fully human monoclonal antibody.

In some examples of any of these activatable antibody embodiments, the activatable antibody includes a combination of a variable heavy chain region comprising an amino acid sequence presented herein and a variable light chain region comprising an amino acid sequence presented herein. In some embodiments, the activatable antibody includes a combination of a variable heavy chain region comprising an amino acid sequence that is at least 90%, 91%, 92%, 93%, 94%, 95%, 96%, 97%, 98%, 99% or more identical to an amino acid sequence presented herein, and a variable light chain region comprising an amino acid sequence that is at least 90%, 91%, 92%, 93%, 94%, 95%, 96%, 97%, 98%, 99% or more identical to an amino acid sequence presented herein.

In some examples of any of these activatable antibody embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the AB via a linker. In some embodiments, the linker is a cleavable linker. In some embodiments, the agent is conjugated to the AB via a noncleavable linker. In some embodiments, the agent is an agent selected from the group listed in Table 3. In some embodiments, the agent is a microtubule inhibitor. In some embodiments, the agent is a nucleic acid damaging agent, such as a DNA alkylator or DNA intercalator, or other DNA damaging agent. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some examples of any of these activatable antibody embodiments, the activatable antibody also includes a detectable moiety. In some embodiments, the detectable moiety is a diagnostic agent.

In some examples of any of these activatable antibody embodiments, the activatable antibody also includes a spacer. In some examples of any of these activatable antibody embodiments, the activatable antibody also includes a signal peptide. In some embodiments, the signal peptide is conjugated to the activatable antibody via a spacer. In some examples of any of these activatable antibody embodiments, the spacer is joined directly to the MM of the activatable antibody.

In some embodiments, the serum half-life of the activatable antibody is longer than that of the corresponding antibody; e.g., the pK of the activatable antibody is longer than that of the corresponding antibody. In some embodiments, the serum half-life of the activatable antibody is similar to that of the corresponding antibody. In some embodiments, the serum half-life of the activatable antibody is at least 15 days when administered to an organism. In some embodiments, the serum half-life of the activatable antibody is at least 12 days when administered to an organism. In some embodiments, the serum half-life of the activatable antibody is at least 11 days when administered to an organism. In some embodiments, the serum half-life of the activatable antibody is at least 10 days when administered to an organism. In some embodiments, the serum half-life of the activatable antibody is at least 9 days when administered to an organism. In some embodiments, the serum half-life of the activatable antibody is at least 8 days when administered to an organism. In some embodiments, the serum half-life of the activatable antibody is at least 7 days when administered to an organism. In some embodiments, the serum half-life of the activatable antibody is at least 6 days when administered to an organism. In some examples of any of these activatable antibody embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

The disclosure also provides an isolated nucleic acid molecule encoding any of these activatable antibodies, as well as vectors that include these isolated nucleic acid sequences. The disclosure provides methods of producing an activatable antibody by culturing a cell under conditions that lead to expression of the activatable antibody, wherein the cell comprises such a nucleic acid sequence. In some embodiments, the cell comprises such a vector.

The dissociation constant ($K_d$) of the NB-containing activatable antibody toward the target is greater than the $K_d$ of the AB towards the target when it is not associated with the NB or NB:BP. The dissociation constant ($K_d$) of the NB-containing activatable antibody toward the target is greater than the $K_d$ of the parental AB towards the target. For example, the $K_d$ of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB when it is not associated with the NB or NB:BP or the $K_d$ of the parental AB towards the target. Conversely, the binding affinity of the NB-containing activatable antibody towards the target is lower than the binding affinity of the AB when it is not associated with the NB or NB:BP or lower than the binding affinity of the parental AB towards the target. For example, the binding affinity of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB when it is not associated with the NB or NB:BP or lower than the binding affinity of the parental AB towards the target.

When the NB-containing activatable antibody is in the presence of the target, specific binding of the AB to the target is reduced or inhibited, as compared to the specific binding of the AB when it is not associated with the NB or NB:BP. When the NB-containing activatable antibody is in the presence of the target, specific binding of the AB to the target is reduced or inhibited, as compared to the specific binding of the parental AB to the target. When compared to the binding of the AB not associated with an NB or NB:BP or the binding of the parental AB to the target, the ability of the NB-containing activatable antibody to bind the target is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

When the NB-containing activatable antibody is in the presence of the target but not in the presence of a modifying agent (for example a protease or other enzyme), specific binding of the AB to the target is reduced or inhibited, as compared to the specific binding of the AB when it is not associated with the NB or NB:BP. When the NB-containing activatable antibody is in the presence of the target but not in the presence of a modifying agent (for example a protease, other enzyme, reduction agent, or light), specific binding of the AB to the target is reduced or inhibited, as compared to the specific binding of the parental AB to the target. When compared to the binding of the AB not associated with an NB or NB:BP or the binding of the parental AB to the target, the ability of the NB-containing activatable antibody to bind the target is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

In some examples of any of these activatable antibody embodiments, the activatable antibody includes an agent conjugated to the AB to produce an activatable antibody conjugate. In some embodiments of the activatable antibody conjugate, the agent is a therapeutic agent. In some embodiments, the agent is a diagnostic agent. In some embodiments, the agent is a detectable marker. In some embodiments of the activatable antibody conjugate, the agent is an antineoplastic agent. In some embodiments of the activatable antibody conjugate, the agent is a toxin or fragment thereof. In some embodiments of the activatable antibody conjugate, the agent is conjugated to the AB via a linker. In some embodiments of the activatable antibody conjugate, the linker is a cleavable linker. In some embodiments, the agent is conjugated to the AB via a noncleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some examples of any of these activatable antibody embodiments, the activatable antibodies are dual-target binding activatable antibodies. Such dual target binding activatable antibodies contain two Abs that may bind the same or different targets. In specific embodiments, dual-targeting activatable antibodies contain bispecific antibodies or antibody fragments.

Dual target binding activatable antibodies are designed so as to have a CM1-CM2 substrate cleavable by a cleaving agent that is co-localized in a target tissue with one or both of the targets capable of binding to the ABs of the activatable antibodies. Dual target binding activatable antibodies with more than one AB to the same or different targets can be designed so as to have more than one CM1-CM2 substrate, wherein the first CM1-CM2 substrate is cleavable by a cleaving agent in a first target tissue and wherein the second CM1-CM2 substrate is cleavable by a cleaving agent in a second target tissue, with one or more of the targets binding to the ABs of the activatable antibodies. In one embodiment, the first and second target tissues are spatially separated, for example, at different sites in the organism. In one embodiment, the first and second target tissues are the same tissue temporally separated, for example the same tissue at two different points in time, for example the first time point is when the tissue is an early stage tumor, and the second time point is when the tissue is a late stage tumor.

The disclosure also provides nucleic acid molecules encoding the activatable antibodies described herein. The disclosure also provides vectors that include these nucleic acids. The activatable antibodies described herein are produced by culturing a cell under conditions that lead to expression of the activatable antibody, wherein the cell includes these nucleic acid molecules or vectors.

The disclosure also provides methods of manufacturing activatable antibodies. In one embodiment, the method includes the steps of (a) culturing a cell that includes a nucleic acid construct that encodes the activatable antibody under conditions that lead to expression of the activatable antibody, wherein the activatable antibody includes (i) a non-binding steric moiety (NB); (ii) a CM1-CM2 substrate; and (iii) an antibody or an antigen binding fragment thereof (AB) that specifically binds a target, wherein (1) the NB does not bind specifically to the AB; (2) the CM1-CM2 substrate is a polypeptide that includes a substrate (S) for an enzyme; (3) the CM1-CM2 substrate is positioned such that in an uncleaved state, the NB interferes with binding of the AB to the target and in a cleaved state, the NB does not interfere with binding of the AB to the target; and (4) the NB does not inhibit cleavage of the CM1-CM2 substrate by the enzyme; and (b) recovering the activatable antibody.

In some embodiments, the method includes the steps of (a) culturing a cell that includes a nucleic acid construct that encodes the activatable antibody under conditions that lead to expression of the activatable antibody, wherein the activatable antibody includes (i) a binding partner (BP) for a non-binding steric moiety (NB); (ii) a CM1-CM2 substrate; and (iii) an antibody or an antigen binding fragment thereof (AB) that specifically binds a target, wherein (1) the NB does not bind specifically to the AB; (2) the CM1-CM2 substrate is a polypeptide that includes a substrate (S) for an enzyme; (3) the CM1-CM2 substrate is positioned such that in an uncleaved state in the presence of the NB, the NB interferes with binding of the AB to the target and in a cleaved state, the NB does not interfere with binding of the AB to the target and the BP does not interfere with binding of the AB to the target; and (4) the NB and the BP do not inhibit cleavage of the CM1-CM2 substrate by the enzyme; and (b) recovering the activatable antibody. In some examples of this embodiment, the BP of the activatable antibody is bound to the NB.

Use of Activatable Antibodies and Conjugated Activatable Antibodies

It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci.89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the disclosure, which include a conjugated antibody, an activatable antibody and/or a conjugated activatable antibody, are used to prevent, treat or otherwise ameliorate a disease or disorder associated with aberrant target expression and/or activity. For example, therapeutic formulations of the disclosure, which include a conjugated antibody, an activatable antibody and/or a conjugated activatable antibody, are used to treat or otherwise ameliorate inflammation, an inflammatory disorder, an autoimmune disease and/or a cancer or other neoplastic condition. In some embodiments, the cancer is a solid tumor or a hematologic malignancy where the target is expressed. In some embodiments, the cancer is a solid tumor where the target is expressed. In some embodiments, the cancer is a hematologic malignancy where the target is expressed. In some embodiments, the target is expressed on parenchyma (e.g., in cancer, the portion of an organ or tissue that often carries out function(s) of the organ or tissue). In some embodiments, the target is expressed on a cell, tissue, or organ. In some embodiments, the target is expressed on stroma (i.e., the connective supportive framework of a cell, tissue, or organ). In some embodiments, the target is expressed on an osteoblast. In some embodiments, the target is expressed on the endothelium (vasculature). In some embodiments, the target is expressed on a cancer stem cell. In some embodiments, the agent to which the activatable antibody is conjugated is a microtubule inhibitor. In some embodiments, the agent to which the activatable antibody is conjugated is a nucleic acid damaging agent.

Efficaciousness of prevention, amelioration or treatment is determined in association with any known method for diagnosing or treating the disease or disorder associated with target expression and/or activity, such as, for example, aberrant target expression and/or activity. Prolonging the survival of a subject or otherwise delaying the progression of the disease or disorder associated with target expression and/or activity, e.g., aberrant target expression and/or activity, in a subject indicates that the conjugated antibody, activatable antibody and/or conjugated activatable antibody confers a clinical benefit.

A conjugated antibody, an activatable antibody and/or a conjugated activatable antibody can be administered in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

In some embodiments where antibody fragments are used, the smallest fragment that specifically binds to the binding domain of the target protein is selected. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compounds as necessary for the particular indication being treated, for example, in some embodiments, those with complementary activities that do not adversely affect each other. In some embodiments, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

In some embodiments, the conjugated antibody, activatable antibody and/or conjugated activatable antibody contains a detectable label. An intact antibody, or a fragment thereof (e.g., Fab, scFv, or $F(ab)_2$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the disclosure can be used to detect an analyte mRNA, protein, or genomic DNA in a biological sample in vitro as well as in vivo. For example, in vitro techniques for detection of an analyte mRNA include Northern hybridizations and in situ hybridizations.

In vitro techniques for detection of an analyte protein include enzyme linked immunosorbent assays (ELISAs), Western blots, immunoprecipitations, immunochemical staining, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

The conjugated antibodies, activatable antibodies and/or conjugated activatable antibodies of the disclosure are also useful in a variety of diagnostic and prophylactic formulations. In one embodiment, a conjugated antibody, an activatable antibody and/or a conjugated activatable antibody is administered to patients that are at risk of developing one or more of the aforementioned disorders. A patient's or organ's predisposition to one or more of the aforementioned disorders can be determined using genotypic, serological or biochemical markers.

In some embodiments, a conjugated antibody, an activatable antibody and/or a conjugated activatable antibody is administered to human individuals diagnosed with a clinical indication associated with one or more of the aforementioned disorders. Upon diagnosis, a conjugated antibody, an activatable antibody and/or a conjugated activatable antibody is administered to mitigate or reverse the effects of the clinical indication.

A conjugated antibody, an activatable antibody and/or a conjugated activatable antibody of the disclosure is also useful in the detection of a target in patient samples and accordingly are useful as diagnostics. For example, the antibodies and/or activatable antibodies, and conjugated versions thereof, of the disclosure are used in in vitro assays, e.g., ELISA, to detect target levels in a patient sample.

In one embodiment, a conjugated antibody, an activatable antibody and/or a conjugated activatable antibody of the disclosure is immobilized on a solid support (e.g., the well(s) of a microtiter plate). The immobilized conjugated antibody, activatable antibody and/or conjugated activatable antibody serves as a capture antibody for any target that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen in the test sample is determined by comparison with a standard curve developed from the standard samples.

It will be appreciated that based on the results obtained using the antibodies of the disclosure, and conjugated versions thereof, in an in vitro diagnostic assay, it is possible to stage a disease in a subject based on expression levels of the target antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

A conjugated antibody, an activatable antibody and/or a conjugated activatable antibody can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable antibodies having an enzymatically cleavable CM1-CM2 substrate can be used to detect the presence or absence of an enzyme that is capable of cleaving the CM1-CM2 substrate. Such activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of an activatable antibody) in a given cell or tissue of a given host organism. Such accumulation of activated antibodies indicates not only that the tissue expresses enzymatic activity (or an increased reduction potential depending on the nature of the CM1-CM2 substrate) but also that the tissue expresses target to which the activated antibody binds.

For example, the CM1-CM2 substrate can be selected to be substrate for a matrix metalloprotease (MMP) and a serine protease (SP) found at the site of a tumor, at the site of a viral or bacterial infection at a biologically confined site (e.g., such as in an abscess, in an organ, and the like), and the like. The AB can be one that binds a target antigen. Using methods as disclosed herein, or when appropriate, methods familiar to one skilled in the art, a detectable label (e.g., a fluorescent label or radioactive label or radiotracer) can be conjugated to an AB or other region of an antibody and/or activatable antibody. Suitable detectable labels are discussed in the context of the above screening methods and additional specific examples are provided below. Using an AB specific to a protein or peptide of the disease state, along with an MMP whose activity is elevated in the disease tissue of interest, activatable antibodies will exhibit an increased rate of binding to disease tissue relative to tissues where the CM1-CM2 substrate specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM1-CM2 substrate is not present at a detectable level (or is present at lower levels in non-disease tissues or is present in inactive conformation), accumulation of activated antibodies in the disease tissue is enhanced relative to non-disease tissues.

In another example, activatable antibodies can be used to detect the presence or absence of a cleaving agent in a sample. For example, where the activatable antibodies contain a CM1-CM2 substrate susceptible to cleavage by an enzyme, the activatable antibodies can be used to detect (either qualitatively or quantitatively) the presence of an enzyme in the sample. In another example, where the activatable antibodies contain a CM1-CM2 substrate susceptible to cleavage by reducing agent, the activatable antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable antibody that is not released following cleavage, for example, the detectable label can be a quenched fluorescent label or other label that is not detectable until cleavage has occurred. The assay can be conducted by, for example, contacting the immobilized, detectably labeled activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable antibodies as described above, and the presence or absence of the target can be detected by detection of a target-AB complex e.g., by use of a detectably labeled anti-target antibody.

Activatable antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody is labeled with a detectable label. The detectable label may be a fluorescent dye, (e.g. a fluorophore, Fluorescein Isothiocyanate (FITC), Rhodamine Isothiocyanate (TRITC), an Alexa Fluor® label), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable antibody indicates that the sample contains the target and contains a matrix metalloprotease (MMP) and one serine protease (SP) that are specific for the CM1-CM2 substrate of the activatable antibody. In some embodiments, the presence of the MMP can be confirmed using broad spectrum protease inhibitors such as those described herein, and/or by using an agent that is specific for the protease, for example, an antibody such as A11, which is specific for the protease matriptase (MT-SP1) and inhibits the proteolytic activity of matriptase; see e.g., International Publication Number WO 2010/129609, published 11 Nov. 2010. The same approach of using broad spectrum protease inhibitors such as those described herein, and/or by using a more selective inhibitory agent can be used to identify a MMP and a SP specific for the CM1-CM2 substrate of the activatable antibody. In some embodiments, the presence of the target can be confirmed using an agent that is specific for the target, e.g., another antibody, or the detectable label can be competed with unlabeled target. In some embodiments, unlabeled activatable antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a MMP and a SP that is specific for the CM1-CM2 substrate of the activatable antibody.

These techniques are also useful in kits and/or as reagents for the detection, identification or characterization of protease activity in a variety of cells, tissues, and organisms based on the protease-specific CM1-CM2 substrate in the activatable antibody.

The disclosure provides methods of using the antibodies and/or activatable antibodies in a variety of diagnostic and/or prophylactic indications. For example, the disclosure provides methods of detecting presence or absence of a cleaving agent and a target of interest in a subject or a sample by (i) contacting a subject or sample with an activatable antibody, wherein the activatable antibody comprises a masking moiety (MM), a CM1-CM2 substrate that is cleaved by the cleaving agent, and an antigen binding domain or fragment thereof (AB) that specifically binds the target of interest, wherein the activatable antibody in an uncleaved, non-activated state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent and the target are present in the subject or sample and wherein no detectable level of activated activatable antibody in the subject or sample indicates that the cleaving agent, the target or both the cleaving agent and the target are absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides methods of detecting presence or absence of a cleaving agent in a subject or a sample by (i) contacting a subject or sample with an activatable antibody in the presence of a target of interest, e.g., the target, wherein the activatable antibody comprises a masking moiety (MM), a CM1-CM2 substrate that is cleaved by the cleaving agent, and an antigen binding domain or fragment thereof (AB) that specifically binds the target of interest, wherein the activatable antibody in an uncleaved, non-activated state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent is present in the subject or sample and wherein no detectable level of activated activatable antibody in the subject or sample indicates that the cleaving agent is absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody comprises a masking moiety (MM), a CM1-CM2 substrate that is cleaved by the cleaving agent, and an antigen binding domain or fragment thereof (AB) that specifically binds the target of interest, wherein the activatable antibody in an uncleaved, non-activated state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent is present in the subject or sample and wherein no detectable level of activated activatable antibody in the subject or sample indicates that the cleaving agent is absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides methods of detecting presence or absence of a cleaving agent in a subject or a sample by (i) contacting a subject or sample with an activatable antibody, wherein the activatable antibody comprises a masking moiety (MM), a CM1-CM2 substrate that is cleaved by the cleaving agent, an antigen binding domain (AB) that specifically binds the target, and a detectable label, wherein the activatable antibody in an uncleaved, non-activated state comprises a structural arrangement from N-terminus to C-terminus as follows: MM-CM1-CM2 substrate-AB or AB-CM1-CM2 substrate-MM; wherein the MM is a peptide that inhibits binding of the AB to the target, and wherein the MM does not have an amino acid sequence of a naturally occurring binding partner of the AB and is not a modified form of a natural binding partner of the AB; wherein, in an uncleaved, non-activated state, the MM interferes with specific binding of the AB to the target, and in a cleaved, activated state the MM does not interfere or compete with specific binding of the AB to the target; and wherein the detectable label is positioned on a portion of the activatable antibody that is released following cleavage of the CM1-CM2 substrate; and (ii) measuring a level of detectable label in the subject or sample, wherein a detectable level of the detectable label in the subject or sample indicates that the cleaving agent is absent and/or not sufficiently present in the subject or sample and wherein no detectable level of the detectable label in the subject or sample indicates that the cleaving agent is present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody and/or conjugated activatable antibody (e.g., an activatable antibody to which a therapeutic agent is conjugated) described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent and the target are present in the subject or biological sample and wherein no detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample.

The disclosure also provides methods of detecting presence or absence of a cleaving agent in a subject or a sample by (i) contacting a subject or biological sample with an activatable antibody in the presence of the target, and (ii) measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample. Such an activatable antibody includes a masking moiety (MM), a CM1-CM2 substrate that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments, all antigen binding sites are masked. In some embodiments, the measuring step includes use of a secondary reagent comprising a detectable label.

The disclosure also provides kits for use in methods of detecting presence or absence of a cleaving agent and the target in a subject or a sample, where the kits include at least an activatable antibody and/or conjugated activatable antibody described herein for use in contacting a subject or biological sample with an activatable antibody in the presence of the target, and measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample. Such an activatable antibody includes a masking moiety (MM), a CM1-CM2 substrate that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments, all antigen binding sites are masked. In some embodiments, the measuring step includes use of a secondary reagent comprising a detectable label.

The disclosure also provides kits for use in methods of detecting presence or absence of a cleaving agent in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM1-CM2 substrate, wherein a detectable level of activated activatable antibody in the subject or biological sample indicates that the cleaving agent is absent and/or not sufficiently present in the subject or biological sample such that the target binding and/or protease cleavage of the activatable antibody cannot be detected in the subject or biological sample, and wherein no detectable level of activated activatable antibody in the subject or biological sample indicates that the cleaving agent is present in the subject or biological sample at a detectable level.

The disclosure provides methods of detecting presence or absence of a cleaving agent and the target in a subject or a sample by (i) contacting a subject or biological sample with an activatable antibody, wherein the activatable antibody includes a detectable label that is positioned on a portion of the activatable antibody that is released following cleavage of the CM1-CM2 substrate and (ii) measuring a level of activated activatable antibody in the subject or biological sample, wherein a detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a masking moiety (MM), a CM1-CM2 substrate that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

The disclosure also provides methods of detecting presence or absence of a cleaving agent in a subject or a sample by (i) contacting a subject or biological sample with an activatable antibody, wherein the activatable antibody includes a detectable label that is positioned on a portion of the activatable antibody that is released following cleavage of the CM1-CM2 substrate; and (ii) measuring a level of detectable label in the subject or biological sample, wherein a detectable level of the detectable label in the subject or biological sample indicates that the cleaving agent is absent and/or not sufficiently present in the subject or biological sample at a detectable level, such that protease cleavage of the activatable antibody cannot be detected in the subject or biological sample, and wherein a reduced detectable level of the detectable label in the subject or biological sample indicates that the cleaving agent is present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a masking moiety (MM), a CM1-CM2 substrate that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent of interest in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM1-CM2 substrate, wherein a detectable level of the detectable label in the subject or biological sample indicates that the cleaving agent, the target, or both the cleaving agent and the target are absent and/or not sufficiently present in the subject or biological sample, such that the target binding and/or protease cleavage of the activatable antibody cannot be detected in the subject or biological sample, and wherein a reduced detectable level of the detectable label in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

In some embodiments of these methods and kits, the activatable antibody includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or 0-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor® 680 or Alexa Fluor® 750. In some embodiments of these methods and kits, the ligand-based label comprises biotin, avidin, streptavidin or one or more haptens.

In some embodiments of these methods and kits, the subject is a mammal. In some embodiments of these methods and kits, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments, in situ imaging and/or in vivo imaging are useful in methods to identify which patients to treat. For example, in in situ imaging, the activatable antibodies are used to screen patient samples to identify those patients having the appropriate protease(s) and target(s) at the appropriate location, e.g., at a tumor site.

In some embodiments, in situ imaging is used to identify or otherwise refine a patient population suitable for treatment with an activatable antibody of the disclosure. For example, patients that test positive for both the target (e.g., the target) and a protease that cleaves the substrate in the CM1-CM2 substrate of the activatable antibody being tested (e.g., accumulate activated antibodies at the disease site) are identified as suitable candidates for treatment with such an activatable antibody comprising such a CM1-CM2 substrate. Likewise, patients that test negative for either or both of the target (e.g., the target) and the protease that cleaves the substrate in the CM1-CM2 substrate in the activatable antibody being tested using these methods might be identified as suitable candidates for another form of therapy. In some embodiments, such patients that test negative with respect to a first activatable antibody can be tested with other activatable antibodies comprising different CM1-CM2 substrates until a suitable activatable antibody for treatment is identified (e.g., an activatable antibody comprising a CM1-CM2 substrate that is cleaved by the patient at the site of disease). In some embodiments, the patient is then administered a therapeutically effective amount of the conjugated activatable antibody for which the patient tested positive.

In some embodiments, in vivo imaging is used to identify or otherwise refine a patient population suitable for treatment with an activatable antibody of the disclosure. For example, patients that test positive for both the target (e.g., the target) and a protease that cleaves the substrate in the CM1-CM2 substrate of the activatable antibody being tested (e.g., accumulate activated antibodies at the disease site) are identified as suitable candidates for treatment with such an activatable antibody comprising such a CM1-CM2 substrate. Likewise, patients that test negative might be identified as suitable candidates for another form of therapy. In some embodiments, such patients that test negative with respect to a first activatable antibody can be tested with other activatable antibodies comprising different CM1-CM2 substrates until a suitable activatable antibody for treatment is identified (e.g., an activatable antibody comprising a CM1-CM2 substrate that is cleaved by the patient at the site of disease). In some embodiments, the patient is then administered a therapeutically effective amount of the conjugated activatable antibody for which the patient tested positive.

In some embodiments of the methods and kits, the method or kit is used to identify or otherwise refine a patient population suitable for treatment with an activatable antibody of the disclosure. For example, patients that test positive for both the target (e.g., the target) and a protease that cleaves the substrate in the CM1-CM2 substrate of the activatable antibody being tested in these methods are identified as suitable candidates for treatment with such an activatable antibody comprising such a CM1-CM2 substrate. Likewise, patients that test negative for both of the targets (e.g., the target) and the protease that cleaves the substrate in the CM1-CM2 substrate in the activatable antibody being tested using these methods might be identified as suitable candidates for another form of therapy. In some embodiments, such patients can be tested with other activatable antibodies until a suitable activatable antibody for treatment is identified (e.g., an activatable antibody comprising a CM1-CM2 substrate that is cleaved by the patient at the site of disease). In some embodiments, patients that test negative for either of the target (e.g., the target) are identified as suitable candidates for treatment with such an activatable antibody comprising such a CM1-CM2 substrate. In some embodiments, patients that test negative for either of the target (e.g., the target) are identified as not being suitable candidates for treatment with such an activatable antibody comprising such a CM1-CM2 substrate. In some embodiments, such patients can be tested with other activatable antibodies until a suitable activatable antibody for treatment is identified (e.g., an activatable antibody comprising a CM1-CM2 substrate that is cleaved by the patient at the site of disease). In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

In some embodiments, a method or kit is used to identify or otherwise refine a patient population suitable for treatment with an anti—the target activatable antibody and/or conjugated activatable antibody (e.g., activatable antibody to which a therapeutic agent is conjugated) of the disclosure, followed by treatment by administering that activatable antibody and/or conjugated activatable antibody to a subject in need thereof. For example, patients that test positive for both the targets (e.g., the target) and a protease that cleaves the CM1-CM2 substrate of the activatable antibody and/or conjugated activatable antibody being tested in these methods are identified as suitable candidates for treatment with such antibody and/or such a conjugated activatable antibody comprising such a CM1-CM2 substrate, and the patient is then administered a therapeutically effective amount of the activatable antibody and/or conjugated activatable antibody that was tested. Likewise, patients that test negative for either or both of the target (e.g., the target) and the protease that cleaves the substrate in the CM1-CM2 substrate in the activatable antibody being tested using these methods might be identified as suitable candidates for another form of therapy. In some embodiments, such patients can be tested with other antibody and/or conjugated activatable antibody until a suitable antibody and/or conjugated activatable antibody for treatment is identified (e.g., an activatable antibody and/or conjugated activatable antibody comprising a CM1-CM2 substrate that is cleaved by the patient at the site of disease). In some embodiments, the patient is then administered a therapeutically effective amount of the activatable antibody and/or conjugated for which the patient tested positive.

In some embodiments of these methods and kits, the MM is a peptide having a length from about 4 to 40 amino acids. In some embodiments of these methods and kits, the activatable antibody comprises a linker peptide, wherein the linker peptide is positioned between the MM and the CM1-CM2 substrate. In some embodiments of these methods and kits, the activatable antibody comprises a linker peptide, where the linker peptide is positioned between the AB and the CM1-CM2 substrate. In some embodiments of these methods and kits, the activatable antibody comprises a first linker peptide (L1) and a second linker peptide (L2), wherein the first linker peptide is positioned between the MM and the CM1-CM2 substrate and the second linker peptide is positioned between the AB and the CM1-CM2 substrate. In some embodiments of these methods and kits, each of L1 and L2 is a peptide of about 1 to 20 amino acids in length, and wherein each of L1 and L2 need not be the same linker. In some embodiments of these methods and kits, one or both of L1 and L2 comprises a glycine-serine polymer. In some embodiments of these methods and kits, at least one of L1 and L2 comprises an amino acid sequence selected from the group consisting of (GS)n, (GSGGS)n (SEQ ID NO: 381) and (GGGS)n (SEQ ID NO: 382), where n is an integer of at least one. In some embodiments of these methods and kits, at least one of L1 and L2 comprises an amino acid sequence having the formula (GGS)n, where n is an integer of at least one. In some embodiments of these methods and kits, at least one of L1 and L2 comprises an amino acid sequence selected from the group consisting of Gly-Gly-Ser-Gly (SEQ ID NO: 383), Gly-Gly-Ser-Gly-Gly (SEQ ID NO: 384), Gly-Ser-Gly-Ser-Gly (SEQ ID NO: 385), Gly-Ser-Gly-Gly-Gly (SEQ ID NO: 386), Gly-Gly-Gly-Ser-Gly (SEQ ID NO: 387), and Gly-Ser-Ser-Ser-Gly (SEQ ID NO: 388).

In some embodiments of these methods and kits, the AB comprises an antibody or antibody fragment sequence selected from the cross-reactive antibody sequences presented herein. In some embodiments of these methods and kits, the AB comprises a Fab fragment, a scFv or a single chain antibody (scAb).

In some embodiments of these methods and kits, the cleaving agent is a protease that is co-localized in the subject or sample with the target and the CM1-CM2 substrate is a polypeptide that functions as a substrate for the protease, wherein the protease cleaves the CM1-CM2 substrate in the activatable antibody when the activatable antibody is exposed to the protease. In some embodiments of these methods and kits, each of the CM1 substrate sequence and the CM2 substrate sequence in the CM1-CM2 substrate is independently a polypeptide of up to 15 amino acids in length. In some embodiments of these methods and kits, the CM1-CM2 substrate is coupled to the N-terminus of the AB. In some embodiments of these methods and kits, the CM1-CM2 substrate is coupled to the C-terminus of the AB. In some embodiments of these methods and kits, the CM1-CM2 substrate is coupled to the N-terminus of a VL chain of the AB.

The activatable antibodies and/or conjugated activatable antibodies of the disclosure are used in diagnostic and prophylactic formulations. In one embodiment, an activatable antibody is administered to patients that are at risk of developing one or more of the aforementioned inflammation, inflammatory disorders, cancer or other disorders.

A patient's or organ's predisposition to one or more of the aforementioned disorders can be determined using genotypic, serological or biochemical markers.

In some embodiments, an activatable antibody and/or conjugated activatable antibodies is administered to human individuals diagnosed with a clinical indication associated with one or more of the aforementioned disorders. Upon diagnosis, an activatable antibody and/or conjugated activatable antibodies is administered to mitigate or reverse the effects of the clinical indication.

Activatable antibodies and/or conjugated activatable antibodies of the disclosure are also useful in the detection of the target in patient samples and accordingly are useful as diagnostics. For example, the activatable antibodies and/or conjugated activatable antibodies of the disclosure are used in in vitro assays, e.g., ELISA, to detect target levels in a patient sample.

In one embodiment, an activatable antibody of the disclosure is immobilized on a solid support (e.g., the well(s) of a microtiter plate). The immobilized activatable antibody serves as a capture antibody for any target that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen in the test sample is determined by comparison with a standard curve developed from the standard samples.

It will be appreciated that based on the results obtained using the antibodies of the disclosure in an in vitro diagnostic assay, it is possible to stage a disease in a subject based on expression levels of the Target antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Activatable antibodies and/or conjugated activatable antibodies can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable antibodies having an enzymatically cleavable CM1-CM2 substrate can be used to detect the presence or absence of an enzyme that is capable of cleaving the CM1-CM2 substrate. Such activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of an activatable antibody) in a given cell or tissue of a given host organism. Such accumulation of activated antibodies indicates not only that the tissue expresses enzymatic activity (or an increased reduction potential depending on the nature of the CM1-CM2 substrate) but also that the tissue expresses target to which the activated antibody binds.

For example, the CM1-CM2 substrate can be selected to be a protease substrate for a protease found at the site of a tumor, at the site of a viral or bacterial infection at a biologically confined site (e.g., such as in an abscess, in an organ, and the like), and the like. The AB can be one that binds a target antigen. Using methods familiar to one skilled in the art, a detectable label (e.g., a fluorescent label or radioactive label or radiotracer) can be conjugated to an AB or other region of an activatable antibody. Suitable detectable labels are discussed in the context of the above screening methods and additional specific examples are provided below. Using an AB specific to a protein or peptide of the disease state, along with a protease whose activity is elevated in the disease tissue of interest, activatable antibodies will exhibit an increased rate of binding to disease tissue relative to tissues where the CM1-CM2 substrate specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM1-CM2 substrate is not present at a detectable level (or is present at lower levels in non-disease tissues or is present in inactive conformation), accumulation of activated antibodies in the disease tissue is enhanced relative to non-disease tissues.

In another example, activatable antibodies can be used to detect the presence or absence of a cleaving agent in a sample. For example, where the activatable antibodies contain a CM1-CM2 substrate susceptible to cleavage by an enzyme, the activatable antibodies can be used to detect (either qualitatively or quantitatively) the presence of an enzyme in the sample. In another example, where the activatable antibodies contain a CM1-CM2 substrate susceptible to cleavage by reducing agent, the activatable antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable antibody that is not released following cleavage, for example, the detectable label can be a quenched fluorescent label or other label that is not detectable until cleavage has occurred. The assay can be conducted by, for example, contacting the immobilized, detectably labeled activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable antibodies as described above, and the presence or absence of the target can be detected by detection of a target-AB complex e.g., by use of a detectably labeled anti-target antibody.

Activatable antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody is labeled with a detectable label. The detectable label may be a fluorescent dye, (e.g. Fluorescein Isothiocyanate (FITC), Rhodamine Isothiocyanate (TRITC), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable antibody indicates that the sample contains the target and contains a protease that is specific for the CM1-CM2 substrate of the activatable antibody. In some embodiments, the presence of the protease can be confirmed using broad spectrum protease inhibitors such as those described herein, and/or by using an agent that is specific for the protease, for example, an antibody such as A11, which is specific for the protease matriptase (MT-SP1) and inhibits the proteolytic activity of matriptase; see e.g., International Publication Number WO 2010/129609, published 11 Nov. 2010. The same approach of using broad spectrum protease inhibitors such as those described herein, and/or by using a more selective inhibitory agent can be used to identify a protease or class of proteases specific for the CM1-CM2 substrate of the activatable antibody. In some embodiments, the presence of the target can be confirmed using an agent that is specific for the target, e.g., another antibody, or the detectable label can be competed with unlabeled target. In some embodiments, unlabeled activatable antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a protease that is specific for the CM1-CM2 substrate of the activatable antibody.

These techniques are also useful in kits and/or as reagents for the detection, identification or characterization of protease activity in a variety of cells, tissues, and organisms based on the protease-specific CM1-CM2 substrate in the activatable antibody.

In some embodiments, in situ imaging and/or in vivo imaging are useful in methods to identify which patients to treat. For example, in in situ imaging, the activatable antibodies are used to screen patient samples to identify those patients having the appropriate protease(s) and target(s) at the appropriate location, e.g., at a tumor site.

In some embodiments, in situ imaging is used to identify or otherwise refine a patient population suitable for treatment with an activatable antibody of the disclosure. For example, patients that test positive for both the target and a protease that cleaves the substrate in the cleavable moiety (CM1-CM2 substrate) of the activatable antibody being tested (e.g., accumulate activated antibodies at the disease site) are identified as suitable candidates for treatment with such an activatable antibody comprising such a CM1-CM2 substrate. Likewise, patients that test negative for either or both of the target and the protease that cleaves the substrate in the CM1-CM2 substrate in the activatable antibody being tested using these methods are identified as suitable candidates for another form of therapy (i.e., not suitable for treatment with the activatable antibody being tested). In some embodiments, such patients that test negative with respect to a first activatable antibody can be tested with other activatable antibodies comprising different CMs until a suitable activatable antibody for treatment is identified (e.g., an activatable antibody comprising a CM1-CM2 substrate that is cleaved by the patient at the site of disease).

In some embodiments, in vivo imaging is used to identify or otherwise refine a patient population suitable for treatment with an activatable antibody of the disclosure. For example, patients that test positive for both the target and a protease that cleaves the substrate in the cleavable moiety (CM1-CM2 substrate) of the activatable antibody being tested (e.g., accumulate activated antibodies at the disease site) are identified as suitable candidates for treatment with such an activatable antibody comprising such a CM1-CM2 substrate. Likewise, patients that test negative are identified as suitable candidates for another form of therapy (i.e., not suitable for treatment with the activatable antibody being tested). In some embodiments, such patients that test negative with respect to a first activatable antibody can be tested with other activatable antibodies comprising different CMs until a suitable activatable antibody for treatment is identified (e.g., an activatable antibody comprising a CM1-CM2 substrate that is cleaved by the patient at the site of disease).

Pharmaceutical Compositions

The conjugated antibodies, activatable antibodies and/or conjugated activatable antibodies of the disclosure (also referred to herein as "active compounds"), and derivatives, fragments, analogs and homologs thereof, can be incorporated into pharmaceutical compositions suitable for administration. Such compositions typically comprise the conjugated antibody, activatable antibody and/or conjugated activatable antibody and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL" (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1. Matrix Metalloprotease (MMP) and Serine Protease (SP) Cleavable Anti-Jagged Activatable Antibodies This Example demonstrates the generation and evaluation of activatable antibodies that bind a Jagged target, e.g., Jagged 1 and/or Jagged 2, where the activatable antibodies are activated in the presence of at least one matrix metalloprotease (MMP) and at least one serine protease.

The studies described herein used the following substrate sequences, where LP' is a linking peptide between CM1 and CM2. For the CM1-CM2 substrate 1001/LP'/0001, LP' is GGSGGS (SEQ ID NO: 350), and for all other CM1-CM2 in the Table below, LP' is GG:

| CM1-CM2 Substrate | AA sequence | SEQ ID NO: |
|---|---|---|
| 2001 | ISSGLLSGRSDNH | 1 |
| 1001/LP'/0001 | ISSGLLSSGGSGGSLSGRSDNH | 2 |
| 1004/LP'/0003 | AVGLLAPPGGTSTSGRSANPRG | 3 |
| 0003/LP'/1004 | TSTSGRSANPRGGGAVGLLAPP | 4 |
| 1003/LP'/0003 | VHMPLGFLGPGGTSTSGRSANPRG | 5 |
| 0003/LP'/1003 | TSTSGRSANPRGGGVHMPLGFLGP | 6 |
| 1004/LP'/0001 | AVGLLAPPGGLSGRSDNH | 7 |
| 0001/LP'/1004 | LSGRSDNHGGAVGLLAPP | 8 |
| 1003/LP'/0001 | VHMPLGFLGPGGLSGRSDNH | 9 |
| 0001/LP'/1003 | LSGRSDNHGGVHMPLGFLGP | 10 |

Construction of the Anti-Jagged activatable antibody light chains was performed as follows.

The CM1-CM2 substrates were incorporated into the Jagged activatable antibody vector (described in PCT Publication No. WO2013/192550) as follows. Using standard molecular biology techniques, the forward (F) primers encoding the CM1-CM2 substrates (see Table A) and the reverse (R) primer CX1198 were used to amplify the substrate and VL domain of the Jagged activatable antibody and were subsequently cloned into the activatable antibody vector using the XhoI and BsiWI restriction sites. The resulting vectors encoded the following anti-Jagged activatable antibody light chains.

TABLE A

| | Primers used to construct the CM1-CM2 expression vectors | |
|---|---|---|
| CX1198 | Light chain R | Gtgcagccaccgtacgtttgatttccaccttggtccc (SEQ ID NO: 37) |
| CX2066 | 2001 F | CaggggggctcgagcGGCGGCTCTATCTCTTCCGGACTGCTGTCCGGCAGATCCGACAATCACGGCGGAGGCTCTGacatccagatgacccagtctc (SEQ ID NO: 38) |
| CX2067 | 1001/LP'/0001 F | CaggggggctcgagcGGCGGCTCTATCTCTTCTGGCCTGCTGTCTAGCGGCGGCTCCGGCGGATCTCTGTCTGGCAGATCTGACAACCACGGCGGAGGCTCCGacatccagatgacccagtctc (SEQ ID NO: 39) |
| CX2190 | 1004/LP'/0003 F | CaggggggctcgagcGGAGGATCTGCTGTGGGACTGCTGGCTCCTCCTGGCGGCACATCTACCTCTGGCAGATCCGCCAACCCTCGGGGCGGAGGATCTGacatccagatgacccagtctc (SEQ ID NO: 40) |
| CX2191 | 0003/LP'/1004 F | CaggggggctcgagcGGCGGCTCCACATCTACCTCTGGCAGATCCGCCAACCCCAGAGGTGGCGGAGCTGTGGGACTGCTGGCTCCACCAGGCGGATCTGacatccagatgacccagtctc (SEQ ID NO: 41) |
| CX2192 | 1003/LP'/0003 F | CaggggggctcgagcGGCGGCTCTGTGCATATGCCCCTGGGCTTTCTGGGCCCTGGCGGCACATCTACCTCTGGCAGATCCGCCAACCCTCGGGGCGGAGGATCTGacatccagatgacccagtctc (SEQ ID NO: 42) |
| CX2193 | 0003/LP'/1003 F | CaggggggctcgagcGGCGGCTCCACATCTACCTCTGGCAGATCCGCCAACCCCAGAGGCGGCGGAGTGCATATGCCTCTGGGCTTTCTGGGACCTGGCGGCTCTGacatccagatgacccag/tctc (SEQ ID NO: 43) |
| CX2242 | 1004/LP'/0001 F | CaggggggctcgagcGGAGGATCTGCTGTGGGACTGCTGGCTCCTCCTGGTGGCCTGTCTGGCAGATCTGATAACCACGGCGGCTCCGacatccagatgacccagtctc (SEQ ID NO: 44) |
| CX2243 | 0001/LP'/1004 F | CaggggggctcgagcGGAGGCTCTGGCCTGTCTGGCAGATCCGATAACCATGGCGGCGCTGTGGGACTGCTGGCTCCTCCTGGTGGATCTGacatccagatgacccagtctc (SEQ ID NO: 45) |
| CX2244 | 1003/LP'/0001 F | CaggggggctcgagcGGCGGCTCTGTGCATATGCCCCTGGGCTTTCTGGGACCTGGCGGCCTGTCTGGCAGATCCGATAATCACGGCGGCTCCGacatccagatgacccagtctc (SEQ ID NO: 46) |
| CX2245 | 0001/LP'/1003 F | CaggggggctcgagcGGAGGCTCTGGCCTGTCTGGCAGATCTGATAACCACGGCGGCGTGCACATGCCCCTGGGCTTTCTGGGACCTGGCGGATCTGacatccagatgacccagtctc (SEQ ID NO: 47) |

Anti-Jagged 2001 activatable antibody Lc with spacer sequence
Nucleotide sequence
(SEQ ID NO: 48)

Caaggccagtctggccagtgcaatatttggctcgtaggtggtgattgcaggggctggcaggggg gctcgagcggcggctctatctcttccggactgctgtccggcagatccgacaatcacggcggagg ctctgacatccagatgacccagtctccatcctccctgtctgcatctgtaggagacagagtcacc atcacttgccgggcaagtcagagcattagcagctatttaaattggtatcagcagaaaccaggga aagcccctaagctcctgatctatgcggcatccagtttgcaaagtggggtcccatcaaggttcag tggcagtggatctgggacagatttcactctcaccatcagcagtctgcaacctgaagattttgca acttactactgtcaacagacggttgtggcgcctccgttattcggccaagggaccaaggtggaaa tcaaacgtacggtggctgcaccatctgtcttcatcttcccgccatctgatgagcagttgaaatc tggaactgcctctgttgtgtgcctgctgaataacttctatcccagagaggccaaagtacagtgg aaggtggataacgcccctccaatcgggtaactcccaggagagtgtcacagagcaggacagcaagg -continued acagcacctacagcctcagcagcaccctgacgctgagcaaagcagactacgagaaacacaaagt ctacgcctgcgaagtcacccatcagggcctgagctcgcccgtcacaaagagcttcaacagggga gagtgt Amino Acid sequence (SEQ ID NO: 49)

QGQSGQCNIWLVGGDCRGWQGGSSGGSISSGLLSGRSDNHGGGSDIQMTQSPSSLSASVGDRVT

ITCRASQSISSYLNWYQQKPGKAPKLLIYAASSLQSGVPSRFSGSGSGTDFTLTISSLQPEDFA

TYYCQQTVVAPPLFGQGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQGLSSPVTKSFNRG

EC

Anti-Jagged 2001 activatable antibody Lc
Nucleotide sequence (SEQ ID NO: 419)

Tgcaatatttggctcgtaggtggtgattgcaggggctggcagggggggctcgagcggcggctcta tctcttccggactgctgtccggcagatccgacaatcacggcggaggctctgacatccagatgac ccagtctccatcctccctgtctgcatctgtaggagacagagtcaccatcacttgccgggcaagt cagagcattagcagctatttaaattggtatcagcagaaaccagggaaagcccctaagctcctga tctatgcggcatccagtttgcaaagtggggtcccatcaaggttcagtggcagtggatctgggac agatttcactctcaccatcagcagtctgcaacctgaagattttgcaacttactactgtcaacag acggttgtggcgcctccgttattcggccaagggaccaaggtggaaatcaaacgtacggtggctg caccatctgtcttcatcttcccgccatctgatgagcagttgaaatctggaactgcctctgttgt gtgcctgctgaataacttctatcccagagaggccaaagtacagtggaaggtggataacgccctc caatcgggtaactcccaggagagtgtcacagagcaggacagcaaggacagcacctacagcctca gcagcaccctgacgctgagcaaagcagactacgagaaacacaaagtctacgcctgcgaagtcac ccatcagggcctgagctcgcccgtcacaaagagcttcaacaggggagagtgt Amino Acid sequence (SEQ ID NO: 420)

CNIWLVGGDCRGWQGGSSGGSISSGLLSGRSDNHGGGSDIQMTQSPSSLSASVGDRVTITCRAS

QSISSYLNWYQQKPGKAPKLLIYAASSLQSGVPSRFSGSGSGTDFTLTISSLQPEDFATYYCQQ

TVVAPPLFGQGTKVEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

Anti-Jagged activatable antibody 1001/LP'/0001 Lc with spacer
sequence
Nucleotide sequence (SEQ ID NO: 50)

Caaggccagtctggccagtgcaatatttggctcgtaggtggtgattgcaggggctggcaggggg gctcgagcggcggctctatctcttctggcctgctgtctagcggcggctccggcggatctctgtc tggcagatctgacaaccacggcggaggctccgacatccagatgacccagtctccatcctccctg tctgcatctgtaggagacagagtcaccatcacttgccgggcaagtcagagcattagcagctatt taaattggtatcagcagaaaccagggaaagcccctaagctcctgatctatgcggcatccagttt gcaaagtggggtcccatcaaggttcagtggcagtggatctgggacagatttcactctcaccatc agcagtctgcaacctgaagattttgcaacttactactgtcaacagacggttgtggcgcctccgt tattcggccaagggaccaaggtggaaatcaaacgtacggtggctgcaccatctgtcttcatctt cccgccatctgatgagcagttgaaatctggaactgcctctgttgtgtgcctgctgaataacttc tatcccagagaggccaaagtacagtggaaggtggataacgccctccaatcgggtaactcccagg agagtgtcacagagcaggacagcaaggacagcacctacagcctcagcagcaccctgacgctgag -continued caaagcagactacgagaaacacaaagtctacgcctgcgaagtcacccatcagggcctgagctcg cccgtcacaaagagcttcaacaggggagagtgt Amino Acid sequence (SEQ ID NO: 51)

QGQSGQCNIWLVGGDCRGWQGGSSGGSISSGLLSSGGSGGSLSGRSDNHGGGSDIQMTQSPSSL

SASVGDRVTITCRASQSISSYLNWYQQKPGKAPKLLIYAASSLQSGVPSRFSGSGSGTDFTLTI

SSLQPEDFATYYCQQTVVAPPLFGQGTKVEIKRTVAAPSVFIFPPSDEQLKSGTASVVCLLNNF

YPREAKVQWKVDNALQSGNSQESVTEQDSKDSTYSLSSTLTLSKADYEKHKVYACEVTHQGLSS

PVTKSFNRGEC

Anti-Jagged activatable antibody 1001/LP'/0001 Lc
Nucleotide sequence (SEQ ID NO: 421)

Tgcaatatttggctcgtaggtggtgattgcaggggctggcagggggctcgagcggcggctcta tctcttctggcctgctgtctagcggcggctccggcggatctctgtctggcagatctgacaacca cggcggaggctccgacatccagatgacccagtctccatcctccctgtctgcatctgtaggagac agagtcaccatcacttgccgggcaagtcagagcattagcagctatttaaattggtatcagcaga aaccagggaaagcccctaagctcctgatctatgcggcatccagtttgcaaagtggggtcccatc aaggttcagtggcagtggatctgggacagatttcactctcaccatcagcagtctgcaacctgaa gattttgcaacttactactgtcaacagacggttgtggcgcctccgttattcggccaagggacca aggtggaaatcaaacgtacggtggctgcaccatctgtcttcatcttcccgccatctgatgagca gttgaaatctggaactgcctctgttgtgtgcctgctgaataacttctatcccagagaggccaaa gtacagtggaaggtggataacgccctccaatcgggtaactcccaggagagtgtcacagagcagg acagcaaggacagcacctacagcctcagcagcaccctgacgctgagcaaagcagactacgagaa acacaaagtctacgcctgcgaagtcacccatcagggcctgagctcgcccgtcacaaagagcttc aacaggggagagtgt Amino Acid sequence (SEQ ID NO: 422)

CNIWLVGGDCRGWQGGSSGGSISSGLLSSGGSGGSLSGRSDNHGGGSDIQMTQSPSSLSASVGD

RVTITCRASQSISSYLNWYQQKPGKAPKLLIYAASSLQSGVPSRFSGSGSGTDFTLTISSLQPE

DFATYYCQQTVVAPPLFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACEVTHQGLSSPVTKSF

NRGEC

Anti-Jagged 1004/LP'/0003 activatable antibody Lc with spacer sequence
Nucleotide sequence (SEQ ID NO: 52)

Caaggccagtctggccagtgcaatatttggctcgtaggtggtgattgcaggggctggcaggggg gctcgagcggaggatctgctgtgggactgctggctcctcctggcggcacatctacctctggcag atccgccaaccctcggggcggaggatctgacatccagatgacccagtctccatcctccctgtct gcatctgtaggagacagagtcaccatcacttgccgggcaagtcagagcattagcagctatttaa attggtatcagcagaaaccagggaaagcccctaagctcctgatctatgcggcatccagtttgca aagtggggtcccatcaaggttcagtggcagtggatctgggacagatttcactctcaccatcagc agtctgcaacctgaagattttgcaacttactactgtcaacagacggttgtggcgcctccgttat tcggccaagggaccaaggtggaaatcaaacgtacggtggctgcaccatctgtcttcatcttccc gccatctgatgagcagttgaaatctggaactgcctctgttgtgtgcctgctgaataacttctat cccagagaggccaaagtacagtggaaggtggataacgccctccaatcgggtaactcccaggaga -continued gtgtcacagagcaggacagcaaggacagcacctacagcctcagcagcaccctgacgctgagcaa agcagactacgagaaacacaaagtctacgcctgcgaagtcacccatcagggcctgagctcgccc gtcacaaagagcttcaacaggggagagtgt Amino Acid sequence (SEQ ID NO: 53)

QGQSGQCNIWLVGGDCRGWQGGSSGGSAVGLLAPPGGTSTSGRSANPRGGGSDIQMTQSPSSLS

ASVGDRVTITCRASQSISSYLNWYQQKPGKAPKLLIYAASSLQSGVPSRFSGSGSGTDFTLTIS

SLQPEDFATYYCQQTVVAPPLFGQGTKVEIKRTVAAPSVFIFPPSDEQLKSGTASVVCLLNNFY

PREAKVQWKVDNALQSGNSQESVTEQDSKDSTYSLSSTLTLSKADYEKHKVYACEVTHQGLSSP

VTKSFNRGEC

Anti-Jagged 1004/LP'/0003 activatable antibody Lc
Nucleotide sequence (SEQ ID NO: 423)

Tgcaatatttggctcgtaggtggtgattgcaggggctggcagggggctcgagcggaggatctg ctgtgggactgctggctcctcctggcggcacatctacctctggcagatccgccaaccctcgggg cggaggatctgacatccagatgacccagtctccatcctccctgtctgcatctgtaggagacaga gtcaccatcacttgccgggcaagtcagagcattagcagctatttaaattggtatcagcagaaac cagggaaagcccctaagctcctgatctatgcggcatccagtttgcaaagtggggtcccatcaag gttcagtggcagtggatctgggacagatttcactctcaccatcagcagtctgcaacctgaagat tttgcaacttactactgtcaacagacggttgtggcgcctccgttattcggccaagggaccaagg tggaaatcaaacgtacggtggctgcaccatctgtcttcatcttcccgccatctgatgagcagtt gaaatctggaactgcctctgttgtgtgcctgctgaataacttctatcccagagaggccaaagta cagtggaaggtggataacgccctccaatcgggtaactcccaggagagtgtcacagagcaggaca gcaaggacagcacctacagcctcagcagcaccctgacgctgagcaaagcagactacgagaaaca caaagtctacgcctgcgaagtcacccatcagggcctgagctcgcccgtcacaaagagcttcaac aggggagagtgt Amino Acid sequence (SEQ ID NO: 424)

CNIWLVGGDCRGWQGGSSGGSAVGLLAPPGGTSTSGRSANPRGGGSDIQMTQSPSSLSASVGDR

VTITCRASQSISSYLNWYQQKPGKAPKLLIYAASSLQSGVPSRFSGSGSGTDFTLTISSLQPED

FATYYCQQTVVAPPLFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEVTHQGLSSPVTKSFN

RGEC

Anti-Jagged 0003/LP'/1004 activatable antibody Lc with spacer
sequence
Nucleotide sequence (SEQ ID NO: 54)

Caaggccagtctggccagtgcaatatttggctcgtaggtggtgattgcaggggctggcaggggg gctcgagcggcggctccacatctacctctggcagatccgccaaccccagaggtggcggagctgt gggactgctggctccaccaggcggatctgacatccagatgacccagtctccatcctccctgtct gcatctgtaggagacagagtcaccatcacttgccgggcaagtcagagcattagcagctatttaa attggtatcagcagaaaccagggaaagcccctaagctcctgatctatgcggcatccagtttgca aagtggggtcccatcaaggttcagtggcagtggatctgggacagatttcactctcaccatcagc agtctgcaacctgaagattttgcaacttactactgtcaacagacggttgtggcgcctccgttat tcggccaagggaccaaggtggaaatcaaacgtacggtggctgcaccatctgtcttcatcttccc gccatctgatgagcagttgaaatctggaactgcctctgttgtgtgcctgctgaataacttctat -continued cccagagaggccaaagtacagtggaaggtggataacgccctccaatcgggtaactcccaggaga gtgtcacagagcaggacagcaaggacagcacctacagcctcagcagcaccctgacgctgagcaa agcagactacgagaaacacaaagtctacgcctgcgaagtcacccatcagggcctgagctcgccc gtcacaaagagcttcaacaggggagagtgt Amino Acid sequence (SEQ ID NO: 55)

QGQSGQCNIWLVGGDCRGWQGGSSGGSTSTSGRSANPRGGGAVGLLAPPGGSDIQMTQSPSSLS

ASVGDRVTITCRASQSISSYLNWYQQKPGKAPKLLIYAASSLQSGVPSRFSGSGSGTDFTLTIS

SLQPEDFATYYCQQTVVAPPLFGQGTKVEIKRTVAAPSVFIFPPSDEQLKSGTASVVCLLNNFY

PREAKVQWKVDNALQSGNSQESVTEQDSKDSTYSLSSTLTLSKADYEKHKVYACEVTHQGLSSP

VTKSFNRGEC

Anti-Jagged 0003/LP'/1004 activatable antibody Lc
Nucleotide sequence (SEQ ID NO: 425)

Tgcaatatttggctcgtaggtggtgattgcaggggctggcagggggggctcgagcggcggctcca catctacctctggcagatccgccaaccccagaggtggcggagctgtgggactgctggctccacc aggcggatctgacatccagatgacccagtctccatcctccctgtctgcatctgtaggagacaga gtcaccatcacttgccgggcaagtcagagcattagcagctatttaaattggtatcagcagaaac cagggaaagcccctaagctcctgatctatgcggcatccagtttgcaaagtggggtcccatcaag gttcagtggcagtggatctgggacagatttcactctcaccatcagcagtctgcaacctgaagat tttgcaacttactactgtcaacagacggttgtggcgcctccgttattcggccaagggaccaagg tggaaatcaaacgtacggtggctgcaccatctgtcttcatcttcccgccatctgatgagcagtt gaaatctggaactgcctctgttgtgtgcctgctgaataacttctatcccagagaggccaaagta cagtggaaggtggataacgccctccaatcgggtaactcccaggagagtgtcacagagcaggaca gcaaggacagcacctacagcctcagcagcaccctgacgctgagcaaagcagactacgagaaaca caaagtctacgcctgcgaagtcacccatcagggcctgagctcgcccgtcacaaagagcttcaac aggggagagtgt Amino Acid sequence (SEQ ID NO: 426)

CNIWLVGGDCRGWQGGSSGGSTSTSGRSANPRGGGAVGLLAPPGGSDIQMTQSPSSLSASVGDR

VTITCRASQSISSYLNWYQQKPGKAPKLLIYAASSLQSGVPSRFSGSGSGTDFTLTISSLQPED

FATYYCQQTVVAPPLFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEVTHQGLSSPVTKSFN

RGEC

Anti-Jagged 1003/LP'/0003 activatable antibody Lc with spacer
sequence
Nucleotide sequence (SEQ ID NO: 56)

Caaggccagtctggccagtgcaatatttggctcgtaggtggtgattgcaggggctggcaggggg gctcgagcggcggctctgtgcatatgcccctgggctttctgggccctggcggcacatctacctc tggcagatccgccaaccctcggggcggaggatctgacatccagatgacccagtctccatcctcc ctgtctgcatctgtaggagacagagtcaccatcacttgccgggcaagtcagagcattagcagct atttaaattggtatcagcagaaaccagggaaagcccctaagctcctgatctatgcggcatccag tttgcaaagtggggtcccatcaaggttcagtggcagtggatctgggacagatttcactctcacc atcagcagtctgcaacctgaagattttgcaacttactactgtcaacagacggttgtggcgcctc cgttattcggccaagggaccaaggtggaaatcaaacgtacggtggctgcaccatctgtcttcat -continued cttcccgccatctgatgagcagttgaaatctggaactgcctctgttgtgtgcctgctgaataac ttctatcccagagaggccaaagtacagtggaaggtggataacgccctccaatcgggtaactccc aggagagtgtcacagagcaggacagcaaggacagcacctacagcctcagcagcaccctgacgct gagcaaagcagactacgagaaacacaaagtctacgcctgcgaagtcacccatcagggcctgagc tcgcccgtcacaaagagcttcaacaggggagagtgt Amino Acid sequence (SEQ ID NO: 57)

QGQSGQCNIWLVGGDCRGWQGGSSGGSVHMPLGFLGPGGTSTSGRSANPRGGGSDIQMTQSPSS

LSASVGDRVTITCRASQSISSYLNWYQQKPGKAPKLLIYAASSLQSGVPSRFSGSGSGTDFTLT

ISSLQPEDFATYYCQQTVVAPPLFGQGTKVEIKRTVAAPSVFIFPPSDEQLKSGTASVVCLLNN

FYPREAKVQWKVDNALQSGNSQESVTEQDSKDSTYSLSSTLTLSKADYEKHKVYACEVTHQGLS

SPVTKSFNRGEC

Anti-Jagged 1003/LP'/0003 activatable antibody Lc
Nucleotide sequence (SEQ ID NO: 427)

Tgcaatatttggctcgtaggtggtgattgcaggggctggcagggggggctcgagcggcggctctg tgcatatgcccctgggctttctgggccctggcggcacatctacctctggcagatccgccaaccc tcggggcggaggatctgacatccagatgacccagtctccatcctccctgtctgcatctgtagga gacagagtcaccatcacttgccgggcaagtcagagcattagcagctatttaaattggtatcagc agaaaccagggaaagcccctaagctcctgatctatgcggcatccagtttgcaaagtggggtccc atcaaggttcagtggcagtggatctgggacagatttcactctcaccatcagcagtctgcaacct gaagattttgcaacttactactgtcaacagacggttgtggcgcctccgttattcggccaaggga ccaaggtggaaatcaaacgtacggtggctgcaccatctgtcttcatcttcccgccatctgatga gcagttgaaatctggaactgcctctgttgtgtgcctgctgaataacttctatcccagagaggcc aaagtacagtggaaggtggataacgccctccaatcgggtaactcccaggagagtgtcacagagc aggacagcaaggacagcacctacagcctcagcagcaccctgacgctgagcaaagcagactacga gaaacacaaagtctacgcctgcgaagtcacccatcagggcctgagctcgcccgtcacaaagagc ttcaacaggggagagtgt Amino Acid sequence (SEQ ID NO: 428)

CNIWLVGGDCRGWQGGSSGGSVHMPLGFLGPGGTSTSGRSANPRGGGSDIQMTQSPSSLSASVG

DRVTITCRASQSISSYLNWYQQKPGKAPKLLIYAASSLQSGVPSRFSGSGSGTDFTLTISSLQP

EDFATYYCQQTVVAPPLFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVYACEVTHQGLSSPVTKS

FNRGEC

Anti-Jagged 0003/LP'/1003 activatable antibody Lc with spacer
sequence
Nucleotide sequence (SEQ ID NO: 58)

Caaggccagtctggccagtgcaatatttggctcgtaggtggtgattgcaggggctggcaggggg gctcgagcggcggctccacatctacctctggcagatccgccaaccccagaggcggcggagtgca tatgcctctgggctttctgggacctggcggctctgacatccagatgacccagtctccatcctcc ctgtctgcatctgtaggagacagagtcaccatcacttgccgggcaagtcagagcattagcagct atttaaattggtatcagcagaaaccagggaaagcccctaagctcctgatctatgcggcatccag tttgcaaagtggggtcccatcaaggttcagtggcagtggatctgggacagatttcactctcacc atcagcagtctgcaacctgaagattttgcaacttactactgtcaacagacggttgtggcgcctc -continued cgttattcggccaagggaccaaggtggaaatcaaacgtacggtggctgcaccatctgtcttcat cttcccgccatctgatgagcagttgaaatctggaactgcctctgttgtgtgcctgctgaataac ttctatcccagagaggccaaagtacagtggaaggtggataacgccctccaatcgggtaactccc aggagagtgtcacagagcaggacagcaaggacagcacctacagcctcagcagcaccctgacgct gagcaaagcagactacgagaaacacaaagtctacgcctgcgaagtcacccatcagggcctgagc tcgcccgtcacaaagagcttcaacaggggagagtgt Amino Acid sequence (SEQ ID NO: 59)

QGQSGQCNIWLVGGDCRGWQGGSSGGSTSTSGRSANPRGGGVHMPLGFLGPGGSDIQMTQSPSS

LSASVGDRVTITCRASQSISSYLNWYQQKPGKAPKLLIYAASSLQSGVPSRFSGSGSGTDFTLT

ISSLQPEDFATYYCQQTVVAPPLFGQGTKVEIKRTVAAPSVFIFPPSDEQLKSGTASVVCLLNN

FYPREAKVQWKVDNALQSGNSQESVTEQDSKDSTYSLSSTLTLSKADYEKHKVYACEVTHQGLS

SPVTKSFNRGEC

Anti-Jagged 0003/LP'/1003 activatable antibody Lc
Nucleotide sequence (SEQ ID NO: 429)

Tgcaatatttggctcgtaggtggtgattgcaggggctggcagggggctcgagcggcggctcca catctacctctggcagatccgccaaccccagaggcggcggagtgcatatgcctctgggctttct gggacctggcggctctgacatccagatgacccagtctccatcctccctgtctgcatctgtagga gacagagtcaccatcacttgccgggcaagtcagagcattagcagctatttaaattggtatcagc agaaaccagggaaagcccctaagctcctgatctatgcggcatccagtttgcaaagtggggtccc atcaaggttcagtggcagtggatctgggacagatttcactctcaccatcagcagtctgcaacct gaagattttgcaacttactactgtcaacagacggttgtggcgcctccgttattcggccaaggga ccaaggtggaaatcaaacgtacggtggctgcaccatctgtcttcatcttcccgccatctgatga gcagttgaaatctggaactgcctctgttgtgtgcctgctgaataacttctatcccagagaggcc aaagtacagtggaaggtggataacgccctccaatcgggtaactcccaggagagtgtcacagagc aggacagcaaggacagcacctacagcctcagcagcaccctgacgctgagcaaagcagactacga gaaacacaaagtctacgcctgcgaagtcacccatcagggcctgagctcgcccgtcacaaagagc ttcaacaggggagagtgt Amino Acid sequence (SEQ ID NO: 430)

CNIWLVGGDCRGWQGGSSGGSTSTSGRSANPRGGGVHMPLGFLGPGGSDIQMTQSPSSLSASVG

DRVTITCRASQSISSYLNWYQQKPGKAPKLLIYAASSLQSGVPSRFSGSGSGTDFTLTISSLQP

EDFATYYCQQTVVAPPLFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVYACEVTHQGLSSPVTKS

FNRGEC

Anti-Jagged 1004/LP'/0001 activatable antibody Lc with spacer
sequence
Nucleotide sequence (SEQ ID NO: 60)

Caaggccagtctggccagtgcaatatttggctcgtaggtggtgattgcaggggctggcaggggg gctcgagcggaggatctgctgtgggactgctggctcctcctggtggcctgtctggcagatctga taaccacggcggctccgacatccagatgacccagtctccatcctccctgtctgcatctgtagga gacagagtcaccatcacttgccgggcaagtcagagcattagcagctatttaaattggtatcagc agaaaccagggaaagcccctaagctcctgatctatgcggcatccagtttgcaaagtggggtccc atcaaggttcagtggcagtggatctgggacagatttcactctcaccatcagcagtctgcaacct -continued gaagattttgcaacttactactgtcaacagacggttgtggcgcctccgttattcggccaaggga ccaaggtggaaatcaaacgtacggtggctgcaccatctgtcttcatcttcccgccatctgatga gcagttgaaatctggaactgcctctgttgtgtgcctgctgaataacttctatcccagagaggcc aaagtacagtggaaggtggataacgccctccaatcgggtaactcccaggagagtgtcacagagc aggacagcaaggacagcacctacagcctcagcagcaccctgacgctgagcaaagcagactacga gaaacacaaagtctacgcctgcgaagtcacccatcagggcctgagctcgcccgtcacaaagagc ttcaacaggggagagtgt Amino Acid sequence (SEQ ID NO: 61)

QGQSGQCNIWLVGGDCRGWQGGSSGGSAVGLLAPPGGLSGRSDNHGGSDIQMTQSPSSLSASVG

DRVTITCRASQSISSYLNWYQQKPGKAPKLLIYAASSLQSGVPSRFSGSGSGTDFTLTISSLQP

EDFATYYCQQTVVAPPLFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVYACEVTHQGLSSPVTKS

FNRGEC

Anti-Jagged 1004/LP'/0001 activatable antibody Lc
Nucleotide sequence (SEQ ID NO: 431)

Tgcaatatttggctcgtaggtggtgattgcaggggctggcagggggctcgagcggaggatctg ctgtgggactgctggctcctcctggtggcctgtctggcagatctgataaccacggcggctccga catccagatgacccagtctccatcctccctgtctgcatctgtaggagacagagtcaccatcact tgccgggcaagtcagagcattagcagctatttaaattggtatcagcagaaaccagggaaagccc ctaagctcctgatctatgcggcatccagtttgcaaagtggggtcccatcaaggttcagtggcag tggatctgggacagatttcactctcaccatcagcagtctgcaacctgaagattttgcaacttac tactgtcaacagacggttgtggcgcctccgttattcggccaagggaccaaggtggaaatcaaac gtacggtggctgcaccatctgtcttcatcttcccgccatctgatgagcagttgaaatctggaac tgcctctgttgtgtgcctgctgaataacttctatcccagagaggccaaagtacagtggaaggtg gataacgccctccaatcgggtaactcccaggagagtgtcacagagcaggacagcaaggacagca cctacagcctcagcagcaccctgacgctgagcaaagcagactacgagaaacacaaagtctacgc ctgcgaagtcacccatcagggcctgagctcgcccgtcacaaagagcttcaacaggggagagtgt Amino Acid sequence (SEQ ID NO: 432)

CNIWLVGGDCRGWQGGSSGGSAVGLLAPPGGLSGRSDNHGGSDIQMTQSPSSLSASVGDRVTIT

CRASQSISSYLNWYQQKPGKAPKLLIYAASSLQSGVPSRFSGSGSGTDFTLTISSLQPEDFATY

YCQQTVVAPPLFGQGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC

Anti-Jagged 0001/LP'/1004 activatable antibody Lc with spacer
sequence
Nucleotide sequence (SEQ ID NO: 62)

Caaggccagtctggccagtgcaatatttggctcgtaggtggtgattgcaggggctggcaggggg gctcgagcggaggctctggcctgtctggcagatccgataaccatggcggcgctgtgggactgct ggctcctcctggtggatctgacatccagatgacccagtctccatcctccctgtctgcatctgta ggagacagagtcaccatcacttgccgggcaagtcagagcattagcagctatttaaattggtatc agcagaaaccagggaaagcccctaagctcctgatctatgcggcatccagtttgcaaagtggggt cccatcaaggttcagtggcagtggatctgggacagatttcactctcaccatcagcagtctgcaa cctgaagattttgcaacttactactgtcaacagacggttgtggcgcctccgttattcggccaag -continued ggaccaaggtggaaatcaaacgtacggtggctgcaccatctgtcttcatcttcccgccatctga tgagcagttgaaatctggaactgcctctgttgtgtgcctgctgaataacttctatcccagagag gccaaagtacagtggaaggtggataacgccctccaatcgggtaactcccaggagagtgtcacag agcaggacagcaaggacagcacctacagcctcagcagcaccctgacgctgagcaaagcagacta cgagaaacacaaagtctacgcctgcgaagtcacccatcagggcctgagctcgcccgtcacaaag agcttcaacaggggagagtgt Amino Acid sequence (SEQ ID NO: 63)

QGQSGQCNIWLVGGDCRGWQGGSSGGSGLSGRSDNHGGAVGLLAPPGGSDIQMTQSPSSLSASV

GDRVTITCRASQSISSYLNWYQQKPGKAPKLLIYAASSLQSGVPSRFSGSGSGTDFTLTISSLQ

PEDFATYYCQQTVVAPPLFGQGTKVEIKRTVAAPSVFIFPPSDEQLKSGTASVVCLLNNFYPRE

AKVQWKVDNALQSGNSQESVTEQDSKDSTYSLSSTLTLSKADYEKHKVYACEVTHQGLSSPVTK

SFNRGEC

Anti-Jagged 0001/LP'/1004 activatable antibody Lc
Nucleotide sequence (SEQ ID NO: 433)

Tgcaatatttggctcgtaggtggtgattgcaggggctggcagggggggctcgagcggaggctctg gcctgtctggcagatccgataaccatggcggcgctgtgggactgctggctcctcctggtggatc tgacatccagatgacccagtctccatcctccctgtctgcatctgtaggagacagagtcaccatc acttgccgggcaagtcagagcattagcagctatttaaattggtatcagcagaaaccagggaaag cccctaagctcctgatctatgcggcatccagtttgcaaagtggggtcccatcaaggttcagtgg cagtggatctgggacagatttcactctcaccatcagcagtctgcaacctgaagattttgcaact tactactgtcaacagacggttgtggcgcctccgttattcggccaagggaccaaggtggaaatca aacgtacggtggctgcaccatctgtcttcatcttcccgccatctgatgagcagttgaaatctgg aactgcctctgttgtgtgcctgctgaataacttctatcccagagaggccaaagtacagtggaag gtggataacgccctccaatcgggtaactcccaggagagtgtcacagagcaggacagcaaggaca gcacctacagcctcagcagcaccctgacgctgagcaaagcagactacgagaaacacaaagtcta cgcctgcgaagtcacccatcagggcctgagctcgcccgtcacaaagagcttcaacaggggagag tgt Amino Acid sequence (SEQ ID NO: 434)

CNIWLVGGDCRGWQGGSSGGSGLSGRSDNHGGAVGLLAPPGGSDIQMTQSPSSLSASVGDRVTI

TCRASQSISSYLNWYQQKPGKAPKLLIYAASSLQSGVPSRFSGSGSGTDFTLTISSLQPEDFAT

YYCQQTVVAPPLFGQGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQGLSSPVTKSFNRGE

C

Anti-Jagged 1003/LP'/0001 activatable antibody Lc with spacer sequence
Nucleotide sequence (SEQ ID NO: 64)

Caaggccagtctggccagtgcaatatttggctcgtaggtggtgattgcaggggctggcaggggg gctcgagcggcggctctgtgcatatgcccctgggctttctgggacctggcggcctgtctggcag atccgataatcacggcggctccgacatccagatgacccagtctccatcctccctgtctgcatct gtaggagacagagtcaccatcacttgccgggcaagtcagagcattagcagctatttaaattggt atcagcagaaaccagggaaagcccctaagctcctgatctatgcggcatccagtttgcaaagtgg ggtcccatcaaggttcagtggcagtggatctgggacagatttcactctcaccatcagcagtctg -continued caacctgaagattttgcaacttactactgtcaacagacggttgtggcgcctccgttattcggcc aagggaccaaggtggaaatcaaacgtacggtggctgcaccatctgtcttcatcttcccgccatc tgatgagcagttgaaatctggaactgcctctgttgtgtgcctgctgaataacttctatcccaga gaggccaaagtacagtggaaggtggataacgccctccaatcgggtaactcccaggagagtgtca cagagcaggacagcaaggacagcacctacagcctcagcagcaccctgacgctgagcaaagcaga ctacgagaaacacaaagtctacgcctgcgaagtcacccatcagggcctgagctcgcccgtcaca aagagcttcaacaggggagagtgt Amino Acid sequence (SEQ ID NO: 65)

QGQSGQCNIWLVGGDCRGWQGGSSGGSVHMPLGFLGPGGLSGRSDNHGGSDIQMTQSPSSLSAS

VGDRVTITCRASQSISSYLNWYQQKPGKAPKLLIYAASSLQSGVPSRFSGSGSGTDFTLTISSL

QPEDFATYYCQQTVVAPPLFGQGTKVEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVT

KSFNRGEC

Anti-Jagged 1003/LP'/0001 activatable antibody Lc
Nucleotide sequence (SEQ ID NO: 435)

Tgcaatatttggctcgtaggtggtgattgcaggggctggcagggggggctcgagcggcggctctg tgcatatgcccctgggctttctgggacctggcggcctgtctggcagatccgataatcacggcgg ctccgacatccagatgacccagtctccatcctccctgtctgcatctgtaggagacagagtcacc atcacttgccgggcaagtcagagcattagcagctatttaaattggtatcagcagaaaccaggga aagcccctaagctcctgatctatgcggcatccagtttgcaaagtggggtcccatcaaggttcag tggcagtggatctgggacagatttcactctcaccatcagcagtctgcaacctgaagattttgca acttactactgtcaacagacggttgtggcgcctccgttattcggccaagggaccaaggtggaaa tcaaacgtacggtggctgcaccatctgtcttcatcttcccgccatctgatgagcagttgaaatc tggaactgcctctgttgtgtgcctgctgaataacttctatcccagagaggccaaagtacagtgg aaggtggataacgccctccaatcgggtaactcccaggagagtgtcacagagcaggacagcaagg acagcacctacagcctcagcagcaccctgacgctgagcaaagcagactacgagaaacacaaagt ctacgcctgcgaagtcacccatcagggcctgagctcgcccgtcacaaagagcttcaacagggga gagtgt Amino Acid sequence (SEQ ID NO: 436)

CNIWLVGGDCRGWQGGSSGGSVHMPLGFLGPGGLSGRSDNHGGSDIQMTQSPSSLSASVGDRVT

ITCRASQSISSYLNWYQQKPGKAPKLLIYAASSLQSGVPSRFSGSGSGTDFTLTISSLQPEDFA

TYYCQQTVVAPPLFGQGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQGLSSPVTKSFNRG

EC

Anti-Jagged 0001/LP'/1003 activatable antibody Lc with spacer
sequence
Nucleotide sequence (SEQ ID NO: 66)

Caaggccagtctggccagtgcaatatttggctcgtaggtggtgattgcaggggctggcaggggg gctcgagcggaggctctggcctgtctggcagatctgataaccacggcggcgtgcacatgcccct gggctttctgggacctggcggatctgacatccagatgacccagtctccatcctccctgtctgca tctgtaggagacagagtcaccatcacttgccgggcaagtcagagcattagcagctatttaaatt ggtatcagcagaaaccagggaaagcccctaagctcctgatctatgcggcatccagtttgcaaag -continued tggggtcccatcaaggttcagtggcagtggatctgggacagatttcactctcaccatcagcagt ctgcaacctgaagattttgcaacttactactgtcaacagacggttgtggcgcctccgttattcg gccaagggaccaaggtggaaatcaaacgtacggtggctgcaccatctgtcttcatcttcccgcc atctgatgagcagttgaaatctggaactgcctctgttgtgtgcctgctgaataacttctatccc agagaggccaaagtacagtggaaggtggataacgccctccaatcgggtaactcccaggagagtg tcacagagcaggacagcaaggacagcacctacagcctcagcagcaccctgacgctgagcaaagc agactacgagaaacacaaagtctacgcctgcgaagtcacccatcagggcctgagctcgcccgtc acaaagagcttcaacaggggagagtgt Amino Acid sequence (SEQ ID NO: 437)

QGQSGQCNIWLVGGDCRGWQGGSSGGSGLSGRSDNHGGVHMPLGFLGPGGSDIQMTQSPSSLSA

SVGDRVTITCRASQSISSYLNWYQQKPGKAPKLLIYAASSLQSGVPSRFSGSGSGTDFTLTISS

LQPEDFATYYCQQTVVAPPLFGQGTKVEIKRTVAAPSVFIFPPSDEQLKSGTASVVCLLNNFYP

REAKVQWKVDNALQSGNSQESVTEQDSKDSTYSLSSTLTLSKADYEKHKVYACEVTHQGLSSPV

TKSFNRGEC

Anti-Jagged 0001/LP'/1003 activatable antibody Lc
Nucleotide sequence (SEQ ID NO: 438)

Tgcaatatttggctcgtaggtggtgattgcaggggctggcagggggctcgagcggaggctctg gcctgtctggcagatctgataaccacggcggcgtgcacatgcccctgggctttctgggacctgg cggatctgacatccagatgacccagtctccatcctccctgtctgcatctgtaggagacagagtc accatcacttgccgggcaagtcagagcattagcagctatttaaattggtatcagcagaaaccag ggaaagcccctaagctcctgatctatgcggcatccagtttgcaaagtggggtcccatcaaggtt cagtggcagtggatctgggacagatttcactctcaccatcagcagtctgcaacctgaagatttt gcaacttactactgtcaacagacggttgtggcgcctccgttattcggccaagggaccaaggtgg aaatcaaacgtacggtggctgcaccatctgtcttcatcttcccgccatctgatgagcagttgaa atctggaactgcctctgttgtgtgcctgctgaataacttctatcccagagaggccaaagtacag tggaaggtggataacgccctccaatcgggtaactcccaggagagtgtcacagagcaggacagca aggacagcacctacagcctcagcagcaccctgacgctgagcaaagcagactacgagaaacacaa agtctacgcctgcgaagtcacccatcagggcctgagctcgcccgtcacaaagagcttcaacagg ggagagtgt Amino Acid sequence (SEQ ID NO: 439)

CNIWLVGGDCRGWQGGSSGGSGLSGRSDNHGGVHMPLGFLGPGGSDIQMTQSPSSLSASVGDRV

TITCRASQSISSYLNWYQQKPGKAPKLLIYAASSLQSGVPSRFSGSGSGTDFTLTISSLQPEDF

ATYYCQQTVVAPPLFGQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEVTHQGLSSPVTKSFNR

GEC

Anti-Jagged activatable antibody Hc (SEQ ID NO: 67)

EVQLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSSASTKGPSVF

PLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKE

-continued

YKCKVSNKALPAPIEKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEALHNHYTQKSLSLSPG

K

Anti-Jagged CM1-CM2 Activatable antibody in vitro binding and activation was evaluated as follows.

Anti-Jagged activatable antibodies were expressed from transiently transfected HEK-293 cells and purified from the culture supernatant by Protein A chromatography. To verify that the anti-Jagged CM1-CM2 activatable antibodies could be activated by both MMPs and serine proteases, the purified activatable antibodies were digested with uPA and/or MMP14 and subsequently evaluated for their ability to bind to human Jagged 1-Fc by ELISA. ELISA plates (Greiner Bio-One #655061) were coated with human Jag1-Fc (R&D #1277-JG-050) in Hank's Balanced Salt Solution pH 7.4 (HBSS) (Teknova #H8057) at 1 microgram/ml overnight at 4° C.; as used herein, microgram(s) is also represented by ug and μg. Plates were blocked with 2% Nonfat dry milk (NFDM) in HBSS for 1 hour at room temperature (RT). The block was removed and anti-Jagged antibody 4D11, an anti-Jagged CM1-CM2 activatable antibody, or a digested activatable antibody was added to the indicated concentration in 2% NFDM/HBSS and incubated at RT for 1 hours. The ELISA plate was washed 3 times with excess HBSS, 0.05% TWEEN (HBSS-T) before adding the mouse anti-human IgG, F'Ab(2) specific, HRP conjugated (Jackson ImmunoResearch #209-035-097) diluted to 1:30,000 in 2% NFDM/HBSS. The ELISA plate was subsequently washed 3× with HBSS-T and developed using 1-Step TMB Substrate (Pierce/Thermo Fisher #NC0140927). The plates were read at $OD_{450}$ and plotted using Prism software.

Figure 1B:
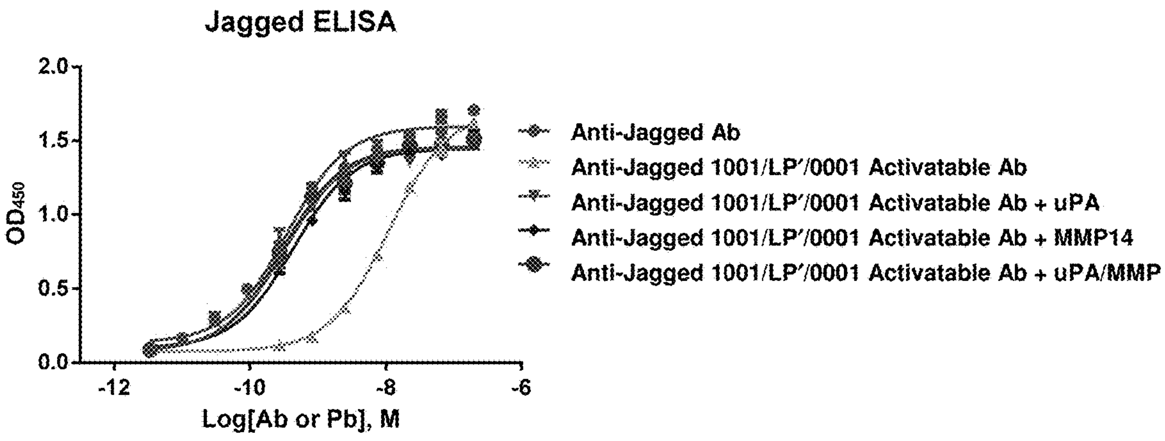

FIG. 1 demonstrates the anti-Jagged CM1-CM2 activatable antibodies (a) were effectively masked prior to cleavage by uPA or MMP14 and (b) showed binding equivalent to the antibody when cleaved by uPA or MMP14 or a combination of uPA and MMP14.

Anti-Jagged activatable antibody containing CM1-CM2 Substrate pharmacokinetics were evaluated in non-tumor bearing nude mice as follows.

As a surrogate for the stability of the mask and substrate, the pharmacokinetics of the anti-Jagged activatable antibodies containing the CM1-CM2 substrates 2001 and 1001/LP'/0001 were compared to that of the anti-Jagged antibody in non-tumor bearing mice. The mouse/human cross-reactive anti-Jagged antibody shows rapid clearance in mice due to the binding of Jagged 1/2 in normal tissues. If the anti-Jagged CM1-CM2 Activatable antibody remains masked (stable) in circulation, then the activatable antibody should avoid target-mediated clearance and show prolonged serum half-life.

The plasma pharmacokinetics of the anti-Jagged antibody and activatable antibodies were evaluated as follows. As shown in Table B, each group consisted of 2 cohorts of 5 mice. Mice were given a single intravenous dose of 5 mg/kg of the indicated compound. Lithium heparinized plasma was collected from cohort 1 at 24 hours, 96 hours, and 10 days post dose while plasma was collected from cohort 2 at 48 hours, 7 days, and 14 days by the retro-orbital route with isoflurane anesthesia. Total plasma human IgG levels were detected using a human IgG sandwich ELISA. Briefly, ELISA plates (Costar 3590 Fisher Scientific Cat. #07-200-35) were coated with AffiniPure Goat Anti-Human IgG F(ab')2 Fragment Specific, (Jackson ImmunoResearch Cat. #109-006-097) in phosphate buffered saline (PBS) at 1 ug/ml overnight at 4° C. Plates were blocked with Superblock (ScyTek Laboratories Cat. #AAA500) for 1 hour at room temperature (RT). The block was removed and an appropriate dilution of standard (test article) and test samples (plasma samples) were added to the plate and incubated at RT for 1 hour. The ELISA plate was washed 3 times with excess PBS, 0.05% TWEEN (PBS-T) before adding the AffiniPure Goat Anti-Human IgG F(ab')2 Fragment Specific Horseradish Peroxidase (HRP) (Jackson ImmunoResearch Cat. #109-035-097) diluted to 1:25,000. The ELISA plate was subsequently washed 3× with PBS-T and developed using 1-Step TMB Substrate (Pierce/Thermo Fisher #NC0140927) following the manufacturers protocol. Serum human IgG levels were calculated by comparing the test sample values to the standard curve. Pharmacokinetic parameters were calculated using a noncompartmental analysis with sparse sampling (Phoenix WinNonlin v6.3).

Figure 2:
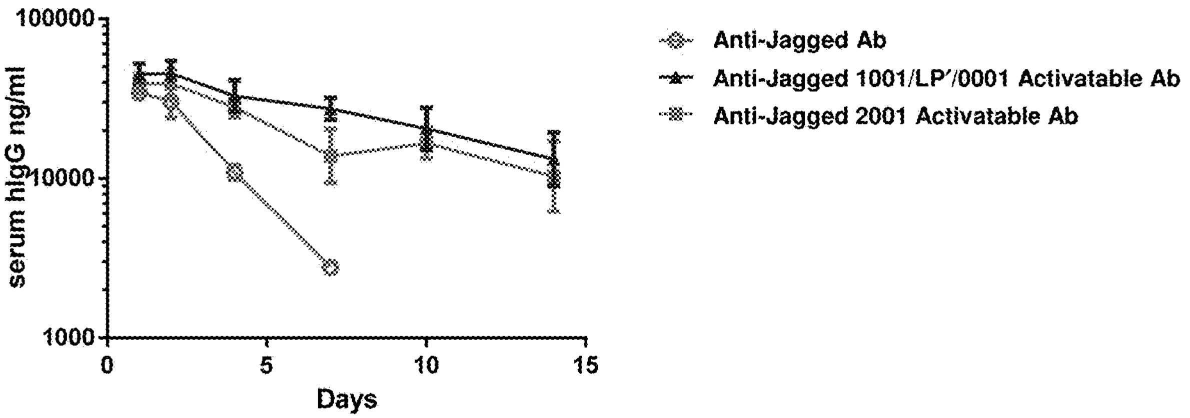
FIG. 2 is a graph depicting human IgG serum concentrations for anti-Jagged antibody and the 1001/LP'/0001 and 2001 activatable antibodies following a single 5 mg/kg intravenous dose. The anti-Jagged antibody is rapidly cleared due to target-mediated clearance. In contrast, the anti-Jagged activatable antibodies remain masked in circulation.

As shown in FIG. 2, the anti-Jagged antibody was rapidly cleared and was below the detection limit of the assay by day 10. In contrast, the anti-Jagged CM1-CM2 activatable antibodies 1001/LP'/0001 and 2001 showed significantly extended half-life indicating that the activatable antibodies remained stable and well masked in circulation.

TABLE B

Groups and dosing for the pharmacokinetic analysis of the anti-Jagged CM1-CM2 Activatable antibodies 2001 and 1001/LP'/0001.

| Group | N | Treatment | Dose (mg/kg) | Dose volume (mL/kg) | Schedule | Route |
|---|---|---|---|---|---|---|
| 1 | 2 × 5 | Anti-Jagged | 5 | 10 | Single | IP |
| 2 | 2 × 5 | Anti-Jagged Activatable antibody 2001 | 5 | 10 | Single | IP |
| 3 | 2 × 5 | Anti-Jagged Activatable antibody 1001/LP'/0001 | 5 | 10 | Single | IP |

In vivo evaluation of the safety and efficacy of an anti-Jagged CM1-CM2 substrate containing activatable antibody drug conjugate was performed as follows.

The efficacy of the anti-Jagged CM1-CM2 substrate containing 2001 activatable antibody drug conjugate, which comprised the anti-Jagged 2001 activatable antibody conjugated to maytansinoid DM4 (see, e.g., U.S. Pat. No. 7,276,497) via a SPDB linker, was evaluated in the human breast cancer cell line HCC1806 xenograft tumor model. HCC1806 cells were harvested during log phase growth and resuspended in 50% Matrigel (BD Biosciences) in PBS at a concentration of $5\times10^7$ cells/ml. Mice were injected subcutaneously in the right flank with $5\times10^6$ cells and allowed to grow to a mean volume of 100-150 $mm^3$. Mice were randomized and dosed as indicated in Table C. Tumor volume and body weight were measured twice weekly for the duration of the study, and measures of efficacy and safety, respectively were obtained.

Figure 3:
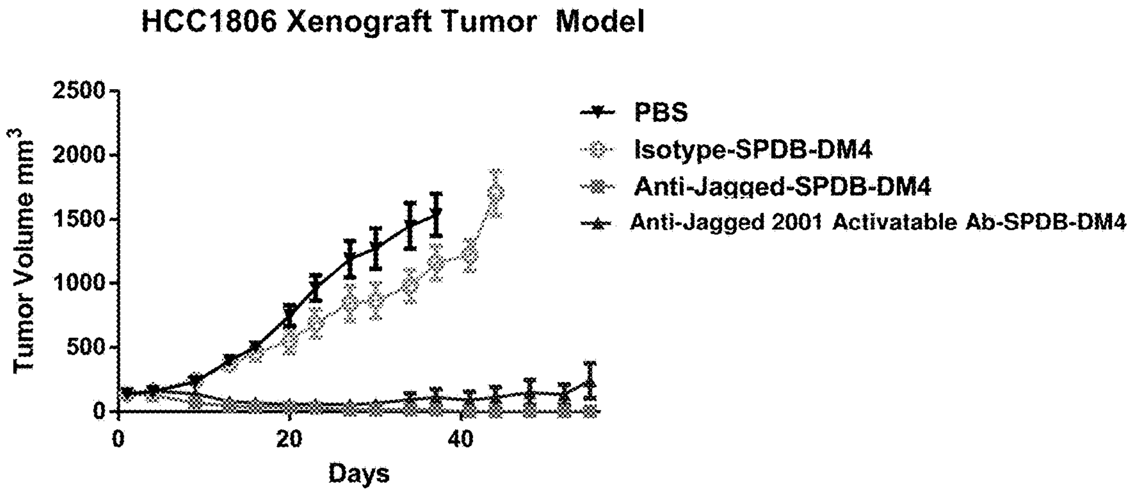
FIG. 3 is a graph depicting HCC1806 tumor volume (group mean±SEM n=8) plotted vs time post initial dose. Groups were dosed on day 1 and day 8 of the study. The anti-Jagged-SPDB-DM4 antibody and anti-Jagged 2001 activatable antibody-SPDB-DM4 groups both showed tumor regression while the isotype-SPDB-DM4 group did not show tumor growth inhibition.
Figure 4:
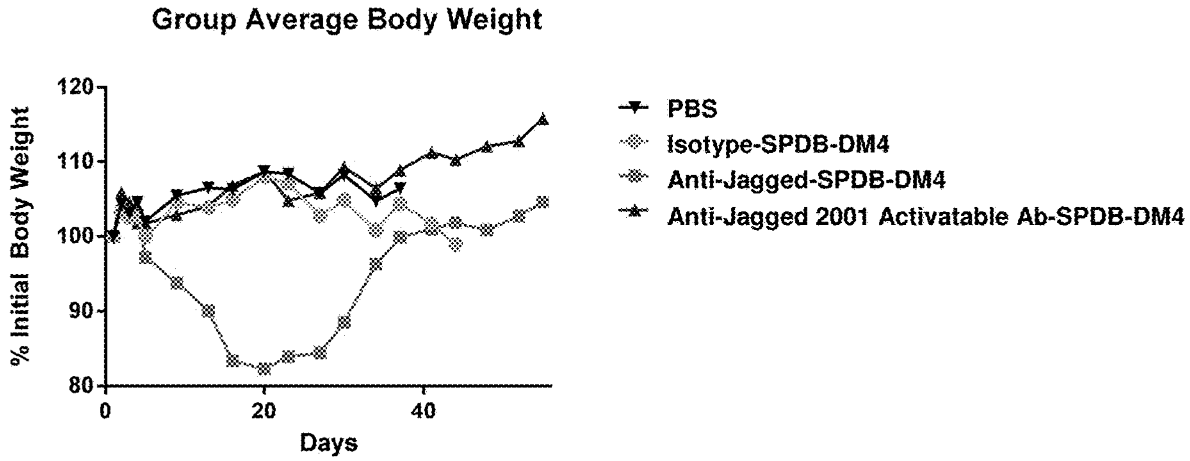
FIG. 4 is a graph depicting percent initial body weight (group mean n=8) plotted vs time post initial dose. Groups were dosed on day 1 and day 8 of the study. Animals in the anti-Jagged-SPDB-DM4 ADC treated group showed significant body weight loss, whereas the PBS, Isotype-SPDB-DM4 ADC, and anti-Jagged 2001 activatable antibody-SPDB-DM4 treated animals showed no significant weight loss.
Figure 5:
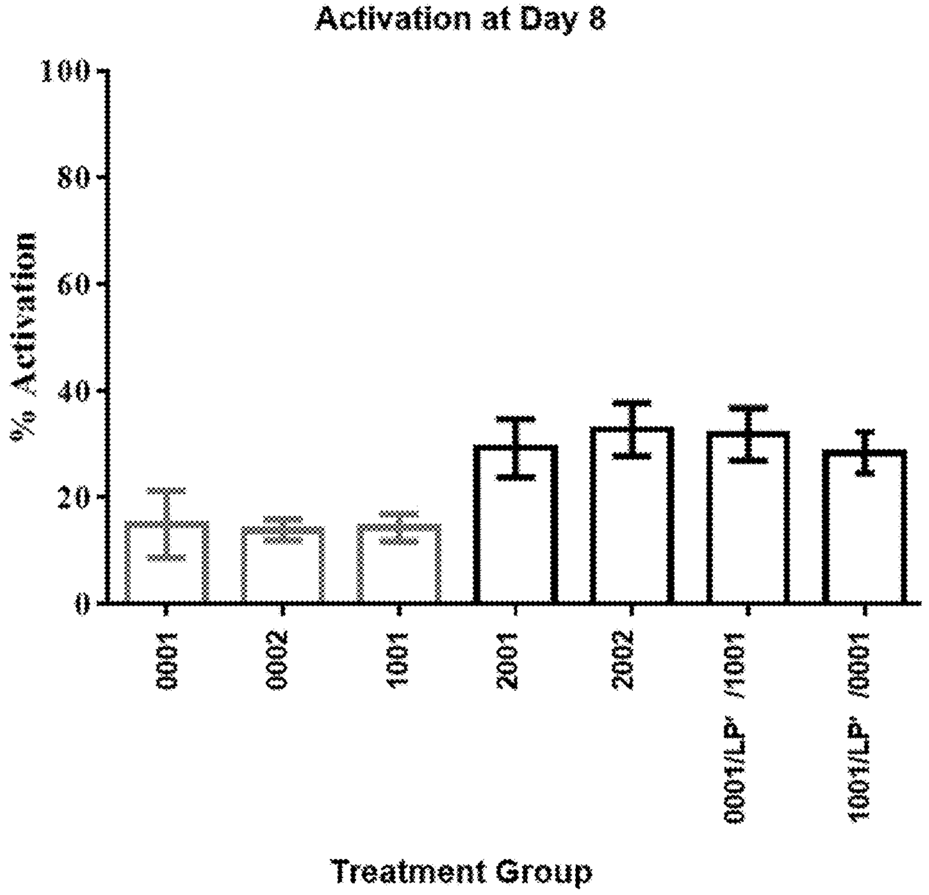
FIG. 5 is a graph depicting in vivo activation of EGFR activatable antibodies measured in plasma 8 days post-dose of 12.5 mg/kg of such EGFR activatable antibodies in H292 xenograft tumor-bearing mice.

FIG. 3 shows the group mean tumor volume±the standard error of the mean (SEM) for the PBS, Isotype-SPDB-DM4, anti-Jagged-SPDB-DM4 drug conjugate (ADC), and anti-Jagged 2001 activatable antibody drug conjugate treated animals. Neither control group (PBS nor Isotype-SPDB-DM4) showed tumor growth inhibition while both the anti-Jagged ADC and anti-Jagged 2001 activatable antibody drug conjugate groups showed tumor regression. The animals treated with the anti-Jagged ADC showed significant side effects as measured by weight loss, as shown in FIG. 4. However, animals treated with anti-Jagged 2001 activatable antibody drug conjugate showed no weight loss (also shown in FIG. 4) demonstrating that the anti-Jagged CM1-CM2 activatable antibody drug conjugate's activity was localized to the tumor.

TABLE C

Groups and dose schedule for the HCC1806 study

| Group | Count | Treatment | Dose (mg/kg) | Schedule | Route |
|---|---|---|---|---|---|
| 1 | 8 | PBS | 10 | q7d × 2 | IV |
| 3 | 8 | Isotype-SPDB-DM4 | 10 | q7d × 2 | IV |
| 4 | 8 | Anti-Jagged-SPDB-DM4 | 10 | q7d × 2 | IV |

TABLE C-continued

Groups and dose schedule for the HCC1806 study

| Group | Count | Treatment | Dose (mg/kg) | Schedule | Route |
|---|---|---|---|---|---|
| 5 | 8 | Anti-Jagged 2001 activatable antibody-SPDB-DM4 | 10 | q7d × 2 | IV |

Example 2. Matrix Metalloprotease (MMP) and Serine Protease (SP) Cleavable Anti-EGFR Activatable Antibodies This Example demonstrates the generation and evaluation of activatable antibodies that bind Epidermal Growth Factor Receptor (EGFR), where the activatable antibodies are activated in the presence of at least one matrix metalloprotease (MMP) and at least one serine protease.

The activatable anti-EGFR antibodies used in this Example were generated using a method similar to the methods used in Example 1 to generate activatable anti-Jagged antibodies.

The studies described herein used the following substrate sequences, where LP' is a linking peptide between CM1 and CM2. For all CM1-CM2 substrates in the Table below, LP' is GGSGGS (SEQ ID NO: 350):

| CM1-CM2 Substrate | Amino Acid Sequence | Nucleotide Sequence |
|---|---|---|
| 0001 | LSGRSDNH (SEQ ID NO: 18) | TTAAGCGGGCGGTCGGACAACCAC (SEQ ID NO: 23) |
| 0002 | LSGRSGNH (SEQ ID NO: 19) | CTTAGCGGGCGGAGCGGCAACCAC (SEQ ID NO: 24) |
| 1001 | ISSGLLSS (SEQ ID NO: 20) | ATCTCCTCCGGGCTACTGAGTTCT (SEQ ID NO: 25) |
| 1002 | QNQALRMA (SEQ ID NO: 21) | CAGAACCAGGCGCTCAGAATGGCA (SEQ ID NO: 26) |
| 2001 | ISSGLLSGRSDNH (SEQ ID NO: 1) | ATATCATCCGGCCTCCTTAGCGGC CGTTCCGACAATCAC (SEQ ID NO: 27) |
| 2002 | ISSGLLSGRSGNH (SEQ ID NO: 22) | ATAAGTTCTGGGCTCCTGTCGGGC CGGAGTGGAAATCAC (SEQ ID NO: 28) |
| 0001/LP'/1001 | LSGRSDNHGGSGGSISSGLLSS (SEQ ID NO: 11) | CTGAGCGGGCGGTCCGATAATCAT GGTGGTTCAGGAGGGAGTATTTCT TCCGGCTTACTGAGTAGC (SEQ ID NO: 29) |
| 1001/LP'/0001 | ISSGLLSSGGSGGSLSGRSDNH (SEQ ID NO: 2) | ATCTCCTCTGGGTTGCTTTCTTCA GGAGGTTCAGGGGGGAGCCTGAGC GGACGCTCCGACAACCAT (SEQ ID NO: 30) |
| 0002/LP'/1001 | LSGRSGNHGGSGGSISSGLLSS (SEQ ID NO: 12) | CTCTCAGGAAGATCCGGAAATCAT GGGGGGTCTGGGGGGAGTATCTCA TCAGGTCTGCTGAGCAGC (SEQ ID NO: 31) |
| 1001/LP'/0002 | ISSGLLSSGGSGGSLSGRSGNH (SEQ ID NO: 13) | ATCTCAAGTGGGCTGTTAAGTTCC GGCGGCAGTGGAGGGTCCCTAAGC GGCCGCAGCGGGAATCAC (SEQ ID NO: 32) |

-continued

| CM1-CM2 Substrate | Amino Acid Sequence | Nucleotide Sequence |
|---|---|---|
| 0001/LP'/1002 | LSGRSDNHGGSGGSQNQALRMA (SEQ ID NO: 14) | CTCTCTGGCCGCTCCGATAATCAT GGTGGATCCGGTGGCTCTCAGAAC CAGGCACTACGGATGGCA (SEQ ID NO: 33) |
| 1002/LP'/0001 | QNQALRMAGGSGGSLSGRSDNH (SEQ ID NO: 15) | CAGAACCAGGCGCTCAGGATGGCA GGGGGGAGTGGCGGAAGCCTTTCT GGTCGATCCGATAATCAC (SEQ ID NO: 34) |
| 0002/LP'/1002 | LSGRSGNHGGSGGSQNQALRMA (SEQ ID NO: 16) | CTTAGCGGACGCTCTGGCAACCAC GGAGGATCTGGAGGAAGTCAGAAC CAGGCCTTGCGCATGGCC (SEQ ID NO: 35) |
| 1002/LP'/0002 | QNQALRMAGGSGGSLSGRSGNH (SEQ ID NO: 17) | CAAAACCAGGCTCTGCGCATGGCT GGGGGGTCTGGTGGGAGCCTGAGC GGGCGGTCAGGAAACCAC (SEQ ID NO: 36) |

Anti-EGFR Heavy Chain (Hc):
Nucleotide sequence:
(SEQ ID NO: 68)

CAGGTACAGCTGAAACAGTCTGGACCCGGGCTTGTACAGCCTAGTCAGTCACTGTCTATCACCT

GTACCGTCTCAGGTTTTAGCCTGACAAATTACGGTGTGCATTGGGTACGCCAGTCTCCCGGTAA

GGGGCTGGAGTGGCTCGGCGTGATCTGGTCCGGGGGGAACACAGATTATAATACTCCTTTCACA

TCTAGACTGTCCATCAACAAAGACAACTCCAAATCGCAGGTTTTTTTCAAGATGAATTCCCTGC

AATCACAGGACACTGCCATCTATTATTGCGCGAGGGCCCTGACTTATTATGACTATGAGTTCGC

TTATTGGGGCCAGGGGACGCTTGTGACCGTAAGCGCTGCTAGTACCAAGGGCCCCAGTGTGTTC

CCCCTTGCCCCCAGCAGTAAGTCCACCTCAGGTGGCACAGCTGCCCTTGGGTGCCTTGTGAAGG

ATTACTTCCCAGAACCAGTGACCGTGAGCTGGAATTCCGGAGCCCTTACCAGCGGTGTGCATAC

CTTTCCGGCCGTCCTGCAAAGCAGCGGACTTTACAGTCTGTCTAGCGTGGTCACCGTGCCCAGC

AGCAGCCTGGGTACACAGACGTATATTTGCAACGTTAATCACAAACCCTCAAACACAAAGGTGG

ACAAGAAAGTGGAGCCTAAATCATGTGATAAGACACATACATGCCCTCCCTGCCCTGCACCGGA

GCTCTTAGGTGGACCTTCAGTCTTTTTATTTCCACCTAAACCCAAAGATACACTTATGATCTCA

CGGACACCCGAGGTGACCTGCGTTGTCGTGGATGTCTCACACGAAGACCCTGAAGTGAAATTCA

ATTGGTATGTTGACGGTGTTGAGGTGCATAACGCAAAGACCAAGCCACGCGAGGAGCAGTATAA

TAGCACCTATAGGGTAGTCAGCGTACTGACTGTTCTGCATCAGGATTGGCTGAACGGTAAAGAG

TACAAATGCAAGGTCTCAAACAAGGCTCTCCCTGCCCCGATCGAGAAGACAATTTCTAAGGCCA

AAGGGCAGCCCCGGGAACCACAAGTCTATACCCTGCCACCCAGTCGGGATGAACTAACAAAAAA

TCAGGTGTCTCTAACCTGCCTGGTGAAGGGATTTTACCCTTCCGATATAGCTGTGGAGTGGGAG

TCTAATGGCCAACCAGAGAATAATTACAAGACTACCCCCCCCGTTCTTGACAGTGATGGCTCGT

TCTTCTTATACTCAAAATTAACAGTCGACAAATCCCGATGGCAACAGGGCAATGTGTTTAGCTG

TAGCGTGATGCATGAAGCCCTGCACAACCATTACACACAGAAGTCTCTGTCCTTGTCACCTGGC

AAG

Amino acid Sequence:
(SEQ ID NO: 69)

QVQLKQSGPGLVQPSQSLSITCTVSGFSLTNYGVHWVRQSPGKGLEWLGVIWSGGNTDYNTPFT

SRLSINKDNSKSQVFFKSLQSQDTAIYYCARALTYYDYEFAYWGQGTLVTVSAASTKGPSVFPL

-continued

APSSKSTSGGTAALGCLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVFLFPPKPKDTLMISRT

PEVTCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHNHYTQKSLSLSPGK

Anti-EGFR Light Chain:
Nucleotide Sequence:
(SEQ ID NO: 70)
ACCCAAATCCTCCTGACCCAGTCCCCTGTTATCCTTTCTGTGTCGCCCGGGGAGCGCGTTAGCT

TTAGCTGCCGCGCCAGTCAGTCAATCGGAACAAACATCCATTGGTACCAGCAGCGTACGAACGG

CAGTCCAAGGCTGCTGATCAAATACGCAAGTGAATCTATATCGGGGATTCCGTCTCGGTTCAGC

GGATCCGGAAGCGGGACTGACTTTACGCTCTCCATAAATAGCGTCGAAAGTGAGGACATTGCAG

ACTATTACTGTCAGCAGAATAACAACTGGCCGACCACATTTGGGGCCGGAACCAAGTTGGAACT

GAAGCGCACTGTGGCAGCTCCTAGTGTTTTTATTTTCCCCCCTTCTGACGAGCAACTGAAAAGT

GGTACAGCTTCAGTAGTTTGTTTGCTCAATAATTTCTACCCACGGGAAGCAAAGGTGCAGTGGA

AAGTCGACAACGCATTACAGAGCGGCAACTCTCAAGAAAGCGTGACGGAGCAGGATAGCAAGGA

CTCAACATATTCCTTGTCTTCCACTCTCACTCTGTCAAAGGCTGATTATGAGAAGCATAAGGTG

TATGCGTGCGAAGTGACACACCAGGGATTATCAAGCCCAGTGACCAAGTCCTTTAACCGTGGCG

AATGC

Amino acid Sequence:
(SEQ ID NO: 111)
QILLTQSPVILSVSPGERVSFSCRASQSIGTNIHWYQQRTNGSPRLLIKYASESISGIPSRFSG

SGSGTDFTLSINSVESEDIADYYCQQNNNWPTTFGAGTKLELKRTVAAPSVFIFPPSDEQLKSG

TASVVCLLNNFYPREAKVQWKVDNALQSGNSQESVTEQDSKDSTYSLSSTLTLSKADYEKHKVY

ACEVTHQGLSSPVTKSFNRGEC

Anti-EGFR 0001 Activatable Antibody Light Chain with spacer
sequence:
Nucleotide sequence:
(SEQ ID NO: 72)
CAGGGCCAGAGCGGCCAATGCATCTCCCCCCGCGGTTGTCCCGACGGGCCGTACGTGATGTACG

GCAGCTCCGGCGGCAGTGGGGGTAGCGGTGGGTCCGGGCTGAGTGGCCGGTCCGACAATCACGG

GAGCTCGGGAACACAGATTCTGCTGACGCAATCTCCCGTGATCCTCTCGGTCTCACCCGGCGAA

CGGGTCTCGTTCAGCTGCAGAGCGTCCCAATCAATCGGGACCAATATTCACTGGTACCAGCAAA

GGACTAATGGGTCTCCCCGGCTGCTGATAAAATACGCCTCCGAGTCTATCTCGGGCATCCCATC

CCGATTTAGTGGTAGCGGAAGCGGCACTGATTTCACCTTGTCTATTAACAGCGTAGAATCTGAG

GACATTGCAGACTATTACTGTCAGCAGAATAACAATTGGCCTACAACTTTCGGCGCCGGGACCA

AACTAGAGTTAAAGCGTACTGTGGCTGCCCCCAGCGTTTTTATTTTTCCGCCCAGCGACGAACA

GCTGAAGTCAGGCACAGCCTCTGTGGTGTGTCTCCTGAATAACTTCTACCCCAGAGAGGCCAAA

GTTCAGTGGAAAGTGGACAATGCCTTGCAGTCCGGAAACAGTCAAGAGTCCGTGACCGAGCAGG

ACAGTAAGGATAGCACGTATAGCCTCTCTAGTACTTTAACACTGTCCAAGGCCGACTACGAGAA

GCACAAGGTGTACGCATGCGAAGTGACCCATCAGGGGCTTTCCTCCCCCGTCACCAAGTCTTTC

AATCGCGGGGAGTGT

Amino acid Sequence:
(SEQ ID NO: 73)
QGQSGQCISPRGCPDGPYVMYGSSGGSGGSGGSGLSGRSDNHGSSGTQILLTQSPVILSVSPGE

RVSFSCRASQSIGTNIHWYQQRTNGSPRLLIKYASESISGIPSRFSGSGSGTDFTLSINSVESE

-continued

DIADYYCQQNNNWPTTFGAGTKLELKRTVAAPSVFIFPPSDEQLKSGTASVVCLLNNFYPREAK

VQWKVDNALQSGNSQESVTEQDSKDSTYSLSSTLTLSKADYEKHKVYACEVTHQGLSSPVTKSF

NRGEC

Anti-EGFR 0001 Activatable Antibody Light Chain:
Nucleotide sequence:

(SEQ ID NO: 440)

TGCATCTCCCCCCGCGGTTGTCCCGACGGGCCGTACGTGATGTACGGCAGCTCCGGCGGCAGTG

GGGGTAGCGGTGGGTCCGGGCTGAGTGGCCGGTCCGACAATCACGGGAGCTCGGGAACACAGAT

TCTGCTGACGCAATCTCCCGTGATCCTCTCGGTCTCACCCGGCGAACGGGTCTCGTTCAGCTGC

AGAGCGTCCCAATCAATCGGGACCAATATTCACTGGTACCAGCAAAGGACTAATGGGTCTCCCC

GGCTGCTGATAAAATACGCCTCCGAGTCTATCTCGGGCATCCCATCCCGATTTAGTGGTAGCGG

AAGCGGCACTGATTTCACCTTGTCTATTAACAGCGTAGAATCTGAGGACATTGCAGACTATTAC

TGTCAGCAGAATAACAATTGGCCTACAACTTTCGGCGCCGGGACCAAACTAGAGTTAAAGCGTA

CTGTGGCTGCCCCCAGCGTTTTTATTTTTCCGCCCAGCGACGAACAGCTGAAGTCAGGCACAGC

CTCTGTGGTGTGTCTCCTGAATAACTTCTACCCCAGAGAGGCCAAAGTTCAGTGGAAAGTGGAC

AATGCCTTGCAGTCCGGAAACAGTCAAGAGTCCGTGACCGAGCAGGACAGTAAGGATAGCACGT

ATAGCCTCTCTAGTACTTTAACACTGTCCAAGGCCGACTACGAGAAGCACAAGGTGTACGCATG

CGAAGTGACCCATCAGGGGCTTTCCTCCCCCGTCACCAAGTCTTTCAATCGCGGGGAGTGT

Amino acid Sequence:

(SEQ ID NO: 441)

CISPRGCPDGPYVMYGSSGGSGGSGGSGLSGRSDNHGSSGTQILLTQSPVILSVSPGERVSFSC

RASQSIGTNIHWYQQRTNGSPRLLIKYASESISGIPSRFSGSGSGTDFTLSINSVESEDIADYY

CQQNNNWPTTFGAGTKLELKRTVAAPSVFIFPPSDEQLKSGTASVVCLLNNFYPREAKVQWKVD

NALQSGNSQESVTEQDSKDSTYSLSSTLTLSKADYEKHKVYACEVTHQGLSSPVTKSFNRGEC

Anti-EGFR 0002 Activatable Antibody Light Chain with spacer
sequence:
Nucleotide sequence:

(SEQ ID NO: 74)

CAAGGTCAGTCCGGACAGTGTATTTCCCCTAGAGGTTGCCCTGACGGGCCGTATGTCATGTACG

GTAGTTCTGGCGGTAGTGGCGGATCTGGCGGCAGTGGGCTGAGCGGACGTAGCGGGAATCACGG

CTCATCCGGGACGCAGATACTGCTGACCCAGTCCCCCGTGATCCTGTCCGTGTCACCGGGCGAA

AGGGTCAGTTTCTCTTGCCGAGCATCACAGTCCATAGGTACGAATATCCATTGGTACCAGCAGC

GGACCAATGGGAGCCCAAGACTGCTCATTAAGTACGCATCTGAGAGTATCTCAGGCATTCCAAG

CAGGTTTTCCGGCAGTGGGAGCGGCACTGACTTCACCCTCAGCATTAACAGCGTGGAAAGCGAA

GACATTGCAGATTACTACTGCCAACAGAACAATAACTGGCCTACTACATTCGGGGCAGGAACTA

AGTTGGAGCTCAAACGTACCGTCGCTGCTCCTAGCGTATTTATTTTCCCTCCTAGCGATGAACA

GTTGAAATCTGGTACCGCTAGTGTTGTGTGCTTACTGAACAACTTTTATCCCCGGGAGGCCAAG

GTACAATGGAAGGTGGACAATGCCCTCCAATCAGGGAACAGCCAGGAGTCTGTTACCGAGCAGG

ACTCCAAGGACAGCACCTACAGCCTGAGCTCTACCCTTACATTGAGCAAGGCTGATTATGAGAA

GCATAAGGTCTACGCTTGTGAGGTGACCCATCAGGGGCTCAGCAGCCCGGTGACAAAAAGCTTT

AACCGGGGGGAATGC

Amino acid Sequence:

(SEQ ID NO: 75)

QGQSGQCISPRGCPDGPYVMYGSSGGSGGSGGSGLSGRSGNHGSSGTQILLTQSPVILSVSPGE

RVSFSCRASQSIGTNIHWYQQRTNGSPRLLIKYASESISGIPSRFSGSGSGTDFTLSINSVESE

DIADYYCQQNNNWPTTFGAGTKLELKRTVAAPSVFIFPPSDEQLKSGTASVVCLLNNFYPREAK

-continued

VQWKVDNALQSGNSQESVTEQDSKDSTYSLSSTLTLSKADYEKHKVYACEVTHQGLSSPVTKSF

NRGEC

Anti-EGFR 0002 Activatable Antibody Light Chain:
Nucleotide sequence:

(SEQ ID NO: 442)

TGTATTTCCCCTAGAGGTTGCCCTGACGGGCCGTATGTCATGTACGGTAGTTCTGGCGGTAGTG

GCGGATCTGGCGGCAGTGGGCTGAGCGGACGTAGCGGGAATCACGGCTCATCCGGGACGCAGAT

ACTGCTGACCCAGTCCCCCGTGATCCTGTCCGTGTCACCGGGCGAAAGGGTCAGTTTCTCTTGC

CGAGCATCACAGTCCATAGGTACGAATATCCATTGGTACCAGCAGCGGACCAATGGGAGCCCAA

GACTGCTCATTAAGTACGCATCTGAGAGTATCTCAGGCATTCCAAGCAGGTTTTCCGGCAGTGG

GAGCGGCACTGACTTCACCCTCAGCATTAACAGCGTGGAAAGCGAAGACATTGCAGATTACTAC

TGCCAACAGAACAATAACTGGCCTACTACATTCGGGGCAGGAACTAAGTTGGAGCTCAAACGTA

CCGTCGCTGCTCCTAGCGTATTTATTTTCCCTCCTAGCGATGAACAGTTGAAATCTGGTACCGC

TAGTGTTGTGTGCTTACTGAACAACTTTTATCCCCGGGAGGCCAAGGTACAATGGAAGGTGGAC

AATGCCCTCCAATCAGGGAACAGCCAGGAGTCTGTTACCGAGCAGGACTCCAAGGACAGCACCT

ACAGCCTGAGCTCTACCCTTACATTGAGCAAGGCTGATTATGAGAAGCATAAGGTCTACGCTTG

TGAGGTGACCCATCAGGGGCTCAGCAGCCCGGTGACAAAAAGCTTTAACCGGGGGGAATGC

Amino acid Sequence:

(SEQ ID NO: 443)

CISPRGCPDGPYVMYGSSGGSGGSGGSGLSGRSGNHGSSGTQILLTQSPVILSVSPGERVSFSC

RASQSIGTNIHWYQQRTNGSPRLLIKYASESISGIPSRFSGSGSGTDFTLSINSVESEDIADYY

CQQNNNWPTTFGAGTKLELKRTVAAPSVFIFPPSDEQLKSGTASVVCLLNNFYPREAKVQWKVD

NALQSGNSQESVTEQDSKDSTYSLSSTLTLSKADYEKHKVYACEVTHQGLSSPVTKSFNRGEC

Anti-EGFR 1001 Activatable Antibody Light Chain with spacer
sequence:
Nucleotide sequence:

(SEQ ID NO: 76)

CAGGGGCAGTCTGGGCAGTGTATTAGCCCCAGGGGGTGCCCCGACGGGCCTTACGTGATGTATG

GCAGCTCCGGTGGCAGCGGAGGCTCTGGCGGGAGTGGGATCAGTTCCGGCCTGCTGAGCTCCGG

GTCAAGCGGGACCCAGATCTTGCTCACCCAATCACCAGTGATCCTAAGCGTGAGCCCTGGCGAA

CGGGTCAGCTTCTCTTGCCGGGCATCTCAGAGTATTGGCACTAACATACACTGGTACCAGCAGC

GAACCAATGGGTCCCCCCGCCTTCTAATCAAATATGCTAGCGAATCCATTTCAGGAATTCCTAG

CCGATTTAGCGGCAGCGGATCAGGCACTGACTTCACTCTGTCAATCAACTCAGTTGAAAGCGAG

GACATTGCAGACTACTATTGCCAGCAGAATAATAATTGGCCCACTACATTTGGAGCTGGAACAA

AATTGGAGCTTAAGAGGACAGTGGCTGCGCCTAGTGTATTTATCTTTCCCCCCTCTGACGAACA

GTTGAAATCGGGAACCGCATCCGTCGTCTGTTTACTGAACAACTTCTATCCCAGAGAGGCCAAA

GTGCAGTGGAAAGTGGATAATGCTTTGCAGTCTGGCAACAGCCAGGAAAGCGTGACGGAGCAGG

ACTCAAAGGATAGTACATACTCCCTGTCCTCCACCCTGACTCTGAGTAAGGCCGACTACGAGAA

GCACAAGGTCTACGCCTGCGAAGTGACGCACCAAGGGCTATCGAGCCCGGTCACCAAGTCTTTC

AATCGTGGAGAATGC

Amino acid Sequence:

(SEQ ID NO: 77)

QGQSGQCISPRGCPDGPYVMYGSSGGSGGSGGSGISSGLLSSGSSGTQILLTQSPVILSVSPGE

RVSFSCRASQSIGTNIHWYQQRTNGSPRLLIKYASESISGIPSRFSGSGSGTDFTLSINSVESE

-continued

DIADYYCQQNNNWPTTFGAGTKLELKRTVAAPSVFIFPPSDEQLKSGTASVVCLLNNFYPREAK

VQWKVDNALQSGNSQESVTEQDSKDSTYSLSSTLTLSKADYEKHKVYACEVTHQGLSSPVTKSF

NRGEC

Anti-EGFR 1001 Activatable Antibody Light Chain:
Nucleotide sequence:

(SEQ ID NO: 444)

TGTATTAGCCCCAGGGGGTGCCCCGACGGGCCTTACGTGATGTATGGCAGCTCCGGTGGCAGCG

GAGGCTCTGGCGGGAGTGGGATCAGTTCCGGCCTGCTGAGCTCCGGGTCAAGCGGGACCCAGAT

CTTGCTCACCCAATCACCAGTGATCCTAAGCGTGAGCCCTGGCGAACGGGTCAGCTTCTCTTGC

CGGGCATCTCAGAGTATTGGCACTAACATACACTGGTACCAGCAGCGAACCAATGGGTCCCCCC

GCCTTCTAATCAAATATGCTAGCGAATCCATTTCAGGAATTCCTAGCCGATTTAGCGGCAGCGG

ATCAGGCACTGACTTCACTCTGTCAATCAACTCAGTTGAAAGCGAGGACATTGCAGACTACTAT

TGCCAGCAGAATAATAATTGGCCCACTACATTTGGAGCTGGAACAAAATTGGAGCTTAAGAGGA

CAGTGGCTGCGCCTAGTGTATTTATCTTTCCCCCCTCTGACGAACAGTTGAAATCGGGAACCGC

ATCCGTCGTCTGTTTACTGAACAACTTCTATCCCAGAGAGGCCAAAGTGCAGTGGAAAGTGGAT

AATGCTTTGCAGTCTGGCAACAGCCAGGAAAGCGTGACGGAGCAGGACTCAAAGGATAGTACAT

ACTCCCTGTCCTCCACCCTGACTCTGAGTAAGGCCGACTACGAGAAGCACAAGGTCTACGCCTG

CGAAGTGACGCACCAAGGGCTATCGAGCCCGGTCACCAAGTCTTTCAATCGTGGAGAATGC

Amino acid Sequence:

(SEQ ID NO: 445)

CISPRGCPDGPYVMYGSSGGSGGSGGSGISSGLLSSGSSGTQILLTQSPVILSVSPGERVSFSC

RASQSIGTNIHWYQQRTNGSPRLLIKYASESISGIPSRFSGSGSGTDFTLSINSVESEDIADYY

CQQNNNWPTTFGAGTKLELKRTVAAPSVFIFPPSDEQLKSGTASVVCLLNNFYPREAKVQWKVD

NALQSGNSQESVTEQDSKDSTYSLSSTLTLSKADYEKHKVYACEVTHQGLSSPVTKSFNRGEC

Anti-EGFR 1002 Activatable Antibody Light Chain with spacer
sequence:
Nucleotide sequence:

(SEQ ID NO: 78)

CAGGGGCAATCAGGACAATGCATCAGCCCTAGGGGCTGCCCAGACGGCCCATATGTGATGTACG

GTAGCTCTGGGGGCTCAGGAGGCAGCGGGGGAAGCGGACAAAACCAGGCCTTACGAATGGCTGG

CAGCTCTGGCACCCAGATATTGCTGACGCAGAGTCCAGTTATCCTTAGTGTCAGCCCTGGTGAA

CGGGTTTCATTTAGTTGCCGTGCCTCCCAGTCTATTGGAACGAACATTCATTGGTACCAGCAAA

GGACCAACGGTTCACCCAGGTTGCTTATCAAGTATGCTTCAGAGTCAATCTCCGGGATTCCCTC

AAGGTTTTCAGGCTCTGGCTCAGGTACCGATTTTACGCTGAGCATCAACTCCGTGGAGAGTGAG

GACATTGCTGATTATTACTGTCAGCAGAATAACAATTGGCCGACAACTTTCGGCGCCGGCACAA

AGCTGGAACTTAAGCGTACTGTGGCTGCGCCATCTGTCTTCATTTTTCCGCCCTCGGACGAGCA

GTTGAAGTCAGGGACCGCCTCTGTCGTGTGCCTTCTCAATAACTTCTATCCCAGAGAGGCTAAA

GTCCAGTGGAAAGTTGATAATGCACTTCAGAGCGGGAATAGCCAGGAGAGCGTGACGGAACAGG

ACTCTAAGGACTCCACCTATTCTCTCTCATCCACCCTTACTCTCTCTAAAGCCGACTACGAAAA

GCATAAGGTTTATGCTTGCGAAGTCACTCATCAAGGGCTATCTAGTCCGGTCACTAAAAGCTTC

AACAGAGGTGAATGT

Amino acid Sequence:

(SEQ ID NO: 79)

QGQSGQCISPRGCPDGPYVMYGSSGGSGGSGGSGQNQALRMAGSSGTQILLTQSPVILSVSPGE

RVSFSCRASQSIGTNIHWYQQRTNGSPRLLIKYASESISGIPSRFSGSGSGTDFTLSINSVESE

DIADYYCQQNNNWPTTFGAGTKLELKRTVAAPSVFIFPPSDEQLKSGTASVVCLLNNFYPREAK

-continued

VQWKVDNALQSGNSQESVTEQDSKDSTYSLSSTLTLSKADYEKHKVYACEVTHQGLSSPVTKSF

NRGEC

Anti-EGFR 1002 Activatable Antibody Light Chain:
Nucleotide sequence:

(SEQ ID NO: 446)

TGCATCAGCCCTAGGGGCTGCCCAGACGGCCCATATGTGATGTACGGTAGCTCTGGGGGCTCAG

GAGGCAGCGGGGGAAGCGGACAAAACCAGGCCTTACGAATGGCTGGCAGCTCTGGCACCCAGAT

ATTGCTGACGCAGAGTCCAGTTATCCTTAGTGTCAGCCCTGGTGAACGGGTTTCATTTAGTTGC

CGTGCCTCCCAGTCTATTGGAACGAACATTCATTGGTACCAGCAAAGGACCAACGGTTCACCCA

GGTTGCTTATCAAGTATGCTTCAGAGTCAATCTCCGGGATTCCCTCAAGGTTTTCAGGCTCTGG

CTCAGGTACCGATTTTACGCTGAGCATCAACTCCGTGGAGAGTGAGGACATTGCTGATTATTAC

TGTCAGCAGAATAACAATTGGCCGACAACTTTCGGCGCCGGCACAAAGCTGGAACTTAAGCGTA

CTGTGGCTGCGCCATCTGTCTTCATTTTTCCGCCCTCGGACGAGCAGTTGAAGTCAGGGACCGC

CTCTGTCGTGTGCCTTCTCAATAACTTCTATCCCAGAGAGGCTAAAGTCCAGTGGAAAGTTGAT

AATGCACTTCAGAGCGGGAATAGCCAGGAGAGCGTGACGGAACAGGACTCTAAGGACTCCACCT

ATTCTCTCTCATCCACCCTTACTCTCTCTAAAGCCGACTACGAAAAGCATAAGGTTTATGCTTG

CGAAGTCACTCATCAAGGGCTATCTAGTCCGGTCACTAAAAGCTTCAACAGAGGTGAATGT

Amino acid Sequence:

(SEQ ID NO: 447)

CISPRGCPDGPYVMYGSSGGSGGSGGSGQNQALRMAGSSGTQILLTQSPVILSVSPGERVSFSC

RASQSIGTNIHWYQQRTNGSPRLLIKYASESISGIPSRFSGSGSGTDFTLSINSVESEDIADYY

CQQNNNWPTTFGAGTKLELKRTVAAPSVFIFPPSDEQLKSGTASVVCLLNNFYPREAKVQWKVD

NALQSGNSQESVTEQDSKDSTYSLSSTLTLSKADYEKHKVYACEVTHQGLSSPVTKSFNRGEC

Anti-EGFR 2001 Activatable Antibody Light Chain with spacer sequence:
Nucleotide sequence:

(SEQ ID NO: 80)

CAAGGCCAGTCTGGACAATGTATCAGCCCCCGTGGCTGTCCAGACGGTCCTTACGTTATGTATG

GATCTAGCGGGGGCTCTGGAGGGTCTGGCGGCTCTGGAATCTCTAGTGGACTTCTCTCCGGAAG

AAGCGATAATCATGGATCCAGCGGGACACAAATCCTGTTGACACAGTCCCCAGTGATCCTGTCA

GTCTCGCCCGGAGAAAGGGTGTCTTTCTCTTGTAGGGCTAGTCAGTCTATCGGAACTAACATCC

ATTGGTACCAGCAGCGGACAAATGGGAGCCCGAGGCTTCTGATCAAGTATGCTTCAGAGAGTAT

AAGCGGCATCCCCTCAAGATTTAGTGGCAGCGGGTCCGGGACAGATTTCACCTTGTCAATCAAT

TCTGTCGAATCCGAAGACATTGCAGACTACTATTGCCAGCAAAACAACAACTGGCCCACCACTT

TCGGTGCTGGAACCAAACTCGAGCTGAAACGCACTGTGGCAGCTCCTTCAGTGTTCATCTTCCC

ACCTAGCGACGAGCAGTTGAAATCGGGGACAGCCTCAGTGGTGTGTCTACTGAACAACTTTTAC

CCCCGGGAAGCCAAAGTGCAGTGGAAGGTCGACAATGCGCTGCAATCAGGGAACAGTCAGGAGT

CAGTTACAGAGCAGGACTCTAAGGACAGTACATATTCTTTGAGTTCCACCTTGACATTAAGCAA

GGCAGACTACGAGAAACACAAGGTGTACGCATGTGAAGTTACACACCAGGGCCTTTCCTCCCCA

GTTACGAAAAGCTTCAACAGAGGCGAATGC

Amino acid Sequence:

(SEQ ID NO: 81)

QGQSGQCISPRGCPDGPYVMYGSSGGSGGSGGSGISSGLLSGRSDNHGSSGTQILLTQSPVILS

VSPGERVSFSCRASQSIGTNIHWYQQRTNGSPRLLIKYASESISGIPSRFSGSGSGTDFTLSIN

SVESEDIADYYCQQNNNWPTTFGAGTKLELKRTVAAPSVFIFPPSDEQLKSGTASVVCLLNNFY

-continued

PREAKVQWKVDNALQSGNSQESVTEQDSKDSTYSLSSTLTLSKADYEKHKVYACEVTHQGLSSP

VTKSFNRGEC

Anti-EGFR 2001 Activatable Antibody Light Chain:
Nucleotide sequence:

(SEQ ID NO: 448)

TGTATCAGCCCCCGTGGCTGTCCAGACGGTCCTTACGTTATGTATGGATCTAGCGGGGGCTCTG

GAGGGTCTGGCGGCTCTGGAATCTCTAGTGGACTTCTCTCCGGAAGAAGCGATAATCATGGATC

CAGCGGGACACAAATCCTGTTGACACAGTCCCCAGTGATCCTGTCAGTCTCGCCCGGAGAAAGG

GTGTCTTTCTCTTGTAGGGCTAGTCAGTCTATCGGAACTAACATCCATTGGTACCAGCAGCGGA

CAAATGGGAGCCCGAGGCTTCTGATCAAGTATGCTTCAGAGAGTATAAGCGGCATCCCCTCAAG

ATTTAGTGGCAGCGGGTCCGGGACAGATTTCACCTTGTCAATCAATTCTGTCGAATCCGAAGAC

ATTGCAGACTACTATTGCCAGCAAAACAACAACTGGCCCACCACTTTCGGTGCTGGAACCAAAC

TCGAGCTGAAACGCACTGTGGCAGCTCCTTCAGTGTTCATCTTCCCACCTAGCGACGAGCAGTT

GAAATCGGGGACAGCCTCAGTGGTGTGTCTACTGAACAACTTTTACCCCCGGGAAGCCAAAGTG

CAGTGGAAGGTCGACAATGCGCTGCAATCAGGGAACAGTCAGGAGTCAGTTACAGAGCAGGACT

CTAAGGACAGTACATATTCTTTGAGTTCCACCTTGACATTAAGCAAGGCAGACTACGAGAAACA

CAAGGTGTACGCATGTGAAGTTACACACCAGGGCCTTTCCTCCCCAGTTACGAAAAGCTTCAAC

AGAGGCGAATGC

Amino acid Sequence:

(SEQ ID NO: 449)

CISPRGCPDGPYVMYGSSGGSGGSGGSGISSGLLSGRSDNHGSSGTQILLTQSPVILSVSPGER

VSFSCRASQSIGTNIHWYQQRTNGSPRLLIKYASESISGIPSRFSGSGSGTDFTLSINSVESED

IADYYCQQNNNWPTTFGAGTKLELKRTVAAPSVFIFPPSDEQLKSGTASVVCLLNNFYPREAKV

QWKVDNALQSGNSQESVTEQDSKDSTYSLSSTLTLSKADYEKHKVYACEVTHQGLSSPVTKSFN

RGEC

Anti-EGFR 2002 Activatable Antibody Light Chain with spacer
sequence:
Nucleotide sequence:

(SEQ ID NO: 82)

CAAGGTCAGAGTGGCCAATGCATATCGCCCAGAGGATGTCCTGACGGACCCTACGTGATGTACG

GGAGTTCTGGGGGGAGTGGAGGCTCTGGCGGGTCAGGGATTAGTTCCGGCCTCTTGTCTGGACG

CTCCGGAAATCACGGATCATCTGGGACCCAGATCCTCCTGACCCAGTCTCCCGTCATTCTGTCT

GTTTCTCCAGGCGAGCGGGTTTCATTTAGCTGTAGGGCCAGTCAGAGCATTGGCACCAACATCC

ATTGGTACCAGCAGAGAACTAATGGCAGTCCCAGACTGCTCATTAAATATGCAAGCGAATCAAT

TTCCGGGATTCCTTCTCGCTTCTCGGGATCTGGATCTGGCACCGACTTCACGCTGTCCATCAAC

AGCGTGGAGAGTGAGGACATCGCCGATTACTACTGCCAGCAGAACAACAACTGGCCAACAACTT

TTGGCGCCGGGACCAAGCTTGAGTTAAAGAGAACCGTAGCTGCACCCTCTGTTTTCATTTTCCC

ACCCTCAGACGAGCAGCTTAAGTCAGGAACTGCCAGTGTGGTGTGCCTGCTGAACAACTTCTAC

CCGAGAGAGGCTAAAGTCCAGTGGAAGGTAGACAATGCCCTTCAGTCTGGCAACTCTCAGGAGA

GTGTCACAGAGCAGGATTCTAAGGACTCCACGTACAGTCTGAGTTCCACCCTCACCCTCAGTAA

GGCAGACTACGAGAAGCACAAAGTCTACGCATGTGAGGTTACTCACCAGGGGCTCAGCTCTCCC

GTGACGAAGTCATTTAACAGAGGTGAGTGC

Amino acid Sequence:

(SEQ ID NO: 83)

QGQSGQCISPRGCPDGPYVMYGSSGGSGGSGGSGISSGLLSGRSGNHGSSGTQILLTQSPVILS

VSPGERVSFSCRASQSIGTNIHWYQQRTNGSPRLLIKYASESISGIPSRFSGSGSGTDFTLSIN

-continued

SVESEDIADYYCQQNNNWPTTFGAGTKLELKRTVAAPSVFIFPPSDEQLKSGTASVVCLLNNFY

PREAKVQWKVDNALQSGNSQESVTEQDSKDSTYSLSSTLTLSKADYEKHKVYACEVTHQGLSSP

VTKSFNRGEC

Anti-EGFR 2002 Activatable Antibody Light Chain:
Nucleotide sequence:

(SEQ ID NO: 450)

TGCATATCGCCCAGAGGATGTCCTGACGGACCCTACGTGATGTACGGGAGTTCTGGGGGGAGTG

GAGGCTCTGGCGGGTCAGGGATTAGTTCCGGCCTCTTGTCTGGACGCTCCGGAAATCACGGATC

ATCTGGGACCCAGATCCTCCTGACCCAGTCTCCCGTCATTCTGTCTGTTTCTCCAGGCGAGCGG

GTTTCATTTAGCTGTAGGGCCAGTCAGAGCATTGGCACCAACATCCATTGGTACCAGCAGAGAA

CTAATGGCAGTCCCAGACTGCTCATTAAATATGCAAGCGAATCAATTTCCGGGATTCCTTCTCG

CTTCTCGGGATCTGGATCTGGCACCGACTTCACGCTGTCCATCAACAGCGTGGAGAGTGAGGAC

ATCGCCGATTACTACTGCCAGCAGAACAACAACTGGCCAACAACTTTTGGCGCCGGGACCAAGC

TTGAGTTAAAGAGAACCGTAGCTGCACCCTCTGTTTTCATTTTCCCACCCTCAGACGAGCAGCT

TAAGTCAGGAACTGCCAGTGTGGTGTGCCTGCTGAACAACTTCTACCCGAGAGAGGCTAAAGTC

CAGTGGAAGGTAGACAATGCCCTTCAGTCTGGCAACTCTCAGGAGAGTGTCACAGAGCAGGATT

CTAAGGACTCCACGTACAGTCTGAGTTCCACCCTCACCCTCAGTAAGGCAGACTACGAGAAGCA

CAAAGTCTACGCATGTGAGGTTACTCACCAGGGGCTCAGCTCTCCCGTGACGAAGTCATTTAAC

AGAGGTGAGTGC

Amino acid Sequence:

(SEQ ID NO: 451)

CISPRGCPDGPYVMYGSSGGSGGSGGSGISSGLLSGRSGNHGSSGTQILLTQSPVILSVSPGER

VSFSCRASQSIGTNIHWYQQRTNGSPRLLIKYASESISGIPSRFSGSGSGTDFTLSINSVESED

IADYYCQQNNNWPTTFGAGTKLELKRTVAAPSVFIFPPSDEQLKSGTASVVCLLNNFYPREAKV

QWKVDNALQSGNSQESVTEQDSKDSTYSLSSTLTLSKADYEKHKVYACEVTHQGLSSPVTKSFN

RGEC

Anti-EGFR 0001/LP'/1001 Activatable Antibody Light Chain with
spacer sequence:
Nucleotide sequence:

(SEQ ID NO: 84)

CAGGGACAGTCGGGACAGTGCATTTCTCCGAGAGGCTGCCCTGACGGCCCATACGTAATGTACG

GATCATCCGGTGGCAGTGGAGGGTCCGGGGGATCCGGTCTAAGCGGCAGAAGTGATAATCATGG

AGGCTCTGGCGGGAGCATCAGCTCCGGATTGCTTTCCAGCGGAAGTTCTGGCACTCAAATTCTG

CTGACACAAAGCCCTGTGATCTTGTCAGTCTCACCTGGCGAGCGGGTGAGCTTTTCATGCCGGG

CTTCCCAGAGCATCGGTACAAATATTCACTGGTATCAGCAGAGAACCAATGGCAGTCCGCGGTT

GCTGATTAAGTATGCGAGCGAGAGCATATCAGGCATACCAAGCAGATTTAGCGGGAGTGGCTCT

GGGACCGATTTTACACTCAGTATAAATTCAGTGGAGAGCGAGGATATAGCCGACTACTACTGCC

AGCAAAACAATAACTGGCCCACCACCTTCGGCGCAGGGACCAAGCTTGAACTGAAGCGTACAGT

TGCCGCCCCAAGCGTATTTATTTTCCCTCCAAGCGACGAACAGCTGAAAAGCGGTACCGCAAGC

GTTGTGTGCCTGCTGAATAACTTTTACCCAAGGGAAGCTAAGGTGCAGTGGAAGGTTGACAATG

CGCTGCAGTCAGGCAACTCCCAGGAATCGGTAACAGAGCAGGACTCCAAGGATTCAACTTATAG

TCTTAGTAGTACCCTTACTCTTTCCAAAGCTGATTATGAAAAACACAAAGTGTATGCATGCGAG

GTGACCCACCAAGGACTGTCATCTCCTGTCACCAAGTCCTTCAACCGGGGAGAGTGT

-continued

Substitute Specification-clean copy
Amino acid Sequence:

(SEQ ID NO: 85)

QGQSGQCISPRGCPDGPYVMYGSSGGSGGSGGSGLSGRSDNHGGSGGSISSGLLSSGSSGTQIL

LTQSPVILSVSPGERVSFSCRASQSIGTNIHWYQQRTNGSPRLLIKYASESISGIPSRFSGSGS

GTDFTLSINSVESEDIADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTLTLSKADYEKHKVYACE

VTHQGLSSPVTKSFNRGEC

Anti-EGFR 0001/LP'/1001 Activatable Antibody Light Chain:
Nucleotide sequence:

(SEQ ID NO: 452)

TGCATTTCTCCGAGAGGCTGCCCTGACGGCCCATACGTAATGTACGGATCATCCGGTGGCAGTG

GAGGGTCCGGGGGATCCGGTCTAAGCGGCAGAAGTGATAATCATGGAGGCTCTGGCGGGAGCAT

CAGCTCCGGATTGCTTTCCAGCGGAAGTTCTGGCACTCAAATTCTGCTGACACAAAGCCCTGTG

ATCTTGTCAGTCTCACCTGGCGAGCGGGTGAGCTTTTCATGCCGGGCTTCCCAGAGCATCGGTA

CAAATATTCACTGGTATCAGCAGAGAACCAATGGCAGTCCGCGGTTGCTGATTAAGTATGCGAG

CGAGAGCATATCAGGCATACCAAGCAGATTTAGCGGGAGTGGCTCTGGGACCGATTTTACACTC

AGTATAAATTCAGTGGAGAGCGAGGATATAGCCGACTACTACTGCCAGCAAAACAATAACTGGC

CCACCACCTTCGGCGCAGGGACCAAGCTTGAACTGAAGCGTACAGTTGCCGCCCCAAGCGTATT

TATTTTCCCTCCAAGCGACGAACAGCTGAAAAGCGGTACCGCAAGCGTTGTGTGCCTGCTGAAT

AACTTTTACCCAAGGGAAGCTAAGGTGCAGTGGAAGGTTGACAATGCGCTGCAGTCAGGCAACT

CCCAGGAATCGGTAACAGAGCAGGACTCCAAGGATTCAACTTATAGTCTTAGTAGTACCCTTAC

TCTTTCCAAAGCTGATTATGAAAAACACAAAGTGTATGCATGCGAGGTGACCCACCAAGGACTG

TCATCTCCTGTCACCAAGTCCTTCAACCGGGGAGAGTGT

Amino acid Sequence:

(SEQ ID NO: 453)

CISPRGCPDGPYVMYGSSGGSGGSGGSGLSGRSDNHGGSGGSISSGLLSSGSSGTQILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC

Anti-EGFR 1001/LP'/0001 Activatable Antibody Light Chain with
spacer sequence:
Nucleotide sequence:

(SEQ ID NO: 86)

CAAGGTCAGAGCGGCCAGTGCATTAGTCCTCGCGGTTGCCCTGATGGACCATACGTAATGTATG

GAAGCTCTGGTGGATCCGGGGGCTCTGGCGGATCAGGAATCTCCAGCGGGCTGCTCTCATCAGG

TGGCAGCGGGGGCTCATTAAGCGGCCGAAGTGACAATCACGGCTCGTCCGGTACACAGATTCTG

CTCACTCAGTCACCCGTTATACTGTCTGTGTCGCCTGGAGAGCGTGTCAGCTTTTCATGTAGAG

CCTCGCAGTCAATAGGCACGAATATACACTGGTACCAGCAGAGAACTAATGGAAGCCCAAGGTT

GCTCATCAAATACGCATCTGAGTCGATTAGCGGCATTCCGTCCAGGTTTAGTGGCAGTGGAAGC

GGCACCGATTTCACTTTGTCTATTAACTCTGTGGAAAGCGAGGACATCGCCGATTATTATTGTC

AGCAGAATAACAATTGGCCCACCACCTTCGGTGCCGGTACTAAGCTGGAGCTGAAACGTACAGT

TGCCGCTCCCTCTGTGTTTATTTTCCCTCCCTCGGATGAGCAACTCAAATCAGGGACAGCGAGT

GTCGTATGTCTCCTGAACAATTTTTACCCACGTGAAGCTAAAGTTCAGTGGAAGGTGGACAACG

CTCTGCAGTCCGGCAACAGTCAGGAAAGCGTAACTGAACAGGACTCAAAGGATAGCACTTACTC

-continued

CTTGAGCAGCACTCTCACTCTTTCCAAGGCTGATTATGAGAAGCACAAGGTGTACGCGTGTGAA

GTCACCCATCAGGGACTGTCAAGTCCGGTGACTAAATCATTTAACAGGGGCGAATGC

Amino acid Sequence:

(SEQ ID NO: 87)

QGQSGQCISPRGCPDGPYVMYGSSGGSGGSGGSGISSGLLSSGGSGGSLSGRSDNHGSSGTQIL

LTQSPVILSVSPGERVSFSCRASQSIGTNIHWYQQRTNGSPRLLIKYASESISGIPSRFSGSGS

GTDFTLSINSVESEDIADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTLTLSKADYEKHKVYACE

VTHQGLSSPVTKSFNRGEC

Anti-EGFR 1001/LP'/0001 Activatable Antibody Light Chain:
Nucleotide sequence:

(SEQ ID NO: 454)

TGCATTAGTCCTCGCGGTTGCCCTGATGGACCATACGTAATGTATGGAAGCTCTGGTGGATCCG

GGGGCTCTGGCGGATCAGGAATCTCCAGCGGGCTGCTCTCATCAGGTGGCAGCGGGGGCTCATT

AAGCGGCCGAAGTGACAATCACGGCTCGTCCGGTACACAGATTCTGCTCACTCAGTCACCCGTT

ATACTGTCTGTGTCGCCTGGAGAGCGTGTCAGCTTTTCATGTAGAGCCTCGCAGTCAATAGGCA

CGAATATACACTGGTACCAGCAGAGAACTAATGGAAGCCCAAGGTTGCTCATCAAATACGCATC

TGAGTCGATTAGCGGCATTCCGTCCAGGTTTAGTGGCAGTGGAAGCGGCACCGATTTCACTTTG

TCTATTAACTCTGTGGAAAGCGAGGACATCGCCGATTATTATTGTCAGCAGAATAACAATTGGC

CCACCACCTTCGGTGCCGGTACTAAGCTGGAGCTGAAACGTACAGTTGCCGCTCCCTCTGTGTT

TATTTTCCCTCCCTCGGATGAGCAACTCAAATCAGGGACAGCGAGTGTCGTATGTCTCCTGAAC

AATTTTTACCCACGTGAAGCTAAAGTTCAGTGGAAGGTGGACAACGCTCTGCAGTCCGGCAACA

GTCAGGAAAGCGTAACTGAACAGGACTCAAAGGATAGCACTTACTCCTTGAGCAGCACTCTCAC

TCTTTCCAAGGCTGATTATGAGAAGCACAAGGTGTACGCGTGTGAAGTCACCCATCAGGGACTG

TCAAGTCCGGTGACTAAATCATTTAACAGGGGCGAATGC

Amino acid Sequence:

(SEQ ID NO: 455)

CISPRGCPDGPYVMYGSSGGSGGSGGSGISSGLLSSGGSGGSLSGRSDNHGSSGTQILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC

Anti-EGFR 0002/LP'/1001 Activatable Antibody Light Chain with
spacer sequence:
Nucleotide sequence:

(SEQ ID NO: 88)

CAGGGCCAGAGTGGGCAGTGTATTTCCCCTCGCGGATGTCCCGACGGTCCATACGTAATGTATG

GGTCAAGCGGGGGATCAGGAGGAAGTGGAGGCTCCGGACTCAGCGGTCGCTCCGGCAATCACGG

GGGGTCTGGCGGATCAATAAGTTCGGGCCTCCTGAGCTCCGGTTCATCTGGCACTCAGATCCTG

CTCACGCAGTCGCCGGTAATACTGAGTGTCTCACCAGGCGAGCGTGTCAGCTTCAGCTGTCGCG

CCTCACAGTCAATCGGCACAAATATCCATTGGTACCAGCAAAGGACCAATGGCAGCCCTAGGCT

GCTGATAAAATACGCATCCGAGTCAATTTCAGGGATTCCATCGAGATTCTCGGGCAGCGGAAGT

GGGACCGACTTTACTCTCTCCATCAACAGCGTCGAGTCGGAGGACATCGCGGACTACTACTGCC

AGCAGAATAACAATTGGCCAACAACATTCGGCGCAGGAACAAAGCTAGAGCTCAAGAGGACAGT

GGCTGCACCCAGTGTATTCATCTTCCCACCTAGCGACGAGCAACTGAAGAGCGGGACGGCTTCC

GTCGTTTGTCTATTAAATAATTTCTATCCCCGTGAGGCTAAAGTTCAGTGGAAGGTTGATAATG

-continued

CGTTGCAGTCCGGCAACTCCCAGGAATCCGTCACAGAGCAGGATTCTAAGGATTCAACCTATAG

CTTAAGCTCTACACTTACGCTTTCTAAAGCCGATTATGAAAAACACAAGGTGTACGCTTGTGAG

GTTACCCACCAGGGCCTGAGCAGCCCCGTGACCAAGTCGTTCAACCGGGGCGAGTGT

Amino acid Sequence:

(SEQ ID NO: 89)

QGQSGQCISPRGCPDGPYVMYGSSGGSGGSGGSGLSGRSGNHGGSGGSISSGLLSSGSSGTQIL

LTQSPVILSVSPGERVSFSCRASQSIGTNIHWYQQRTNGSPRLLIKYASESISGIPSRFSGSGS

GTDFTLSINSVESEDIADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTLTLSKADYEKHKVYACE

VTHQGLSSPVTKSFNRGEC

Anti-EGFR 0002/LP'/1001 Activatable Antibody Light Chain:
Nucleotide sequence:

(SEQ ID NO: 456)

TGTATTTCCCCTCGCGGATGTCCCGACGGTCCATACGTAATGTATGGGTCAAGCGGGGGATCAG

GAGGAAGTGGAGGCTCCGGACTCAGCGGTCGCTCCGGCAATCACGGGGGGTCTGGCGGATCAAT

AAGTTCGGGCCTCCTGAGCTCCGGTTCATCTGGCACTCAGATCCTGCTCACGCAGTCGCCGGTA

ATACTGAGTGTCTCACCAGGCGAGCGTGTCAGCTTCAGCTGTCGCGCCTCACAGTCAATCGGCA

CAAATATCCATTGGTACCAGCAAAGGACCAATGGCAGCCCTAGGCTGCTGATAAAATACGCATC

CGAGTCAATTTCAGGGATTCCATCGAGATTCTCGGGCAGCGGAAGTGGGACCGACTTTACTCTC

TCCATCAACAGCGTCGAGTCGGAGGACATCGCGGACTACTACTGCCAGCAGAATAACAATTGGC

CAACAACATTCGGCGCAGGAACAAAGCTAGAGCTCAAGAGGACAGTGGCTGCACCCAGTGTATT

CATCTTCCCACCTAGCGACGAGCAACTGAAGAGCGGGACGGCTTCCGTCGTTTGTCTATTAAAT

AATTTCTATCCCCGTGAGGCTAAAGTTCAGTGGAAGGTTGATAATGCGTTGCAGTCCGGCAACT

CCCAGGAATCCGTCACAGAGCAGGATTCTAAGGATTCAACCTATAGCTTAAGCTCTACACTTAC

GCTTTCTAAAGCCGATTATGAAAAACACAAGGTGTACGCTTGTGAGGTTACCCACCAGGGCCTG

AGCAGCCCCGTGACCAAGTCGTTCAACCGGGGCGAGTGT

Amino acid Sequence:

(SEQ ID NO: 457)

CISPRGCPDGPYVMYGSSGGSGGSGGSGLSGRSGNHGGSGGSISSGLLSSGSSGTQILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC

Anti-EGFR 1001/LP'/0002 Activatable Antibody Light Chain with
spacer sequence:
Nucleotide sequence:

(SEQ ID NO: 90)

CAAGGACAGAGCGGACAGTGTATCTCACCTCGCGGCTGCCCCGACGGCCCTTACGTCATGTACG

GCTCCTCGGGTGGGTCCGGGGGAAGTGGCGGGTCTGGCATTAGTTCAGGGCTCTTATCTTCCGG

CGGAAGCGGGGGATCTCTTTCCGGGCGGAGTGGCAATCACGGCAGTAGCGGAACTCAGATCCTA

CTCACTCAGTCACCAGTGATCCTGTCTGTCAGTCCAGGGGAGAGAGTGTCTTTCAGTTGTAGAG

CTTCCCAGTCTATTGGGACAAACATTCACTGGTATCAACAGCGAACTAATGGATCGCCAAGACT

CCTGATTAAATATGCTTCTGAGAGCATCTCTGGAATTCCATCAAGATTCTCAGGGAGTGGTAGC

GGCACCGATTTTACGTTATCGATCAATTCCGTTGAGAGCGAAGATATCGCGGACTATTACTGTC

AGCAGAACAATAACTGGCCTACAACGTTCGGGGCAGGGACGAAATTGGAGCTGAAGCGGACCGT

CGCCGCGCCAAGCGTGTTCATCTTCCCCCCTAGCGACGAGCAATTGAAAAGCGGCACCGCAAGT

-continued

GTGGTTTGCCTGCTGAACAACTTTTATCCTCGCGAGGCGAAAGTGCAGTGGAAAGTCGACAATG

CACTCCAGTCAGGGAACAGCCAAGAGTCCGTTACTGAACAAGACTCTAAAGATAGTACTTATAG

CTTATCCAGCACACTGACGCTCAGTAAGGCCGATTATGAAAAACATAAGGTGTATGCGTGTGAG

GTTACCCATCAAGGATTGTCATCACCCGTCACCAAATCCTTTAACAGAGGAGAATGT

Amino acid Sequence:

(SEQ ID NO: 91)

QGQSGQCISPRGCPDGPYVMYGSSGGSGGSGGSGISSGLLSSGGSGGSLSGRSGNHGSSGTQIL

LTQSPVILSVSPGERVSFSCRASQSIGTNIHWYQQRTNGSPRLLIKYASESISGIPSRFSGSGS

GTDFTLSINSVESEDIADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTLTLSKADYEKHKVYACE

VTHQGLSSPVTKSFNRGEC

Anti-EGFR 1001/LP'/0002 Activatable Antibody Light Chain:
Nucleotide sequence:

(SEQ ID NO: 458)

TGTATCTCACCTCGCGGCTGCCCCGACGGCCCTTACGTCATGTACGGCTCCTCGGGTGGGTCCG

GGGGAAGTGGCGGGTCTGGCATTAGTTCAGGGCTCTTATCTTCCGGCGGAAGCGGGGGATCTCT

TTCCGGGCGGAGTGGCAATCACGGCAGTAGCGGAACTCAGATCCTACTCACTCAGTCACCAGTG

ATCCTGTCTGTCAGTCCAGGGGAGAGAGTGTCTTTCAGTTGTAGAGCTTCCCAGTCTATTGGGA

CAAACATTCACTGGTATCAACAGCGAACTAATGGATCGCCAAGACTCCTGATTAAATATGCTTC

TGAGAGCATCTCTGGAATTCCATCAAGATTCTCAGGGAGTGGTAGCGGCACCGATTTTACGTTA

TCGATCAATTCCGTTGAGAGCGAAGATATCGCGGACTATTACTGTCAGCAGAACAATAACTGGC

CTACAACGTTCGGGGCAGGGACGAAATTGGAGCTGAAGCGGACCGTCGCCGCGCCAAGCGTGTT

CATCTTCCCCCCTAGCGACGAGCAATTGAAAAGCGGCACCGCAAGTGTGGTTTGCCTGCTGAAC

AACTTTTATCCTCGCGAGGCGAAAGTGCAGTGGAAAGTCGACAATGCACTCCAGTCAGGGAACA

GCCAAGAGTCCGTTACTGAACAAGACTCTAAAGATAGTACTTATAGCTTATCCAGCACACTGAC

GCTCAGTAAGGCCGATTATGAAAAACATAAGGTGTATGCGTGTGAGGTTACCCATCAAGGATTG

TCATCACCCGTCACCAAATCCTTTAACAGAGGAGAATGT

Amino acid Sequence:

(SEQ ID NO: 459)

CISPRGCPDGPYVMYGSSGGSGGSGGSGISSGLLSSGGSGGSLSGRSGNHGSSGTQILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC

Anti-EGFR 0001/LP'/1002 Activatable Antibody Light Chain with
spacer sequence:
Nucleotide sequence:

(SEQ ID NO: 92)

CAGGGTCAAAGTGGACAGTGTATCTCGCCCCGCGGCTGCCCAGACGGCCCATATGTGATGTATG

GTTCTTCCGGTGGATCCGGCGGATCAGGTGGGTCTGGCCTCTCAGGTCGTTCCGACAACCACGG

CGGCTCAGGTGGGTCTCAGAATCAGGCACTGCGGATGGCCGGATCTTCTGGCACCCAGATATTG

CTCACACAGTCACCAGTTATTCTGTCCGTATCTCCAGGAGAACGGGTATCTTTCTCTTGTAGGG

CAAGCCAGTCCATCGGAACAAACATCCATTGGTACCAGCAGCGGACCAATGGCAGTCCACGGCT

TCTGATCAAGTATGCTAGTGAAAGCATTAGCGGGATTCCAAGCCGATTTTCTGGGTCGGGTAGT

GGAACCGACTTCACCCTGAGCATTAACTCTGTCGAATCCGAAGATATTGCTGACTATTACTGTC

AGCAGAACAACAATTGGCCGACTACGTTTGGCGCCGGAACCAAATTAGAACTTAAGAGAACCGT

-continued

GGCCGCTCCCTCTGTCTTCATTTTCCCGCCTTCCGACGAACAGCTGAAGAGCGGAACTGCCTCC

GTGGTGTGCCTGTTGAATAACTTTTATCCAAGGGAAGCAAAGGTGCAGTGGAAAGTGGACAATG

CTCTGCAGTCTGGCAATAGCCAGGAGTCCGTGACTGAACAGGACAGTAAAGACTCAACCTACTC

ACTGAGCAGTACTCTCACATTATCCAAAGCCGATTATGAAAAGCATAAGGTTTATGCATGCGAG

GTTACCCACCAGGGACTGAGCTCCCCCGTGACCAAAAGCTTCAATAGGGGTGAGTGC

Amino acid Sequence:

(SEQ ID NO: 93)

QGQSGQCISPRGCPDGPYVMYGSSGGSGGSGGSGLSGRSDNHGGSGGSQNQALRMAGSSGTQIL

LTQSPVILSVSPGERVSFSCRASQSIGTNIHWYQQRTNGSPRLLIKYASESISGIPSRFSGSGS

GTDFTLSINSVESEDIADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTLTLSKADYEKHKVYACE

VTHQGLSSPVTKSFNRGEC

Anti-EGFR 0001/LP'/1002 Activatable Antibody Light Chain:
Nucleotide sequence:

(SEQ ID NO: 460)

TGTATCTCGCCCCGCGGCTGCCCAGACGGCCCATATGTGATGTATGGTTCTTCCGGTGGATCCG

GCGGATCAGGTGGGTCTGGCCTCTCAGGTCGTTCCGACAACCACGGCGGCTCAGGTGGGTCTCA

GAATCAGGCACTGCGGATGGCCGGATCTTCTGGCACCCAGATATTGCTCACACAGTCACCAGTT

ATTCTGTCCGTATCTCCAGGAGAACGGGTATCTTTCTCTTGTAGGGCAAGCCAGTCCATCGGAA

CAAACATCCATTGGTACCAGCAGCGGACCAATGGCAGTCCACGGCTTCTGATCAAGTATGCTAG

TGAAAGCATTAGCGGGATTCCAAGCCGATTTTCTGGGTCGGGTAGTGGAACCGACTTCACCCTG

AGCATTAACTCTGTCGAATCCGAAGATATTGCTGACTATTACTGTCAGCAGAACAACAATTGGC

CGACTACGTTTGGCGCCGGAACCAAATTAGAACTTAAGAGAACCGTGGCCGCTCCCTCTGTCTT

CATTTTCCCGCCTTCCGACGAACAGCTGAAGAGCGGAACTGCCTCCGTGGTGTGCCTGTTGAAT

AACTTTTATCCAAGGGAAGCAAAGGTGCAGTGGAAAGTGGACAATGCTCTGCAGTCTGGCAATA

GCCAGGAGTCCGTGACTGAACAGGACAGTAAAGACTCAACCTACTCACTGAGCAGTACTCTCAC

ATTATCCAAAGCCGATTATGAAAAGCATAAGGTTTATGCATGCGAGGTTACCCACCAGGGACTG

AGCTCCCCCGTGACCAAAAGCTTCAATAGGGGTGAGTGC

Amino acid Sequence:

(SEQ ID NO: 461)

CISPRGCPDGPYVMYGSSGGSGGSGGSGLSGRSDNHGGSGGSQNQALRMAGSSGTQILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC

Anti-EGFR 1002/LP'/0001 Activatable Antibody Light Chain with
spacer sequence:
Nucleotide sequence:

(SEQ ID NO: 94)

CAGGGGCAGTCCGGACAATGCATCAGCCCCCGAGGCTGCCCTGATGGCCCCTACGTGATGTACG

GGTCCAGCGGTGGCAGCGGGGGCTCAGGGGGGAGCGGGCAGAATCAGGCCCTGAGAATGGCGGG

TGGATCCGGGGGGTCCCTTTCTGGCAGGTCCGATAACCACGGTTCTAGTGGAACACAGATTTTG

CTGACACAAAGTCCCGTCATCCTCTCTGTGTCTCCCGGTGAGCGGGTCAGTTTTTCCTGCCGAG

CGTCCCAGAGCATCGGGACAAATATCCATTGGTACCAGCAGAGAACGAACGGCTCTCCTAGACT

GCTCATCAAGTACGCCTCGGAAAGTATTTCCGGCATTCCCTCCCGTTTCAGCGGCTCCGGAAGT

GGTACAGATTTTACCCTGAGTATTAATTCCGTCGAATCTGAGGACATAGCCGACTACTATTGCC

-continued

AACAGAATAACAATTGGCCAACAACTTTTGGCGCCGGGACTAAGCTGGAGCTGAAACGGACCGT

CGCAGCACCAAGTGTTTTCATCTTCCCACCAAGTGACGAGCAGCTGAAATCCGGAACAGCGAGC

GTGGTGTGCCTACTCAATAACTTCTATCCACGCGAAGCCAAGGTGCAGTGGAAAGTGGACAACG

CTCTGCAGTCCGGCAATAGCCAGGAAAGCGTGACAGAGCAAGATTCTAAGGACAGTACGTATTC

ACTGTCCAGTACGCTCACCTTAAGCAAGGCTGACTACGAAAAACACAAGGTCTACGCCTGTGAG

GTCACACATCAGGGCCTCTCCAGTCCGGTTACAAAAAGTTTCAATCGCGGGGAATGT

Amino acid Sequence:

(SEQ ID NO: 95)

QGQSGQCISPRGCPDGPYVMYGSSGGSGGSGGSGQNQALRMAGGSGGSLSGRSDNHGSSGTQIL

LTQSPVILSVSPGERVSFSCRASQSIGTNIHWYQQRTNGSPRLLIKYASESISGIPSRFSGSGS

GTDFTLSINSVESEDIADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTLTLSKADYEKHKVYACE

VTHQGLSSPVTKSFNRGEC

Anti-EGFR 1002/LP'/0001 Activatable Antibody Light Chain:
Nucleotide sequence:

(SEQ ID NO: 462)

TGCATCAGCCCCCGAGGCTGCCCTGATGGCCCCTACGTGATGTACGGGTCCAGCGGTGGCAGCG

GGGGCTCAGGGGGGAGCGGGCAGAATCAGGCCCTGAGAATGGCGGGTGGATCCGGGGGGTCCCT

TTCTGGCAGGTCCGATAACCACGGTTCTAGTGGAACACAGATTTTGCTGACACAAAGTCCCGTC

ATCCTCTCTGTGTCTCCCGGTGAGCGGGTCAGTTTTTCCTGCCGAGCGTCCCAGAGCATCGGGA

CAAATATCCATTGGTACCAGCAGAGAACGAACGGCTCTCCTAGACTGCTCATCAAGTACGCCTC

GGAAAGTATTTCCGGCATTCCCTCCCGTTTCAGCGGCTCCGGAAGTGGTACAGATTTTACCCTG

AGTATTAATTCCGTCGAATCTGAGGACATAGCCGACTACTATTGCCAACAGAATAACAATTGGC

CAACAACTTTTGGCGCCGGGACTAAGCTGGAGCTGAAACGGACCGTCGCAGCACCAAGTGTTTT

CATCTTCCCACCAAGTGACGAGCAGCTGAAATCCGGAACAGCGAGCGTGGTGTGCCTACTCAAT

AACTTCTATCCACGCGAAGCCAAGGTGCAGTGGAAAGTGGACAACGCTCTGCAGTCCGGCAATA

GCCAGGAAAGCGTGACAGAGCAAGATTCTAAGGACAGTACGTATTCACTGTCCAGTACGCTCAC

CTTAAGCAAGGCTGACTACGAAAAACACAAGGTCTACGCCTGTGAGGTCACACATCAGGGCCTC

TCCAGTCCGGTTACAAAAAGTTTCAATCGCGGGGAATGT

Amino acid Sequence:

(SEQ ID NO: 463)

CISPRGCPDGPYVMYGSSGGSGGSGGSGQNQALRMAGGSGGSLSGRSDNHGSSGTQILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC

Anti-EGFR 0002/LP'/1002 Activatable Antibody Light Chain with spacer sequence:
Nucleotide sequence:

(SEQ ID NO: 96)

CAAGGCCAATCCGGTCAGTGCATCAGTCCCAGAGGCTGCCCTGACGGGCCCTACGTGATGTATG

GTAGCTCAGGGGGCTCCGGCGGCTCCGGCGGAAGCGGACTTAGCGGCCGTAGCGGCAACCATGG

GGGTTCTGGAGGATCCCAGAATCAGGCTCTGCGCATGGCTGGAAGCAGCGGTACCCAGATCCTG

CTCACCCAATCACCCGTCATCTTGTCTGTGAGTCCTGGCGAAAGGGTGTCGTTCTCTTGTCGCG

CGTCCCAGTCCATTGGGACCAACATTCATTGGTACCAGCAGAGGACTAACGGGAGCCCCCGCCT

GCTGATCAAATACGCCAGTGAATCTATCTCTGGAATCCCATCACGATTTTCAGGGTCCGGTAGT

-continued

GGGACCGACTTCACTTTGAGTATTAACAGTGTGGAATCCGAGGACATAGCCGACTATTACTGTC

AGCAGAACAATAACTGGCCAACAACCTTTGGCGCCGGGACAAAGTTAGAGCTTAAGCGGACTGT

TGCAGCCCCCTCCGTTTTTATCTTCCCGCCCAGTGATGAACAGCTGAAAAGCGGTACCGCCTCC

GTAGTGTGCCTTCTCAATAATTTTTACCCCAGAGAAGCTAAAGTACAGTGGAAAGTCGACAACG

CCCTCCAGAGCGGCAACAGTCAGGAGTCCGTCACCGAGCAGGATTCTAAAGACTCAACATATAG

CCTTTCGTCCACCCTAACACTTTCAAAAGCAGACTATGAAAAACATAAGGTGTATGCCTGCGAG

GTCACACACCAGGGGCTCAGCTCTCCAGTTACTAAGTCATTCAACCGCGGAGAGTGT

Amino acid Sequence:

(SEQ ID NO: 97)

QGQSGQCISPRGCPDGPYVMYGSSGGSGGSGGSGLSGRSGNHGGSGGSQNQALRMAGSSGTQIL

LTQSPVILSVSPGERVSFSCRASQSIGTNIHWYQQRTNGSPRLLIKYASESISGIPSRFSGSGS

GTDFTLSINSVESEDIADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTLTLSKADYEKHKVYACE

VTHQGLSSPVTKSFNRGEC

Anti-EGFR 0002/LP'/1002 Activatable Antibody Light Chain:
Nucleotide sequence:

(SEQ ID NO: 464)

TGCATCAGTCCCAGAGGCTGCCCTGACGGGCCCTACGTGATGTATGGTAGCTCAGGGGGCTCCG

GCGGCTCCGGCGGAAGCGGACTTAGCGGCCGTAGCGGCAACCATGGGGGTTCTGGAGGATCCCA

GAATCAGGCTCTGCGCATGGCTGGAAGCAGCGGTACCCAGATCCTGCTCACCCAATCACCCGTC

ATCTTGTCTGTGAGTCCTGGCGAAAGGGTGTCGTTCTCTTGTCGCGCGTCCCAGTCCATTGGGA

CCAACATTCATTGGTACCAGCAGAGGACTAACGGGAGCCCCCGCCTGCTGATCAAATACGCCAG

TGAATCTATCTCTGGAATCCCATCACGATTTTCAGGGTCCGGTAGTGGGACCGACTTCACTTTG

AGTATTAACAGTGTGGAATCCGAGGACATAGCCGACTATTACTGTCAGCAGAACAATAACTGGC

CAACAACCTTTGGCGCCGGGACAAAGTTAGAGCTTAAGCGGACTGTTGCAGCCCCCTCCGTTTT

TATCTTCCCGCCCAGTGATGAACAGCTGAAAAGCGGTACCGCCTCCGTAGTGTGCCTTCTCAAT

AATTTTTACCCCAGAGAAGCTAAAGTACAGTGGAAAGTCGACAACGCCCTCCAGAGCGGCAACA

GTCAGGAGTCCGTCACCGAGCAGGATTCTAAAGACTCAACATATAGCCTTTCGTCCACCCTAAC

ACTTTCAAAAGCAGACTATGAAAAACATAAGGTGTATGCCTGCGAGGTCACACACCAGGGGCTC

AGCTCTCCAGTTACTAAGTCATTCAACCGCGGAGAGTGT

Amino acid Sequence:

(SEQ ID NO: 465)

CISPRGCPDGPYVMYGSSGGSGGSGGSGLSGRSGNHGGSGGSQNQALRMAGSSGTQILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC

Anti-EGFR 1002/LP'/0002 Activatable Antibody Light Chain with
spacer sequence:
Nucleotide sequence:

(SEQ ID NO: 98)

CAGGGCCAATCAGGTCAGTGCATTAGCCCCCGAGGGTGTCCCGATGGGCCCTACGTAATGTACG

GATCATCGGGCGGATCTGGGGGCTCCGGTGGCTCTGGTCAGAATCAAGCTCTGCGCATGGCCGG

AGGTAGCGGTGGAAGCCTGAGCGGCCGAAGTGGAAACCACGGCTCCTCTGGCACTCAGATTCTT

CTCACGCAGTCGCCCGTGATCTTGTCCGTGAGCCCAGGCGAGCGGGTGAGCTTCTCTTGCCGGG

CCAGCCAAAGTATAGGTACAAATATTCACTGGTACCAACAGCGAACCAACGGGTCGCCTAGGTT

-continued

GCTCATAAAGTACGCATCCGAGAGTATAAGCGGCATACCATCTAGGTTCTCAGGTAGCGGCAGC

GGGACCGATTTTACCCTCAGCATTAATTCGGTTGAATCTGAAGATATCGCCGATTATTATTGTC

AGCAGAATAACAATTGGCCTACTACTTTCGGCGCCGGAACAAAGCTGGAACTTAAGCGCACAGT

GGCCGCTCCTTCTGTCTTTATCTTCCCTCCATCTGACGAGCAATTAAAGAGTGGGACAGCCTCG

GTGGTGTGTTTGCTCAATAACTTCTATCCAAGGGAGGCAAAGGTGCAGTGGAAGGTCGATAACG

CTCTCCAGAGTGGGAATTCCCAGGAGTCCGTGACCGAGCAGGATTCTAAAGATAGCACATACTC

ACTGTCTTCCACCCTGACCCTGTCCAAGGCAGACTACGAGAAGCACAAAGTTTACGCCTGTGAA

GTGACACACCAGGGCCTCAGCTCTCCTGTCACAAAGAGTTTTAATCGGGGCGAGTGT

Amino acid Sequence:

(SEQ ID NO: 99)

QGQSGQCISPRGCPDGPYVMYGSSGGSGGSGGSGQNQALRMAGGSGGSLSGRSGNHGSSGTQIL

LTQSPVILSVSPGERVSFSCRASQSIGTNIHWYQQRTNGSPRLLIKYASESISGIPSRFSGSGS

GTDFTLSINSVESEDIADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTLTLSKADYEKHKVYACE

VTHQGLSSPVTKSFNRGEC

Anti-EGFR 1002/LP'/000 Activatable Antibody Light Chain:
Nucleotide sequence:

(SEQ ID NO: 466)

TGCATTAGCCCCCGAGGGTGTCCCGATGGGCCCTACGTAATGTACGGATCATCGGGCGGATCTG

GGGGCTCCGGTGGCTCTGGTCAGAATCAAGCTCTGCGCATGGCCGGAGGTAGCGGTGGAAGCCT

GAGCGGCCGAAGTGGAAACCACGGCTCCTCTGGCACTCAGATTCTTCTCACGCAGTCGCCCGTG

ATCTTGTCCGTGAGCCCAGGCGAGCGGGTGAGCTTCTCTTGCCGGGCCAGCCAAAGTATAGGTA

CAAATATTCACTGGTACCAACAGCGAACCAACGGGTCGCCTAGGTTGCTCATAAAGTACGCATC

CGAGAGTATAAGCGGCATACCATCTAGGTTCTCAGGTAGCGGCAGCGGGACCGATTTTACCCTC

AGCATTAATTCGGTTGAATCTGAAGATATCGCCGATTATTATTGTCAGCAGAATAACAATTGGC

CTACTACTTTCGGCGCCGGAACAAAGCTGGAACTTAAGCGCACAGTGGCCGCTCCTTCTGTCTT

TATCTTCCCTCCATCTGACGAGCAATTAAAGAGTGGGACAGCCTCGGTGGTGTGTTTGCTCAAT

AACTTCTATCCAAGGGAGGCAAAGGTGCAGTGGAAGGTCGATAACGCTCTCCAGAGTGGGAATT

CCCAGGAGTCCGTGACCGAGCAGGATTCTAAAGATAGCACATACTCACTGTCTTCCACCCTGAC

CCTGTCCAAGGCAGACTACGAGAAGCACAAAGTTTACGCCTGTGAAGTGACACACCAGGGCCTC

AGCTCTCCTGTCACAAAGAGTTTTAATCGGGGCGAGTGT

Amino acid Sequence:

(SEQ ID NO: 467)

CISPRGCPDGPYVMYGSSGGSGGSGGSGQNQALRMAGGSGGSLSGRSGNHGSSGTQILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC

The following materials were used in the studies described herein.

Reagents and Strains: Human u-PA (Research & Diagnostics Systems, Inc.) was used without modifications. Human matriptase (Research & Diagnostics Systems, Inc.) was used without modifications. Human MMP14 (Research & Diagnostics Systems, Inc.) was activated following the supplied protocol and used without modifications. MMP14 Buffer HCM (50 mM HEPES (pH 6.8), 10 mM $CaCl_2$), 0.5 mM $MgCl_2$) was used, u-PA and Matriptase Buffer TBST (50 mM Tris-HCl, 150 mM NaCl, 0.05% Tween20, pH 7.4) was used.

The following methods were used to evaluate in Vitro substrate activity in activatable antibodies.

Substrate Proteolysis: The ability of substrates in the activatable antibodies to be cleaved by u-PA, matriptase and/or MMP14 was determined as follows. Samples were incubated overnight for 16 to 24 hours at 37° C. in the presence or absence of protease in PBS pH 7.2. Protease digests were prepared to maintain an activatable antibody to protease ratio of 9-to-1. Proteolysis was confirmed by capillary electrophoresis, ELISA, or SDS-PAGE.

Substrate Cleavage Kinetics ($k_{cat}/K_m$): The ability of EGFR activatable antibodies containing substrates, 2001, 2002, 0001/LP'/1001 or 1001/LP'/0001, to be cleaved by matriptase and/or MMP14 was determined as follows. Matriptase protease digests were performed in TBST, 50 mM Tris-HCl, 150 mM NaCl, 0.05% Tween20, pH 7.4. MMP14 protease digests were performed in HCM, 50 mM HEPES (pH 6.8), 10 mM $CaCl_2$), 0.5 mM $MgCl_2$. Varying concentrations of active site titrated matriptase or MMP14 were combined with a fixed activatable antibody concentration to maintain a substrate to protease ratio of at least 50. Samples comprising these substrates were incubated at 37° C. for up to 24 hr. To stop the reaction, 5 µl of the digest was added to 7 µl of HT Protein Express Sample Buffer (Caliper LifeSciences) containing 20 mM 2-Mercaptoethanol for 10 minutes at 95° C. After heat denaturation, 32 µl of $ddH_2O$ was added and samples analyzed on a LabChip GXII per manufacturer's instructions. The LabChip GXII software was used to quantify light chain peak area. Product conversion was calculated by plugging the light chain peak areas into the following equation: cleaved LC/(cleaved LC+uncleaved LC), LC=light chain peak area. $k_{cat}/K_m$ values were determined with the following equation $$\frac{k_{cat}}{K_m} = -\ln(1-C)/(t^*p)$$

where C is product conversion, t is time (s), and p is protease concentration (M), which assumes that the substrate concentration is below the $K_m$ and in excess of the protease concentration.

The following methods can be used to evaluate the in vivo substrate stability of activatable antibodies described herein.

This section describes the experimental method for evaluating in vivo stability of substrates of the embodiments when they were incorporated into EGFR activatable antibodies and injected into mice.

Three nude mice (Crl:NU-Foxn1nu) received a single IP dose of each EGFR activatable antibodies containing 2001, 2002, 0001/LP'/1001, 1001/LP'/0001, 1001/LP'/0002, 0001/LP'/1002, or 0002/LP'/1002 substrates at 12.5 mg/kg on Day 0. Mice were euthanized on day 4 (~96 hours post-dose) by CO2 asphyxiation, and blood was collected immediately as plasma-EDTA and stored at −80° C.

The EGFR activatable antibodies were purified from plasma by anti-human IgG immunoprecipitation using magnetic beads. Eluted EGFR activatable antibodies were prepared for analysis by capillary electrophoresis as described in the $k_{cat}/K_m$ section. Briefly, 5 µl of eluted IgG was added to 7 µl Protein Express Sample Buffer with 2-mercaptoethanol. The method of quantification of circulating stability was identical to quantification of product conversion.

The following methods are used to evaluate in vivo efficacy of activatable antibodies.

This section describes the experimental method for evaluating that EGFR activatable antibodies comprising matriptase-cleavable substrates, MMP14-cleavable substrates, or substrates of the embodiments, i.e., substrates cleavable by matriptase and MMP14, are efficacious in vivo. Seven EGFR activatable antibodies comprising substrate sequences of 0001, 0002, 1001, 2001, 2002, 0001/LP'/1001 or 1001/LP'/0001, cleavable by either or both matriptase and/or MMP14 were administered at 12.5 mg/kg intraperitoneally (i.p.) to H292 xenograft tumor-bearing (lung cancer) mice on Day 0. Mice were retro-orbitally bled on day 8 (~192 hours post-dose). Blood was collected immediately as plasma-EDTA and stored at −80° C. EGFR activatable antibodies were purified from plasma by anti-human IgG immunoprecipitation using magnetic beads. Eluted EGFR activatable antibodies were prepared for analysis by capillary electrophoresis. Briefly, 5 µl of eluted IgG was added to 7 µl Protein Express Sample Buffer with 2-mercaptoethanol. Quantification of circulating stability was identical to quantification of product conversion.

At day 8, the three EGFR activatable antibodies containing matriptase-cleavable substrates or MMP14-cleavable substrates, 0001, 0002 or 1001, demonstrated mean percent (%) activation values ranging from 14% to 15% and the four EGFR activatable antibodies containing substrates, 2001, 2002, 0001/LP'/1001 or 1001/LP'/0001, of the embodiments, i.e., substrates cleavable by matriptase and MMP14, demonstrated mean % activation values of 28% to 33%. Mean % activation is calculated as ((product conversion sum of the test group)*100%)/(number of animals in the test group).

All seven EGFR activatable antibodies containing substrate sequences of 0001, 0002, 1001, 2001, 2002, 0001/LP'/1001 or 1001/LP'/0001 also comprised the masking moiety comprising the amino acid sequence CISPRGCPDGPYVMY (SEQ ID NO: 168) and anti-EGFR antibody C225v5 antibody comprising a light chain (SEQ ID NO: 111) and a heavy chain (SEQ ID NO: 108). The configuration of the light chain of the activatable antibody was masking moiety—substrate—light chain of C225v5.

At day 21, the three EGFR activatable antibodies containing matriptase-cleavable substrates or MMP14-cleavable substrates, 0001, 0002 or 1001, demonstrated tumor growth inhibition ranging from 41% to 57% as measured by mean percent (%) inhibition and the four EGFR activatable antibodies containing substrates, 2001, 2002, 0001/LP'/1001 or 1001/LP'/0001, of the embodiments, i.e., substrates cleavable by matriptase and MMP14, demonstrated tumor growth inhibition ranging from 77% to 80% as measured by mean % inhibition. Mean % inhibition is calculated as (mean(C)−mean(C0))−(mean(T)−mean(T0))/(mean(C)−mean(C0)) *100%, wherein T is the current test group value, T0 is the current test group initial value, C is the control group value, and C0 is the control group initial value. The EGFR antibody cetuximab at day 21 demonstrated 86% inhibition in this study.

Example 3. In Situ Imaging of Anti-EGFR Activatable Antibodies

The present Example describes the use of in situ imaging of non-labeled anti-EGFR activatable antibodies. The cleavage and binding was detected using a secondary antibody that specifically binds to the AB portion of the activatable antibody.

Figure 6:
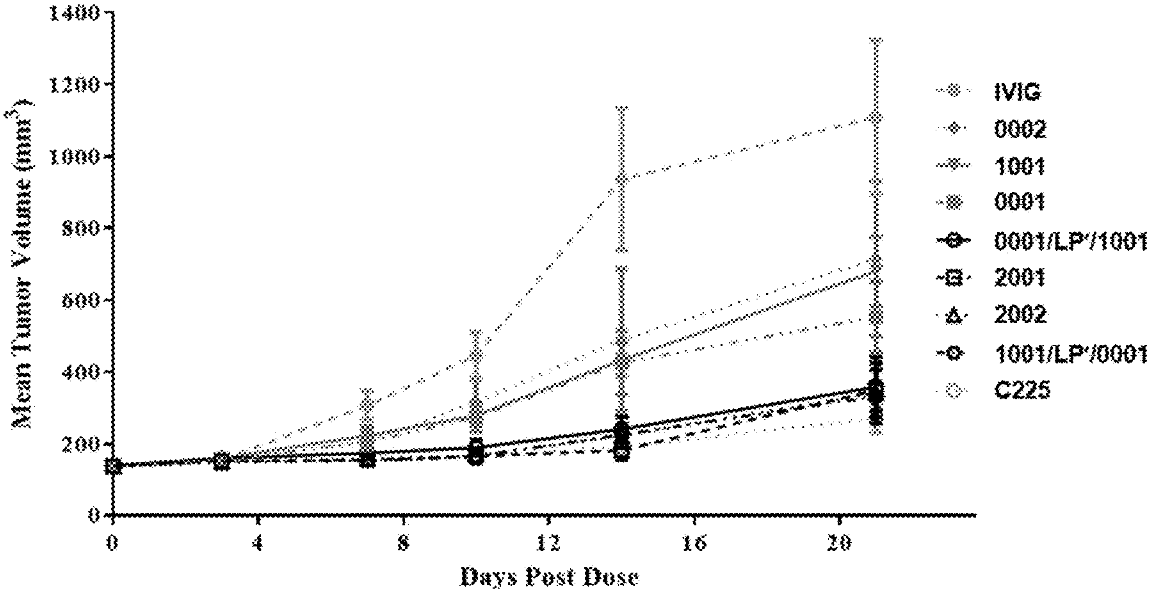
FIG. 6 is a graph depicting in vivo efficacy of EGFR activatable antibodies in H292 xenograft tumor-bearing mice.
Figure 7:
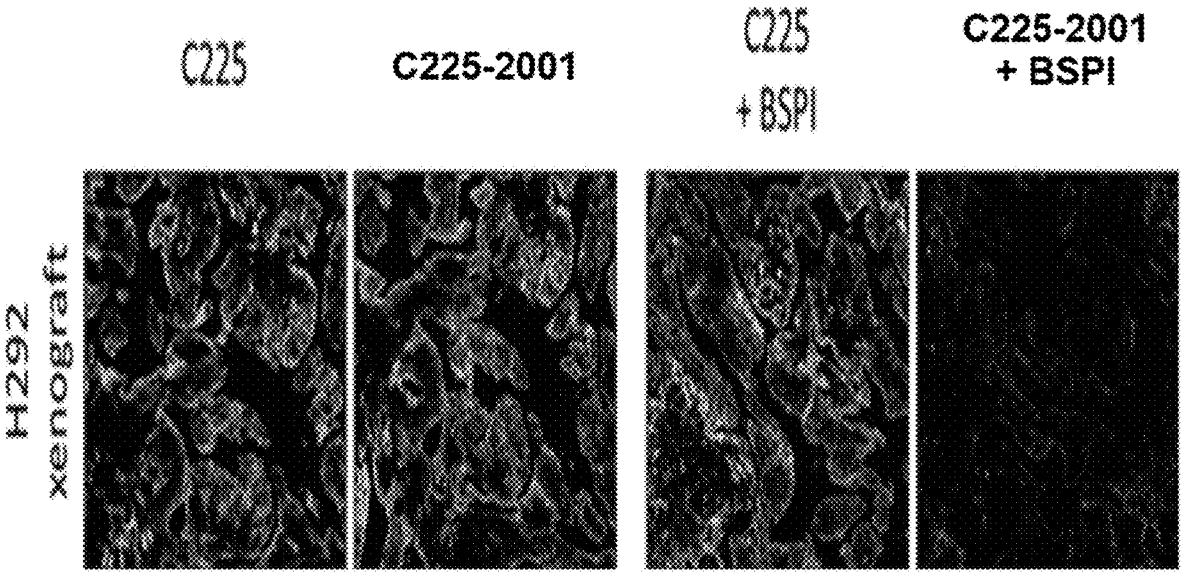
FIG. 7 is a graph depicting in situ evaluation of EGFR activatable antibody activation in a H292 xenograft tumor microenvironment.
Figure 8A:
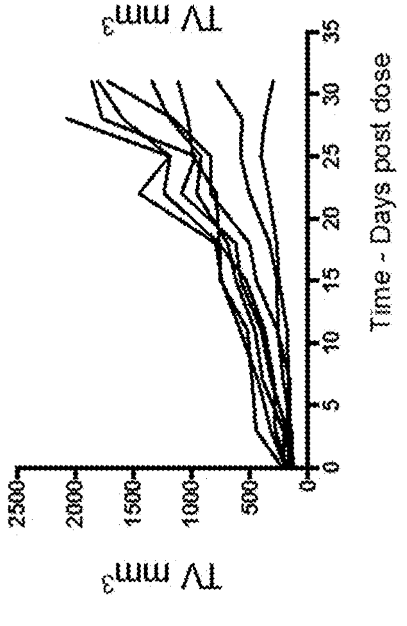
FIGS. 8A, 8B, 8C, 8D, 8E, and 8F are a series of graphs depicting the tumor volume of H292 xenograft tumors in nu/nu mice at various time points following administration with a control intravenous immunoglobulin (IVIG, FIG. 8A), the anti-EGFR antibody cetuximab (FIG. 8B), the anti-EGFR activatable antibody referred to herein as anti-EGFR 2001 activatable antibody, which includes the heavy chain sequence of SEQ ID NO: 108, and the light chain sequence of SEQ ID NO: 449 (FIG. 8C); the anti-EGFR activatable antibody referred to herein as anti-EGFR 2003 activatable antibody, which includes the heavy chain sequence of SEQ ID NO: 108, and the light chain sequence of SEQ ID NO: 472 (FIG. 8D); or the anti-EGFR activatable antibody referred to herein as anti-EGFR 2005 activatable antibody, which includes the heavy chain sequence of SEQ ID NO: 108, and the light chain sequence of SEQ ID NO: 474 (FIG. 8E). For the data shown in FIGS. 8C and 8D, each group lost one animal each due to body weight loss.
Figure 8B:
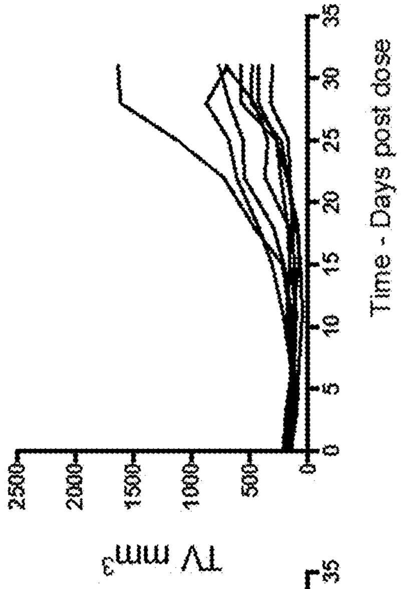
Figure 8C:
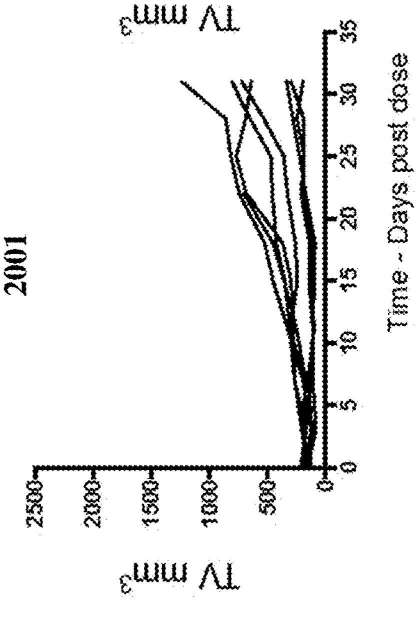
Figure 8D:
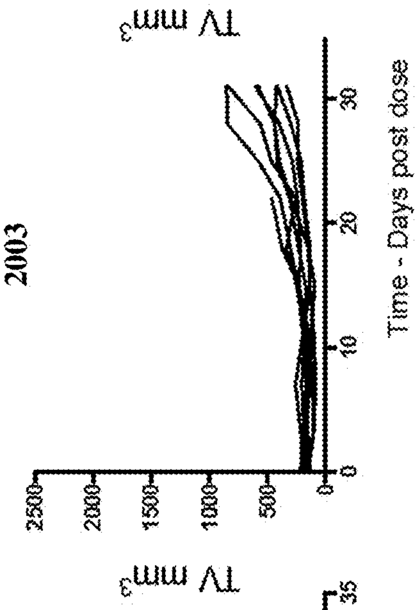
Figure 8E:
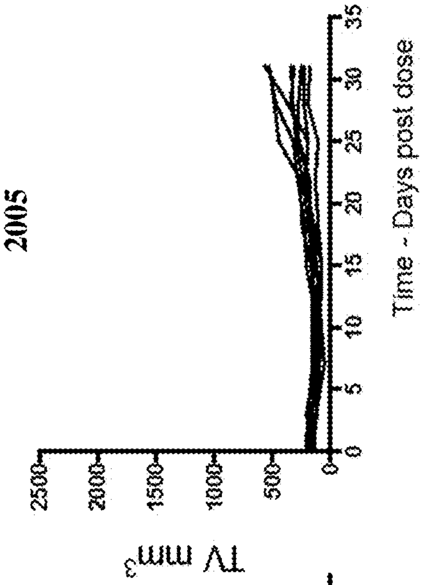
Figure 8F:
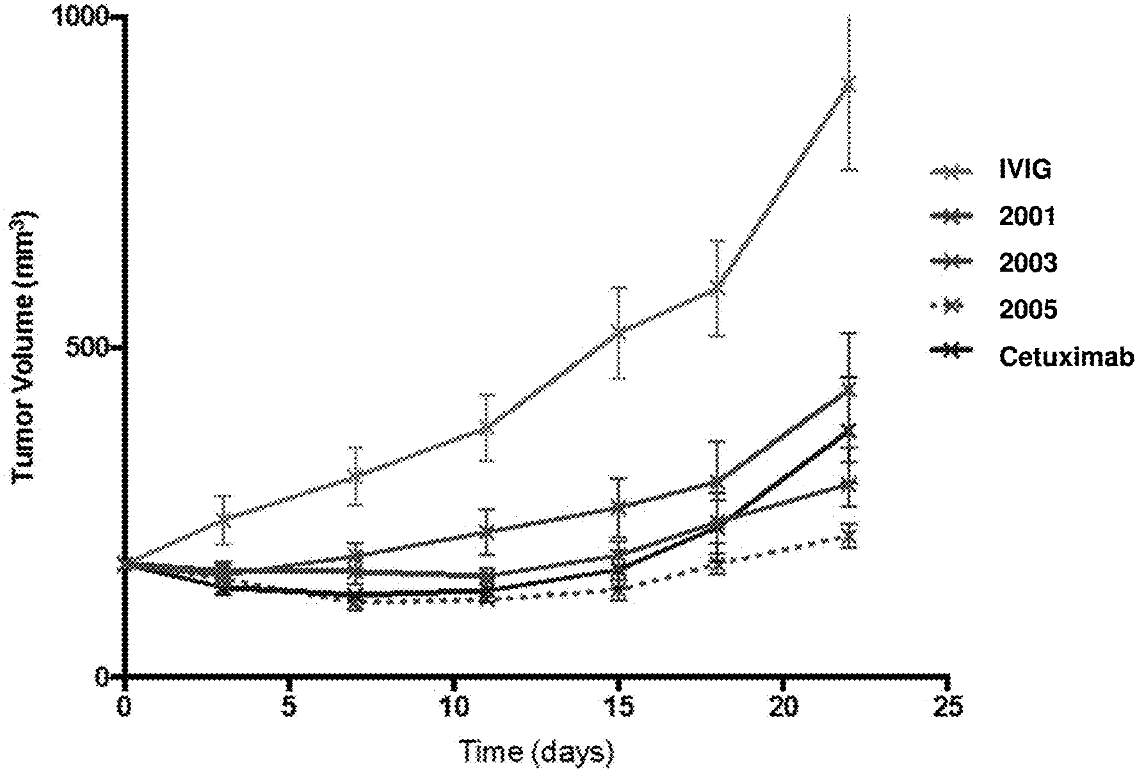

In situ imaging of the activation and binding of a non-labeled anti-EGFR activatable antibody 3954-2001-C225v5 on H292 lung cancer tumor tissue was conducted as follows: Frozen tissue sections were laid over glass slides. A solution containing non-labeled anti-EGFR activatable antibodies was applied on the tissue and incubated, e.g., for 1 hour at room temperature (about 22-24° C.) in an incubation buffer of 10 mM Hepes buffer pH 7.4, containing 150 mM NaCl, 10 µM $ZnCl_2$, 2 mM $CaCl_2$) and 0.005% Tween 20; activatable antibody at a concentration of about 1 µg/ml. The conditions of such an incubation can be adjusted to be conducive to the cleavage agent in the tissue section by, for example, varying the pH of the solution (e.g., within a range of about pH 7 to about pH 8.5), the temperature of the incubation (e.g., within a range of about 20° C. to about 40° C., e.g., room temperature or 37° C.), the incubation time (e.g., within a range of about 15 minutes to about 150 minutes, and/or the activatable antibody concentrations (e.g., within a range of about 0.05 μg/ml to about 10 μg/ml). The tissue was then extensively washed to remove non-bound material. The presence of activated antibody on the tissue was detected using a secondary anti-human IgG antibody labeled with AlexaFluor-647. The conditions of that detection can be adjusted to the detecting reagent and detection modality (e.g., fluorescently labeled). For example, when a fluorescent tag was used, the tissue was submitted to fluorescent microscopy. As shown in FIG. 6, anti-EGFR activatable antibody 3954-2001-C225v5 demonstrated staining with comparable intensity and pattern as parental anti-EGFR antibody. The fluorescent signal of anti-EGFR activatable antibody 3954-2001-C225v5 was significantly inhibited by pre-treatment of the tissue with a 1:100 dilution of broad spectrum inhibitor cocktail set III (539134, EMD Millipore, Billerica, Mass.) and 50 mM EDTA.

Example 4. Additional Matrix Metalloprotease (MMP) and Serine Protease (SP) Activatable Antibodies This Example demonstrates the generation and evaluation of additional substrate sequences that are activated in the presence of at least one matrix metalloprotease (MMP) and at least one serine protease.

The studies described herein used the following substrate sequences:

| CM1-CM2 Substrate | AA sequence | SEQ ID NO: |
|---|---|---|
| 2001 | ISSGLLSGRSDNH | 1 |
| 1004/LP'/0003 | AVGLLAPPGGTSTSGRSANPRG | 3 |
| 1004/LP'/0001 | AVGLLAPPGGLSGRSDNH | 7 |
| 2003 | ISSGLLSGRSANPRG | 469 |
| 2004 | AVGLLAPPTSGRSANPRG | 470 |
| 2005 | AVGLLAPPSGRSANPRG | 471 |

The ability of substrates, 2001, 1004/LP'/0001, 1004/LP'/0003, 2003, 2004, or 2005 to be cleaved by human matriptase and/or human uPA was determined as described above in Example 2.

Substrate 2003 demonstrated approximately a 50-fold increase in the cleavage kinetics for matriptase as compared to substrate 2001, and substrate 2005 demonstrated approximately a 50-fold increase in the cleavage kinetics for matriptase as compared to substrate 1004/LP'/0001.

Substrates 2003 and 2005 also demonstrated modest increases in the range of about 3- to 4-fold in uPA kinetics as compared to 2001 and 1004/LP'/0001, respectively. Substrates 2003 and 2005 were found to be cleaved in the presence of mouse uPA as well.

Substrates 2003, 2004, and 2005 were incorporated in the following activatable antibodies:

Anti-EGFR Heavy Chain:
Amino acid Sequence:
(SEQ ID NO: 108)

QVQLKQSGPGLVQPSQSLSITCTVSGFSLTNYGVHWVRQSPGKGLEWLG

VIWSGGNTDYNTPFTSRLSINKDNSKSQVFFKMNSLQSQDTAIYYCARA

LTYYDYEFAYWGQGTLVTVSAASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK

Anti-EGFR Light Chain:
Amino acid Sequence:
(SEQ ID NO: 111)

QILLTQSPVILSVSPGERVSFSCRASQSIGTNIHWYQQRTNGSPRLLIK

YASESISGIPSRFSGSGSGTDFTLSINSVESEDIADYYCQQNNNWPTTF

GAGTKLELKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

Anti-EGFR 2003 Activatable Antibody Light Chain:
Amino acid Sequence:
(SEQ ID NO: 472)

CISPRGCPDGPYVMYGSSGGSGGSGGSGISSGLLSGRSANPRGGSSGTQ

ILLTQSPVILSVSPGERVSFSCRASQSIGTNIHWYQQRTNGSPRLLIKY

ASESISGIPSRFSGSGSGTDFTLSINSVESEDIADYYCQQNNNWPTTFG

AGTKLELKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC

Anti-EGFR 2003 Activatable Antibody Light Chain
with spacer sequence:
Amino acid Sequence:
(SEQ ID NO: 473)

QGQSGQCISPRGCPDGPYVMYGSSGGSGGSGGSGISSGLLSGRSANPRG

GSSGTQILLTQSPVILSVSPGERVSFSCRASQSIGTNIHWYQQRTNGSP

RLLIKYASESISGIPSRFSGSGSGTDFTLSINSVESEDIADYYCQQNNN

WPTTFGAGTKLELKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC

Anti-EGFR 2005 Activatable Antibody Light Chain:
Amino acid Sequence:
(SEQ ID NO: 474)

CISPRGCPDGPYVMYGSSGGSGGSGGSGAVGLLAPPSGRSANPRGGSSG

TQILLTQSPVILSVSPGERVSFSCRASQSIGTNIHWYQQRTNGSPRLLI

KYASESISGIPSRFSGSGSGTDFTLSINSVESEDIADYYCQQNNNWPTT

FGAGTKLELKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC

-continued

Anti-EGFR 2005 Activatable Antibody Light Chain with spacer sequence:
Amino acid Sequence:

(SEQ ID NO: 475)
QGQSGQCISPRGCPDGPYVMYGSSGGSGGSGGSGAVGLLAPPSGRSANP

RGGSSGTQILLTQSPVILSVSPGERVSFSCRASQSIGTNIHWYQQRTNG

SPRLLIKYASESISGIPSRFSGSGSGTDFTLSINSVESEDIADYYCQQN

NNWPTTFGAGTKLELKRTVAAPSVFIFPPSDEQLKSGTASVVCLLNNFY

PREAKVQWKVDNALQSGNSQESVTEQDSKDSTYSLSSTLTLSKADYEKH

KVYACEVTHQGLSSPVTKSFNRGEC

The substrates used in all of the anti-EGFR activatable antibodies shown above were cleaved by human matriptase, by human uPA, by human matrix metalloprotease 14 (MMP14), and human matrix metalloprotease 9 (MMP9).

This section describes the evaluation of various anti-EGFR activatable antibodies shown above in a H292 tumor efficacy study using H292 xenograft tumors in nu/nu mice. The H292 tumor efficacy study is described in Example 2 and is also described in PCT Publication No. WO 2013/163631.

In this study, the mice were group and dosed as shown in the Table below using a control intravenous immunoglobulin (IVIG), the anti-EGFR antibody cetuximab, the anti-EGFR activatable antibody referred to herein as anti-EGFR 2001 activatable antibody, which includes the heavy chain sequence of SEQ ID NO: 108, and the light chain sequence of SEQ ID NO: 449; the anti-EGFR activatable antibody referred to herein as anti-EGFR 2003 activatable antibody, which includes the heavy chain sequence of SEQ ID NO: 108, and the light chain sequence of SEQ ID NO: 472; or the anti-EGFR activatable antibody referred to herein as anti-EGFR 2005 activatable antibody, which includes the heavy chain sequence of SEQ ID NO: 108, and the light chain sequence of SEQ ID NO: 474:

| Group | Count | Treatment | Dose (mg/kg) | Schedule |
|---|---|---|---|---|
| 1 | 8 | IVIG | 9 | Single Dose |
| 2 | 8 | Cetuximab | 9 | Single Dose |
| 3 | 8 | Anti-EGFR 2001 Activatable Antibody | 9 | Single Dose |
| 4 | 8 | Anti-EGFR 2003 Activatable Antibody | 9 | Single Dose |
| 5 | 8 | Anti-EGFR 2005 Activatable Antibody | 9 | Single Dose |

The efficacy of the substrates used in the anti-EGFR antibodies shown above was evaluated by measuring tumor volume (TV $mm^3$) at various time points post-administration. The results of this study are shown in FIGS. 8A-8F.

This section describes the evaluation of various anti-Jagged activatable antibodies in a toxicology study using methods similar to those described in Example 2 with regard to the data shown in FIG. 4.

In this study, toxicity was measured as a function of body weight (BW) loss in DBA/1 mice following administration with a control intravenous immunoglobulin (IVIG), a 20 mg/kg dose of the anti-Jagged antibody referred to herein as 4D11, which includes the heavy chain sequence of SEQ ID NO: 67 and the light chain sequence of SEQ ID NO: 162, a 10 mg/kg dose of the 4D11 antibody, a 5 mg/kg dose of the 4D11 antibody, the anti-Jagged activatable antibody referred to herein as anti-Jagged 2001 activatable antibody, which includes the heavy chain sequence of SEQ ID NO: 67, and the light chain sequence of SEQ ID NO: 420, the anti-Jagged activatable antibody referred to herein as anti-Jagged 1004/LP'/0001 activatable antibody, which includes the heavy chain sequence of SEQ ID NO: 67, and the light chain sequence of SEQ ID NO: 432, the anti-Jagged activatable antibody referred to herein as anti-Jagged 1004/LP'/0003 activatable antibody, which includes the heavy chain sequence of SEQ ID NO: 67, and the light chain sequence of SEQ ID NO: 424, the anti-Jagged activatable antibody referred to herein as anti-Jagged 2003 activatable antibody, which includes the heavy chain sequence of SEQ ID NO: 67, and the light chain sequence of SEQ ID NO: 477 shown below, and the anti-Jagged activatable antibody referred to herein as anti-Jagged 2005 activatable antibody, which includes the heavy chain sequence of SEQ ID NO: 67, and the light chain sequence of SEQ ID NO: 479 shown below.

Anti-Jagged 2003 activatable antibody Lc with spacer sequence
Amino Acid sequence (SEQ ID NO: 476)
QGQSGQCNIWLVGGDCRGWQGGSSGGSISSGLLSGRSANPRGGGSDIQMT

QSPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKVE

IKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPV

TKSFNRGEC

Anti-Jagged 2003 activatable antibody Lc
Amino Acid sequence (SEQ ID NO: 477)
CNIWLVGGDCRGWQGGSSGGSISSGLLSGRSANPRGGGSDIQMTQSPSSL

SASVGDRVTITCRASQSISSYLNWYQQKPGKAPKLLIYAASSLQSGVPSR

FSGSGSGTDFTLTISSLQPEDFATYYCQQTVVAPPLFGQGTKVEIKRTVA

APSVFIFPPSDEQLKSGTASVVCLLNNFYPREAKVQWKVDNALQSGNSQE

SVTEQDSKDSTYSLSSTLTLSKADYEKHKVYACEVTHQGLSSPVTKSFNR

GEC

Anti-Jagged 2005 activatable antibody Lc with spacer sequence
Amino Acid sequence (SEQ ID NO: 478)
QGQSGQCNIWLVGGDCRGWQGGSSGGSAVGLLAPPSGRSANPRGGGSDIQ

MTQSPSSLSASVGDRVTITCRASQSISSYLNWYQQKPGKAPKLLIYAASS

LQSGVPSRFSGSGSGTDFTLTISSLQPEDFATYYCQQTVVAPPLFGQGTK

VEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSS

PVTKSFNRGEC

Anti-Jagged 2005 activatable antibody Lc
Amino Acid sequence (SEQ ID NO: 479)
CNIWLVGGDCRGWQGGSSGGSAVGLLAPPSGRSANPRGGGSDIQMTQSPS

SLSASVGDRVTITCRASQSISSYLNWYQQKPGKAPKLLIYAASSLQSGVP

SRFSGSGSGTDFTLTISSLQPEDFATYYCQQTVVAPPLFGQGTKVEIKRT

VAAPSVFIFPPSDEQLKSGTASVVCLLNNFYPREAKVQWKVDNALQSGNS

-continued

QESVTEQDSKDSTYSLSSTLTLSKADYEKHKVYACEVTHQGLSSPVTKSF

NRGEC

In the study depicted in FIG. 9, the mice were group and dosed as shown in the Table below:

| Group | Count | Treatment | Dose (mg/kg) | Schedule | Route |
|---|---|---|---|---|---|
| 1 | 3 | IVIG | — | Single dose | IP |
| 2 | 3 | 4D11 | 20 mg/kg | Single dose | IP |
| 3 | 3 | 4D11 | 10 mg/kg | Single dose | IP |
| 4 | 3 | 4D11 | 5 mg/kg | Single dose | IP |
| 5 | 3 | Anti-Jagged 2001 Activatable Antibody | 20 mg/kg | Single dose | IP |
| 6 | 3 | Anti-Jagged 1004/LP'/0001 Activatable Antibody | 20 mg/kg | Single dose | IP |
| 7 | 3 | Anti-Jagged 2003 Activatable Antibody | 20 mg/kg | Single dose | IP |
| 8 | 3 | Anti-Jagged 2005 Activatable Antibody | 20 mg/kg | Single dose | IP |

Figure 9:
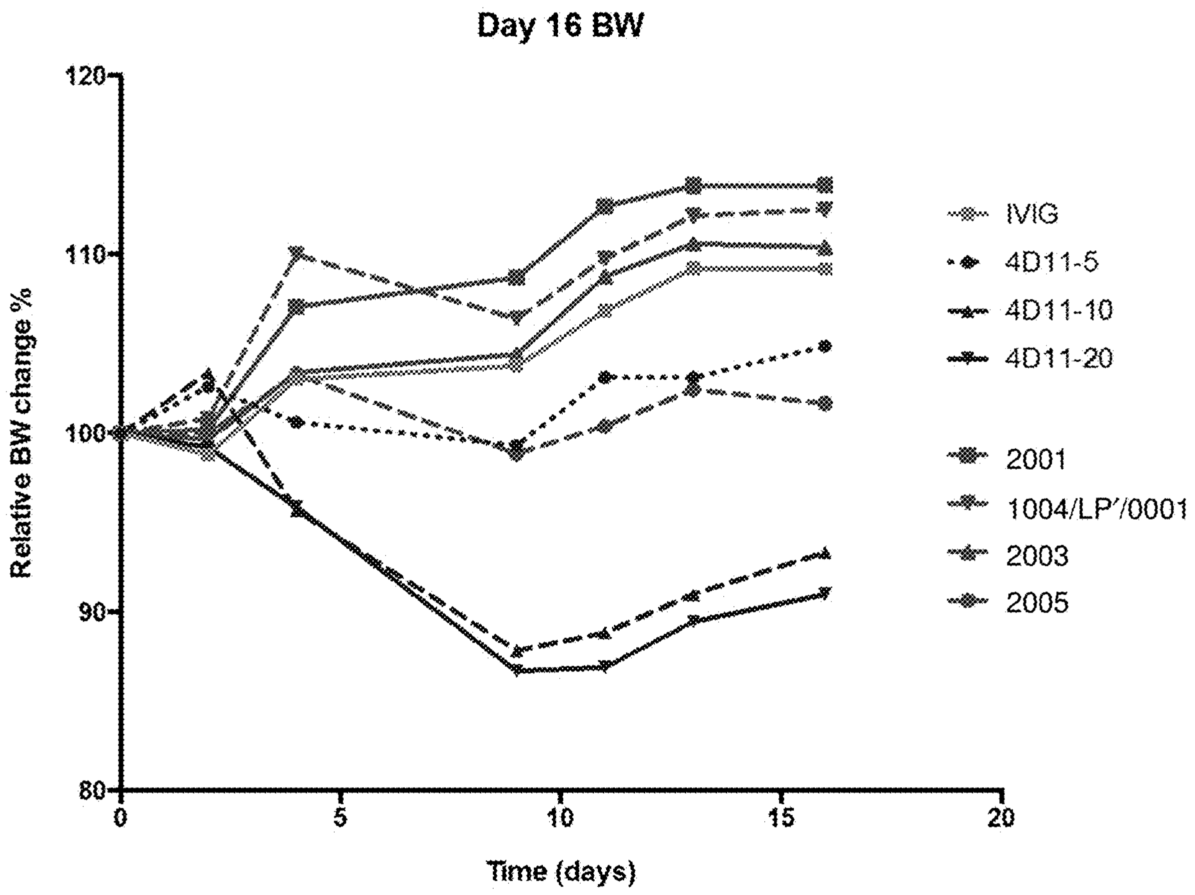
FIG. 9 is a graph depicting toxicity as measured by body weight (BW) loss following administration with an isotype control intravenous immunoglobulin (IVIG), a 20 mg/kg dose of the anti-Jagged antibody referred to herein as 4D11, which includes the heavy chain sequence of SEQ ID NO: 67 and the light chain sequence of SEQ ID NO: 162, a 10 mg/kg dose of the 4D11 antibody, a 5 mg/kg dose of the 4D11 antibody, the anti-Jagged activatable antibody referred to herein as anti-Jagged 2001 activatable antibody, which includes the heavy chain sequence of SEQ ID NO: 67, and the light chain sequence of SEQ ID NO: 420, the anti-Jagged activatable antibody referred to herein as anti-Jagged 1004/LP'/0001 activatable antibody, which includes the heavy chain sequence of SEQ ID NO: 67, and the light chain sequence of SEQ ID NO: 432, the anti-Jagged activatable antibody referred to herein as anti-Jagged 2003 activatable antibody, which includes the heavy chain sequence of SEQ ID NO: 67, and the light chain sequence of SEQ ID NO: 477, and the anti-Jagged activatable antibody referred to herein as anti-Jagged 2005 activatable antibody, which includes the heavy chain sequence of SEQ ID NO: 67, and the light chain sequence of SEQ ID NO: 479. The results are shown as relative body weight (BW) change percent (%) at various time points during the study.

The results are shown in FIG. 9 as relative body weight (BW) change percent (%) at various time points during the study.

Figure 10:
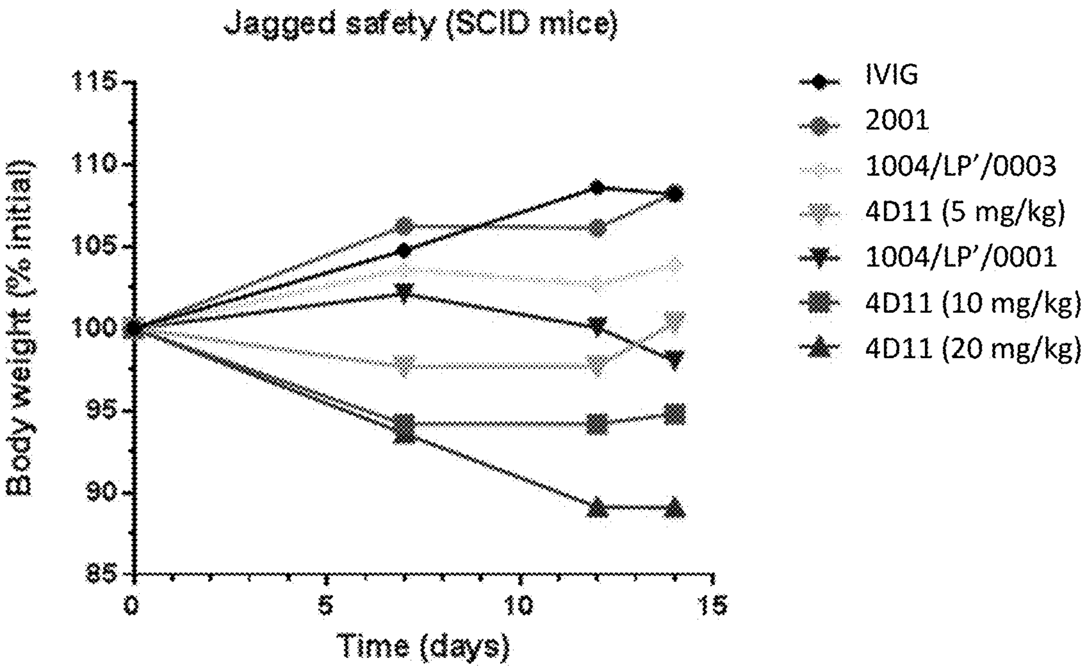
FIG. 10 is a graph depicting toxicity as measured by body weight (BW) loss following administration with an isotype control intravenous immunoglobulin (IVIG), a 20 mg/kg dose of the anti-Jagged antibody referred to herein as 4D11, which includes the heavy chain sequence of SEQ ID NO: 67 and the light chain sequence of SEQ ID NO: 162, a 10 mg/kg dose of the 4D11 antibody, a 5 mg/kg dose of the 4D11 antibody, the anti-Jagged activatable antibody referred to herein as anti-Jagged 2001 activatable antibody ("2001"), which includes the heavy chain sequence of SEQ ID NO: 67, and the light chain sequence of SEQ ID NO: 420, the anti-Jagged activatable antibody referred to herein as anti-Jagged 1004/LP'/0001 activatable antibody, which includes the heavy chain sequence of SEQ ID NO: 67, and the light chain sequence of SEQ ID NO: 432, and the anti-Jagged activatable antibody referred to herein as anti-Jagged 1004/LP'/0003 activatable antibody, which includes the heavy chain sequence of SEQ ID NO: 67, and the light chain sequence of SEQ ID NO: 424. The results are shown as relative body weight (BW) change percent (%) at various time points during the study.
Figure 11A:
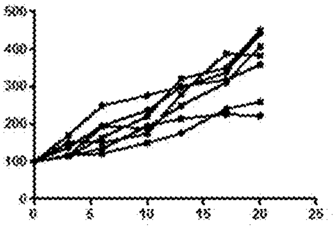
FIGS. 11A, 11B, 11C, 11D, 11E, 11F, 11G, and 11H and FIG. 12 are a series of graphs depicting the efficacy of various substrates of the disclosure when incorporated in activatable anti-EGFR antibodies of the disclosure. Efficacy of the substrates was evaluated by measuring tumor volume (TV $mm^3$) at various time points post-administration.
Figure 11B:
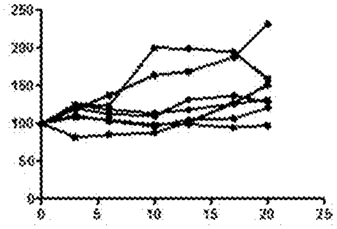
Figure 11C:
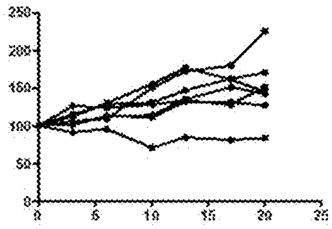
Figure 11D:
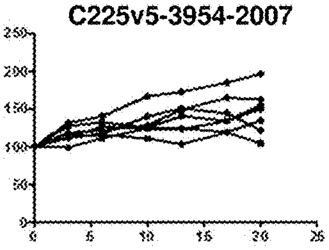
Figure 11E:
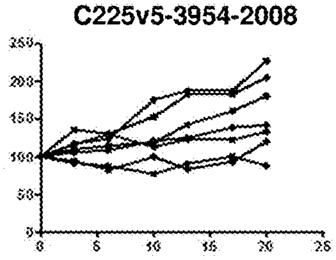
Figure 11F:
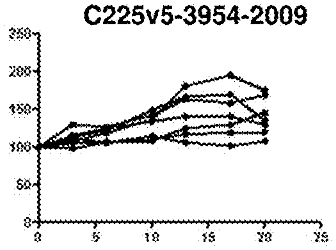
Figure 11G:
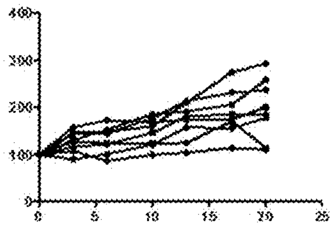
Figure 11H:
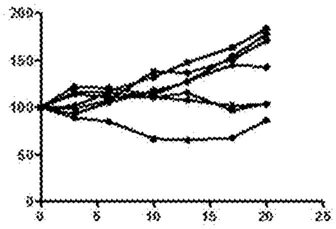
Figure 12:
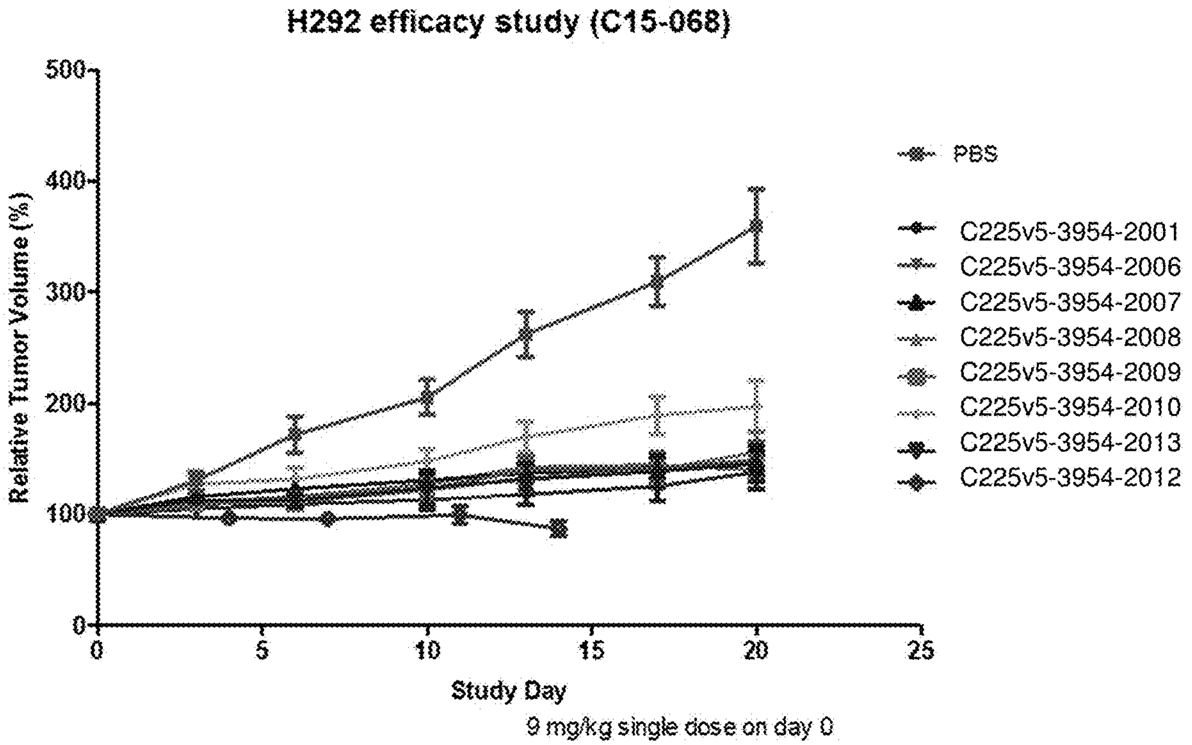

The results are shown in FIG. 10 as relative body weight (BW) change percent (%) at various time points during the study.

As shown in FIGS. 8A-8F, FIG. 9, and FIG. 10, activatable antibodies including the cleavable substrates of the disclosure are safe and efficacious. In particular, the 2003 substrate has demonstrated efficacy comparable to the 2001 substrate and safety comparable to IVIG, and the 2005 substrate has demonstrated efficacy comparable to parental and safety comparable to parental dosed 4-fold lower.

Example 5. Additional Matrix Metalloprotease (MMP) and Serine Protease (SP) Activatable Antibodies This Example demonstrates the generation and evaluation of additional substrate sequences that are activated in the presence of at least one matrix metalloprotease (MMP) and at least one serine protease.

The studies described herein used the following substrate sequences:

| CM1-CM2 Substrate | Amino Acid Sequence | Nucleotide Sequence |
|---|---|---|
| 2006 | ISSGLLSGRSDDH (SEQ ID NO: 483) | ATATCGAGTGGATTGCTGTCTGGCAGATCTGACGATCAC (SEQ ID NO: 491) |
| 2007 | ISSGLLSGRSDIH (SEQ ID NO: 484) | ATATCGAGTGGATTGCTGTCTGGCAGATCTGACATACAC (SEQ ID NO: 492) |
| 2008 | ISSGLLSGRSDQH (SEQ ID NO: 485) | ATATCGAGTGGATTGCTGTCTGGCAGATCTGACCAACAC (SEQ ID NO: 493) |
| 2009 | ISSGLLSGRSDTH (SEQ ID NO: 486) | ATATCGAGTGGATTGCTGTCTGGCAGATCTGACACTCAC (SEQ ID NO: 494) |
| 2010 | ISSGLLSGRSDYH (SEQ ID NO: 487) | ATATCGAGTGGATTGCTGTCTGGCAGATCTGACTATCAC (SEQ ID NO: 495) |
| 2011 | ISSGLLSGRSDNP (SEQ ID NO: 488) | ATTAGCTCAGGCCTTCTTAGCGGCCGCAGCGACAATCCC (SEQ ID NO: 496) |
| 2012 | ISSGLLSGRSANP (SEQ ID NO: 489) | ATATCGAGTGGATTGCTGTCTGGCAGATCTGCTAATCCC (SEQ ID NO: 497) |
| 2013 | ISSGLLSGRSANI (SEQ ID NO: 490) | ATATCGAGTGGATTGCTGTCTGGCAGATCTGCTAATATA (SEQ ID NO: 498) |
| 2014 | ISSGLLSGRSDNI (SEQ ID NO: 555) | ATATCGAGTGGATTGCTGTCTGGCAGATCTGACAATATA (SEQ ID NO: 556) |
| 3006 | AVGLLAPPGGLSGRSDDH (SEQ ID NO: 515) | GCTGTGGGACTGCTGGCTCCTCCTGGTGGCCTGTCT GGCAGATCTGACGATCAC (SEQ ID NO: 523) |
| 3007 | AVGLLAPPGGLSGRSDIH (SEQ ID NO: 516) | GCTGTGGGACTGCTGGCTCCTCCTGGTGGCCTGTCT GGCAGATCTGACATACAC (SEQ ID NO: 524) |
| 3008 | AVGLLAPPGGLSGRSDQH (SEQ ID NO: 517) | GCTGTGGGACTGCTGGCTCCTCCTGGTGGCCTGTCT GGCAGATCTGACCAACAC (SEQ ID NO: 525) |
| 3009 | AVGLLAPPGGLSGRSDTH (SEQ ID NO: 518) | GCTGTGGGACTGCTGGCTCCTCCTGGTGGCCTGTCT GGCAGATCTGACACTCAC (SEQ ID NO: 526) |
| 3010 | AVGLLAPPGGLSGRSDYH (SEQ ID NO: 519) | GCTGTGGGACTGCTGGCTCCTCCTGGTGGCCTGTCT GGCAGATCTGACTATCAC (SEQ ID NO: 527) |
| 3011 | AVGLLAPPGGLSGRSDNP (SEQ ID NO: 520) | GCTGTGGGACTGCTGGCTCCTCCTGGTGGCCTGTCT GGCAGATCTGACAATCCC (SEQ ID NO: 528) |

-continued

| CM1-CM2 Substrate | Amino Acid Sequence | Nucleotide Sequence |
|---|---|---|
| 3012 | AVGLLAPPGGLSGRSANP (SEQ ID NO: 521) | GCTGTGGGACTGCTGGCTCCTCCTGGTGGCCTGTCT GGCAGATCTGCTAATCCC (SEQ ID NO: 529) |
| 3013 | AVGLLAPPGGLSGRSANI (SEQ ID NO: 522) | GCTGTGGGACTGCTGGCTCCTCCTGGTGGCCTGTCT GGCAGATCTGCTAATATA (SEQ ID NO: 530) |
| 3014 | AVGLLAPPGGLSGRSDNI (SEQ ID NO: 557) | GCTGTGGGACTGCTGGCTCCTCCTGGTGGCCTGTCTGGCA GATCTGACAATATA (SEQ ID NO: 558) |

Those of ordinary skill in the art will appreciate that the nucleotide sequences presented herein are exemplary, and the skilled artisan can also use other codon combinations and/or degenerate nucleotide sequence(s) to express the same peptide sequence.

Substrates 2006-2014 and substrates 3006-3014 were incorporated in the following activatable antibodies:

Anti-EGFR Heavy Chain:
Amino acid Sequence:
(SEQ ID NO: 108)

QVQLKQSGPGLVQPSQSLSITCTVSGFSLTNYGVHWVRQSPGKGLEWLG
VIWSGGNTDYNTPFTSRLSINKDNSKSQVFFKMNSLQSQDTAIYYCARA
LTYYDYEFAYWGQGTLVTVSAASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQK
SLSLSPGK

Anti-EGFR Light Chain:
Amino acid Sequence:
(SEQ ID NO: 111)

QILLTQSPVILSVSPGERVSFSCRASQSIGTNIHWYQQRTNGSPRLLIK
YASESISGIPSRFSGSGSGTDFTLSINSVESEDIADYYCQQNNNWPTTF
GAGTKLELKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC

Anti-EGFR 2006 Activatable Antibody Light Chain:
Amino acid Sequence:
(SEQ ID NO: 499)

CISPRGCPDGPYVMYGSSGGSGGSGGSGISSGLLSGRSDDHGSSGTQIL
LTQSPVILSVSPGERVSFSCRASQSIGTNIHWYQQRTNGSPRLLIKYAS
ESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC

-continued

Anti-EGFR 2007 Activatable Antibody Light Chain:
Amino acid Sequence:
(SEQ ID NO: 500)

CISPRGCPDGPYVMYGSSGGSGGSGGSGISSGLLSGRSDIHGSSGTQIL
LTQSPVILSVSPGERVSFSCRASQSIGTNIHWYQQRTNGSPRLLIKYAS
ESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC

Anti-EGFR 2008 Activatable Antibody Light Chain:
Amino acid Sequence:
(SEQ ID NO: 501)

CISPRGCPDGPYVMYGSSGGSGGSGGSGISSGLLSGRSDQHGSSGTQIL
LTQSPVILSVSPGERVSFSCRASQSIGTNIHWYQQRTNGSPRLLIKYAS
ESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC

Anti-EGFR 2009 Activatable Antibody Light Chain:
Amino acid Sequence:
(SEQ ID NO: 502)

CISPRGCPDGPYVMYGSSGGSGGSGGSGISSGLLSGRSDTHGSSGTQIL
LTQSPVILSVSPGERVSFSCRASQSIGTNIHWYQQRTNGSPRLLIKYAS
ESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC

Anti-EGFR 2010 Activatable Antibody Light Chain:
Amino acid Sequence:
(SEQ ID NO: 503)

CISPRGCPDGPYVMYGSSGGSGGSGGSGISSGLLSGRSDYHGSSGTQIL
LTQSPVILSVSPGERVSFSCRASQSIGTNIHWYQQRTNGSPRLLIKYAS
ESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC

-continued

Anti-EGFR 2011 Activatable Antibody Light Chain: Amino acid Sequence:
(SEQ ID NO: 504)
CISPRGCPDGPYVMYGSSGGSGGSGGSGISSGLLSGRSDNPGSSGTQIL
LTQSPVILSVSPGERVSFSCRASQSIGTNIHWYQQRTNGSPRLLIKYAS
ESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC Anti-EGFR 2012 Activatable Antibody Light Chain: Amino acid Sequence:
(SEQ ID NO: 505)
CISPRGCPDGPYVMYGSSGGSGGSGGSGISSGLLSGRSANPGSSGTQIL
LTQSPVILSVSPGERVSFSCRASQSIGTNIHWYQQRTNGSPRLLIKYAS
ESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC Anti-EGFR 2013 Activatable Antibody Light Chain: Amino acid Sequence:
(SEQ ID NO: 506)
CISPRGCPDGPYVMYGSSGGSGGSGGSGISSGLLSGRSANIGSSGTQIL
LTQSPVILSVSPGERVSFSCRASQSIGTNIHWYQQRTNGSPRLLIKYAS
ESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC Anti-EGFR 2014 Activatable Antibody Light Chain: Amino acid Sequence:
(SEQ ID NO: 559)
CISPRGCPDGPYVMYGSSGGSGGSGGSGISSGLLSGRSDNIGSSGTQIL
LTQSPVILSVSPGERVSFSCRASQSIGTNIHWYQQRTNGSPRLLIKYAS
ESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC Anti-EGFR 3006 Activatable Antibody Light Chain: Amino acid Sequence:
(SEQ ID NO: 531)
CISPRGCPDGPYVMYGSSGGSGGSGGSGAVGLLAPPGGLSGRSDDHGSS
GTQILLTQSPVILSVSPGERVSFSCRASQSIGTNIHWYQQRTNGSPRLL
IKYASESISGIPSRFSGSGSGTDFTLSINSVESEDIADYYCQQNNNWPT
TFGAGTKLELKRTVAAPSVFIFPPSDEQLKSGTASVVCLLNNFYPREAK
VQWKVDNALQSGNSQESVTEQDSKDSTYSLSSTLTLSKADYEKHKVYAC
EVTHQGLSSPVTKSFNRGEC -continued Anti-EGFR 3007 Activatable Antibody Light Chain: Amino acid Sequence:
(SEQ ID NO: 532)
CISPRGCPDGPYVMYGSSGGSGGSGGSGAVGLLAPPGGLSGRSDIHGSS
GTQILLTQSPVILSVSPGERVSFSCRASQSIGTNIHWYQQRTNGSPRLL
IKYASESISGIPSRFSGSGSGTDFTLSINSVESEDIADYYCQQNNNWPT
TFGAGTKLELKRTVAAPSVFIFPPSDEQLKSGTASVVCLLNNFYPREAK
VQWKVDNALQSGNSQESVTEQDSKDSTYSLSSTLTLSKADYEKHKVYAC
EVTHQGLSSPVTKSFNRGEC Anti-EGFR 3008 Activatable Antibody Light Chain: Amino acid Sequence:
(SEQ ID NO: 533)
CISPRGCPDGPYVMYGSSGGSGGSGGSGAVGLLAPPGGLSGRSDQHGSS
GTQILLTQSPVILSVSPGERVSFSCRASQSIGTNIHWYQQRTNGSPRLL
IKYASESISGIPSRFSGSGSGTDFTLSINSVESEDIADYYCQQNNNWPT
TFGAGTKLELKRTVAAPSVFIFPPSDEQLKSGTASVVCLLNNFYPREAK
VQWKVDNALQSGNSQESVTEQDSKDSTYSLSSTLTLSKADYEKHKVYAC
EVTHQGLSSPVTKSFNRGEC Anti-EGFR 3009 Activatable Antibody Light Chain: Amino acid Sequence:
(SEQ ID NO: 534)
CISPRGCPDGPYVMYGSSGGSGGSGGSGAVGLLAPPGGLSGRSDTHGSS
GTQILLTQSPVILSVSPGERVSFSCRASQSIGTNIHWYQQRTNGSPRLL
IKYASESISGIPSRFSGSGSGTDFTLSINSVESEDIADYYCQQNNNWPT
TFGAGTKLELKRTVAAPSVFIFPPSDEQLKSGTASVVCLLNNFYPREAK
VQWKVDNALQSGNSQESVTEQDSKDSTYSLSSTLTLSKADYEKHKVYAC
EVTHQGLSSPVTKSFNRGEC Anti-EGFR 3010 Activatable Antibody Light Chain: Amino acid Sequence:
(SEQ ID NO: 535)
CISPRGCPDGPYVMYGSSGGSGGSGGSGAVGLLAPPGGLSGRSDYHGSS
GTQILLTQSPVILSVSPGERVSFSCRASQSIGTNIHWYQQRTNGSPRLL
IKYASESISGIPSRFSGSGSGTDFTLSINSVESEDIADYYCQQNNNWPT
TFGAGTKLELKRTVAAPSVFIFPPSDEQLKSGTASVVCLLNNFYPREAK
VQWKVDNALQSGNSQESVTEQDSKDSTYSLSSTLTLSKADYEKHKVYAC
EVTHQGLSSPVTKSFNRGEC Anti-EGFR 3011 Activatable Antibody Light Chain: Amino acid Sequence:
(SEQ ID NO: 536)
CISPRGCPDGPYVMYGSSGGSGGSGGSGAVGLLAPPGGLSGRSDNPGSS
GTQILLTQSPVILSVSPGERVSFSCRASQSIGTNIHWYQQRTNGSPRLL
IKYASESISGIPSRFSGSGSGTDFTLSINSVESEDIADYYCQQNNNWPT
TFGAGTKLELKRTVAAPSVFIFPPSDEQLKSGTASVVCLLNNFYPREAK
VQWKVDNALQSGNSQESVTEQDSKDSTYSLSSTLTLSKADYEKHKVYAC
EVTHQGLSSPVTKSFNRGEC -continued Anti-EGFR 3012 Activatable Antibody Light Chain:
Amino acid Sequence:
(SEQ ID NO: 537)
CISPRGCPDGPYVMYGSSGGSGGSGGSGAVGLLAPPGGLSGRSANPGSS
GTQILLTQSPVILSVSPGERVSFSCRASQSIGTNIHWYQQRTNGSPRLL
IKYASESISGIPSRFSGSGSGTDFTLSINSVESEDIADYYCQQNNNWPT
TFGAGTKLELKRTVAAPSVFIFPPSDEQLKSGTASVVCLLNNFYPREAK
VQWKVDNALQSGNSQESVTEQDSKDSTYSLSSTLTLSKADYEKHKVYAC
EVTHQGLSSPVTKSFNRGEC Anti-EGFR 3013 Activatable Antibody Light Chain:
Amino acid Sequence:
(SEQ ID NO: 538)
CISPRGCPDGPYVMYGSSGGSGGSGGSGAVGLLAPPGGLSGRSANIGSS
GTQILLTQSPVILSVSPGERVSFSCRASQSIGTNIHWYQQRTNGSPRLL
IKYASESISGIPSRFSGSGSGTDFTLSINSVESEDIADYYCQQNNNWPT
TFGAGTKLELKRTVAAPSVFIFPPSDEQLKSGTASVVCLLNNFYPREAK
VQWKVDNALQSGNSQESVTEQDSKDSTYSLSSTLTLSKADYEKHKVYAC
EVTHQGLSSPVTKSFNRGEC Anti-EGFR 3014 Activatable Antibody Light Chain:
Amino acid Sequence:
(SEQ ID NO: 560)
CISPRGCPDGPYVMYGSSGGSGGSGGSGAVGLLAPPGGLSGRSDNIGSS
GTQILLTQSPVILSVSPGERVSFSCRASQSIGTNIHWYQQRTNGSPRLL
IKYASESISGIPSRFSGSGSGTDFTLSINSVESEDIADYYCQQNNNWPT
TFGAGTKLELKRTVAAPSVFIFPPSDEQLKSGTASVVCLLNNFYPREAK
VQWKVDNALQSGNSQESVTEQDSKDSTYSLSSTLTLSKADYEKHKVYAC
EVTHQGLSSPVTKSFNRGEC All eighteen EGFR activatable antibodies containing substrate sequences of substrate 2006 (SEQ ID NO: 483), substrate 2007 (SEQ ID NO: 484), substrate 2008 (SEQ ID NO: 485), substrate 2009 (SEQ ID NO: 486), substrate 2010 (SEQ ID NO: 487), substrate 2011 (SEQ ID NO: 488), substrate 2012 (SEQ ID NO: 489), substrate 2013 (SEQ ID NO: 490), 2014 (SEQ ID NO: 555), substrate 3006 (SEQ ID NO: 515), substrate 3007 (SEQ ID NO: 516), substrate 3008 (SEQ ID NO: 517), substrate 3009 (SEQ ID NO: 518), substrate 3010 (SEQ ID NO: 519), substrate 3011 (SEQ ID NO: 520), substrate 3012 (SEQ ID NO: 521), substrate 3013 (SEQ ID NO: 522), or substrate 3014 (SEQ ID NO: 557) also comprised the masking moiety comprising the amino acid sequence CISPRGCPDGPYVMY (SEQ ID NO: 168) and anti-EGFR antibody C225v5 antibody comprising a light chain (SEQ ID NO: 111) and a heavy chain (SEQ ID NO: 108). The configuration of the light chain of the activatable antibody was masking moiety—substrate—light chain of C225v5.

Cleavage of anti-EGFR activatable antibodies comprising substrates 2001, 2006-2010 and 2012 by human matriptase using techniques similar to those described herein exhibited a range of $k_{cat}/K_m$ values ranging from 6E+02 to 2E+04. Cleavage of anti-EGFR activatable antibodies comprising substrates 2001, 2006-2010, 2012 and 2013 by human matrix metalloprotease 14 (MMP14) using techniques similar to those described herein exhibited a range of $k_{cat}/K_m$ values ranging from 1E+04 to 5E+04. In vivo, these antibodies also exhibited comparable 4-day stability in both normal and tumor-bearing mice using techniques similar to those described herein.

This section describes the evaluation of various anti-EGFR activatable antibodies shown above in a H292 tumor efficacy study using H292 xenograft tumors in nu/nu mice. The H292 tumor efficacy study is described in Example 2 and is also described in PCT Publication No. WO 2013/163631, the contents of each of which are hereby incorporated by reference in their entireties.

In this study, the mice were group and dosed as shown in the Table below using a control PBS, activatable antibody, which includes the heavy chain sequence of SEQ ID NO: 108, and the light chain sequence of SEQ ID NO: 111; the anti-EGFR C225v5-3954-2001 activatable antibody, anti-EGFR C225v5-3954-2006 activatable antibody, anti-EGFR C225v5-3954-2007 activatable antibody, etc., as shown in the Table below:

| Group | Count | Treatment | Dose (mg/kg) | Schedule |
|---|---|---|---|---|
| 1 | 8 | IVIG | 9 | Single Dose |
| 2 | 8 | C225v5-3954-2001 | 9 | Single Dose |
| 3 | 8 | C225v5-3954-2007 | 9 | Single Dose |
| 4 | 8 | C225v5-3954-2006 | 9 | Single Dose |
| 5 | 8 | C225v5-3954-2008 | 9 | Single Dose |
| 6 | 8 | C225v5-3954-2009 | 9 | Single Dose |
| 7 | 8 | C225v5-3954-2010 | 9 | Single Dose |
| 8 | 8 | C225v5-3954-2012 | 9 | Single Dose |
| 9 | 8 | C225v5-3954-2013 | 9 | Single Dose |

The efficacy of the substrates used in the anti-EGFR antibodies shown above was evaluated by measuring tumor volume (TV $mm^3$) at various time points post-administration. The results of this study are shown in FIGS. 11A-11H and 12.

This section describes the evaluation of various anti-Jagged activatable antibodies in a toxicology study using methods similar to those described in Example 2 with regard to the data shown in FIG. 4.

In this study, 20 mg/kg dose of the anti-Jagged antibody referred to herein as 4D11, which includes the heavy chain sequence of SEQ ID NO: 67 and the light chain sequence of SEQ ID NO: 162, a 10 mg/kg dose of the 4D11 antibody, a 5 mg/kg dose of the 4D11 antibody, the anti-Jagged activatable antibody referred to herein as anti-Jagged 2006 activatable antibody, which includes the heavy chain sequence of SEQ ID NO: 67, and the light chain sequence of SEQ ID NO: 507-514 shown below.

Anti-Jagged 2006 activatable antibody Lc
Amino Acid sequence
(SEQ ID NO: 507)
CNIWLVGGDCRGWQGGSSGGSISSGLLSGRSDDHGGGSDIQMTQSPSSL
SASVGDRVTITCRASQSISSYLNWYQQKPGKAPKLLIYAASSLQSGVPS
RFSGSGSGTDFTLTISSLQPEDFATYYCQQTVVAPPLFGQGTKVEIKRT
VAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTK
SFNRGEC -continued Anti-Jagged 2007 activatable antibody Lc Amino Acid sequence (SEQ ID NO: 508)

CNIWLVGGDCRGWQGGSSGGSISSGLLSGRSDIHGGGSDIQMTQSPSSL

SASVGDRVTITCRASQSISSYLNWYQQKPGKAPKLLIYAASSLQSGVPS

RFSGSGSGTDFTLTISSLQPEDFATYYCQQTVVAPPLFGQGTKVEIKRT

VAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTK

SFNRGEC

Anti-Jagged 2008 activatable antibody Lc Amino Acid sequence (SEQ ID NO: 509)

CNIWLVGGDCRGWQGGSSGGSISSGLLSGRSDQHGGGSDIQMTQSPSSL

SASVGDRVTITCRASQSISSYLNWYQQKPGKAPKLLIYAASSLQSGVPS

RFSGSGSGTDFTLTISSLQPEDFATYYCQQTVVAPPLFGQGTKVEIKRT

VAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTK

SFNRGEC

Anti-Jagged 2009 activatable antibody Lc Amino Acid sequence (SEQ ID NO: 510)

CNIWLVGGDCRGWQGGSSGGSISSGLLSGRSDTHGGGSDIQMTQSPSSL

SASVGDRVTITCRASQSISSYLNWYQQKPGKAPKLLIYAASSLQSGVPS

RFSGSGSGTDFTLTISSLQPEDFATYYCQQTVVAPPLFGQGTKVEIKRT

VAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTK

SFNRGEC

Anti-Jagged 2010 activatable antibody Lc Amino Acid sequence (SEQ ID NO: 511)

CNIWLVGGDCRGWQGGSSGGSISSGLLSGRSDYHGGGSDIQMTQSPSSL

SASVGDRVTITCRASQSISSYLNWYQQKPGKAPKLLIYAASSLQSGVPS

RFSGSGSGTDFTLTISSLQPEDFATYYCQQTVVAPPLFGQGTKVEIKRT

VAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTK

SFNRGEC

Anti-Jagged 2011 activatable antibody Lc Amino Acid sequence (SEQ ID NO: 512)

CNIWLVGGDCRGWQGGSSGGSISSGLLSGRSDNPGGGSDIQMTQSPSSL

SASVGDRVTITCRASQSISSYLNWYQQKPGKAPKLLIYAASSLQSGVPS

RFSGSGSGTDFTLTISSLQPEDFATYYCQQTVVAPPLFGQGTKVEIKRT

VAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTK

SFNRGEC

-continued

Anti-Jagged 2012 activatable antibody Lc Amino Acid sequence (SEQ ID NO: 513)

CNIWLVGGDCRGWQGGSSGGSISSGLLSGRSANPGGGSDIQMTQSPSSL

SASVGDRVTITCRASQSISSYLNWYQQKPGKAPKLLIYAASSLQSGVPS

RFSGSGSGTDFTLTISSLQPEDFATYYCQQTVVAPPLFGQGTKVEIKRT

VAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTK

SFNRGEC

Anti-Jagged 2013 activatable antibody Lc Amino Acid sequence (SEQ ID NO: 514)

CNIWLVGGDCRGWQGGSSGGSISSGLLSGRSANIGGGSDIQMTQSPSSL

SASVGDRVTITCRASQSISSYLNWYQQKPGKAPKLLIYAASSLQSGVPS

RFSGSGSGTDFTLTISSLQPEDFATYYCQQTVVAPPLFGQGTKVEIKRT

VAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTK

SFNRGEC

Anti-Jagged 2014 activatable antibody Lc Amino Acid sequence (SEQ ID NO: 561)

CNIWLVGGDCRGWQGGSSGGSISSGLLSGRSDNIGGGSDIQMTQSPSSL

SASVGDRVTITCRASQSISSYLNWYQQKPGKAPKLLIYAASSLQSGVPS

RFSGSGSGTDFTLTISSLQPEDFATYYCQQTVVAPPLFGQGTKVEIKRT

VAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTK

SFNRGEC

Anti-Jagged 3006 activatable antibody Lc Amino Acid sequence (SEQ ID NO: 539)

CNIWLVGGDCRGWQGGSSGGSAVGLLAPPGGLSGRSDDHGGGSDIQMTQ

SPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKV

EIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC

Anti-Jagged 3007 activatable antibody Lc Amino Acid sequence (SEQ ID NO: 540)

CNIWLVGGDCRGWQGGSSGGSAVGLLAPPGGLSGRSDIHGGGSDIQMTQ

SPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKV

EIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC

-continued

Anti-Jagged 3008 activatable antibody Lc
Amino Acid sequence (SEQ ID NO: 541)

CNIWLVGGDCRGWQGGSSGGSAVGLLAPPGGLSGRSDQHGGGSDIQMTQ

SPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKV

EIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC

Anti-Jagged 3009 activatable antibody Lc
Amino Acid sequence (SEQ ID NO: 542)

CNIWLVGGDCRGWQGGSSGGSAVGLLAPPGGLSGRSDTHGGGSDIQMTQ

SPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKV

EIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC

Anti-Jagged 3010 activatable antibody Lc
Amino Acid sequence (SEQ ID NO: 543)

CNIWLVGGDCRGWQGGSSGGSAVGLLAPPGGLSGRSDYHGGGSDIQMTQ

SPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKV

EIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC

Anti-Jagged 3011 activatable antibody Lc
Amino Acid sequence (SEQ ID NO: 544)

CNIWLVGGDCRGWQGGSSGGSAVGLLAPPGGLSGRSDNPGGGSDIQMTQ

SPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKV

EIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC

Anti-Jagged 3012 activatable antibody Lc
Amino Acid sequence (SEQ ID NO: 545)

CNIWLVGGDCRGWQGGSSGGSAVGLLAPPGGLSGRSANPGGGSDIQMTQ

SPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKV

EIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC

-continued

Anti-Jagged 3013 activatable antibody Lc
Amino Acid sequence (SEQ ID NO: 546)

CNIWLVGGDCRGWQGGSSGGSAVGLLAPPGGLSGRSANIGGGSDIQMTQ

SPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKV

EIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC

Anti-Jagged 3014 activatable antibody Lc
Amino Acid sequence (SEQ ID NO: 562)

CNIWLVGGDCRGWQGGSSGGSAVGLLAPPGGLSGRSDNIGGGSDIQMTQ

SPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKV

EIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC

All eighteen anti-Jagged activatable antibodies containing substrate sequences of substrate 2006 (SEQ ID NO: 483), substrate 2007 (SEQ ID NO: 484), substrate 2008 (SEQ ID NO: 485), substrate 2009 (SEQ ID NO: 486), substrate 2010 (SEQ ID NO: 487), substrate 2011 (SEQ ID NO: 488), substrate 2012 (SEQ ID NO: 489), substrate 2013 (SEQ ID NO: 490), 2014 (SEQ ID NO: 555); substrate 3006 (SEQ ID NO: 515); substrate 3007 (SEQ ID NO: 516); substrate 3008 (SEQ ID NO: 517); substrate 3009 (SEQ ID NO: 518); substrate 3010 (SEQ ID NO: 519); substrate 3011 (SEQ ID NO: 520); substrate 3012 (SEQ ID NO: 521); substrate 3013 (SEQ ID NO: 522); or substrate 3014 (SEQ ID NO: 557) also comprised the masking moiety comprising the amino acid sequence and anti-Jagged antibody 4D11 antibody comprising a light chain (SEQ ID NO: 162) and a heavy chain (SEQ ID NO: 67). The configuration of the light chain of the activatable antibody was masking moiety—substrate—light chain of 4D11.

In this study, the mice were group and dosed as shown in the Table below:

| Group | Count | Treatment | Dose (mg/kg) | Schedule |
|---|---|---|---|---|
| A | 3 | IVIG | 20 | Single Dose |
| B | 4 | 4D11 | 5 | Single Dose |
| C | 4 | 4D11 | 10 | Single Dose |
| D | 4 | 4D11 | 20 | Single Dose |
| E | 4 | 4D11-5342-2001 | 20 | Single Dose |
| F | 3 | 4D11-5342-2006 | 20 | Single Dose |
| G | 3 | 4D11-5342-2007 | 20 | Single Dose |
| H | 3 | 4D11-5342-2008 | 20 | Single Dose |
| I | 3 | 4D11-5342-2009 | 20 | Single Dose |
| J | 3 | 4D11-5342-2010 | 20 | Single Dose |
| K | 3 | 4D11-5342-2012 | 20 | Single Dose |
| L | 3 | 4D11-5342-2013 | 20 | Single Dose |

Figure 13:
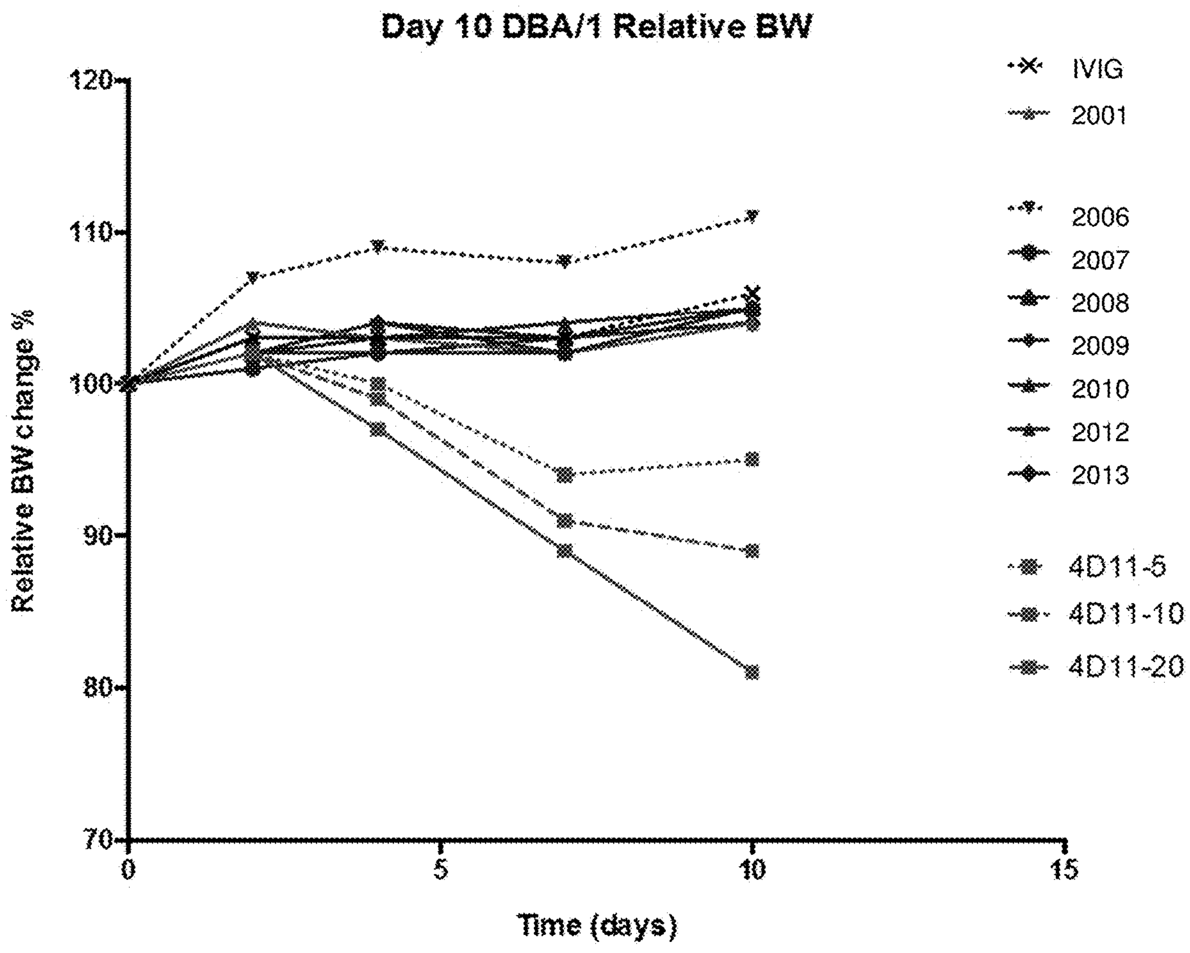
FIG. 13 is a graph depicting toxicity as measured as a function of body weight (BW) loss in DBA/1 mice following administration with a control intravenous immunoglobulin (IVIG), with anti-Jagged antibodies of the disclosure, and with activatable anti-Jagged antibodies of the disclosure that include various substrates of the disclosure.

The results are shown in FIG. 13 as relative body weight (BW) change percent (%) at various time points during the study.

As shown in FIGS. 11A-11H, FIG. 12, and FIG. 13, activatable antibodies including the cleavable substrates of the disclosure are safe and efficacious.

Figure 14:
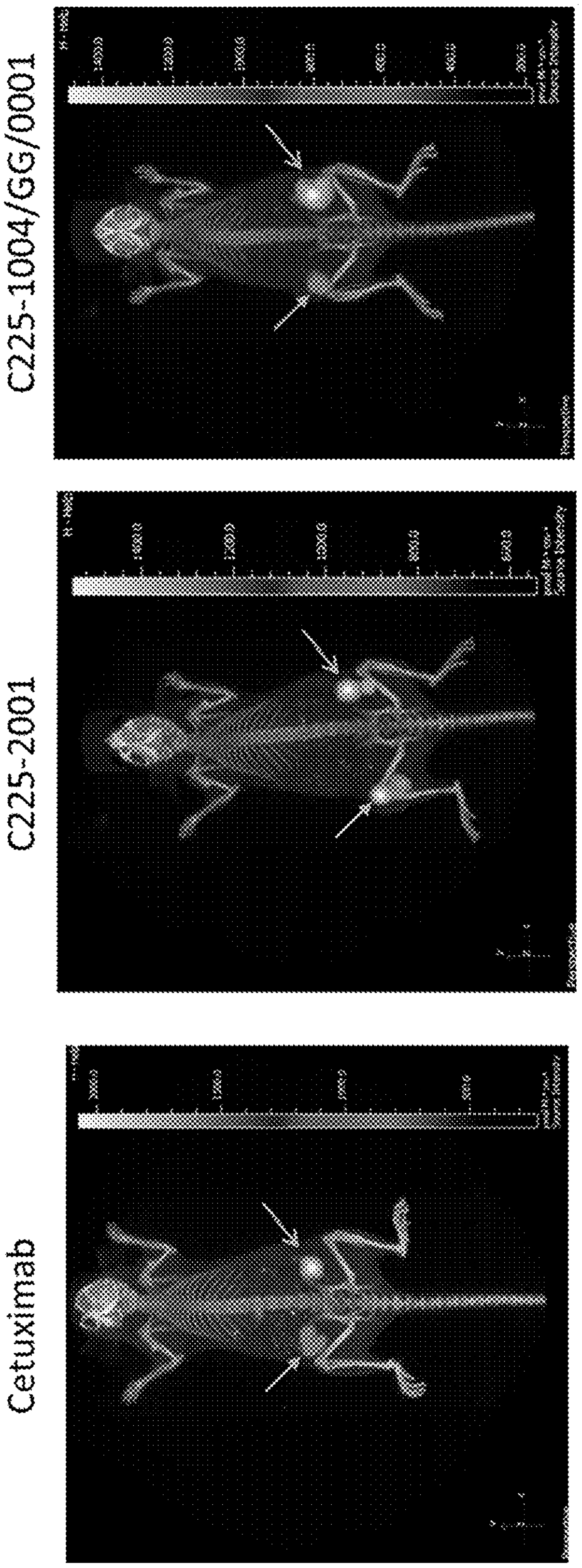
FIG. 14 is a graph depicting 3D reconstruction of FLIT-CT imaging data for cetuximab and two EGFR activatable antibodies containing tandem substrates in H292 (open arrows) and FaDu (filled arrows) co-implanted xenograft tumor model.

Example 6. In Vivo Imaging 7- to 9-week-old female athymic nu/nu (Charles River Laboratories) mice were inoculated subcutaneously with $5\times10^6$ NCI-H292 (left hind flank) and FaDu cells (right hind flank). The NCI-H292 cells (ATCC) and FaDu cells (ATCC) were suspended 1:1 with Matrigel in serum-free or without Matrigel in serum free medium, respectively. Clinical observations, body weights, and digital caliper tumor volume measurements were made two times weekly once tumors become measureable. Tumor volumes were calculated with the formula (ab^2)/2, where a is the longer and b is the smaller of two perpendicular diameters. H292 and FaDu xenograft tumor-bearing mice with tumor volumes of 250-500 mm3 were distributed by tumor size into 3 groups with n=3 per group. The animals were injected intraperitoneally with 15 mg/kg of AlexaFluor 750 (AF750)-conjugated cetuximab (Cetuximab-AF750) or activatable antibodies containing 2001 and 1004/LP'/0001 substrates (Pb2001-AF750 and Pb1004/LP'/0001-SF750). Computed tomography (CT) scans with subsequent fluorescent images were obtained with an IVIS Spectrum/CT imaging system (Caliper Life Sciences, PE). A series of fluorescent surface radiance images were acquired at multiple transillumination locations encompassing the region of interest at excitation and emission wavelengths of 745 nm and 800 nm, respectively (FIG. 14). Three-dimensional reconstruction of the optical and CT images and their co-registration were performed with the Living Image software 4.2 (Caliper Life Sciences). Obtained imaging data demonstrate accumulation of activatable antibodies in both xenograft tumors with the fluorescent signal similar to cetuximab parental antibody.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed:

1. An isolated polypeptide comprising a CM1-CM2 substrate comprising a first cleavable moiety (CM1) that is a substrate for a matrix metalloprotease (MMP) and a second cleavable moiety (CM2) that is a substrate for a serine protease (SP), wherein the CM1-CM2 substrate comprises the amino acid sequence selected from the group consisting of SEQ ID NOs: 483-490 and 555.

2. The isolated polypeptide of claim 1, wherein the CM1-CM2 substrate comprises the amino acid sequence of SEQ ID NO: 483.

3. The isolated polypeptide of claim 1, wherein the CM1-CM2 substrate comprises the amino acid sequence of SEQ ID NO: 484.

4. The isolated polypeptide of claim 1, wherein the CM1-CM2 substrate comprises the amino acid sequence of SEQ ID NO: 485.

5. The isolated polypeptide of claim 1, wherein the CM1-CM2 substrate comprises the amino acid sequence of SEQ ID NO: 486.

6. The isolated polypeptide of claim 1, wherein the CM1-CM2 substrate comprises the amino acid sequence of SEQ ID NO: 487.

7. The isolated polypeptide of claim 1, wherein the CM1-CM2 substrate comprises the amino acid sequence of SEQ ID NO: 488.

8. The isolated polypeptide of claim 1, wherein the CM1-CM2 substrate comprises the amino acid sequence of SEQ ID NO: 489.

9. The isolated polypeptide of claim 1, wherein the CM1-CM2 substrate comprises the amino acid sequence of SEQ ID NO: 490.

10. The isolated polypeptide of claim 1, wherein the CM1-CM2 substrate comprises the amino acid sequence of SEQ ID NO: 555.

* * * * *

SEQUENCE LISTING

```
<160> NUMBER OF SEQ ID NOS: 562

<210> SEQ ID NO 1
<211> LENGTH: 13
<212> TYPE: PRT
<213> ORGANISM: Artificial Sequence
<220> FEATURE:
<223> OTHER INFORMATION: chemically synthesized

<400> SEQUENCE: 1

Ile Ser Ser Gly Leu Leu Ser Gly Arg Ser Asp Asn His
1               5                   10


<210> SEQ ID NO 2
<211> LENGTH: 22
<212> TYPE: PRT
<213> ORGANISM: Artificial Sequence
<220> FEATURE:
<223> OTHER INFORMATION: chemically synthesized

<400> SEQUENCE: 2

Ile Ser Ser Gly Leu Leu Ser Ser Gly Gly Ser Gly Gly Ser Leu Ser
1               5                   10                  15

Gly Arg Ser Asp Asn His
            20


<210> SEQ ID NO 3
<211> LENGTH: 22
<212> TYPE: PRT
<213> ORGANISM: Artificial Sequence
<220> FEATURE:
<223> OTHER INFORMATION: chemically synthesized

<400> SEQUENCE: 3

Ala Val Gly Leu Leu Ala Pro Pro Gly Gly Thr Ser Thr Ser Gly Arg
1               5                   10                  15

Ser Ala Asn Pro Arg Gly
            20


<210> SEQ ID NO 4
<211> LENGTH: 22
```

<212> TYPE: PRT
<213> ORGANISM: Artificial Sequence
<220> FEATURE:
<223> OTHER INFORMATION: chemically synthesized

<400> SEQUENCE: 4

Thr Ser Thr Ser Gly Arg Ser Ala Asn Pro Arg Gly Gly Gly Ala Val
1               5                   10                  15

Gly Leu Leu Ala Pro Pro
            20

<210> SEQ ID NO 5
<211> LENGTH: 24
<212> TYPE: PRT
<213> ORGANISM: Artificial Sequence
<220> FEATURE:
<223> OTHER INFORMATION: chemically synthesized

<400> SEQUENCE: 5

Val His Met Pro Leu Gly Phe Leu Gly Pro Gly Gly Thr Ser Thr Ser
1               5                   10                  15

Gly Arg Ser Ala Asn Pro Arg Gly
            20

<210> SEQ ID NO 6
<211> LENGTH: 24
<212> TYPE: PRT
<213> ORGANISM: Artificial Sequence
<220> FEATURE:
<223> OTHER INFORMATION: chemically synthesized

<400> SEQUENCE: 6

Thr Ser Thr Ser Gly Arg Ser Ala Asn Pro Arg Gly Gly Gly Val His
1               5                   10                  15

Met Pro Leu Gly Phe Leu Gly Pro
            20

<210> SEQ ID NO 7
<211> LENGTH: 18
<212> TYPE: PRT
<213> ORGANISM: Artificial Sequence
<220> FEATURE:
<223> OTHER INFORMATION: chemically synthesized

<400> SEQUENCE: 7

Ala Val Gly Leu Leu Ala Pro Pro Gly Gly Leu Ser Gly Arg Ser Asp
1               5                   10                  15

Asn His

<210> SEQ ID NO 8
<211> LENGTH: 18
<212> TYPE: PRT
<213> ORGANISM: Artificial Sequence
<220> FEATURE:
<223> OTHER INFORMATION: chemically synthesized

<400> SEQUENCE: 8

Leu Ser Gly Arg Ser Asp Asn His Gly Gly Ala Val Gly Leu Leu Ala
1               5                   10                  15

Pro Pro

<210> SEQ ID NO 9
<211> LENGTH: 20
<212> TYPE: PRT

<213> ORGANISM: Artificial Sequence
<220> FEATURE:
<223> OTHER INFORMATION: chemically synthesized

<400> SEQUENCE: 9

Val His Met Pro Leu Gly Phe Leu Gly Pro Gly Gly Leu Ser Gly Arg
1 5 10 15

Ser Asp Asn His
20

<210> SEQ ID NO 10
<211> LENGTH: 20
<212> TYPE: PRT
<213> ORGANISM: Artificial Sequence
<220> FEATURE:
<223> OTHER INFORMATION: chemically synthesized

<400> SEQUENCE: 10

Leu Ser Gly Arg Ser Asp Asn His Gly Gly Val His Met Pro Leu Gly
1 5 10 15

Phe Leu Gly Pro
20

<210> SEQ ID NO 11
<211> LENGTH: 22
<212> TYPE: PRT
<213> ORGANISM: Artificial Sequence
<220> FEATURE:
<223> OTHER INFORMATION: chemically synthesized

<400> SEQUENCE: 11

Leu Ser Gly Arg Ser Asp Asn His Gly Gly Ser Gly Gly Ser Ile Ser
1 5 10 15

Ser Gly Leu Leu Ser Ser
20

<210> SEQ ID NO 12
<211> LENGTH: 22
<212> TYPE: PRT
<213> ORGANISM: Artificial Sequence
<220> FEATURE:
<223> OTHER INFORMATION: chemically synthesized

<400> SEQUENCE: 12

Leu Ser Gly Arg Ser Gly Asn His Gly Gly Ser Gly Gly Ser Ile Ser
1 5 10 15

Ser Gly Leu Leu Ser Ser
20

<210> SEQ ID NO 13
<211> LENGTH: 22
<212> TYPE: PRT
<213> ORGANISM: Artificial Sequence
<220> FEATURE:
<223> OTHER INFORMATION: chemically synthesized

<400> SEQUENCE: 13

Ile Ser Ser Gly Leu Leu Ser Ser Gly Gly Ser Gly Gly Ser Leu Ser
1 5 10 15

Gly Arg Ser Gly Asn His
20

<210> SEQ ID NO 14
<211> LENGTH: 22

<212> TYPE: PRT
<213> ORGANISM: Artificial Sequence
<220> FEATURE:
<223> OTHER INFORMATION: chemically synthesized

<400> SEQUENCE: 14

```
Leu Ser Gly Arg Ser Asp Asn His Gly Gly Ser Gly Gly Ser Gln Asn
1               5                   10                  15

Gln Ala Leu Arg Met Ala
            20
```

<210> SEQ ID NO 15
<211> LENGTH: 22
<212> TYPE: PRT
<213> ORGANISM: Artificial Sequence
<220> FEATURE:
<223> OTHER INFORMATION: chemically synthesized

<400> SEQUENCE: 15

```
Gln Asn Gln Ala Leu Arg Met Ala Gly Gly Ser Gly Gly Ser Leu Ser
1               5                   10                  15

Gly Arg Ser Asp Asn His
            20
```

<210> SEQ ID NO 16
<211> LENGTH: 22
<212> TYPE: PRT
<213> ORGANISM: Artificial Sequence
<220> FEATURE:
<223> OTHER INFORMATION: chemically synthesized

<400> SEQUENCE: 16

```
Leu Ser Gly Arg Ser Gly Asn His Gly Gly Ser Gly Gly Ser Gln Asn
1               5                   10                  15

Gln Ala Leu Arg Met Ala
            20
```

<210> SEQ ID NO 17
<211> LENGTH: 22
<212> TYPE: PRT
<213> ORGANISM: Artificial Sequence
<220> FEATURE:
<223> OTHER INFORMATION: chemically synthesized

<400> SEQUENCE: 17

```
Gln Asn Gln Ala Leu Arg Met Ala Gly Gly Ser Gly Gly Ser Leu Ser
1               5                   10                  15

Gly Arg Ser Gly Asn His
            20
```

<210> SEQ ID NO 18
<211> LENGTH: 8
<212> TYPE: PRT
<213> ORGANISM: Artificial Sequence
<220> FEATURE:
<223> OTHER INFORMATION: chemically synthesized

<400> SEQUENCE: 18

```
Leu Ser Gly Arg Ser Asp Asn His
1               5
```

<210> SEQ ID NO 19
<211> LENGTH: 8
<212> TYPE: PRT
<213> ORGANISM: Artificial Sequence
<220> FEATURE:
<223> OTHER INFORMATION: chemically synthesized

<400> SEQUENCE: 19

Leu Ser Gly Arg Ser Gly Asn His
1               5

<210> SEQ ID NO 20
<211> LENGTH: 8
<212> TYPE: PRT
<213> ORGANISM: Artificial Sequence
<220> FEATURE:
<223> OTHER INFORMATION: chemically synthesized

<400> SEQUENCE: 20

Ile Ser Ser Gly Leu Leu Ser Ser
1               5

<210> SEQ ID NO 21
<211> LENGTH: 8
<212> TYPE: PRT
<213> ORGANISM: Artificial Sequence
<220> FEATURE:
<223> OTHER INFORMATION: chemically synthesized

<400> SEQUENCE: 21

Gln Asn Gln Ala Leu Arg Met Ala
1               5

<210> SEQ ID NO 22
<211> LENGTH: 13
<212> TYPE: PRT
<213> ORGANISM: Artificial Sequence
<220> FEATURE:
<223> OTHER INFORMATION: chemically synthesized

<400> SEQUENCE: 22

Ile Ser Ser Gly Leu Leu Ser Gly Arg Ser Gly Asn His
1               5                   10

<210> SEQ ID NO 23
<211> LENGTH: 24
<212> TYPE: DNA
<213> ORGANISM: Artificial Sequence
<220> FEATURE:
<223> OTHER INFORMATION: chemically synthesized

<400> SEQUENCE: 23
ttaagcgggc ggtcggacaa ccac 24

<210> SEQ ID NO 24
<211> LENGTH: 24
<212> TYPE: DNA
<213> ORGANISM: Artificial Sequence
<220> FEATURE:
<223> OTHER INFORMATION: chemically synthesized

<400> SEQUENCE: 24
cttagcgggc ggagcggcaa ccac 24

<210> SEQ ID NO 25
<211> LENGTH: 24
<212> TYPE: DNA
<213> ORGANISM: Artificial Sequence
<220> FEATURE:
<223> OTHER INFORMATION: chemically synthesized

```
<400> SEQUENCE: 25

atctcctccg ggctactgag ttct                                              24

<210> SEQ ID NO 26
<211> LENGTH: 24
<212> TYPE: DNA
<213> ORGANISM: Artificial Sequence
<220> FEATURE:
<223> OTHER INFORMATION: chemically synthesized

<400> SEQUENCE: 26

cagaaccagg cgctcagaat ggca                                              24

<210> SEQ ID NO 27
<211> LENGTH: 39
<212> TYPE: DNA
<213> ORGANISM: Artificial Sequence
<220> FEATURE:
<223> OTHER INFORMATION: chemically synthesized

<400> SEQUENCE: 27

atatcatccg gcctccttag cggccgttcc gacaatcac                               39

<210> SEQ ID NO 28
<211> LENGTH: 39
<212> TYPE: DNA
<213> ORGANISM: Artificial Sequence
<220> FEATURE:
<223> OTHER INFORMATION: chemically synthesized

<400> SEQUENCE: 28

ataagttctg ggctcctgtc gggccggagt ggaaatcac                               39

<210> SEQ ID NO 29
<211> LENGTH: 66
<212> TYPE: DNA
<213> ORGANISM: Artificial Sequence
<220> FEATURE:
<223> OTHER INFORMATION: chemically synthesized

<400> SEQUENCE: 29

ctgagcgggc ggtccgataa tcatggtggt tcaggaggga gtatttcttc cggcttactg        60

agtagc                                                                  66

<210> SEQ ID NO 30
<211> LENGTH: 66
<212> TYPE: DNA
<213> ORGANISM: Artificial Sequence
<220> FEATURE:
<223> OTHER INFORMATION: chemically synthesized

<400> SEQUENCE: 30

atctcctctg ggttgctttc ttcaggaggt tcagggggga gcctgagcgg acgctccgac        60

aaccat                                                                  66

<210> SEQ ID NO 31
<211> LENGTH: 66
<212> TYPE: DNA
<213> ORGANISM: Artificial Sequence
<220> FEATURE:
<223> OTHER INFORMATION: chemically synthesized

<400> SEQUENCE: 31

ctctcaggaa gatccggaaa tcatgggggg tctgggggga gtatctcatc aggtctgctg        60
```

agcagc 66

<210> SEQ ID NO 32
<211> LENGTH: 66
<212> TYPE: DNA
<213> ORGANISM: Artificial Sequence
<220> FEATURE:
<223> OTHER INFORMATION: chemically synthesized

<400> SEQUENCE: 32
atctcaagtg ggctgttaag ttccggcggc agtggagggt ccctaagcgg ccgcagcggg 60
aatcac 66

<210> SEQ ID NO 33
<211> LENGTH: 66
<212> TYPE: DNA
<213> ORGANISM: Artificial Sequence
<220> FEATURE:
<223> OTHER INFORMATION: chemically synthesized

<400> SEQUENCE: 33
ctctctggcc gctccgataa tcatggtgga tccggtggct ctcagaacca ggcactacgg 60
atggca 66

<210> SEQ ID NO 34
<211> LENGTH: 66
<212> TYPE: DNA
<213> ORGANISM: Artificial Sequence
<220> FEATURE:
<223> OTHER INFORMATION: chemically synthesized

<400> SEQUENCE: 34
cagaaccagg cgctcaggat ggcagggggg agtggcggaa gcctttctgg tcgatccgat 60
aatcac 66

<210> SEQ ID NO 35
<211> LENGTH: 66
<212> TYPE: DNA
<213> ORGANISM: Artificial Sequence
<220> FEATURE:
<223> OTHER INFORMATION: chemically synthesized

<400> SEQUENCE: 35
cttagcggac gctctggcaa ccacggagga tctggaggaa gtcagaacca ggccttgcgc 60
atggcc 66

<210> SEQ ID NO 36
<211> LENGTH: 66
<212> TYPE: DNA
<213> ORGANISM: Artificial Sequence
<220> FEATURE:
<223> OTHER INFORMATION: chemically synthesized

<400> SEQUENCE: 36
caaaaccagg ctctgcgcat ggctgggggg tctggtggga gcctgagcgg gcggtcagga 60
aaccac 66

<210> SEQ ID NO 37
<211> LENGTH: 37
<212> TYPE: DNA
<213> ORGANISM: Artificial Sequence
<220> FEATURE:

<223> OTHER INFORMATION: chemically synthesized

<400> SEQUENCE: 37
gtgcagccac cgtacgtttg atttccacct tggtccc 37

<210> SEQ ID NO 38
<211> LENGTH: 97
<212> TYPE: DNA
<213> ORGANISM: Artificial Sequence
<220> FEATURE:
<223> OTHER INFORMATION: chemically synthesized

<400> SEQUENCE: 38
caggggggct cgagcggcgg ctctatctct tccggactgc tgtccggcag atccgacaat 60
cacggcggag gctctgacat ccagatgacc cagtctc 97

<210> SEQ ID NO 39
<211> LENGTH: 124
<212> TYPE: DNA
<213> ORGANISM: Artificial Sequence
<220> FEATURE:
<223> OTHER INFORMATION: chemically synthesized

<400> SEQUENCE: 39
caggggggct cgagcggcgg ctctatctct tctggcctgc tgtctagcgg cggctccggc 60
ggatctctgt ctggcagatc tgacaaccac ggcggaggct ccgacatcca gatgacccag 120
tctc 124

<210> SEQ ID NO 40
<211> LENGTH: 121
<212> TYPE: DNA
<213> ORGANISM: Artificial Sequence
<220> FEATURE:
<223> OTHER INFORMATION: chemically synthesized

<400> SEQUENCE: 40
caggggggct cgagcggagg atctgctgtg ggactgctgg ctcctcctgg cggcacatct 60
acctctggca gatccgccaa ccctcggggc ggaggatctg acatccagat gacccagtct 120
c 121

<210> SEQ ID NO 41
<211> LENGTH: 121
<212> TYPE: DNA
<213> ORGANISM: Artificial Sequence
<220> FEATURE:
<223> OTHER INFORMATION: chemically synthesized

<400> SEQUENCE: 41
caggggggct cgagcggcgg ctccacatct acctctggca gatccgccaa ccccagaggt 60
ggcggagctg tgggactgct ggctccacca ggcggatctg acatccagat gacccagtct 120
c 121

<210> SEQ ID NO 42
<211> LENGTH: 127
<212> TYPE: DNA
<213> ORGANISM: Artificial Sequence
<220> FEATURE:
<223> OTHER INFORMATION: chemically synthesized

<400> SEQUENCE: 42
caggggggct cgagcggcgg ctctgtgcat atgcccctgg gctttctggg ccctggcggc 60
acatctacct ctggcagatc cgccaaccct cggggcggag gatctgacat ccagatgacc 120
cagtctc 127

<210> SEQ ID NO 43
<211> LENGTH: 127
<212> TYPE: DNA
<213> ORGANISM: Artificial Sequence
<220> FEATURE:
<223> OTHER INFORMATION: chemically synthesized

<400> SEQUENCE: 43
caggggggct cgagcggcgg ctccacatct acctctggca gatccgccaa ccccagaggc 60
ggcggagtgc atatgcctct gggctttctg ggacctggcg gctctgacat ccagatgacc 120
cagtctc 127

<210> SEQ ID NO 44
<211> LENGTH: 109
<212> TYPE: DNA
<213> ORGANISM: Artificial Sequence
<220> FEATURE:
<223> OTHER INFORMATION: chemically synthesized

<400> SEQUENCE: 44
caggggggct cgagcggagg atctgctgtg ggactgctgg ctcctcctgg tggcctgtct 60
ggcagatctg ataaccacgg cggctccgac atccagatga cccagtctc 109

<210> SEQ ID NO 45
<211> LENGTH: 112
<212> TYPE: DNA
<213> ORGANISM: Artificial Sequence
<220> FEATURE:
<223> OTHER INFORMATION: chemically synthesized

<400> SEQUENCE: 45
caggggggct cgagcggagg ctctggcctg tctggcagat ccgataacca tggcggcgct 60
gtgggactgc tggctcctcc tggtggatct gacatccaga tgacccagtc tc 112

<210> SEQ ID NO 46
<211> LENGTH: 115
<212> TYPE: DNA
<213> ORGANISM: Artificial Sequence
<220> FEATURE:
<223> OTHER INFORMATION: chemically synthesized

<400> SEQUENCE: 46
caggggggct cgagcggcgg ctctgtgcat atgcccctgg gctttctggg acctggcggc 60
ctgtctggca gatccgataa tcacggcggc tccgacatcc agatgaccca gtctc 115

<210> SEQ ID NO 47
<211> LENGTH: 118
<212> TYPE: DNA
<213> ORGANISM: Artificial Sequence
<220> FEATURE:
<223> OTHER INFORMATION: chemically synthesized

<400> SEQUENCE: 47
caggggggct cgagcggagg ctctggcctg tctggcagat ctgataacca cggcggcgtg 60
cacatgcccc tgggctttct gggacctggc ggatctgaca tccagatgac ccagtctc 118

<210> SEQ ID NO 48

<211> LENGTH: 774
<212> TYPE: DNA
<213> ORGANISM: Artificial Sequence
<220> FEATURE:
<223> OTHER INFORMATION: chemically synthesized

<400> SEQUENCE: 48

```
caaggccagt ctggccagtg caatatttgg ctcgtaggtg gtgattgcag ggctggcag      60

gggggctcga gcggcggctc tatctcttcc ggactgctgt ccggcagatc cgacaatcac    120

ggcggaggct ctgacatcca gatgacccag tctccatcct ccctgtctgc atctgtagga    180

gacagagtca ccatcacttg ccgggcaagt cagagcatta gcagctattt aaattggtat    240

cagcagaaac cagggaaagc ccctaagctc ctgatctatg cggcatccag tttgcaaagt    300

ggggtcccat caaggttcag tggcagtgga tctgggacag atttcactct caccatcagc    360

agtctgcaac ctgaagattt tgcaacttac tactgtcaac agacggttgt ggcgcctccg    420

ttattcggcc aagggaccaa ggtggaaatc aaacgtacgg tggctgcacc atctgtcttc    480

atcttcccgc catctgatga gcagttgaaa tctggaactg cctctgttgt gtgcctgctg    540

aataacttct atcccagaga ggccaaagta cagtggaagg tggataacgc cctccaatcg    600

ggtaactccc aggagagtgt cacagagcag gacagcaagg acagcaccta cagcctcagc    660

agcaccctga cgctgagcaa agcagactac gagaaacaca aagtctacgc ctgcgaagtc    720

acccatcagg gcctgagctc gcccgtcaca aagagcttca acaggggaga gtgt          774
```

<210> SEQ ID NO 49
<211> LENGTH: 258
<212> TYPE: PRT
<213> ORGANISM: Artificial Sequence
<220> FEATURE:
<223> OTHER INFORMATION: chemically synthesized

<400> SEQUENCE: 49

```
Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Ile Ser Ser Gly Leu
            20                  25                  30

Leu Ser Gly Arg Ser Asp Asn His Gly Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Ser Ile Ser Ser Tyr Leu Asn Trp Tyr
65                  70                  75                  80

Gln Gln Lys Pro Gly Lys Ala Pro Lys Leu Leu Ile Tyr Ala Ala Ser
                85                  90                  95

Ser Leu Gln Ser Gly Val Pro Ser Arg Phe Ser Gly Ser Gly Ser Gly
            100                 105                 110

Thr Asp Phe Thr Leu Thr Ile Ser Ser Leu Gln Pro Glu Asp Phe Ala
        115                 120                 125

Thr Tyr Tyr Cys Gln Gln Thr Val Val Ala Pro Pro Leu Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190
```

```
Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys


<210> SEQ ID NO 50
<211> LENGTH: 801
<212> TYPE: DNA
<213> ORGANISM: Artificial Sequence
<220> FEATURE:
<223> OTHER INFORMATION: chemically synthesized

<400> SEQUENCE: 50

caaggccagt ctggccagtg caatatttgg ctcgtaggtg gtgattgcag ggctggcag     60

gggggctcga gcggcggctc tatctcttct ggcctgctgt ctagcggcgg ctccggcgga    120

tctctgtctg gcagatctga caaccacggc ggaggctccg acatccagat gacccagtct    180

ccatcctccc tgtctgcatc tgtaggagac agagtcacca tcacttgccg ggcaagtcag    240

agcattagca gctatttaaa ttggtatcag cagaaaccag ggaaagcccc taagctcctg    300

atctatgcgg catccagttt gcaaagtggg gtcccatcaa ggttcagtgg cagtggatct    360

gggacagatt tcactctcac catcagcagt ctgcaacctg aagattttgc aacttactac    420

tgtcaacaga cggttgtggc gcctccgtta ttcggccaag ggaccaaggt ggaaatcaaa    480

cgtacggtgg ctgcaccatc tgtcttcatc ttcccgccat ctgatgagca gttgaaatct    540

ggaactgcct ctgttgtgtg cctgctgaat aacttctatc ccagagaggc caaagtacag    600

tggaaggtgg ataacgccct ccaatcgggt aactcccagg agagtgtcac agagcaggac    660

agcaaggaca gcacctacag cctcagcagc accctgacgc tgagcaaagc agactacgag    720

aaacacaaag tctacgcctg cgaagtcacc catcagggcc tgagctcgcc cgtcacaaag    780

agcttcaaca ggggagagtg t                                              801


<210> SEQ ID NO 51
<211> LENGTH: 267
<212> TYPE: PRT
<213> ORGANISM: Artificial Sequence
<220> FEATURE:
<223> OTHER INFORMATION: chemically synthesized

<400> SEQUENCE: 51

Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Ile Ser Ser Gly Leu
            20                  25                  30

Leu Ser Ser Gly Gly Ser Gly Gly Ser Leu Ser Gly Arg Ser Asp Asn
        35                  40                  45

His Gly Gly Gly Ser Asp Ile Gln Met Thr Gln Ser Pro Ser Ser Leu
    50                  55                  60

Ser Ala Ser Val Gly Asp Arg Val Thr Ile Thr Cys Arg Ala Ser Gln
65                  70                  75                  80

Ser Ile Ser Ser Tyr Leu Asn Trp Tyr Gln Gln Lys Pro Gly Lys Ala
```

```
                85                  90                  95

Pro Lys Leu Leu Ile Tyr Ala Ala Ser Ser Leu Gln Ser Gly Val Pro
            100                 105                 110

Ser Arg Phe Ser Gly Ser Gly Ser Gly Thr Asp Phe Thr Leu Thr Ile
        115                 120                 125

Ser Ser Leu Gln Pro Glu Asp Phe Ala Thr Tyr Tyr Cys Gln Gln Thr
    130                 135                 140

Val Val Ala Pro Pro Leu Phe Gly Gln Gly Thr Lys Val Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265
```

<210> SEQ ID NO 52
<211> LENGTH: 798
<212> TYPE: DNA
<213> ORGANISM: Artificial Sequence
<220> FEATURE:
<223> OTHER INFORMATION: chemically synthesized

<400> SEQUENCE: 52

```
caaggccagt ctggccagtg caatatttgg ctcgtaggtg gtgattgcag ggctggcag     60

gggggctcga gcggaggatc tgctgtggga ctgctggctc ctcctggcgg cacatctacc    120

tctggcagat ccgccaaccc tcggggcgga ggatctgaca tccagatgac ccagtctcca    180

tcctccctgt ctgcatctgt aggagacaga gtcaccatca cttgccgggc aagtcagagc    240

attagcagct atttaaattg gtatcagcag aaaccaggga aagcccctaa gctcctgatc    300

tatgcggcat ccagtttgca aagtggggtc ccatcaaggt tcagtggcag tggatctggg    360

acagatttca ctctcaccat cagcagtctg caacctgaag attttgcaac ttactactgt    420

caacagacgg ttgtggcgcc tccgttattc ggccaaggga ccaaggtgga aatcaaacgt    480

acggtggctg caccatctgt cttcatcttc ccgccatctg atgagcagtt gaaatctgga    540

actgcctctg ttgtgtgcct gctgaataac ttctatccca gagaggccaa agtacagtgg    600

aaggtggata acgccctcca atcgggtaac tcccaggaga gtgtcacaga gcaggacagc    660

aaggacagca cctacagcct cagcagcacc ctgacgctga gcaaagcaga ctacgagaaa    720

cacaaagtct acgcctgcga agtcacccat cagggcctga gctcgcccgt cacaaagagc    780

ttcaacaggg gagagtgt                                                  798
```

<210> SEQ ID NO 53
<211> LENGTH: 266
<212> TYPE: PRT
<213> ORGANISM: Artificial Sequence
<220> FEATURE:

<223> OTHER INFORMATION: chemically synthesized

<400> SEQUENCE: 53

Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Ala Val Gly Leu Leu
            20                  25                  30

Ala Pro Pro Gly Gly Thr Ser Thr Ser Gly Arg Ser Ala Asn Pro Arg
        35                  40                  45

Gly Gly Gly Ser Asp Ile Gln Met Thr Gln Ser Pro Ser Ser Leu Ser
    50                  55                  60

Ala Ser Val Gly Asp Arg Val Thr Ile Thr Cys Arg Ala Ser Gln Ser
65                  70                  75                  80

Ile Ser Ser Tyr Leu Asn Trp Tyr Gln Gln Lys Pro Gly Lys Ala Pro
                85                  90                  95

Lys Leu Leu Ile Tyr Ala Ala Ser Ser Leu Gln Ser Gly Val Pro Ser
            100                 105                 110

Arg Phe Ser Gly Ser Gly Ser Gly Thr Asp Phe Thr Leu Thr Ile Ser
        115                 120                 125

Ser Leu Gln Pro Glu Asp Phe Ala Thr Tyr Tyr Cys Gln Gln Thr Val
    130                 135                 140

Val Ala Pro Pro Leu Phe Gly Gln Gly Thr Lys Val Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265

<210> SEQ ID NO 54
<211> LENGTH: 798
<212> TYPE: DNA
<213> ORGANISM: Artificial Sequence
<220> FEATURE:
<223> OTHER INFORMATION: chemically synthesized

<400> SEQUENCE: 54
caaggccagt ctggccagtg caatatttgg ctcgtaggtg gtgattgcag ggctggcag 60 gggggctcga gcggcggctc cacatctacc tctggcagat ccgccaaccc cagaggtggc 120
ggagctgtgg gactgctggc tccaccaggc ggatctgaca tccagatgac ccagtctcca 180
tcctccctgt ctgcatctgt aggagacaga gtcaccatca cttgccgggc aagtcagagc 240
attagcagct atttaaattg gtatcagcag aaaccaggga aagcccctaa gctcctgatc 300
tatgcggcat ccagtttgca aagtggggtc ccatcaaggt tcagtggcag tggatctggg 360
acagatttca ctctcaccat cagcagtctg caacctgaag attttgcaac ttactactgt 420

```
caacagacgg ttgtggcgcc tccgttattc ggccaaggga ccaaggtgga aatcaaacgt    480

acggtggctg caccatctgt cttcatcttc ccgccatctg atgagcagtt gaaatctgga    540

actgcctctg ttgtgtgcct gctgaataac ttctatccca gagaggccaa agtacagtgg    600

aaggtggata acgccctcca atcgggtaac tcccaggaga gtgtcacaga gcaggacagc    660

aaggacagca cctacagcct cagcagcacc ctgacgctga gcaaagcaga ctacgagaaa    720

cacaaagtct acgcctgcga agtcacccat cagggcctga gctcgcccgt cacaaagagc    780

ttcaacaggg gagagtgt                                                  798


<210> SEQ ID NO 55
<211> LENGTH: 266
<212> TYPE: PRT
<213> ORGANISM: Artificial Sequence
<220> FEATURE:
<223> OTHER INFORMATION: chemically synthesized

<400> SEQUENCE: 55

Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Thr Ser Thr Ser Gly
            20                  25                  30

Arg Ser Ala Asn Pro Arg Gly Gly Gly Ala Val Gly Leu Leu Ala Pro
        35                  40                  45

Pro Gly Gly Ser Asp Ile Gln Met Thr Gln Ser Pro Ser Ser Leu Ser
    50                  55                  60

Ala Ser Val Gly Asp Arg Val Thr Ile Thr Cys Arg Ala Ser Gln Ser
65                  70                  75                  80

Ile Ser Ser Tyr Leu Asn Trp Tyr Gln Gln Lys Pro Gly Lys Ala Pro
                85                  90                  95

Lys Leu Leu Ile Tyr Ala Ala Ser Ser Leu Gln Ser Gly Val Pro Ser
            100                 105                 110

Arg Phe Ser Gly Ser Gly Ser Gly Thr Asp Phe Thr Leu Thr Ile Ser
        115                 120                 125

Ser Leu Gln Pro Glu Asp Phe Ala Thr Tyr Tyr Cys Gln Gln Thr Val
    130                 135                 140

Val Ala Pro Pro Leu Phe Gly Gln Gly Thr Lys Val Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265


<210> SEQ ID NO 56
<211> LENGTH: 804
<212> TYPE: DNA
```

<213> ORGANISM: Artificial Sequence
<220> FEATURE:
<223> OTHER INFORMATION: chemically synthesized

<400> SEQUENCE: 56
caaggccagt ctggccagtg caatatttgg ctcgtaggtg gtgattgcag gggctggcag 60
gggggctcga gcggcggctc tgtgcatatg cccctgggct ttctgggccc tggcggcaca 120
tctacctctg gcagatccgc caaccctcgg ggcggaggat ctgacatcca gatgacccag 180
tctccatcct ccctgtctgc atctgtagga gacagagtca ccatcacttg ccgggcaagt 240
cagagcatta gcagctattt aaattggtat cagcagaaac cagggaaagc ccctaagctc 300
ctgatctatg cggcatccag tttgcaaagt ggggtcccat caaggttcag tggcagtgga 360
tctgggacag atttcactct caccatcagc agtctgcaac ctgaagattt tgcaacttac 420
tactgtcaac agacggttgt ggcgcctccg ttattcggcc aagggaccaa ggtggaaatc 480
aaacgtacgg tggctgcacc atctgtcttc atcttcccgc catctgatga gcagttgaaa 540
tctggaactg cctctgttgt gtgcctgctg aataacttct atcccagaga ggccaaagta 600
cagtggaagg tggataacgc cctccaatcg ggtaactccc aggagagtgt cacagagcag 660
gacagcaagg acagcaccta cagcctcagc agcaccctga cgctgagcaa agcagactac 720
gagaaacaca aagtctacgc ctgcgaagtc acccatcagg gcctgagctc gcccgtcaca 780
aagagcttca acaggggaga gtgt 804

<210> SEQ ID NO 57
<211> LENGTH: 268
<212> TYPE: PRT
<213> ORGANISM: Artificial Sequence
<220> FEATURE:
<223> OTHER INFORMATION: chemically synthesized

<400> SEQUENCE: 57

Gln Gly Gln Ser Gly Gln Cys Asn Ile Trp Leu Val Gly Gly Asp Cys
1 5 10 15

Arg Gly Trp Gln Gly Gly Ser Ser Gly Gly Ser Val His Met Pro Leu
20 25 30

Gly Phe Leu Gly Pro Gly Gly Thr Ser Thr Ser Gly Arg Ser Ala Asn
35 40 45

Pro Arg Gly Gly Gly Ser Asp Ile Gln Met Thr Gln Ser Pro Ser Ser
50 55 60

Leu Ser Ala Ser Val Gly Asp Arg Val Thr Ile Thr Cys Arg Ala Ser
65 70 75 80

Gln Ser Ile Ser Ser Tyr Leu Asn Trp Tyr Gln Gln Lys Pro Gly Lys
85 90 95

Ala Pro Lys Leu Leu Ile Tyr Ala Ala Ser Ser Leu Gln Ser Gly Val
100 105 110

Pro Ser Arg Phe Ser Gly Ser Gly Ser Gly Thr Asp Phe Thr Leu Thr
115 120 125

Ile Ser Ser Leu Gln Pro Glu Asp Phe Ala Thr Tyr Tyr Cys Gln Gln
130 135 140

Thr Val Val Ala Pro Pro Leu Phe Gly Gln Gly Thr Lys Val Glu Ile
145 150 155 160

Lys Arg Thr Val Ala Ala Pro Ser Val Phe Ile Phe Pro Pro Ser Asp
165 170 175

Glu Gln Leu Lys Ser Gly Thr Ala Ser Val Val Cys Leu Leu Asn Asn
180 185 190

```
Phe Tyr Pro Arg Glu Ala Lys Val Gln Trp Lys Val Asp Asn Ala Leu
        195                 200                 205

Gln Ser Gly Asn Ser Gln Glu Ser Val Thr Glu Gln Asp Ser Lys Asp
    210                 215                 220

Ser Thr Tyr Ser Leu Ser Ser Thr Leu Thr Leu Ser Lys Ala Asp Tyr
225                 230                 235                 240

Glu Lys His Lys Val Tyr Ala Cys Glu Val Thr His Gln Gly Leu Ser
                245                 250                 255

Ser Pro Val Thr Lys Ser Phe Asn Arg Gly Glu Cys
            260                 265
```

<210> SEQ ID NO 58
<211> LENGTH: 804
<212> TYPE: DNA
<213> ORGANISM: Artificial Sequence
<220> FEATURE:
<223> OTHER INFORMATION: chemically synthesized

<400> SEQUENCE: 58

```
caaggccagt ctggccagtg caatatttgg ctcgtaggtg gtgattgcag ggctggcag      60

gggggctcga gcggcggctc cacatctacc tctggcagat ccgccaaccc cagaggcggc    120

ggagtgcata tgcctctggg ctttctggga cctggcggct ctgacatcca gatgacccag    180

tctccatcct ccctgtctgc atctgtagga gacagagtca ccatcacttg ccgggcaagt    240

cagagcatta gcagctattt aaattggtat cagcagaaac cagggaaagc ccctaagctc    300

ctgatctatg cggcatccag tttgcaaagt ggggtcccat caaggttcag tggcagtgga    360

tctgggacag atttcactct caccatcagc agtctgcaac ctgaagattt tgcaacttac    420

tactgtcaac agacggttgt ggcgcctccg ttattcggcc aagggaccaa ggtggaaatc    480

aaacgtacgg tggctgcacc atctgtcttc atcttcccgc catctgatga gcagttgaaa    540

tctggaactg cctctgttgt gtgcctgctg aataacttct atcccagaga ggccaaagta    600

cagtggaagg tggataacgc cctccaatcg ggtaactccc aggagagtgt cacagagcag    660

gacagcaagg acagcaccta cagcctcagc agcaccctga cgctgagcaa agcagactac    720

gagaaacaca aagtctacgc ctgcgaagtc acccatcagg gcctgagctc gcccgtcaca    780

aagagcttca acaggggaga gtgt                                           804
```

<210> SEQ ID NO 59
<211> LENGTH: 268
<212> TYPE: PRT
<213> ORGANISM: Artificial Sequence
<220> FEATURE:
<223> OTHER INFORMATION: chemically synthesized

<400> SEQUENCE: 59

```
Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Thr Ser Thr Ser Gly
            20                  25                  30

Arg Ser Ala Asn Pro Arg Gly Gly Gly Val His Met Pro Leu Gly Phe
        35                  40                  45

Leu Gly Pro Gly Gly Ser Asp Ile Gln Met Thr Gln Ser Pro Ser Ser
    50                  55                  60

Leu Ser Ala Ser Val Gly Asp Arg Val Thr Ile Thr Cys Arg Ala Ser
65                  70                  75                  80
```

-continued

```
Gln Ser Ile Ser Ser Tyr Leu Asn Trp Tyr Gln Gln Lys Pro Gly Lys
                85                  90                  95

Ala Pro Lys Leu Leu Ile Tyr Ala Ala Ser Ser Leu Gln Ser Gly Val
            100                 105                 110

Pro Ser Arg Phe Ser Gly Ser Gly Ser Gly Thr Asp Phe Thr Leu Thr
        115                 120                 125

Ile Ser Ser Leu Gln Pro Glu Asp Phe Ala Thr Tyr Tyr Cys Gln Gln
    130                 135                 140

Thr Val Val Ala Pro Pro Leu Phe Gly Gln Gly Thr Lys Val Glu Ile
145                 150                 155                 160

Lys Arg Thr Val Ala Ala Pro Ser Val Phe Ile Phe Pro Pro Ser Asp
                165                 170                 175

Glu Gln Leu Lys Ser Gly Thr Ala Ser Val Val Cys Leu Leu Asn Asn
            180                 185                 190

Phe Tyr Pro Arg Glu Ala Lys Val Gln Trp Lys Val Asp Asn Ala Leu
        195                 200                 205

Gln Ser Gly Asn Ser Gln Glu Ser Val Thr Glu Gln Asp Ser Lys Asp
    210                 215                 220

Ser Thr Tyr Ser Leu Ser Ser Thr Leu Thr Leu Ser Lys Ala Asp Tyr
225                 230                 235                 240

Glu Lys His Lys Val Tyr Ala Cys Glu Val Thr His Gln Gly Leu Ser
                245                 250                 255

Ser Pro Val Thr Lys Ser Phe Asn Arg Gly Glu Cys
            260                 265
```

<210> SEQ ID NO 60
<211> LENGTH: 786
<212> TYPE: DNA
<213> ORGANISM: Artificial Sequence
<220> FEATURE:
<223> OTHER INFORMATION: chemically synthesized

<400> SEQUENCE: 60

```
caaggccagt ctggccagtg caatatttgg ctcgtaggtg gtgattgcag ggctggcag      60

gggggctcga gcggaggatc tgctgtggga ctgctggctc ctcctggtgg cctgtctggc    120

agatctgata accacggcgg ctccgacatc cagatgaccc agtctccatc ctccctgtct    180

gcatctgtag gagacagagt caccatcact tgccgggcaa gtcagagcat tagcagctat    240

ttaaattggt atcagcagaa accagggaaa gcccctaagc tcctgatcta tgcggcatcc    300

agtttgcaaa gtggggtccc atcaaggttc agtggcagtg gatctgggac agatttcact    360

ctcaccatca gcagtctgca acctgaagat tttgcaactt actactgtca acagacggtt    420

gtggcgcctc cgttattcgg ccaagggacc aaggtggaaa tcaaacgtac ggtggctgca    480

ccatctgtct tcatcttccc gccatctgat gagcagttga aatctggaac tgcctctgtt    540

gtgtgcctgc tgaataactt ctatcccaga gaggccaaag tacagtggaa ggtggataac    600

gccctccaat cgggtaactc ccaggagagt gtcacagagc aggacagcaa ggacagcacc    660

tacagcctca gcagcaccct gacgctgagc aaagcagact acgagaaaca caaagtctac    720

gcctgcgaag tcacccatca gggcctgagc tcgcccgtca caaagagctt caacagggga    780

gagtgt                                                               786
```

<210> SEQ ID NO 61
<211> LENGTH: 262
<212> TYPE: PRT
<213> ORGANISM: Artificial Sequence
<220> FEATURE:
<223> OTHER INFORMATION: chemically synthesized

<400> SEQUENCE: 61

```
Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Ala Val Gly Leu Leu
            20                  25                  30

Ala Pro Pro Gly Gly Leu Ser Gly Arg Ser Asp Asn His Gly Gly Ser
        35                  40                  45

Asp Ile Gln Met Thr Gln Ser Pro Ser Ser Leu Ser Ala Ser Val Gly
    50                  55                  60

Asp Arg Val Thr Ile Thr Cys Arg Ala Ser Gln Ser Ile Ser Ser Tyr
65                  70                  75                  80

Leu Asn Trp Tyr Gln Gln Lys Pro Gly Lys Ala Pro Lys Leu Leu Ile
                85                  90                  95

Tyr Ala Ala Ser Ser Leu Gln Ser Gly Val Pro Ser Arg Phe Ser Gly
            100                 105                 110

Ser Gly Ser Gly Thr Asp Phe Thr Leu Thr Ile Ser Ser Leu Gln Pro
        115                 120                 125

Glu Asp Phe Ala Thr Tyr Tyr Cys Gln Gln Thr Val Val Ala Pro Pro
    130                 135                 140

Leu Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
            260
```

<210> SEQ ID NO 62
<211> LENGTH: 789
<212> TYPE: DNA
<213> ORGANISM: Artificial Sequence
<220> FEATURE:
<223> OTHER INFORMATION: chemically synthesized

<400> SEQUENCE: 62

```
caaggccagt ctggccagtg caatatttgg ctcgtaggtg gtgattgcag gggctggcag     60

gggggctcga gcggaggctc tggcctgtct ggcagatccg ataaccatgg cggcgctgtg    120

ggactgctgg ctcctcctgg tggatctgac atccagatga cccagtctcc atcctccctg    180

tctgcatctg taggagacag agtcaccatc acttgccggg caagtcagag cattagcagc    240

tatttaaatt ggtatcagca gaaaccaggg aaagccccta agctcctgat ctatgcggca    300

tccagtttgc aaagtggggt cccatcaagg ttcagtggca gtggatctgg gacagatttc    360

actctcacca tcagcagtct gcaacctgaa gattttgcaa cttactactg tcaacagacg    420
```

-continued

```
gttgtggcgc ctccgttatt cggccaaggg accaaggtgg aaatcaaacg tacggtggct    480

gcaccatctg tcttcatctt cccgccatct gatgagcagt tgaaatctgg aactgcctct    540

gttgtgtgcc tgctgaataa cttctatccc agagaggcca aagtacagtg gaaggtggat    600

aacgccctcc aatcgggtaa ctcccaggag agtgtcacag agcaggacag caaggacagc    660

acctacagcc tcagcagcac cctgacgctg agcaaagcag actacgagaa acacaaagtc    720

tacgcctgcg aagtcaccca tcagggcctg agctcgcccg tcacaaagag cttcaacagg    780

ggagagtgt                                                            789
```

```
<210> SEQ ID NO 63
<211> LENGTH: 263
<212> TYPE: PRT
<213> ORGANISM: Artificial Sequence
<220> FEATURE:
<223> OTHER INFORMATION: chemically synthesized

<400> SEQUENCE: 63

Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Gly Leu Ser Gly Arg
            20                  25                  30

Ser Asp Asn His Gly Gly Ala Val Gly Leu Leu Ala Pro Pro Gly Gly
        35                  40                  45

Ser Asp Ile Gln Met Thr Gln Ser Pro Ser Ser Leu Ser Ala Ser Val
    50                  55                  60

Gly Asp Arg Val Thr Ile Thr Cys Arg Ala Ser Gln Ser Ile Ser Ser
65                  70                  75                  80

Tyr Leu Asn Trp Tyr Gln Gln Lys Pro Gly Lys Ala Pro Lys Leu Leu
                85                  90                  95

Ile Tyr Ala Ala Ser Ser Leu Gln Ser Gly Val Pro Ser Arg Phe Ser
            100                 105                 110

Gly Ser Gly Ser Gly Thr Asp Phe Thr Leu Thr Ile Ser Ser Leu Gln
        115                 120                 125

Pro Glu Asp Phe Ala Thr Tyr Tyr Cys Gln Gln Thr Val Val Ala Pro
    130                 135                 140

Pro Leu Phe Gly Gln Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 64
<211> LENGTH: 792
```

<212> TYPE: DNA
<213> ORGANISM: Artificial Sequence
<220> FEATURE:
<223> OTHER INFORMATION: chemically synthesized

<400> SEQUENCE: 64
caaggccagt ctggccagtg caatatttgg ctcgtaggtg gtgattgcag gggctggcag 60
gggggctcga gcggcggctc tgtgcatatg cccctgggct ttctgggacc tggcggcctg 120
tctggcagat ccgataatca cggcggctcc gacatccaga tgacccagtc tccatcctcc 180
ctgtctgcat ctgtaggaga cagagtcacc atcacttgcc gggcaagtca gagcattagc 240
agctatttaa attggtatca gcagaaacca gggaaagccc ctaagctcct gatctatgcg 300
gcatccagtt tgcaaagtgg ggtcccatca aggttcagtg gcagtggatc tgggacagat 360
ttcactctca ccatcagcag tctgcaacct gaagattttg caacttacta ctgtcaacag 420
acggttgtgg cgcctccgtt attcggccaa gggaccaagg tggaaatcaa acgtacggtg 480
gctgcaccat ctgtcttcat cttcccgcca tctgatgagc agttgaaatc tggaactgcc 540
tctgttgtgt gcctgctgaa taacttctat cccagagagg ccaaagtaca gtggaaggtg 600
gataacgccc tccaatcggg taactcccag gagagtgtca cagagcagga cagcaaggac 660
agcacctaca gcctcagcag caccctgacg ctgagcaaag cagactacga gaaacacaaa 720
gtctacgcct gcgaagtcac ccatcagggc ctgagctcgc ccgtcacaaa gagcttcaac 780
aggggagagt gt 792

<210> SEQ ID NO 65
<211> LENGTH: 264
<212> TYPE: PRT
<213> ORGANISM: Artificial Sequence
<220> FEATURE:
<223> OTHER INFORMATION: chemically synthesized

<400> SEQUENCE: 65

Gln Gly Gln Ser Gly Gln Cys Asn Ile Trp Leu Val Gly Gly Asp Cys
1 5 10 15

Arg Gly Trp Gln Gly Gly Ser Ser Gly Gly Ser Val His Met Pro Leu
20 25 30

Gly Phe Leu Gly Pro Gly Gly Leu Ser Gly Arg Ser Asp Asn His Gly
35 40 45

Gly Ser Asp Ile Gln Met Thr Gln Ser Pro Ser Ser Leu Ser Ala Ser
50 55 60

Val Gly Asp Arg Val Thr Ile Thr Cys Arg Ala Ser Gln Ser Ile Ser
65 70 75 80

Ser Tyr Leu Asn Trp Tyr Gln Gln Lys Pro Gly Lys Ala Pro Lys Leu
85 90 95

Leu Ile Tyr Ala Ala Ser Ser Leu Gln Ser Gly Val Pro Ser Arg Phe
100 105 110

Ser Gly Ser Gly Ser Gly Thr Asp Phe Thr Leu Thr Ile Ser Ser Leu
115 120 125

Gln Pro Glu Asp Phe Ala Thr Tyr Tyr Cys Gln Gln Thr Val Val Ala
130 135 140

Pro Pro Leu Phe Gly Gln Gly Thr Lys Val Glu Ile Lys Arg Thr Val
145 150 155 160

Ala Ala Pro Ser Val Phe Ile Phe Pro Pro Ser Asp Glu Gln Leu Lys
165 170 175

Ser Gly Thr Ala Ser Val Val Cys Leu Leu Asn Asn Phe Tyr Pro Arg

```
            180                 185                 190

Glu Ala Lys Val Gln Trp Lys Val Asp Asn Ala Leu Gln Ser Gly Asn
        195                 200                 205

Ser Gln Glu Ser Val Thr Glu Gln Asp Ser Lys Asp Ser Thr Tyr Ser
    210                 215                 220

Leu Ser Ser Thr Leu Thr Leu Ser Lys Ala Asp Tyr Glu Lys His Lys
225                 230                 235                 240

Val Tyr Ala Cys Glu Val Thr His Gln Gly Leu Ser Ser Pro Val Thr
                245                 250                 255

Lys Ser Phe Asn Arg Gly Glu Cys
            260
```

<210> SEQ ID NO 66
<211> LENGTH: 795
<212> TYPE: DNA
<213> ORGANISM: Artificial Sequence
<220> FEATURE:
<223> OTHER INFORMATION: chemically synthesized

<400> SEQUENCE: 66

```
caaggccagt ctggccagtg caatatttgg ctcgtaggtg gtgattgcag ggctggcag      60

gggggctcga gcggaggctc tggcctgtct ggcagatctg ataaccacgg cggcgtgcac    120

atgcccctgg gctttctggg acctggcgga tctgacatcc agatgaccca gtctccatcc    180

tccctgtctg catctgtagg agacagagtc accatcactt gccgggcaag tcagagcatt    240

agcagctatt taaattggta tcagcagaaa ccagggaaag cccctaagct cctgatctat    300

gcggcatcca gtttgcaaag tggggtccca tcaaggttca gtggcagtgg atctgggaca    360

gatttcactc tcaccatcag cagtctgcaa cctgaagatt ttgcaactta ctactgtcaa    420

cagacggttg tggcgcctcc gttattcggc caagggacca aggtggaaat caaacgtacg    480

gtggctgcac catctgtctt catcttcccg ccatctgatg agcagttgaa atctggaact    540

gcctctgttg tgtgcctgct gaataacttc tatcccagag aggccaaagt acagtggaag    600

gtggataacg ccctccaatc gggtaactcc caggagagtg tcacagagca ggacagcaag    660

gacagcacct acagcctcag cagcaccctg acgctgagca aagcagacta cgagaaacac    720

aaagtctacg cctgcgaagt cacccatcag ggcctgagct cgcccgtcac aaagagcttc    780

aacaggggag agtgt                                                      795
```

<210> SEQ ID NO 67
<211> LENGTH: 449
<212> TYPE: PRT
<213> ORGANISM: Artificial Sequence
<220> FEATURE:
<223> OTHER INFORMATION: chemically synthesized

<400> SEQUENCE: 67

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 68
<211> LENGTH: 1347
<212> TYPE: PRT
<213> ORGANISM: Artificial Sequence
<220> FEATURE:
<223> OTHER INFORMATION: chemically synthesized -continued

<400> SEQUENCE: 68

Cys Ala Gly Gly Thr Ala Cys Ala Gly Cys Thr Gly Ala Ala Ala Cys
1 5 10 15

Ala Gly Thr Cys Thr Gly Gly Ala Cys Cys Cys Gly Gly Gly Cys Thr
20 25 30

Thr Gly Thr Ala Cys Ala Gly Cys Cys Thr Ala Gly Thr Cys Ala Gly
35 40 45

Thr Cys Ala Cys Thr Gly Thr Cys Thr Ala Thr Cys Ala Cys Cys Thr
50 55 60

Gly Thr Ala Cys Cys Gly Thr Cys Thr Cys Ala Gly Gly Thr Thr Thr
65 70 75 80

Thr Ala Gly Cys Cys Thr Gly Ala Cys Ala Ala Ala Thr Thr Ala Cys
85 90 95

Gly Gly Thr Gly Thr Gly Cys Ala Thr Thr Gly Gly Gly Thr Ala Cys
100 105 110

Gly Cys Cys Ala Gly Thr Cys Thr Cys Cys Cys Gly Gly Thr Ala Ala
115 120 125

Gly Gly Gly Gly Cys Thr Gly Gly Ala Gly Thr Gly Gly Cys Thr Cys
130 135 140

Gly Gly Cys Gly Thr Gly Ala Thr Cys Thr Gly Gly Thr Cys Cys Gly
145 150 155 160

Gly Gly Gly Gly Gly Ala Ala Cys Ala Cys Ala Gly Ala Thr Thr Ala
165 170 175

Thr Ala Ala Thr Ala Cys Thr Cys Cys Thr Thr Thr Cys Ala Cys Ala
180 185 190

Thr Cys Thr Ala Gly Ala Cys Thr Gly Thr Cys Cys Ala Thr Cys Ala
195 200 205

Ala Cys Ala Ala Ala Gly Ala Cys Ala Ala Cys Thr Cys Cys Ala Ala
210 215 220

Ala Thr Cys Gly Cys Ala Gly Gly Thr Thr Thr Thr Thr Thr Thr Cys
225 230 235 240

Ala Ala Gly Ala Thr Gly Ala Ala Thr Thr Cys Cys Cys Thr Gly Cys
245 250 255

Ala Ala Thr Cys Ala Cys Ala Gly Gly Ala Cys Ala Cys Thr Gly Cys
260 265 270

Cys Ala Thr Cys Thr Ala Thr Thr Ala Thr Thr Gly Cys Gly Cys Gly
275 280 285

Ala Gly Gly Gly Cys Cys Cys Thr Gly Ala Cys Thr Thr Ala Thr Thr
290 295 300

Ala Thr Gly Ala Cys Thr Ala Thr Gly Ala Gly Thr Thr Cys Gly Cys
305 310 315 320

Thr Thr Ala Thr Thr Gly Gly Gly Gly Cys Cys Ala Gly Gly Gly Gly
325 330 335

Ala Cys Gly Cys Thr Thr Gly Thr Gly Ala Cys Cys Gly Thr Ala Ala
340 345 350

Gly Cys Gly Cys Thr Gly Cys Thr Ala Gly Thr Ala Cys Cys Ala Ala
355 360 365

Gly Gly Gly Cys Cys Cys Cys Ala Gly Thr Gly Thr Gly Thr Thr Cys
370 375 380

Cys Cys Cys Cys Thr Thr Gly Cys Cys Cys Cys Cys Ala Gly Cys Ala
385 390 395 400

Gly Thr Ala Ala Gly Thr Cys Cys Ala Cys Cys Thr Cys Ala Gly Gly

```
                405                 410                 415

Thr Gly Gly Cys Ala Cys Ala Gly Cys Thr Gly Cys Cys Cys Thr Thr
            420                 425                 430

Gly Gly Gly Thr Gly Cys Cys Thr Thr Gly Thr Gly Ala Ala Gly Gly
        435                 440                 445

Ala Thr Thr Ala Cys Thr Thr Cys Cys Cys Ala Gly Ala Ala Cys Cys
    450                 455                 460

Ala Gly Thr Gly Ala Cys Cys Gly Thr Gly Ala Gly Cys Thr Gly Gly
465                 470                 475                 480

Ala Ala Thr Thr Cys Cys Gly Gly Ala Gly Cys Cys Cys Thr Thr Ala
                485                 490                 495

Cys Cys Ala Gly Cys Gly Gly Thr Gly Thr Gly Cys Ala Thr Ala Cys
            500                 505                 510

Cys Thr Thr Thr Cys Cys Gly Gly Cys Cys Gly Thr Cys Cys Thr Gly
        515                 520                 525

Cys Ala Ala Ala Gly Cys Ala Gly Cys Gly Gly Ala Cys Thr Thr Thr
    530                 535                 540

Ala Cys Ala Gly Thr Cys Thr Gly Thr Cys Thr Ala Gly Cys Gly Thr
545                 550                 555                 560

Gly Gly Thr Cys Ala Cys Cys Gly Thr Gly Cys Cys Cys Ala Gly Cys
                565                 570                 575

Ala Gly Cys Ala Gly Cys Cys Thr Gly Gly Gly Thr Ala Cys Ala Cys
            580                 585                 590

Ala Gly Ala Cys Gly Thr Ala Thr Ala Thr Thr Thr Gly Cys Ala Ala
        595                 600                 605

Cys Gly Thr Thr Ala Ala Thr Cys Ala Cys Ala Ala Ala Cys Cys Cys
    610                 615                 620

Thr Cys Ala Ala Ala Cys Ala Cys Ala Ala Ala Gly Gly Thr Gly Gly
625                 630                 635                 640

Ala Cys Ala Ala Gly Ala Ala Ala Gly Thr Gly Gly Ala Gly Cys Cys
                645                 650                 655

Thr Ala Ala Ala Thr Cys Ala Thr Gly Thr Gly Ala Thr Ala Ala Gly
            660                 665                 670

Ala Cys Ala Cys Ala Thr Ala Cys Ala Thr Gly Cys Cys Cys Thr Cys
        675                 680                 685

Cys Cys Thr Gly Cys Cys Cys Thr Gly Cys Ala Cys Cys Gly Gly Ala
    690                 695                 700

Gly Cys Thr Cys Thr Thr Ala Gly Gly Thr Gly Gly Ala Cys Cys Thr
705                 710                 715                 720

Thr Cys Ala Gly Thr Cys Thr Thr Thr Thr Thr Ala Thr Thr Thr Cys
                725                 730                 735

Cys Ala Cys Cys Thr Ala Ala Ala Cys Cys Cys Ala Ala Ala Gly Ala
            740                 745                 750

Thr Ala Cys Ala Cys Thr Thr Ala Thr Gly Ala Thr Cys Thr Cys Ala
        755                 760                 765

Cys Gly Gly Ala Cys Ala Cys Cys Cys Gly Ala Gly Gly Thr Gly Ala
    770                 775                 780

Cys Cys Thr Gly Cys Gly Thr Thr Gly Thr Cys Gly Thr Gly Gly Ala
785                 790                 795                 800

Thr Gly Thr Cys Thr Cys Ala Cys Ala Cys Gly Ala Ala Gly Ala Cys
                805                 810                 815

Cys Cys Thr Gly Ala Ala Gly Thr Gly Ala Ala Ala Thr Thr Cys Ala
            820                 825                 830
```

```
Ala Thr Thr Gly Gly Thr Ala Thr Gly Thr Thr Gly Ala Cys Gly Gly
        835                 840                 845

Thr Gly Thr Thr Gly Ala Gly Gly Thr Gly Cys Ala Thr Ala Ala Cys
    850                 855                 860

Gly Cys Ala Ala Ala Gly Ala Cys Cys Ala Ala Gly Cys Cys Ala Cys
865                 870                 875                 880

Gly Cys Gly Ala Gly Gly Ala Gly Cys Ala Gly Thr Ala Thr Ala Ala
                885                 890                 895

Thr Ala Gly Cys Ala Cys Cys Thr Ala Thr Ala Gly Gly Gly Thr Ala
            900                 905                 910

Gly Thr Cys Ala Gly Cys Gly Thr Ala Cys Thr Gly Ala Cys Thr Gly
        915                 920                 925

Thr Thr Cys Thr Gly Cys Ala Thr Cys Ala Gly Gly Ala Thr Thr Gly
    930                 935                 940

Gly Cys Thr Gly Ala Ala Cys Gly Gly Thr Ala Ala Ala Gly Ala Gly
945                 950                 955                 960

Thr Ala Cys Ala Ala Ala Thr Gly Cys Ala Ala Gly Gly Thr Cys Thr
                965                 970                 975

Cys Ala Ala Ala Cys Ala Ala Gly Gly Cys Thr Cys Thr Cys Cys Cys
            980                 985                 990

Thr Gly Cys Cys Cys Cys Gly Ala  Thr Cys Gly Ala Gly  Ala Ala Gly
        995                 1000                1005

Ala Cys  Ala Ala Thr Thr Thr  Cys Thr Ala Ala Gly  Gly Cys Cys
    1010                1015                1020

Ala Ala  Ala Gly Gly Gly Cys  Ala Gly Cys Cys Cys  Cys Gly Gly
    1025                1030                1035

Gly Ala  Ala Cys Cys Ala Cys  Ala Ala Gly Thr Cys  Thr Ala Thr
    1040                1045                1050

Ala Cys  Cys Cys Thr Gly Cys  Cys Ala Cys Cys Cys  Ala Gly Thr
    1055                1060                1065

Cys Gly  Gly Gly Ala Thr Gly  Ala Ala Cys Thr Ala  Ala Cys Ala
    1070                1075                1080

Ala Ala  Ala Ala Ala Thr Cys  Ala Gly Gly Thr Gly  Thr Cys Thr
    1085                1090                1095

Cys Thr  Ala Ala Cys Cys Thr  Gly Cys Cys Thr Gly  Gly Thr Gly
    1100                1105                1110

Ala Ala  Gly Gly Gly Ala Thr  Thr Thr Thr Ala Cys  Cys Cys Thr
    1115                1120                1125

Thr Cys  Cys Gly Ala Thr Ala  Thr Ala Gly Cys Thr  Gly Thr Gly
    1130                1135                1140

Gly Ala  Gly Thr Gly Gly Gly  Ala Gly Thr Cys Thr  Ala Ala Thr
    1145                1150                1155

Gly Gly  Cys Cys Ala Ala Cys  Cys Ala Gly Ala Gly  Ala Ala Thr
    1160                1165                1170

Ala Ala  Thr Thr Ala Cys Ala  Ala Gly Ala Cys Thr  Ala Cys Cys
    1175                1180                1185

Cys Cys  Cys Cys Cys Cys Gly  Thr Thr Cys Thr Thr  Gly Ala Cys
    1190                1195                1200

Ala Gly  Thr Gly Ala Thr Gly  Gly Cys Thr Cys Gly  Thr Thr Cys
    1205                1210                1215

Thr Thr  Cys Thr Thr Ala Thr  Ala Cys Thr Cys Ala  Ala Ala Ala
    1220                1225                1230
```

```
Thr Thr  Ala Ala Cys Ala Gly  Thr Cys Gly Ala Cys  Ala Ala Ala
    1235                 1240                 1245

Thr Cys  Cys Cys Gly Ala Thr  Gly Gly Cys Ala Ala  Cys Ala Gly
    1250                 1255                 1260

Gly Gly  Cys Ala Ala Thr Gly  Thr Gly Thr Thr Thr  Ala Gly Cys
    1265                 1270                 1275

Thr Gly  Thr Ala Gly Cys Gly  Thr Gly Ala Thr Gly  Cys Ala Thr
    1280                 1285                 1290

Gly Ala  Ala Gly Cys Cys Cys  Thr Gly Cys Ala Cys  Ala Ala Cys
    1295                 1300                 1305

Cys Ala  Thr Thr Ala Cys Ala  Cys Ala Cys Ala Gly  Ala Ala Gly
    1310                 1315                 1320

Thr Cys  Thr Cys Thr Gly Thr  Cys Cys Thr Thr Gly  Thr Cys Ala
    1325                 1330                 1335

Cys Cys  Thr Gly Gly Cys Ala  Ala Gly
    1340                 1345


<210> SEQ ID NO 69
<211> LENGTH: 447
<212> TYPE: PRT
<213> ORGANISM: Artificial Sequence
<220> FEATURE:
<223> OTHER INFORMATION: chemically synthesized

<400> SEQUENCE: 69

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Ser Leu Gln Ser Gln Asp Thr Ala Ile Tyr Tyr Cys Ala Arg Ala
                85                  90                  95

Leu Thr Tyr Tyr Asp Tyr Glu Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 70
<211> LENGTH: 645
<212> TYPE: DNA
<213> ORGANISM: Artificial Sequence
<220> FEATURE:
<223> OTHER INFORMATION: chemically synthesized

<400> SEQUENCE: 70

```
acccaaatcc tcctgaccca gtcccctgtt atcctttctg tgtcgcccgg ggagcgcgtt     60

agctttagct gccgcgccag tcagtcaatc ggaacaaaca tccattggta ccagcagcgt    120

acgaacggca gtccaaggct gctgatcaaa tacgcaagtg aatctatatc ggggattccg    180

tctcggttca gcggatccgg aagcgggact gactttacgc tctccataaa tagcgtcgaa    240

agtgaggaca ttgcagacta ttactgtcag cagaataaca actggccgac cacatttggg    300

gccggaacca agttggaact gaagcgcact gtggcagctc ctagtgtttt tattttcccc    360

ccttctgacg agcaactgaa aagtggtaca gcttcagtag tttgtttgct caataatttc    420

tacccacggg aagcaaaggt gcagtggaaa gtcgacaacg cattacagag cggcaactct    480

caagaaagcg tgacggagca ggatagcaag gactcaacat attccttgtc ttccactctc    540

actctgtcaa aggctgatta tgagaagcat aaggtgtatg cgtgcgaagt gacacaccag    600

ggattatcaa gcccagtgac caagtccttt aaccgtggcg aatgc                    645
```

<210> SEQ ID NO 71
<211> LENGTH: 8
<212> TYPE: PRT
<213> ORGANISM: Artificial Sequence
<220> FEATURE:
<223> OTHER INFORMATION: chemically synthesized

<400> SEQUENCE: 71

Leu Ser Gly Arg Ser Asp Asn Ile
1 5

<210> SEQ ID NO 72
<211> LENGTH: 783
<212> TYPE: DNA
<213> ORGANISM: Artificial Sequence
<220> FEATURE:
<223> OTHER INFORMATION: chemically synthesized

<400> SEQUENCE: 72
cagggccaga gcggccaatg catctccccc cgcggttgtc ccgacgggcc gtacgtgatg 60
tacggcagct ccggcggcag tgggggtagc ggtgggtccg ggctgagtgg ccggtccgac 120
aatcacggga gctcgggaac acagattctg ctgacgcaat ctcccgtgat cctctcggtc 180
tcacccggcg aacgggtctc gttcagctgc agagcgtccc aatcaatcgg gaccaatatt 240
cactggtacc agcaaaggac taatgggtct ccccggctgc tgataaaata cgcctccgag 300
tctatctcgg gcatcccatc ccgatttagt ggtagcggaa gcggcactga tttcaccttg 360
tctattaaca gcgtagaatc tgaggacatt gcagactatt actgtcagca gaataacaat 420
tggcctacaa ctttcggcgc cggaccaaa ctagagttaa agcgtactgt ggctgccccc 480
agcgttttta tttttccgcc cagcgacgaa cagctgaagt caggcacagc ctctgtggtg 540
tgtctcctga ataacttcta ccccagagag gccaaagttc agtggaaagt ggacaatgcc 600
ttgcagtccg gaaacagtca agagtccgtg accgagcagg acagtaagga tagcacgtat 660
agcctctcta gtactttaac actgtccaag gccgactacg agaagcacaa ggtgtacgca 720
tgcgaagtga cccatcaggg gctttcctcc cccgtcacca agtctttcaa tcgcggggag 780
tgt 783

<210> SEQ ID NO 73
<211> LENGTH: 261
<212> TYPE: PRT
<213> ORGANISM: Artificial Sequence
<220> FEATURE:
<223> OTHER INFORMATION: chemically synthesized

<400> SEQUENCE: 73

Gln Gly Gln Ser Gly Gln Cys Ile Ser Pro Arg Gly Cys Pro Asp Gly
1 5 10 15

Pro Tyr Val Met Tyr Gly Ser Ser Gly Gly Ser Gly Gly Ser Gly Gly
20 25 30

Ser Gly Leu Ser Gly Arg Ser Asp Asn His Gly Ser Ser Gly Thr Gln
35 40 45

Ile Leu Leu Thr Gln Ser Pro Val Ile Leu Ser Val Ser Pro Gly Glu
50 55 60

Arg Val Ser Phe Ser Cys Arg Ala Ser Gln Ser Ile Gly Thr Asn Ile
65 70 75 80

His Trp Tyr Gln Gln Arg Thr Asn Gly Ser Pro Arg Leu Leu Ile Lys
85 90 95

Tyr Ala Ser Glu Ser Ile Ser Gly Ile Pro Ser Arg Phe Ser Gly Ser
100 105 110

Gly Ser Gly Thr Asp Phe Thr Leu Ser Ile Asn Ser Val Glu Ser Glu
115 120 125

Asp Ile Ala Asp Tyr Tyr Cys Gln Gln Asn Asn Asn Trp Pro Thr Thr
130 135 140

-continued

Phe Gly Ala Gly Thr Lys Leu Glu Leu Lys Arg Thr Val Ala Ala Pro
145 150 155 160

Ser Val Phe Ile Phe Pro Pro Ser Asp Glu Gln Leu Lys Ser Gly Thr
165 170 175

Ala Ser Val Val Cys Leu Leu Asn Asn Phe Tyr Pro Arg Glu Ala Lys
180 185 190

Val Gln Trp Lys Val Asp Asn Ala Leu Gln Ser Gly Asn Ser Gln Glu
195 200 205

Ser Val Thr Glu Gln Asp Ser Lys Asp Ser Thr Tyr Ser Leu Ser Ser
210 215 220

Thr Leu Thr Leu Ser Lys Ala Asp Tyr Glu Lys His Lys Val Tyr Ala
225 230 235 240

Cys Glu Val Thr His Gln Gly Leu Ser Ser Pro Val Thr Lys Ser Phe
245 250 255

Asn Arg Gly Glu Cys
260

<210> SEQ ID NO 74
<211> LENGTH: 783
<212> TYPE: DNA
<213> ORGANISM: Artificial Sequence
<220> FEATURE:
<223> OTHER INFORMATION: chemically synthesized

<400> SEQUENCE: 74
caaggtcagt ccggacagtg tatttcccct agaggttgcc ctgacgggcc gtatgtcatg 60
tacggtagtt ctggcggtag tggcggatct ggcggcagtg ggctgagcgg acgtagcggg 120
aatcacggct catccgggac gcagatactg ctgacccagt cccccgtgat cctgtccgtg 180
tcaccgggcg aaagggtcag tttctcttgc cgagcatcac agtccatagg tacgaatatc 240
cattggtacc agcagcggac caatgggagc ccaagactgc tcattaagta cgcatctgag 300
agtatctcag gcattccaag caggttttcc ggcagtggga gcggcactga cttcaccctc 360
agcattaaca gcgtggaaag cgaagacatt gcagattact actgccaaca gaacaataac 420
tggcctacta cattcggggc aggaactaag ttggagctca aacgtaccgt cgctgctcct 480
agcgtattta ttttccctcc tagcgatgaa cagttgaaat ctggtaccgc tagtgttgtg 540
tgcttactga acaactttta tccccgggag gccaaggtac aatggaaggt ggacaatgcc 600
ctccaatcag ggaacagcca ggagtctgtt accgagcagg actccaagga cagcacctac 660
agcctgagct ctacccttac attgagcaag gctgattatg agaagcataa ggtctacgct 720
tgtgaggtga cccatcaggg gctcagcagc ccggtgacaa aaagctttaa ccgggggggaa 780 tgc 783

<210> SEQ ID NO 75
<211> LENGTH: 261
<212> TYPE: PRT
<213> ORGANISM: Artificial Sequence
<220> FEATURE:
<223> OTHER INFORMATION: chemically synthesized

<400> SEQUENCE: 75

Gln Gly Gln Ser Gly Gln Cys Ile Ser Pro Arg Gly Cys Pro Asp Gly
1 5 10 15

Pro Tyr Val Met Tyr Gly Ser Ser Gly Gly Ser Gly Gly Ser Gly Gly
20 25 30

```
Ser Gly Leu Ser Gly Arg Ser Gly Asn His Gly Ser Ser Gly Thr Gln
        35                  40                  45

Ile Leu Leu Thr Gln Ser Pro Val Ile Leu Ser Val Ser Pro Gly Glu
    50                  55                  60

Arg Val Ser Phe Ser Cys Arg Ala Ser Gln Ser Ile Gly Thr Asn Ile
65                  70                  75                  80

His Trp Tyr Gln Gln Arg Thr Asn Gly Ser Pro Arg Leu Leu Ile Lys
                85                  90                  95

Tyr Ala Ser Glu Ser Ile Ser Gly Ile Pro Ser Arg Phe Ser Gly Ser
            100                 105                 110

Gly Ser Gly Thr Asp Phe Thr Leu Ser Ile Asn Ser Val Glu Ser Glu
        115                 120                 125

Asp Ile Ala Asp Tyr Tyr Cys Gln Gln Asn Asn Asn Trp Pro Thr Thr
    130                 135                 140

Phe Gly Ala Gly Thr Lys Leu Glu Leu Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260


<210> SEQ ID NO 76
<211> LENGTH: 783
<212> TYPE: DNA
<213> ORGANISM: Artificial Sequence
<220> FEATURE:
<223> OTHER INFORMATION: chemically synthesized

<400> SEQUENCE: 76

caggggcagt ctgggcagtg tattagcccc agggggtgcc ccgacgggcc ttacgtgatg      60

tatggcagct ccggtggcag cggaggctct ggcgggagtg ggatcagttc cggcctgctg     120

agctccgggt caagcgggac ccagatcttg ctcacccaat caccagtgat cctaagcgtg     180

agccctggcg aacgggtcag cttctcttgc cgggcatctc agagtattgg cactaacata     240

cactggtacc agcagcgaac caatgggtcc ccccgccttc taatcaaata tgctagcgaa     300

tccatttcag gaattcctag ccgatttagc ggcagcggat caggcactga cttcactctg     360

tcaatcaact cagttgaaag cgaggacatt gcagactact attgccagca gaataataat     420

tggcccacta catttggagc tggaacaaaa ttggagctta agaggacagt ggctgcgcct     480

agtgtattta tctttccccc ctctgacgaa cagttgaaat cgggaaccgc atccgtcgtc     540

tgtttactga acaacttcta tcccagagag gccaaagtgc agtggaaagt ggataatgct     600

ttgcagtctg gcaacagcca ggaaagcgtg acggagcagg actcaaagga tagtacatac     660

tccctgtcct ccaccctgac tctgagtaag gccgactacg agaagcacaa ggtctacgcc     720
```

```
tgcgaagtga cgcaccaagg gctatcgagc ccggtcacca agtctttcaa tcgtggagaa    780

tgc                                                                  783


<210> SEQ ID NO 77
<211> LENGTH: 261
<212> TYPE: PRT
<213> ORGANISM: Artificial Sequence
<220> FEATURE:
<223> OTHER INFORMATION: chemically synthesized

<400> SEQUENCE: 77

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Ile Ser Ser Gly Leu Leu Ser Ser Gly Ser Ser Gly Thr Gln
        35                  40                  45

Ile Leu Leu Thr Gln Ser Pro Val Ile Leu Ser Val Ser Pro Gly Glu
    50                  55                  60

Arg Val Ser Phe Ser Cys Arg Ala Ser Gln Ser Ile Gly Thr Asn Ile
65                  70                  75                  80

His Trp Tyr Gln Gln Arg Thr Asn Gly Ser Pro Arg Leu Leu Ile Lys
                85                  90                  95

Tyr Ala Ser Glu Ser Ile Ser Gly Ile Pro Ser Arg Phe Ser Gly Ser
            100                 105                 110

Gly Ser Gly Thr Asp Phe Thr Leu Ser Ile Asn Ser Val Glu Ser Glu
        115                 120                 125

Asp Ile Ala Asp Tyr Tyr Cys Gln Gln Asn Asn Asn Trp Pro Thr Thr
    130                 135                 140

Phe Gly Ala Gly Thr Lys Leu Glu Leu Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260


<210> SEQ ID NO 78
<211> LENGTH: 783
<212> TYPE: DNA
<213> ORGANISM: Artificial Sequence
<220> FEATURE:
<223> OTHER INFORMATION: chemically synthesized

<400> SEQUENCE: 78

caggggcaat caggacaatg catcagccct aggggctgcc cagacggccc atatgtgatg     60

tacggtagct ctgggggctc aggaggcagc gggggaagcg gacaaaacca ggccttacga    120
```

```
atggctggca gctctggcac ccagatattg ctgacgcaga gtccagttat ccttagtgtc    180

agccctggtg aacgggtttc atttagttgc cgtgcctccc agtctattgg aacgaacatt    240

cattggtacc agcaaaggac caacggttca cccaggttgc ttatcaagta tgcttcagag    300

tcaatctccg ggattccctc aaggttttca ggctctggct caggtaccga ttttacgctg    360

agcatcaact ccgtggagag tgaggacatt gctgattatt actgtcagca gaataacaat    420

tggccgacaa ctttcggcgc cggcacaaag ctggaactta agcgtactgt ggctgcgcca    480

tctgtcttca tttttccgcc ctcggacgag cagttgaagt cagggaccgc ctctgtcgtg    540

tgccttctca ataacttcta tcccagagag gctaaagtcc agtggaaagt tgataatgca    600

cttcagagcg ggaatagcca ggagagcgtg acggaacagg actctaagga ctccacctat    660

tctctctcat ccacccttac tctctctaaa gccgactacg aaaagcataa ggtttatgct    720

tgcgaagtca ctcatcaagg gctatctagt ccggtcacta aaagcttcaa cagaggtgaa    780

tgt                                                                  783


<210> SEQ ID NO 79
<211> LENGTH: 261
<212> TYPE: PRT
<213> ORGANISM: Artificial Sequence
<220> FEATURE:
<223> OTHER INFORMATION: chemically synthesized

<400> SEQUENCE: 79

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Gln Asn Gln Ala Leu Arg Met Ala Gly Ser Ser Gly Thr Gln
        35                  40                  45

Ile Leu Leu Thr Gln Ser Pro Val Ile Leu Ser Val Ser Pro Gly Glu
    50                  55                  60

Arg Val Ser Phe Ser Cys Arg Ala Ser Gln Ser Ile Gly Thr Asn Ile
65                  70                  75                  80

His Trp Tyr Gln Gln Arg Thr Asn Gly Ser Pro Arg Leu Leu Ile Lys
                85                  90                  95

Tyr Ala Ser Glu Ser Ile Ser Gly Ile Pro Ser Arg Phe Ser Gly Ser
            100                 105                 110

Gly Ser Gly Thr Asp Phe Thr Leu Ser Ile Asn Ser Val Glu Ser Glu
        115                 120                 125

Asp Ile Ala Asp Tyr Tyr Cys Gln Gln Asn Asn Asn Trp Pro Thr Thr
    130                 135                 140

Phe Gly Ala Gly Thr Lys Leu Glu Leu Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240
```

Cys Glu Val Thr His Gln Gly Leu Ser Ser Pro Val Thr Lys Ser Phe
245 250 255

Asn Arg Gly Glu Cys
260

<210> SEQ ID NO 80
<211> LENGTH: 798
<212> TYPE: DNA
<213> ORGANISM: Artificial Sequence
<220> FEATURE:
<223> OTHER INFORMATION: chemically synthesized

<400> SEQUENCE: 80
caaggccagt ctggacaatg tatcagcccc cgtggctgtc cagacggtcc ttacgttatg 60
tatggatcta gcgggggctc tggagggtct ggcggctctg gaatctctag tggacttctc 120
tccggaagaa gcgataatca tggatccagc gggacacaaa tcctgttgac acagtcccca 180
gtgatcctgt cagtctcgcc cggagaaagg gtgtctttct cttgtagggc tagtcagtct 240
atcggaacta acatccattg gtaccagcag cggacaaatg ggagcccgag gcttctgatc 300
aagtatgctt cagagagtat aagcggcatc ccctcaagat ttagtggcag cgggtccggg 360
acagatttca ccttgtcaat caattctgtc gaatccgaag acattgcaga ctactattgc 420
cagcaaaaca acaactggcc caccactttc ggtgctggaa ccaaactcga gctgaaacgc 480
actgtggcag ctccttcagt gttcatcttc ccacctagcg acgagcagtt gaaatcgggg 540
acagcctcag tggtgtgtct actgaacaac ttttaccccc gggaagccaa agtgcagtgg 600
aaggtcgaca atgcgctgca atcagggaac agtcaggagt cagttacaga gcaggactct 660
aaggacagta catattcttt gagttccacc ttgacattaa gcaaggcaga ctacgagaaa 720
cacaaggtgt acgcatgtga agttacacac cagggccttt cctccccagt tacgaaaagc 780
ttcaacagag gcgaatgc 798

<210> SEQ ID NO 81
<211> LENGTH: 266
<212> TYPE: PRT
<213> ORGANISM: Artificial Sequence
<220> FEATURE:
<223> OTHER INFORMATION: chemically synthesized

<400> SEQUENCE: 81

Gln Gly Gln Ser Gly Gln Cys Ile Ser Pro Arg Gly Cys Pro Asp Gly
1 5 10 15

Pro Tyr Val Met Tyr Gly Ser Ser Gly Gly Ser Gly Gly Ser Gly Gly
20 25 30

Ser Gly Ile Ser Ser Gly Leu Leu Ser Gly Arg Ser Asp Asn His Gly
35 40 45

Ser Ser Gly Thr Gln Ile Leu Leu Thr Gln Ser Pro Val Ile Leu Ser
50 55 60

Val Ser Pro Gly Glu Arg Val Ser Phe Ser Cys Arg Ala Ser Gln Ser
65 70 75 80

Ile Gly Thr Asn Ile His Trp Tyr Gln Gln Arg Thr Asn Gly Ser Pro
85 90 95

Arg Leu Leu Ile Lys Tyr Ala Ser Glu Ser Ile Ser Gly Ile Pro Ser
100 105 110

Arg Phe Ser Gly Ser Gly Ser Gly Thr Asp Phe Thr Leu Ser Ile Asn
115 120 125

Ser Val Glu Ser Glu Asp Ile Ala Asp Tyr Tyr Cys Gln Gln Asn Asn

```
    130                 135                 140

Asn Trp Pro Thr Thr Phe Gly Ala Gly Thr Lys Leu Glu Leu Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265
```

<210> SEQ ID NO 82
<211> LENGTH: 798
<212> TYPE: DNA
<213> ORGANISM: Artificial Sequence
<220> FEATURE:
<223> OTHER INFORMATION: chemically synthesized

<400> SEQUENCE: 82

```
caaggtcaga gtggccaatg catatcgccc agaggatgtc ctgacggacc ctacgtgatg     60

tacgggagtt ctggggggag tggaggctct ggcgggtcag ggattagttc cggcctcttg    120

tctggacgct ccggaaatca cggatcatct gggacccaga tcctcctgac ccagtctccc    180

gtcattctgt ctgtttctcc aggcgagcgg gtttcattta gctgtagggc cagtcagagc    240

attggcacca acatccattg gtaccagcag agaactaatg gcagtcccag actgctcatt    300

aaatatgcaa gcgaatcaat ttccgggatt ccttctcgct tctcgggatc tggatctggc    360

accgacttca cgctgtccat caacagcgtg gagagtgagg acatcgccga ttactactgc    420

cagcagaaca acaactggcc aacaactttt ggcgccggga ccaagcttga gttaaagaga    480

accgtagctg caccctctgt tttcattttc ccaccctcag acgagcagct taagtcagga    540

actgccagtg tggtgtgcct gctgaacaac ttctacccga gagaggctaa agtccagtgg    600

aaggtagaca atgcccttca gtctggcaac tctcaggaga gtgtcacaga gcaggattct    660

aaggactcca cgtacagtct gagttccacc ctcaccctca gtaaggcaga ctacgagaag    720

cacaaagtct acgcatgtga ggttactcac caggggctca gctctcccgt gacgaagtca    780

tttaacagag gtgagtgc                                                  798
```

<210> SEQ ID NO 83
<211> LENGTH: 266
<212> TYPE: PRT
<213> ORGANISM: Artificial Sequence
<220> FEATURE:
<223> OTHER INFORMATION: chemically synthesized

<400> SEQUENCE: 83

```
Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30
```

```
Ser Gly Ile Ser Ser Gly Leu Leu Ser Gly Arg Ser Gly Asn His Gly
        35                  40                  45

Ser Ser Gly Thr Gln Ile Leu Leu Thr Gln Ser Pro Val Ile Leu Ser
    50                  55                  60

Val Ser Pro Gly Glu Arg Val Ser Phe Ser Cys Arg Ala Ser Gln Ser
65                  70                  75                  80

Ile Gly Thr Asn Ile His Trp Tyr Gln Gln Arg Thr Asn Gly Ser Pro
                85                  90                  95

Arg Leu Leu Ile Lys Tyr Ala Ser Glu Ser Ile Ser Gly Ile Pro Ser
            100                 105                 110

Arg Phe Ser Gly Ser Gly Ser Gly Thr Asp Phe Thr Leu Ser Ile Asn
        115                 120                 125

Ser Val Glu Ser Glu Asp Ile Ala Asp Tyr Tyr Cys Gln Gln Asn Asn
    130                 135                 140

Asn Trp Pro Thr Thr Phe Gly Ala Gly Thr Lys Leu Glu Leu Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265
```

<210> SEQ ID NO 84
<211> LENGTH: 825
<212> TYPE: DNA
<213> ORGANISM: Artificial Sequence
<220> FEATURE:
<223> OTHER INFORMATION: chemically synthesized

<400> SEQUENCE: 84

```
cagggacagt cgggacagtg catttctccg agaggctgcc ctgacggccc atacgtaatg      60

tacggatcat ccggtggcag tggagggtcc gggggatccg gtctaagcgg cagaagtgat     120

aatcatggag gctctggcgg gagcatcagc tccggattgc tttccagcgg aagttctggc     180

actcaaattc tgctgacaca aagccctgtg atcttgtcag tctcacctgg cgagcgggtg     240

agcttttcat gccgggcttc ccagagcatc ggtacaaata ttcactggta tcagcagaga     300

accaatggca gtccgcggtt gctgattaag tatgcgagcg agagcatatc aggcatacca     360

agcagattta gcgggagtgg ctctgggacc gattttacac tcagtataaa ttcagtggag     420

agcgaggata tagccgacta ctactgccag caaaacaata actggcccac caccttcggc     480

gcagggacca agcttgaact gaagcgtaca gttgccgccc caagcgtatt tattttccct     540

ccaagcgacg aacagctgaa aagcggtacc gcaagcgttg tgtgcctgct gaataacttt     600

tacccaaggg aagctaaggt gcagtggaag gttgacaatg cgctgcagtc aggcaactcc     660

caggaatcgg taacagagca ggactccaag gattcaactt atagtcttag tagtaccctt     720
```

actctttcca aagctgatta tgaaaaacac aaagtgtatg catgcgaggt gacccaccaa 780
ggactgtcat ctcctgtcac caagtccttc aaccggggag agtgt 825

<210> SEQ ID NO 85
<211> LENGTH: 275
<212> TYPE: PRT
<213> ORGANISM: Artificial Sequence
<220> FEATURE:
<223> OTHER INFORMATION: chemically synthesized

<400> SEQUENCE: 85

Gln Gly Gln Ser Gly Gln Cys Ile Ser Pro Arg Gly Cys Pro Asp Gly
1 5 10 15

Pro Tyr Val Met Tyr Gly Ser Ser Gly Gly Ser Gly Gly Ser Gly Gly
20 25 30

Ser Gly Leu Ser Gly Arg Ser Asp Asn His Gly Gly Ser Gly Gly Ser
35 40 45

Ile Ser Ser Gly Leu Leu Ser Ser Gly Ser Ser Gly Thr Gln Ile Leu
50 55 60

Leu Thr Gln Ser Pro Val Ile Leu Ser Val Ser Pro Gly Glu Arg Val
65 70 75 80

Ser Phe Ser Cys Arg Ala Ser Gln Ser Ile Gly Thr Asn Ile His Trp
85 90 95

Tyr Gln Gln Arg Thr Asn Gly Ser Pro Arg Leu Leu Ile Lys Tyr Ala
100 105 110

Ser Glu Ser Ile Ser Gly Ile Pro Ser Arg Phe Ser Gly Ser Gly Ser
115 120 125

Gly Thr Asp Phe Thr Leu Ser Ile Asn Ser Val Glu Ser Glu Asp Ile
130 135 140

Ala Asp Tyr Tyr Cys Gln Gln Asn Asn Asn Trp Pro Thr Thr Phe Gly
145 150 155 160

Ala Gly Thr Lys Leu Glu Leu Lys Arg Thr Val Ala Ala Pro Ser Val
165 170 175

Phe Ile Phe Pro Pro Ser Asp Glu Gln Leu Lys Ser Gly Thr Ala Ser
180 185 190

Val Val Cys Leu Leu Asn Asn Phe Tyr Pro Arg Glu Ala Lys Val Gln
195 200 205

Trp Lys Val Asp Asn Ala Leu Gln Ser Gly Asn Ser Gln Glu Ser Val
210 215 220

Thr Glu Gln Asp Ser Lys Asp Ser Thr Tyr Ser Leu Ser Ser Thr Leu
225 230 235 240

Thr Leu Ser Lys Ala Asp Tyr Glu Lys His Lys Val Tyr Ala Cys Glu
245 250 255

Val Thr His Gln Gly Leu Ser Ser Pro Val Thr Lys Ser Phe Asn Arg
260 265 270

Gly Glu Cys
275

<210> SEQ ID NO 86
<211> LENGTH: 825
<212> TYPE: DNA
<213> ORGANISM: Artificial Sequence
<220> FEATURE:
<223> OTHER INFORMATION: chemically synthesized

<400> SEQUENCE: 86

-continued

```
caaggtcaga gcggccagtg cattagtcct cgcggttgcc ctgatggacc atacgtaatg     60

tatggaagct ctggtggatc cgggggctct ggcggatcag gaatctccag cgggctgctc    120

tcatcaggtg gcagcggggg ctcattaagc ggccgaagtg acaatcacgg ctcgtccggt    180

acacagattc tgctcactca gtcacccgtt atactgtctg tgtcgcctgg agagcgtgtc    240

agcttttcat gtagagcctc gcagtcaata ggcacgaata tacactggta ccagcagaga    300

actaatggaa gcccaaggtt gctcatcaaa tacgcatctg agtcgattag cggcattccg    360

tccaggttta gtggcagtgg aagcggcacc gatttcactt tgtctattaa ctctgtggaa    420

agcgaggaca tcgccgatta ttattgtcag cagaataaca attggcccac caccttcggt    480

gccggtacta agctggagct gaaacgtaca gttgccgctc cctctgtgtt tattttccct    540

ccctcggatg agcaactcaa atcagggaca gcgagtgtcg tatgtctcct gaacaatttt    600

tacccacgtg aagctaaagt tcagtggaag gtggacaacg ctctgcagtc cggcaacagt    660

caggaaagcg taactgaaca ggactcaaag gatagcactt actccttgag cagcactctc    720

actctttcca aggctgatta tgagaagcac aaggtgtacg cgtgtgaagt cacccatcag    780

ggactgtcaa gtccggtgac taaatcattt aacaggggcg aatgc                   825
```

```
<210> SEQ ID NO 87
<211> LENGTH: 275
<212> TYPE: PRT
<213> ORGANISM: Artificial Sequence
<220> FEATURE:
<223> OTHER INFORMATION: chemically synthesized

<400> SEQUENCE: 87

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Ile Ser Ser Gly Leu Leu Ser Ser Gly Gly Ser Gly Gly Ser
        35                  40                  45

Leu Ser Gly Arg Ser Asp Asn His Gly Ser Ser Gly Thr Gln Ile Leu
    50                  55                  60

Leu Thr Gln Ser Pro Val Ile Leu Ser Val Ser Pro Gly Glu Arg Val
65                  70                  75                  80

Ser Phe Ser Cys Arg Ala Ser Gln Ser Ile Gly Thr Asn Ile His Trp
                85                  90                  95

Tyr Gln Gln Arg Thr Asn Gly Ser Pro Arg Leu Leu Ile Lys Tyr Ala
            100                 105                 110

Ser Glu Ser Ile Ser Gly Ile Pro Ser Arg Phe Ser Gly Ser Gly Ser
        115                 120                 125

Gly Thr Asp Phe Thr Leu Ser Ile Asn Ser Val Glu Ser Glu Asp Ile
    130                 135                 140

Ala Asp Tyr Tyr Cys Gln Gln Asn Asn Asn Trp Pro Thr Thr Phe Gly
145                 150                 155                 160

Ala Gly Thr Lys Leu Glu Leu Lys Arg Thr Val Ala Ala Pro Ser Val
                165                 170                 175

Phe Ile Phe Pro Pro Ser Asp Glu Gln Leu Lys Ser Gly Thr Ala Ser
            180                 185                 190

Val Val Cys Leu Leu Asn Asn Phe Tyr Pro Arg Glu Ala Lys Val Gln
        195                 200                 205

Trp Lys Val Asp Asn Ala Leu Gln Ser Gly Asn Ser Gln Glu Ser Val
    210                 215                 220
```

```
Thr Glu Gln Asp Ser Lys Asp Ser Thr Tyr Ser Leu Ser Ser Thr Leu
225                 230                 235                 240

Thr Leu Ser Lys Ala Asp Tyr Glu Lys His Lys Val Tyr Ala Cys Glu
                245                 250                 255

Val Thr His Gln Gly Leu Ser Ser Pro Val Thr Lys Ser Phe Asn Arg
            260                 265                 270

Gly Glu Cys
        275


<210> SEQ ID NO 88
<211> LENGTH: 825
<212> TYPE: DNA
<213> ORGANISM: Artificial Sequence
<220> FEATURE:
<223> OTHER INFORMATION: chemically synthesized

<400> SEQUENCE: 88

cagggccaga gtgggcagtg tatttcccct cgcggatgtc ccgacggtcc atacgtaatg      60

tatgggtcaa gcgggggatc aggaggaagt ggaggctccg gactcagcgg tcgctccggc     120

aatcacgggg ggtctggcgg atcaataagt tcgggcctcc tgagctccgg ttcatctggc     180

actcagatcc tgctcacgca gtcgccggta atactgagtg tctcaccagg cgagcgtgtc     240

agcttcagct gtcgcgcctc acagtcaatc ggcacaaata tccattggta ccagcaaagg     300

accaatggca gccctaggct gctgataaaa tacgcatccg agtcaatttc agggattcca     360

tcgagattct cgggcagcgg aagtgggacc gactttactc tctccatcaa cagcgtcgag     420

tcggaggaca tcgcggacta ctactgccag cagaataaca attggccaac aacattcggc     480

gcaggaacaa agctagagct caagaggaca gtggctgcac ccagtgtatt catcttccca     540

cctagcgacg agcaactgaa gagcgggacg gcttccgtcg tttgtctatt aaataatttc     600

tatccccgtg aggctaaagt tcagtggaag gttgataatg cgttgcagtc cggcaactcc     660

caggaatccg tcacagagca ggattctaag gattcaacct atagcttaag ctctacactt     720

acgctttcta aagccgatta tgaaaaacac aaggtgtacg cttgtgaggt tacccaccag     780

ggcctgagca gccccgtgac caagtcgttc aaccggggcg agtgt                     825


<210> SEQ ID NO 89
<211> LENGTH: 275
<212> TYPE: PRT
<213> ORGANISM: Artificial Sequence
<220> FEATURE:
<223> OTHER INFORMATION: chemically synthesized

<400> SEQUENCE: 89

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Leu Ser Gly Arg Ser Gly Asn His Gly Gly Ser Gly Gly Ser
        35                  40                  45

Ile Ser Ser Gly Leu Leu Ser Ser Gly Ser Ser Gly Thr Gln Ile Leu
    50                  55                  60

Leu Thr Gln Ser Pro Val Ile Leu Ser Val Ser Pro Gly Glu Arg Val
65                  70                  75                  80

Ser Phe Ser Cys Arg Ala Ser Gln Ser Ile Gly Thr Asn Ile His Trp
                85                  90                  95
```

```
Tyr Gln Gln Arg Thr Asn Gly Ser Pro Arg Leu Leu Ile Lys Tyr Ala
            100                 105                 110

Ser Glu Ser Ile Ser Gly Ile Pro Ser Arg Phe Ser Gly Ser Gly Ser
        115                 120                 125

Gly Thr Asp Phe Thr Leu Ser Ile Asn Ser Val Glu Ser Glu Asp Ile
    130                 135                 140

Ala Asp Tyr Tyr Cys Gln Gln Asn Asn Asn Trp Pro Thr Thr Phe Gly
145                 150                 155                 160

Ala Gly Thr Lys Leu Glu Leu Lys Arg Thr Val Ala Ala Pro Ser Val
                165                 170                 175

Phe Ile Phe Pro Pro Ser Asp Glu Gln Leu Lys Ser Gly Thr Ala Ser
            180                 185                 190

Val Val Cys Leu Leu Asn Asn Phe Tyr Pro Arg Glu Ala Lys Val Gln
        195                 200                 205

Trp Lys Val Asp Asn Ala Leu Gln Ser Gly Asn Ser Gln Glu Ser Val
    210                 215                 220

Thr Glu Gln Asp Ser Lys Asp Ser Thr Tyr Ser Leu Ser Ser Thr Leu
225                 230                 235                 240

Thr Leu Ser Lys Ala Asp Tyr Glu Lys His Lys Val Tyr Ala Cys Glu
                245                 250                 255

Val Thr His Gln Gly Leu Ser Ser Pro Val Thr Lys Ser Phe Asn Arg
            260                 265                 270

Gly Glu Cys
        275
```

<210> SEQ ID NO 90
<211> LENGTH: 825
<212> TYPE: DNA
<213> ORGANISM: Artificial Sequence
<220> FEATURE:
<223> OTHER INFORMATION: chemically synthesized

<400> SEQUENCE: 90

```
caaggacaga gcggacagtg tatctcacct cgcggctgcc ccgacggccc ttacgtcatg      60

tacggctcct cgggtgggtc cgggggaagt ggcgggtctg gcattagttc agggctctta     120

tcttccggcg gaagcggggg atctctttcc gggcggagtg gcaatcacgg cagtagcgga     180

actcagatcc tactcactca gtcaccagtg atcctgtctg tcagtccagg ggagagagtg     240

tctttcagtt gtagagcttc ccagtctatt gggacaaaca ttcactggta tcaacagcga     300

actaatggat cgccaagact cctgattaaa tatgcttctg agagcatctc tggaattcca     360

tcaagattct cagggagtgg tagcggcacc gattttacgt tatcgatcaa ttccgttgag     420

agcgaagata tcgcggacta ttactgtcag cagaacaata actggcctac aacgttcggg     480

gcagggacga aattggagct gaagcggacc gtcgccgcgc caagcgtgtt catcttcccc     540

cctagcgacg agcaattgaa aagcggcacc gcaagtgtgg tttgcctgct gaacaacttt     600

tatcctcgcg aggcgaaagt gcagtggaaa gtcgacaatg cactccagtc agggaacagc     660

caagagtccg ttactgaaca agactctaaa gatagtactt atagcttatc cagcacactg     720

acgctcagta aggccgatta tgaaaaacat aaggtgtatg cgtgtgaggt tacccatcaa     780

ggattgtcat cacccgtcac caaatccttt aacagaggag aatgt                     825
```

<210> SEQ ID NO 91
<211> LENGTH: 275
<212> TYPE: PRT
<213> ORGANISM: Artificial Sequence
<220> FEATURE:
<223> OTHER INFORMATION: chemically synthesized

<400> SEQUENCE: 91

```
Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Ile Ser Ser Gly Leu Leu Ser Ser Gly Gly Ser Gly Gly Ser
        35                  40                  45

Leu Ser Gly Arg Ser Gly Asn His Gly Ser Ser Gly Thr Gln Ile Leu
    50                  55                  60

Leu Thr Gln Ser Pro Val Ile Leu Ser Val Ser Pro Gly Glu Arg Val
65                  70                  75                  80

Ser Phe Ser Cys Arg Ala Ser Gln Ser Ile Gly Thr Asn Ile His Trp
                85                  90                  95

Tyr Gln Gln Arg Thr Asn Gly Ser Pro Arg Leu Leu Ile Lys Tyr Ala
            100                 105                 110

Ser Glu Ser Ile Ser Gly Ile Pro Ser Arg Phe Ser Gly Ser Gly Ser
        115                 120                 125

Gly Thr Asp Phe Thr Leu Ser Ile Asn Ser Val Glu Ser Glu Asp Ile
    130                 135                 140

Ala Asp Tyr Tyr Cys Gln Gln Asn Asn Asn Trp Pro Thr Thr Phe Gly
145                 150                 155                 160

Ala Gly Thr Lys Leu Glu Leu Lys Arg Thr Val Ala Ala Pro Ser Val
                165                 170                 175

Phe Ile Phe Pro Pro Ser Asp Glu Gln Leu Lys Ser Gly Thr Ala Ser
            180                 185                 190

Val Val Cys Leu Leu Asn Asn Phe Tyr Pro Arg Glu Ala Lys Val Gln
        195                 200                 205

Trp Lys Val Asp Asn Ala Leu Gln Ser Gly Asn Ser Gln Glu Ser Val
    210                 215                 220

Thr Glu Gln Asp Ser Lys Asp Ser Thr Tyr Ser Leu Ser Ser Thr Leu
225                 230                 235                 240

Thr Leu Ser Lys Ala Asp Tyr Glu Lys His Lys Val Tyr Ala Cys Glu
                245                 250                 255

Val Thr His Gln Gly Leu Ser Ser Pro Val Thr Lys Ser Phe Asn Arg
            260                 265                 270

Gly Glu Cys
        275
```

<210> SEQ ID NO 92
<211> LENGTH: 825
<212> TYPE: DNA
<213> ORGANISM: Artificial Sequence
<220> FEATURE:
<223> OTHER INFORMATION: chemically synthesized

<400> SEQUENCE: 92

```
cagggtcaaa gtggacagtg tatctcgccc cgcggctgcc cagacggccc atatgtgatg      60

tatggttctt ccggtggatc cggcggatca ggtgggtctg gcctctcagg tcgttccgac     120

aaccacggcg gctcaggtgg gtctcagaat caggcactgc ggatggccgg atcttctggc     180

acccagatat tgctcacaca gtcaccagtt attctgtccg tatctccagg agaacgggta     240

tctttctctt gtagggcaag ccagtccatc ggaacaaaca tccattggta ccagcagcgg     300
```

```
accaatggca gtccacggct tctgatcaag tatgctagtg aaagcattag cgggattcca    360

agccgatttt ctgggtcggg tagtggaacc gacttcaccc tgagcattaa ctctgtcgaa    420

tccgaagata ttgctgacta ttactgtcag cagaacaaca attggccgac tacgtttggc    480

gccggaacca aattagaact taagagaacc gtggccgctc cctctgtctt cattttcccg    540

ccttccgacg aacagctgaa gagcggaact gcctccgtgg tgtgcctgtt gaataacttt    600

tatccaaggg aagcaaaggt gcagtggaaa gtggacaatg ctctgcagtc tggcaatagc    660

caggagtccg tgactgaaca ggacagtaaa gactcaacct actcactgag cagtactctc    720

acattatcca aagccgatta tgaaaagcat aaggtttatg catgcgaggt tacccaccag    780

ggactgagct cccccgtgac caaaagcttc aatagggtg agtgc                     825
```

<210> SEQ ID NO 93
<211> LENGTH: 275
<212> TYPE: PRT
<213> ORGANISM: Artificial Sequence
<220> FEATURE:
<223> OTHER INFORMATION: chemically synthesized

<400> SEQUENCE: 93

```
Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Leu Ser Gly Arg Ser Asp Asn His Gly Gly Ser Gly Gly Ser
        35                  40                  45

Gln Asn Gln Ala Leu Arg Met Ala Gly Ser Ser Gly Thr Gln Ile Leu
    50                  55                  60

Leu Thr Gln Ser Pro Val Ile Leu Ser Val Ser Pro Gly Glu Arg Val
65                  70                  75                  80

Ser Phe Ser Cys Arg Ala Ser Gln Ser Ile Gly Thr Asn Ile His Trp
                85                  90                  95

Tyr Gln Gln Arg Thr Asn Gly Ser Pro Arg Leu Leu Ile Lys Tyr Ala
            100                 105                 110

Ser Glu Ser Ile Ser Gly Ile Pro Ser Arg Phe Ser Gly Ser Gly Ser
        115                 120                 125

Gly Thr Asp Phe Thr Leu Ser Ile Asn Ser Val Glu Ser Glu Asp Ile
    130                 135                 140

Ala Asp Tyr Tyr Cys Gln Gln Asn Asn Asn Trp Pro Thr Thr Phe Gly
145                 150                 155                 160

Ala Gly Thr Lys Leu Glu Leu Lys Arg Thr Val Ala Ala Pro Ser Val
                165                 170                 175

Phe Ile Phe Pro Pro Ser Asp Glu Gln Leu Lys Ser Gly Thr Ala Ser
            180                 185                 190

Val Val Cys Leu Leu Asn Asn Phe Tyr Pro Arg Glu Ala Lys Val Gln
        195                 200                 205

Trp Lys Val Asp Asn Ala Leu Gln Ser Gly Asn Ser Gln Glu Ser Val
    210                 215                 220

Thr Glu Gln Asp Ser Lys Asp Ser Thr Tyr Ser Leu Ser Ser Thr Leu
225                 230                 235                 240

Thr Leu Ser Lys Ala Asp Tyr Glu Lys His Lys Val Tyr Ala Cys Glu
                245                 250                 255

Val Thr His Gln Gly Leu Ser Ser Pro Val Thr Lys Ser Phe Asn Arg
            260                 265                 270
```

Gly Glu Cys
        275

<210> SEQ ID NO 94
<211> LENGTH: 825
<212> TYPE: DNA
<213> ORGANISM: Artificial Sequence
<220> FEATURE:
<223> OTHER INFORMATION: chemically synthesized

<400> SEQUENCE: 94
caggggcagt ccggacaatg catcagcccc cgaggctgcc ctgatggccc ctacgtgatg 60
tacgggtcca gcggtggcag cgggggctca ggggggagcg ggcagaatca ggccctgaga 120
atggcgggtg gatccggggg gtccctttct ggcaggtccg ataaccacgg ttctagtgga 180
acacagattt tgctgacaca aagtcccgtc atcctctctg tgtctcccgg tgagcgggtc 240
agtttttcct gccgagcgtc ccagagcatc gggacaaata tccattggta ccagcagaga 300
acgaacggct ctcctagact gctcatcaag tacgcctcgg aaagtatttc cggcattccc 360
tcccgtttca gcggctccgg aagtggtaca gattttaccc tgagtattaa ttccgtcgaa 420
tctgaggaca tagccgacta ctattgccaa cagaataaca attggccaac aacttttggc 480
gccgggacta agctggagct gaaacggacc gtcgcagcac caagtgtttt catcttccca 540
ccaagtgacg agcagctgaa atccggaaca gcgagcgtgg tgtgcctact caataacttc 600
tatccacgcg aagccaaggt gcagtggaaa gtggacaacg ctctgcagtc cggcaatagc 660
caggaaagcg tgacagagca agattctaag gacagtacgt attcactgtc cagtacgctc 720
accttaagca aggctgacta cgaaaaacac aaggtctacg cctgtgaggt cacacatcag 780
ggcctctcca gtccggttac aaaaagtttc aatcgcgggg aatgt 825

<210> SEQ ID NO 95
<211> LENGTH: 275
<212> TYPE: PRT
<213> ORGANISM: Artificial Sequence
<220> FEATURE:
<223> OTHER INFORMATION: chemically synthesized

<400> SEQUENCE: 95

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Gln Asn Gln Ala Leu Arg Met Ala Gly Gly Ser Gly Gly Ser
        35                  40                  45

Leu Ser Gly Arg Ser Asp Asn His Gly Ser Ser Gly Thr Gln Ile Leu
    50                  55                  60

Leu Thr Gln Ser Pro Val Ile Leu Ser Val Ser Pro Gly Glu Arg Val
65                  70                  75                  80

Ser Phe Ser Cys Arg Ala Ser Gln Ser Ile Gly Thr Asn Ile His Trp
                85                  90                  95

Tyr Gln Gln Arg Thr Asn Gly Ser Pro Arg Leu Leu Ile Lys Tyr Ala
            100                 105                 110

Ser Glu Ser Ile Ser Gly Ile Pro Ser Arg Phe Ser Gly Ser Gly Ser
        115                 120                 125

Gly Thr Asp Phe Thr Leu Ser Ile Asn Ser Val Glu Ser Glu Asp Ile
    130                 135                 140

Ala Asp Tyr Tyr Cys Gln Gln Asn Asn Asn Trp Pro Thr Thr Phe Gly

-continued

```
145                 150                 155                 160

Ala Gly Thr Lys Leu Glu Leu Lys Arg Thr Val Ala Ala Pro Ser Val
                165                 170                 175

Phe Ile Phe Pro Pro Ser Asp Glu Gln Leu Lys Ser Gly Thr Ala Ser
            180                 185                 190

Val Val Cys Leu Leu Asn Asn Phe Tyr Pro Arg Glu Ala Lys Val Gln
        195                 200                 205

Trp Lys Val Asp Asn Ala Leu Gln Ser Gly Asn Ser Gln Glu Ser Val
    210                 215                 220

Thr Glu Gln Asp Ser Lys Asp Ser Thr Tyr Ser Leu Ser Ser Thr Leu
225                 230                 235                 240

Thr Leu Ser Lys Ala Asp Tyr Glu Lys His Lys Val Tyr Ala Cys Glu
                245                 250                 255

Val Thr His Gln Gly Leu Ser Ser Pro Val Thr Lys Ser Phe Asn Arg
            260                 265                 270

Gly Glu Cys
        275


<210> SEQ ID NO 96
<211> LENGTH: 825
<212> TYPE: DNA
<213> ORGANISM: Artificial Sequence
<220> FEATURE:
<223> OTHER INFORMATION: chemically synthesized

<400> SEQUENCE: 96

caaggccaat ccggtcagtg catcagtccc agaggctgcc ctgacgggcc ctacgtgatg      60

tatggtagct caggggggctc cggcggctcc ggcggaagcg gacttagcgg ccgtagcggc     120

aaccatgggg gttctggagg atcccagaat caggctctgc gcatggctgg aagcagcggt     180

acccagatcc tgctcaccca atcacccgtc atcttgtctg tgagtcctgg cgaaagggtg     240

tcgttctctt gtcgcgcgtc ccagtccatt gggaccaaca ttcattggta ccagcagagg     300

actaacggga gcccccgcct gctgatcaaa tacgccagtg aatctatctc tggaatccca     360

tcacgatttt cagggtccgg tagtgggacc gacttcactt tgagtattaa cagtgtggaa     420

tccgaggaca tagccgacta ttactgtcag cagaacaata actggccaac aacctttggc     480

gccgggacaa agttagagct taagcggact gttgcagccc cctccgtttt tatcttcccg     540

cccagtgatg aacagctgaa aagcggtacc gcctccgtag tgtgccttct caataatttt     600

taccccagag aagctaaagt acagtggaaa gtcgacaacg ccctccagag cggcaacagt     660

caggagtccg tcaccgagca ggattctaaa gactcaacat atagcctttc gtccacccta     720

acactttcaa aagcagacta tgaaaaacat aaggtgtatg cctgcgaggt cacacaccag     780

gggctcagct ctccagttac taagtcattc aaccgcggag agtgt                      825


<210> SEQ ID NO 97
<211> LENGTH: 275
<212> TYPE: PRT
<213> ORGANISM: Artificial Sequence
<220> FEATURE:
<223> OTHER INFORMATION: chemically synthesized

<400> SEQUENCE: 97

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30
```

```
Ser Gly Leu Ser Gly Arg Ser Gly Asn His Gly Gly Ser Gly Gly Ser
        35                  40                  45

Gln Asn Gln Ala Leu Arg Met Ala Gly Ser Ser Gly Thr Gln Ile Leu
    50                  55                  60

Leu Thr Gln Ser Pro Val Ile Leu Ser Val Ser Pro Gly Glu Arg Val
65                  70                  75                  80

Ser Phe Ser Cys Arg Ala Ser Gln Ser Ile Gly Thr Asn Ile His Trp
                85                  90                  95

Tyr Gln Gln Arg Thr Asn Gly Ser Pro Arg Leu Leu Ile Lys Tyr Ala
            100                 105                 110

Ser Glu Ser Ile Ser Gly Ile Pro Ser Arg Phe Ser Gly Ser Gly Ser
        115                 120                 125

Gly Thr Asp Phe Thr Leu Ser Ile Asn Ser Val Glu Ser Glu Asp Ile
    130                 135                 140

Ala Asp Tyr Tyr Cys Gln Gln Asn Asn Asn Trp Pro Thr Thr Phe Gly
145                 150                 155                 160

Ala Gly Thr Lys Leu Glu Leu Lys Arg Thr Val Ala Ala Pro Ser Val
                165                 170                 175

Phe Ile Phe Pro Pro Ser Asp Glu Gln Leu Lys Ser Gly Thr Ala Ser
            180                 185                 190

Val Val Cys Leu Leu Asn Asn Phe Tyr Pro Arg Glu Ala Lys Val Gln
        195                 200                 205

Trp Lys Val Asp Asn Ala Leu Gln Ser Gly Asn Ser Gln Glu Ser Val
    210                 215                 220

Thr Glu Gln Asp Ser Lys Asp Ser Thr Tyr Ser Leu Ser Ser Thr Leu
225                 230                 235                 240

Thr Leu Ser Lys Ala Asp Tyr Glu Lys His Lys Val Tyr Ala Cys Glu
                245                 250                 255

Val Thr His Gln Gly Leu Ser Ser Pro Val Thr Lys Ser Phe Asn Arg
            260                 265                 270

Gly Glu Cys
        275
```

<210> SEQ ID NO 98
<211> LENGTH: 825
<212> TYPE: DNA
<213> ORGANISM: Artificial Sequence
<220> FEATURE:
<223> OTHER INFORMATION: chemically synthesized

<400> SEQUENCE: 98

```
cagggccaat caggtcagtg cattagcccc cgagggtgtc ccgatgggcc ctacgtaatg     60

tacggatcat cgggcggatc tgggggctcc ggtggctctg gtcagaatca agctctgcgc    120

atggccggag gtagcggtgg aagcctgagc ggccgaagtg gaaaccacgg ctcctctggc    180

actcagattc ttctcacgca gtcgcccgtg atcttgtccg tgagcccagg cgagcgggtg    240

agcttctctt gccgggccag ccaaagtata ggtacaaata ttcactggta ccaacagcga    300

accaacgggt cgcctaggtt gctcataaag tacgcatccg agagtataag cggcatacca    360

tctaggttct caggtagcgg cagcgggacc gattttaccc tcagcattaa ttcggttgaa    420

tctgaagata tcgccgatta ttattgtcag cagaataaca attggcctac tactttcggc    480

gccggaacaa agctggaact taagcgcaca gtggccgctc cttctgtctt tatcttccct    540

ccatctgacg agcaattaaa gagtgggaca gcctcggtgg tgtgtttgct caataacttc    600
```

```
tatccaaggg aggcaaaggt gcagtggaag gtcgataacg ctctccagag tgggaattcc    660

caggagtccg tgaccgagca ggattctaaa gatagcacat actcactgtc ttccaccctg    720

accctgtcca aggcagacta cgagaagcac aaagtttacg cctgtgaagt gacacaccag    780

ggcctcagct ctcctgtcac aaagagtttt aatcggggcg agtgt                    825
```

<210> SEQ ID NO 99
<211> LENGTH: 275
<212> TYPE: PRT
<213> ORGANISM: Artificial Sequence
<220> FEATURE:
<223> OTHER INFORMATION: chemically synthesized

<400> SEQUENCE: 99

```
Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Gln Asn Gln Ala Leu Arg Met Ala Gly Gly Ser Gly Gly Ser
        35                  40                  45

Leu Ser Gly Arg Ser Gly Asn His Gly Ser Ser Gly Thr Gln Ile Leu
    50                  55                  60

Leu Thr Gln Ser Pro Val Ile Leu Ser Val Ser Pro Gly Glu Arg Val
65                  70                  75                  80

Ser Phe Ser Cys Arg Ala Ser Gln Ser Ile Gly Thr Asn Ile His Trp
                85                  90                  95

Tyr Gln Gln Arg Thr Asn Gly Ser Pro Arg Leu Leu Ile Lys Tyr Ala
            100                 105                 110

Ser Glu Ser Ile Ser Gly Ile Pro Ser Arg Phe Ser Gly Ser Gly Ser
        115                 120                 125

Gly Thr Asp Phe Thr Leu Ser Ile Asn Ser Val Glu Ser Glu Asp Ile
    130                 135                 140

Ala Asp Tyr Tyr Cys Gln Gln Asn Asn Asn Trp Pro Thr Thr Phe Gly
145                 150                 155                 160

Ala Gly Thr Lys Leu Glu Leu Lys Arg Thr Val Ala Ala Pro Ser Val
                165                 170                 175

Phe Ile Phe Pro Pro Ser Asp Glu Gln Leu Lys Ser Gly Thr Ala Ser
            180                 185                 190

Val Val Cys Leu Leu Asn Asn Phe Tyr Pro Arg Glu Ala Lys Val Gln
        195                 200                 205

Trp Lys Val Asp Asn Ala Leu Gln Ser Gly Asn Ser Gln Glu Ser Val
    210                 215                 220

Thr Glu Gln Asp Ser Lys Asp Ser Thr Tyr Ser Leu Ser Ser Thr Leu
225                 230                 235                 240

Thr Leu Ser Lys Ala Asp Tyr Glu Lys His Lys Val Tyr Ala Cys Glu
                245                 250                 255

Val Thr His Gln Gly Leu Ser Ser Pro Val Thr Lys Ser Phe Asn Arg
            260                 265                 270

Gly Glu Cys
        275
```

<210> SEQ ID NO 100
<211> LENGTH: 449
<212> TYPE: PRT
<213> ORGANISM: Artificial Sequence
<220> FEATURE:
<223> OTHER INFORMATION: chemically synthesized

<400> SEQUENCE: 100

Gln Val Gln Leu Gln Glu Ser Gly Pro Gly Leu Val Arg Pro Ser Gln
1 5 10 15

Thr Leu Ser Leu Thr Cys Thr Val Ser Gly Tyr Ser Ile Thr Ser Asp
20 25 30

His Ala Trp Ser Trp Val Arg Gln Pro Pro Gly Arg Gly Leu Glu Trp
35 40 45

Ile Gly Tyr Ile Ser Tyr Ser Gly Ile Thr Thr Tyr Asn Pro Ser Leu
50 55 60

Lys Ser Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Gln Gly
100 105 110

Ser Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys

```
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 101
<211> LENGTH: 214
<212> TYPE: PRT
<213> ORGANISM: Artificial Sequence
<220> FEATURE:
<223> OTHER INFORMATION: chemically synthesized

<400> SEQUENCE: 101

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 102
<211> LENGTH: 15
<212> TYPE: PRT
<213> ORGANISM: Artificial Sequence
<220> FEATURE:
<223> OTHER INFORMATION: chemically synthesized

<400> SEQUENCE: 102

```
Tyr Gly Ser Cys Ser Trp Asn Tyr Val His Ile Phe Met Asp Cys
1               5                   10                  15
```

<210> SEQ ID NO 103
<211> LENGTH: 16
<212> TYPE: PRT

<213> ORGANISM: Artificial Sequence
<220> FEATURE:
<223> OTHER INFORMATION: chemically synthesized

<400> SEQUENCE: 103

Gln Gly Asp Phe Asp Ile Pro Phe Pro Ala His Trp Val Pro Ile Thr
1 5 10 15

<210> SEQ ID NO 104
<211> LENGTH: 18
<212> TYPE: PRT
<213> ORGANISM: Artificial Sequence
<220> FEATURE:
<223> OTHER INFORMATION: chemically synthesized

<400> SEQUENCE: 104

Met Gly Val Pro Ala Gly Cys Val Trp Asn Tyr Ala His Ile Phe Met
1 5 10 15

Asp Cys

<210> SEQ ID NO 105
<211> LENGTH: 21
<212> TYPE: PRT
<213> ORGANISM: Artificial Sequence
<220> FEATURE:
<223> OTHER INFORMATION: chemically synthesized

<400> SEQUENCE: 105

Gln Gly Gln Ser Gly Gln Tyr Gly Ser Cys Ser Trp Asn Tyr Val His
1 5 10 15

Ile Phe Met Asp Cys
20

<210> SEQ ID NO 106
<211> LENGTH: 21
<212> TYPE: PRT
<213> ORGANISM: Artificial Sequence
<220> FEATURE:
<223> OTHER INFORMATION: chemically synthesized

<400> SEQUENCE: 106

Gln Gly Gln Ser Gly Gln Gly Asp Phe Asp Ile Pro Phe Pro Ala His
1 5 10 15

Trp Val Pro Ile Thr
20

<210> SEQ ID NO 107
<211> LENGTH: 24
<212> TYPE: PRT
<213> ORGANISM: Artificial Sequence
<220> FEATURE:
<223> OTHER INFORMATION: chemically synthesized

<400> SEQUENCE: 107

Gln Gly Gln Ser Gly Gln Met Gly Val Pro Ala Gly Cys Val Trp Asn
1 5 10 15

Tyr Ala His Ile Phe Met Asp Cys
20

<210> SEQ ID NO 108
<211> LENGTH: 449
<212> TYPE: PRT
<213> ORGANISM: Artificial Sequence
<220> FEATURE:
<223> OTHER INFORMATION: chemically synthesized

<400> SEQUENCE: 108

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys

```
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 109
<211> LENGTH: 449
<212> TYPE: PRT
<213> ORGANISM: Artificial Sequence
<220> FEATURE:
<223> OTHER INFORMATION: chemically synthesized

<400> SEQUENCE: 109

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 110
<211> LENGTH: 449
<212> TYPE: PRT
<213> ORGANISM: Artificial Sequence
<220> FEATURE:
<223> OTHER INFORMATION: chemically synthesized

<400> SEQUENCE: 110

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Ala Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 111
<211> LENGTH: 214
<212> TYPE: PRT
<213> ORGANISM: Artificial Sequence
<220> FEATURE:
<223> OTHER INFORMATION: chemically synthesized

<400> SEQUENCE: 111

Gln Ile Leu Leu Thr Gln Ser Pro Val Ile Leu Ser Val Ser Pro Gly
1 5 10 15

Glu Arg Val Ser Phe Ser Cys Arg Ala Ser Gln Ser Ile Gly Thr Asn
20 25 30

Ile His Trp Tyr Gln Gln Arg Thr Asn Gly Ser Pro Arg Leu Leu Ile
35 40 45

Lys Tyr Ala Ser Glu Ser Ile Ser Gly Ile Pro Ser Arg Phe Ser Gly
50 55 60

Ser Gly Ser Gly Thr Asp Phe Thr Leu Ser Ile Asn Ser Val Glu Ser
65 70 75 80

Glu Asp Ile Ala Asp Tyr Tyr Cys Gln Gln Asn Asn Asn Trp Pro Thr
85 90 95

Thr Phe Gly Ala Gly Thr Lys Leu Glu Leu Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala

```
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 112
<211> LENGTH: 108
<212> TYPE: PRT
<213> ORGANISM: Artificial Sequence
<220> FEATURE:
<223> OTHER INFORMATION: chemically synthesized

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105


<210> SEQ ID NO 113
<211> LENGTH: 119
<212> TYPE: PRT
<213> ORGANISM: Artificial Sequence
<220> FEATURE:
<223> OTHER INFORMATION: chemically synthesized

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110
```

```
Thr Leu Val Thr Val Ser Ser
        115


<210> SEQ ID NO 114
<211> LENGTH: 108
<212> TYPE: PRT
<213> ORGANISM: Artificial Sequence
<220> FEATURE:
<223> OTHER INFORMATION: chemically synthesized

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105


<210> SEQ ID NO 115
<211> LENGTH: 119
<212> TYPE: PRT
<213> ORGANISM: Artificial Sequence
<220> FEATURE:
<223> OTHER INFORMATION: chemically synthesized

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Tyr His Gly Gln Phe Asp Tyr Trp Gly Gln Gly
            100                 105                 110

Thr Leu Val Thr Val Ser Ser
        115


<210> SEQ ID NO 116
<211> LENGTH: 108
<212> TYPE: PRT
<213> ORGANISM: Artificial Sequence
<220> FEATURE:
<223> OTHER INFORMATION: chemically synthesized

<400> SEQUENCE: 116

Asp Ile Gln Met Thr Gln Ser Pro Ser Ser Leu Ser Ala Ser Val Gly
```

```
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105


<210> SEQ ID NO 117
<211> LENGTH: 119
<212> TYPE: PRT
<213> ORGANISM: Artificial Sequence
<220> FEATURE:
<223> OTHER INFORMATION: chemically synthesized

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Phe Phe Gly Gln Phe Asp Tyr Trp Gly Gln Gly
            100                 105                 110

Thr Leu Val Thr Val Ser Ser
        115


<210> SEQ ID NO 118
<211> LENGTH: 108
<212> TYPE: PRT
<213> ORGANISM: Artificial Sequence
<220> FEATURE:
<223> OTHER INFORMATION: chemically synthesized

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105


<210> SEQ ID NO 119
<211> LENGTH: 119
<212> TYPE: PRT
<213> ORGANISM: Artificial Sequence
<220> FEATURE:
<223> OTHER INFORMATION: chemically synthesized

<400> SEQUENCE: 119

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Ile Gly Arg Thr Asn Pro Phe Asp Tyr Trp Gly Gln Gly
            100                 105                 110

Thr Leu Val Thr Val Ser Ser
        115


<210> SEQ ID NO 120
<211> LENGTH: 108
<212> TYPE: PRT
<213> ORGANISM: Artificial Sequence
<220> FEATURE:
<223> OTHER INFORMATION: chemically synthesized

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105


<210> SEQ ID NO 121
<211> LENGTH: 116
<212> TYPE: PRT
<213> ORGANISM: Artificial Sequence
<220> FEATURE:
<223> OTHER INFORMATION: chemically synthesized
```

<400> SEQUENCE: 121

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ser Ile Glu Gln Met Gly Trp Gln Thr Glu Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ser Ala Ala Ala Phe Asp Tyr Trp Gly Gln Gly Thr Leu Val
100 105 110

Thr Val Ser Ser
115

<210> SEQ ID NO 122
<211> LENGTH: 108
<212> TYPE: PRT
<213> ORGANISM: Artificial Sequence
<220> FEATURE:
<223> OTHER INFORMATION: chemically synthesized

<400> SEQUENCE: 122

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Val Val Ala Pro Leu
85 90 95

Thr Phe Gly Gln Gly Thr Lys Val Glu Ile Lys Arg
100 105

<210> SEQ ID NO 123
<211> LENGTH: 119
<212> TYPE: PRT
<213> ORGANISM: Artificial Sequence
<220> FEATURE:
<223> OTHER INFORMATION: chemically synthesized

<400> SEQUENCE: 123

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ser Ile Glu Gln Met Gly Trp Gln Thr Tyr Tyr Ala Asp Ser Val
50 55 60

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Tyr Tyr Gly Gln Phe Asp Tyr Trp Gly Gln Gly
            100                 105                 110

Thr Leu Val Thr Val Ser Ser
        115


<210> SEQ ID NO 124
<211> LENGTH: 108
<212> TYPE: PRT
<213> ORGANISM: Artificial Sequence
<220> FEATURE:
<223> OTHER INFORMATION: chemically synthesized

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105


<210> SEQ ID NO 125
<211> LENGTH: 119
<212> TYPE: PRT
<213> ORGANISM: Artificial Sequence
<220> FEATURE:
<223> OTHER INFORMATION: chemically synthesized

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Phe Phe Gly Gln Phe Asp Tyr Trp Gly Gln Gly
            100                 105                 110

Thr Leu Val Thr Val Ser Ser
        115


<210> SEQ ID NO 126
```

<211> LENGTH: 108
<212> TYPE: PRT
<213> ORGANISM: Artificial Sequence
<220> FEATURE:
<223> OTHER INFORMATION: chemically synthesized

<400> SEQUENCE: 126

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Val Val Ala Pro Leu
85 90 95

Thr Phe Gly Gln Gly Thr Lys Val Glu Ile Lys Arg
100 105

<210> SEQ ID NO 127
<211> LENGTH: 119
<212> TYPE: PRT
<213> ORGANISM: Artificial Sequence
<220> FEATURE:
<223> OTHER INFORMATION: chemically synthesized

<400> SEQUENCE: 127

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ser Ile Glu Gln Met Gly Trp Gln Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Ile Gly Gly Arg Ser Ala Phe Asp Tyr Trp Gly Gln Gly
100 105 110

Thr Leu Val Thr Val Ser Ser
115

<210> SEQ ID NO 128
<211> LENGTH: 108
<212> TYPE: PRT
<213> ORGANISM: Artificial Sequence
<220> FEATURE:
<223> OTHER INFORMATION: chemically synthesized

<400> SEQUENCE: 128

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

```
Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105
```

<210> SEQ ID NO 129
<211> LENGTH: 116
<212> TYPE: PRT
<213> ORGANISM: Artificial Sequence
<220> FEATURE:
<223> OTHER INFORMATION: chemically synthesized

<400> SEQUENCE: 129

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Glu Met Gly Trp Gln Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
        115
```

<210> SEQ ID NO 130
<211> LENGTH: 108
<212> TYPE: PRT
<213> ORGANISM: Artificial Sequence
<220> FEATURE:
<223> OTHER INFORMATION: chemically synthesized

<400> SEQUENCE: 130

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105
```

<210> SEQ ID NO 131
<211> LENGTH: 119
<212> TYPE: PRT
<213> ORGANISM: Artificial Sequence
<220> FEATURE:
<223> OTHER INFORMATION: chemically synthesized

<400> SEQUENCE: 131

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115
```

<210> SEQ ID NO 132
<211> LENGTH: 108
<212> TYPE: PRT
<213> ORGANISM: Artificial Sequence
<220> FEATURE:
<223> OTHER INFORMATION: chemically synthesized

<400> SEQUENCE: 132

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105
```

<210> SEQ ID NO 133
<211> LENGTH: 119
<212> TYPE: PRT
<213> ORGANISM: Artificial Sequence
<220> FEATURE:
<223> OTHER INFORMATION: chemically synthesized

<400> SEQUENCE: 133

```
Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Phe Tyr Gly Gln Phe Asp Tyr Trp Gly Gln Gly
            100                 105                 110

Thr Leu Val Thr Val Ser Ser
        115


<210> SEQ ID NO 134
<211> LENGTH: 108
<212> TYPE: PRT
<213> ORGANISM: Artificial Sequence
<220> FEATURE:
<223> OTHER INFORMATION: chemically synthesized

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105


<210> SEQ ID NO 135
<211> LENGTH: 119
<212> TYPE: PRT
<213> ORGANISM: Artificial Sequence
<220> FEATURE:
<223> OTHER INFORMATION: chemically synthesized

<400> SEQUENCE: 135

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Ser Pro Pro Phe Phe Gly Gln Phe Asp Tyr Trp Gly Gln Gly
            100                 105                 110

Thr Leu Val Thr Val Ser Ser
        115


<210> SEQ ID NO 136
<211> LENGTH: 108
<212> TYPE: PRT
<213> ORGANISM: Artificial Sequence
<220> FEATURE:
<223> OTHER INFORMATION: chemically synthesized

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105


<210> SEQ ID NO 137
<211> LENGTH: 115
<212> TYPE: PRT
<213> ORGANISM: Artificial Sequence
<220> FEATURE:
<223> OTHER INFORMATION: chemically synthesized

<400> SEQUENCE: 137

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Glu Met Gly Trp Gln Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ala
                85                  90                  95

Lys Ser Ala Ala Ala Phe Asp Tyr Trp Gly Gln Gly Thr Leu Val Thr
            100                 105                 110

Val Ser Ser
        115


<210> SEQ ID NO 138
<211> LENGTH: 108
<212> TYPE: PRT
<213> ORGANISM: Artificial Sequence
<220> FEATURE:
<223> OTHER INFORMATION: chemically synthesized
```

<400> SEQUENCE: 138

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Val Val Ala Pro Leu
85 90 95

Thr Phe Gly Gln Gly Thr Lys Val Glu Ile Lys Arg
100 105

<210> SEQ ID NO 139
<211> LENGTH: 119
<212> TYPE: PRT
<213> ORGANISM: Artificial Sequence
<220> FEATURE:
<223> OTHER INFORMATION: chemically synthesized

<400> SEQUENCE: 139

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ser Ile Glu Gln Met Gly Trp Gln Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Ile Gly Gly Arg Ser Ala Phe Asp Tyr Trp Gly Gln Gly
100 105 110

Thr Leu Val Thr Val Ser Ser
115

<210> SEQ ID NO 140
<211> LENGTH: 108
<212> TYPE: PRT
<213> ORGANISM: Artificial Sequence
<220> FEATURE:
<223> OTHER INFORMATION: chemically synthesized

<400> SEQUENCE: 140

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Val Val Ala Pro Leu
85 90 95

Thr Phe Gly Gln Gly Thr Lys Val Glu Ile Lys Arg
100 105

<210> SEQ ID NO 141
<211> LENGTH: 116
<212> TYPE: PRT
<213> ORGANISM: Artificial Sequence
<220> FEATURE:
<223> OTHER INFORMATION: chemically synthesized

<400> SEQUENCE: 141

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ser Ile Asp Pro Glu Gly Trp Gln Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ser Ala Ala Ala Phe Asp Tyr Trp Gly Gln Gly Thr Leu Val
100 105 110

Thr Val Ser Ser
115

<210> SEQ ID NO 142
<211> LENGTH: 108
<212> TYPE: PRT
<213> ORGANISM: Artificial Sequence
<220> FEATURE:
<223> OTHER INFORMATION: chemically synthesized

<400> SEQUENCE: 142

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Val Val Ala Pro Leu
85 90 95

Thr Phe Gly Gln Gly Thr Lys Val Glu Ile Lys Arg
100 105

<210> SEQ ID NO 143
<211> LENGTH: 119
<212> TYPE: PRT

<213> ORGANISM: Artificial Sequence
<220> FEATURE:
<223> OTHER INFORMATION: chemically synthesized

<400> SEQUENCE: 143

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro His Asn Gly Gln Phe Asp Tyr Trp Gly Gln Gly
            100                 105                 110

Thr Leu Val Thr Val Ser Ser
        115
```

<210> SEQ ID NO 144
<211> LENGTH: 108
<212> TYPE: PRT
<213> ORGANISM: Artificial Sequence
<220> FEATURE:
<223> OTHER INFORMATION: chemically synthesized

<400> SEQUENCE: 144

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105
```

<210> SEQ ID NO 145
<211> LENGTH: 116
<212> TYPE: PRT
<213> ORGANISM: Artificial Sequence
<220> FEATURE:
<223> OTHER INFORMATION: chemically synthesized

<400> SEQUENCE: 145

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ser Ile Glu Gln Met Gly Trp Gln Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
        115


<210> SEQ ID NO 146
<211> LENGTH: 108
<212> TYPE: PRT
<213> ORGANISM: Artificial Sequence
<220> FEATURE:
<223> OTHER INFORMATION: chemically synthesized

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105


<210> SEQ ID NO 147
<211> LENGTH: 119
<212> TYPE: PRT
<213> ORGANISM: Artificial Sequence
<220> FEATURE:
<223> OTHER INFORMATION: chemically synthesized

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Phe Phe Gly Gln Phe Asp Tyr Trp Gly Gln Gly
            100                 105                 110

Thr Leu Val Thr Val Ser Ser
```

115

<210> SEQ ID NO 148
<211> LENGTH: 108
<212> TYPE: PRT
<213> ORGANISM: Artificial Sequence
<220> FEATURE:
<223> OTHER INFORMATION: chemically synthesized

<400> SEQUENCE: 148

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Val Val Ala Pro Leu
85 90 95

Thr Phe Gly Gln Gly Thr Lys Val Glu Ile Lys Arg
100 105

<210> SEQ ID NO 149
<211> LENGTH: 116
<212> TYPE: PRT
<213> ORGANISM: Artificial Sequence
<220> FEATURE:
<223> OTHER INFORMATION: chemically synthesized

<400> SEQUENCE: 149

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ser Ile Asp Glu Met Gly Trp Gln Thr Glu Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ser Ala Ala Ala Phe Asp Tyr Trp Gly Gln Gly Thr Leu Val
100 105 110

Thr Val Ser Ser
115

<210> SEQ ID NO 150
<211> LENGTH: 108
<212> TYPE: PRT
<213> ORGANISM: Artificial Sequence
<220> FEATURE:
<223> OTHER INFORMATION: chemically synthesized

<400> SEQUENCE: 150

Asp Ile Gln Met Thr Gln Ser Pro Ser Ser Leu Ser Ala Ser Val Gly
1 5 10 15

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Leu Asp Ala Pro Pro
                85                  90                  95

Gln Phe Gly Gln Gly Thr Lys Val Glu Ile Lys Arg
            100                 105


<210> SEQ ID NO 151
<211> LENGTH: 119
<212> TYPE: PRT
<213> ORGANISM: Artificial Sequence
<220> FEATURE:
<223> OTHER INFORMATION: chemically synthesized

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115


<210> SEQ ID NO 152
<211> LENGTH: 108
<212> TYPE: PRT
<213> ORGANISM: Artificial Sequence
<220> FEATURE:
<223> OTHER INFORMATION: chemically synthesized

<400> SEQUENCE: 152

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Val Val Ala Pro Pro
```

```
                85                  90                  95

Leu Phe Gly Gln Gly Thr Lys Val Glu Ile Lys Arg
            100                 105


<210> SEQ ID NO 153
<211> LENGTH: 119
<212> TYPE: PRT
<213> ORGANISM: Artificial Sequence
<220> FEATURE:
<223> OTHER INFORMATION: chemically synthesized

<400> SEQUENCE: 153

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115


<210> SEQ ID NO 154
<211> LENGTH: 108
<212> TYPE: PRT
<213> ORGANISM: Artificial Sequence
<220> FEATURE:
<223> OTHER INFORMATION: chemically synthesized

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Val Ala Pro Leu
                85                  90                  95

Thr Phe Gly Gln Gly Thr Lys Val Glu Ile Lys Arg
            100                 105


<210> SEQ ID NO 155
<211> LENGTH: 116
<212> TYPE: PRT
<213> ORGANISM: Artificial Sequence
<220> FEATURE:
<223> OTHER INFORMATION: chemically synthesized

<400> SEQUENCE: 155
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Glu Met Gly Trp Gln Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
        115


<210> SEQ ID NO 156
<211> LENGTH: 108
<212> TYPE: PRT
<213> ORGANISM: Artificial Sequence
<220> FEATURE:
<223> OTHER INFORMATION: chemically synthesized

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Leu Asp Ala Pro Leu
                85                  90                  95

Met Phe Gly Gln Gly Thr Lys Val Glu Ile Lys Arg
            100                 105


<210> SEQ ID NO 157
<211> LENGTH: 119
<212> TYPE: PRT
<213> ORGANISM: Artificial Sequence
<220> FEATURE:
<223> OTHER INFORMATION: chemically synthesized

<400> SEQUENCE: 157

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Pro Met Gly Gln Leu Thr Glu Tyr Ala Asp Ser Val
    50                  55                  60

Lys Gly Arg Phe Thr Ile Ser Arg Asp Asn Ser Lys Asn Thr Leu Tyr
```

```
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115


<210> SEQ ID NO 158
<211> LENGTH: 108
<212> TYPE: PRT
<213> ORGANISM: Artificial Sequence
<220> FEATURE:
<223> OTHER INFORMATION: chemically synthesized

<400> SEQUENCE: 158

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Leu Val Ala Pro Leu
                85                  90                  95

Thr Phe Gly Gln Gly Thr Lys Val Glu Ile Lys Arg
            100                 105


<210> SEQ ID NO 159
<211> LENGTH: 116
<212> TYPE: PRT
<213> ORGANISM: Artificial Sequence
<220> FEATURE:
<223> OTHER INFORMATION: chemically synthesized

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Glu Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
        115


<210> SEQ ID NO 160
<211> LENGTH: 108
```

<212> TYPE: PRT
<213> ORGANISM: Artificial Sequence
<220> FEATURE:
<223> OTHER INFORMATION: chemically synthesized

<400> SEQUENCE: 160

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Leu Val Ala Pro Leu
85 90 95

Thr Phe Gly Gln Gly Thr Lys Val Glu Ile Lys Arg
100 105

<210> SEQ ID NO 161
<211> LENGTH: 116
<212> TYPE: PRT
<213> ORGANISM: Artificial Sequence
<220> FEATURE:
<223> OTHER INFORMATION: chemically synthesized

<400> SEQUENCE: 161

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ser Ile Asp Glu Met Gly Trp Gln Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ser Ala Ala Ala Phe Asp Tyr Trp Gly Gln Gly Thr Leu Val
100 105 110

Thr Val Ser Ser
115

<210> SEQ ID NO 162
<211> LENGTH: 214
<212> TYPE: PRT
<213> ORGANISM: Artificial Sequence
<220> FEATURE:
<223> OTHER INFORMATION: chemically synthesized

<400> SEQUENCE: 162

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile 35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Thr Val Val Ala Pro Pro
85 90 95

Leu Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 163
<211> LENGTH: 449
<212> TYPE: PRT
<213> ORGANISM: Artificial Sequence
<220> FEATURE:
<223> OTHER INFORMATION: chemically synthesized

<400> SEQUENCE: 163

Glu Val His Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ser Ile Asp Pro Glu Gly Arg Gln Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Ile Gly Gly Arg Ser Ala Phe Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser 180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 164
<211> LENGTH: 214
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (182)..(182)
<223> OTHER INFORMATION: X is any amino acid

<400> SEQUENCE: 164

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro

```
65                  70                  75                  80

Glu Asp Phe Ala Thr Tyr Tyr Cys Gln Gln Thr Val Val Ala Pro Pro
                85                  90                  95

Leu Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Xaa Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 165
<211> LENGTH: 6
<212> TYPE: PRT
<213> ORGANISM: Artificial Sequence
<220> FEATURE:
<223> OTHER INFORMATION: chemically synthesized

<400> SEQUENCE: 165

Cys Ile Ser Pro Arg Gly
1               5


<210> SEQ ID NO 166
<211> LENGTH: 7
<212> TYPE: PRT
<213> ORGANISM: Artificial Sequence
<220> FEATURE:
<223> OTHER INFORMATION: chemically synthesized

<400> SEQUENCE: 166

Cys Ile Ser Pro Arg Gly Cys
1               5


<210> SEQ ID NO 167
<211> LENGTH: 8
<212> TYPE: PRT
<213> ORGANISM: Artificial Sequence
<220> FEATURE:
<223> OTHER INFORMATION: chemically synthesized

<400> SEQUENCE: 167

Cys Ile Ser Pro Arg Gly Cys Gly
1               5


<210> SEQ ID NO 168
<211> LENGTH: 15
<212> TYPE: PRT
<213> ORGANISM: Artificial Sequence
<220> FEATURE:
<223> OTHER INFORMATION: chemically synthesized

<400> SEQUENCE: 168

Cys Ile Ser Pro Arg Gly Cys Pro Asp Gly Pro Tyr Val Met Tyr
```

1 5 10 15

<210> SEQ ID NO 169
<211> LENGTH: 14
<212> TYPE: PRT
<213> ORGANISM: Artificial Sequence
<220> FEATURE:
<223> OTHER INFORMATION: chemically synthesized

<400> SEQUENCE: 169

Cys Ile Ser Pro Arg Gly Cys Pro Asp Gly Pro Tyr Val Met
1 5 10

<210> SEQ ID NO 170
<211> LENGTH: 15
<212> TYPE: PRT
<213> ORGANISM: Artificial Sequence
<220> FEATURE:
<223> OTHER INFORMATION: chemically synthesized

<400> SEQUENCE: 170

Cys Ile Ser Pro Arg Gly Cys Glu Pro Gly Thr Tyr Val Pro Thr
1 5 10 15

<210> SEQ ID NO 171
<211> LENGTH: 15
<212> TYPE: PRT
<213> ORGANISM: Artificial Sequence
<220> FEATURE:
<223> OTHER INFORMATION: chemically synthesized

<400> SEQUENCE: 171

Cys Ile Ser Pro Arg Gly Cys Pro Gly Gln Ile Trp His Pro Pro
1 5 10 15

<210> SEQ ID NO 172
<211> LENGTH: 15
<212> TYPE: PRT
<213> ORGANISM: Artificial Sequence
<220> FEATURE:
<223> OTHER INFORMATION: chemically synthesized

<400> SEQUENCE: 172

Gly Ser His Cys Leu Ile Pro Ile Asn Met Gly Ala Pro Ser Cys
1 5 10 15

<210> SEQ ID NO 173
<211> LENGTH: 32
<212> TYPE: PRT
<213> ORGANISM: Artificial Sequence
<220> FEATURE:
<223> OTHER INFORMATION: chemically synthesized

<400> SEQUENCE: 173

Cys Ile Ser Pro Arg Gly Cys Gly Gly Ser Ser Ala Ser Gln Ser Gly
1 5 10 15

Gln Gly Ser His Cys Leu Ile Pro Ile Asn Met Gly Ala Pro Ser Cys
20 25 30

<210> SEQ ID NO 174
<211> LENGTH: 19
<212> TYPE: PRT
<213> ORGANISM: Artificial Sequence
<220> FEATURE:
<223> OTHER INFORMATION: chemically synthesized

<400> SEQUENCE: 174

Cys Asn His His Tyr Phe Tyr Thr Cys Gly Cys Ile Ser Pro Arg Gly
1 5 10 15

Cys Pro Gly

<210> SEQ ID NO 175
<211> LENGTH: 19
<212> TYPE: PRT
<213> ORGANISM: Artificial Sequence
<220> FEATURE:
<223> OTHER INFORMATION: chemically synthesized

<400> SEQUENCE: 175

Ala Asp His Val Phe Trp Gly Ser Tyr Gly Cys Ile Ser Pro Arg Gly
1 5 10 15

Cys Pro Gly

<210> SEQ ID NO 176
<211> LENGTH: 19
<212> TYPE: PRT
<213> ORGANISM: Artificial Sequence
<220> FEATURE:
<223> OTHER INFORMATION: chemically synthesized

<400> SEQUENCE: 176

Cys His His Val Tyr Trp Gly His Cys Gly Cys Ile Ser Pro Arg Gly
1 5 10 15

Cys Pro Gly

<210> SEQ ID NO 177
<211> LENGTH: 19
<212> TYPE: PRT
<213> ORGANISM: Artificial Sequence
<220> FEATURE:
<223> OTHER INFORMATION: chemically synthesized

<400> SEQUENCE: 177

Cys Pro His Phe Thr Thr Thr Ser Cys Gly Cys Ile Ser Pro Arg Gly
1 5 10 15

Cys Pro Gly

<210> SEQ ID NO 178
<211> LENGTH: 19
<212> TYPE: PRT
<213> ORGANISM: Artificial Sequence
<220> FEATURE:
<223> OTHER INFORMATION: chemically synthesized

<400> SEQUENCE: 178

Cys Asn His His Tyr His Tyr Tyr Cys Gly Cys Ile Ser Pro Arg Gly
1 5 10 15

Cys Pro Gly

<210> SEQ ID NO 179
<211> LENGTH: 19
<212> TYPE: PRT
<213> ORGANISM: Artificial Sequence
<220> FEATURE:
<223> OTHER INFORMATION: chemically synthesized

<400> SEQUENCE: 179

Cys Pro His Val Ser Phe Gly Ser Cys Gly Cys Ile Ser Pro Arg Gly
1 5 10 15

Cys Pro Gly

<210> SEQ ID NO 180
<211> LENGTH: 19
<212> TYPE: PRT
<213> ORGANISM: Artificial Sequence
<220> FEATURE:
<223> OTHER INFORMATION: chemically synthesized

<400> SEQUENCE: 180

Cys Pro Tyr Tyr Thr Leu Ser Tyr Cys Gly Cys Ile Ser Pro Arg Gly
1 5 10 15

Cys Pro Gly

<210> SEQ ID NO 181
<211> LENGTH: 19
<212> TYPE: PRT
<213> ORGANISM: Artificial Sequence
<220> FEATURE:
<223> OTHER INFORMATION: chemically synthesized

<400> SEQUENCE: 181

Cys Asn His Val Tyr Phe Gly Thr Cys Gly Cys Ile Ser Pro Arg Gly
1 5 10 15

Cys Pro Gly

<210> SEQ ID NO 182
<211> LENGTH: 19
<212> TYPE: PRT
<213> ORGANISM: Artificial Sequence
<220> FEATURE:
<223> OTHER INFORMATION: chemically synthesized

<400> SEQUENCE: 182

Cys Asn His Phe Thr Leu Thr Thr Cys Gly Cys Ile Ser Pro Arg Gly
1 5 10 15

Cys Pro Gly

<210> SEQ ID NO 183
<211> LENGTH: 19
<212> TYPE: PRT
<213> ORGANISM: Artificial Sequence
<220> FEATURE:
<223> OTHER INFORMATION: chemically synthesized

<400> SEQUENCE: 183

Cys His His Phe Thr Leu Thr Thr Cys Gly Cys Ile Ser Pro Arg Gly
1 5 10 15

Cys Pro Gly

<210> SEQ ID NO 184
<211> LENGTH: 18
<212> TYPE: PRT
<213> ORGANISM: Artificial Sequence
<220> FEATURE:
<223> OTHER INFORMATION: chemically synthesized

<400> SEQUENCE: 184

Tyr Asn Pro Cys Ala Thr Pro Met Cys Cys Ile Ser Pro Arg Gly Cys
1 5 10 15

Pro Gly

<210> SEQ ID NO 185

<211> LENGTH: 18
<212> TYPE: PRT
<213> ORGANISM: Artificial Sequence
<220> FEATURE:
<223> OTHER INFORMATION: chemically synthesized

<400> SEQUENCE: 185

Cys Asn His His Tyr Phe Tyr Thr Cys Gly Cys Ile Ser Pro Arg Gly
1               5                   10                  15

Cys Gly

<210> SEQ ID NO 186
<211> LENGTH: 18
<212> TYPE: PRT
<213> ORGANISM: Artificial Sequence
<220> FEATURE:
<223> OTHER INFORMATION: chemically synthesized

<400> SEQUENCE: 186

Cys Asn His His Tyr His Tyr Tyr Cys Gly Cys Ile Ser Pro Arg Gly
1               5                   10                  15

Cys Gly

<210> SEQ ID NO 187
<211> LENGTH: 18
<212> TYPE: PRT
<213> ORGANISM: Artificial Sequence
<220> FEATURE:
<223> OTHER INFORMATION: chemically synthesized

<400> SEQUENCE: 187

Cys Asn His Val Tyr Phe Gly Thr Cys Gly Cys Ile Ser Pro Arg Gly
1               5                   10                  15

Cys Gly

<210> SEQ ID NO 188
<211> LENGTH: 18
<212> TYPE: PRT
<213> ORGANISM: Artificial Sequence
<220> FEATURE:
<223> OTHER INFORMATION: chemically synthesized

<400> SEQUENCE: 188

Cys His His Val Tyr Trp Gly His Cys Gly Cys Ile Ser Pro Arg Gly
1               5                   10                  15

Cys Gly

<210> SEQ ID NO 189
<211> LENGTH: 18
<212> TYPE: PRT
<213> ORGANISM: Artificial Sequence
<220> FEATURE:
<223> OTHER INFORMATION: chemically synthesized

<400> SEQUENCE: 189

Cys Pro His Phe Thr Thr Thr Ser Cys Gly Cys Ile Ser Pro Arg Gly
1               5                   10                  15

Cys Gly

<210> SEQ ID NO 190
<211> LENGTH: 18
<212> TYPE: PRT
<213> ORGANISM: Artificial Sequence
<220> FEATURE:

-continued

<223> OTHER INFORMATION: chemically synthesized

<400> SEQUENCE: 190

```
Cys Asn His Phe Thr Leu Thr Thr Cys Gly Cys Ile Ser Pro Arg Gly
1               5                   10                  15

Cys Gly
```

<210> SEQ ID NO 191
<211> LENGTH: 18
<212> TYPE: PRT
<213> ORGANISM: Artificial Sequence
<220> FEATURE:
<223> OTHER INFORMATION: chemically synthesized

<400> SEQUENCE: 191

```
Cys His His Phe Thr Leu Thr Thr Cys Gly Cys Ile Ser Pro Arg Gly
1               5                   10                  15

Cys Gly
```

<210> SEQ ID NO 192
<211> LENGTH: 18
<212> TYPE: PRT
<213> ORGANISM: Artificial Sequence
<220> FEATURE:
<223> OTHER INFORMATION: chemically synthesized

<400> SEQUENCE: 192

```
Cys Pro Tyr Tyr Thr Leu Ser Tyr Cys Gly Cys Ile Ser Pro Arg Gly
1               5                   10                  15

Cys Gly
```

<210> SEQ ID NO 193
<211> LENGTH: 18
<212> TYPE: PRT
<213> ORGANISM: Artificial Sequence
<220> FEATURE:
<223> OTHER INFORMATION: chemically synthesized

<400> SEQUENCE: 193

```
Cys Pro His Val Ser Phe Gly Ser Cys Gly Cys Ile Ser Pro Arg Gly
1               5                   10                  15

Cys Gly
```

<210> SEQ ID NO 194
<211> LENGTH: 18
<212> TYPE: PRT
<213> ORGANISM: Artificial Sequence
<220> FEATURE:
<223> OTHER INFORMATION: chemically synthesized

<400> SEQUENCE: 194

```
Ala Asp His Val Phe Trp Gly Ser Tyr Gly Cys Ile Ser Pro Arg Gly
1               5                   10                  15

Cys Gly
```

<210> SEQ ID NO 195
<211> LENGTH: 17
<212> TYPE: PRT
<213> ORGANISM: Artificial Sequence
<220> FEATURE:
<223> OTHER INFORMATION: chemically synthesized

<400> SEQUENCE: 195

Tyr Asn Pro Cys Ala Thr Pro Met Cys Cys Ile Ser Pro Arg Gly Cys
1 5 10 15

Gly

<210> SEQ ID NO 196
<211> LENGTH: 18
<212> TYPE: PRT
<213> ORGANISM: Artificial Sequence
<220> FEATURE:
<223> OTHER INFORMATION: chemically synthesized

<400> SEQUENCE: 196

Cys His His Val Tyr Trp Gly His Cys Gly Cys Ile Ser Pro Arg Gly
1 5 10 15

Cys Gly

<210> SEQ ID NO 197
<211> LENGTH: 18
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (2)..(2)
<223> OTHER INFORMATION: X is N or P
<220> FEATURE:
<221> NAME/KEY: MISC_FEATURE
<222> LOCATION: (4)..(4)
<223> OTHER INFORMATION: X is H, V, or F
<220> FEATURE:
<221> NAME/KEY: MISC_FEATURE
<222> LOCATION: (5)..(5)
<223> OTHER INFORMATION: X is Y or T
<220> FEATURE:
<221> NAME/KEY: MISC_FEATURE
<222> LOCATION: (6)..(6)
<223> OTHER INFORMATION: X is F, W, T, or L
<220> FEATURE:
<221> NAME/KEY: MISC_FEATURE
<222> LOCATION: (7)..(7)
<223> OTHER INFORMATION: X is Y, G, T, or S
<220> FEATURE:
<221> NAME/KEY: MISC_FEATURE
<222> LOCATION: (8)..(8)
<223> OTHER INFORMATION: X is T, S, Y, or H

<400> SEQUENCE: 197

Cys Xaa His Xaa Xaa Xaa Xaa Xaa Cys Gly Cys Ile Ser Pro Arg Gly
1 5 10 15

Cys Gly

<210> SEQ ID NO 198
<211> LENGTH: 15
<212> TYPE: PRT
<213> ORGANISM: Artificial Sequence
<220> FEATURE:
<223> OTHER INFORMATION: chemically synthesized

<400> SEQUENCE: 198

Cys Ile Ser Pro Arg Gly Cys Gly Gln Pro Ile Pro Ser Val Lys
1 5 10 15

<210> SEQ ID NO 199
<211> LENGTH: 15
<212> TYPE: PRT
<213> ORGANISM: Artificial Sequence
<220> FEATURE:
<223> OTHER INFORMATION: chemically synthesized

<400> SEQUENCE: 199

Cys Ile Ser Pro Arg Gly Cys Thr Gln Pro Tyr His Val Ser Arg
1 5 10 15

<210> SEQ ID NO 200
<211> LENGTH: 15
<212> TYPE: PRT
<213> ORGANISM: Artificial Sequence
<220> FEATURE:
<223> OTHER INFORMATION: chemically synthesized

<400> SEQUENCE: 200

Cys Ile Ser Pro Arg Gly Cys Asn Ala Val Ser Gly Leu Gly Ser
1 5 10 15

<210> SEQ ID NO 201
<211> LENGTH: 21
<212> TYPE: PRT
<213> ORGANISM: Artificial Sequence
<220> FEATURE:
<223> OTHER INFORMATION: chemically synthesized

<400> SEQUENCE: 201

Gln Gly Gln Ser Gly Gln Cys Asn Ile Trp Leu Val Gly Gly Asp Cys
1 5 10 15

Arg Gly Trp Gln Gly
20

<210> SEQ ID NO 202
<211> LENGTH: 26
<212> TYPE: PRT
<213> ORGANISM: Artificial Sequence
<220> FEATURE:
<223> OTHER INFORMATION: chemically synthesized

<400> SEQUENCE: 202

Gln Gly Gln Ser Gly Gln Gly Gln Gln Gln Trp Cys Asn Ile Trp Ile
1 5 10 15

Asn Gly Gly Asp Cys Arg Gly Trp Asn Gly
20 25

<210> SEQ ID NO 203
<211> LENGTH: 15
<212> TYPE: PRT
<213> ORGANISM: Artificial Sequence
<220> FEATURE:
<223> OTHER INFORMATION: chemically synthesized

<400> SEQUENCE: 203

Pro Trp Cys Met Gln Arg Gln Asp Phe Leu Arg Cys Pro Gln Pro
1 5 10 15

<210> SEQ ID NO 204
<211> LENGTH: 15
<212> TYPE: PRT
<213> ORGANISM: Artificial Sequence
<220> FEATURE:
<223> OTHER INFORMATION: chemically synthesized

<400> SEQUENCE: 204

Gln Leu Gly Leu Pro Ala Tyr Met Cys Thr Phe Glu Cys Leu Arg
1 5 10 15

<210> SEQ ID NO 205

<211> LENGTH: 15
<212> TYPE: PRT
<213> ORGANISM: Artificial Sequence
<220> FEATURE:
<223> OTHER INFORMATION: chemically synthesized

<400> SEQUENCE: 205

Cys Asn Leu Trp Val Ser Gly Gly Asp Cys Gly Gly Leu Gln Gly
1 5 10 15

<210> SEQ ID NO 206
<211> LENGTH: 15
<212> TYPE: PRT
<213> ORGANISM: Artificial Sequence
<220> FEATURE:
<223> OTHER INFORMATION: chemically synthesized

<400> SEQUENCE: 206

Ser Cys Ser Leu Trp Thr Ser Gly Ser Cys Leu Pro His Ser Pro
1 5 10 15

<210> SEQ ID NO 207
<211> LENGTH: 15
<212> TYPE: PRT
<213> ORGANISM: Artificial Sequence
<220> FEATURE:
<223> OTHER INFORMATION: chemically synthesized

<400> SEQUENCE: 207

Tyr Cys Leu Gln Leu Pro His Tyr Met Gln Ala Met Cys Gly Arg
1 5 10 15

<210> SEQ ID NO 208
<211> LENGTH: 15
<212> TYPE: PRT
<213> ORGANISM: Artificial Sequence
<220> FEATURE:
<223> OTHER INFORMATION: chemically synthesized

<400> SEQUENCE: 208

Cys Phe Leu Tyr Ser Cys Thr Asp Val Ser Tyr Trp Asn Asn Thr
1 5 10 15

<210> SEQ ID NO 209
<211> LENGTH: 15
<212> TYPE: PRT
<213> ORGANISM: Artificial Sequence
<220> FEATURE:
<223> OTHER INFORMATION: chemically synthesized

<400> SEQUENCE: 209

Pro Trp Cys Met Gln Arg Gln Asp Tyr Leu Arg Cys Pro Gln Pro
1 5 10 15

<210> SEQ ID NO 210
<211> LENGTH: 15
<212> TYPE: PRT
<213> ORGANISM: Artificial Sequence
<220> FEATURE:
<223> OTHER INFORMATION: chemically synthesized

<400> SEQUENCE: 210

Cys Asn Leu Trp Ile Ser Gly Gly Asp Cys Arg Gly Leu Ala Gly
1 5 10 15

<210> SEQ ID NO 211
<211> LENGTH: 15

<212> TYPE: PRT
<213> ORGANISM: Artificial Sequence
<220> FEATURE:
<223> OTHER INFORMATION: chemically synthesized

<400> SEQUENCE: 211

Cys Asn Leu Trp Val Ser Gly Gly Asp Cys Arg Gly Val Gln Gly
1               5                   10                  15

<210> SEQ ID NO 212
<211> LENGTH: 15
<212> TYPE: PRT
<213> ORGANISM: Artificial Sequence
<220> FEATURE:
<223> OTHER INFORMATION: chemically synthesized

<400> SEQUENCE: 212

Cys Asn Leu Trp Val Ser Gly Gly Asp Cys Arg Gly Leu Arg Gly
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: chemically synthesized

<400> SEQUENCE: 213

Cys Asn Leu Trp Ile Ser Gly Gly Asp Cys Arg Gly Leu Pro Gly
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: chemically synthesized

<400> SEQUENCE: 214

Cys Asn Leu Trp Val Ser Gly Gly Asp Cys Arg Asp Ala Pro Trp
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: chemically synthesized

<400> SEQUENCE: 215

Cys Asn Leu Trp Val Ser Gly Gly Asp Cys Arg Asp Leu Leu Gly
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: chemically synthesized

<400> SEQUENCE: 216

Cys Asn Leu Trp Val Ser Gly Gly Asp Cys Arg Gly Leu Gln Gly
1               5                   10                  15

<210> SEQ ID NO 217
<211> LENGTH: 15
<212> TYPE: PRT

<213> ORGANISM: Artificial Sequence
<220> FEATURE:
<223> OTHER INFORMATION: chemically synthesized

<400> SEQUENCE: 217

Cys Asn Leu Trp Leu His Gly Gly Asp Cys Arg Gly Trp Gln Gly
1 5 10 15

<210> SEQ ID NO 218
<211> LENGTH: 15
<212> TYPE: PRT
<213> ORGANISM: Artificial Sequence
<220> FEATURE:
<223> OTHER INFORMATION: chemically synthesized

<400> SEQUENCE: 218

Cys Asn Ile Trp Leu Val Gly Gly Asp Cys Arg Gly Trp Gln Gly
1 5 10 15

<210> SEQ ID NO 219
<211> LENGTH: 15
<212> TYPE: PRT
<213> ORGANISM: Artificial Sequence
<220> FEATURE:
<223> OTHER INFORMATION: chemically synthesized

<400> SEQUENCE: 219

Cys Thr Thr Trp Phe Cys Gly Gly Asp Cys Gly Val Met Arg Gly
1 5 10 15

<210> SEQ ID NO 220
<211> LENGTH: 15
<212> TYPE: PRT
<213> ORGANISM: Artificial Sequence
<220> FEATURE:
<223> OTHER INFORMATION: chemically synthesized

<400> SEQUENCE: 220

Cys Asn Ile Trp Gly Pro Ser Val Asp Cys Gly Ala Leu Leu Gly
1 5 10 15

<210> SEQ ID NO 221
<211> LENGTH: 15
<212> TYPE: PRT
<213> ORGANISM: Artificial Sequence
<220> FEATURE:
<223> OTHER INFORMATION: chemically synthesized

<400> SEQUENCE: 221

Cys Asn Ile Trp Val Asn Gly Gly Asp Cys Arg Ser Phe Glu Gly
1 5 10 15

<210> SEQ ID NO 222
<211> LENGTH: 15
<212> TYPE: PRT
<213> ORGANISM: Artificial Sequence
<220> FEATURE:
<223> OTHER INFORMATION: chemically synthesized

<400> SEQUENCE: 222

Tyr Cys Leu Asn Leu Pro Arg Tyr Met Gln Asp Met Cys Trp Ala
1 5 10 15

<210> SEQ ID NO 223
<211> LENGTH: 15
<212> TYPE: PRT
<213> ORGANISM: Artificial Sequence -continued
<220> FEATURE:
<223> OTHER INFORMATION: chemically synthesized

<400> SEQUENCE: 223

Tyr Cys Leu Ala Leu Pro His Tyr Met Gln Ala Asp Cys Ala Arg
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: chemically synthesized

<400> SEQUENCE: 224

Cys Phe Leu Tyr Ser Cys Gly Asp Val Ser Tyr Trp Gly Ser Ala
1               5                   10                  15

<210> SEQ ID NO 225
<211> LENGTH: 15
<212> TYPE: PRT
<213> ORGANISM: Artificial Sequence
<220> FEATURE:
<223> OTHER INFORMATION: chemically synthesized

<400> SEQUENCE: 225

Cys Tyr Leu Tyr Ser Cys Thr Asp Ser Ala Phe Trp Asn Asn Arg
1               5                   10                  15

<210> SEQ ID NO 226
<211> LENGTH: 15
<212> TYPE: PRT
<213> ORGANISM: Artificial Sequence
<220> FEATURE:
<223> OTHER INFORMATION: chemically synthesized

<400> SEQUENCE: 226

Cys Tyr Leu Tyr Ser Cys Asn Asp Val Ser Tyr Trp Ser Asn Thr
1               5                   10                  15

<210> SEQ ID NO 227
<211> LENGTH: 12
<212> TYPE: PRT
<213> ORGANISM: Artificial Sequence
<220> FEATURE:
<223> OTHER INFORMATION: chemically synthesized

<400> SEQUENCE: 227

Cys Phe Leu Tyr Ser Cys Thr Asp Val Ser Tyr Trp
1               5                   10

<210> SEQ ID NO 228
<211> LENGTH: 15
<212> TYPE: PRT
<213> ORGANISM: Artificial Sequence
<220> FEATURE:
<223> OTHER INFORMATION: chemically synthesized

<400> SEQUENCE: 228

Cys Phe Leu Tyr Ser Cys Thr Asp Val Ala Tyr Trp Asn Ser Ala
1               5                   10                  15

<210> SEQ ID NO 229
<211> LENGTH: 15
<212> TYPE: PRT
<213> ORGANISM: Artificial Sequence
<220> FEATURE:

<223> OTHER INFORMATION: chemically synthesized

<400> SEQUENCE: 229

Cys Phe Leu Tyr Ser Cys Thr Asp Val Ser Tyr Trp Gly Asp Thr
1 5 10 15

<210> SEQ ID NO 230
<211> LENGTH: 15
<212> TYPE: PRT
<213> ORGANISM: Artificial Sequence
<220> FEATURE:
<223> OTHER INFORMATION: chemically synthesized

<400> SEQUENCE: 230

Cys Phe Leu Tyr Ser Cys Thr Asp Val Ser Tyr Trp Gly Asn Ser
1 5 10 15

<210> SEQ ID NO 231
<211> LENGTH: 15
<212> TYPE: PRT
<213> ORGANISM: Artificial Sequence
<220> FEATURE:
<223> OTHER INFORMATION: chemically synthesized

<400> SEQUENCE: 231

Cys Phe Leu Tyr Ser Cys Thr Asp Val Ala Tyr Trp Asn Asn Thr
1 5 10 15

<210> SEQ ID NO 232
<211> LENGTH: 18
<212> TYPE: PRT
<213> ORGANISM: Artificial Sequence
<220> FEATURE:
<223> OTHER INFORMATION: chemically synthesized

<400> SEQUENCE: 232

Cys Phe Leu Tyr Ser Cys Gly Asp Val Ser Tyr Trp Gly Asn Pro Gly
1 5 10 15

Leu Ser

<210> SEQ ID NO 233
<211> LENGTH: 15
<212> TYPE: PRT
<213> ORGANISM: Artificial Sequence
<220> FEATURE:
<223> OTHER INFORMATION: chemically synthesized

<400> SEQUENCE: 233

Cys Phe Leu Tyr Ser Cys Thr Asp Val Ala Tyr Trp Ser Gly Leu
1 5 10 15

<210> SEQ ID NO 234
<211> LENGTH: 15
<212> TYPE: PRT
<213> ORGANISM: Artificial Sequence
<220> FEATURE:
<223> OTHER INFORMATION: chemically synthesized

<400> SEQUENCE: 234

Cys Tyr Leu Tyr Ser Cys Thr Asp Gly Ser Tyr Trp Asn Ser Thr
1 5 10 15

<210> SEQ ID NO 235
<211> LENGTH: 15
<212> TYPE: PRT
<213> ORGANISM: Artificial Sequence
<220> FEATURE:
<223> OTHER INFORMATION: chemically synthesized

<400> SEQUENCE: 235

Cys Phe Leu Tyr Ser Cys Ser Asp Val Ser Tyr Trp Gly Asn Ile
1 5 10 15

<210> SEQ ID NO 236
<211> LENGTH: 12
<212> TYPE: PRT
<213> ORGANISM: Artificial Sequence
<220> FEATURE:
<223> OTHER INFORMATION: chemically synthesized

<400> SEQUENCE: 236

Cys Phe Leu Tyr Ser Cys Thr Asp Val Ala Tyr Trp
1 5 10

<210> SEQ ID NO 237
<211> LENGTH: 15
<212> TYPE: PRT
<213> ORGANISM: Artificial Sequence
<220> FEATURE:
<223> OTHER INFORMATION: chemically synthesized

<400> SEQUENCE: 237

Cys Phe Leu Tyr Ser Cys Thr Asp Val Ser Tyr Trp Gly Ser Thr
1 5 10 15

<210> SEQ ID NO 238
<211> LENGTH: 15
<212> TYPE: PRT
<213> ORGANISM: Artificial Sequence
<220> FEATURE:
<223> OTHER INFORMATION: chemically synthesized

<400> SEQUENCE: 238

Cys Phe Leu Tyr Ser Cys Thr Asp Val Ala Tyr Trp Gly Asp Thr
1 5 10 15

<210> SEQ ID NO 239
<211> LENGTH: 20
<212> TYPE: PRT
<213> ORGANISM: Artificial Sequence
<220> FEATURE:
<223> OTHER INFORMATION: chemically synthesized

<400> SEQUENCE: 239

Gly Cys Asn Ile Trp Leu Asn Gly Gly Asp Cys Arg Gly Trp Val Asp
1 5 10 15

Pro Leu Gln Gly
20

<210> SEQ ID NO 240
<211> LENGTH: 20
<212> TYPE: PRT
<213> ORGANISM: Artificial Sequence
<220> FEATURE:
<223> OTHER INFORMATION: chemically synthesized

<400> SEQUENCE: 240

Gly Cys Asn Ile Trp Leu Val Gly Gly Asp Cys Arg Gly Trp Ile Gly
1 5 10 15

Asp Thr Asn Gly
20

<210> SEQ ID NO 241
<211> LENGTH: 20
<212> TYPE: PRT
<213> ORGANISM: Artificial Sequence
<220> FEATURE:
<223> OTHER INFORMATION: chemically synthesized

<400> SEQUENCE: 241

Gly Cys Asn Ile Trp Leu Val Gly Gly Asp Cys Arg Gly Trp Ile Glu
1 5 10 15

Asp Ser Asn Gly
20

<210> SEQ ID NO 242
<211> LENGTH: 20
<212> TYPE: PRT
<213> ORGANISM: Artificial Sequence
<220> FEATURE:
<223> OTHER INFORMATION: chemically synthesized

<400> SEQUENCE: 242

Gly Cys Asn Ile Trp Ala Asn Gly Gly Asp Cys Arg Gly Trp Ile Asp
1 5 10 15

Asn Ile Asp Gly
20

<210> SEQ ID NO 243
<211> LENGTH: 20
<212> TYPE: PRT
<213> ORGANISM: Artificial Sequence
<220> FEATURE:
<223> OTHER INFORMATION: chemically synthesized

<400> SEQUENCE: 243

Gly Cys Asn Ile Trp Leu Val Gly Gly Asp Cys Arg Gly Trp Leu Gly
1 5 10 15

Glu Ala Val Gly
20

<210> SEQ ID NO 244
<211> LENGTH: 20
<212> TYPE: PRT
<213> ORGANISM: Artificial Sequence
<220> FEATURE:
<223> OTHER INFORMATION: chemically synthesized

<400> SEQUENCE: 244

Gly Cys Asn Ile Trp Leu Val Gly Gly Asp Cys Arg Gly Trp Leu Glu
1 5 10 15

Glu Ala Val Gly
20

<210> SEQ ID NO 245
<211> LENGTH: 20
<212> TYPE: PRT
<213> ORGANISM: Artificial Sequence
<220> FEATURE:
<223> OTHER INFORMATION: chemically synthesized

<400> SEQUENCE: 245

Gly Gly Pro Ala Leu Cys Asn Ile Trp Leu Asn Gly Gly Asp Cys Arg
1 5 10 15

Gly Trp Ser Gly
20

<210> SEQ ID NO 246
<211> LENGTH: 20
<212> TYPE: PRT
<213> ORGANISM: Artificial Sequence
<220> FEATURE:
<223> OTHER INFORMATION: chemically synthesized

<400> SEQUENCE: 246

Gly Ala Pro Val Phe Cys Asn Ile Trp Leu Asn Gly Gly Asp Cys Arg
1 5 10 15

Gly Trp Met Gly
20

<210> SEQ ID NO 247
<211> LENGTH: 20
<212> TYPE: PRT
<213> ORGANISM: Artificial Sequence
<220> FEATURE:
<223> OTHER INFORMATION: chemically synthesized

<400> SEQUENCE: 247

Gly Gln Gln Gln Trp Cys Asn Ile Trp Ile Asn Gly Gly Asp Cys Arg
1 5 10 15

Gly Trp Asn Gly
20

<210> SEQ ID NO 248
<211> LENGTH: 20
<212> TYPE: PRT
<213> ORGANISM: Artificial Sequence
<220> FEATURE:
<223> OTHER INFORMATION: chemically synthesized

<400> SEQUENCE: 248

Gly Lys Ser Glu Phe Cys Asn Ile Trp Leu Asn Gly Gly Asp Cys Arg
1 5 10 15

Gly Trp Ile Gly
20

<210> SEQ ID NO 249
<211> LENGTH: 20
<212> TYPE: PRT
<213> ORGANISM: Artificial Sequence
<220> FEATURE:
<223> OTHER INFORMATION: chemically synthesized

<400> SEQUENCE: 249

Gly Thr Pro Gly Gly Cys Asn Ile Trp Ala Asn Gly Gly Asp Cys Arg
1 5 10 15

Gly Trp Glu Gly
20

<210> SEQ ID NO 250
<211> LENGTH: 20
<212> TYPE: PRT
<213> ORGANISM: Artificial Sequence
<220> FEATURE:
<223> OTHER INFORMATION: chemically synthesized

<400> SEQUENCE: 250

Gly Ala Ser Gln Tyr Cys Asn Leu Trp Ile Asn Gly Gly Asp Cys Arg
1 5 10 15

Gly Trp Arg Gly

20

<210> SEQ ID NO 251
<211> LENGTH: 18
<212> TYPE: PRT
<213> ORGANISM: Artificial Sequence
<220> FEATURE:
<223> OTHER INFORMATION: chemically synthesized

<400> SEQUENCE: 251

Gly Cys Asn Ile Trp Leu Val Gly Gly Asp Cys Arg Pro Trp Val Glu
1 5 10 15

Gly Gly

<210> SEQ ID NO 252
<211> LENGTH: 18
<212> TYPE: PRT
<213> ORGANISM: Artificial Sequence
<220> FEATURE:
<223> OTHER INFORMATION: chemically synthesized

<400> SEQUENCE: 252

Gly Cys Asn Ile Trp Ala Val Gly Gly Asp Cys Arg Pro Phe Val Asp
1 5 10 15

Gly Gly

<210> SEQ ID NO 253
<211> LENGTH: 18
<212> TYPE: PRT
<213> ORGANISM: Artificial Sequence
<220> FEATURE:
<223> OTHER INFORMATION: chemically synthesized

<400> SEQUENCE: 253

Gly Cys Asn Ile Trp Leu Asn Gly Gly Asp Cys Arg Ala Trp Val Asp
1 5 10 15

Thr Gly

<210> SEQ ID NO 254
<211> LENGTH: 18
<212> TYPE: PRT
<213> ORGANISM: Artificial Sequence
<220> FEATURE:
<223> OTHER INFORMATION: chemically synthesized

<400> SEQUENCE: 254

Gly Cys Asn Ile Trp Ile Val Gly Gly Asp Cys Arg Pro Phe Ile Asn
1 5 10 15

Asp Gly

<210> SEQ ID NO 255
<211> LENGTH: 18
<212> TYPE: PRT
<213> ORGANISM: Artificial Sequence
<220> FEATURE:
<223> OTHER INFORMATION: chemically synthesized

<400> SEQUENCE: 255

Gly Cys Asn Ile Trp Leu Asn Gly Gly Asp Cys Arg Pro Val Val Phe
1 5 10 15

Gly Gly

<210> SEQ ID NO 256

<211> LENGTH: 18
<212> TYPE: PRT
<213> ORGANISM: Artificial Sequence
<220> FEATURE:
<223> OTHER INFORMATION: chemically synthesized

<400> SEQUENCE: 256

Gly Cys Asn Ile Trp Leu Ser Gly Gly Asp Cys Arg Met Phe Met Asn
1 5 10 15

Glu Gly

<210> SEQ ID NO 257
<211> LENGTH: 18
<212> TYPE: PRT
<213> ORGANISM: Artificial Sequence
<220> FEATURE:
<223> OTHER INFORMATION: chemically synthesized

<400> SEQUENCE: 257

Gly Cys Asn Ile Trp Val Asn Gly Gly Asp Cys Arg Ser Phe Val Tyr
1 5 10 15

Ser Gly

<210> SEQ ID NO 258
<211> LENGTH: 18
<212> TYPE: PRT
<213> ORGANISM: Artificial Sequence
<220> FEATURE:
<223> OTHER INFORMATION: chemically synthesized

<400> SEQUENCE: 258

Gly Cys Asn Ile Trp Leu Asn Gly Gly Asp Cys Arg Gly Trp Glu Ala
1 5 10 15

Ser Gly

<210> SEQ ID NO 259
<211> LENGTH: 18
<212> TYPE: PRT
<213> ORGANISM: Artificial Sequence
<220> FEATURE:
<223> OTHER INFORMATION: chemically synthesized

<400> SEQUENCE: 259

Gly Cys Asn Ile Trp Ala His Gly Gly Asp Cys Arg Gly Phe Ile Glu
1 5 10 15

Pro Gly

<210> SEQ ID NO 260
<211> LENGTH: 18
<212> TYPE: PRT
<213> ORGANISM: Artificial Sequence
<220> FEATURE:
<223> OTHER INFORMATION: chemically synthesized

<400> SEQUENCE: 260

Gly Cys Asn Ile Trp Leu Asn Gly Gly Asp Cys Arg Thr Phe Val Ala
1 5 10 15

Ser Gly

<210> SEQ ID NO 261
<211> LENGTH: 18
<212> TYPE: PRT
<213> ORGANISM: Artificial Sequence
<220> FEATURE:

<223> OTHER INFORMATION: chemically synthesized

<400> SEQUENCE: 261

Gly Cys Asn Ile Trp Ala His Gly Gly Asp Cys Arg Gly Phe Ile Glu
1 5 10 15

Pro Gly

<210> SEQ ID NO 262
<211> LENGTH: 18
<212> TYPE: PRT
<213> ORGANISM: Artificial Sequence
<220> FEATURE:
<223> OTHER INFORMATION: chemically synthesized

<400> SEQUENCE: 262

Gly Phe Leu Glu Asn Cys Asn Ile Trp Leu Asn Gly Gly Asp Cys Arg
1 5 10 15

Thr Gly

<210> SEQ ID NO 263
<211> LENGTH: 18
<212> TYPE: PRT
<213> ORGANISM: Artificial Sequence
<220> FEATURE:
<223> OTHER INFORMATION: chemically synthesized

<400> SEQUENCE: 263

Gly Ile Tyr Glu Asn Cys Asn Ile Trp Leu Asn Gly Gly Asp Cys Arg
1 5 10 15

Met Gly

<210> SEQ ID NO 264
<211> LENGTH: 18
<212> TYPE: PRT
<213> ORGANISM: Artificial Sequence
<220> FEATURE:
<223> OTHER INFORMATION: chemically synthesized

<400> SEQUENCE: 264

Gly Ile Pro Asp Asn Cys Asn Ile Trp Ile Asn Gly Gly Asp Cys Arg
1 5 10 15

Tyr Gly

<210> SEQ ID NO 265
<211> LENGTH: 21
<212> TYPE: PRT
<213> ORGANISM: Artificial Sequence
<220> FEATURE:
<223> OTHER INFORMATION: chemically synthesized

<400> SEQUENCE: 265

Gln Gly Gln Ser Gly Gln Tyr Gly Ser Cys Ser Trp Asn Tyr Val His
1 5 10 15

Ile Phe Met Asp Cys
20

<210> SEQ ID NO 266
<211> LENGTH: 21
<212> TYPE: PRT
<213> ORGANISM: Artificial Sequence
<220> FEATURE:
<223> OTHER INFORMATION: chemically synthesized

<400> SEQUENCE: 266

```
Gln Gly Gln Ser Gly Gln Gly Asp Phe Asp Ile Pro Phe Pro Ala His
1               5                   10                  15

Trp Val Pro Ile Thr
            20


<210> SEQ ID NO 267
<211> LENGTH: 24
<212> TYPE: PRT
<213> ORGANISM: Artificial Sequence
<220> FEATURE:
<223> OTHER INFORMATION: chemically synthesized

<400> SEQUENCE: 267

Gln Gly Gln Ser Gly Gln Met Gly Val Pro Ala Gly Cys Val Trp Asn
1               5                   10                  15

Tyr Ala His Ile Phe Met Asp Cys
            20


<210> SEQ ID NO 268
<211> LENGTH: 15
<212> TYPE: PRT
<213> ORGANISM: Artificial Sequence
<220> FEATURE:
<223> OTHER INFORMATION: chemically synthesized

<400> SEQUENCE: 268

Tyr Arg Ser Cys Asn Trp Asn Tyr Val Ser Ile Phe Leu Asp Cys
1               5                   10                  15


<210> SEQ ID NO 269
<211> LENGTH: 16
<212> TYPE: PRT
<213> ORGANISM: Artificial Sequence
<220> FEATURE:
<223> OTHER INFORMATION: chemically synthesized

<400> SEQUENCE: 269

Pro Gly Ala Phe Asp Ile Pro Phe Pro Ala His Trp Val Pro Asn Thr
1               5                   10                  15


<210> SEQ ID NO 270
<211> LENGTH: 15
<212> TYPE: PRT
<213> ORGANISM: Artificial Sequence
<220> FEATURE:
<223> OTHER INFORMATION: chemically synthesized

<400> SEQUENCE: 270

Glu Ser Ser Cys Val Trp Asn Tyr Val His Ile Tyr Met Asp Cys
1               5                   10                  15


<210> SEQ ID NO 271
<211> LENGTH: 15
<212> TYPE: PRT
<213> ORGANISM: Artificial Sequence
<220> FEATURE:
<223> OTHER INFORMATION: chemically synthesized

<400> SEQUENCE: 271

Tyr Pro Gly Cys Lys Trp Asn Tyr Asp Arg Ile Phe Leu Asp Cys
1               5                   10                  15


<210> SEQ ID NO 272
<211> LENGTH: 15
<212> TYPE: PRT
```

<213> ORGANISM: Artificial Sequence
<220> FEATURE:
<223> OTHER INFORMATION: chemically synthesized

<400> SEQUENCE: 272

Tyr Arg Thr Cys Ser Trp Asn Tyr Val Gly Ile Phe Leu Asp Cys
1 5 10 15

<210> SEQ ID NO 273
<211> LENGTH: 15
<212> TYPE: PRT
<213> ORGANISM: Artificial Sequence
<220> FEATURE:
<223> OTHER INFORMATION: chemically synthesized

<400> SEQUENCE: 273

Tyr Gly Ser Cys Ser Trp Asn Tyr Val His Ile Phe Met Asp Cys
1 5 10 15

<210> SEQ ID NO 274
<211> LENGTH: 15
<212> TYPE: PRT
<213> ORGANISM: Artificial Sequence
<220> FEATURE:
<223> OTHER INFORMATION: chemically synthesized

<400> SEQUENCE: 274

Tyr Gly Ser Cys Ser Trp Asn Tyr Val His Ile Phe Leu Asp Cys
1 5 10 15

<210> SEQ ID NO 275
<211> LENGTH: 15
<212> TYPE: PRT
<213> ORGANISM: Artificial Sequence
<220> FEATURE:
<223> OTHER INFORMATION: chemically synthesized

<400> SEQUENCE: 275

Tyr Gly Ser Cys Asn Trp Asn Tyr Val His Ile Phe Leu Asp Cys
1 5 10 15

<210> SEQ ID NO 276
<211> LENGTH: 15
<212> TYPE: PRT
<213> ORGANISM: Artificial Sequence
<220> FEATURE:
<223> OTHER INFORMATION: chemically synthesized

<400> SEQUENCE: 276

Tyr Thr Ser Cys Asn Trp Asn Tyr Val His Ile Phe Met Asp Cys
1 5 10 15

<210> SEQ ID NO 277
<211> LENGTH: 15
<212> TYPE: PRT
<213> ORGANISM: Artificial Sequence
<220> FEATURE:
<223> OTHER INFORMATION: chemically synthesized

<400> SEQUENCE: 277

Tyr Pro Gly Cys Lys Trp Asn Tyr Asp Arg Ile Phe Leu Asp Cys
1 5 10 15

<210> SEQ ID NO 278
<211> LENGTH: 15
<212> TYPE: PRT
<213> ORGANISM: Artificial Sequence
<220> FEATURE:
<223> OTHER INFORMATION: chemically synthesized

<400> SEQUENCE: 278

Trp Arg Ser Cys Asn Trp Asn Tyr Ala His Ile Phe Leu Asp Cys
1 5 10 15

<210> SEQ ID NO 279
<211> LENGTH: 15
<212> TYPE: PRT
<213> ORGANISM: Artificial Sequence
<220> FEATURE:
<223> OTHER INFORMATION: chemically synthesized

<400> SEQUENCE: 279

Trp Ser Asn Cys His Trp Asn Tyr Val His Ile Phe Leu Asp Cys
1 5 10 15

<210> SEQ ID NO 280
<211> LENGTH: 15
<212> TYPE: PRT
<213> ORGANISM: Artificial Sequence
<220> FEATURE:
<223> OTHER INFORMATION: chemically synthesized

<400> SEQUENCE: 280

Asp Arg Ser Cys Thr Trp Asn Tyr Val Arg Ile Ser Tyr Asp Cys
1 5 10 15

<210> SEQ ID NO 281
<211> LENGTH: 15
<212> TYPE: PRT
<213> ORGANISM: Artificial Sequence
<220> FEATURE:
<223> OTHER INFORMATION: chemically synthesized

<400> SEQUENCE: 281

Ser Gly Ser Cys Lys Trp Asp Tyr Val His Ile Phe Leu Asp Cys
1 5 10 15

<210> SEQ ID NO 282
<211> LENGTH: 15
<212> TYPE: PRT
<213> ORGANISM: Artificial Sequence
<220> FEATURE:
<223> OTHER INFORMATION: chemically synthesized

<400> SEQUENCE: 282

Ser Arg Ser Cys Ile Trp Asn Tyr Ala His Ile His Leu Asp Cys
1 5 10 15

<210> SEQ ID NO 283
<211> LENGTH: 15
<212> TYPE: PRT
<213> ORGANISM: Artificial Sequence
<220> FEATURE:
<223> OTHER INFORMATION: chemically synthesized

<400> SEQUENCE: 283

Ser Met Ser Cys Tyr Trp Gln Tyr Glu Arg Ile Phe Leu Asp Cys
1 5 10 15

<210> SEQ ID NO 284
<211> LENGTH: 15
<212> TYPE: PRT
<213> ORGANISM: Artificial Sequence
<220> FEATURE:

<223> OTHER INFORMATION: chemically synthesized

<400> SEQUENCE: 284

Tyr Arg Ser Cys Asn Trp Asn Tyr Val Ser Ile Phe Leu Asp Cys
1 5 10 15

<210> SEQ ID NO 285
<211> LENGTH: 15
<212> TYPE: PRT
<213> ORGANISM: Artificial Sequence
<220> FEATURE:
<223> OTHER INFORMATION: chemically synthesized

<400> SEQUENCE: 285

Ser Gly Ser Cys Lys Trp Asp Tyr Val His Ile Phe Leu Asp Cys
1 5 10 15

<210> SEQ ID NO 286
<211> LENGTH: 15
<212> TYPE: PRT
<213> ORGANISM: Artificial Sequence
<220> FEATURE:
<223> OTHER INFORMATION: chemically synthesized

<400> SEQUENCE: 286

Tyr Lys Ser Cys His Trp Asp Tyr Val His Ile Phe Leu Asp Cys
1 5 10 15

<210> SEQ ID NO 287
<211> LENGTH: 15
<212> TYPE: PRT
<213> ORGANISM: Artificial Sequence
<220> FEATURE:
<223> OTHER INFORMATION: chemically synthesized

<400> SEQUENCE: 287

Tyr Gly Ser Cys Thr Trp Asn Tyr Val His Ile Phe Met Glu Cys
1 5 10 15

<210> SEQ ID NO 288
<211> LENGTH: 15
<212> TYPE: PRT
<213> ORGANISM: Artificial Sequence
<220> FEATURE:
<223> OTHER INFORMATION: chemically synthesized

<400> SEQUENCE: 288

Phe Ser Ser Cys Asn Trp Asn Tyr Val His Ile Phe Leu Asp Cys
1 5 10 15

<210> SEQ ID NO 289
<211> LENGTH: 15
<212> TYPE: PRT
<213> ORGANISM: Artificial Sequence
<220> FEATURE:
<223> OTHER INFORMATION: chemically synthesized

<400> SEQUENCE: 289

Trp Arg Ser Cys Asn Trp Asn Tyr Ala His Ile Phe Leu Asp Cys
1 5 10 15

<210> SEQ ID NO 290
<211> LENGTH: 15
<212> TYPE: PRT
<213> ORGANISM: Artificial Sequence
<220> FEATURE:
<223> OTHER INFORMATION: chemically synthesized

<400> SEQUENCE: 290

Tyr Gly Ser Cys Gln Trp Asn Tyr Val His Ile Phe Leu Asp Cys
1 5 10 15

<210> SEQ ID NO 291
<211> LENGTH: 15
<212> TYPE: PRT
<213> ORGANISM: Artificial Sequence
<220> FEATURE:
<223> OTHER INFORMATION: chemically synthesized

<400> SEQUENCE: 291

Tyr Arg Ser Cys Asn Trp Asn Tyr Val His Ile Phe Leu Asp Cys
1 5 10 15

<210> SEQ ID NO 292
<211> LENGTH: 15
<212> TYPE: PRT
<213> ORGANISM: Artificial Sequence
<220> FEATURE:
<223> OTHER INFORMATION: chemically synthesized

<400> SEQUENCE: 292

Asn Met Ser Cys His Trp Asp Tyr Val His Ile Phe Leu Asp Cys
1 5 10 15

<210> SEQ ID NO 293
<211> LENGTH: 15
<212> TYPE: PRT
<213> ORGANISM: Artificial Sequence
<220> FEATURE:
<223> OTHER INFORMATION: chemically synthesized

<400> SEQUENCE: 293

Phe Gly Pro Cys Thr Trp Asn Tyr Ala Arg Ile Ser Trp Asp Cys
1 5 10 15

<210> SEQ ID NO 294
<211> LENGTH: 15
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(2)
<223> OTHER INFORMATION: X is any amino acid
<220> FEATURE:
<221> NAME/KEY: MISC_FEATURE
<222> LOCATION: (5)..(5)
<223> OTHER INFORMATION: X is any amino acid
<220> FEATURE:
<221> NAME/KEY: MISC_FEATURE
<222> LOCATION: (7)..(7)
<223> OTHER INFORMATION: X is any amino acid
<220> FEATURE:
<221> NAME/KEY: MISC_FEATURE
<222> LOCATION: (13)..(13)
<223> OTHER INFORMATION: X is any amino acid

<400> SEQUENCE: 294

Xaa Xaa Ser Cys Xaa Trp Xaa Tyr Val His Ile Phe Xaa Asp Cys
1 5 10 15

<210> SEQ ID NO 295
<211> LENGTH: 18
<212> TYPE: PRT
<213> ORGANISM: Artificial Sequence
<220> FEATURE:
<223> OTHER INFORMATION: chemically synthesized

<400> SEQUENCE: 295

Met Gly Val Pro Ala Gly Cys Val Trp Asn Tyr Ala His Ile Phe Met
1 5 10 15

Asp Cys

<210> SEQ ID NO 296
<211> LENGTH: 18
<212> TYPE: PRT
<213> ORGANISM: Artificial Sequence
<220> FEATURE:
<223> OTHER INFORMATION: chemically synthesized

<400> SEQUENCE: 296

Arg Asp Thr Gly Gly Gln Cys Arg Trp Asp Tyr Val His Ile Phe Met
1 5 10 15

Asp Cys

<210> SEQ ID NO 297
<211> LENGTH: 18
<212> TYPE: PRT
<213> ORGANISM: Artificial Sequence
<220> FEATURE:
<223> OTHER INFORMATION: chemically synthesized

<400> SEQUENCE: 297

Ala Gly Val Pro Ala Gly Cys Thr Trp Asn Tyr Val His Ile Phe Met
1 5 10 15

Glu Cys

<210> SEQ ID NO 298
<211> LENGTH: 18
<212> TYPE: PRT
<213> ORGANISM: Artificial Sequence
<220> FEATURE:
<223> OTHER INFORMATION: chemically synthesized

<400> SEQUENCE: 298

Val Gly Val Pro Asn Gly Cys Val Trp Asn Tyr Ala His Ile Phe Met
1 5 10 15

Glu Cys

<210> SEQ ID NO 299
<211> LENGTH: 18
<212> TYPE: PRT
<213> ORGANISM: Artificial Sequence
<220> FEATURE:
<223> OTHER INFORMATION: chemically synthesized

<400> SEQUENCE: 299

Asp Gly Gly Pro Ala Gly Cys Ser Trp Asn Tyr Val His Ile Phe Met
1 5 10 15

Glu Cys

<210> SEQ ID NO 300
<211> LENGTH: 18
<212> TYPE: PRT
<213> ORGANISM: Artificial Sequence
<220> FEATURE:
<223> OTHER INFORMATION: chemically synthesized

<400> SEQUENCE: 300

Ala Val Gly Pro Ala Gly Cys Trp Trp Asn Tyr Val His Ile Phe Met
1 5 10 15

Glu Cys

<210> SEQ ID NO 301
<211> LENGTH: 18
<212> TYPE: PRT
<213> ORGANISM: Artificial Sequence
<220> FEATURE:
<223> OTHER INFORMATION: chemically synthesized

<400> SEQUENCE: 301

Cys Thr Trp Asn Tyr Val His Ile Phe Met Asp Cys Gly Glu Gly Glu
1 5 10 15

Gly Pro

<210> SEQ ID NO 302
<211> LENGTH: 18
<212> TYPE: PRT
<213> ORGANISM: Artificial Sequence
<220> FEATURE:
<223> OTHER INFORMATION: chemically synthesized

<400> SEQUENCE: 302

Gly Gly Val Pro Glu Gly Cys Thr Trp Asn Tyr Ala His Ile Phe Met
1 5 10 15

Glu Cys

<210> SEQ ID NO 303
<211> LENGTH: 18
<212> TYPE: PRT
<213> ORGANISM: Artificial Sequence
<220> FEATURE:
<223> OTHER INFORMATION: chemically synthesized

<400> SEQUENCE: 303

Ala Glu Val Pro Ala Gly Cys Trp Trp Asn Tyr Val His Ile Phe Met
1 5 10 15

Glu Cys

<210> SEQ ID NO 304
<211> LENGTH: 18
<212> TYPE: PRT
<213> ORGANISM: Artificial Sequence
<220> FEATURE:
<223> OTHER INFORMATION: chemically synthesized

<400> SEQUENCE: 304

Ala Gly Val Pro Ala Gly Cys Thr Trp Asn Tyr Val His Ile Phe Met
1 5 10 15

Glu Cys

<210> SEQ ID NO 305
<211> LENGTH: 18
<212> TYPE: PRT
<213> ORGANISM: Artificial Sequence
<220> FEATURE:
<223> OTHER INFORMATION: chemically synthesized

<400> SEQUENCE: 305

Ser Gly Ala Ser Gly Gly Cys Lys Trp Asn Tyr Val His Ile Phe Met
1 5 10 15

Asp Cys

<210> SEQ ID NO 306
<211> LENGTH: 18
<212> TYPE: PRT
<213> ORGANISM: Artificial Sequence
<220> FEATURE:
<223> OTHER INFORMATION: chemically synthesized

<400> SEQUENCE: 306

Thr Pro Gly Cys Arg Trp Asn Tyr Val His Ile Phe Met Glu Cys Glu
1 5 10 15

Ala Leu

<210> SEQ ID NO 307
<211> LENGTH: 18
<212> TYPE: PRT
<213> ORGANISM: Artificial Sequence
<220> FEATURE:
<223> OTHER INFORMATION: chemically synthesized

<400> SEQUENCE: 307

Val Gly Val Pro Asn Gly Cys Val Trp Asn Tyr Ala His Ile Phe Met
1 5 10 15

Glu Cys

<210> SEQ ID NO 308
<211> LENGTH: 16
<212> TYPE: PRT
<213> ORGANISM: Artificial Sequence
<220> FEATURE:
<223> OTHER INFORMATION: chemically synthesized

<400> SEQUENCE: 308

Pro Gly Ala Phe Asp Ile Pro Phe Pro Ala His Trp Val Pro Asn Thr
1 5 10 15

<210> SEQ ID NO 309
<211> LENGTH: 16
<212> TYPE: PRT
<213> ORGANISM: Artificial Sequence
<220> FEATURE:
<223> OTHER INFORMATION: chemically synthesized

<400> SEQUENCE: 309

Arg Gly Ala Cys Asp Ile Pro Phe Pro Ala His Trp Ile Pro Asn Thr
1 5 10 15

<210> SEQ ID NO 310
<211> LENGTH: 16
<212> TYPE: PRT
<213> ORGANISM: Artificial Sequence
<220> FEATURE:
<223> OTHER INFORMATION: chemically synthesized

<400> SEQUENCE: 310

Gln Gly Asp Phe Asp Ile Pro Phe Pro Ala His Trp Val Pro Ile Thr
1 5 10 15

<210> SEQ ID NO 311
<211> LENGTH: 16
<212> TYPE: PRT
<213> ORGANISM: Artificial Sequence
<220> FEATURE:
<223> OTHER INFORMATION: chemically synthesized
<220> FEATURE:

<221> NAME/KEY: MISC_FEATURE
<222> LOCATION: (1)..(1)
<223> OTHER INFORMATION: X is any amino acid

<400> SEQUENCE: 311

Xaa Gly Ala Phe Asp Ile Pro Phe Pro Ala His Trp Val Pro Asn Thr
1 5 10 15

<210> SEQ ID NO 312
<211> LENGTH: 19
<212> TYPE: PRT
<213> ORGANISM: Artificial Sequence
<220> FEATURE:
<223> OTHER INFORMATION: chemically synthesized

<400> SEQUENCE: 312

Arg Gly Asp Gly Asn Asp Ser Asp Ile Pro Phe Pro Ala His Trp Val
1 5 10 15

Pro Arg Thr

<210> SEQ ID NO 313
<211> LENGTH: 19
<212> TYPE: PRT
<213> ORGANISM: Artificial Sequence
<220> FEATURE:
<223> OTHER INFORMATION: chemically synthesized

<400> SEQUENCE: 313

Ser Gly Val Gly Arg Asp Arg Asp Ile Pro Phe Pro Ala His Trp Val
1 5 10 15

Pro Arg Thr

<210> SEQ ID NO 314
<211> LENGTH: 19
<212> TYPE: PRT
<213> ORGANISM: Artificial Sequence
<220> FEATURE:
<223> OTHER INFORMATION: chemically synthesized

<400> SEQUENCE: 314

Trp Ala Gly Gly Asn Asp Cys Asp Ile Pro Phe Pro Ala His Trp Ile
1 5 10 15

Pro Asn Thr

<210> SEQ ID NO 315
<211> LENGTH: 19
<212> TYPE: PRT
<213> ORGANISM: Artificial Sequence
<220> FEATURE:
<223> OTHER INFORMATION: chemically synthesized

<400> SEQUENCE: 315

Trp Gly Asp Gly Met Asp Val Asp Ile Pro Phe Pro Ala His Trp Val
1 5 10 15

Pro Val Thr

<210> SEQ ID NO 316
<211> LENGTH: 19
<212> TYPE: PRT
<213> ORGANISM: Artificial Sequence
<220> FEATURE:
<223> OTHER INFORMATION: chemically synthesized

<400> SEQUENCE: 316

Ala Gly Ser Gly Asn Asp Ser Asp Ile Pro Phe Pro Ala His Trp Val
1               5                   10                  15

Pro Arg Thr

<210> SEQ ID NO 317
<211> LENGTH: 19
<212> TYPE: PRT
<213> ORGANISM: Artificial Sequence
<220> FEATURE:
<223> OTHER INFORMATION: chemically synthesized

<400> SEQUENCE: 317

Glu Ser Arg Ser Gly Tyr Ala Asp Ile Pro Phe Pro Ala His Trp Val
1               5                   10                  15

Pro Arg Thr

<210> SEQ ID NO 318
<211> LENGTH: 19
<212> TYPE: PRT
<213> ORGANISM: Artificial Sequence
<220> FEATURE:
<223> OTHER INFORMATION: chemically synthesized

<400> SEQUENCE: 318

Arg Glu Cys Gly Arg Cys Gly Asp Ile Pro Phe Pro Ala His Trp Val
1               5                   10                  15

Pro Arg Thr

<210> SEQ ID NO 319
<211> LENGTH: 8
<212> TYPE: PRT
<213> ORGANISM: Artificial Sequence
<220> FEATURE:
<223> OTHER INFORMATION: chemically synthesized

<400> SEQUENCE: 319

Pro Arg Phe Lys Ile Ile Gly Gly
1               5

<210> SEQ ID NO 320
<211> LENGTH: 8
<212> TYPE: PRT
<213> ORGANISM: Artificial Sequence
<220> FEATURE:
<223> OTHER INFORMATION: chemically synthesized

<400> SEQUENCE: 320

Pro Arg Phe Arg Ile Ile Gly Gly
1               5

<210> SEQ ID NO 321
<211> LENGTH: 9
<212> TYPE: PRT
<213> ORGANISM: Artificial Sequence
<220> FEATURE:
<223> OTHER INFORMATION: chemically synthesized

<400> SEQUENCE: 321

Ser Ser Arg His Arg Arg Ala Leu Asp
1               5

<210> SEQ ID NO 322
<211> LENGTH: 14
<212> TYPE: PRT
<213> ORGANISM: Artificial Sequence
<220> FEATURE:
<223> OTHER INFORMATION: chemically synthesized

<400> SEQUENCE: 322

Arg Lys Ser Ser Ile Ile Ile Arg Met Arg Asp Val Val Leu
1 5 10

<210> SEQ ID NO 323
<211> LENGTH: 15
<212> TYPE: PRT
<213> ORGANISM: Artificial Sequence
<220> FEATURE:
<223> OTHER INFORMATION: chemically synthesized

<400> SEQUENCE: 323

Ser Ser Ser Phe Asp Lys Gly Lys Tyr Lys Lys Gly Asp Asp Ala
1 5 10 15

<210> SEQ ID NO 324
<211> LENGTH: 15
<212> TYPE: PRT
<213> ORGANISM: Artificial Sequence
<220> FEATURE:
<223> OTHER INFORMATION: chemically synthesized

<400> SEQUENCE: 324

Ser Ser Ser Phe Asp Lys Gly Lys Tyr Lys Arg Gly Asp Asp Ala
1 5 10 15

<210> SEQ ID NO 325
<211> LENGTH: 4
<212> TYPE: PRT
<213> ORGANISM: Artificial Sequence
<220> FEATURE:
<223> OTHER INFORMATION: chemically synthesized

<400> SEQUENCE: 325

Ile Glu Gly Arg
1

<210> SEQ ID NO 326
<211> LENGTH: 4
<212> TYPE: PRT
<213> ORGANISM: Artificial Sequence
<220> FEATURE:
<223> OTHER INFORMATION: chemically synthesized

<400> SEQUENCE: 326

Ile Asp Gly Arg
1

<210> SEQ ID NO 327
<211> LENGTH: 7
<212> TYPE: PRT
<213> ORGANISM: Artificial Sequence
<220> FEATURE:
<223> OTHER INFORMATION: chemically synthesized

<400> SEQUENCE: 327

Gly Gly Ser Ile Asp Gly Arg
1 5

<210> SEQ ID NO 328
<211> LENGTH: 6
<212> TYPE: PRT
<213> ORGANISM: Artificial Sequence
<220> FEATURE:

<223> OTHER INFORMATION: chemically synthesized

<400> SEQUENCE: 328

Pro Leu Gly Leu Trp Ala
1               5

<210> SEQ ID NO 329
<211> LENGTH: 8
<212> TYPE: PRT
<213> ORGANISM: Artificial Sequence
<220> FEATURE:
<223> OTHER INFORMATION: chemically synthesized

<400> SEQUENCE: 329

Gly Pro Gln Gly Ile Ala Gly Gln
1               5

<210> SEQ ID NO 330
<211> LENGTH: 8
<212> TYPE: PRT
<213> ORGANISM: Artificial Sequence
<220> FEATURE:
<223> OTHER INFORMATION: chemically synthesized

<400> SEQUENCE: 330

Gly Pro Gln Gly Leu Leu Gly Ala
1               5

<210> SEQ ID NO 331
<211> LENGTH: 5
<212> TYPE: PRT
<213> ORGANISM: Artificial Sequence
<220> FEATURE:
<223> OTHER INFORMATION: chemically synthesized

<400> SEQUENCE: 331

Gly Ile Ala Gly Gln
1               5

<210> SEQ ID NO 332
<211> LENGTH: 8
<212> TYPE: PRT
<213> ORGANISM: Artificial Sequence
<220> FEATURE:
<223> OTHER INFORMATION: chemically synthesized

<400> SEQUENCE: 332

Gly Pro Leu Gly Ile Ala Gly Ile
1               5

<210> SEQ ID NO 333
<211> LENGTH: 8
<212> TYPE: PRT
<213> ORGANISM: Artificial Sequence
<220> FEATURE:
<223> OTHER INFORMATION: chemically synthesized

<400> SEQUENCE: 333

Gly Pro Glu Gly Leu Arg Val Gly
1               5

<210> SEQ ID NO 334
<211> LENGTH: 8
<212> TYPE: PRT
<213> ORGANISM: Artificial Sequence
<220> FEATURE:
<223> OTHER INFORMATION: chemically synthesized

<400> SEQUENCE: 334

Tyr Gly Ala Gly Leu Gly Val Val
1               5

<210> SEQ ID NO 335
<211> LENGTH: 8
<212> TYPE: PRT
<213> ORGANISM: Artificial Sequence
<220> FEATURE:
<223> OTHER INFORMATION: chemically synthesized

<400> SEQUENCE: 335

Ala Gly Leu Gly Val Val Glu Arg
1               5

<210> SEQ ID NO 336
<211> LENGTH: 8
<212> TYPE: PRT
<213> ORGANISM: Artificial Sequence
<220> FEATURE:
<223> OTHER INFORMATION: chemically synthesized

<400> SEQUENCE: 336

Ala Gly Leu Gly Ile Ser Ser Thr
1               5

<210> SEQ ID NO 337
<211> LENGTH: 8
<212> TYPE: PRT
<213> ORGANISM: Artificial Sequence
<220> FEATURE:
<223> OTHER INFORMATION: chemically synthesized

<400> SEQUENCE: 337

Glu Pro Gln Ala Leu Ala Met Ser
1               5

<210> SEQ ID NO 338
<211> LENGTH: 8
<212> TYPE: PRT
<213> ORGANISM: Artificial Sequence
<220> FEATURE:
<223> OTHER INFORMATION: chemically synthesized

<400> SEQUENCE: 338

Gln Ala Leu Ala Met Ser Ala Ile
1               5

<210> SEQ ID NO 339
<211> LENGTH: 8
<212> TYPE: PRT
<213> ORGANISM: Artificial Sequence
<220> FEATURE:
<223> OTHER INFORMATION: chemically synthesized

<400> SEQUENCE: 339

Ala Ala Tyr His Leu Val Ser Gln
1               5

<210> SEQ ID NO 340
<211> LENGTH: 8
<212> TYPE: PRT
<213> ORGANISM: Artificial Sequence
<220> FEATURE:
<223> OTHER INFORMATION: chemically synthesized

<400> SEQUENCE: 340

Met Asp Ala Phe Leu Glu Ser Ser
1 5

<210> SEQ ID NO 341
<211> LENGTH: 8
<212> TYPE: PRT
<213> ORGANISM: Artificial Sequence
<220> FEATURE:
<223> OTHER INFORMATION: chemically synthesized

<400> SEQUENCE: 341

Glu Ser Leu Pro Val Val Ala Val
1 5

<210> SEQ ID NO 342
<211> LENGTH: 8
<212> TYPE: PRT
<213> ORGANISM: Artificial Sequence
<220> FEATURE:
<223> OTHER INFORMATION: chemically synthesized

<400> SEQUENCE: 342

Ser Ala Pro Ala Val Glu Ser Glu
1 5

<210> SEQ ID NO 343
<211> LENGTH: 8
<212> TYPE: PRT
<213> ORGANISM: Artificial Sequence
<220> FEATURE:
<223> OTHER INFORMATION: chemically synthesized

<400> SEQUENCE: 343

Asp Val Ala Gln Phe Val Leu Thr
1 5

<210> SEQ ID NO 344
<211> LENGTH: 8
<212> TYPE: PRT
<213> ORGANISM: Artificial Sequence
<220> FEATURE:
<223> OTHER INFORMATION: chemically synthesized

<400> SEQUENCE: 344

Val Ala Gln Phe Val Leu Thr Glu
1 5

<210> SEQ ID NO 345
<211> LENGTH: 8
<212> TYPE: PRT
<213> ORGANISM: Artificial Sequence
<220> FEATURE:
<223> OTHER INFORMATION: chemically synthesized

<400> SEQUENCE: 345

Ala Gln Phe Val Leu Thr Glu Gly
1 5

<210> SEQ ID NO 346
<211> LENGTH: 8
<212> TYPE: PRT
<213> ORGANISM: Artificial Sequence
<220> FEATURE:
<223> OTHER INFORMATION: chemically synthesized

<400> SEQUENCE: 346

Pro Val Gln Pro Ile Gly Pro Gln
1 5

<210> SEQ ID NO 347
<211> LENGTH: 273
<212> TYPE: PRT
<213> ORGANISM: Artificial Sequence
<220> FEATURE:
<223> OTHER INFORMATION: chemically synthesized

<400> SEQUENCE: 347

Gly Gly Gly Ser Gly Gly Gly Gly Ser Gly Ser Gly Gly Gly Ser Gly
1 5 10 15

Gly Gly Gly Ser Gly Gly Gly Glu Ile Val Leu Thr Gln Ser Pro Gly
20 25 30

Thr Leu Ser Leu Ser Pro Gly Glu Arg Ala Thr Leu Ser Cys Arg Ala
35 40 45

Ser Gln Ser Val Ser Ser Ser Tyr Leu Ala Trp Tyr Gln Gln Lys Pro
50 55 60

Gly Gln Ala Pro Arg Leu Leu Ile Tyr Gly Ala Ser Ser Arg Ala Thr
65 70 75 80

Gly Ile Pro Asp Arg Phe Ser Gly Ser Gly Ser Gly Thr Asp Phe Thr
85 90 95

Leu Thr Ile Ser Arg Leu Glu Pro Glu Asp Phe Ala Val Tyr Tyr Cys
100 105 110

Gln Gln Tyr Gly Ser Ser Pro Leu Thr Phe Gly Gly Gly Thr Lys Val
115 120 125

Glu Ile Lys Arg Ser Gly Gly Ser Thr Ile Thr Ser Tyr Asn Val Tyr
130 135 140

Tyr Thr Lys Leu Ser Ser Ser Gly Thr Gln Val Gln Leu Val Gln Thr
145 150 155 160

Gly Gly Gly Val Val Gln Pro Gly Arg Ser Leu Arg Leu Ser Cys Ala
165 170 175

Ala Ser Gly Ser Thr Phe Ser Ser Tyr Ala Met Ser Trp Val Arg Gln
180 185 190

Ala Pro Gly Lys Gly Leu Glu Trp Val Ser Ala Ile Ser Gly Ser Gly
195 200 205

Gly Ser Thr Tyr Tyr Ala Asp Ser Val Lys Gly Arg Phe Thr Ile Ser
210 215 220

Arg Asp Asn Ser Lys Asn Thr Leu Tyr Leu Gln Met Asn Ser Leu Arg
225 230 235 240

Ala Glu Asp Thr Ala Val Tyr Tyr Cys Ala Thr Asn Ser Leu Tyr Trp
245 250 255

Tyr Phe Asp Leu Trp Gly Arg Gly Thr Leu Val Thr Val Ser Ser Ala
260 265 270

Ser

<210> SEQ ID NO 348

<400> SEQUENCE: 348

000

<210> SEQ ID NO 349
<211> LENGTH: 264
<212> TYPE: PRT
<213> ORGANISM: Artificial Sequence
<220> FEATURE:
<223> OTHER INFORMATION: chemically synthesized

<400> SEQUENCE: 349

```
Gly Gly Gly Ser Gly Gly Gly Gly Ser Gly Ser Gly Gly Gly Ser Gly
1               5                   10                  15

Gly Gly Gly Ser Gly Gly Gly Gln Val Gln Leu Gln Gln Ser Gly Ala
            20                  25                  30

Glu Leu Ala Arg Pro Gly Ala Ser Val Lys Met Ser Cys Lys Ala Ser
        35                  40                  45

Gly Tyr Thr Phe Thr Arg Tyr Thr Met His Trp Val Lys Gln Arg Pro
    50                  55                  60

Gly Gln Gly Leu Glu Trp Ile Gly Tyr Ile Asn Pro Ser Arg Gly Tyr
65                  70                  75                  80

Thr Asn Tyr Asn Gln Lys Phe Lys Asp Lys Ala Thr Leu Thr Thr Asp
                85                  90                  95

Lys Ser Ser Ser Thr Ala Tyr Met Gln Leu Ser Ser Leu Thr Ser Glu
            100                 105                 110

Asp Ser Ala Val Tyr Tyr Cys Ala Arg Tyr Tyr Asp Asp His Tyr Cys
        115                 120                 125

Leu Asp Tyr Trp Gly Gln Gly Thr Thr Leu Thr Val Ser Ser Gly Gly
    130                 135                 140

Gly Gly Ser Gly Gly Gly Gly Ser Gly Gly Gly Gly Ser Gln Ile Val
145                 150                 155                 160

Leu Thr Gln Ser Pro Ala Ile Met Ser Ala Ser Pro Gly Glu Lys Val
                165                 170                 175

Thr Met Thr Cys Ser Ala Ser Ser Ser Val Ser Tyr Met Asn Trp Tyr
            180                 185                 190

Gln Gln Lys Ser Gly Thr Ser Pro Lys Arg Trp Ile Tyr Asp Thr Ser
        195                 200                 205

Lys Leu Ala Ser Gly Val Pro Ala His Phe Arg Gly Ser Gly Ser Gly
    210                 215                 220

Thr Ser Tyr Ser Leu Thr Ile Ser Gly Met Glu Ala Glu Asp Ala Ala
225                 230                 235                 240

Thr Tyr Tyr Cys Gln Gln Trp Ser Ser Asn Pro Phe Thr Phe Gly Ser
                245                 250                 255

Gly Thr Lys Leu Glu Ile Asn Arg
            260
```

<210> SEQ ID NO 350
<211> LENGTH: 6
<212> TYPE: PRT
<213> ORGANISM: Artificial Sequence
<220> FEATURE:
<223> OTHER INFORMATION: chemically synthesized

<400> SEQUENCE: 350

```
Gly Gly Ser Gly Gly Ser
1               5
```

<210> SEQ ID NO 351
<211> LENGTH: 8
<212> TYPE: PRT
<213> ORGANISM: Artificial Sequence
<220> FEATURE:
<223> OTHER INFORMATION: chemically synthesized

<400> SEQUENCE: 351

Ala Gln Asn Leu Leu Gly Met Val
1 5

<210> SEQ ID NO 352
<211> LENGTH: 8
<212> TYPE: PRT
<213> ORGANISM: Artificial Sequence
<220> FEATURE:
<223> OTHER INFORMATION: chemically synthesized

<400> SEQUENCE: 352

Ser Thr Phe Pro Phe Gly Met Phe
1 5

<210> SEQ ID NO 353
<211> LENGTH: 8
<212> TYPE: PRT
<213> ORGANISM: Artificial Sequence
<220> FEATURE:
<223> OTHER INFORMATION: chemically synthesized

<400> SEQUENCE: 353

Pro Val Gly Tyr Thr Ser Ser Leu
1 5

<210> SEQ ID NO 354
<211> LENGTH: 8
<212> TYPE: PRT
<213> ORGANISM: Artificial Sequence
<220> FEATURE:
<223> OTHER INFORMATION: chemically synthesized

<400> SEQUENCE: 354

Asp Trp Leu Tyr Trp Pro Gly Ile
1 5

<210> SEQ ID NO 355
<211> LENGTH: 8
<212> TYPE: PRT
<213> ORGANISM: Artificial Sequence
<220> FEATURE:
<223> OTHER INFORMATION: chemically synthesized

<400> SEQUENCE: 355

Met Ile Ala Pro Val Ala Tyr Arg
1 5

<210> SEQ ID NO 356
<211> LENGTH: 8
<212> TYPE: PRT
<213> ORGANISM: Artificial Sequence
<220> FEATURE:
<223> OTHER INFORMATION: chemically synthesized

<400> SEQUENCE: 356

Arg Pro Ser Pro Met Trp Ala Tyr
1 5

<210> SEQ ID NO 357
<211> LENGTH: 8
<212> TYPE: PRT
<213> ORGANISM: Artificial Sequence
<220> FEATURE:
<223> OTHER INFORMATION: chemically synthesized

<400> SEQUENCE: 357

Trp Ala Thr Pro Arg Pro Met Arg 1 5

<210> SEQ ID NO 358
<211> LENGTH: 8
<212> TYPE: PRT
<213> ORGANISM: Artificial Sequence
<220> FEATURE:
<223> OTHER INFORMATION: chemically synthesized

<400> SEQUENCE: 358

Phe Arg Leu Leu Asp Trp Gln Trp
1 5

<210> SEQ ID NO 359
<211> LENGTH: 8
<212> TYPE: PRT
<213> ORGANISM: Artificial Sequence
<220> FEATURE:
<223> OTHER INFORMATION: chemically synthesized

<400> SEQUENCE: 359

Leu Lys Ala Ala Pro Arg Trp Ala
1 5

<210> SEQ ID NO 360
<211> LENGTH: 8
<212> TYPE: PRT
<213> ORGANISM: Artificial Sequence
<220> FEATURE:
<223> OTHER INFORMATION: chemically synthesized

<400> SEQUENCE: 360

Gly Pro Ser His Leu Val Leu Thr
1 5

<210> SEQ ID NO 361
<211> LENGTH: 8
<212> TYPE: PRT
<213> ORGANISM: Artificial Sequence
<220> FEATURE:
<223> OTHER INFORMATION: chemically synthesized

<400> SEQUENCE: 361

Leu Pro Gly Gly Leu Ser Pro Trp
1 5

<210> SEQ ID NO 362
<211> LENGTH: 8
<212> TYPE: PRT
<213> ORGANISM: Artificial Sequence
<220> FEATURE:
<223> OTHER INFORMATION: chemically synthesized

<400> SEQUENCE: 362

Met Gly Leu Phe Ser Glu Ala Gly
1 5

<210> SEQ ID NO 363
<211> LENGTH: 8
<212> TYPE: PRT
<213> ORGANISM: Artificial Sequence
<220> FEATURE:
<223> OTHER INFORMATION: chemically synthesized

<400> SEQUENCE: 363

Ser Pro Leu Pro Leu Arg Val Pro
1 5

<210> SEQ ID NO 364
<211> LENGTH: 8
<212> TYPE: PRT
<213> ORGANISM: Artificial Sequence
<220> FEATURE:
<223> OTHER INFORMATION: chemically synthesized

<400> SEQUENCE: 364

Arg Met His Leu Arg Ser Leu Gly
1 5

<210> SEQ ID NO 365
<211> LENGTH: 8
<212> TYPE: PRT
<213> ORGANISM: Artificial Sequence
<220> FEATURE:
<223> OTHER INFORMATION: chemically synthesized

<400> SEQUENCE: 365

Leu Ala Ala Pro Leu Gly Leu Leu
1 5

<210> SEQ ID NO 366
<211> LENGTH: 8
<212> TYPE: PRT
<213> ORGANISM: Artificial Sequence
<220> FEATURE:
<223> OTHER INFORMATION: chemically synthesized

<400> SEQUENCE: 366

Ala Val Gly Leu Leu Ala Pro Pro
1 5

<210> SEQ ID NO 367
<211> LENGTH: 8
<212> TYPE: PRT
<213> ORGANISM: Artificial Sequence
<220> FEATURE:
<223> OTHER INFORMATION: chemically synthesized

<400> SEQUENCE: 367

Leu Leu Ala Pro Ser His Arg Ala
1 5

<210> SEQ ID NO 368
<211> LENGTH: 8
<212> TYPE: PRT
<213> ORGANISM: Artificial Sequence
<220> FEATURE:
<223> OTHER INFORMATION: chemically synthesized

<400> SEQUENCE: 368

Pro Ala Gly Leu Trp Leu Asp Pro
1 5

<210> SEQ ID NO 369
<211> LENGTH: 7
<212> TYPE: PRT
<213> ORGANISM: Artificial Sequence
<220> FEATURE:
<223> OTHER INFORMATION: chemically synthesized

<400> SEQUENCE: 369

Ile Ser Ser Gly Leu Ser Ser
1 5

<210> SEQ ID NO 370
<211> LENGTH: 8
<212> TYPE: PRT
<213> ORGANISM: Artificial Sequence
<220> FEATURE:
<223> OTHER INFORMATION: chemically synthesized

<400> SEQUENCE: 370

Thr Gly Arg Gly Pro Ser Trp Val
1               5

<210> SEQ ID NO 371
<211> LENGTH: 8
<212> TYPE: PRT
<213> ORGANISM: Artificial Sequence
<220> FEATURE:
<223> OTHER INFORMATION: chemically synthesized

<400> SEQUENCE: 371

Ser Ala Arg Gly Pro Ser Arg Trp
1               5

<210> SEQ ID NO 372
<211> LENGTH: 8
<212> TYPE: PRT
<213> ORGANISM: Artificial Sequence
<220> FEATURE:
<223> OTHER INFORMATION: chemically synthesized

<400> SEQUENCE: 372

Thr Ala Arg Gly Pro Ser Phe Lys
1               5

<210> SEQ ID NO 373
<211> LENGTH: 8
<212> TYPE: PRT
<213> ORGANISM: Artificial Sequence
<220> FEATURE:
<223> OTHER INFORMATION: chemically synthesized

<400> SEQUENCE: 373

Gly Gly Trp His Thr Gly Arg Asn
1               5

<210> SEQ ID NO 374
<211> LENGTH: 8
<212> TYPE: PRT
<213> ORGANISM: Artificial Sequence
<220> FEATURE:
<223> OTHER INFORMATION: chemically synthesized

<400> SEQUENCE: 374

His Thr Gly Arg Ser Gly Ala Leu
1               5

<210> SEQ ID NO 375
<211> LENGTH: 8
<212> TYPE: PRT
<213> ORGANISM: Artificial Sequence
<220> FEATURE:
<223> OTHER INFORMATION: chemically synthesized

<400> SEQUENCE: 375

Pro Leu Thr Gly Arg Ser Gly Gly
1               5

<210> SEQ ID NO 376
<211> LENGTH: 8
<212> TYPE: PRT
<213> ORGANISM: Artificial Sequence
<220> FEATURE:
<223> OTHER INFORMATION: chemically synthesized

<400> SEQUENCE: 376

Ala Ala Arg Gly Pro Ala Ile His
1               5

<210> SEQ ID NO 377
<211> LENGTH: 8
<212> TYPE: PRT
<213> ORGANISM: Artificial Sequence
<220> FEATURE:
<223> OTHER INFORMATION: chemically synthesized

<400> SEQUENCE: 377

Arg Gly Pro Ala Phe Asn Pro Met
1               5

<210> SEQ ID NO 378
<211> LENGTH: 8
<212> TYPE: PRT
<213> ORGANISM: Artificial Sequence
<220> FEATURE:
<223> OTHER INFORMATION: chemically synthesized

<400> SEQUENCE: 378

Ser Ser Arg Gly Pro Ala Tyr Leu
1               5

<210> SEQ ID NO 379
<211> LENGTH: 8
<212> TYPE: PRT
<213> ORGANISM: Artificial Sequence
<220> FEATURE:
<223> OTHER INFORMATION: chemically synthesized

<400> SEQUENCE: 379

Arg Gly Pro Ala Thr Pro Ile Met
1               5

<210> SEQ ID NO 380
<211> LENGTH: 4
<212> TYPE: PRT
<213> ORGANISM: Artificial Sequence
<220> FEATURE:
<223> OTHER INFORMATION: chemically synthesized

<400> SEQUENCE: 380

Arg Gly Pro Ala
1

<210> SEQ ID NO 381
<211> LENGTH: 5
<212> TYPE: PRT
<213> ORGANISM: Artificial Sequence
<220> FEATURE:
<223> OTHER INFORMATION: chemically synthesized

<400> SEQUENCE: 381

Gly Ser Gly Gly Ser
1               5

<210> SEQ ID NO 382

<211> LENGTH: 4
<212> TYPE: PRT
<213> ORGANISM: Artificial Sequence
<220> FEATURE:
<223> OTHER INFORMATION: chemically synthesized

<400> SEQUENCE: 382

Gly Gly Gly Ser
1

<210> SEQ ID NO 383
<211> LENGTH: 4
<212> TYPE: PRT
<213> ORGANISM: Artificial Sequence
<220> FEATURE:
<223> OTHER INFORMATION: chemically synthesized

<400> SEQUENCE: 383

Gly Gly Ser Gly
1

<210> SEQ ID NO 384
<211> LENGTH: 5
<212> TYPE: PRT
<213> ORGANISM: Artificial Sequence
<220> FEATURE:
<223> OTHER INFORMATION: chemically synthesized

<400> SEQUENCE: 384

Gly Gly Ser Gly Gly
1 5

<210> SEQ ID NO 385
<211> LENGTH: 5
<212> TYPE: PRT
<213> ORGANISM: Artificial Sequence
<220> FEATURE:
<223> OTHER INFORMATION: chemically synthesized

<400> SEQUENCE: 385

Gly Ser Gly Ser Gly
1 5

<210> SEQ ID NO 386
<211> LENGTH: 5
<212> TYPE: PRT
<213> ORGANISM: Artificial Sequence
<220> FEATURE:
<223> OTHER INFORMATION: chemically synthesized

<400> SEQUENCE: 386

Gly Ser Gly Gly Gly
1 5

<210> SEQ ID NO 387
<211> LENGTH: 5
<212> TYPE: PRT
<213> ORGANISM: Artificial Sequence
<220> FEATURE:
<223> OTHER INFORMATION: chemically synthesized

<400> SEQUENCE: 387

Gly Gly Gly Ser Gly
1 5

<210> SEQ ID NO 388
<211> LENGTH: 5

<212> TYPE: PRT
<213> ORGANISM: Artificial Sequence
<220> FEATURE:
<223> OTHER INFORMATION: chemically synthesized

<400> SEQUENCE: 388

Gly Ser Ser Ser Gly
1               5

<210> SEQ ID NO 389
<211> LENGTH: 13
<212> TYPE: PRT
<213> ORGANISM: Artificial Sequence
<220> FEATURE:
<223> OTHER INFORMATION: chemically synthesized

<400> SEQUENCE: 389

Gly Ser Ser Gly Gly Ser Gly Gly Ser Gly Gly Ser Gly
1               5                   10

<210> SEQ ID NO 390
<211> LENGTH: 11
<212> TYPE: PRT
<213> ORGANISM: Artificial Sequence
<220> FEATURE:
<223> OTHER INFORMATION: chemically synthesized

<400> SEQUENCE: 390

Gly Ser Ser Gly Gly Ser Gly Gly Ser Gly Gly
1               5                   10

<210> SEQ ID NO 391
<211> LENGTH: 12
<212> TYPE: PRT
<213> ORGANISM: Artificial Sequence
<220> FEATURE:
<223> OTHER INFORMATION: chemically synthesized

<400> SEQUENCE: 391

Gly Ser Ser Gly Gly Ser Gly Gly Ser Gly Gly Ser
1               5                   10

<210> SEQ ID NO 392
<211> LENGTH: 16
<212> TYPE: PRT
<213> ORGANISM: Artificial Sequence
<220> FEATURE:
<223> OTHER INFORMATION: chemically synthesized

<400> SEQUENCE: 392

Gly Ser Ser Gly Gly Ser Gly Gly Ser Gly Gly Ser Gly Gly Gly Ser
1               5                   10                  15

<210> SEQ ID NO 393
<211> LENGTH: 10
<212> TYPE: PRT
<213> ORGANISM: Artificial Sequence
<220> FEATURE:
<223> OTHER INFORMATION: chemically synthesized

<400> SEQUENCE: 393

Gly Ser Ser Gly Gly Ser Gly Gly Ser Gly
1               5                   10

<210> SEQ ID NO 394
<211> LENGTH: 11
<212> TYPE: PRT

<213> ORGANISM: Artificial Sequence
<220> FEATURE:
<223> OTHER INFORMATION: chemically synthesized

<400> SEQUENCE: 394

Gly Ser Ser Gly Gly Ser Gly Gly Ser Gly Ser
1 5 10

<210> SEQ ID NO 395
<211> LENGTH: 4
<212> TYPE: PRT
<213> ORGANISM: Artificial Sequence
<220> FEATURE:
<223> OTHER INFORMATION: chemically synthesized

<400> SEQUENCE: 395

Gly Gly Gly Ser
1

<210> SEQ ID NO 396
<211> LENGTH: 5
<212> TYPE: PRT
<213> ORGANISM: Artificial Sequence
<220> FEATURE:
<223> OTHER INFORMATION: chemically synthesized

<400> SEQUENCE: 396

Gly Ser Ser Gly Thr
1 5

<210> SEQ ID NO 397
<211> LENGTH: 4
<212> TYPE: PRT
<213> ORGANISM: Artificial Sequence
<220> FEATURE:
<223> OTHER INFORMATION: chemically synthesized

<400> SEQUENCE: 397

Gly Ser Ser Gly
1

<210> SEQ ID NO 398
<211> LENGTH: 5
<212> TYPE: PRT
<213> ORGANISM: Artificial Sequence
<220> FEATURE:
<223> OTHER INFORMATION: chemically synthesized

<400> SEQUENCE: 398

Ser Tyr Ala Met Ser
1 5

<210> SEQ ID NO 399
<211> LENGTH: 17
<212> TYPE: PRT
<213> ORGANISM: Artificial Sequence
<220> FEATURE:
<223> OTHER INFORMATION: chemically synthesized

<400> SEQUENCE: 399

Ser Ile Asp Pro Glu Gly Arg Gln Thr Tyr Tyr Ala Asp Ser Val Lys
1 5 10 15

Gly

<210> SEQ ID NO 400
<211> LENGTH: 10

<212> TYPE: PRT
<213> ORGANISM: Artificial Sequence
<220> FEATURE:
<223> OTHER INFORMATION: chemically synthesized

<400> SEQUENCE: 400

Asp Ile Gly Gly Arg Ser Ala Phe Asp Tyr
1               5                   10

<210> SEQ ID NO 401
<211> LENGTH: 9
<212> TYPE: PRT
<213> ORGANISM: Artificial Sequence
<220> FEATURE:
<223> OTHER INFORMATION: chemically synthesized

<400> SEQUENCE: 401

Arg Ala Ser Gln Ser Ile Ser Ser Tyr
1               5

<210> SEQ ID NO 402
<211> LENGTH: 7
<212> TYPE: PRT
<213> ORGANISM: Artificial Sequence
<220> FEATURE:
<223> OTHER INFORMATION: chemically synthesized

<400> SEQUENCE: 402

Ala Ala Ser Ser Leu Gln Ser
1               5

<210> SEQ ID NO 403
<211> LENGTH: 9
<212> TYPE: PRT
<213> ORGANISM: Artificial Sequence
<220> FEATURE:
<223> OTHER INFORMATION: chemically synthesized

<400> SEQUENCE: 403

Gln Gln Thr Val Val Ala Pro Pro Leu
1               5

<210> SEQ ID NO 404
<211> LENGTH: 5
<212> TYPE: PRT
<213> ORGANISM: Artificial Sequence
<220> FEATURE:
<223> OTHER INFORMATION: chemically synthesized

<400> SEQUENCE: 404

Asn Tyr Gly Val His
1               5

<210> SEQ ID NO 405
<211> LENGTH: 16
<212> TYPE: PRT
<213> ORGANISM: Artificial Sequence
<220> FEATURE:
<223> OTHER INFORMATION: chemically synthesized

<400> SEQUENCE: 405

Val Ile Trp Ser Gly Gly Asn Thr Asp Tyr Asn Thr Pro Phe Thr Ser
1               5                   10                  15

<210> SEQ ID NO 406
<211> LENGTH: 11
<212> TYPE: PRT

<213> ORGANISM: Artificial Sequence
<220> FEATURE:
<223> OTHER INFORMATION: chemically synthesized

<400> SEQUENCE: 406

Ala Leu Thr Tyr Tyr Asp Tyr Glu Phe Ala Tyr
1 5 10

<210> SEQ ID NO 407
<211> LENGTH: 11
<212> TYPE: PRT
<213> ORGANISM: Artificial Sequence
<220> FEATURE:
<223> OTHER INFORMATION: chemically synthesized

<400> SEQUENCE: 407

Arg Ala Ser Gln Ser Ile Gly Thr Asn Ile His
1 5 10

<210> SEQ ID NO 408
<211> LENGTH: 8
<212> TYPE: PRT
<213> ORGANISM: Artificial Sequence
<220> FEATURE:
<223> OTHER INFORMATION: chemically synthesized

<400> SEQUENCE: 408

Lys Tyr Ala Ser Glu Ser Ile Ser
1 5

<210> SEQ ID NO 409
<211> LENGTH: 9
<212> TYPE: PRT
<213> ORGANISM: Artificial Sequence
<220> FEATURE:
<223> OTHER INFORMATION: chemically synthesized

<400> SEQUENCE: 409

Gln Gln Asn Asn Asn Trp Pro Thr Thr
1 5

<210> SEQ ID NO 410
<211> LENGTH: 6
<212> TYPE: PRT
<213> ORGANISM: Artificial Sequence
<220> FEATURE:
<223> OTHER INFORMATION: chemically synthesized

<400> SEQUENCE: 410

Gln Gly Gln Ser Gly Gln
1 5

<210> SEQ ID NO 411
<211> LENGTH: 10
<212> TYPE: PRT
<213> ORGANISM: Artificial Sequence
<220> FEATURE:
<223> OTHER INFORMATION: chemically synthesized

<400> SEQUENCE: 411

Val His Met Pro Leu Gly Phe Leu Gly Pro
1 5 10

<210> SEQ ID NO 412
<211> LENGTH: 8
<212> TYPE: PRT
<213> ORGANISM: Artificial Sequence
<220> FEATURE:
<223> OTHER INFORMATION: chemically synthesized

<400> SEQUENCE: 412

Leu Ser Gly Arg Ser Gly Asn His
1 5

<210> SEQ ID NO 413
<211> LENGTH: 12
<212> TYPE: PRT
<213> ORGANISM: Artificial Sequence
<220> FEATURE:
<223> OTHER INFORMATION: chemically synthesized

<400> SEQUENCE: 413

Thr Ser Thr Ser Gly Arg Ser Ala Asn Pro Arg Gly
1 5 10

<210> SEQ ID NO 414
<211> LENGTH: 8
<212> TYPE: PRT
<213> ORGANISM: Artificial Sequence
<220> FEATURE:
<223> OTHER INFORMATION: chemically synthesized

<400> SEQUENCE: 414

Thr Ser Gly Arg Ser Ala Asn Pro
1 5

<210> SEQ ID NO 415
<211> LENGTH: 8
<212> TYPE: PRT
<213> ORGANISM: Artificial Sequence
<220> FEATURE:
<223> OTHER INFORMATION: chemically synthesized

<400> SEQUENCE: 415

Val Ala Gly Arg Ser Met Arg Pro
1 5

<210> SEQ ID NO 416
<211> LENGTH: 5
<212> TYPE: PRT
<213> ORGANISM: Artificial Sequence
<220> FEATURE:
<223> OTHER INFORMATION: chemically synthesized

<400> SEQUENCE: 416

Gly Gln Ser Gly Gln
1 5

<210> SEQ ID NO 417
<211> LENGTH: 4
<212> TYPE: PRT
<213> ORGANISM: Artificial Sequence
<220> FEATURE:
<223> OTHER INFORMATION: chemically synthesized

<400> SEQUENCE: 417

Gln Ser Gly Gln
1

<210> SEQ ID NO 418
<211> LENGTH: 3
<212> TYPE: PRT
<213> ORGANISM: Artificial Sequence
<220> FEATURE:

<223> OTHER INFORMATION: chemically synthesized

<400> SEQUENCE: 418

Ser Gly Gln
1

<210> SEQ ID NO 419
<211> LENGTH: 756
<212> TYPE: DNA
<213> ORGANISM: Artificial Sequence
<220> FEATURE:
<223> OTHER INFORMATION: chemically synthesized

<400> SEQUENCE: 419

```
tgcaatattt ggctcgtagg tggtgattgc aggggctggc agggggctc gagcggcggc      60

tctatctctt ccggactgct gtccggcaga tccgacaatc acggcggagg ctctgacatc    120

cagatgaccc agtctccatc ctccctgtct gcatctgtag gagacagagt caccatcact    180

tgccgggcaa gtcagagcat tagcagctat ttaaattggt atcagcagaa accagggaaa    240

gcccctaagc tcctgatcta tgcggcatcc agtttgcaaa gtggggtccc atcaaggttc    300

agtggcagtg gatctgggac agatttcact ctcaccatca gcagtctgca acctgaagat    360

tttgcaactt actactgtca acagacggtt gtggcgcctc cgttattcgg ccaagggacc    420

aaggtggaaa tcaaacgtac ggtggctgca ccatctgtct tcatcttccc gccatctgat    480

gagcagttga aatctggaac tgcctctgtt gtgtgcctgc tgaataactt ctatcccaga    540

gaggccaaag tacagtggaa ggtggataac gccctccaat cgggtaactc ccaggagagt    600

gtcacagagc aggacagcaa ggacagcacc tacagcctca gcagcaccct gacgctgagc    660

aaagcagact acgagaaaca caaagtctac gcctgcgaag tcacccatca gggcctgagc    720

tcgcccgtca caaagagctt caacagggga gagtgt                              756
```

<210> SEQ ID NO 420
<211> LENGTH: 252
<212> TYPE: PRT
<213> ORGANISM: Artificial Sequence
<220> FEATURE:
<223> OTHER INFORMATION: chemically synthesized

<400> SEQUENCE: 420

```
Cys Asn Ile Trp Leu Val Gly Gly Asp Cys Arg Gly Trp Gln Gly Gly
1               5                   10                  15

Ser Ser Gly Gly Ser Ile Ser Ser Gly Leu Leu Ser Gly Arg Ser Asp
            20                  25                  30

Asn His Gly Gly Gly Ser Asp Ile Gln Met Thr Gln Ser Pro Ser Ser
        35                  40                  45

Leu Ser Ala Ser Val Gly Asp Arg Val Thr Ile Thr Cys Arg Ala Ser
    50                  55                  60

Gln Ser Ile Ser Ser Tyr Leu Asn Trp Tyr Gln Gln Lys Pro Gly Lys
65                  70                  75                  80

Ala Pro Lys Leu Leu Ile Tyr Ala Ala Ser Ser Leu Gln Ser Gly Val
                85                  90                  95

Pro Ser Arg Phe Ser Gly Ser Gly Ser Gly Thr Asp Phe Thr Leu Thr
            100                 105                 110

Ile Ser Ser Leu Gln Pro Glu Asp Phe Ala Thr Tyr Tyr Cys Gln Gln
        115                 120                 125

Thr Val Val Ala Pro Pro Leu Phe Gly Gln Gly Thr Lys Val Glu Ile
    130                 135                 140
```

```
Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250


<210> SEQ ID NO 421
<211> LENGTH: 783
<212> TYPE: DNA
<213> ORGANISM: Artificial Sequence
<220> FEATURE:
<223> OTHER INFORMATION: chemically synthesized

<400> SEQUENCE: 421

tgcaatattt ggctcgtagg tggtgattgc aggggctggc agggggggctc gagcggcggc      60

tctatctctt ctggcctgct gtctagcggc ggctccggcg gatctctgtc tggcagatct     120

gacaaccacg gcggaggctc cgacatccag atgacccagt ctccatcctc cctgtctgca     180

tctgtaggag acagagtcac catcacttgc cgggcaagtc agagcattag cagctattta     240

aattggtatc agcagaaacc agggaaagcc cctaagctcc tgatctatgc ggcatccagt     300

ttgcaaagtg gggtcccatc aaggttcagt ggcagtggat ctgggacaga tttcactctc     360

accatcagca gtctgcaacc tgaagatttt gcaacttact actgtcaaca gacggttgtg     420

gcgcctccgt tattcggcca agggaccaag gtggaaatca aacgtacggt ggctgcacca     480

tctgtcttca tcttcccgcc atctgatgag cagttgaaat ctggaactgc ctctgttgtg     540

tgcctgctga ataacttcta tcccagagag gccaaagtac agtggaaggt ggataacgcc     600

ctccaatcgg gtaactccca ggagagtgtc acagagcagg acagcaagga cagcacctac     660

agcctcagca gcaccctgac gctgagcaaa gcagactacg agaaacacaa agtctacgcc     720

tgcgaagtca cccatcaggg cctgagctcg cccgtcacaa agagcttcaa caggggagag     780

tgt                                                                   783


<210> SEQ ID NO 422
<211> LENGTH: 261
<212> TYPE: PRT
<213> ORGANISM: Artificial Sequence
<220> FEATURE:
<223> OTHER INFORMATION: chemically synthesized

<400> SEQUENCE: 422

Cys Asn Ile Trp Leu Val Gly Gly Asp Cys Arg Gly Trp Gln Gly Gly
1               5                   10                  15

Ser Ser Gly Gly Ser Ile Ser Ser Gly Leu Leu Ser Ser Gly Gly Ser
            20                  25                  30

Gly Gly Ser Leu Ser Gly Arg Ser Asp Asn His Gly Gly Gly Ser Asp
        35                  40                  45
```

```
Ile Gln Met Thr Gln Ser Pro Ser Ser Leu Ser Ala Ser Val Gly Asp
    50                  55                  60

Arg Val Thr Ile Thr Cys Arg Ala Ser Gln Ser Ile Ser Ser Tyr Leu
65                  70                  75                  80

Asn Trp Tyr Gln Gln Lys Pro Gly Lys Ala Pro Lys Leu Leu Ile Tyr
                85                  90                  95

Ala Ala Ser Ser Leu Gln Ser Gly Val Pro Ser Arg Phe Ser Gly Ser
            100                 105                 110

Gly Ser Gly Thr Asp Phe Thr Leu Thr Ile Ser Ser Leu Gln Pro Glu
        115                 120                 125

Asp Phe Ala Thr Tyr Tyr Cys Gln Gln Thr Val Val Ala Pro Pro Leu
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260
```

<210> SEQ ID NO 423
<211> LENGTH: 780
<212> TYPE: DNA
<213> ORGANISM: Artificial Sequence
<220> FEATURE:
<223> OTHER INFORMATION: chemically synthesized

<400> SEQUENCE: 423

```
tgcaatattt ggctcgtagg tggtgattgc aggggctggc agggggctc gagcggagga     60

tctgctgtgg gactgctggc tcctcctggc ggcacatcta cctctggcag atccgccaac    120

cctcggggcg gaggatctga catccagatg acccagtctc catcctccct gtctgcatct    180

gtaggagaca gagtcaccat cacttgccgg gcaagtcaga gcattagcag ctatttaaat    240

tggtatcagc agaaaccagg gaaagcccct aagctcctga tctatgcggc atccagtttg    300

caaagtgggg tcccatcaag gttcagtggc agtggatctg ggacagattt cactctcacc    360

atcagcagtc tgcaacctga agattttgca acttactact gtcaacagac ggttgtggcg    420

cctccgttat tcggccaagg gaccaaggtg gaaatcaaac gtacggtggc tgcaccatct    480

gtcttcatct tcccgccatc tgatgagcag ttgaaatctg gaactgcctc tgttgtgtgc    540

ctgctgaata acttctatcc cagagaggcc aaagtacagt ggaaggtgga taacgccctc    600

caatcgggta actcccagga gagtgtcaca gagcaggaca gcaaggacag cacctacagc    660

ctcagcagca ccctgacgct gagcaaagca gactacgaga aacacaaagt ctacgcctgc    720

gaagtcaccc atcagggcct gagctcgccc gtcacaaaga gcttcaacag gggagagtgt    780
```

<210> SEQ ID NO 424
<211> LENGTH: 260
<212> TYPE: PRT
<213> ORGANISM: Artificial Sequence
<220> FEATURE:
<223> OTHER INFORMATION: chemically synthesized

<400> SEQUENCE: 424

```
Cys Asn Ile Trp Leu Val Gly Gly Asp Cys Arg Gly Trp Gln Gly Gly
1               5                   10                  15

Ser Ser Gly Gly Ser Ala Val Gly Leu Leu Ala Pro Pro Gly Gly Thr
            20                  25                  30

Ser Thr Ser Gly Arg Ser Ala Asn Pro Arg Gly Gly Gly Ser Asp Ile
        35                  40                  45

Gln Met Thr Gln Ser Pro Ser Ser Leu Ser Ala Ser Val Gly Asp Arg
    50                  55                  60

Val Thr Ile Thr Cys Arg Ala Ser Gln Ser Ile Ser Ser Tyr Leu Asn
65                  70                  75                  80

Trp Tyr Gln Gln Lys Pro Gly Lys Ala Pro Lys Leu Leu Ile Tyr Ala
                85                  90                  95

Ala Ser Ser Leu Gln Ser Gly Val Pro Ser Arg Phe Ser Gly Ser Gly
            100                 105                 110

Ser Gly Thr Asp Phe Thr Leu Thr Ile Ser Ser Leu Gln Pro Glu Asp
        115                 120                 125

Phe Ala Thr Tyr Tyr Cys Gln Gln Thr Val Val Ala Pro Pro Leu Phe
    130                 135                 140

Gly Gln Gly Thr Lys Val Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260
```

<210> SEQ ID NO 425
<211> LENGTH: 780
<212> TYPE: DNA
<213> ORGANISM: Artificial Sequence
<220> FEATURE:
<223> OTHER INFORMATION: chemically synthesized

<400> SEQUENCE: 425

```
tgcaatattt ggctcgtagg tggtgattgc aggggctggc agggggggctc gagcggcggc      60

tccacatcta cctctggcag atccgccaac cccagaggtg gcggagctgt gggactgctg     120

gctccaccag gcggatctga catccagatg acccagtctc catcctccct gtctgcatct     180

gtaggagaca gagtcaccat cacttgccgg gcaagtcaga gcattagcag ctatttaaat     240

tggtatcagc agaaaccagg gaaagcccct aagctcctga tctatgcggc atccagtttg     300
```

```
caaagtgggg tcccatcaag gttcagtggc agtggatctg ggacagattt cactctcacc    360

atcagcagtc tgcaacctga agattttgca acttactact gtcaacagac ggttgtggcg    420

cctccgttat tcggccaagg gaccaaggtg gaaatcaaac gtacggtggc tgcaccatct    480

gtcttcatct tcccgccatc tgatgagcag ttgaaatctg gaactgcctc tgttgtgtgc    540

ctgctgaata acttctatcc cagagaggcc aaagtacagt ggaaggtgga taacgccctc    600

caatcgggta actcccagga gagtgtcaca gagcaggaca gcaaggacag cacctacagc    660

ctcagcagca ccctgacgct gagcaaagca gactacgaga aacacaaagt ctacgcctgc    720

gaagtcaccc atcagggcct gagctcgccc gtcacaaaga gcttcaacag gggagagtgt    780
```

```
<210> SEQ ID NO 426
<211> LENGTH: 260
<212> TYPE: PRT
<213> ORGANISM: Artificial Sequence
<220> FEATURE:
<223> OTHER INFORMATION: chemically synthesized

<400> SEQUENCE: 426

Cys Asn Ile Trp Leu Val Gly Gly Asp Cys Arg Gly Trp Gln Gly Gly
1               5                   10                  15

Ser Ser Gly Gly Ser Thr Ser Thr Ser Gly Arg Ser Ala Asn Pro Arg
            20                  25                  30

Gly Gly Gly Ala Val Gly Leu Leu Ala Pro Pro Gly Gly Ser Asp Ile
        35                  40                  45

Gln Met Thr Gln Ser Pro Ser Ser Leu Ser Ala Ser Val Gly Asp Arg
    50                  55                  60

Val Thr Ile Thr Cys Arg Ala Ser Gln Ser Ile Ser Ser Tyr Leu Asn
65                  70                  75                  80

Trp Tyr Gln Gln Lys Pro Gly Lys Ala Pro Lys Leu Leu Ile Tyr Ala
                85                  90                  95

Ala Ser Ser Leu Gln Ser Gly Val Pro Ser Arg Phe Ser Gly Ser Gly
            100                 105                 110

Ser Gly Thr Asp Phe Thr Leu Thr Ile Ser Ser Leu Gln Pro Glu Asp
        115                 120                 125

Phe Ala Thr Tyr Tyr Cys Gln Gln Thr Val Val Ala Pro Pro Leu Phe
    130                 135                 140

Gly Gln Gly Thr Lys Val Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260
```

<210> SEQ ID NO 427
<211> LENGTH: 786
<212> TYPE: DNA
<213> ORGANISM: Artificial Sequence
<220> FEATURE:
<223> OTHER INFORMATION: chemically synthesized

<400> SEQUENCE: 427

```
tgcaatattt ggctcgtagg tggtgattgc aggggctggc agggggctc gagcggcggc     60

tctgtgcata tgcccctggg ctttctgggc cctggcggca catctacctc tggcagatcc    120

gccaaccctc ggggcggagg atctgacatc cagatgaccc agtctccatc ctccctgtct    180

gcatctgtag gagacagagt caccatcact tgccgggcaa gtcagagcat tagcagctat    240

ttaaattggt atcagcagaa accagggaaa gcccctaagc tcctgatcta tgcggcatcc    300

agtttgcaaa gtggggtccc atcaaggttc agtggcagtg gatctgggac agatttcact    360

ctcaccatca gcagtctgca acctgaagat tttgcaactt actactgtca acagacggtt    420

gtggcgcctc cgttattcgg ccaagggacc aaggtggaaa tcaaacgtac ggtggctgca    480

ccatctgtct tcatcttccc gccatctgat gagcagttga aatctggaac tgcctctgtt    540

gtgtgcctgc tgaataactt ctatcccaga gaggccaaag tacagtggaa ggtggataac    600

gccctccaat cgggtaactc ccaggagagt gtcacagagc aggacagcaa ggacagcacc    660

tacagcctca gcagcaccct gacgctgagc aaagcagact acgagaaaca caaagtctac    720

gcctgcgaag tcacccatca gggcctgagc tcgcccgtca caaagagctt caacagggga    780

gagtgt                                                                786
```

<210> SEQ ID NO 428
<211> LENGTH: 262
<212> TYPE: PRT
<213> ORGANISM: Artificial Sequence
<220> FEATURE:
<223> OTHER INFORMATION: chemically synthesized

<400> SEQUENCE: 428

```
Cys Asn Ile Trp Leu Val Gly Gly Asp Cys Arg Gly Trp Gln Gly Gly
1               5                   10                  15

Ser Ser Gly Gly Ser Val His Met Pro Leu Gly Phe Leu Gly Pro Gly
            20                  25                  30

Gly Thr Ser Thr Ser Gly Arg Ser Ala Asn Pro Arg Gly Gly Gly Ser
        35                  40                  45

Asp Ile Gln Met Thr Gln Ser Pro Ser Ser Leu Ser Ala Ser Val Gly
    50                  55                  60

Asp Arg Val Thr Ile Thr Cys Arg Ala Ser Gln Ser Ile Ser Ser Tyr
65                  70                  75                  80

Leu Asn Trp Tyr Gln Gln Lys Pro Gly Lys Ala Pro Lys Leu Leu Ile
                85                  90                  95

Tyr Ala Ala Ser Ser Leu Gln Ser Gly Val Pro Ser Arg Phe Ser Gly
            100                 105                 110

Ser Gly Ser Gly Thr Asp Phe Thr Leu Thr Ile Ser Ser Leu Gln Pro
        115                 120                 125

Glu Asp Phe Ala Thr Tyr Tyr Cys Gln Gln Thr Val Val Ala Pro Pro
    130                 135                 140

Leu Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175
```

```
Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
            260


<210> SEQ ID NO 429
<211> LENGTH: 786
<212> TYPE: DNA
<213> ORGANISM: Artificial Sequence
<220> FEATURE:
<223> OTHER INFORMATION: chemically synthesized

<400> SEQUENCE: 429

tgcaatattt ggctcgtagg tggtgattgc aggggctggc agggggggctc gagcggcggc      60

tccacatcta cctctggcag atccgccaac cccagaggcg gcggagtgca tatgcctctg     120

ggctttctgg gacctggcgg ctctgacatc cagatgaccc agtctccatc ctccctgtct     180

gcatctgtag gagacagagt caccatcact tgccgggcaa gtcagagcat tagcagctat     240

ttaaattggt atcagcagaa accagggaaa gcccctaagc tcctgatcta tgcggcatcc     300

agtttgcaaa gtggggtccc atcaaggttc agtggcagtg gatctgggac agatttcact     360

ctcaccatca gcagtctgca acctgaagat tttgcaactt actactgtca acagacggtt     420

gtggcgcctc cgttattcgg ccaagggacc aaggtggaaa tcaaacgtac ggtggctgca     480

ccatctgtct tcatcttccc gccatctgat gagcagttga aatctggaac tgcctctgtt     540

gtgtgcctgc tgaataactt ctatcccaga gaggccaaag tacagtggaa ggtggataac     600

gccctccaat cgggtaactc ccaggagagt gtcacagagc aggacagcaa ggacagcacc     660

tacagcctca gcagcaccct gacgctgagc aaagcagact acgagaaaca caaagtctac     720

gcctgcgaag tcacccatca gggcctgagc tcgcccgtca caaagagctt caacagggga     780

gagtgt                                                                786


<210> SEQ ID NO 430
<211> LENGTH: 262
<212> TYPE: PRT
<213> ORGANISM: Artificial Sequence
<220> FEATURE:
<223> OTHER INFORMATION: chemically synthesized

<400> SEQUENCE: 430

Cys Asn Ile Trp Leu Val Gly Gly Asp Cys Arg Gly Trp Gln Gly Gly
1               5                   10                  15

Ser Ser Gly Gly Ser Thr Ser Thr Ser Gly Arg Ser Ala Asn Pro Arg
            20                  25                  30

Gly Gly Gly Val His Met Pro Leu Gly Phe Leu Gly Pro Gly Gly Ser
        35                  40                  45

Asp Ile Gln Met Thr Gln Ser Pro Ser Ser Leu Ser Ala Ser Val Gly
    50                  55                  60
```

```
Asp Arg Val Thr Ile Thr Cys Arg Ala Ser Gln Ser Ile Ser Ser Tyr
65                  70                  75                  80

Leu Asn Trp Tyr Gln Gln Lys Pro Gly Lys Ala Pro Lys Leu Leu Ile
                85                  90                  95

Tyr Ala Ala Ser Ser Leu Gln Ser Gly Val Pro Ser Arg Phe Ser Gly
            100                 105                 110

Ser Gly Ser Gly Thr Asp Phe Thr Leu Thr Ile Ser Ser Leu Gln Pro
        115                 120                 125

Glu Asp Phe Ala Thr Tyr Tyr Cys Gln Gln Thr Val Val Ala Pro Pro
    130                 135                 140

Leu Phe Gly Gln Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
            260
```

<210> SEQ ID NO 431
<211> LENGTH: 768
<212> TYPE: DNA
<213> ORGANISM: Artificial Sequence
<220> FEATURE:
<223> OTHER INFORMATION: chemically synthesized

<400> SEQUENCE: 431

```
tgcaatattt ggctcgtagg tggtgattgc aggggctggc agggggggctc gagcggagga     60

tctgctgtgg gactgctggc tcctcctggt ggcctgtctg gcagatctga taaccacggc    120

ggctccgaca tccagatgac ccagtctcca tcctccctgt ctgcatctgt aggagacaga    180

gtcaccatca cttgccgggc aagtcagagc attagcagct atttaaattg gtatcagcag    240

aaaccaggga aagcccctaa gctcctgatc tatgcggcat ccagtttgca aagtggggtc    300

ccatcaaggt tcagtggcag tggatctggg acagatttca ctctcaccat cagcagtctg    360

caacctgaag attttgcaac ttactactgt caacagacgg ttgtggcgcc tccgttattc    420

ggccaaggga ccaaggtgga aatcaaacgt acggtggctg caccatctgt cttcatcttc    480

ccgccatctg atgagcagtt gaaatctgga actgcctctg ttgtgtgcct gctgaataac    540

ttctatccca gagaggccaa agtacagtgg aaggtggata acgccctcca atcgggtaac    600

tcccaggaga gtgtcacaga gcaggacagc aaggacagca cctacagcct cagcagcacc    660

ctgacgctga gcaaagcaga ctacgagaaa cacaaagtct acgcctgcga agtcacccat    720

cagggcctga gctcgcccgt cacaaagagc ttcaacaggg gagagtgt                 768
```

<210> SEQ ID NO 432
<211> LENGTH: 256
<212> TYPE: PRT

<213> ORGANISM: Artificial Sequence
<220> FEATURE:
<223> OTHER INFORMATION: chemically synthesized

<400> SEQUENCE: 432

```
Cys Asn Ile Trp Leu Val Gly Gly Asp Cys Arg Gly Trp Gln Gly Gly
1               5                   10                  15

Ser Ser Gly Gly Ser Ala Val Gly Leu Leu Ala Pro Pro Gly Gly Leu
            20                  25                  30

Ser Gly Arg Ser Asp Asn His Gly Gly Ser Asp Ile Gln Met Thr Gln
        35                  40                  45

Ser Pro Ser Ser Leu Ser Ala Ser Val Gly Asp Arg Val Thr Ile Thr
    50                  55                  60

Cys Arg Ala Ser Gln Ser Ile Ser Ser Tyr Leu Asn Trp Tyr Gln Gln
65                  70                  75                  80

Lys Pro Gly Lys Ala Pro Lys Leu Leu Ile Tyr Ala Ala Ser Ser Leu
                85                  90                  95

Gln Ser Gly Val Pro Ser Arg Phe Ser Gly Ser Gly Ser Gly Thr Asp
            100                 105                 110

Phe Thr Leu Thr Ile Ser Ser Leu Gln Pro Glu Asp Phe Ala Thr Tyr
        115                 120                 125

Tyr Cys Gln Gln Thr Val Val Ala Pro Pro Leu Phe Gly Gln Gly Thr
    130                 135                 140

Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Ser Thr Leu Thr Leu Ser
    210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255
```

<210> SEQ ID NO 433
<211> LENGTH: 771
<212> TYPE: DNA
<213> ORGANISM: Artificial Sequence
<220> FEATURE:
<223> OTHER INFORMATION: chemically synthesized

<400> SEQUENCE: 433

```
tgcaatattt ggctcgtagg tggtgattgc aggggctggc aggggggctc gagcggaggc      60

tctggcctgt ctggcagatc cgataaccat ggcggcgctg tgggactgct ggctcctcct     120

ggtggatctg acatccagat gacccagtct ccatcctccc tgtctgcatc tgtaggagac     180

agagtcacca tcacttgccg ggcaagtcag agcattagca gctatttaaa ttggtatcag     240

cagaaaccag ggaaagcccc taagctcctg atctatgcgg catccagttt gcaaagtggg     300

gtcccatcaa ggttcagtgg cagtggatct gggacagatt tcactctcac catcagcagt     360

ctgcaacctg aagattttgc aacttactac tgtcaacaga cggttgtggc gcctccgtta     420

ttcggccaag ggaccaaggt ggaaatcaaa cgtacggtgg ctgcaccatc tgtcttcatc     480
```

```
ttcccgccat ctgatgagca gttgaaatct ggaactgcct ctgttgtgtg cctgctgaat    540

aacttctatc ccagagaggc caaagtacag tggaaggtgg ataacgccct ccaatcgggt    600

aactcccagg agagtgtcac agagcaggac agcaaggaca gcacctacag cctcagcagc    660

accctgacgc tgagcaaagc agactacgag aaacacaaag tctacgcctg cgaagtcacc    720

catcagggcc tgagctcgcc cgtcacaaag agcttcaaca ggggagagtg t             771
```

<210> SEQ ID NO 434
<211> LENGTH: 257
<212> TYPE: PRT
<213> ORGANISM: Artificial Sequence
<220> FEATURE:
<223> OTHER INFORMATION: chemically synthesized

<400> SEQUENCE: 434

```
Cys Asn Ile Trp Leu Val Gly Gly Asp Cys Arg Gly Trp Gln Gly Gly
1               5                   10                  15

Ser Ser Gly Gly Ser Gly Leu Ser Gly Arg Ser Asp Asn His Gly Gly
            20                  25                  30

Ala Val Gly Leu Leu Ala Pro Pro Gly Gly Ser Asp Ile Gln Met Thr
        35                  40                  45

Gln Ser Pro Ser Ser Leu Ser Ala Ser Val Gly Asp Arg Val Thr Ile
    50                  55                  60

Thr Cys Arg Ala Ser Gln Ser Ile Ser Ser Tyr Leu Asn Trp Tyr Gln
65                  70                  75                  80

Gln Lys Pro Gly Lys Ala Pro Lys Leu Leu Ile Tyr Ala Ala Ser Ser
                85                  90                  95

Leu Gln Ser Gly Val Pro Ser Arg Phe Ser Gly Ser Gly Ser Gly Thr
            100                 105                 110

Asp Phe Thr Leu Thr Ile Ser Ser Leu Gln Pro Glu Asp Phe Ala Thr
        115                 120                 125

Tyr Tyr Cys Gln Gln Thr Val Val Ala Pro Pro Leu Phe Gly Gln Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys
```

<210> SEQ ID NO 435
<211> LENGTH: 774
<212> TYPE: DNA
<213> ORGANISM: Artificial Sequence
<220> FEATURE:
<223> OTHER INFORMATION: chemically synthesized

<400> SEQUENCE: 435
tgcaatattt ggctcgtagg tggtgattgc aggggctggc aggggggctc gagcggcggc 60
tctgtgcata tgcccctggg ctttctggga cctggcggcc tgtctggcag atccgataat 120
cacggcggct ccgacatcca gatgacccag tctccatcct ccctgtctgc atctgtagga 180
gacagagtca ccatcacttg ccgggcaagt cagagcatta gcagctattt aaattggtat 240
cagcagaaac cagggaaagc ccctaagctc ctgatctatg cggcatccag tttgcaaagt 300
ggggtcccat caaggttcag tggcagtgga tctgggacag atttcactct caccatcagc 360
agtctgcaac ctgaagattt tgcaacttac tactgtcaac agacggttgt ggcgcctccg 420
ttattcggcc aagggaccaa ggtggaaatc aaacgtacgg tggctgcacc atctgtcttc 480
atcttcccgc catctgatga gcagttgaaa tctggaactg cctctgttgt gtgcctgctg 540
aataacttct atcccagaga ggccaaagta cagtggaagg tggataacgc cctccaatcg 600
ggtaactccc aggagagtgt cacagagcag gacagcaagg acagcaccta cagcctcagc 660
agcaccctga cgctgagcaa agcagactac gagaaacaca aagtctacgc ctgcgaagtc 720
acccatcagg gcctgagctc gcccgtcaca aagagcttca acaggggaga gtgt 774

<210> SEQ ID NO 436
<211> LENGTH: 258
<212> TYPE: PRT
<213> ORGANISM: Artificial Sequence
<220> FEATURE:
<223> OTHER INFORMATION: chemically synthesized

<400> SEQUENCE: 436

Cys Asn Ile Trp Leu Val Gly Gly Asp Cys Arg Gly Trp Gln Gly Gly
1 5 10 15

Ser Ser Gly Gly Ser Val His Met Pro Leu Gly Phe Leu Gly Pro Gly
20 25 30

Gly Leu Ser Gly Arg Ser Asp Asn His Gly Gly Ser Asp Ile Gln Met
35 40 45

Thr Gln Ser Pro Ser Ser Leu Ser Ala Ser Val Gly Asp Arg Val Thr
50 55 60

Ile Thr Cys Arg Ala Ser Gln Ser Ile Ser Ser Tyr Leu Asn Trp Tyr
65 70 75 80

Gln Gln Lys Pro Gly Lys Ala Pro Lys Leu Leu Ile Tyr Ala Ala Ser
85 90 95

Ser Leu Gln Ser Gly Val Pro Ser Arg Phe Ser Gly Ser Gly Ser Gly
100 105 110

Thr Asp Phe Thr Leu Thr Ile Ser Ser Leu Gln Pro Glu Asp Phe Ala
115 120 125

Thr Tyr Tyr Cys Gln Gln Thr Val Val Ala Pro Pro Leu Phe Gly Gln
130 135 140

Gly Thr Lys Val Glu Ile Lys Arg Thr Val Ala Ala Pro Ser Val Phe
145 150 155 160

Ile Phe Pro Pro Ser Asp Glu Gln Leu Lys Ser Gly Thr Ala Ser Val
165 170 175

Val Cys Leu Leu Asn Asn Phe Tyr Pro Arg Glu Ala Lys Val Gln Trp
180 185 190

Lys Val Asp Asn Ala Leu Gln Ser Gly Asn Ser Gln Glu Ser Val Thr
195 200 205

Glu Gln Asp Ser Lys Asp Ser Thr Tyr Ser Leu Ser Ser Thr Leu Thr
210 215 220

```
Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys


<210> SEQ ID NO 437
<211> LENGTH: 265
<212> TYPE: PRT
<213> ORGANISM: Artificial Sequence
<220> FEATURE:
<223> OTHER INFORMATION: chemically synthesized

<400> SEQUENCE: 437

Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Gly Leu Ser Gly Arg
            20                  25                  30

Ser Asp Asn His Gly Gly Val His Met Pro Leu Gly Phe Leu Gly Pro
        35                  40                  45

Gly Gly Ser Asp Ile Gln Met Thr Gln Ser Pro Ser Ser Leu Ser Ala
    50                  55                  60

Ser Val Gly Asp Arg Val Thr Ile Thr Cys Arg Ala Ser Gln Ser Ile
65                  70                  75                  80

Ser Ser Tyr Leu Asn Trp Tyr Gln Gln Lys Pro Gly Lys Ala Pro Lys
                85                  90                  95

Leu Leu Ile Tyr Ala Ala Ser Ser Leu Gln Ser Gly Val Pro Ser Arg
            100                 105                 110

Phe Ser Gly Ser Gly Ser Gly Thr Asp Phe Thr Leu Thr Ile Ser Ser
        115                 120                 125

Leu Gln Pro Glu Asp Phe Ala Thr Tyr Tyr Cys Gln Gln Thr Val Val
    130                 135                 140

Ala Pro Pro Leu Phe Gly Gln Gly Thr Lys Val Glu Ile Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265


<210> SEQ ID NO 438
<211> LENGTH: 777
<212> TYPE: DNA
<213> ORGANISM: Artificial Sequence
<220> FEATURE:
<223> OTHER INFORMATION: chemically synthesized

<400> SEQUENCE: 438
```

```
tgcaatattt ggctcgtagg tggtgattgc aggggctggc agggggggctc gagcggaggc     60

tctggcctgt ctggcagatc tgataaccac ggcggcgtgc acatgcccct gggctttctg    120

ggacctggcg gatctgacat ccagatgacc cagtctccat cctccctgtc tgcatctgta    180

ggagacagag tcaccatcac ttgccgggca agtcagagca ttagcagcta tttaaattgg    240

tatcagcaga aaccagggaa agcccctaag ctcctgatct atgcggcatc cagtttgcaa    300

agtggggtcc catcaaggtt cagtggcagt ggatctggga cagatttcac tctcaccatc    360

agcagtctgc aacctgaaga ttttgcaact tactactgtc aacagacggt tgtggcgcct    420

ccgttattcg gccaagggac caaggtggaa atcaaacgta cggtggctgc accatctgtc    480

ttcatcttcc cgccatctga tgagcagttg aaatctggaa ctgcctctgt tgtgtgcctg    540

ctgaataact tctatcccag agaggccaaa gtacagtgga aggtggataa cgccctccaa    600

tcgggtaact cccaggagag tgtcacagag caggacagca aggacagcac ctacagcctc    660

agcagcaccc tgacgctgag caaagcagac tacgagaaac acaaagtcta cgcctgcgaa    720

gtcacccatc agggcctgag ctcgcccgtc acaaagagct tcaacagggg agagtgt       777
```

<210> SEQ ID NO 439
<211> LENGTH: 259
<212> TYPE: PRT
<213> ORGANISM: Artificial Sequence
<220> FEATURE:
<223> OTHER INFORMATION: chemically synthesized

<400> SEQUENCE: 439

```
Cys Asn Ile Trp Leu Val Gly Gly Asp Cys Arg Gly Trp Gln Gly Gly
1               5                   10                  15

Ser Ser Gly Gly Ser Gly Leu Ser Gly Arg Ser Asp Asn His Gly Gly
            20                  25                  30

Val His Met Pro Leu Gly Phe Leu Gly Pro Gly Gly Ser Asp Ile Gln
        35                  40                  45

Met Thr Gln Ser Pro Ser Ser Leu Ser Ala Ser Val Gly Asp Arg Val
    50                  55                  60

Thr Ile Thr Cys Arg Ala Ser Gln Ser Ile Ser Ser Tyr Leu Asn Trp
65                  70                  75                  80

Tyr Gln Gln Lys Pro Gly Lys Ala Pro Lys Leu Leu Ile Tyr Ala Ala
                85                  90                  95

Ser Ser Leu Gln Ser Gly Val Pro Ser Arg Phe Ser Gly Ser Gly Ser
            100                 105                 110

Gly Thr Asp Phe Thr Leu Thr Ile Ser Ser Leu Gln Pro Glu Asp Phe
        115                 120                 125

Ala Thr Tyr Tyr Cys Gln Gln Thr Val Val Ala Pro Pro Leu Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220
```

-continued

```
Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys


<210> SEQ ID NO 440
<211> LENGTH: 765
<212> TYPE: DNA
<213> ORGANISM: Artificial Sequence
<220> FEATURE:
<223> OTHER INFORMATION: chemically synthesized

<400> SEQUENCE: 440

tgcatctccc cccgcggttg tcccgacggg ccgtacgtga tgtacggcag ctccggcggc      60

agtgggggta gcggtgggtc cgggctgagt ggccggtccg acaatcacgg gagctcggga     120

acacagattc tgctgacgca atctcccgtg atcctctcgg tctcacccgg cgaacgggtc     180

tcgttcagct gcagagcgtc ccaatcaatc gggaccaata ttcactggta ccagcaaagg     240

actaatgggt ctccccggct gctgataaaa tacgcctccg agtctatctc gggcatccca     300

tcccgattta gtggtagcgg aagcggcact gatttcacct tgtctattaa cagcgtagaa     360

tctgaggaca ttgcagacta ttactgtcag cagaataaca attggcctac aactttcggc     420

gccgggacca aactagagtt aaagcgtact gtggctgccc ccagcgtttt tatttttccg     480

cccagcgacg aacagctgaa gtcaggcaca gcctctgtgg tgtgtctcct gaataacttc     540

taccccagag aggccaaagt tcagtggaaa gtggacaatg ccttgcagtc cggaaacagt     600

caagagtccg tgaccgagca ggacagtaag gatagcacgt atagcctctc tagtacttta     660

acactgtcca aggccgacta cgagaagcac aaggtgtacg catgcgaagt gacccatcag     720

gggctttcct cccccgtcac caagtctttc aatcgcgggg agtgt                     765


<210> SEQ ID NO 441
<211> LENGTH: 255
<212> TYPE: PRT
<213> ORGANISM: Artificial Sequence
<220> FEATURE:
<223> OTHER INFORMATION: chemically synthesized

<400> SEQUENCE: 441

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Leu Ser Gly Arg
            20                  25                  30

Ser Asp Asn His Gly Ser Ser Gly Thr Gln Ile Leu Leu Thr Gln Ser
        35                  40                  45

Pro Val Ile Leu Ser Val Ser Pro Gly Glu Arg Val Ser Phe Ser Cys
    50                  55                  60

Arg Ala Ser Gln Ser Ile Gly Thr Asn Ile His Trp Tyr Gln Gln Arg
65                  70                  75                  80

Thr Asn Gly Ser Pro Arg Leu Leu Ile Lys Tyr Ala Ser Glu Ser Ile
                85                  90                  95

Ser Gly Ile Pro Ser Arg Phe Ser Gly Ser Gly Ser Gly Thr Asp Phe
            100                 105                 110

Thr Leu Ser Ile Asn Ser Val Glu Ser Glu Asp Ile Ala Asp Tyr Tyr
        115                 120                 125

Cys Gln Gln Asn Asn Asn Trp Pro Thr Thr Phe Gly Ala Gly Thr Lys
```

```
    130                 135                 140

Leu Glu Leu Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 442
<211> LENGTH: 765
<212> TYPE: DNA
<213> ORGANISM: Artificial Sequence
<220> FEATURE:
<223> OTHER INFORMATION: chemically synthesized

<400> SEQUENCE: 442

tgtatttccc ctagaggttg ccctgacggg ccgtatgtca tgtacggtag ttctggcggt     60

agtggcggat ctggcggcag tgggctgagc ggacgtagcg ggaatcacgg ctcatccggg    120

acgcagatac tgctgaccca gtcccccgtg atcctgtccg tgtcaccggg cgaaagggtc    180

agtttctctt gccgagcatc acagtccata ggtacgaata tccattggta ccagcagcgg    240

accaatggga gcccaagact gctcattaag tacgcatctg agagtatctc aggcattcca    300

agcaggtttt ccggcagtgg gagcggcact gacttcaccc tcagcattaa cagcgtggaa    360

agcgaagaca ttgcagatta ctactgccaa cagaacaata actggcctac tacattcggg    420

gcaggaacta agttggagct caaacgtacc gtcgctgctc ctagcgtatt tattttccct    480

cctagcgatg aacagttgaa atctggtacc gctagtgttg tgtgcttact gaacaacttt    540

tatccccggg aggccaaggt acaatggaag gtggacaatg ccctccaatc agggaacagc    600

caggagtctg ttaccgagca ggactccaag gacagcacct acagcctgag ctctaccctt    660

acattgagca aggctgatta tgagaagcat aaggtctacg cttgtgaggt gacccatcag    720

gggctcagca gcccggtgac aaaaagcttt aaccgggggg aatgc                    765


<210> SEQ ID NO 443
<211> LENGTH: 255
<212> TYPE: PRT
<213> ORGANISM: Artificial Sequence
<220> FEATURE:
<223> OTHER INFORMATION: chemically synthesized

<400> SEQUENCE: 443

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Leu Ser Gly Arg
            20                  25                  30

Ser Gly Asn His Gly Ser Ser Gly Thr Gln Ile Leu Leu Thr Gln Ser
        35                  40                  45

Pro Val Ile Leu Ser Val Ser Pro Gly Glu Arg Val Ser Phe Ser Cys
```

```
    50                  55                  60

Arg Ala Ser Gln Ser Ile Gly Thr Asn Ile His Trp Tyr Gln Gln Arg
65                  70                  75                  80

Thr Asn Gly Ser Pro Arg Leu Leu Ile Lys Tyr Ala Ser Glu Ser Ile
                85                  90                  95

Ser Gly Ile Pro Ser Arg Phe Ser Gly Ser Gly Ser Gly Thr Asp Phe
            100                 105                 110

Thr Leu Ser Ile Asn Ser Val Glu Ser Glu Asp Ile Ala Asp Tyr Tyr
        115                 120                 125

Cys Gln Gln Asn Asn Asn Trp Pro Thr Thr Phe Gly Ala Gly Thr Lys
    130                 135                 140

Leu Glu Leu Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 444
<211> LENGTH: 765
<212> TYPE: DNA
<213> ORGANISM: Artificial Sequence
<220> FEATURE:
<223> OTHER INFORMATION: chemically synthesized

<400> SEQUENCE: 444

tgtattagcc ccaggggggtg ccccgacggg ccttacgtga tgtatggcag ctccggtggc      60

agcggaggct ctggcgggag tgggatcagt tccggcctgc tgagctccgg gtcaagcggg     120

acccagatct tgctcaccca atcaccagtg atcctaagcg tgagccctgg cgaacgggtc     180

agcttctctt gccgggcatc tcagagtatt ggcactaaca tacactggta ccagcagcga     240

accaatgggt ccccccgcct tctaatcaaa tatgctagcg aatccatttc aggaattcct     300

agccgattta gcggcagcgg atcaggcact gacttcactc tgtcaatcaa ctcagttgaa     360

agcgaggaca ttgcagacta ctattgccag cagaataata attggcccac tacatttgga     420

gctggaacaa aattggagct taagaggaca gtggctgcgc ctagtgtatt tatctttccc     480

ccctctgacg aacagttgaa atcgggaacc gcatccgtcg tctgtttact gaacaacttc     540

tatcccagag aggccaaagt gcagtggaaa gtggataatg ctttgcagtc tggcaacagc     600

caggaaagcg tgacggagca ggactcaaag gatagtacat actccctgtc ctccaccctg     660

actctgagta aggccgacta cgagaagcac aaggtctacg cctgcgaagt gacgcaccaa     720

gggctatcga gcccggtcac caagtctttc aatcgtggag aatgc                     765


<210> SEQ ID NO 445
<211> LENGTH: 255
<212> TYPE: PRT
<213> ORGANISM: Artificial Sequence
```

<220> FEATURE:
<223> OTHER INFORMATION: chemically synthesized

<400> SEQUENCE: 445

```
Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ile Ser Ser Gly
            20                  25                  30

Leu Leu Ser Ser Gly Ser Ser Gly Thr Gln Ile Leu Leu Thr Gln Ser
        35                  40                  45

Pro Val Ile Leu Ser Val Ser Pro Gly Glu Arg Val Ser Phe Ser Cys
    50                  55                  60

Arg Ala Ser Gln Ser Ile Gly Thr Asn Ile His Trp Tyr Gln Gln Arg
65                  70                  75                  80

Thr Asn Gly Ser Pro Arg Leu Leu Ile Lys Tyr Ala Ser Glu Ser Ile
                85                  90                  95

Ser Gly Ile Pro Ser Arg Phe Ser Gly Ser Gly Ser Gly Thr Asp Phe
            100                 105                 110

Thr Leu Ser Ile Asn Ser Val Glu Ser Glu Asp Ile Ala Asp Tyr Tyr
        115                 120                 125

Cys Gln Gln Asn Asn Asn Trp Pro Thr Thr Phe Gly Ala Gly Thr Lys
    130                 135                 140

Leu Glu Leu Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255
```

<210> SEQ ID NO 446
<211> LENGTH: 765
<212> TYPE: DNA
<213> ORGANISM: Artificial Sequence
<220> FEATURE:
<223> OTHER INFORMATION: chemically synthesized

<400> SEQUENCE: 446

```
tgcatcagcc ctaggggctg cccagacggc ccatatgtga tgtacggtag ctctgggggc     60

tcaggaggca gcgggggaag cggacaaaac caggccttac gaatggctgg cagctctggc    120

acccagatat tgctgacgca gagtccagtt atccttagtg tcagccctgg tgaacgggtt    180

tcatttagtt gccgtgcctc ccagtctatt ggaacgaaca ttcattggta ccagcaaagg    240

accaacggtt cacccaggtt gcttatcaag tatgcttcag agtcaatctc cgggattccc    300

tcaaggtttt caggctctgg ctcaggtacc gattttacgc tgagcatcaa ctccgtggag    360

agtgaggaca ttgctgatta ttactgtcag cagaataaca attggccgac aactttcggc    420

gccggcacaa agctggaact taagcgtact gtggctgcgc catctgtctt cattttccg     480
```

ccctcggacg agcagttgaa gtcagggacc gcctctgtcg tgtgccttct caataacttc 540
tatcccagag aggctaaagt ccagtggaaa gttgataatg cacttcagag cgggaatagc 600
caggagagcg tgacggaaca ggactctaag gactccacct attctctctc atccaccctt 660
actctctcta aagccgacta cgaaaagcat aaggtttatg cttgcgaagt cactcatcaa 720
gggctatcta gtccggtcac taaaagcttc aacagaggtg aatgt 765

<210> SEQ ID NO 447
<211> LENGTH: 255
<212> TYPE: PRT
<213> ORGANISM: Artificial Sequence
<220> FEATURE:
<223> OTHER INFORMATION: chemically synthesized

<400> SEQUENCE: 447

Cys Ile Ser Pro Arg Gly Cys Pro Asp Gly Pro Tyr Val Met Tyr Gly
1 5 10 15

Ser Ser Gly Gly Ser Gly Gly Ser Gly Gly Ser Gly Gln Asn Gln Ala
20 25 30

Leu Arg Met Ala Gly Ser Ser Gly Thr Gln Ile Leu Leu Thr Gln Ser
35 40 45

Pro Val Ile Leu Ser Val Ser Pro Gly Glu Arg Val Ser Phe Ser Cys
50 55 60

Arg Ala Ser Gln Ser Ile Gly Thr Asn Ile His Trp Tyr Gln Gln Arg
65 70 75 80

Thr Asn Gly Ser Pro Arg Leu Leu Ile Lys Tyr Ala Ser Glu Ser Ile
85 90 95

Ser Gly Ile Pro Ser Arg Phe Ser Gly Ser Gly Ser Gly Thr Asp Phe
100 105 110

Thr Leu Ser Ile Asn Ser Val Glu Ser Glu Asp Ile Ala Asp Tyr Tyr
115 120 125

Cys Gln Gln Asn Asn Asn Trp Pro Thr Thr Phe Gly Ala Gly Thr Lys
130 135 140

Leu Glu Leu Lys Arg Thr Val Ala Ala Pro Ser Val Phe Ile Phe Pro
145 150 155 160

Pro Ser Asp Glu Gln Leu Lys Ser Gly Thr Ala Ser Val Val Cys Leu
165 170 175

Leu Asn Asn Phe Tyr Pro Arg Glu Ala Lys Val Gln Trp Lys Val Asp
180 185 190

Asn Ala Leu Gln Ser Gly Asn Ser Gln Glu Ser Val Thr Glu Gln Asp
195 200 205

Ser Lys Asp Ser Thr Tyr Ser Leu Ser Ser Thr Leu Thr Leu Ser Lys
210 215 220

Ala Asp Tyr Glu Lys His Lys Val Tyr Ala Cys Glu Val Thr His Gln
225 230 235 240

Gly Leu Ser Ser Pro Val Thr Lys Ser Phe Asn Arg Gly Glu Cys
245 250 255

<210> SEQ ID NO 448
<211> LENGTH: 780
<212> TYPE: DNA
<213> ORGANISM: Artificial Sequence
<220> FEATURE:
<223> OTHER INFORMATION: chemically synthesized

<400> SEQUENCE: 448
tgtatcagcc cccgtggctg tccagacggt ccttacgtta tgtatggatc tagcgggggc 60

```
tctggagggt ctggcggctc tggaatctct agtggacttc tctccggaag aagcgataat    120

catggatcca gcgggacaca aatcctgttg acacagtccc cagtgatcct gtcagtctcg    180

cccggagaaa gggtgtcttt ctcttgtagg gctagtcagt ctatcggaac taacatccat    240

tggtaccagc agcggacaaa tgggagcccg aggcttctga tcaagtatgc ttcagagagt    300

ataagcggca tcccctcaag atttagtggc agcgggtccg ggacagattt caccttgtca    360

atcaattctg tcgaatccga agacattgca gactactatt gccagcaaaa caacaactgg    420

cccaccactt tcggtgctgg aaccaaactc gagctgaaac gcactgtggc agctccttca    480

gtgttcatct tcccacctag cgacgagcag ttgaaatcgg ggacagcctc agtggtgtgt    540

ctactgaaca acttttaccc ccgggaagcc aaagtgcagt ggaaggtcga caatgcgctg    600

caatcaggga acagtcagga gtcagttaca gagcaggact ctaaggacag tacatattct    660

ttgagttcca ccttgacatt aagcaaggca gactacgaga aacacaaggt gtacgcatgt    720

gaagttacac accagggcct ttcctcccca gttacgaaaa gcttcaacag aggcgaatgc    780
```

<210> SEQ ID NO 449
<211> LENGTH: 260
<212> TYPE: PRT
<213> ORGANISM: Artificial Sequence
<220> FEATURE:
<223> OTHER INFORMATION: chemically synthesized

<400> SEQUENCE: 449

```
Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ile Ser Ser Gly
            20                  25                  30

Leu Leu Ser Gly Arg Ser Asp Asn His Gly Ser Ser Gly Thr Gln Ile
        35                  40                  45

Leu Leu Thr Gln Ser Pro Val Ile Leu Ser Val Ser Pro Gly Glu Arg
    50                  55                  60

Val Ser Phe Ser Cys Arg Ala Ser Gln Ser Ile Gly Thr Asn Ile His
65                  70                  75                  80

Trp Tyr Gln Gln Arg Thr Asn Gly Ser Pro Arg Leu Leu Ile Lys Tyr
                85                  90                  95

Ala Ser Glu Ser Ile Ser Gly Ile Pro Ser Arg Phe Ser Gly Ser Gly
            100                 105                 110

Ser Gly Thr Asp Phe Thr Leu Ser Ile Asn Ser Val Glu Ser Glu Asp
        115                 120                 125

Ile Ala Asp Tyr Tyr Cys Gln Gln Asn Asn Asn Trp Pro Thr Thr Phe
    130                 135                 140

Gly Ala Gly Thr Lys Leu Glu Leu Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240
```

```
Glu Val Thr His Gln Gly Leu Ser Ser Pro Val Thr Lys Ser Phe Asn
                245                 250                 255

Arg Gly Glu Cys
            260


<210> SEQ ID NO 450
<211> LENGTH: 780
<212> TYPE: DNA
<213> ORGANISM: Artificial Sequence
<220> FEATURE:
<223> OTHER INFORMATION: chemically synthesized

<400> SEQUENCE: 450

tgcatatcgc ccagaggatg tcctgacgga ccctacgtga tgtacgggag ttctgggggg      60

agtggaggct ctggcgggtc agggattagt tccggcctct tgtctggacg ctccggaaat     120

cacggatcat ctgggaccca gatcctcctg acccagtctc ccgtcattct gtctgtttct     180

ccaggcgagc gggtttcatt tagctgtagg gccagtcaga gcattggcac caacatccat     240

tggtaccagc agagaactaa tggcagtccc agactgctca ttaaatatgc aagcgaatca     300

atttccggga ttccttctcg cttctcggga tctggatctg gcaccgactt cacgctgtcc     360

atcaacagcg tggagagtga ggacatcgcc gattactact gccagcagaa caacaactgg     420

ccaacaactt ttggcgccgg gaccaagctt gagttaaaga gaaccgtagc tgcaccctct     480

gttttcattt tcccaccctc agacgagcag cttaagtcag gaactgccag tgtggtgtgc     540

ctgctgaaca acttctaccc gagagaggct aaagtccagt ggaaggtaga caatgccctt     600

cagtctggca actctcagga gagtgtcaca gagcaggatt ctaaggactc cacgtacagt     660

ctgagttcca ccctcaccct cagtaaggca gactacgaga agcacaaagt ctacgcatgt     720

gaggttactc accaggggct cagctctccc gtgacgaagt catttaacag aggtgagtgc     780


<210> SEQ ID NO 451
<211> LENGTH: 260
<212> TYPE: PRT
<213> ORGANISM: Artificial Sequence
<220> FEATURE:
<223> OTHER INFORMATION: chemically synthesized

<400> SEQUENCE: 451

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ile Ser Ser Gly
            20                  25                  30

Leu Leu Ser Gly Arg Ser Gly Asn His Gly Ser Ser Gly Thr Gln Ile
        35                  40                  45

Leu Leu Thr Gln Ser Pro Val Ile Leu Ser Val Ser Pro Gly Glu Arg
    50                  55                  60

Val Ser Phe Ser Cys Arg Ala Ser Gln Ser Ile Gly Thr Asn Ile His
65                  70                  75                  80

Trp Tyr Gln Gln Arg Thr Asn Gly Ser Pro Arg Leu Leu Ile Lys Tyr
                85                  90                  95

Ala Ser Glu Ser Ile Ser Gly Ile Pro Ser Arg Phe Ser Gly Ser Gly
            100                 105                 110

Ser Gly Thr Asp Phe Thr Leu Ser Ile Asn Ser Val Glu Ser Glu Asp
        115                 120                 125

Ile Ala Asp Tyr Tyr Cys Gln Gln Asn Asn Asn Trp Pro Thr Thr Phe
    130                 135                 140
```

Gly Ala Gly Thr Lys Leu Glu Leu Lys Arg Thr Val Ala Ala Pro Ser
145 150 155 160

Val Phe Ile Phe Pro Pro Ser Asp Glu Gln Leu Lys Ser Gly Thr Ala
165 170 175

Ser Val Val Cys Leu Leu Asn Asn Phe Tyr Pro Arg Glu Ala Lys Val
180 185 190

Gln Trp Lys Val Asp Asn Ala Leu Gln Ser Gly Asn Ser Gln Glu Ser
195 200 205

Val Thr Glu Gln Asp Ser Lys Asp Ser Thr Tyr Ser Leu Ser Ser Thr
210 215 220

Leu Thr Leu Ser Lys Ala Asp Tyr Glu Lys His Lys Val Tyr Ala Cys
225 230 235 240

Glu Val Thr His Gln Gly Leu Ser Ser Pro Val Thr Lys Ser Phe Asn
245 250 255

Arg Gly Glu Cys
260

<210> SEQ ID NO 452
<211> LENGTH: 807
<212> TYPE: DNA
<213> ORGANISM: Artificial Sequence
<220> FEATURE:
<223> OTHER INFORMATION: chemically synthesized

<400> SEQUENCE: 452
tgcatttctc cgagaggctg ccctgacggc ccatacgtaa tgtacggatc atccggtggc 60
agtggagggt ccgggggatc cggtctaagc ggcagaagtg ataatcatgg aggctctggc 120
gggagcatca gctccggatt gctttccagc ggaagttctg gcactcaaat tctgctgaca 180
caaagccctg tgatcttgtc agtctcacct ggcgagcggg tgagcttttc atgccgggct 240
tcccagagca tcggtacaaa tattcactgg tatcagcaga gaaccaatgg cagtccgcgg 300
ttgctgatta agtatgcgag cgagagcata tcaggcatac caagcagatt tagcgggagt 360
ggctctggga ccgattttac actcagtata aattcagtgg agagcgagga tatagccgac 420
tactactgcc agcaaaacaa taactggccc accaccttcg gcgcagggac caagcttgaa 480
ctgaagcgta cagttgccgc cccaagcgta tttattttcc ctccaagcga cgaacagctg 540
aaaagcggta ccgcaagcgt tgtgtgcctg ctgaataact tttacccaag ggaagctaag 600
gtgcagtgga aggttgacaa tgcgctgcag tcaggcaact cccaggaatc ggtaacagag 660
caggactcca aggattcaac ttatagtctt agtagtaccc ttactctttc caaagctgat 720
tatgaaaaac acaaagtgta tgcatgcgag gtgacccacc aaggactgtc atctcctgtc 780
accaagtcct tcaaccgggg agagtgt 807

<210> SEQ ID NO 453
<211> LENGTH: 269
<212> TYPE: PRT
<213> ORGANISM: Artificial Sequence
<220> FEATURE:
<223> OTHER INFORMATION: chemically synthesized

<400> SEQUENCE: 453

Cys Ile Ser Pro Arg Gly Cys Pro Asp Gly Pro Tyr Val Met Tyr Gly
1 5 10 15

Ser Ser Gly Gly Ser Gly Gly Ser Gly Gly Ser Gly Leu Ser Gly Arg
20 25 30

-continued

```
Ser Asp Asn His Gly Gly Ser Gly Gly Ser Ile Ser Ser Gly Leu Leu
        35                  40                  45

Ser Ser Gly Ser Ser Gly Thr Gln Ile Leu Leu Thr Gln Ser Pro Val
    50                  55                  60

Ile Leu Ser Val Ser Pro Gly Glu Arg Val Ser Phe Ser Cys Arg Ala
65                  70                  75                  80

Ser Gln Ser Ile Gly Thr Asn Ile His Trp Tyr Gln Gln Arg Thr Asn
                85                  90                  95

Gly Ser Pro Arg Leu Leu Ile Lys Tyr Ala Ser Glu Ser Ile Ser Gly
            100                 105                 110

Ile Pro Ser Arg Phe Ser Gly Ser Gly Ser Gly Thr Asp Phe Thr Leu
        115                 120                 125

Ser Ile Asn Ser Val Glu Ser Glu Asp Ile Ala Asp Tyr Tyr Cys Gln
    130                 135                 140

Gln Asn Asn Asn Trp Pro Thr Thr Phe Gly Ala Gly Thr Lys Leu Glu
145                 150                 155                 160

Leu Lys Arg Thr Val Ala Ala Pro Ser Val Phe Ile Phe Pro Pro Ser
                165                 170                 175

Asp Glu Gln Leu Lys Ser Gly Thr Ala Ser Val Val Cys Leu Leu Asn
            180                 185                 190

Asn Phe Tyr Pro Arg Glu Ala Lys Val Gln Trp Lys Val Asp Asn Ala
        195                 200                 205

Leu Gln Ser Gly Asn Ser Gln Glu Ser Val Thr Glu Gln Asp Ser Lys
    210                 215                 220

Asp Ser Thr Tyr Ser Leu Ser Ser Thr Leu Thr Leu Ser Lys Ala Asp
225                 230                 235                 240

Tyr Glu Lys His Lys Val Tyr Ala Cys Glu Val Thr His Gln Gly Leu
                245                 250                 255

Ser Ser Pro Val Thr Lys Ser Phe Asn Arg Gly Glu Cys
            260                 265
```

```
<210> SEQ ID NO 454
<211> LENGTH: 807
<212> TYPE: DNA
<213> ORGANISM: Artificial Sequence
<220> FEATURE:
<223> OTHER INFORMATION: chemically synthesized

<400> SEQUENCE: 454

tgcattagtc ctcgcggttg ccctgatgga ccatacgtaa tgtatggaag ctctggtgga     60

tccgggggct ctggcggatc aggaatctcc agcgggctgc tctcatcagg tggcagcggg    120

ggctcattaa gcggccgaag tgacaatcac ggctcgtccg gtacacagat tctgctcact    180

cagtcacccg ttatactgtc tgtgtcgcct ggagagcgtg tcagcttttc atgtagagcc    240

tcgcagtcaa taggcacgaa tatacactgg taccagcaga gaactaatgg aagcccaagg    300

ttgctcatca aatacgcatc tgagtcgatt agcggcattc cgtccaggtt tagtggcagt    360

ggaagcggca ccgatttcac tttgtctatt aactctgtgg aaagcgagga catcgccgat    420

tattattgtc agcagaataa caattggccc accaccttcg gtgccggtac taagctggag    480

ctgaaacgta cagttgccgc tccctctgtg tttattttcc ctccctcgga tgagcaactc    540

aaatcaggga cagcgagtgt cgtatgtctc ctgaacaatt tttacccacg tgaagctaaa    600

gttcagtgga aggtggacaa cgctctgcag tccggcaaca gtcaggaaag cgtaactgaa    660

caggactcaa aggatagcac ttactccttg agcagcactc tcactctttc caaggctgat    720
```

```
tatgagaagc acaaggtgta cgcgtgtgaa gtcacccatc agggactgtc aagtccggtg    780

actaaatcat ttaacagggg cgaatgc                                        807


<210> SEQ ID NO 455
<211> LENGTH: 269
<212> TYPE: PRT
<213> ORGANISM: Artificial Sequence
<220> FEATURE:
<223> OTHER INFORMATION: chemically synthesized

<400> SEQUENCE: 455

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ile Ser Ser Gly
            20                  25                  30

Leu Leu Ser Ser Gly Gly Ser Gly Gly Ser Leu Ser Gly Arg Ser Asp
        35                  40                  45

Asn His Gly Ser Ser Gly Thr Gln Ile Leu Leu Thr Gln Ser Pro Val
    50                  55                  60

Ile Leu Ser Val Ser Pro Gly Glu Arg Val Ser Phe Ser Cys Arg Ala
65                  70                  75                  80

Ser Gln Ser Ile Gly Thr Asn Ile His Trp Tyr Gln Gln Arg Thr Asn
                85                  90                  95

Gly Ser Pro Arg Leu Leu Ile Lys Tyr Ala Ser Glu Ser Ile Ser Gly
            100                 105                 110

Ile Pro Ser Arg Phe Ser Gly Ser Gly Ser Gly Thr Asp Phe Thr Leu
        115                 120                 125

Ser Ile Asn Ser Val Glu Ser Glu Asp Ile Ala Asp Tyr Tyr Cys Gln
    130                 135                 140

Gln Asn Asn Asn Trp Pro Thr Thr Phe Gly Ala Gly Thr Lys Leu Glu
145                 150                 155                 160

Leu Lys Arg Thr Val Ala Ala Pro Ser Val Phe Ile Phe Pro Pro Ser
                165                 170                 175

Asp Glu Gln Leu Lys Ser Gly Thr Ala Ser Val Val Cys Leu Leu Asn
            180                 185                 190

Asn Phe Tyr Pro Arg Glu Ala Lys Val Gln Trp Lys Val Asp Asn Ala
        195                 200                 205

Leu Gln Ser Gly Asn Ser Gln Glu Ser Val Thr Glu Gln Asp Ser Lys
    210                 215                 220

Asp Ser Thr Tyr Ser Leu Ser Ser Thr Leu Thr Leu Ser Lys Ala Asp
225                 230                 235                 240

Tyr Glu Lys His Lys Val Tyr Ala Cys Glu Val Thr His Gln Gly Leu
                245                 250                 255

Ser Ser Pro Val Thr Lys Ser Phe Asn Arg Gly Glu Cys
            260                 265


<210> SEQ ID NO 456
<211> LENGTH: 807
<212> TYPE: DNA
<213> ORGANISM: Artificial Sequence
<220> FEATURE:
<223> OTHER INFORMATION: chemically synthesized

<400> SEQUENCE: 456

tgtatttccc ctcgcggatg tcccgacggt ccatacgtaa tgtatgggtc aagcggggga     60

tcaggaggaa gtggaggctc cggactcagc ggtcgctccg gcaatcacgg ggggtctggc    120
```

-continued

```
ggatcaataa gttcgggcct cctgagctcc ggttcatctg gcactcagat cctgctcacg    180

cagtcgccgg taatactgag tgtctcacca ggcgagcgtg tcagcttcag ctgtcgcgcc    240

tcacagtcaa tcggcacaaa tatccattgg taccagcaaa ggaccaatgg cagccctagg    300

ctgctgataa aatacgcatc cgagtcaatt tcagggattc catcgagatt ctcgggcagc    360

ggaagtggga ccgactttac tctctccatc aacagcgtcg agtcggagga catcgcggac    420

tactactgcc agcagaataa caattggcca acaacattcg gcgcaggaac aaagctagag    480

ctcaagagga cagtggctgc acccagtgta ttcatcttcc cacctagcga cgagcaactg    540

aagagcggga cggcttccgt cgtttgtcta ttaaataatt tctatccccg tgaggctaaa    600

gttcagtgga aggttgataa tgcgttgcag tccggcaact cccaggaatc cgtcacagag    660

caggattcta aggattcaac ctatagctta agctctacac ttacgctttc taaagccgat    720

tatgaaaaac acaaggtgta cgcttgtgag gttacccacc agggcctgag cagccccgtg    780

accaagtcgt tcaaccgggg cgagtgt                                        807
```

<210> SEQ ID NO 457
<211> LENGTH: 269
<212> TYPE: PRT
<213> ORGANISM: Artificial Sequence
<220> FEATURE:
<223> OTHER INFORMATION: chemically synthesized

<400> SEQUENCE: 457

```
Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Leu Ser Gly Arg
            20                  25                  30

Ser Gly Asn His Gly Gly Ser Gly Gly Ser Ile Ser Ser Gly Leu Leu
        35                  40                  45

Ser Ser Gly Ser Ser Gly Thr Gln Ile Leu Leu Thr Gln Ser Pro Val
    50                  55                  60

Ile Leu Ser Val Ser Pro Gly Glu Arg Val Ser Phe Ser Cys Arg Ala
65                  70                  75                  80

Ser Gln Ser Ile Gly Thr Asn Ile His Trp Tyr Gln Gln Arg Thr Asn
                85                  90                  95

Gly Ser Pro Arg Leu Leu Ile Lys Tyr Ala Ser Glu Ser Ile Ser Gly
            100                 105                 110

Ile Pro Ser Arg Phe Ser Gly Ser Gly Ser Gly Thr Asp Phe Thr Leu
        115                 120                 125

Ser Ile Asn Ser Val Glu Ser Glu Asp Ile Ala Asp Tyr Tyr Cys Gln
    130                 135                 140

Gln Asn Asn Asn Trp Pro Thr Thr Phe Gly Ala Gly Thr Lys Leu Glu
145                 150                 155                 160

Leu Lys Arg Thr Val Ala Ala Pro Ser Val Phe Ile Phe Pro Pro Ser
                165                 170                 175

Asp Glu Gln Leu Lys Ser Gly Thr Ala Ser Val Val Cys Leu Leu Asn
            180                 185                 190

Asn Phe Tyr Pro Arg Glu Ala Lys Val Gln Trp Lys Val Asp Asn Ala
        195                 200                 205

Leu Gln Ser Gly Asn Ser Gln Glu Ser Val Thr Glu Gln Asp Ser Lys
    210                 215                 220

Asp Ser Thr Tyr Ser Leu Ser Ser Thr Leu Thr Leu Ser Lys Ala Asp
225                 230                 235                 240
```

```
Tyr Glu Lys His Lys Val Tyr Ala Cys Glu Val Thr His Gln Gly Leu
                245                 250                 255

Ser Ser Pro Val Thr Lys Ser Phe Asn Arg Gly Glu Cys
            260                 265
```

<210> SEQ ID NO 458
<211> LENGTH: 807
<212> TYPE: DNA
<213> ORGANISM: Artificial Sequence
<220> FEATURE:
<223> OTHER INFORMATION: chemically synthesized

<400> SEQUENCE: 458

```
tgtatctcac ctcgcggctg ccccgacggc ccttacgtca tgtacggctc ctcgggtggg      60

tccgggggaa gtggcgggtc tggcattagt tcagggctct tatcttccgg cggaagcggg     120

ggatctcttt ccgggcggag tggcaatcac ggcagtagcg gaactcagat cctactcact     180

cagtcaccag tgatcctgtc tgtcagtcca ggggagagag tgtctttcag ttgtagagct     240

tcccagtcta ttgggacaaa cattcactgg tatcaacagc gaactaatgg atcgccaaga     300

ctcctgatta aatatgcttc tgagagcatc tctggaattc catcaagatt ctcagggagt     360

ggtagcggca ccgattttac gttatcgatc aattccgttg agagcgaaga tatcgcggac     420

tattactgtc agcagaacaa taactggcct acaacgttcg ggcagggac gaaattggag      480

ctgaagcgga ccgtcgccgc gccaagcgtg ttcatcttcc cccctagcga cgagcaattg     540

aaaagcggca ccgcaagtgt ggtttgcctg ctgaacaact tttatcctcg cgaggcgaaa     600

gtgcagtgga aagtcgacaa tgcactccag tcagggaaca gccaagagtc cgttactgaa     660

caagactcta aagatagtac ttatagctta tccagcacac tgacgctcag taaggccgat     720

tatgaaaaac ataaggtgta tgcgtgtgag gttacccatc aaggattgtc atcacccgtc     780

accaaatcct ttaacagagg agaatgt                                          807
```

<210> SEQ ID NO 459
<211> LENGTH: 269
<212> TYPE: PRT
<213> ORGANISM: Artificial Sequence
<220> FEATURE:
<223> OTHER INFORMATION: chemically synthesized

<400> SEQUENCE: 459

```
Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ile Ser Ser Gly
            20                  25                  30

Leu Leu Ser Ser Gly Gly Ser Gly Gly Ser Leu Ser Gly Arg Ser Gly
        35                  40                  45

Asn His Gly Ser Ser Gly Thr Gln Ile Leu Leu Thr Gln Ser Pro Val
    50                  55                  60

Ile Leu Ser Val Ser Pro Gly Glu Arg Val Ser Phe Ser Cys Arg Ala
65                  70                  75                  80

Ser Gln Ser Ile Gly Thr Asn Ile His Trp Tyr Gln Gln Arg Thr Asn
                85                  90                  95

Gly Ser Pro Arg Leu Leu Ile Lys Tyr Ala Ser Glu Ser Ile Ser Gly
            100                 105                 110

Ile Pro Ser Arg Phe Ser Gly Ser Gly Ser Gly Thr Asp Phe Thr Leu
        115                 120                 125

Ser Ile Asn Ser Val Glu Ser Glu Asp Ile Ala Asp Tyr Tyr Cys Gln
```

```
    130                 135                 140

Gln Asn Asn Asn Trp Pro Thr Thr Phe Gly Ala Gly Thr Lys Leu Glu
145                 150                 155                 160

Leu Lys Arg Thr Val Ala Ala Pro Ser Val Phe Ile Phe Pro Pro Ser
                165                 170                 175

Asp Glu Gln Leu Lys Ser Gly Thr Ala Ser Val Val Cys Leu Leu Asn
            180                 185                 190

Asn Phe Tyr Pro Arg Glu Ala Lys Val Gln Trp Lys Val Asp Asn Ala
        195                 200                 205

Leu Gln Ser Gly Asn Ser Gln Glu Ser Val Thr Glu Gln Asp Ser Lys
    210                 215                 220

Asp Ser Thr Tyr Ser Leu Ser Ser Thr Leu Thr Leu Ser Lys Ala Asp
225                 230                 235                 240

Tyr Glu Lys His Lys Val Tyr Ala Cys Glu Val Thr His Gln Gly Leu
                245                 250                 255

Ser Ser Pro Val Thr Lys Ser Phe Asn Arg Gly Glu Cys
            260                 265


<210> SEQ ID NO 460
<211> LENGTH: 807
<212> TYPE: DNA
<213> ORGANISM: Artificial Sequence
<220> FEATURE:
<223> OTHER INFORMATION: chemically synthesized

<400> SEQUENCE: 460

tgtatctcgc cccgcggctg cccagacggc ccatatgtga tgtatggttc ttccggtgga      60

tccggcggat caggtgggtc tggcctctca ggtcgttccg acaaccacgg cggctcaggt     120

gggtctcaga atcaggcact gcggatggcc ggatcttctg gcacccagat attgctcaca     180

cagtcaccag ttattctgtc cgtatctcca ggagaacggg tatctttctc ttgtagggca     240

agccagtcca tcggaacaaa catccattgg taccagcagc ggaccaatgg cagtccacgg     300

cttctgatca agtatgctag tgaaagcatt agcgggattc caagccgatt ttctgggtcg     360

ggtagtggaa ccgacttcac cctgagcatt aactctgtcg aatccgaaga tattgctgac     420

tattactgtc agcagaacaa caattggccg actacgtttg gcgccggaac caaattagaa     480

cttaagagaa ccgtggccgc tccctctgtc ttcatttttcc cgccttccga cgaacagctg     540

aagagcggaa ctgcctccgt ggtgtgcctg ttgaataact tttatccaag ggaagcaaag     600

gtgcagtgga aagtggacaa tgctctgcag tctggcaata gccaggagtc cgtgactgaa     660

caggacagta aagactcaac ctactcactg agcagtactc tcacattatc caaagccgat     720

tatgaaaagc ataaggttta tgcatgcgag gttacccacc agggactgag ctcccccgtg     780

accaaaagct tcaatagggg tgagtgc                                         807


<210> SEQ ID NO 461
<211> LENGTH: 269
<212> TYPE: PRT
<213> ORGANISM: Artificial Sequence
<220> FEATURE:
<223> OTHER INFORMATION: chemically synthesized

<400> SEQUENCE: 461

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Leu Ser Gly Arg
            20                  25                  30
```

```
Ser Asp Asn His Gly Gly Ser Gly Gly Ser Gln Asn Gln Ala Leu Arg
        35                  40                  45

Met Ala Gly Ser Ser Gly Thr Gln Ile Leu Leu Thr Gln Ser Pro Val
    50                  55                  60

Ile Leu Ser Val Ser Pro Gly Glu Arg Val Ser Phe Ser Cys Arg Ala
65                  70                  75                  80

Ser Gln Ser Ile Gly Thr Asn Ile His Trp Tyr Gln Gln Arg Thr Asn
                85                  90                  95

Gly Ser Pro Arg Leu Leu Ile Lys Tyr Ala Ser Glu Ser Ile Ser Gly
            100                 105                 110

Ile Pro Ser Arg Phe Ser Gly Ser Gly Ser Gly Thr Asp Phe Thr Leu
        115                 120                 125

Ser Ile Asn Ser Val Glu Ser Glu Asp Ile Ala Asp Tyr Tyr Cys Gln
    130                 135                 140

Gln Asn Asn Asn Trp Pro Thr Thr Phe Gly Ala Gly Thr Lys Leu Glu
145                 150                 155                 160

Leu Lys Arg Thr Val Ala Ala Pro Ser Val Phe Ile Phe Pro Pro Ser
                165                 170                 175

Asp Glu Gln Leu Lys Ser Gly Thr Ala Ser Val Val Cys Leu Leu Asn
            180                 185                 190

Asn Phe Tyr Pro Arg Glu Ala Lys Val Gln Trp Lys Val Asp Asn Ala
        195                 200                 205

Leu Gln Ser Gly Asn Ser Gln Glu Ser Val Thr Glu Gln Asp Ser Lys
    210                 215                 220

Asp Ser Thr Tyr Ser Leu Ser Ser Thr Leu Thr Leu Ser Lys Ala Asp
225                 230                 235                 240

Tyr Glu Lys His Lys Val Tyr Ala Cys Glu Val Thr His Gln Gly Leu
                245                 250                 255

Ser Ser Pro Val Thr Lys Ser Phe Asn Arg Gly Glu Cys
            260                 265
```

```
<210> SEQ ID NO 462
<211> LENGTH: 807
<212> TYPE: DNA
<213> ORGANISM: Artificial Sequence
<220> FEATURE:
<223> OTHER INFORMATION: chemically synthesized

<400> SEQUENCE: 462

tgcatcagcc cccgaggctg ccctgatggc ccctacgtga tgtacgggtc cagcggtggc      60

agcgggggct caggggggag cgggcagaat caggccctga gaatggcggg tggatccggg     120

gggtcccttt ctggcaggtc cgataaccac ggttctagtg gaacacagat tttgctgaca     180

caaagtcccg tcatcctctc tgtgtctccc ggtgagcggg tcagtttttc ctgccgagcg     240

tcccagagca tcgggacaaa tatccattgg taccagcaga gaacgaacgg ctctcctaga     300

ctgctcatca agtacgcctc ggaaagtatt tccggcattc cctcccgttt cagcggctcc     360

ggaagtggta cagattttac cctgagtatt aattccgtcg aatctgagga catagccgac     420

tactattgcc aacagaataa caattggcca acaacttttg gcgccgggac taagctggag     480

ctgaaacgga ccgtcgcagc accaagtgtt ttcatcttcc caccaagtga cgagcagctg     540

aaatccggaa cagcgagcgt ggtgtgccta ctcaataact tctatccacg cgaagccaag     600

gtgcagtgga aagtggacaa cgctctgcag tccggcaata gccaggaaag cgtgacagag     660

caagattcta aggacagtac gtattcactg tccagtacgc tcaccttaag caaggctgac     720
```

tacgaaaaac acaaggtcta cgcctgtgag gtcacacatc agggcctctc cagtccggtt 780
acaaaaagtt tcaatcgcgg ggaatgt 807

<210> SEQ ID NO 463
<211> LENGTH: 269
<212> TYPE: PRT
<213> ORGANISM: Artificial Sequence
<220> FEATURE:
<223> OTHER INFORMATION: chemically synthesized

<400> SEQUENCE: 463

Cys Ile Ser Pro Arg Gly Cys Pro Asp Gly Pro Tyr Val Met Tyr Gly
1 5 10 15

Ser Ser Gly Gly Ser Gly Gly Ser Gly Gly Ser Gly Gln Asn Gln Ala
20 25 30

Leu Arg Met Ala Gly Gly Ser Gly Gly Ser Leu Ser Gly Arg Ser Asp
35 40 45

Asn His Gly Ser Ser Gly Thr Gln Ile Leu Leu Thr Gln Ser Pro Val
50 55 60

Ile Leu Ser Val Ser Pro Gly Glu Arg Val Ser Phe Ser Cys Arg Ala
65 70 75 80

Ser Gln Ser Ile Gly Thr Asn Ile His Trp Tyr Gln Gln Arg Thr Asn
85 90 95

Gly Ser Pro Arg Leu Leu Ile Lys Tyr Ala Ser Glu Ser Ile Ser Gly
100 105 110

Ile Pro Ser Arg Phe Ser Gly Ser Gly Ser Gly Thr Asp Phe Thr Leu
115 120 125

Ser Ile Asn Ser Val Glu Ser Glu Asp Ile Ala Asp Tyr Tyr Cys Gln
130 135 140

Gln Asn Asn Asn Trp Pro Thr Thr Phe Gly Ala Gly Thr Lys Leu Glu
145 150 155 160

Leu Lys Arg Thr Val Ala Ala Pro Ser Val Phe Ile Phe Pro Pro Ser
165 170 175

Asp Glu Gln Leu Lys Ser Gly Thr Ala Ser Val Val Cys Leu Leu Asn
180 185 190

Asn Phe Tyr Pro Arg Glu Ala Lys Val Gln Trp Lys Val Asp Asn Ala
195 200 205

Leu Gln Ser Gly Asn Ser Gln Glu Ser Val Thr Glu Gln Asp Ser Lys
210 215 220

Asp Ser Thr Tyr Ser Leu Ser Ser Thr Leu Thr Leu Ser Lys Ala Asp
225 230 235 240

Tyr Glu Lys His Lys Val Tyr Ala Cys Glu Val Thr His Gln Gly Leu
245 250 255

Ser Ser Pro Val Thr Lys Ser Phe Asn Arg Gly Glu Cys
260 265

<210> SEQ ID NO 464
<211> LENGTH: 807
<212> TYPE: DNA
<213> ORGANISM: Artificial Sequence
<220> FEATURE:
<223> OTHER INFORMATION: chemically synthesized

<400> SEQUENCE: 464
tgcatcagtc ccagaggctg ccctgacggg ccctacgtga tgtatggtag ctcagggggc 60
tccggcggct ccggcggaag cggacttagc ggccgtagcg gcaaccatgg gggttctgga 120

```
ggatcccaga atcaggctct gcgcatggct ggaagcagcg gtacccagat cctgctcacc    180

caatcacccg tcatcttgtc tgtgagtcct ggcgaaaggg tgtcgttctc ttgtcgcgcg    240

tcccagtcca ttgggaccaa cattcattgg taccagcaga ggactaacgg gagccccgc     300

ctgctgatca aatacgccag tgaatctatc tctggaatcc catcacgatt ttcagggtcc    360

ggtagtggga ccgacttcac tttgagtatt aacagtgtgg aatccgagga catagccgac    420

tattactgtc agcagaacaa taactggcca acaacctttg gcgccgggac aaagttagag    480

cttaagcgga ctgttgcagc cccctccgtt tttatcttcc cgcccagtga tgaacagctg    540

aaaagcggta ccgcctccgt agtgtgcctt ctcaataatt tttaccccag agaagctaaa    600

gtacagtgga aagtcgacaa cgccctccag agcggcaaca gtcaggagtc cgtcaccgag    660

caggattcta aagactcaac atatagcctt tcgtccaccc taacactttc aaaagcagac    720

tatgaaaaac ataaggtgta tgcctgcgag gtcacacacc aggggctcag ctctccagtt    780

actaagtcat tcaaccgcgg agagtgt                                        807


<210> SEQ ID NO 465
<211> LENGTH: 269
<212> TYPE: PRT
<213> ORGANISM: Artificial Sequence
<220> FEATURE:
<223> OTHER INFORMATION: chemically synthesized

<400> SEQUENCE: 465

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Leu Ser Gly Arg
            20                  25                  30

Ser Gly Asn His Gly Gly Ser Gly Gly Ser Gln Asn Gln Ala Leu Arg
        35                  40                  45

Met Ala Gly Ser Ser Gly Thr Gln Ile Leu Leu Thr Gln Ser Pro Val
    50                  55                  60

Ile Leu Ser Val Ser Pro Gly Glu Arg Val Ser Phe Ser Cys Arg Ala
65                  70                  75                  80

Ser Gln Ser Ile Gly Thr Asn Ile His Trp Tyr Gln Gln Arg Thr Asn
                85                  90                  95

Gly Ser Pro Arg Leu Leu Ile Lys Tyr Ala Ser Glu Ser Ile Ser Gly
            100                 105                 110

Ile Pro Ser Arg Phe Ser Gly Ser Gly Ser Gly Thr Asp Phe Thr Leu
        115                 120                 125

Ser Ile Asn Ser Val Glu Ser Glu Asp Ile Ala Asp Tyr Tyr Cys Gln
    130                 135                 140

Gln Asn Asn Asn Trp Pro Thr Thr Phe Gly Ala Gly Thr Lys Leu Glu
145                 150                 155                 160

Leu Lys Arg Thr Val Ala Ala Pro Ser Val Phe Ile Phe Pro Pro Ser
                165                 170                 175

Asp Glu Gln Leu Lys Ser Gly Thr Ala Ser Val Val Cys Leu Leu Asn
            180                 185                 190

Asn Phe Tyr Pro Arg Glu Ala Lys Val Gln Trp Lys Val Asp Asn Ala
        195                 200                 205

Leu Gln Ser Gly Asn Ser Gln Glu Ser Val Thr Glu Gln Asp Ser Lys
    210                 215                 220

Asp Ser Thr Tyr Ser Leu Ser Ser Thr Leu Thr Leu Ser Lys Ala Asp
225                 230                 235                 240
```

```
Tyr Glu Lys His Lys Val Tyr Ala Cys Glu Val Thr His Gln Gly Leu
                245                 250                 255

Ser Ser Pro Val Thr Lys Ser Phe Asn Arg Gly Glu Cys
            260                 265
```

<210> SEQ ID NO 466
<211> LENGTH: 807
<212> TYPE: DNA
<213> ORGANISM: Artificial Sequence
<220> FEATURE:
<223> OTHER INFORMATION: chemically synthesized

<400> SEQUENCE: 466

```
tgcattagcc cccgagggtg tcccgatggg ccctacgtaa tgtacggatc atcgggcgga     60

tctgggggct ccggtggctc tggtcagaat caagctctgc gcatggccgg aggtagcggt    120

ggaagcctga gcggccgaag tggaaaccac ggctcctctg gcactcagat tcttctcacg    180

cagtcgcccg tgatcttgtc cgtgagccca ggcgagcggg tgagcttctc ttgccgggcc    240

agccaaagta taggtacaaa tattcactgg taccaacagc gaaccaacgg gtcgcctagg    300

ttgctcataa agtacgcatc cgagagtata agcggcatac catctaggtt ctcaggtagc    360

ggcagcggga ccgattttac cctcagcatt aattcggttg aatctgaaga tatcgccgat    420

tattattgtc agcagaataa caattggcct actactttcg gcgccggaac aaagctggaa    480

cttaagcgca cagtggccgc tccttctgtc tttatcttcc ctccatctga cgagcaatta    540

aagagtggga cagcctcggt ggtgtgtttg ctcaataact tctatccaag ggaggcaaag    600

gtgcagtgga aggtcgataa cgctctccag agtgggaatt cccaggagtc cgtgaccgag    660

caggattcta aagatagcac atactcactg tcttccaccc tgaccctgtc caaggcagac    720

tacgagaagc acaaagttta cgcctgtgaa gtgacacacc agggcctcag ctctcctgtc    780

acaaagagtt ttaatcgggg cgagtgt                                         807
```

<210> SEQ ID NO 467
<211> LENGTH: 269
<212> TYPE: PRT
<213> ORGANISM: Artificial Sequence
<220> FEATURE:
<223> OTHER INFORMATION: chemically synthesized

<400> SEQUENCE: 467

```
Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Gln Asn Gln Ala
            20                  25                  30

Leu Arg Met Ala Gly Gly Ser Gly Gly Ser Leu Ser Gly Arg Ser Gly
        35                  40                  45

Asn His Gly Ser Ser Gly Thr Gln Ile Leu Leu Thr Gln Ser Pro Val
    50                  55                  60

Ile Leu Ser Val Ser Pro Gly Glu Arg Val Ser Phe Ser Cys Arg Ala
65                  70                  75                  80

Ser Gln Ser Ile Gly Thr Asn Ile His Trp Tyr Gln Gln Arg Thr Asn
                85                  90                  95

Gly Ser Pro Arg Leu Leu Ile Lys Tyr Ala Ser Glu Ser Ile Ser Gly
            100                 105                 110

Ile Pro Ser Arg Phe Ser Gly Ser Gly Ser Gly Thr Asp Phe Thr Leu
        115                 120                 125
```

-continued

```
Ser Ile Asn Ser Val Glu Ser Glu Asp Ile Ala Asp Tyr Tyr Cys Gln
    130                 135                 140

Gln Asn Asn Asn Trp Pro Thr Thr Phe Gly Ala Gly Thr Lys Leu Glu
145                 150                 155                 160

Leu Lys Arg Thr Val Ala Ala Pro Ser Val Phe Ile Phe Pro Pro Ser
                165                 170                 175

Asp Glu Gln Leu Lys Ser Gly Thr Ala Ser Val Val Cys Leu Leu Asn
            180                 185                 190

Asn Phe Tyr Pro Arg Glu Ala Lys Val Gln Trp Lys Val Asp Asn Ala
        195                 200                 205

Leu Gln Ser Gly Asn Ser Gln Glu Ser Val Thr Glu Gln Asp Ser Lys
    210                 215                 220

Asp Ser Thr Tyr Ser Leu Ser Ser Thr Leu Thr Leu Ser Lys Ala Asp
225                 230                 235                 240

Tyr Glu Lys His Lys Val Tyr Ala Cys Glu Val Thr His Gln Gly Leu
                245                 250                 255

Ser Ser Pro Val Thr Lys Ser Phe Asn Arg Gly Glu Cys
            260                 265


<210> SEQ ID NO 468
<211> LENGTH: 9
<212> TYPE: PRT
<213> ORGANISM: Artificial Sequence
<220> FEATURE:
<223> OTHER INFORMATION: chemically synthesized

<400> SEQUENCE: 468

Ser Gly Arg Ser Ala Asn Pro Arg Gly
1               5


<210> SEQ ID NO 469
<211> LENGTH: 15
<212> TYPE: PRT
<213> ORGANISM: Artificial Sequence
<220> FEATURE:
<223> OTHER INFORMATION: chemically synthesized

<400> SEQUENCE: 469

Ile Ser Ser Gly Leu Leu Ser Gly Arg Ser Ala Asn Pro Arg Gly
1               5                   10                  15


<210> SEQ ID NO 470
<211> LENGTH: 18
<212> TYPE: PRT
<213> ORGANISM: Artificial Sequence
<220> FEATURE:
<223> OTHER INFORMATION: chemically synthesized

<400> SEQUENCE: 470

Ala Val Gly Leu Leu Ala Pro Pro Thr Ser Gly Arg Ser Ala Asn Pro
1               5                   10                  15

Arg Gly


<210> SEQ ID NO 471
<211> LENGTH: 17
<212> TYPE: PRT
<213> ORGANISM: Artificial Sequence
<220> FEATURE:
<223> OTHER INFORMATION: chemically synthesized

<400> SEQUENCE: 471

Ala Val Gly Leu Leu Ala Pro Pro Ser Gly Arg Ser Ala Asn Pro Arg
```

```
1               5                   10                  15

Gly


<210> SEQ ID NO 472
<211> LENGTH: 262
<212> TYPE: PRT
<213> ORGANISM: Artificial Sequence
<220> FEATURE:
<223> OTHER INFORMATION: chemically synthesized

<400> SEQUENCE: 472

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ile Ser Ser Gly
            20                  25                  30

Leu Leu Ser Gly Arg Ser Ala Asn Pro Arg Gly Gly Ser Ser Gly Thr
        35                  40                  45

Gln Ile Leu Leu Thr Gln Ser Pro Val Ile Leu Ser Val Ser Pro Gly
    50                  55                  60

Glu Arg Val Ser Phe Ser Cys Arg Ala Ser Gln Ser Ile Gly Thr Asn
65                  70                  75                  80

Ile His Trp Tyr Gln Gln Arg Thr Asn Gly Ser Pro Arg Leu Leu Ile
                85                  90                  95

Lys Tyr Ala Ser Glu Ser Ile Ser Gly Ile Pro Ser Arg Phe Ser Gly
            100                 105                 110

Ser Gly Ser Gly Thr Asp Phe Thr Leu Ser Ile Asn Ser Val Glu Ser
        115                 120                 125

Glu Asp Ile Ala Asp Tyr Tyr Cys Gln Gln Asn Asn Asn Trp Pro Thr
    130                 135                 140

Thr Phe Gly Ala Gly Thr Lys Leu Glu Leu Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
            260


<210> SEQ ID NO 473
<211> LENGTH: 268
<212> TYPE: PRT
<213> ORGANISM: Artificial Sequence
<220> FEATURE:
<223> OTHER INFORMATION: chemically synthesized

<400> SEQUENCE: 473

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
```

```
            20                  25                  30

Ser Gly Ile Ser Ser Gly Leu Leu Ser Gly Arg Ser Ala Asn Pro Arg
        35                  40                  45

Gly Gly Ser Ser Gly Thr Gln Ile Leu Leu Thr Gln Ser Pro Val Ile
    50                  55                  60

Leu Ser Val Ser Pro Gly Glu Arg Val Ser Phe Ser Cys Arg Ala Ser
65                  70                  75                  80

Gln Ser Ile Gly Thr Asn Ile His Trp Tyr Gln Gln Arg Thr Asn Gly
                85                  90                  95

Ser Pro Arg Leu Leu Ile Lys Tyr Ala Ser Glu Ser Ile Ser Gly Ile
            100                 105                 110

Pro Ser Arg Phe Ser Gly Ser Gly Ser Gly Thr Asp Phe Thr Leu Ser
        115                 120                 125

Ile Asn Ser Val Glu Ser Glu Asp Ile Ala Asp Tyr Tyr Cys Gln Gln
    130                 135                 140

Asn Asn Asn Trp Pro Thr Thr Phe Gly Ala Gly Thr Lys Leu Glu Leu
145                 150                 155                 160

Lys Arg Thr Val Ala Ala Pro Ser Val Phe Ile Phe Pro Pro Ser Asp
                165                 170                 175

Glu Gln Leu Lys Ser Gly Thr Ala Ser Val Val Cys Leu Leu Asn Asn
            180                 185                 190

Phe Tyr Pro Arg Glu Ala Lys Val Gln Trp Lys Val Asp Asn Ala Leu
        195                 200                 205

Gln Ser Gly Asn Ser Gln Glu Ser Val Thr Glu Gln Asp Ser Lys Asp
    210                 215                 220

Ser Thr Tyr Ser Leu Ser Ser Thr Leu Thr Leu Ser Lys Ala Asp Tyr
225                 230                 235                 240

Glu Lys His Lys Val Tyr Ala Cys Glu Val Thr His Gln Gly Leu Ser
                245                 250                 255

Ser Pro Val Thr Lys Ser Phe Asn Arg Gly Glu Cys
            260                 265


<210> SEQ ID NO 474
<211> LENGTH: 264
<212> TYPE: PRT
<213> ORGANISM: Artificial Sequence
<220> FEATURE:
<223> OTHER INFORMATION: chemically synthesized

<400> SEQUENCE: 474

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ala Val Gly Leu
            20                  25                  30

Leu Ala Pro Pro Ser Gly Arg Ser Ala Asn Pro Arg Gly Gly Ser Ser
        35                  40                  45

Gly Thr Gln Ile Leu Leu Thr Gln Ser Pro Val Ile Leu Ser Val Ser
    50                  55                  60

Pro Gly Glu Arg Val Ser Phe Ser Cys Arg Ala Ser Gln Ser Ile Gly
65                  70                  75                  80

Thr Asn Ile His Trp Tyr Gln Gln Arg Thr Asn Gly Ser Pro Arg Leu
                85                  90                  95

Leu Ile Lys Tyr Ala Ser Glu Ser Ile Ser Gly Ile Pro Ser Arg Phe
            100                 105                 110

Ser Gly Ser Gly Ser Gly Thr Asp Phe Thr Leu Ser Ile Asn Ser Val
```

```
        115                 120                 125

Glu Ser Glu Asp Ile Ala Asp Tyr Tyr Cys Gln Gln Asn Asn Asn Trp
    130                 135                 140

Pro Thr Thr Phe Gly Ala Gly Thr Lys Leu Glu Leu Lys Arg Thr Val
145                 150                 155                 160

Ala Ala Pro Ser Val Phe Ile Phe Pro Pro Ser Asp Glu Gln Leu Lys
                165                 170                 175

Ser Gly Thr Ala Ser Val Val Cys Leu Leu Asn Asn Phe Tyr Pro Arg
            180                 185                 190

Glu Ala Lys Val Gln Trp Lys Val Asp Asn Ala Leu Gln Ser Gly Asn
        195                 200                 205

Ser Gln Glu Ser Val Thr Glu Gln Asp Ser Lys Asp Ser Thr Tyr Ser
    210                 215                 220

Leu Ser Ser Thr Leu Thr Leu Ser Lys Ala Asp Tyr Glu Lys His Lys
225                 230                 235                 240

Val Tyr Ala Cys Glu Val Thr His Gln Gly Leu Ser Ser Pro Val Thr
                245                 250                 255

Lys Ser Phe Asn Arg Gly Glu Cys
            260


<210> SEQ ID NO 475
<211> LENGTH: 270
<212> TYPE: PRT
<213> ORGANISM: Artificial Sequence
<220> FEATURE:
<223> OTHER INFORMATION: chemically synthesized

<400> SEQUENCE: 475

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Ala Val Gly Leu Leu Ala Pro Pro Ser Gly Arg Ser Ala Asn
        35                  40                  45

Pro Arg Gly Gly Ser Ser Gly Thr Gln Ile Leu Leu Thr Gln Ser Pro
    50                  55                  60

Val Ile Leu Ser Val Ser Pro Gly Glu Arg Val Ser Phe Ser Cys Arg
65                  70                  75                  80

Ala Ser Gln Ser Ile Gly Thr Asn Ile His Trp Tyr Gln Gln Arg Thr
                85                  90                  95

Asn Gly Ser Pro Arg Leu Leu Ile Lys Tyr Ala Ser Glu Ser Ile Ser
            100                 105                 110

Gly Ile Pro Ser Arg Phe Ser Gly Ser Gly Ser Gly Thr Asp Phe Thr
        115                 120                 125

Leu Ser Ile Asn Ser Val Glu Ser Glu Asp Ile Ala Asp Tyr Tyr Cys
    130                 135                 140

Gln Gln Asn Asn Asn Trp Pro Thr Thr Phe Gly Ala Gly Thr Lys Leu
145                 150                 155                 160

Glu Leu Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
            180                 185                 190

Asn Asn Phe Tyr Pro Arg Glu Ala Lys Val Gln Trp Lys Val Asp Asn
        195                 200                 205

Ala Leu Gln Ser Gly Asn Ser Gln Glu Ser Val Thr Glu Gln Asp Ser
```

```
    210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
            260                 265                 270
```

<210> SEQ ID NO 476
<211> LENGTH: 259
<212> TYPE: PRT
<213> ORGANISM: Artificial Sequence
<220> FEATURE:
<223> OTHER INFORMATION: chemically synthesized

<400> SEQUENCE: 476

```
Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Ile Ser Ser Gly Leu
            20                  25                  30

Leu Ser Gly Arg Ser Ala Asn Pro Arg Gly Gly Gly Ser Asp Ile Gln
        35                  40                  45

Met Thr Gln Ser Pro Ser Ser Leu Ser Ala Ser Val Gly Asp Arg Val
    50                  55                  60

Thr Ile Thr Cys Arg Ala Ser Gln Ser Ile Ser Ser Tyr Leu Asn Trp
65                  70                  75                  80

Tyr Gln Gln Lys Pro Gly Lys Ala Pro Lys Leu Leu Ile Tyr Ala Ala
                85                  90                  95

Ser Ser Leu Gln Ser Gly Val Pro Ser Arg Phe Ser Gly Ser Gly Ser
            100                 105                 110

Gly Thr Asp Phe Thr Leu Thr Ile Ser Ser Leu Gln Pro Glu Asp Phe
        115                 120                 125

Ala Thr Tyr Tyr Cys Gln Gln Thr Val Val Ala Pro Pro Leu Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys
```

<210> SEQ ID NO 477
<211> LENGTH: 253
<212> TYPE: PRT
<213> ORGANISM: Artificial Sequence
<220> FEATURE:
<223> OTHER INFORMATION: chemically synthesized -continued

<400> SEQUENCE: 477

Cys Asn Ile Trp Leu Val Gly Gly Asp Cys Arg Gly Trp Gln Gly Gly
1 5 10 15

Ser Ser Gly Gly Ser Ile Ser Ser Gly Leu Leu Ser Gly Arg Ser Ala
20 25 30

Asn Pro Arg Gly Gly Gly Ser Asp Ile Gln Met Thr Gln Ser Pro Ser
35 40 45

Ser Leu Ser Ala Ser Val Gly Asp Arg Val Thr Ile Thr Cys Arg Ala
50 55 60

Ser Gln Ser Ile Ser Ser Tyr Leu Asn Trp Tyr Gln Gln Lys Pro Gly
65 70 75 80

Lys Ala Pro Lys Leu Leu Ile Tyr Ala Ala Ser Ser Leu Gln Ser Gly
85 90 95

Val Pro Ser Arg Phe Ser Gly Ser Gly Ser Gly Thr Asp Phe Thr Leu
100 105 110

Thr Ile Ser Ser Leu Gln Pro Glu Asp Phe Ala Thr Tyr Tyr Cys Gln
115 120 125

Gln Thr Val Val Ala Pro Pro Leu Phe Gly Gln Gly Thr Lys Val Glu
130 135 140

Ile Lys Arg Thr Val Ala Ala Pro Ser Val Phe Ile Phe Pro Pro Ser
145 150 155 160

Asp Glu Gln Leu Lys Ser Gly Thr Ala Ser Val Val Cys Leu Leu Asn
165 170 175

Asn Phe Tyr Pro Arg Glu Ala Lys Val Gln Trp Lys Val Asp Asn Ala
180 185 190

Leu Gln Ser Gly Asn Ser Gln Glu Ser Val Thr Glu Gln Asp Ser Lys
195 200 205

Asp Ser Thr Tyr Ser Leu Ser Ser Thr Leu Thr Leu Ser Lys Ala Asp
210 215 220

Tyr Glu Lys His Lys Val Tyr Ala Cys Glu Val Thr His Gln Gly Leu
225 230 235 240

Ser Ser Pro Val Thr Lys Ser Phe Asn Arg Gly Glu Cys
245 250

<210> SEQ ID NO 478
<211> LENGTH: 261
<212> TYPE: PRT
<213> ORGANISM: Artificial Sequence
<220> FEATURE:
<223> OTHER INFORMATION: chemically synthesized

<400> SEQUENCE: 478

Gln Gly Gln Ser Gly Gln Cys Asn Ile Trp Leu Val Gly Gly Asp Cys
1 5 10 15

Arg Gly Trp Gln Gly Gly Ser Ser Gly Gly Ser Ala Val Gly Leu Leu
20 25 30

Ala Pro Pro Ser Gly Arg Ser Ala Asn Pro Arg Gly Gly Gly Ser Asp
35 40 45

Ile Gln Met Thr Gln Ser Pro Ser Ser Leu Ser Ala Ser Val Gly Asp
50 55 60

Arg Val Thr Ile Thr Cys Arg Ala Ser Gln Ser Ile Ser Ser Tyr Leu
65 70 75 80

Asn Trp Tyr Gln Gln Lys Pro Gly Lys Ala Pro Lys Leu Leu Ile Tyr
85 90 95

Ala Ala Ser Ser Leu Gln Ser Gly Val Pro Ser Arg Phe Ser Gly Ser

```
            100                 105                 110

Gly Ser Gly Thr Asp Phe Thr Leu Thr Ile Ser Ser Leu Gln Pro Glu
        115                 120                 125

Asp Phe Ala Thr Tyr Tyr Cys Gln Gln Thr Val Val Ala Pro Pro Leu
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260


<210> SEQ ID NO 479
<211> LENGTH: 255
<212> TYPE: PRT
<213> ORGANISM: Artificial Sequence
<220> FEATURE:
<223> OTHER INFORMATION: chemically synthesized

<400> SEQUENCE: 479

Cys Asn Ile Trp Leu Val Gly Gly Asp Cys Arg Gly Trp Gln Gly Gly
1               5                   10                  15

Ser Ser Gly Gly Ser Ala Val Gly Leu Leu Ala Pro Pro Ser Gly Arg
            20                  25                  30

Ser Ala Asn Pro Arg Gly Gly Gly Ser Asp Ile Gln Met Thr Gln Ser
        35                  40                  45

Pro Ser Ser Leu Ser Ala Ser Val Gly Asp Arg Val Thr Ile Thr Cys
    50                  55                  60

Arg Ala Ser Gln Ser Ile Ser Ser Tyr Leu Asn Trp Tyr Gln Gln Lys
65                  70                  75                  80

Pro Gly Lys Ala Pro Lys Leu Leu Ile Tyr Ala Ala Ser Ser Leu Gln
                85                  90                  95

Ser Gly Val Pro Ser Arg Phe Ser Gly Ser Gly Ser Gly Thr Asp Phe
            100                 105                 110

Thr Leu Thr Ile Ser Ser Leu Gln Pro Glu Asp Phe Ala Thr Tyr Tyr
        115                 120                 125

Cys Gln Gln Thr Val Val Ala Pro Pro Leu Phe Gly Gln Gly Thr Lys
    130                 135                 140

Val Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
```

```
        195                 200                 205

Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 480
<211> LENGTH: 5
<212> TYPE: PRT
<213> ORGANISM: Artificial Sequence
<220> FEATURE:
<223> OTHER INFORMATION: chemically synthesized

<400> SEQUENCE: 480

Ile Ser Ser Gly Leu
1               5


<210> SEQ ID NO 481
<211> LENGTH: 7
<212> TYPE: PRT
<213> ORGANISM: Artificial Sequence
<220> FEATURE:
<223> OTHER INFORMATION: chemically synthesized

<400> SEQUENCE: 481

Ile Ser Ser Gly Leu Leu Ser
1               5


<210> SEQ ID NO 482
<211> LENGTH: 6
<212> TYPE: PRT
<213> ORGANISM: Artificial Sequence
<220> FEATURE:
<223> OTHER INFORMATION: chemically synthesized

<400> SEQUENCE: 482

Ile Ser Ser Gly Leu Leu
1               5


<210> SEQ ID NO 483
<211> LENGTH: 13
<212> TYPE: PRT
<213> ORGANISM: Artificial Sequence
<220> FEATURE:
<223> OTHER INFORMATION: chemically synthesized

<400> SEQUENCE: 483

Ile Ser Ser Gly Leu Leu Ser Gly Arg Ser Asp Asp His
1               5                   10


<210> SEQ ID NO 484
<211> LENGTH: 13
<212> TYPE: PRT
<213> ORGANISM: Artificial Sequence
<220> FEATURE:
<223> OTHER INFORMATION: chemically synthesized

<400> SEQUENCE: 484

Ile Ser Ser Gly Leu Leu Ser Gly Arg Ser Asp Ile His
1               5                   10


<210> SEQ ID NO 485
<211> LENGTH: 13
```

<212> TYPE: PRT
<213> ORGANISM: Artificial Sequence
<220> FEATURE:
<223> OTHER INFORMATION: chemically synthesized

<400> SEQUENCE: 485

Ile Ser Ser Gly Leu Leu Ser Gly Arg Ser Asp Gln His
1 5 10

<210> SEQ ID NO 486
<211> LENGTH: 13
<212> TYPE: PRT
<213> ORGANISM: Artificial Sequence
<220> FEATURE:
<223> OTHER INFORMATION: chemically synthesized

<400> SEQUENCE: 486

Ile Ser Ser Gly Leu Leu Ser Gly Arg Ser Asp Thr His
1 5 10

<210> SEQ ID NO 487
<211> LENGTH: 13
<212> TYPE: PRT
<213> ORGANISM: Artificial Sequence
<220> FEATURE:
<223> OTHER INFORMATION: chemically synthesized

<400> SEQUENCE: 487

Ile Ser Ser Gly Leu Leu Ser Gly Arg Ser Asp Tyr His
1 5 10

<210> SEQ ID NO 488
<211> LENGTH: 13
<212> TYPE: PRT
<213> ORGANISM: Artificial Sequence
<220> FEATURE:
<223> OTHER INFORMATION: chemically synthesized

<400> SEQUENCE: 488

Ile Ser Ser Gly Leu Leu Ser Gly Arg Ser Asp Asn Pro
1 5 10

<210> SEQ ID NO 489
<211> LENGTH: 13
<212> TYPE: PRT
<213> ORGANISM: Artificial Sequence
<220> FEATURE:
<223> OTHER INFORMATION: chemically synthesized

<400> SEQUENCE: 489

Ile Ser Ser Gly Leu Leu Ser Gly Arg Ser Ala Asn Pro
1 5 10

<210> SEQ ID NO 490
<211> LENGTH: 13
<212> TYPE: PRT
<213> ORGANISM: Artificial Sequence
<220> FEATURE:
<223> OTHER INFORMATION: chemically synthesized

<400> SEQUENCE: 490

Ile Ser Ser Gly Leu Leu Ser Gly Arg Ser Ala Asn Ile
1 5 10

<210> SEQ ID NO 491
<211> LENGTH: 39
<212> TYPE: DNA

<213> ORGANISM: Artificial Sequence
<220> FEATURE:
<223> OTHER INFORMATION: chemically synthesized

<400> SEQUENCE: 491
atatcgagtg gattgctgtc tggcagatct gacgatcac 39

<210> SEQ ID NO 492
<211> LENGTH: 39
<212> TYPE: DNA
<213> ORGANISM: Artificial Sequence
<220> FEATURE:
<223> OTHER INFORMATION: chemically synthesized

<400> SEQUENCE: 492
atatcgagtg gattgctgtc tggcagatct gacatacac 39

<210> SEQ ID NO 493
<211> LENGTH: 39
<212> TYPE: DNA
<213> ORGANISM: Artificial Sequence
<220> FEATURE:
<223> OTHER INFORMATION: chemically synthesized

<400> SEQUENCE: 493
atatcgagtg gattgctgtc tggcagatct gaccaacac 39

<210> SEQ ID NO 494
<211> LENGTH: 39
<212> TYPE: DNA
<213> ORGANISM: Artificial Sequence
<220> FEATURE:
<223> OTHER INFORMATION: chemically synthesized

<400> SEQUENCE: 494
atatcgagtg gattgctgtc tggcagatct gacactcac 39

<210> SEQ ID NO 495
<211> LENGTH: 39
<212> TYPE: DNA
<213> ORGANISM: Artificial Sequence
<220> FEATURE:
<223> OTHER INFORMATION: chemically synthesized

<400> SEQUENCE: 495
atatcgagtg gattgctgtc tggcagatct gactatcac 39

<210> SEQ ID NO 496
<211> LENGTH: 39
<212> TYPE: DNA
<213> ORGANISM: Artificial Sequence
<220> FEATURE:
<223> OTHER INFORMATION: chemically synthesized

<400> SEQUENCE: 496
attagctcag gccttcttag cggccgcagc gacaatccc 39

<210> SEQ ID NO 497
<211> LENGTH: 39
<212> TYPE: DNA
<213> ORGANISM: Artificial Sequence
<220> FEATURE:
<223> OTHER INFORMATION: chemically synthesized

<400> SEQUENCE: 497
atatcgagtg gattgctgtc tggcagatct gctaatccc 39

<210> SEQ ID NO 498
<211> LENGTH: 39
<212> TYPE: DNA
<213> ORGANISM: Artificial Sequence
<220> FEATURE:
<223> OTHER INFORMATION: chemically synthesized

<400> SEQUENCE: 498
atatcgagtg gattgctgtc tggcagatct gctaatata 39

<210> SEQ ID NO 499
<211> LENGTH: 260
<212> TYPE: PRT
<213> ORGANISM: Artificial Sequence
<220> FEATURE:
<223> OTHER INFORMATION: chemically synthesized

<400> SEQUENCE: 499

```
Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ile Ser Ser Gly
            20                  25                  30

Leu Leu Ser Gly Arg Ser Asp Asp His Gly Ser Ser Gly Thr Gln Ile
        35                  40                  45

Leu Leu Thr Gln Ser Pro Val Ile Leu Ser Val Ser Pro Gly Glu Arg
    50                  55                  60

Val Ser Phe Ser Cys Arg Ala Ser Gln Ser Ile Gly Thr Asn Ile His
65                  70                  75                  80

Trp Tyr Gln Gln Arg Thr Asn Gly Ser Pro Arg Leu Leu Ile Lys Tyr
                85                  90                  95

Ala Ser Glu Ser Ile Ser Gly Ile Pro Ser Arg Phe Ser Gly Ser Gly
            100                 105                 110

Ser Gly Thr Asp Phe Thr Leu Ser Ile Asn Ser Val Glu Ser Glu Asp
        115                 120                 125

Ile Ala Asp Tyr Tyr Cys Gln Gln Asn Asn Asn Trp Pro Thr Thr Phe
    130                 135                 140

Gly Ala Gly Thr Lys Leu Glu Leu Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260
```

<210> SEQ ID NO 500
<211> LENGTH: 260
<212> TYPE: PRT
<213> ORGANISM: Artificial Sequence
<220> FEATURE:
<223> OTHER INFORMATION: chemically synthesized

<400> SEQUENCE: 500

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ile Ser Ser Gly
            20                  25                  30

Leu Leu Ser Gly Arg Ser Asp Ile His Gly Ser Ser Gly Thr Gln Ile
        35                  40                  45

Leu Leu Thr Gln Ser Pro Val Ile Leu Ser Val Ser Pro Gly Glu Arg
    50                  55                  60

Val Ser Phe Ser Cys Arg Ala Ser Gln Ser Ile Gly Thr Asn Ile His
65                  70                  75                  80

Trp Tyr Gln Gln Arg Thr Asn Gly Ser Pro Arg Leu Leu Ile Lys Tyr
                85                  90                  95

Ala Ser Glu Ser Ile Ser Gly Ile Pro Ser Arg Phe Ser Gly Ser Gly
            100                 105                 110

Ser Gly Thr Asp Phe Thr Leu Ser Ile Asn Ser Val Glu Ser Glu Asp
        115                 120                 125

Ile Ala Asp Tyr Tyr Cys Gln Gln Asn Asn Asn Trp Pro Thr Thr Phe
    130                 135                 140

Gly Ala Gly Thr Lys Leu Glu Leu Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260

<210> SEQ ID NO 501
<211> LENGTH: 260
<212> TYPE: PRT
<213> ORGANISM: Artificial Sequence
<220> FEATURE:
<223> OTHER INFORMATION: chemically synthesized

<400> SEQUENCE: 501

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ile Ser Ser Gly
            20                  25                  30

Leu Leu Ser Gly Arg Ser Asp Gln His Gly Ser Ser Gly Thr Gln Ile
        35                  40                  45

Leu Leu Thr Gln Ser Pro Val Ile Leu Ser Val Ser Pro Gly Glu Arg
    50                  55                  60

Val Ser Phe Ser Cys Arg Ala Ser Gln Ser Ile Gly Thr Asn Ile His

```
65                  70                  75                  80

Trp Tyr Gln Gln Arg Thr Asn Gly Ser Pro Arg Leu Leu Ile Lys Tyr
                85                  90                  95

Ala Ser Glu Ser Ile Ser Gly Ile Pro Ser Arg Phe Ser Gly Ser Gly
            100                 105                 110

Ser Gly Thr Asp Phe Thr Leu Ser Ile Asn Ser Val Glu Ser Glu Asp
        115                 120                 125

Ile Ala Asp Tyr Tyr Cys Gln Gln Asn Asn Asn Trp Pro Thr Thr Phe
    130                 135                 140

Gly Ala Gly Thr Lys Leu Glu Leu Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260


<210> SEQ ID NO 502
<211> LENGTH: 260
<212> TYPE: PRT
<213> ORGANISM: Artificial Sequence
<220> FEATURE:
<223> OTHER INFORMATION: chemically synthesized

<400> SEQUENCE: 502

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ile Ser Ser Gly
            20                  25                  30

Leu Leu Ser Gly Arg Ser Asp Thr His Gly Ser Ser Gly Thr Gln Ile
        35                  40                  45

Leu Leu Thr Gln Ser Pro Val Ile Leu Ser Val Ser Pro Gly Glu Arg
    50                  55                  60

Val Ser Phe Ser Cys Arg Ala Ser Gln Ser Ile Gly Thr Asn Ile His
65                  70                  75                  80

Trp Tyr Gln Gln Arg Thr Asn Gly Ser Pro Arg Leu Leu Ile Lys Tyr
                85                  90                  95

Ala Ser Glu Ser Ile Ser Gly Ile Pro Ser Arg Phe Ser Gly Ser Gly
            100                 105                 110

Ser Gly Thr Asp Phe Thr Leu Ser Ile Asn Ser Val Glu Ser Glu Asp
        115                 120                 125

Ile Ala Asp Tyr Tyr Cys Gln Gln Asn Asn Asn Trp Pro Thr Thr Phe
    130                 135                 140

Gly Ala Gly Thr Lys Leu Glu Leu Lys Arg Thr Val Ala Ala Pro Ser
145                 150                 155                 160

Val Phe Ile Phe Pro Pro Ser Asp Glu Gln Leu Lys Ser Gly Thr Ala
```

```
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260


<210> SEQ ID NO 503
<211> LENGTH: 260
<212> TYPE: PRT
<213> ORGANISM: Artificial Sequence
<220> FEATURE:
<223> OTHER INFORMATION: chemically synthesized

<400> SEQUENCE: 503

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ile Ser Ser Gly
            20                  25                  30

Leu Leu Ser Gly Arg Ser Asp Tyr His Gly Ser Ser Gly Thr Gln Ile
        35                  40                  45

Leu Leu Thr Gln Ser Pro Val Ile Leu Ser Val Ser Pro Gly Glu Arg
    50                  55                  60

Val Ser Phe Ser Cys Arg Ala Ser Gln Ser Ile Gly Thr Asn Ile His
65                  70                  75                  80

Trp Tyr Gln Gln Arg Thr Asn Gly Ser Pro Arg Leu Leu Ile Lys Tyr
                85                  90                  95

Ala Ser Glu Ser Ile Ser Gly Ile Pro Ser Arg Phe Ser Gly Ser Gly
            100                 105                 110

Ser Gly Thr Asp Phe Thr Leu Ser Ile Asn Ser Val Glu Ser Glu Asp
        115                 120                 125

Ile Ala Asp Tyr Tyr Cys Gln Gln Asn Asn Asn Trp Pro Thr Thr Phe
    130                 135                 140

Gly Ala Gly Thr Lys Leu Glu Leu Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
```

260

<210> SEQ ID NO 504
<211> LENGTH: 260
<212> TYPE: PRT
<213> ORGANISM: Artificial Sequence
<220> FEATURE:
<223> OTHER INFORMATION: chemically synthesized

<400> SEQUENCE: 504

Cys Ile Ser Pro Arg Gly Cys Pro Asp Gly Pro Tyr Val Met Tyr Gly
1 5 10 15

Ser Ser Gly Gly Ser Gly Gly Ser Gly Gly Ser Gly Ile Ser Ser Gly
20 25 30

Leu Leu Ser Gly Arg Ser Asp Asn Pro Gly Ser Ser Gly Thr Gln Ile
35 40 45

Leu Leu Thr Gln Ser Pro Val Ile Leu Ser Val Ser Pro Gly Glu Arg
50 55 60

Val Ser Phe Ser Cys Arg Ala Ser Gln Ser Ile Gly Thr Asn Ile His
65 70 75 80

Trp Tyr Gln Gln Arg Thr Asn Gly Ser Pro Arg Leu Leu Ile Lys Tyr
85 90 95

Ala Ser Glu Ser Ile Ser Gly Ile Pro Ser Arg Phe Ser Gly Ser Gly
100 105 110

Ser Gly Thr Asp Phe Thr Leu Ser Ile Asn Ser Val Glu Ser Glu Asp
115 120 125

Ile Ala Asp Tyr Tyr Cys Gln Gln Asn Asn Asn Trp Pro Thr Thr Phe
130 135 140

Gly Ala Gly Thr Lys Leu Glu Leu Lys Arg Thr Val Ala Ala Pro Ser
145 150 155 160

Val Phe Ile Phe Pro Pro Ser Asp Glu Gln Leu Lys Ser Gly Thr Ala
165 170 175

Ser Val Val Cys Leu Leu Asn Asn Phe Tyr Pro Arg Glu Ala Lys Val
180 185 190

Gln Trp Lys Val Asp Asn Ala Leu Gln Ser Gly Asn Ser Gln Glu Ser
195 200 205

Val Thr Glu Gln Asp Ser Lys Asp Ser Thr Tyr Ser Leu Ser Ser Thr
210 215 220

Leu Thr Leu Ser Lys Ala Asp Tyr Glu Lys His Lys Val Tyr Ala Cys
225 230 235 240

Glu Val Thr His Gln Gly Leu Ser Ser Pro Val Thr Lys Ser Phe Asn
245 250 255

Arg Gly Glu Cys
260

<210> SEQ ID NO 505
<211> LENGTH: 260
<212> TYPE: PRT
<213> ORGANISM: Artificial Sequence
<220> FEATURE:
<223> OTHER INFORMATION: chemically synthesized

<400> SEQUENCE: 505

Cys Ile Ser Pro Arg Gly Cys Pro Asp Gly Pro Tyr Val Met Tyr Gly
1 5 10 15

Ser Ser Gly Gly Ser Gly Gly Ser Gly Gly Ser Gly Ile Ser Ser Gly
20 25 30

-continued

Leu Leu Ser Gly Arg Ser Ala Asn Pro Gly Ser Ser Gly Thr Gln Ile
35 40 45

Leu Leu Thr Gln Ser Pro Val Ile Leu Ser Val Ser Pro Gly Glu Arg
50 55 60

Val Ser Phe Ser Cys Arg Ala Ser Gln Ser Ile Gly Thr Asn Ile His
65 70 75 80

Trp Tyr Gln Gln Arg Thr Asn Gly Ser Pro Arg Leu Leu Ile Lys Tyr
85 90 95

Ala Ser Glu Ser Ile Ser Gly Ile Pro Ser Arg Phe Ser Gly Ser Gly
100 105 110

Ser Gly Thr Asp Phe Thr Leu Ser Ile Asn Ser Val Glu Ser Glu Asp
115 120 125

Ile Ala Asp Tyr Tyr Cys Gln Gln Asn Asn Asn Trp Pro Thr Thr Phe
130 135 140

Gly Ala Gly Thr Lys Leu Glu Leu Lys Arg Thr Val Ala Ala Pro Ser
145 150 155 160

Val Phe Ile Phe Pro Pro Ser Asp Glu Gln Leu Lys Ser Gly Thr Ala
165 170 175

Ser Val Val Cys Leu Leu Asn Asn Phe Tyr Pro Arg Glu Ala Lys Val
180 185 190

Gln Trp Lys Val Asp Asn Ala Leu Gln Ser Gly Asn Ser Gln Glu Ser
195 200 205

Val Thr Glu Gln Asp Ser Lys Asp Ser Thr Tyr Ser Leu Ser Ser Thr
210 215 220

Leu Thr Leu Ser Lys Ala Asp Tyr Glu Lys His Lys Val Tyr Ala Cys
225 230 235 240

Glu Val Thr His Gln Gly Leu Ser Ser Pro Val Thr Lys Ser Phe Asn
245 250 255

Arg Gly Glu Cys
260

<210> SEQ ID NO 506
<211> LENGTH: 260
<212> TYPE: PRT
<213> ORGANISM: Artificial Sequence
<220> FEATURE:
<223> OTHER INFORMATION: chemically synthesized

<400> SEQUENCE: 506

Cys Ile Ser Pro Arg Gly Cys Pro Asp Gly Pro Tyr Val Met Tyr Gly
1 5 10 15

Ser Ser Gly Gly Ser Gly Gly Ser Gly Gly Ser Gly Ile Ser Ser Gly
20 25 30

Leu Leu Ser Gly Arg Ser Ala Asn Ile Gly Ser Ser Gly Thr Gln Ile
35 40 45

Leu Leu Thr Gln Ser Pro Val Ile Leu Ser Val Ser Pro Gly Glu Arg
50 55 60

Val Ser Phe Ser Cys Arg Ala Ser Gln Ser Ile Gly Thr Asn Ile His
65 70 75 80

Trp Tyr Gln Gln Arg Thr Asn Gly Ser Pro Arg Leu Leu Ile Lys Tyr
85 90 95

Ala Ser Glu Ser Ile Ser Gly Ile Pro Ser Arg Phe Ser Gly Ser Gly
100 105 110

Ser Gly Thr Asp Phe Thr Leu Ser Ile Asn Ser Val Glu Ser Glu Asp
115 120 125

```
Ile Ala Asp Tyr Tyr Cys Gln Gln Asn Asn Asn Trp Pro Thr Thr Phe
    130                 135                 140

Gly Ala Gly Thr Lys Leu Glu Leu Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260


<210> SEQ ID NO 507
<211> LENGTH: 252
<212> TYPE: PRT
<213> ORGANISM: Artificial Sequence
<220> FEATURE:
<223> OTHER INFORMATION: chemically synthesized

<400> SEQUENCE: 507

Cys Asn Ile Trp Leu Val Gly Gly Asp Cys Arg Gly Trp Gln Gly Gly
1               5                   10                  15

Ser Ser Gly Gly Ser Ile Ser Ser Gly Leu Leu Ser Gly Arg Ser Asp
            20                  25                  30

Asp His Gly Gly Gly Ser Asp Ile Gln Met Thr Gln Ser Pro Ser Ser
        35                  40                  45

Leu Ser Ala Ser Val Gly Asp Arg Val Thr Ile Thr Cys Arg Ala Ser
    50                  55                  60

Gln Ser Ile Ser Ser Tyr Leu Asn Trp Tyr Gln Gln Lys Pro Gly Lys
65                  70                  75                  80

Ala Pro Lys Leu Leu Ile Tyr Ala Ala Ser Ser Leu Gln Ser Gly Val
                85                  90                  95

Pro Ser Arg Phe Ser Gly Ser Gly Ser Gly Thr Asp Phe Thr Leu Thr
            100                 105                 110

Ile Ser Ser Leu Gln Pro Glu Asp Phe Ala Thr Tyr Tyr Cys Gln Gln
        115                 120                 125

Thr Val Val Ala Pro Pro Leu Phe Gly Gln Gly Thr Lys Val Glu Ile
    130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220
```

```
Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250
```

<210> SEQ ID NO 508
<211> LENGTH: 252
<212> TYPE: PRT
<213> ORGANISM: Artificial Sequence
<220> FEATURE:
<223> OTHER INFORMATION: chemically synthesized

<400> SEQUENCE: 508

```
Cys Asn Ile Trp Leu Val Gly Gly Asp Cys Arg Gly Trp Gln Gly Gly
1               5                   10                  15

Ser Ser Gly Gly Ser Ile Ser Ser Gly Leu Leu Ser Gly Arg Ser Asp
            20                  25                  30

Ile His Gly Gly Gly Ser Asp Ile Gln Met Thr Gln Ser Pro Ser Ser
        35                  40                  45

Leu Ser Ala Ser Val Gly Asp Arg Val Thr Ile Thr Cys Arg Ala Ser
    50                  55                  60

Gln Ser Ile Ser Ser Tyr Leu Asn Trp Tyr Gln Gln Lys Pro Gly Lys
65                  70                  75                  80

Ala Pro Lys Leu Leu Ile Tyr Ala Ala Ser Ser Leu Gln Ser Gly Val
                85                  90                  95

Pro Ser Arg Phe Ser Gly Ser Gly Ser Gly Thr Asp Phe Thr Leu Thr
            100                 105                 110

Ile Ser Ser Leu Gln Pro Glu Asp Phe Ala Thr Tyr Tyr Cys Gln Gln
        115                 120                 125

Thr Val Val Ala Pro Pro Leu Phe Gly Gln Gly Thr Lys Val Glu Ile
    130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250
```

<210> SEQ ID NO 509
<211> LENGTH: 252
<212> TYPE: PRT
<213> ORGANISM: Artificial Sequence
<220> FEATURE:
<223> OTHER INFORMATION: chemically synthesized

<400> SEQUENCE: 509

```
Cys Asn Ile Trp Leu Val Gly Gly Asp Cys Arg Gly Trp Gln Gly Gly
1               5                   10                  15

Ser Ser Gly Gly Ser Ile Ser Ser Gly Leu Leu Ser Gly Arg Ser Asp
            20                  25                  30
```

Gln His Gly Gly Gly Ser Asp Ile Gln Met Thr Gln Ser Pro Ser Ser
35 40 45

Leu Ser Ala Ser Val Gly Asp Arg Val Thr Ile Thr Cys Arg Ala Ser
50 55 60

Gln Ser Ile Ser Ser Tyr Leu Asn Trp Tyr Gln Gln Lys Pro Gly Lys
65 70 75 80

Ala Pro Lys Leu Leu Ile Tyr Ala Ala Ser Ser Leu Gln Ser Gly Val
85 90 95

Pro Ser Arg Phe Ser Gly Ser Gly Ser Gly Thr Asp Phe Thr Leu Thr
100 105 110

Ile Ser Ser Leu Gln Pro Glu Asp Phe Ala Thr Tyr Tyr Cys Gln Gln
115 120 125

Thr Val Val Ala Pro Pro Leu Phe Gly Gln Gly Thr Lys Val Glu Ile
130 135 140

Lys Arg Thr Val Ala Ala Pro Ser Val Phe Ile Phe Pro Pro Ser Asp
145 150 155 160

Glu Gln Leu Lys Ser Gly Thr Ala Ser Val Val Cys Leu Leu Asn Asn
165 170 175

Phe Tyr Pro Arg Glu Ala Lys Val Gln Trp Lys Val Asp Asn Ala Leu
180 185 190

Gln Ser Gly Asn Ser Gln Glu Ser Val Thr Glu Gln Asp Ser Lys Asp
195 200 205

Ser Thr Tyr Ser Leu Ser Ser Thr Leu Thr Leu Ser Lys Ala Asp Tyr
210 215 220

Glu Lys His Lys Val Tyr Ala Cys Glu Val Thr His Gln Gly Leu Ser
225 230 235 240

Ser Pro Val Thr Lys Ser Phe Asn Arg Gly Glu Cys
245 250

<210> SEQ ID NO 510
<211> LENGTH: 252
<212> TYPE: PRT
<213> ORGANISM: Artificial Sequence
<220> FEATURE:
<223> OTHER INFORMATION: chemically synthesized

<400> SEQUENCE: 510

Cys Asn Ile Trp Leu Val Gly Gly Asp Cys Arg Gly Trp Gln Gly Gly
1 5 10 15

Ser Ser Gly Gly Ser Ile Ser Ser Gly Leu Leu Ser Gly Arg Ser Asp
20 25 30

Thr His Gly Gly Gly Ser Asp Ile Gln Met Thr Gln Ser Pro Ser Ser
35 40 45

Leu Ser Ala Ser Val Gly Asp Arg Val Thr Ile Thr Cys Arg Ala Ser
50 55 60

Gln Ser Ile Ser Ser Tyr Leu Asn Trp Tyr Gln Gln Lys Pro Gly Lys
65 70 75 80

Ala Pro Lys Leu Leu Ile Tyr Ala Ala Ser Ser Leu Gln Ser Gly Val
85 90 95

Pro Ser Arg Phe Ser Gly Ser Gly Ser Gly Thr Asp Phe Thr Leu Thr
100 105 110

Ile Ser Ser Leu Gln Pro Glu Asp Phe Ala Thr Tyr Tyr Cys Gln Gln
115 120 125

Thr Val Val Ala Pro Pro Leu Phe Gly Gln Gly Thr Lys Val Glu Ile
130 135 140

```
Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250


<210> SEQ ID NO 511
<211> LENGTH: 252
<212> TYPE: PRT
<213> ORGANISM: Artificial Sequence
<220> FEATURE:
<223> OTHER INFORMATION: chemically synthesized

<400> SEQUENCE: 511

Cys Asn Ile Trp Leu Val Gly Gly Asp Cys Arg Gly Trp Gln Gly Gly
1               5                   10                  15

Ser Ser Gly Gly Ser Ile Ser Ser Gly Leu Leu Ser Gly Arg Ser Asp
            20                  25                  30

Tyr His Gly Gly Gly Ser Asp Ile Gln Met Thr Gln Ser Pro Ser Ser
        35                  40                  45

Leu Ser Ala Ser Val Gly Asp Arg Val Thr Ile Thr Cys Arg Ala Ser
    50                  55                  60

Gln Ser Ile Ser Ser Tyr Leu Asn Trp Tyr Gln Gln Lys Pro Gly Lys
65                  70                  75                  80

Ala Pro Lys Leu Leu Ile Tyr Ala Ala Ser Ser Leu Gln Ser Gly Val
                85                  90                  95

Pro Ser Arg Phe Ser Gly Ser Gly Ser Gly Thr Asp Phe Thr Leu Thr
            100                 105                 110

Ile Ser Ser Leu Gln Pro Glu Asp Phe Ala Thr Tyr Tyr Cys Gln Gln
        115                 120                 125

Thr Val Val Ala Pro Pro Leu Phe Gly Gln Gly Thr Lys Val Glu Ile
    130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250
```

<210> SEQ ID NO 512
<211> LENGTH: 252
<212> TYPE: PRT
<213> ORGANISM: Artificial Sequence
<220> FEATURE:
<223> OTHER INFORMATION: chemically synthesized

<400> SEQUENCE: 512

```
Cys Asn Ile Trp Leu Val Gly Gly Asp Cys Arg Gly Trp Gln Gly Gly
1               5                   10                  15

Ser Ser Gly Gly Ser Ile Ser Ser Gly Leu Leu Ser Gly Arg Ser Asp
            20                  25                  30

Asn Pro Gly Gly Gly Ser Asp Ile Gln Met Thr Gln Ser Pro Ser Ser
        35                  40                  45

Leu Ser Ala Ser Val Gly Asp Arg Val Thr Ile Thr Cys Arg Ala Ser
    50                  55                  60

Gln Ser Ile Ser Ser Tyr Leu Asn Trp Tyr Gln Gln Lys Pro Gly Lys
65                  70                  75                  80

Ala Pro Lys Leu Leu Ile Tyr Ala Ala Ser Ser Leu Gln Ser Gly Val
                85                  90                  95

Pro Ser Arg Phe Ser Gly Ser Gly Ser Gly Thr Asp Phe Thr Leu Thr
            100                 105                 110

Ile Ser Ser Leu Gln Pro Glu Asp Phe Ala Thr Tyr Tyr Cys Gln Gln
        115                 120                 125

Thr Val Val Ala Pro Pro Leu Phe Gly Gln Gly Thr Lys Val Glu Ile
    130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250
```

<210> SEQ ID NO 513
<211> LENGTH: 252
<212> TYPE: PRT
<213> ORGANISM: Artificial Sequence
<220> FEATURE:
<223> OTHER INFORMATION: chemically synthesized

<400> SEQUENCE: 513

```
Cys Asn Ile Trp Leu Val Gly Gly Asp Cys Arg Gly Trp Gln Gly Gly
1               5                   10                  15

Ser Ser Gly Gly Ser Ile Ser Ser Gly Leu Leu Ser Gly Arg Ser Ala
            20                  25                  30

Asn Pro Gly Gly Gly Ser Asp Ile Gln Met Thr Gln Ser Pro Ser Ser
        35                  40                  45

Leu Ser Ala Ser Val Gly Asp Arg Val Thr Ile Thr Cys Arg Ala Ser
```

```
    50                  55                  60

Gln Ser Ile Ser Ser Tyr Leu Asn Trp Tyr Gln Gln Lys Pro Gly Lys
65                  70                  75                  80

Ala Pro Lys Leu Leu Ile Tyr Ala Ala Ser Ser Leu Gln Ser Gly Val
                85                  90                  95

Pro Ser Arg Phe Ser Gly Ser Gly Ser Gly Thr Asp Phe Thr Leu Thr
            100                 105                 110

Ile Ser Ser Leu Gln Pro Glu Asp Phe Ala Thr Tyr Tyr Cys Gln Gln
        115                 120                 125

Thr Val Val Ala Pro Pro Leu Phe Gly Gln Gly Thr Lys Val Glu Ile
    130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250


<210> SEQ ID NO 514
<211> LENGTH: 252
<212> TYPE: PRT
<213> ORGANISM: Artificial Sequence
<220> FEATURE:
<223> OTHER INFORMATION: chemically synthesized

<400> SEQUENCE: 514

Cys Asn Ile Trp Leu Val Gly Gly Asp Cys Arg Gly Trp Gln Gly Gly
1               5                   10                  15

Ser Ser Gly Gly Ser Ile Ser Ser Gly Leu Leu Ser Gly Arg Ser Ala
            20                  25                  30

Asn Ile Gly Gly Gly Ser Asp Ile Gln Met Thr Gln Ser Pro Ser Ser
        35                  40                  45

Leu Ser Ala Ser Val Gly Asp Arg Val Thr Ile Thr Cys Arg Ala Ser
    50                  55                  60

Gln Ser Ile Ser Ser Tyr Leu Asn Trp Tyr Gln Gln Lys Pro Gly Lys
65                  70                  75                  80

Ala Pro Lys Leu Leu Ile Tyr Ala Ala Ser Ser Leu Gln Ser Gly Val
                85                  90                  95

Pro Ser Arg Phe Ser Gly Ser Gly Ser Gly Thr Asp Phe Thr Leu Thr
            100                 105                 110

Ile Ser Ser Leu Gln Pro Glu Asp Phe Ala Thr Tyr Tyr Cys Gln Gln
        115                 120                 125

Thr Val Val Ala Pro Pro Leu Phe Gly Gln Gly Thr Lys Val Glu Ile
    130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
```

```
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250


<210> SEQ ID NO 515
<211> LENGTH: 18
<212> TYPE: PRT
<213> ORGANISM: Artificial Sequence
<220> FEATURE:
<223> OTHER INFORMATION: chemically synthesized

<400> SEQUENCE: 515

Ala Val Gly Leu Leu Ala Pro Pro Gly Gly Leu Ser Gly Arg Ser Asp
1               5                   10                  15

Asp His


<210> SEQ ID NO 516
<211> LENGTH: 18
<212> TYPE: PRT
<213> ORGANISM: Artificial Sequence
<220> FEATURE:
<223> OTHER INFORMATION: chemically synthesized

<400> SEQUENCE: 516

Ala Val Gly Leu Leu Ala Pro Pro Gly Gly Leu Ser Gly Arg Ser Asp
1               5                   10                  15

Ile His


<210> SEQ ID NO 517
<211> LENGTH: 18
<212> TYPE: PRT
<213> ORGANISM: Artificial Sequence
<220> FEATURE:
<223> OTHER INFORMATION: chemically synthesized

<400> SEQUENCE: 517

Ala Val Gly Leu Leu Ala Pro Pro Gly Gly Leu Ser Gly Arg Ser Asp
1               5                   10                  15

Gln His


<210> SEQ ID NO 518
<211> LENGTH: 18
<212> TYPE: PRT
<213> ORGANISM: Artificial Sequence
<220> FEATURE:
<223> OTHER INFORMATION: chemically synthesized

<400> SEQUENCE: 518

Ala Val Gly Leu Leu Ala Pro Pro Gly Gly Leu Ser Gly Arg Ser Asp
1               5                   10                  15

Thr His


<210> SEQ ID NO 519
```

<211> LENGTH: 18
<212> TYPE: PRT
<213> ORGANISM: Artificial Sequence
<220> FEATURE:
<223> OTHER INFORMATION: chemically synthesized

<400> SEQUENCE: 519

Ala Val Gly Leu Leu Ala Pro Pro Gly Gly Leu Ser Gly Arg Ser Asp
1 5 10 15

Tyr His

<210> SEQ ID NO 520
<211> LENGTH: 18
<212> TYPE: PRT
<213> ORGANISM: Artificial Sequence
<220> FEATURE:
<223> OTHER INFORMATION: chemically synthesized

<400> SEQUENCE: 520

Ala Val Gly Leu Leu Ala Pro Pro Gly Gly Leu Ser Gly Arg Ser Asp
1 5 10 15

Asn Pro

<210> SEQ ID NO 521
<211> LENGTH: 18
<212> TYPE: PRT
<213> ORGANISM: Artificial Sequence
<220> FEATURE:
<223> OTHER INFORMATION: chemically synthesized

<400> SEQUENCE: 521

Ala Val Gly Leu Leu Ala Pro Pro Gly Gly Leu Ser Gly Arg Ser Ala
1 5 10 15

Asn Pro

<210> SEQ ID NO 522
<211> LENGTH: 18
<212> TYPE: PRT
<213> ORGANISM: Artificial Sequence
<220> FEATURE:
<223> OTHER INFORMATION: chemically synthesized

<400> SEQUENCE: 522

Ala Val Gly Leu Leu Ala Pro Pro Gly Gly Leu Ser Gly Arg Ser Ala
1 5 10 15

Asn Ile

<210> SEQ ID NO 523
<211> LENGTH: 54
<212> TYPE: DNA
<213> ORGANISM: Artificial Sequence
<220> FEATURE:
<223> OTHER INFORMATION: chemically synthesized

<400> SEQUENCE: 523
gctgtgggac tgctggctcc tcctggtggc ctgtctggca gatctgacga tcac 54

<210> SEQ ID NO 524
<211> LENGTH: 54
<212> TYPE: DNA
<213> ORGANISM: Artificial Sequence
<220> FEATURE:
<223> OTHER INFORMATION: chemically synthesized

<400> SEQUENCE: 524
gctgtgggac tgctggctcc tcctggtggc ctgtctggca gatctgacat acac 54

<210> SEQ ID NO 525
<211> LENGTH: 54
<212> TYPE: DNA
<213> ORGANISM: Artificial Sequence
<220> FEATURE:
<223> OTHER INFORMATION: chemically synthesized

<400> SEQUENCE: 525
gctgtgggac tgctggctcc tcctggtggc ctgtctggca gatctgacca acac 54

<210> SEQ ID NO 526
<211> LENGTH: 54
<212> TYPE: DNA
<213> ORGANISM: Artificial Sequence
<220> FEATURE:
<223> OTHER INFORMATION: chemically synthesized

<400> SEQUENCE: 526
gctgtgggac tgctggctcc tcctggtggc ctgtctggca gatctgacac tcac 54

<210> SEQ ID NO 527
<211> LENGTH: 54
<212> TYPE: DNA
<213> ORGANISM: Artificial Sequence
<220> FEATURE:
<223> OTHER INFORMATION: chemically synthesized

<400> SEQUENCE: 527
gctgtgggac tgctggctcc tcctggtggc ctgtctggca gatctgacta tcac 54

<210> SEQ ID NO 528
<211> LENGTH: 54
<212> TYPE: DNA
<213> ORGANISM: Artificial Sequence
<220> FEATURE:
<223> OTHER INFORMATION: chemically synthesized

<400> SEQUENCE: 528
gctgtgggac tgctggctcc tcctggtggc ctgtctggca gatctgacaa tccc 54

<210> SEQ ID NO 529
<211> LENGTH: 54
<212> TYPE: DNA
<213> ORGANISM: Artificial Sequence
<220> FEATURE:
<223> OTHER INFORMATION: chemically synthesized

<400> SEQUENCE: 529
gctgtgggac tgctggctcc tcctggtggc ctgtctggca gatctgctaa tccc 54

<210> SEQ ID NO 530
<211> LENGTH: 54
<212> TYPE: DNA
<213> ORGANISM: Artificial Sequence
<220> FEATURE:
<223> OTHER INFORMATION: chemically synthesized

<400> SEQUENCE: 530
gctgtgggac tgctggctcc tcctggtggc ctgtctggca gatctgctaa tata 54

<210> SEQ ID NO 531
<211> LENGTH: 265
<212> TYPE: PRT

<213> ORGANISM: Artificial Sequence
<220> FEATURE:
<223> OTHER INFORMATION: chemically synthesized

<400> SEQUENCE: 531

```
Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ala Val Gly Leu
            20                  25                  30

Leu Ala Pro Pro Gly Gly Leu Ser Gly Arg Ser Asp Asp His Gly Ser
        35                  40                  45

Ser Gly Thr Gln Ile Leu Leu Thr Gln Ser Pro Val Ile Leu Ser Val
    50                  55                  60

Ser Pro Gly Glu Arg Val Ser Phe Ser Cys Arg Ala Ser Gln Ser Ile
65                  70                  75                  80

Gly Thr Asn Ile His Trp Tyr Gln Gln Arg Thr Asn Gly Ser Pro Arg
                85                  90                  95

Leu Leu Ile Lys Tyr Ala Ser Glu Ser Ile Ser Gly Ile Pro Ser Arg
            100                 105                 110

Phe Ser Gly Ser Gly Ser Gly Thr Asp Phe Thr Leu Ser Ile Asn Ser
        115                 120                 125

Val Glu Ser Glu Asp Ile Ala Asp Tyr Tyr Cys Gln Gln Asn Asn Asn
    130                 135                 140

Trp Pro Thr Thr Phe Gly Ala Gly Thr Lys Leu Glu Leu Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265
```

<210> SEQ ID NO 532
<211> LENGTH: 265
<212> TYPE: PRT
<213> ORGANISM: Artificial Sequence
<220> FEATURE:
<223> OTHER INFORMATION: chemically synthesized

<400> SEQUENCE: 532

```
Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ala Val Gly Leu
            20                  25                  30

Leu Ala Pro Pro Gly Gly Leu Ser Gly Arg Ser Asp Ile His Gly Ser
        35                  40                  45

Ser Gly Thr Gln Ile Leu Leu Thr Gln Ser Pro Val Ile Leu Ser Val
    50                  55                  60
```

```
Ser Pro Gly Glu Arg Val Ser Phe Ser Cys Arg Ala Ser Gln Ser Ile
65                  70                  75                  80

Gly Thr Asn Ile His Trp Tyr Gln Gln Arg Thr Asn Gly Ser Pro Arg
                85                  90                  95

Leu Leu Ile Lys Tyr Ala Ser Glu Ser Ile Ser Gly Ile Pro Ser Arg
            100                 105                 110

Phe Ser Gly Ser Gly Ser Gly Thr Asp Phe Thr Leu Ser Ile Asn Ser
        115                 120                 125

Val Glu Ser Glu Asp Ile Ala Asp Tyr Tyr Cys Gln Gln Asn Asn Asn
    130                 135                 140

Trp Pro Thr Thr Phe Gly Ala Gly Thr Lys Leu Glu Leu Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265


<210> SEQ ID NO 533
<211> LENGTH: 265
<212> TYPE: PRT
<213> ORGANISM: Artificial Sequence
<220> FEATURE:
<223> OTHER INFORMATION: chemically synthesized

<400> SEQUENCE: 533

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ala Val Gly Leu
            20                  25                  30

Leu Ala Pro Pro Gly Gly Leu Ser Gly Arg Ser Asp Gln His Gly Ser
        35                  40                  45

Ser Gly Thr Gln Ile Leu Leu Thr Gln Ser Pro Val Ile Leu Ser Val
    50                  55                  60

Ser Pro Gly Glu Arg Val Ser Phe Ser Cys Arg Ala Ser Gln Ser Ile
65                  70                  75                  80

Gly Thr Asn Ile His Trp Tyr Gln Gln Arg Thr Asn Gly Ser Pro Arg
                85                  90                  95

Leu Leu Ile Lys Tyr Ala Ser Glu Ser Ile Ser Gly Ile Pro Ser Arg
            100                 105                 110

Phe Ser Gly Ser Gly Ser Gly Thr Asp Phe Thr Leu Ser Ile Asn Ser
        115                 120                 125

Val Glu Ser Glu Asp Ile Ala Asp Tyr Tyr Cys Gln Gln Asn Asn Asn
    130                 135                 140

Trp Pro Thr Thr Phe Gly Ala Gly Thr Lys Leu Glu Leu Lys Arg Thr
145                 150                 155                 160
```

```
Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265


<210> SEQ ID NO 534
<211> LENGTH: 265
<212> TYPE: PRT
<213> ORGANISM: Artificial Sequence
<220> FEATURE:
<223> OTHER INFORMATION: chemically synthesized

<400> SEQUENCE: 534

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ala Val Gly Leu
            20                  25                  30

Leu Ala Pro Pro Gly Gly Leu Ser Gly Arg Ser Asp Thr His Gly Ser
        35                  40                  45

Ser Gly Thr Gln Ile Leu Leu Thr Gln Ser Pro Val Ile Leu Ser Val
    50                  55                  60

Ser Pro Gly Glu Arg Val Ser Phe Ser Cys Arg Ala Ser Gln Ser Ile
65                  70                  75                  80

Gly Thr Asn Ile His Trp Tyr Gln Gln Arg Thr Asn Gly Ser Pro Arg
                85                  90                  95

Leu Leu Ile Lys Tyr Ala Ser Glu Ser Ile Ser Gly Ile Pro Ser Arg
            100                 105                 110

Phe Ser Gly Ser Gly Ser Gly Thr Asp Phe Thr Leu Ser Ile Asn Ser
        115                 120                 125

Val Glu Ser Glu Asp Ile Ala Asp Tyr Tyr Cys Gln Gln Asn Asn Asn
    130                 135                 140

Trp Pro Thr Thr Phe Gly Ala Gly Thr Lys Leu Glu Leu Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255
```

```
Thr Lys Ser Phe Asn Arg Gly Glu Cys
            260                 265


<210> SEQ ID NO 535
<211> LENGTH: 265
<212> TYPE: PRT
<213> ORGANISM: Artificial Sequence
<220> FEATURE:
<223> OTHER INFORMATION: chemically synthesized

<400> SEQUENCE: 535

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ala Val Gly Leu
            20                  25                  30

Leu Ala Pro Pro Gly Gly Leu Ser Gly Arg Ser Asp Tyr His Gly Ser
        35                  40                  45

Ser Gly Thr Gln Ile Leu Leu Thr Gln Ser Pro Val Ile Leu Ser Val
    50                  55                  60

Ser Pro Gly Glu Arg Val Ser Phe Ser Cys Arg Ala Ser Gln Ser Ile
65                  70                  75                  80

Gly Thr Asn Ile His Trp Tyr Gln Gln Arg Thr Asn Gly Ser Pro Arg
                85                  90                  95

Leu Leu Ile Lys Tyr Ala Ser Glu Ser Ile Ser Gly Ile Pro Ser Arg
            100                 105                 110

Phe Ser Gly Ser Gly Ser Gly Thr Asp Phe Thr Leu Ser Ile Asn Ser
        115                 120                 125

Val Glu Ser Glu Asp Ile Ala Asp Tyr Tyr Cys Gln Gln Asn Asn Asn
    130                 135                 140

Trp Pro Thr Thr Phe Gly Ala Gly Thr Lys Leu Glu Leu Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265


<210> SEQ ID NO 536
<211> LENGTH: 265
<212> TYPE: PRT
<213> ORGANISM: Artificial Sequence
<220> FEATURE:
<223> OTHER INFORMATION: chemically synthesized

<400> SEQUENCE: 536

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ala Val Gly Leu
            20                  25                  30
```

```
Leu Ala Pro Pro Gly Gly Leu Ser Gly Arg Ser Asp Asn Pro Gly Ser
        35                  40                  45

Ser Gly Thr Gln Ile Leu Leu Thr Gln Ser Pro Val Ile Leu Ser Val
    50                  55                  60

Ser Pro Gly Glu Arg Val Ser Phe Ser Cys Arg Ala Ser Gln Ser Ile
65                  70                  75                  80

Gly Thr Asn Ile His Trp Tyr Gln Gln Arg Thr Asn Gly Ser Pro Arg
                85                  90                  95

Leu Leu Ile Lys Tyr Ala Ser Glu Ser Ile Ser Gly Ile Pro Ser Arg
            100                 105                 110

Phe Ser Gly Ser Gly Ser Gly Thr Asp Phe Thr Leu Ser Ile Asn Ser
        115                 120                 125

Val Glu Ser Glu Asp Ile Ala Asp Tyr Tyr Cys Gln Gln Asn Asn Asn
    130                 135                 140

Trp Pro Thr Thr Phe Gly Ala Gly Thr Lys Leu Glu Leu Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265
```

<210> SEQ ID NO 537
<211> LENGTH: 265
<212> TYPE: PRT
<213> ORGANISM: Artificial Sequence
<220> FEATURE:
<223> OTHER INFORMATION: chemically synthesized

<400> SEQUENCE: 537

```
Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ala Val Gly Leu
            20                  25                  30

Leu Ala Pro Pro Gly Gly Leu Ser Gly Arg Ser Ala Asn Pro Gly Ser
        35                  40                  45

Ser Gly Thr Gln Ile Leu Leu Thr Gln Ser Pro Val Ile Leu Ser Val
    50                  55                  60

Ser Pro Gly Glu Arg Val Ser Phe Ser Cys Arg Ala Ser Gln Ser Ile
65                  70                  75                  80

Gly Thr Asn Ile His Trp Tyr Gln Gln Arg Thr Asn Gly Ser Pro Arg
                85                  90                  95

Leu Leu Ile Lys Tyr Ala Ser Glu Ser Ile Ser Gly Ile Pro Ser Arg
            100                 105                 110

Phe Ser Gly Ser Gly Ser Gly Thr Asp Phe Thr Leu Ser Ile Asn Ser
        115                 120                 125
```

```
Val Glu Ser Glu Asp Ile Ala Asp Tyr Tyr Cys Gln Gln Asn Asn Asn
    130                 135                 140

Trp Pro Thr Thr Phe Gly Ala Gly Thr Lys Leu Glu Leu Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265


<210> SEQ ID NO 538
<211> LENGTH: 265
<212> TYPE: PRT
<213> ORGANISM: Artificial Sequence
<220> FEATURE:
<223> OTHER INFORMATION: chemically synthesized

<400> SEQUENCE: 538

Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ala Val Gly Leu
            20                  25                  30

Leu Ala Pro Pro Gly Gly Leu Ser Gly Arg Ser Ala Asn Ile Gly Ser
        35                  40                  45

Ser Gly Thr Gln Ile Leu Leu Thr Gln Ser Pro Val Ile Leu Ser Val
    50                  55                  60

Ser Pro Gly Glu Arg Val Ser Phe Ser Cys Arg Ala Ser Gln Ser Ile
65                  70                  75                  80

Gly Thr Asn Ile His Trp Tyr Gln Gln Arg Thr Asn Gly Ser Pro Arg
                85                  90                  95

Leu Leu Ile Lys Tyr Ala Ser Glu Ser Ile Ser Gly Ile Pro Ser Arg
            100                 105                 110

Phe Ser Gly Ser Gly Ser Gly Thr Asp Phe Thr Leu Ser Ile Asn Ser
        115                 120                 125

Val Glu Ser Glu Asp Ile Ala Asp Tyr Tyr Cys Gln Gln Asn Asn Asn
    130                 135                 140

Trp Pro Thr Thr Phe Gly Ala Gly Thr Lys Leu Glu Leu Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220
```

```
Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265


<210> SEQ ID NO 539
<211> LENGTH: 257
<212> TYPE: PRT
<213> ORGANISM: Artificial Sequence
<220> FEATURE:
<223> OTHER INFORMATION: chemically synthesized

<400> SEQUENCE: 539

Cys Asn Ile Trp Leu Val Gly Gly Asp Cys Arg Gly Trp Gln Gly Gly
1               5                   10                  15

Ser Ser Gly Gly Ser Ala Val Gly Leu Leu Ala Pro Pro Gly Gly Leu
            20                  25                  30

Ser Gly Arg Ser Asp Asp His Gly Gly Gly Ser Asp Ile Gln Met Thr
        35                  40                  45

Gln Ser Pro Ser Ser Leu Ser Ala Ser Val Gly Asp Arg Val Thr Ile
    50                  55                  60

Thr Cys Arg Ala Ser Gln Ser Ile Ser Ser Tyr Leu Asn Trp Tyr Gln
65                  70                  75                  80

Gln Lys Pro Gly Lys Ala Pro Lys Leu Leu Ile Tyr Ala Ala Ser Ser
                85                  90                  95

Leu Gln Ser Gly Val Pro Ser Arg Phe Ser Gly Ser Gly Ser Gly Thr
            100                 105                 110

Asp Phe Thr Leu Thr Ile Ser Ser Leu Gln Pro Glu Asp Phe Ala Thr
        115                 120                 125

Tyr Tyr Cys Gln Gln Thr Val Val Ala Pro Pro Leu Phe Gly Gln Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys


<210> SEQ ID NO 540
<211> LENGTH: 257
<212> TYPE: PRT
<213> ORGANISM: Artificial Sequence
<220> FEATURE:
<223> OTHER INFORMATION: chemically synthesized

<400> SEQUENCE: 540
```

```
Cys Asn Ile Trp Leu Val Gly Gly Asp Cys Arg Gly Trp Gln Gly Gly
1               5                   10                  15

Ser Ser Gly Gly Ser Ala Val Gly Leu Leu Ala Pro Pro Gly Gly Leu
            20                  25                  30

Ser Gly Arg Ser Asp Ile His Gly Gly Gly Ser Asp Ile Gln Met Thr
        35                  40                  45

Gln Ser Pro Ser Ser Leu Ser Ala Ser Val Gly Asp Arg Val Thr Ile
    50                  55                  60

Thr Cys Arg Ala Ser Gln Ser Ile Ser Ser Tyr Leu Asn Trp Tyr Gln
65                  70                  75                  80

Gln Lys Pro Gly Lys Ala Pro Lys Leu Leu Ile Tyr Ala Ala Ser Ser
                85                  90                  95

Leu Gln Ser Gly Val Pro Ser Arg Phe Ser Gly Ser Gly Ser Gly Thr
            100                 105                 110

Asp Phe Thr Leu Thr Ile Ser Ser Leu Gln Pro Glu Asp Phe Ala Thr
        115                 120                 125

Tyr Tyr Cys Gln Gln Thr Val Val Ala Pro Pro Leu Phe Gly Gln Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys
```

<210> SEQ ID NO 541
<211> LENGTH: 257
<212> TYPE: PRT
<213> ORGANISM: Artificial Sequence
<220> FEATURE:
<223> OTHER INFORMATION: chemically synthesized

<400> SEQUENCE: 541

```
Cys Asn Ile Trp Leu Val Gly Gly Asp Cys Arg Gly Trp Gln Gly Gly
1               5                   10                  15

Ser Ser Gly Gly Ser Ala Val Gly Leu Leu Ala Pro Pro Gly Gly Leu
            20                  25                  30

Ser Gly Arg Ser Asp Gln His Gly Gly Gly Ser Asp Ile Gln Met Thr
        35                  40                  45

Gln Ser Pro Ser Ser Leu Ser Ala Ser Val Gly Asp Arg Val Thr Ile
    50                  55                  60

Thr Cys Arg Ala Ser Gln Ser Ile Ser Ser Tyr Leu Asn Trp Tyr Gln
65                  70                  75                  80

Gln Lys Pro Gly Lys Ala Pro Lys Leu Leu Ile Tyr Ala Ala Ser Ser
                85                  90                  95
```

```
Leu Gln Ser Gly Val Pro Ser Arg Phe Ser Gly Ser Gly Ser Gly Thr
            100                 105                 110

Asp Phe Thr Leu Thr Ile Ser Ser Leu Gln Pro Glu Asp Phe Ala Thr
        115                 120                 125

Tyr Tyr Cys Gln Gln Thr Val Val Ala Pro Pro Leu Phe Gly Gln Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys


<210> SEQ ID NO 542
<211> LENGTH: 257
<212> TYPE: PRT
<213> ORGANISM: Artificial Sequence
<220> FEATURE:
<223> OTHER INFORMATION: chemically synthesized

<400> SEQUENCE: 542

Cys Asn Ile Trp Leu Val Gly Gly Asp Cys Arg Gly Trp Gln Gly Gly
1               5                   10                  15

Ser Ser Gly Gly Ser Ala Val Gly Leu Leu Ala Pro Pro Gly Gly Leu
            20                  25                  30

Ser Gly Arg Ser Asp Thr His Gly Gly Gly Ser Asp Ile Gln Met Thr
        35                  40                  45

Gln Ser Pro Ser Ser Leu Ser Ala Ser Val Gly Asp Arg Val Thr Ile
    50                  55                  60

Thr Cys Arg Ala Ser Gln Ser Ile Ser Ser Tyr Leu Asn Trp Tyr Gln
65                  70                  75                  80

Gln Lys Pro Gly Lys Ala Pro Lys Leu Leu Ile Tyr Ala Ala Ser Ser
                85                  90                  95

Leu Gln Ser Gly Val Pro Ser Arg Phe Ser Gly Ser Gly Ser Gly Thr
            100                 105                 110

Asp Phe Thr Leu Thr Ile Ser Ser Leu Gln Pro Glu Asp Phe Ala Thr
        115                 120                 125

Tyr Tyr Cys Gln Gln Thr Val Val Ala Pro Pro Leu Phe Gly Gln Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
```

```
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys


<210> SEQ ID NO 543
<211> LENGTH: 257
<212> TYPE: PRT
<213> ORGANISM: Artificial Sequence
<220> FEATURE:
<223> OTHER INFORMATION: chemically synthesized

<400> SEQUENCE: 543

Cys Asn Ile Trp Leu Val Gly Gly Asp Cys Arg Gly Trp Gln Gly Gly
1               5                   10                  15

Ser Ser Gly Gly Ser Ala Val Gly Leu Leu Ala Pro Pro Gly Gly Leu
            20                  25                  30

Ser Gly Arg Ser Asp Tyr His Gly Gly Gly Ser Asp Ile Gln Met Thr
        35                  40                  45

Gln Ser Pro Ser Ser Leu Ser Ala Ser Val Gly Asp Arg Val Thr Ile
    50                  55                  60

Thr Cys Arg Ala Ser Gln Ser Ile Ser Ser Tyr Leu Asn Trp Tyr Gln
65                  70                  75                  80

Gln Lys Pro Gly Lys Ala Pro Lys Leu Leu Ile Tyr Ala Ala Ser Ser
                85                  90                  95

Leu Gln Ser Gly Val Pro Ser Arg Phe Ser Gly Ser Gly Ser Gly Thr
            100                 105                 110

Asp Phe Thr Leu Thr Ile Ser Ser Leu Gln Pro Glu Asp Phe Ala Thr
        115                 120                 125

Tyr Tyr Cys Gln Gln Thr Val Val Ala Pro Pro Leu Phe Gly Gln Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys


<210> SEQ ID NO 544
<211> LENGTH: 257
<212> TYPE: PRT
<213> ORGANISM: Artificial Sequence
<220> FEATURE:
```

<223> OTHER INFORMATION: chemically synthesized

<400> SEQUENCE: 544

Cys Asn Ile Trp Leu Val Gly Gly Asp Cys Arg Gly Trp Gln Gly Gly
1 5 10 15

Ser Ser Gly Gly Ser Ala Val Gly Leu Leu Ala Pro Pro Gly Gly Leu
20 25 30

Ser Gly Arg Ser Asp Asn Pro Gly Gly Gly Ser Asp Ile Gln Met Thr
35 40 45

Gln Ser Pro Ser Ser Leu Ser Ala Ser Val Gly Asp Arg Val Thr Ile
50 55 60

Thr Cys Arg Ala Ser Gln Ser Ile Ser Ser Tyr Leu Asn Trp Tyr Gln
65 70 75 80

Gln Lys Pro Gly Lys Ala Pro Lys Leu Leu Ile Tyr Ala Ala Ser Ser
85 90 95

Leu Gln Ser Gly Val Pro Ser Arg Phe Ser Gly Ser Gly Ser Gly Thr
100 105 110

Asp Phe Thr Leu Thr Ile Ser Ser Leu Gln Pro Glu Asp Phe Ala Thr
115 120 125

Tyr Tyr Cys Gln Gln Thr Val Val Ala Pro Pro Leu Phe Gly Gln Gly
130 135 140

Thr Lys Val Glu Ile Lys Arg Thr Val Ala Ala Pro Ser Val Phe Ile
145 150 155 160

Phe Pro Pro Ser Asp Glu Gln Leu Lys Ser Gly Thr Ala Ser Val Val
165 170 175

Cys Leu Leu Asn Asn Phe Tyr Pro Arg Glu Ala Lys Val Gln Trp Lys
180 185 190

Val Asp Asn Ala Leu Gln Ser Gly Asn Ser Gln Glu Ser Val Thr Glu
195 200 205

Gln Asp Ser Lys Asp Ser Thr Tyr Ser Leu Ser Ser Thr Leu Thr Leu
210 215 220

Ser Lys Ala Asp Tyr Glu Lys His Lys Val Tyr Ala Cys Glu Val Thr
225 230 235 240

His Gln Gly Leu Ser Ser Pro Val Thr Lys Ser Phe Asn Arg Gly Glu
245 250 255

Cys

<210> SEQ ID NO 545
<211> LENGTH: 257
<212> TYPE: PRT
<213> ORGANISM: Artificial Sequence
<220> FEATURE:
<223> OTHER INFORMATION: chemically synthesized

<400> SEQUENCE: 545

Cys Asn Ile Trp Leu Val Gly Gly Asp Cys Arg Gly Trp Gln Gly Gly
1 5 10 15

Ser Ser Gly Gly Ser Ala Val Gly Leu Leu Ala Pro Pro Gly Gly Leu
20 25 30

Ser Gly Arg Ser Ala Asn Pro Gly Gly Gly Ser Asp Ile Gln Met Thr
35 40 45

Gln Ser Pro Ser Ser Leu Ser Ala Ser Val Gly Asp Arg Val Thr Ile
50 55 60

Thr Cys Arg Ala Ser Gln Ser Ile Ser Ser Tyr Leu Asn Trp Tyr Gln
65 70 75 80

```
Gln Lys Pro Gly Lys Ala Pro Lys Leu Leu Ile Tyr Ala Ala Ser Ser
                85                  90                  95

Leu Gln Ser Gly Val Pro Ser Arg Phe Ser Gly Ser Gly Ser Gly Thr
            100                 105                 110

Asp Phe Thr Leu Thr Ile Ser Ser Leu Gln Pro Glu Asp Phe Ala Thr
        115                 120                 125

Tyr Tyr Cys Gln Gln Thr Val Val Ala Pro Pro Leu Phe Gly Gln Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys


<210> SEQ ID NO 546
<211> LENGTH: 257
<212> TYPE: PRT
<213> ORGANISM: Artificial Sequence
<220> FEATURE:
<223> OTHER INFORMATION: chemically synthesized

<400> SEQUENCE: 546

Cys Asn Ile Trp Leu Val Gly Gly Asp Cys Arg Gly Trp Gln Gly Gly
1               5                   10                  15

Ser Ser Gly Gly Ser Ala Val Gly Leu Leu Ala Pro Pro Gly Gly Leu
            20                  25                  30

Ser Gly Arg Ser Ala Asn Ile Gly Gly Gly Ser Asp Ile Gln Met Thr
        35                  40                  45

Gln Ser Pro Ser Ser Leu Ser Ala Ser Val Gly Asp Arg Val Thr Ile
    50                  55                  60

Thr Cys Arg Ala Ser Gln Ser Ile Ser Ser Tyr Leu Asn Trp Tyr Gln
65                  70                  75                  80

Gln Lys Pro Gly Lys Ala Pro Lys Leu Leu Ile Tyr Ala Ala Ser Ser
                85                  90                  95

Leu Gln Ser Gly Val Pro Ser Arg Phe Ser Gly Ser Gly Ser Gly Thr
            100                 105                 110

Asp Phe Thr Leu Thr Ile Ser Ser Leu Gln Pro Glu Asp Phe Ala Thr
        115                 120                 125

Tyr Tyr Cys Gln Gln Thr Val Val Ala Pro Pro Leu Phe Gly Gln Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
```

-continued

```
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys


<210> SEQ ID NO 547
<211> LENGTH: 8
<212> TYPE: PRT
<213> ORGANISM: Artificial Sequence
<220> FEATURE:
<223> OTHER INFORMATION: chemically synthesized

<400> SEQUENCE: 547

Leu Ser Gly Arg Ser Asp Asp His
1               5


<210> SEQ ID NO 548
<211> LENGTH: 8
<212> TYPE: PRT
<213> ORGANISM: Artificial Sequence
<220> FEATURE:
<223> OTHER INFORMATION: chemically synthesized

<400> SEQUENCE: 548

Leu Ser Gly Arg Ser Asp Ile His
1               5


<210> SEQ ID NO 549
<211> LENGTH: 8
<212> TYPE: PRT
<213> ORGANISM: Artificial Sequence
<220> FEATURE:
<223> OTHER INFORMATION: chemically synthesized

<400> SEQUENCE: 549

Leu Ser Gly Arg Ser Asp Gln His
1               5


<210> SEQ ID NO 550
<211> LENGTH: 8
<212> TYPE: PRT
<213> ORGANISM: Artificial Sequence
<220> FEATURE:
<223> OTHER INFORMATION: chemically synthesized

<400> SEQUENCE: 550

Leu Ser Gly Arg Ser Asp Thr His
1               5


<210> SEQ ID NO 551
<211> LENGTH: 8
<212> TYPE: PRT
<213> ORGANISM: Artificial Sequence
<220> FEATURE:
<223> OTHER INFORMATION: chemically synthesized

<400> SEQUENCE: 551

Leu Ser Gly Arg Ser Asp Tyr His
```

1 5

<210> SEQ ID NO 552
<211> LENGTH: 8
<212> TYPE: PRT
<213> ORGANISM: Artificial Sequence
<220> FEATURE:
<223> OTHER INFORMATION: chemically synthesized

<400> SEQUENCE: 552

Leu Ser Gly Arg Ser Asp Asn Pro
1 5

<210> SEQ ID NO 553
<211> LENGTH: 8
<212> TYPE: PRT
<213> ORGANISM: Artificial Sequence
<220> FEATURE:
<223> OTHER INFORMATION: chemically synthesized

<400> SEQUENCE: 553

Leu Ser Gly Arg Ser Ala Asn Pro
1 5

<210> SEQ ID NO 554
<211> LENGTH: 8
<212> TYPE: PRT
<213> ORGANISM: Artificial Sequence
<220> FEATURE:
<223> OTHER INFORMATION: chemically synthesized

<400> SEQUENCE: 554

Leu Ser Gly Arg Ser Ala Asn Ile
1 5

<210> SEQ ID NO 555
<211> LENGTH: 13
<212> TYPE: PRT
<213> ORGANISM: Artificial Sequence
<220> FEATURE:
<223> OTHER INFORMATION: chemically synthesized

<400> SEQUENCE: 555

Ile Ser Ser Gly Leu Leu Ser Gly Arg Ser Asp Asn Ile
1 5 10

<210> SEQ ID NO 556
<211> LENGTH: 39
<212> TYPE: DNA
<213> ORGANISM: Artificial Sequence
<220> FEATURE:
<223> OTHER INFORMATION: chemically synthesized

<400> SEQUENCE: 556
atatcgagtg gattgctgtc tggcagatct gacaatata 39

<210> SEQ ID NO 557
<211> LENGTH: 18
<212> TYPE: PRT
<213> ORGANISM: Artificial Sequence
<220> FEATURE:
<223> OTHER INFORMATION: chemically synthesized

<400> SEQUENCE: 557

Ala Val Gly Leu Leu Ala Pro Pro Gly Gly Leu Ser Gly Arg Ser Asp
1 5 10 15

Asn Ile

<210> SEQ ID NO 558
<211> LENGTH: 54
<212> TYPE: DNA
<213> ORGANISM: Artificial Sequence
<220> FEATURE:
<223> OTHER INFORMATION: chemically synthesized

<400> SEQUENCE: 558
gctgtgggac tgctggctcc tcctggtggc ctgtctggca gatctgacaa tata 54

<210> SEQ ID NO 559
<211> LENGTH: 260
<212> TYPE: PRT
<213> ORGANISM: Artificial Sequence
<220> FEATURE:
<223> OTHER INFORMATION: chemically synthesized

<400> SEQUENCE: 559

Cys Ile Ser Pro Arg Gly Cys Pro Asp Gly Pro Tyr Val Met Tyr Gly
1 5 10 15

Ser Ser Gly Gly Ser Gly Gly Ser Gly Gly Ser Gly Ile Ser Ser Gly
20 25 30

Leu Leu Ser Gly Arg Ser Asp Asn Ile Gly Ser Ser Gly Thr Gln Ile
35 40 45

Leu Leu Thr Gln Ser Pro Val Ile Leu Ser Val Ser Pro Gly Glu Arg
50 55 60

Val Ser Phe Ser Cys Arg Ala Ser Gln Ser Ile Gly Thr Asn Ile His
65 70 75 80

Trp Tyr Gln Gln Arg Thr Asn Gly Ser Pro Arg Leu Leu Ile Lys Tyr
85 90 95

Ala Ser Glu Ser Ile Ser Gly Ile Pro Ser Arg Phe Ser Gly Ser Gly
100 105 110

Ser Gly Thr Asp Phe Thr Leu Ser Ile Asn Ser Val Glu Ser Glu Asp
115 120 125

Ile Ala Asp Tyr Tyr Cys Gln Gln Asn Asn Asn Trp Pro Thr Thr Phe
130 135 140

Gly Ala Gly Thr Lys Leu Glu Leu Lys Arg Thr Val Ala Ala Pro Ser
145 150 155 160

Val Phe Ile Phe Pro Pro Ser Asp Glu Gln Leu Lys Ser Gly Thr Ala
165 170 175

Ser Val Val Cys Leu Leu Asn Asn Phe Tyr Pro Arg Glu Ala Lys Val
180 185 190

Gln Trp Lys Val Asp Asn Ala Leu Gln Ser Gly Asn Ser Gln Glu Ser
195 200 205

Val Thr Glu Gln Asp Ser Lys Asp Ser Thr Tyr Ser Leu Ser Ser Thr
210 215 220

Leu Thr Leu Ser Lys Ala Asp Tyr Glu Lys His Lys Val Tyr Ala Cys
225 230 235 240

Glu Val Thr His Gln Gly Leu Ser Ser Pro Val Thr Lys Ser Phe Asn
245 250 255

Arg Gly Glu Cys
260

<210> SEQ ID NO 560
<211> LENGTH: 265
<212> TYPE: PRT

<213> ORGANISM: Artificial Sequence
<220> FEATURE:
<223> OTHER INFORMATION: chemically synthesized

<400> SEQUENCE: 560

```
Cys Ile Ser Pro Arg Gly Cys Pro Asp Gly Pro Tyr Val Met Tyr Gly
1               5                   10                  15

Ser Ser Gly Gly Ser Gly Gly Ser Gly Gly Ser Gly Ala Val Gly Leu
            20                  25                  30

Leu Ala Pro Pro Gly Gly Leu Ser Gly Arg Ser Asp Asn Ile Gly Ser
        35                  40                  45

Ser Gly Thr Gln Ile Leu Leu Thr Gln Ser Pro Val Ile Leu Ser Val
    50                  55                  60

Ser Pro Gly Glu Arg Val Ser Phe Ser Cys Arg Ala Ser Gln Ser Ile
65                  70                  75                  80

Gly Thr Asn Ile His Trp Tyr Gln Gln Arg Thr Asn Gly Ser Pro Arg
                85                  90                  95

Leu Leu Ile Lys Tyr Ala Ser Glu Ser Ile Ser Gly Ile Pro Ser Arg
            100                 105                 110

Phe Ser Gly Ser Gly Ser Gly Thr Asp Phe Thr Leu Ser Ile Asn Ser
        115                 120                 125

Val Glu Ser Glu Asp Ile Ala Asp Tyr Tyr Cys Gln Gln Asn Asn Asn
    130                 135                 140

Trp Pro Thr Thr Phe Gly Ala Gly Thr Lys Leu Glu Leu Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265
```

<210> SEQ ID NO 561
<211> LENGTH: 252
<212> TYPE: PRT
<213> ORGANISM: Artificial Sequence
<220> FEATURE:
<223> OTHER INFORMATION: chemically synthesized

<400> SEQUENCE: 561

```
Cys Asn Ile Trp Leu Val Gly Gly Asp Cys Arg Gly Trp Gln Gly Gly
1               5                   10                  15

Ser Ser Gly Gly Ser Ile Ser Ser Gly Leu Leu Ser Gly Arg Ser Asp
            20                  25                  30

Asn Ile Gly Gly Gly Ser Asp Ile Gln Met Thr Gln Ser Pro Ser Ser
        35                  40                  45

Leu Ser Ala Ser Val Gly Asp Arg Val Thr Ile Thr Cys Arg Ala Ser
    50                  55                  60
```

-continued

```
Gln Ser Ile Ser Ser Tyr Leu Asn Trp Tyr Gln Gln Lys Pro Gly Lys
65                  70                  75                  80

Ala Pro Lys Leu Leu Ile Tyr Ala Ala Ser Ser Leu Gln Ser Gly Val
                85                  90                  95

Pro Ser Arg Phe Ser Gly Ser Gly Ser Gly Thr Asp Phe Thr Leu Thr
            100                 105                 110

Ile Ser Ser Leu Gln Pro Glu Asp Phe Ala Thr Tyr Tyr Cys Gln Gln
        115                 120                 125

Thr Val Val Ala Pro Pro Leu Phe Gly Gln Gly Thr Lys Val Glu Ile
    130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250


<210> SEQ ID NO 562
<211> LENGTH: 257
<212> TYPE: PRT
<213> ORGANISM: Artificial Sequence
<220> FEATURE:
<223> OTHER INFORMATION: chemically synthesized

<400> SEQUENCE: 562

Cys Asn Ile Trp Leu Val Gly Gly Asp Cys Arg Gly Trp Gln Gly Gly
1               5                   10                  15

Ser Ser Gly Gly Ser Ala Val Gly Leu Leu Ala Pro Pro Gly Gly Leu
            20                  25                  30

Ser Gly Arg Ser Asp Asn Ile Gly Gly Gly Ser Asp Ile Gln Met Thr
        35                  40                  45

Gln Ser Pro Ser Ser Leu Ser Ala Ser Val Gly Asp Arg Val Thr Ile
    50                  55                  60

Thr Cys Arg Ala Ser Gln Ser Ile Ser Ser Tyr Leu Asn Trp Tyr Gln
65                  70                  75                  80

Gln Lys Pro Gly Lys Ala Pro Lys Leu Leu Ile Tyr Ala Ala Ser Ser
                85                  90                  95

Leu Gln Ser Gly Val Pro Ser Arg Phe Ser Gly Ser Gly Ser Gly Thr
            100                 105                 110

Asp Phe Thr Leu Thr Ile Ser Ser Leu Gln Pro Glu Asp Phe Ala Thr
        115                 120                 125

Tyr Tyr Cys Gln Gln Thr Val Val Ala Pro Pro Leu Phe Gly Gln Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175
```

-continued

```
Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys
```